(12) United States Patent
Dunn-Coleman et al.

(10) Patent No.: US 7,453,023 B2
(45) Date of Patent: Nov. 18, 2008

(54) MANIPULATION OF THE PHENOLIC ACID CONTENT AND DIGESTIBILITY OF PLANT CELL WALLS BY TARGETED EXPRESSION OF GENES ENCODING CELL WALL DEGRADING ENZYMES

(75) Inventors: Nigel Dunn-Coleman, Los Gatos, CA (US); Timothy Langdon, Aberystwyth (GB); Phillip Morris, Aberystwyth (GB)

(73) Assignee: Genencor International, Inc., Palo Alto, CA (US)

( * ) Notice: Subject to any disclaimer, the term of this patent is extended or adjusted under 35 U.S.C. 154(b) by 164 days.

(21) Appl. No.: 11/214,613

(22) Filed: Aug. 30, 2005

(65) Prior Publication Data

US 2006/0005270 A1 Jan. 5, 2006

Related U.S. Application Data

(63) Continuation of application No. 09/991,209, filed on Nov. 16, 2001, now Pat. No. 7,132,589.

(60) Provisional application No. 60/249,608, filed on Nov. 17, 2000.

(51) Int. Cl.
C12N 15/52 (2006.01)
C12N 15/82 (2006.01)

(52) U.S. Cl. .................. 800/288; 800/287; 800/298; 800/320

(58) Field of Classification Search ................... None
See application file for complete search history.

(56) References Cited

U.S. PATENT DOCUMENTS 6,143,543 A * 11/2000 Michelsen et al. .......... 435/196

6,602,700 B1 * 8/2003 Li et al. ...................... 435/267

FOREIGN PATENT DOCUMENTS

GB 2 301 103 A 11/1996

OTHER PUBLICATIONS

Kroon P. et al. Biochemical Society Transactions, 1998; vol. 26; p. S167.*
*Darnowski, D. W. et al., << A soybean lectin-GFP fusion labels the vacuoles in developing *Arabidopsis thaliana* embryos, >> Plant Cell Reports, vol. 20, No. 11, pp. 1033-1038, May 2002.
*De Vries. R. P. et al., "The faeA genes from *Aspergillus niger* and *Aspergillus tubingensis* encode ferulic acid esterases involved in degradation of complex cell wall polysaccharides," Applied and Environmental Microbiology, vol. 63, No. 12, Dec. 1997 pp. 4638-4644, XP00203731.
*Garcia-Conesa, Maria-Teresa et al., "A cinnamoyl esterase from *Aspergillus niger* can break plant cell wall cross-links without release of free diferulic acids." European Journal of Biochemistry, vol. 266, No. 2, Dec. 1999, pp. 644-652, XP002203732.

* cited by examiner

*Primary Examiner*—Russell Kallis

(57) ABSTRACT

Described herein are methods to enhance the production of more highly fermentable carbohydrates in plants, especially forage grasses. The invention provides for transgenic plants transformed with expression vectors containing a DNA sequence encoding ferulic acid esterase I from *Aspergillus*, preferably *A. niger*. The expression vectors may optionally comprise a DNA sequence encoding xylanase from *Trichoderma*, preferably *T. reesei*. Expression of the enzyme(s) is targeted to specific cellular compartments, in specific tissues and under specific environmental conditions. Uses of this invention include, but are not limited to, forage with improved digestibility for livestock, and enhanced biomass conversion.

25 Claims, 154 Drawing Sheets

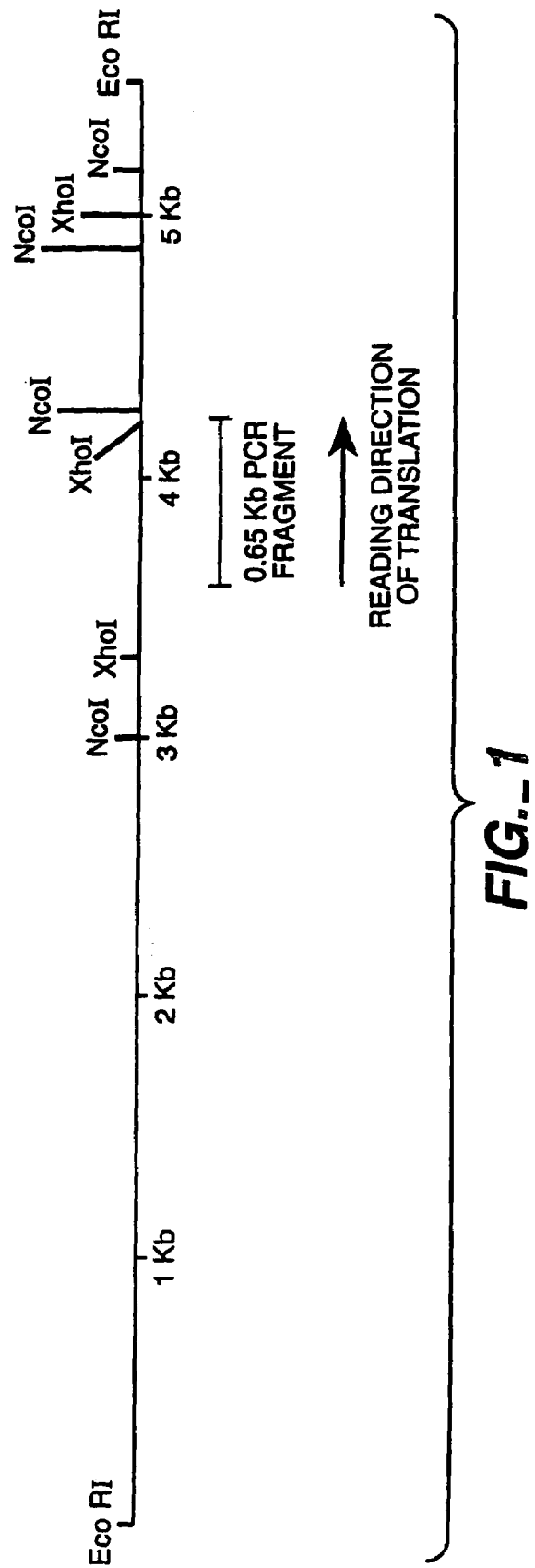
FIG._1

```
Nco I    EcoR V                    Psp1406 I
CCATGGTGGTGTCGATATCGGGCAGTAGTCTTTGCCGAAACGTTGAGGGTTACAGTGATCTGCGTCGGACATATACTTCGGGGAATTCTACGGC
                                                                                            |
                                                                                           90

Sac I
GGAATATCAAAGTCTTTCGGAATATCCATATTGGGAAAGGAGACAGAAGCTTCCGGGGTAGTTTGATAGATGAGCTCCGGTGTATTAAATCGGG
                                                                                            |
                                                                                           180

BssH II
AGCTGACACAGGAGTGAGGCGTCATGTAGACCATCTAGTAATGTCAGTCGCGCGCCAATTTCGCACATGAAACAAGTTGATTTCGGGACCCCAT
                                                                                            |
                                                                                           270

Xho I            Bst1107 I                                                  EclHK I
TGTTACATCTCTCGGCTACAGCTCGAGATGTGCCTGCCGAGTATACTTAGAAGCCATGCCAGCGTGTTGTTATACGACCAAAAGTCAGGG
                                                                                            |
                                                                                           360

Pvu I
AATATGAAACGATCGTCGGATATTTCTTGTTTTTATCCTAAATTAGTCTTCCAGTGGTTTATTTAAGAGATAGATCCCTTCACAAACACT
                                                                                            |
                                                                                           450

Xmn I
CATCCAACGGACTTCTCATACCACTCATTGACATAATTTCAAACAGCTCCAGGGCGCATTTAGTTCAACATGAAGCAATTCTCCGCCAAAC
                                                                                            |
                                                                                           540

┌─────────────────┐
                                                                    │ signal sequence │
                                                                    └─────────────────┘
                                                                     M  K  Q  F  S  A  K

FIG._2A
```

```
                                                                                                                    PstI    Bpu10I
ACGTCCTCGCAGTTGTGGTGACTGCAGGGCACGCCTTAGCAGCCCTCTACGCAAGGCATCTCCGAAGACCTTCCGACAGCCGTTTAGTCGAAA
  H  V  L  A  V  V  V  T  A  G  H  A  L  A  A  S  T  Q  G  I  S  E  D  L  Y  S  R  L  V  E
                                              |―――――――signal sequence―――――――|
                                                                        SalI
TGGCCACTATCTCCCAAGCTGCCTACGCCGACCTGTGCAACATTCCGTCGACTATTATCAAGGGAGAGAAAATTTACAATTCTCAAACTG
  M  A  T  I  S  Q  A  A  Y  A  D  L  C  N  I  P  S  T  I  I  K  G  E  K  I  Y  N  S  Q  T
 MscI
                                                                                BsaBI
ACATTAAACGGGATGGATCCTCCGGACAGCAGCAAAGAAATAATCACCGTCTTCCGTGGCACTGGTAGTGATACGAATCTACAACTCG
  D  I  N  G  W  I  L  R  D  D  S  S  K  E  I  I  T  V  F  R  G  T  G  S  D  T  N  L  Q  L
         BamHI
                                                                                       Eco31I
ATACTAACTACACCCTCACGCCCTTTGACACCCTACCACAATGCAACGGTTGTGAAGTACACGGGTGGATATATTATTGGATGGGTCTCCG
  Q  T  N  Y  T  L  T  P  F  D  T  L  P  Q  C  N  G  C  E  V  H  G  G  Y  Y  I  G  W  V  S
```

*FIG._2B*

Tth111 I      BspM I           Acc III

TCCAGGACCAAGTCGAGTCGCTTGTCAAACAGCAGGTTAGCCAGTATCCGGACTGTGACGGGCCACAGGTATGCCCTCG     990

V  Q  D  Q  V  E  S  L  V  K  Q  Q  V  S  Q  Y  P  D  Y  A  L  T  V  T  G  H

ApaB I      Pvu II

TGATTTCTTTCAATTAAGTGTATAATACTCACTAACTCTACGATAGTCTCGGAGGTCCCTGGCAGCACTCGCCGCCAGCTGTCTG     1080 intron                                          L  G  A  S  L  A  A  L  T  A  A  Q  L  S BsrG I                                                          Stu I CGACATACGAGACAACATCCGCCTGTACACCTTCGGGGAACCGCGCAGGGCAATCAGGCCTTCGCGTCGTACATGAACGATGCCTTCCAAG     1170

A  T  Y  D  N  I  R  L  Y  T  F  G  E  P  R  S  G  N  Q  A  F  A  S  Y  M  N  D  A  F  Q

Xho I                                           BspM I                       Nco I

CCTCGAGCCCCAGATACGACGCAGTATTTCCGGGTCACTCATGCCAATGACGGCATCCCAAACCTGCCCCCGGTGGAGCAGGGGTACGCCC     1260

A  S  S  P  D  T  T  Q  Y  F  R  V  T  H  A  N  D  G  I  P  N  L  P  P  V  E  Q  G  Y  A

Sca I

ATGGGCGGTGTAGAGTACTGGAGCGTTGATCCTTACAGCGCCCAGAACACATTTGTCTGCACTGGGGATGAAGTGCAGTGTGTGAGGCCC     1350

```
                                    Fsp I                    BsrB I         BsrG I      Bcl I
AGGGCGGACAGGGTGTGAATAATGCGCACACGACTTATTTTGGGATGACGAGCGGAGCCTGTACACATGGTGATCAGTCATTTCAGCCTCCC    1440
 Q  G  G  Q  G  V  N  N  A  H  T  T  Y  F  G  M  T  S  G  A  C  T  W

Ppu10 I
                               BfrB I  SnaB I
                               Sph I   Bst1107 I                                      BspLU11 I
CGAGTGTACCAGGAAAGATGTCCTGGAGAGGGCATGCATGTACGTATACCCGAAGCACACTTTTCGGTAAATCAGGACACATGTAAT         1530

BstE II
AAGTTCCTTCCATGAATAGATATGGTTACCCTCACCATAAGCCTTGAGGTTGCCTTTCTCTTTTGATTGTGAATATATATTTAAAGTAGA      1620

EcoR V
TGACAGATATCTCTAAACACCCTTATCCGCTTAAACCCATCATAGATTGTGTCACGTGATGAGCGAAATGTATCA                    1710

Dra I                                                                Sca I         Ppu10 I
GTCCCGTTTAAATCAAACCCTTTCAGCCTAGACACAGTCAGAATACACCAACCCCATTCTAAGGTAGTACTAAATATGAATACAGCCTAAA    1800

Ear I                                  Eco31 I
                                   Bgl II         Sap I        Nhe I    Nco I
TGCATCGCTATATGATCCCATAAAGAAGCAACAACCTTTCAGATCTCGTTTGCGCTGCGAAGAGCTAGCTCTACCATGGTCTCTCAATTAT     1890
BfrB I
```

FIG._2D

```
                                                  BamH I
                                                   Xma I
                                 BspLU11 I          Sma I
                                  BsrG I
GAGTGGAGCGTTAGTCTCGTTTAAGCCTAGTCTATCTTATAAGGACAACACATGTACATGGGCTTACTTGTAGAGAGGTAGGATCCCGGG
                                                                                         1980
        Xho I        BseR I                              Tth111 I
CTTCTTCACATCTCGAGGAGTTGTCTACACGTCGCGTCCATGTCATAAGCCGGTACTCGACCGTTGTCGTGACCGTGACCCAGACCCTGT
                                                                                         2070
                                                     Nco I                          BsaB I
TGATAGCGGTTGAGAAGGCCCTATATTTGAATTTCCAATCTCCAGCTTTACGAAGATATGCCATGGTGGAGGGTTAGTAAACCGATGATGA
                                                                                         2160
        Eco31 I      Msc I                                       BspLU11 I
TCGTGTGCAGCATGAGAGATGAGACCGTTGGCCAATCCTGTTCAAATGCCAAGACCCGCCTCTACCACATGTAAGGCATCCGTCGGCCGCAC
                                                                                         2250
                                             Xcm I                          Msc I
                                                                                   BsrD I
GTTGAATTGTGTCAAATGCCGAGATCATAAAAGGCGGCCACACTTCCACGTGTACTGGATGGGTTGCCGTGGCCATACTGTGTTTCCA
                                                                                         2340
                        Alwn I                       Ear I           Vsp I
TTGCCGTGGGTCGTTACTGCGACGCAGATTCTGTAGGCAAGGCGCAGGGCTCTCTTCTTCTGAGGTAGAAAACACCCCATATTAATCT
                                                                                         2430
EcoR I
GAATTC   2436
```

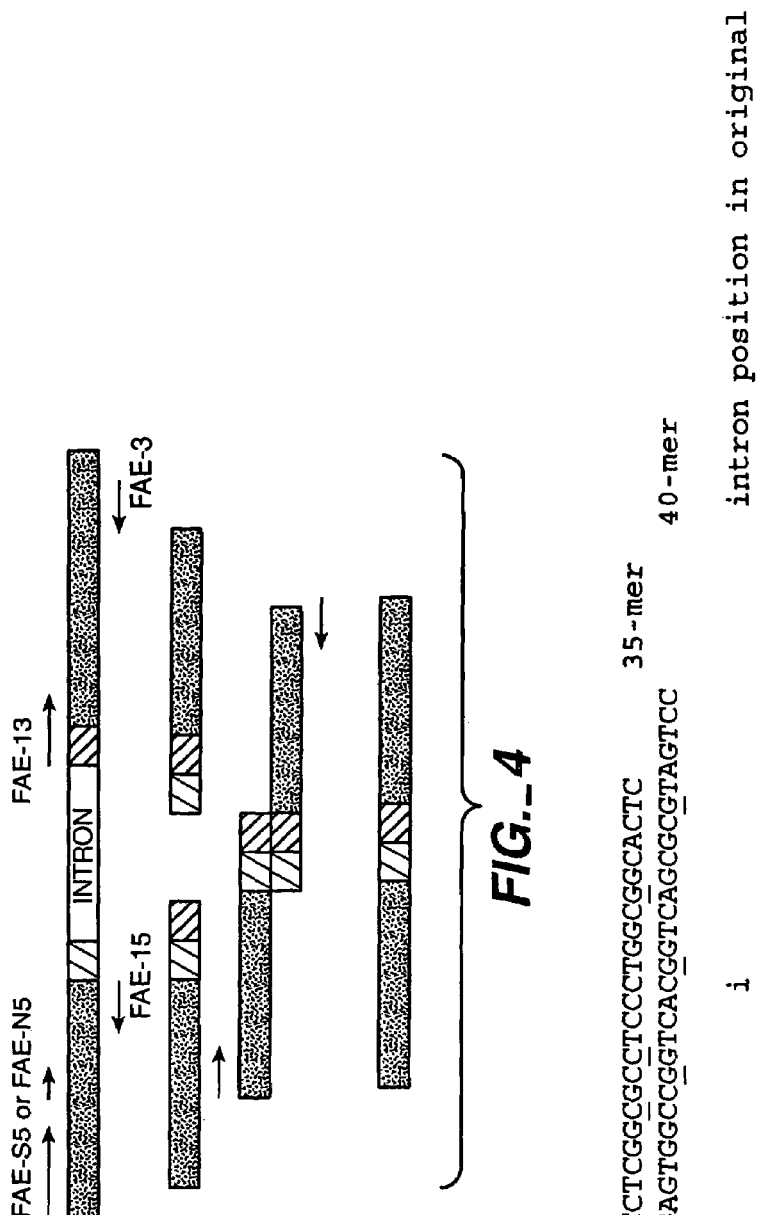

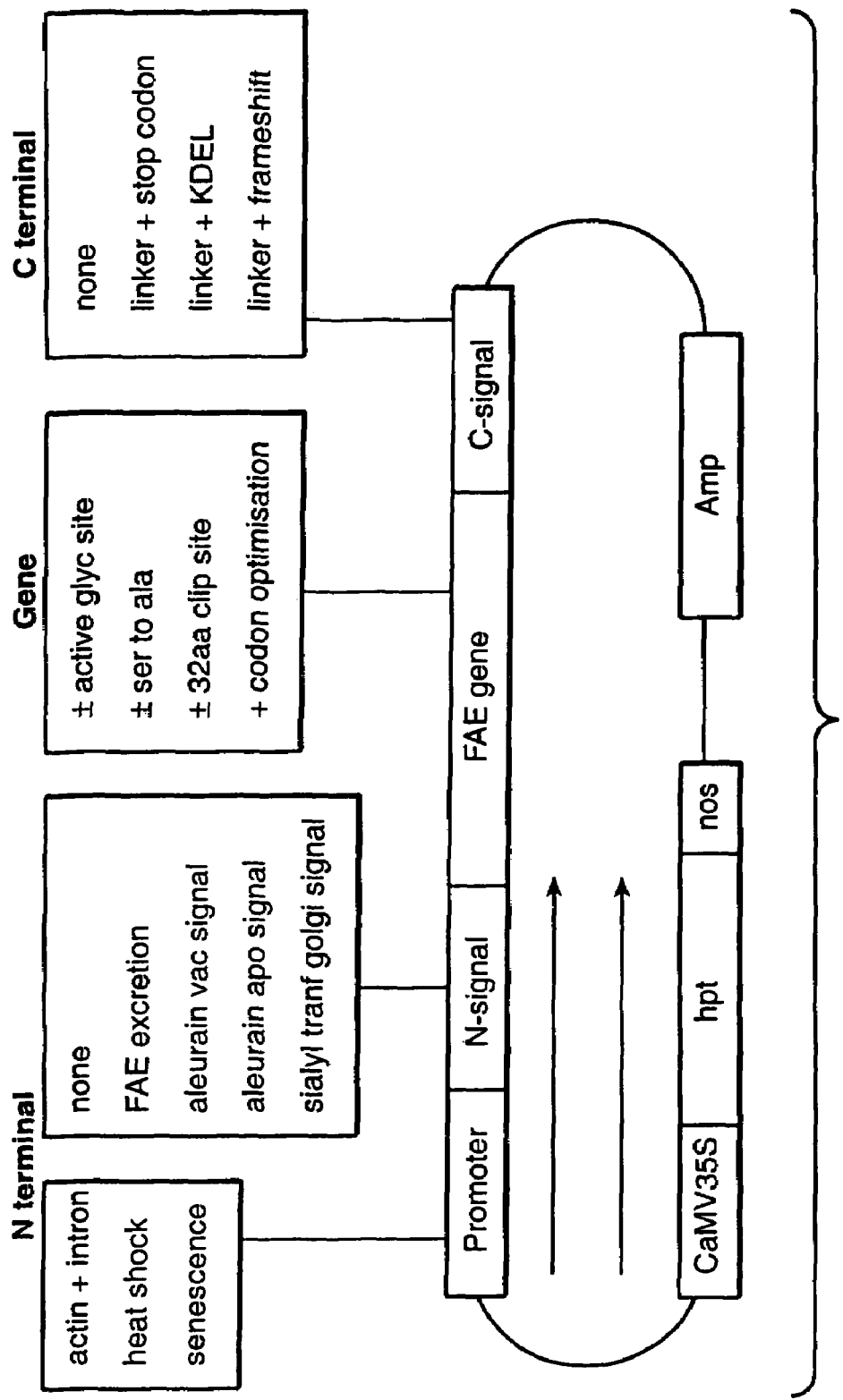
FIG._6

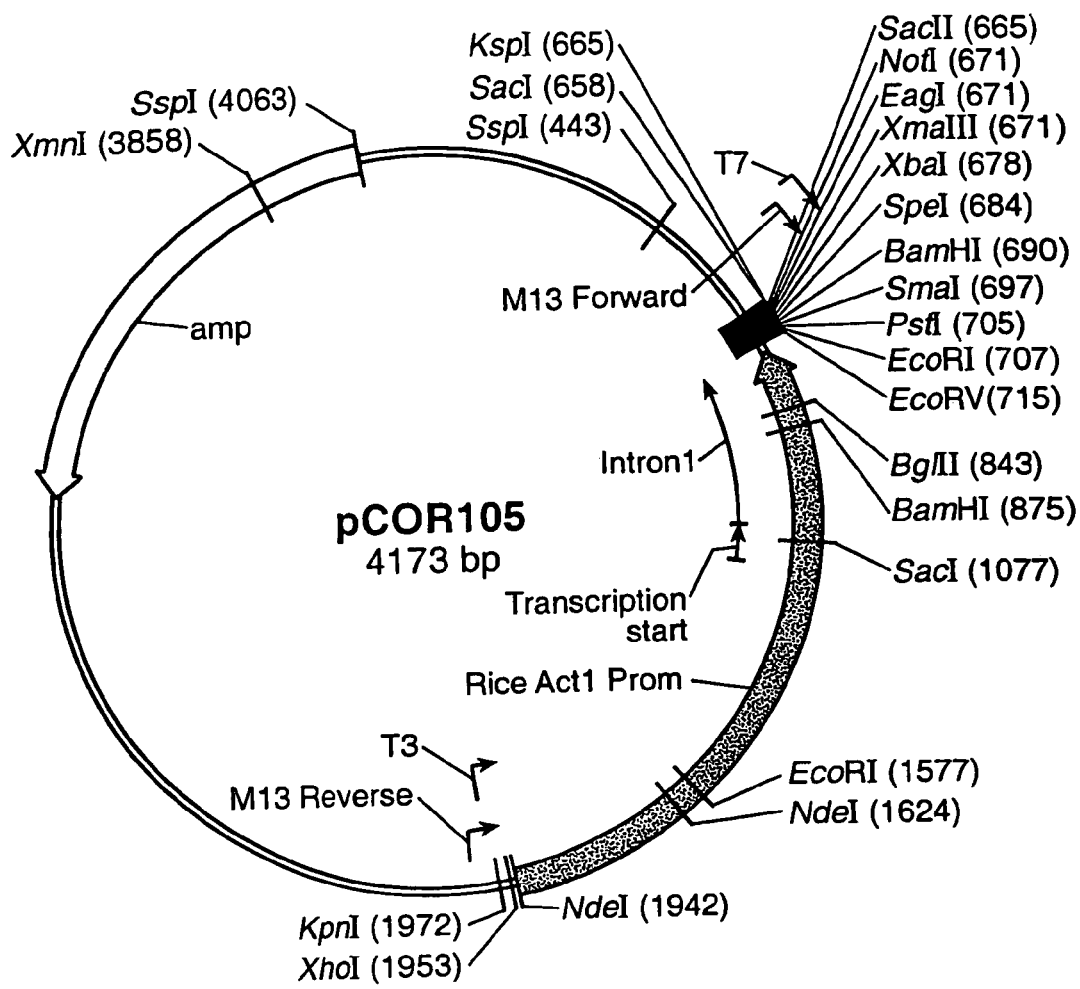
FIG._7

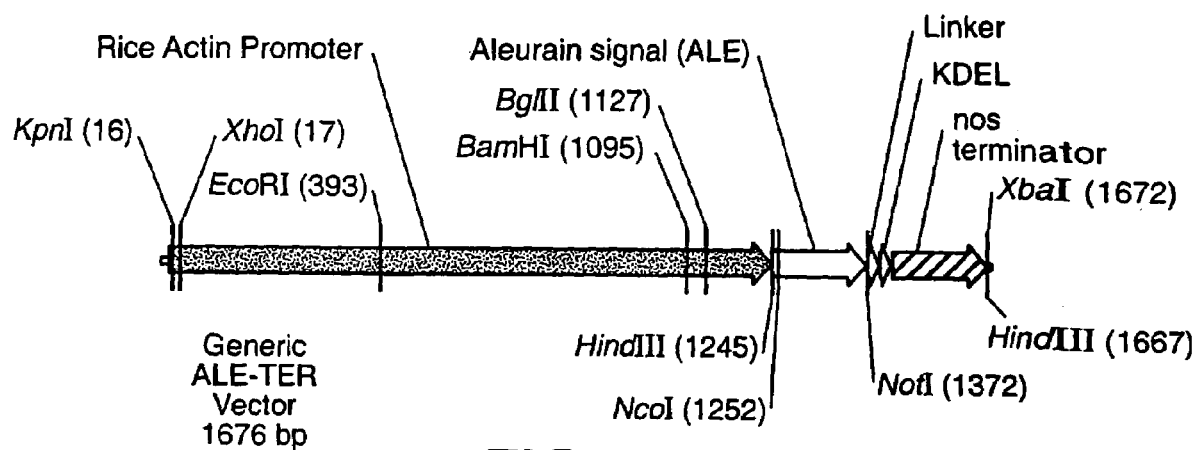
FIG._8
KDEL-COOH ER retention sequence
```
          NotI
      --------
       A   A   A   K   P   L   K   D   E   L   *
    1 GCGGCCGCGA AACCACTGAA GGATGAGCTG TAA
```
FIG._9
FAE-LINKER-FRAMESHIFT Structure and Sequence
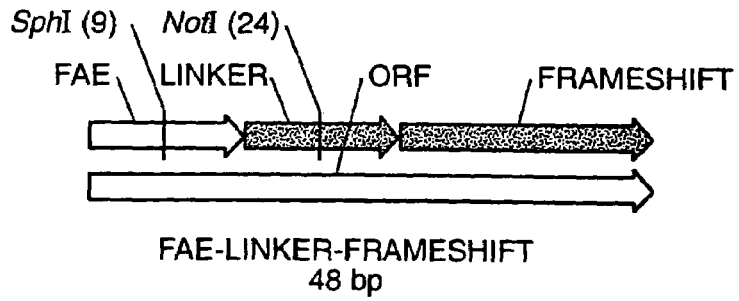
```
   +1  G   A   C   T   W   P   V   A   A   A   E   T   T   E   G
         SphI                         NotI
         ------                       --------
      1 GGCGCATGCA CCTGGCCGGT CGCGGCCGCG AAACCACTG AAGGATGA
        CCGCGTACGT GGACCGGCCA GCGCCGGCGC TTTGGTGAC TTCCTACT
```
FIG._10

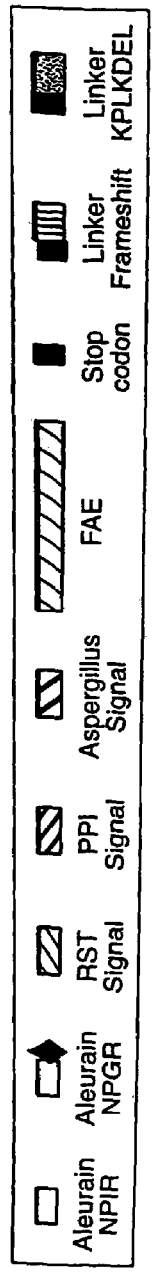
FIG._11

Vectors

Original Actin promoter in pCOR105

| | Target | Signal sequences | Vectors |
|---|---|---|---|
| (i) | APO | - aleurain-NPGR-FAE | pUH6, pTT5, TT5.5, pTT5.1 |
| | | - aleurain-delNPIR -FAE | pUH7, pUA4.4, |
| (ii) | ER | - aleurain-NPGR-FAE-linker-KDEL | pTU5, pUH8, |
| | | - aleurain-delNPIR-FAE-linker-KDEL | pUG4, pUH9, |
| (iii) | VAC | - aleurain-NPIR-FAE | pTP11.1, pTR9.4, pUH4, pUK3, |
| (iv) | ER/VAC | - aleurain-NPIR-FAE-linker-KDEL | pTU4, pUH3, |
| (v) | VAC | - aleurain-NPIR-FAE-linker-frameshift | pUA1K3, pTP3.1, pUC5.11 |
| (vi) | VAC | - aleurain-NPIR-FAE-linker-stop | pTP8.5, pUH5 |
| (vii) | ER | - Aspergillus signal -FAE-KDEL | pTP5.1, pTP6.1, pUF1, |

Modified actin promoter (Kpn1-EcoR1 deletion and restored NCO site)

| | Target | Signal sequences | Vectors |
|---|---|---|---|
| (i) | VAC | - aleurain-NPIR-FAE-linker-frameshift | pJO6.3 |
| (ii) | GOLGI | - RST-FAE-linker-frameshift | pJQ3.2 |
| (iii) | APO | - PPI-FAE-linker-frameshift | pJQ4.9 |

Heat-shock promoter

| | Target | Signal sequences | Vectors |
|---|---|---|---|
| (i) | APO | - aleurain-NPGR-FAE | pUH12 |
| | | - aleurain-delNPIR-FAE | pUH13 |
| | | - Aspergillus signal-FAE | pTP4a2, pTR2.22, |
| (ii) | ER | - aleurain-NPGR-FAE-linker-KDEL | pUH10 |
| | | - aleurain-delNPIR-FAE-linker-KDEL | pUH11 |
| (iii) | VAC | - aleurain-NPIR -FAE | pUK3, pTT3 |
| (iv) | ER/VAC | - aleurain-NPIR-FAE-linker-KDEL | pUK2 |
| (v) | VAC | - aleurain-NPIR-FAE-linker-frameshift | pUC5.11, pHOX3 |
| (vi) | VAC | - aleurain-NPIR-FAE-linker-stop | pUK6 |
| (vii) | ER | - Aspergillus signal -FAE-KDEL | pUK1, pTT2 |

Senescence promoter

| | Target | Signal sequences | Vectors |
|---|---|---|---|
| (i) | APO | - See1-PPI-FAE-linker-frameshift | pJQ5.2 |
| (ii) | VAC | - See1-aleurain-deleted NPIR-FAE | pUB8.1 |

FIG._12

RAT SIALYL TRANSFERASE Golgi signal sequence

```
    HindIII
    ------
          M   I   H   T   N   L   K   K   F   S   L   F   I   L   V   F   L   L   F   A
  1  AAGCTTACCA TGATCCACAC CAACCTCAAA AAGAAGTTCT CCCTCTTCAT CCTCGTCTTC CTCCTCTTCG .   V   I   C   V   W   K   K   G   S   D   Y   E   A   L   T   L   Q   A   K   E   F   Q   M
 71  CCGTGATCTG CGTGTGGAAG AAGGGCTCCG ACTACGAGGC CCTCACCCTC CAAGCCAAGG AGTTCCAAAT NotI
         ----
     .   A   A
141  GGCGGCCGC
```

FIG._14

POTATO PROTEASE INHIBITOR II Apoplast signal sequence

```
    HindIII
    ------
          M   X   V   H   K   E   V   N   F   V   A   Y   L   L   L   I   V   L   G   L   L   L
  1  AAGCTTACMA TGGMCGTGCA CAAGGAGTS AACTTCGTSG CCTACCTCCT GATCGTSCTC
     GGCCTCCTCT NcoI
                   ----
     .   L   V   S   A   M   E   H   V   D   A   K   A   C   T   X   E   C   G   N   L
 71  TGCTCGTSTC CGCCATGGAG CACGTGGACG CCAAGGCCTG CACCCKCGAG TGCGGCAACC
     TCGGCTTCGG NotI
         ----
     G   F   G   .
     .   I   C   P   A   A   A
141  CATCTGCCCG GCGGCCGCC
```

FIG._15

Targeting Expression of gfp to Different Cell Compartments
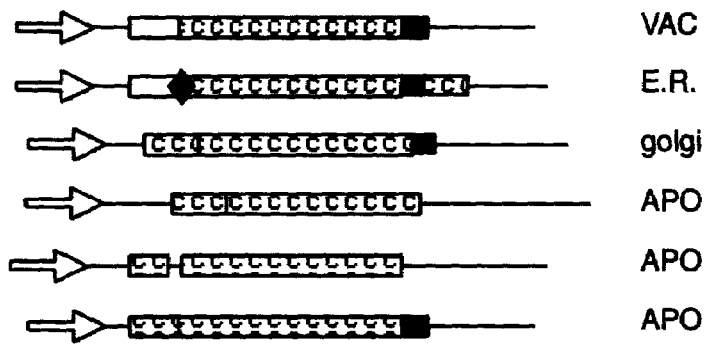
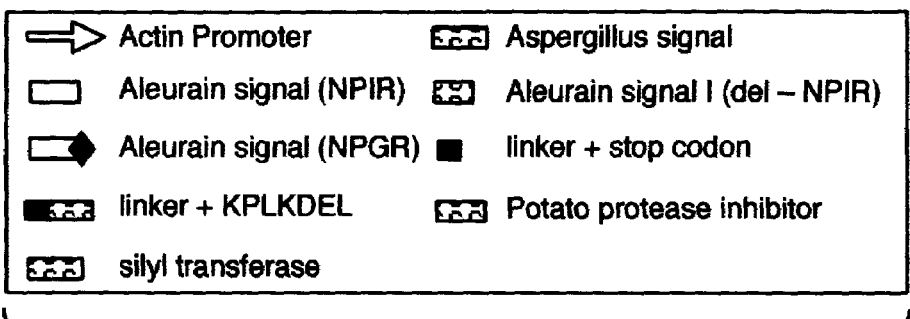
FIG._16A
FIG._16B
FIG._16C
FIG._16D
FIG._16E
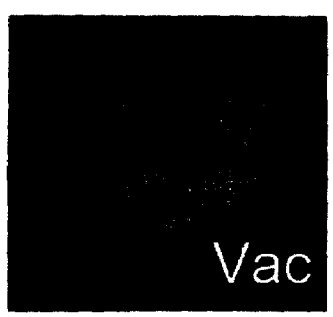
FIG._16F
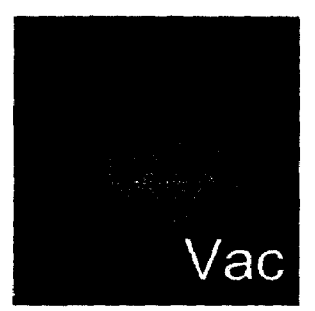
FIG._16G

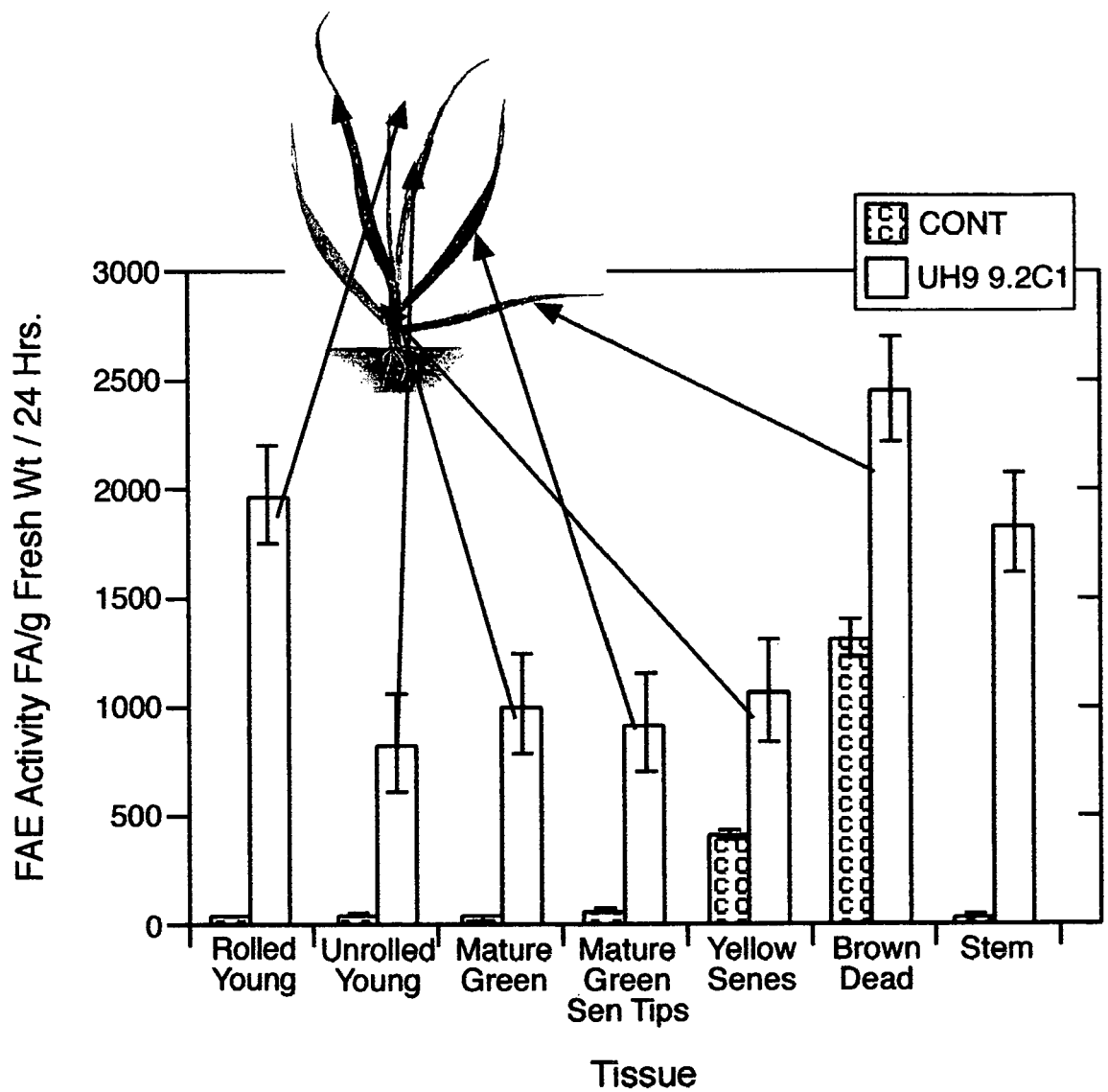
FIG._17A

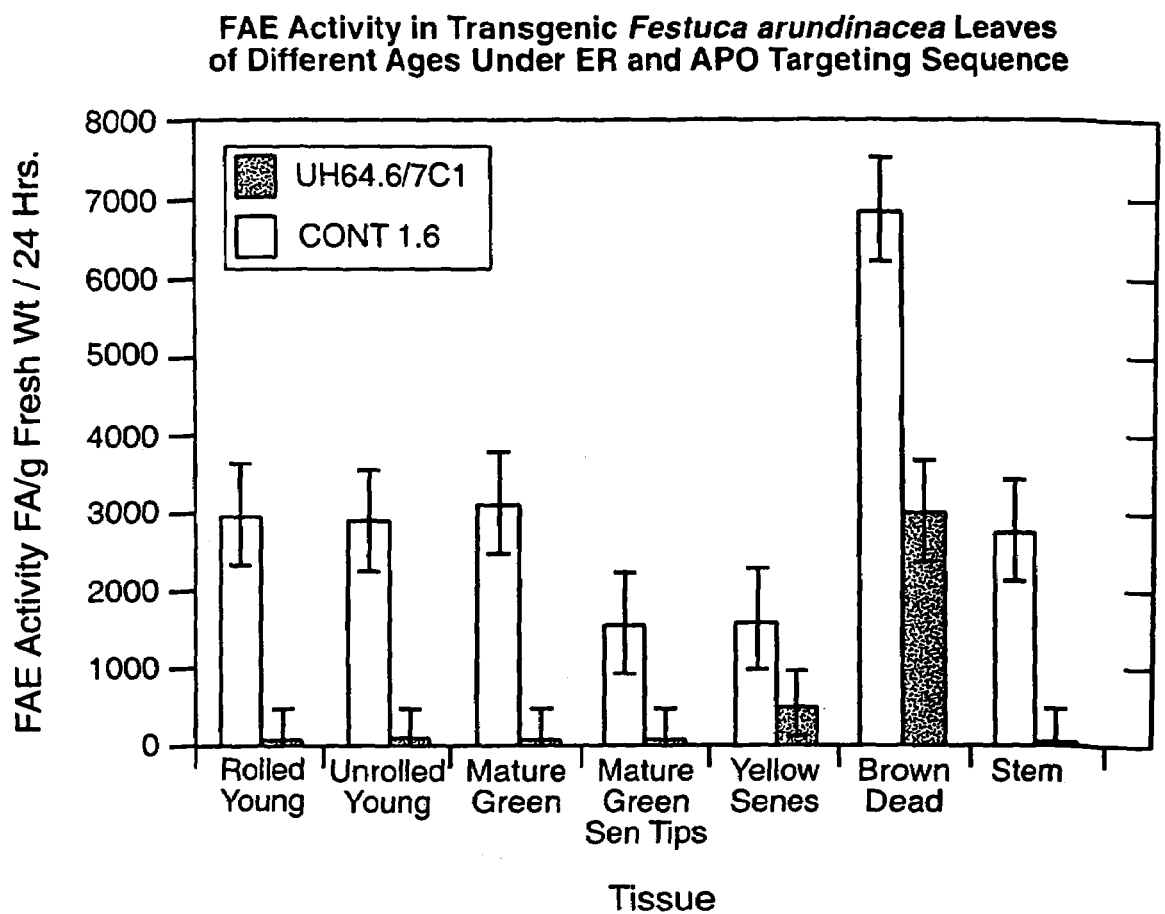
FIG._17B

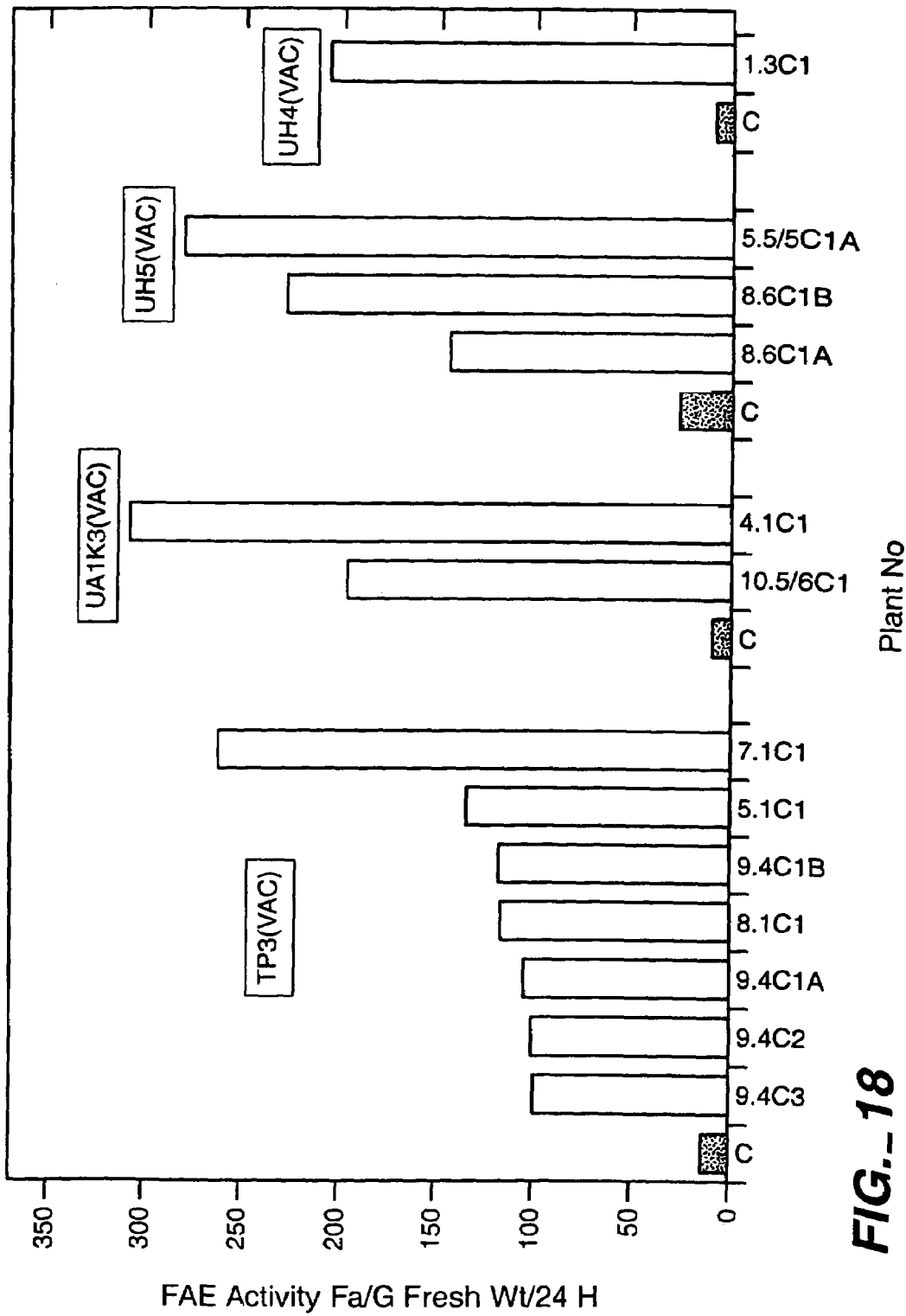
FIG._18

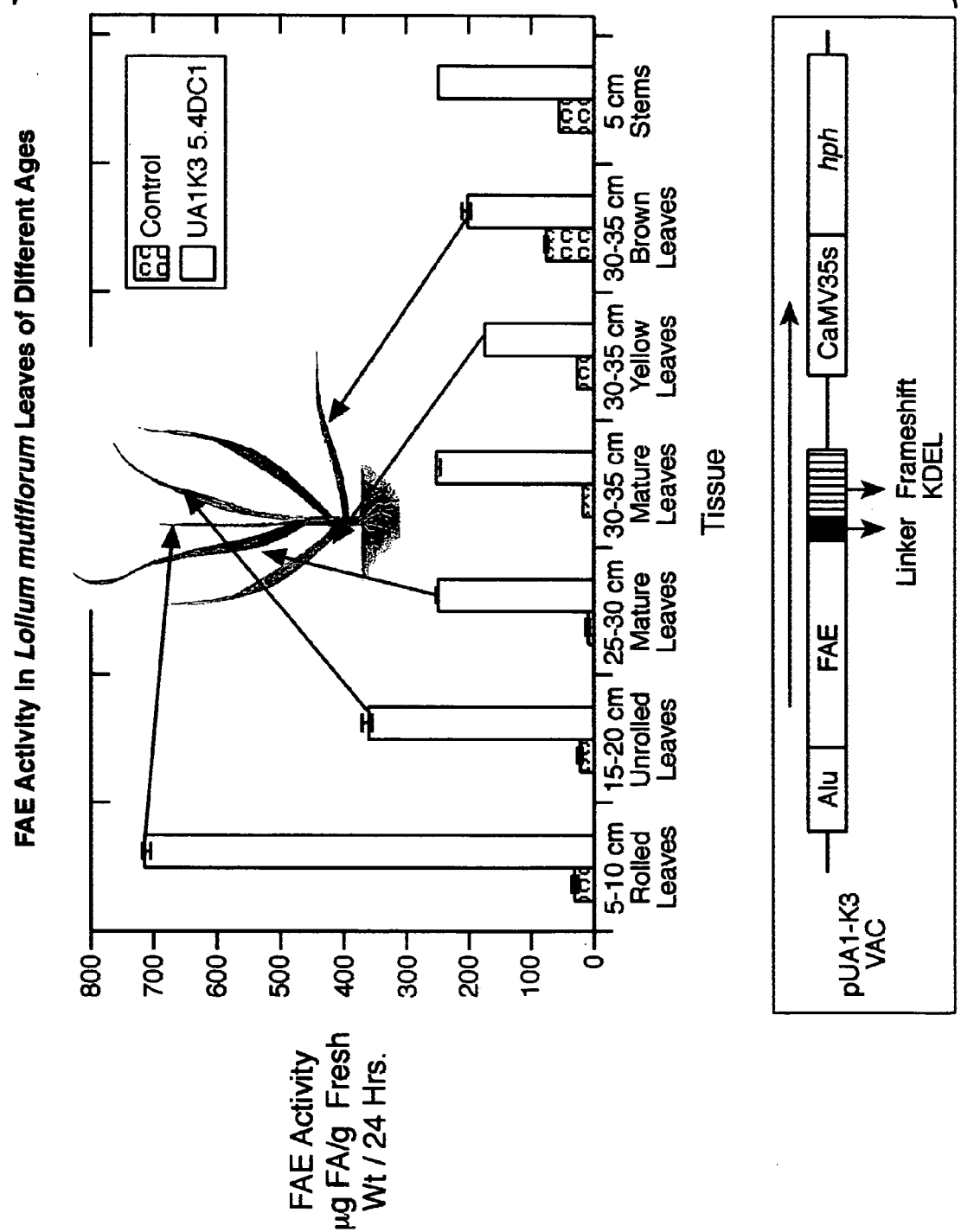
FIG._19

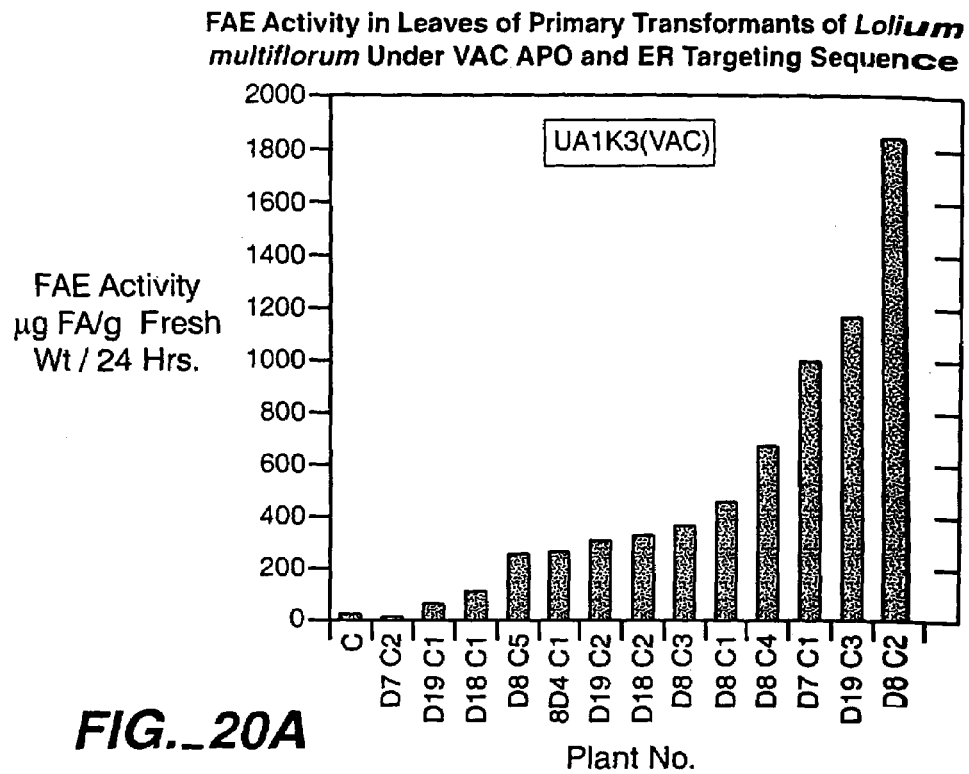
FIG._20A
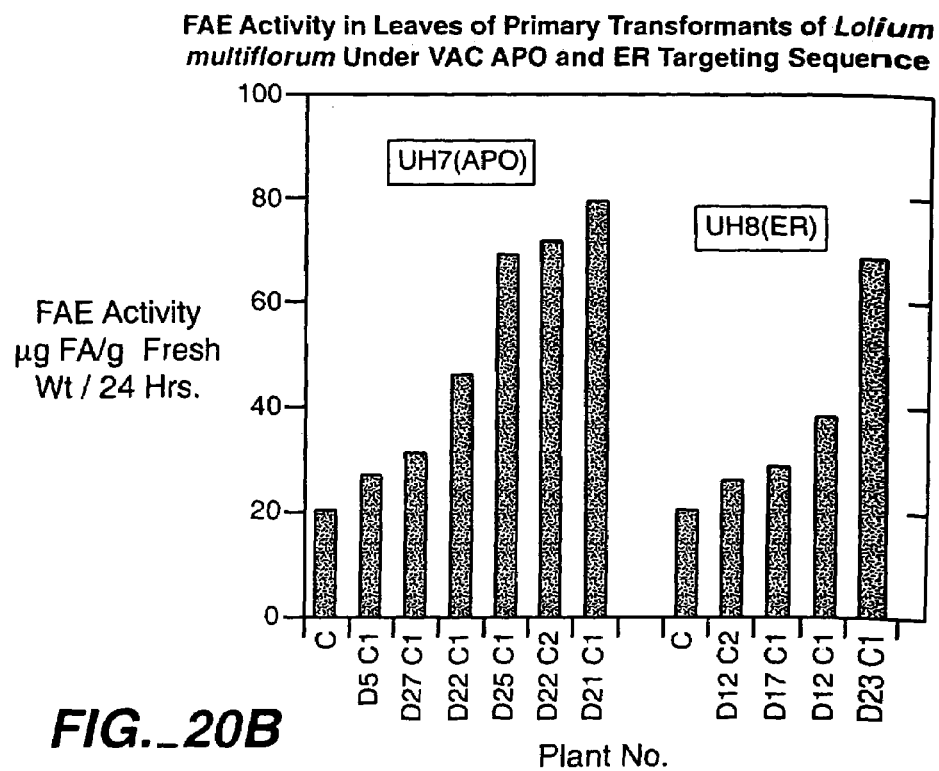
FIG._20B

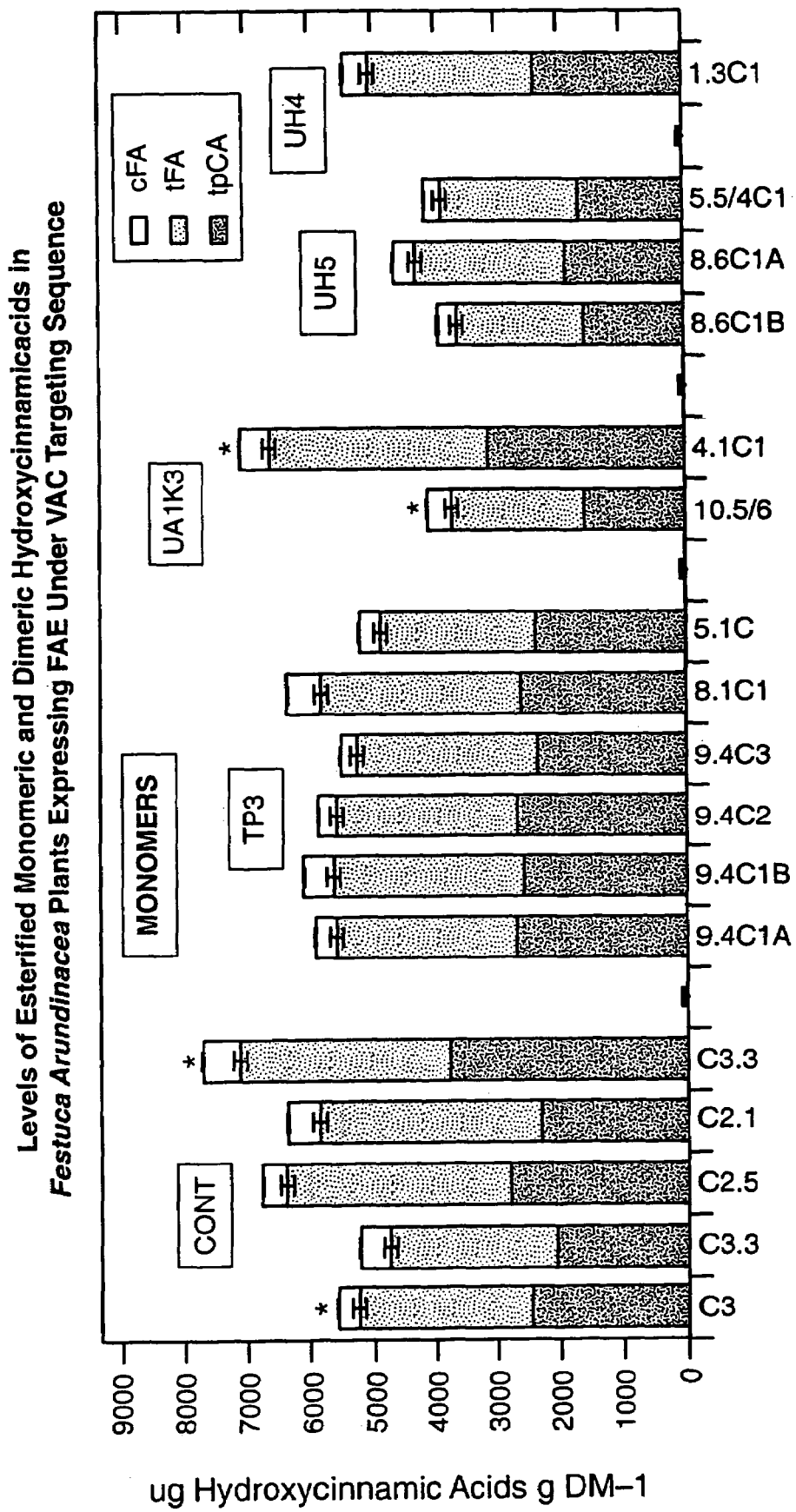
FIG._21A

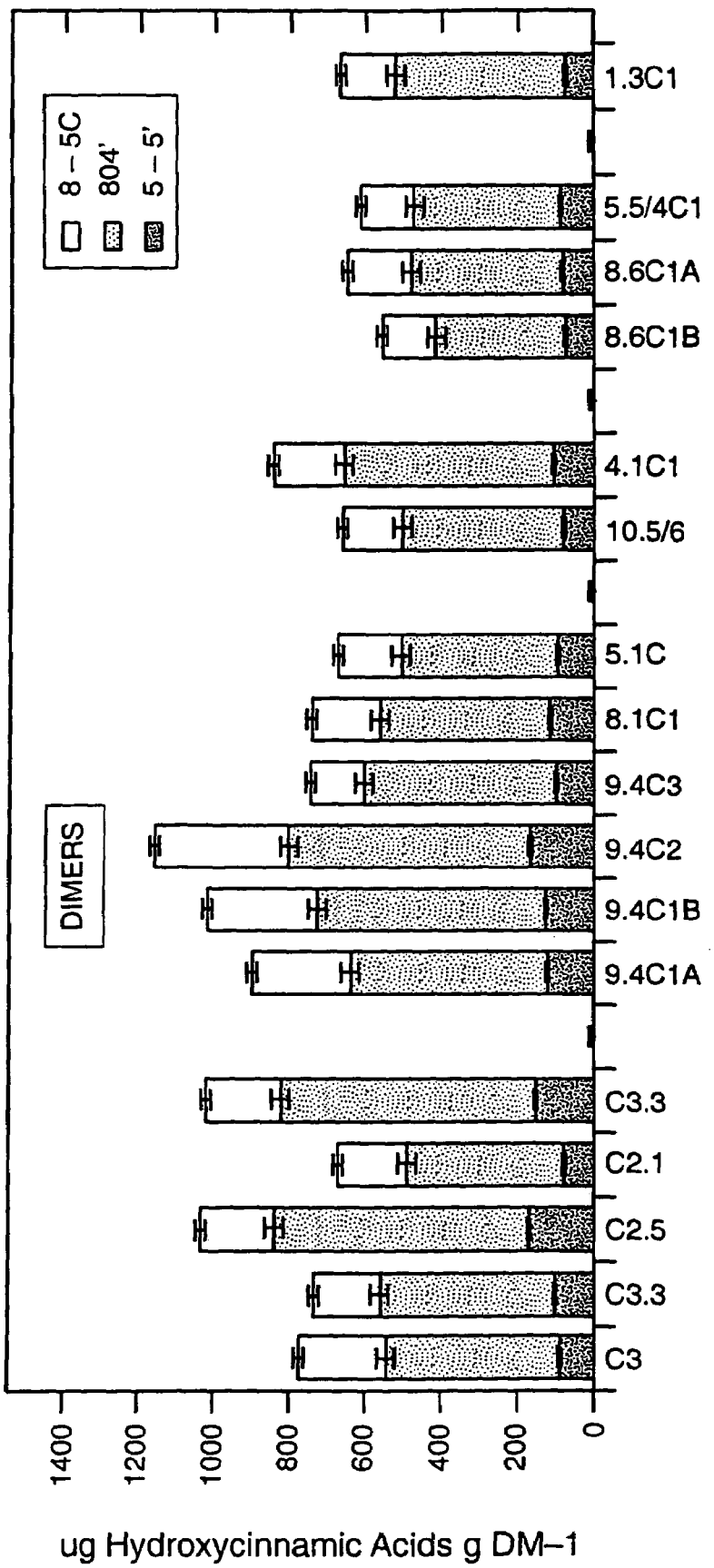
FIG._21B

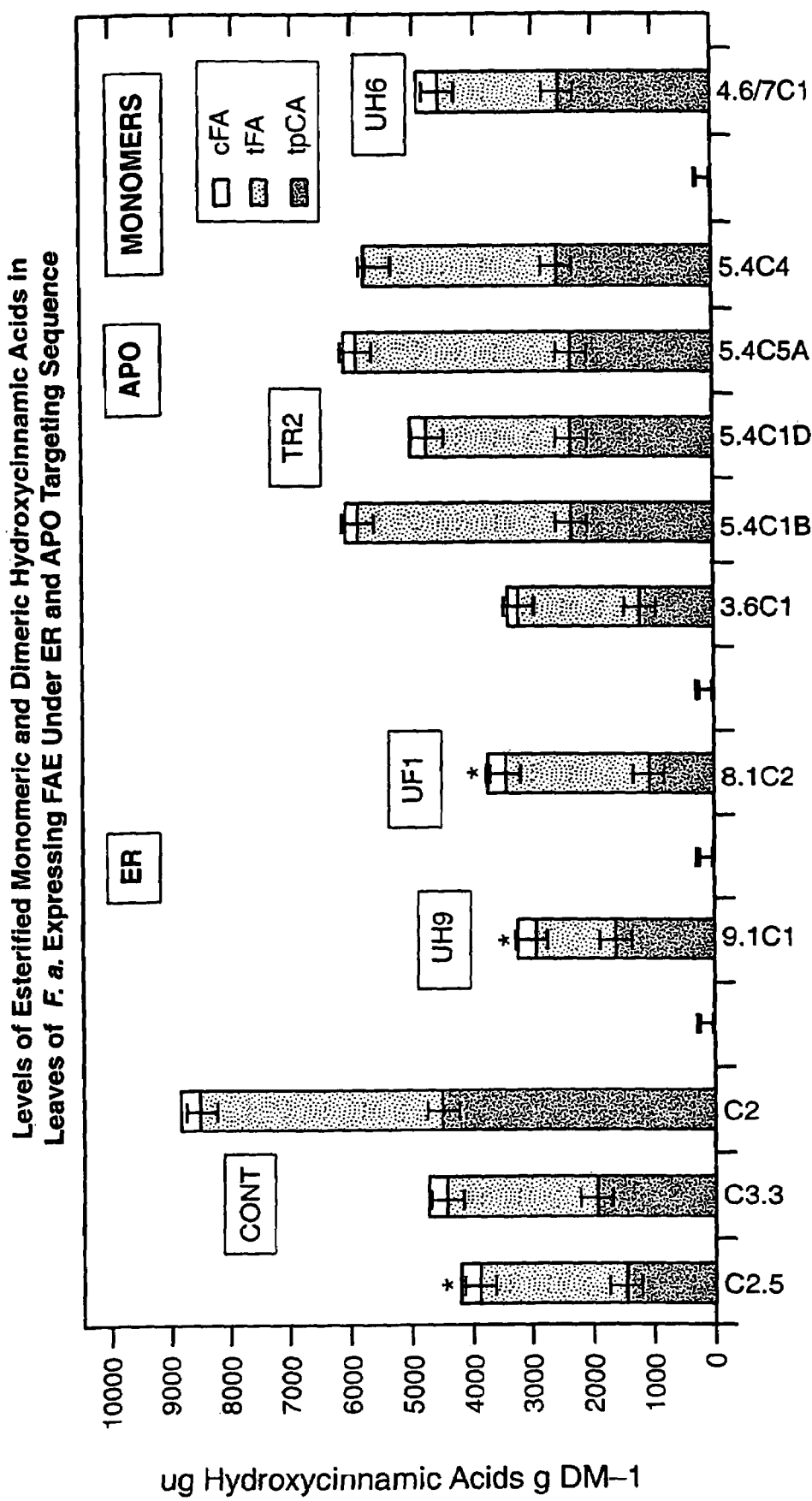
FIG._22A

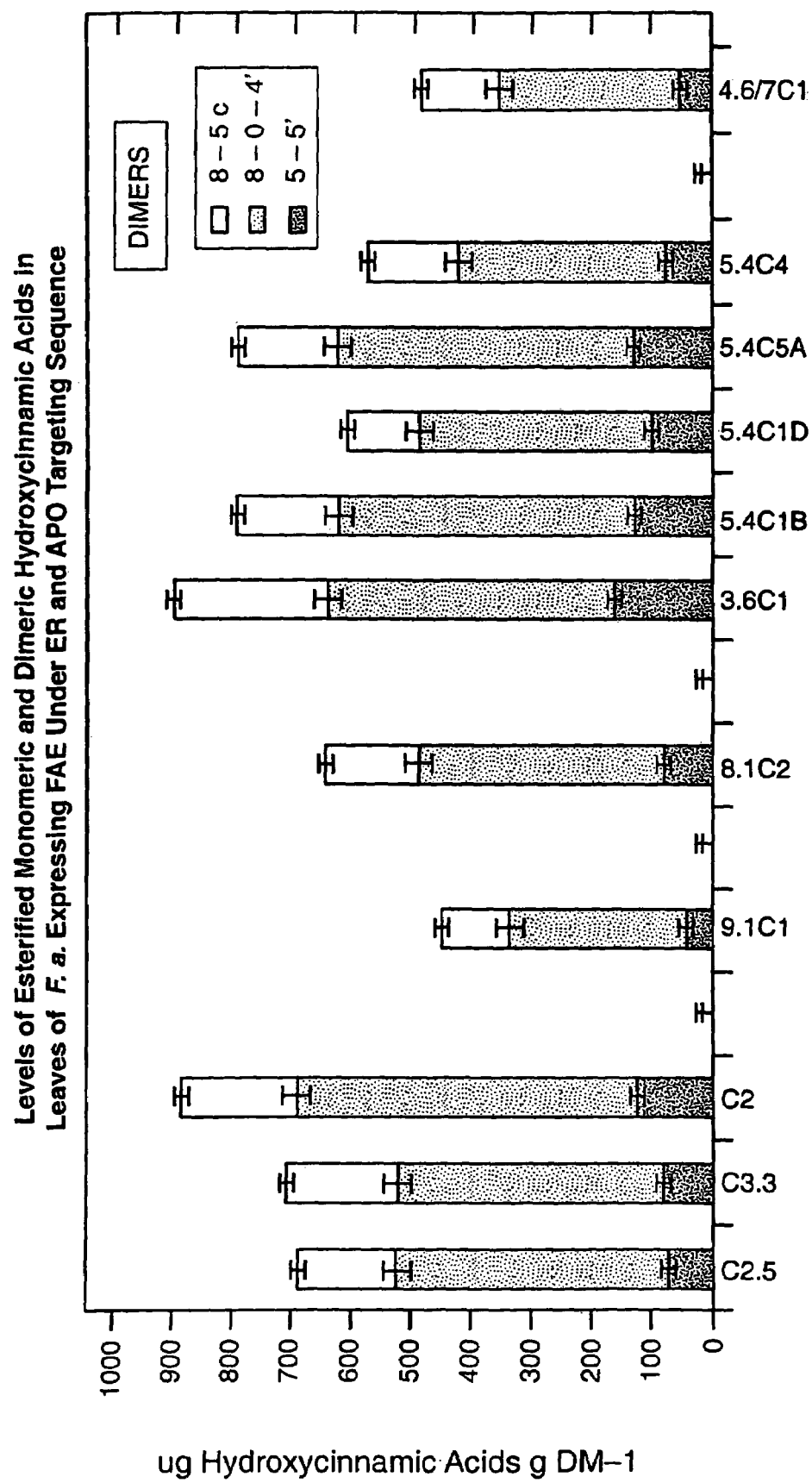
FIG._22B

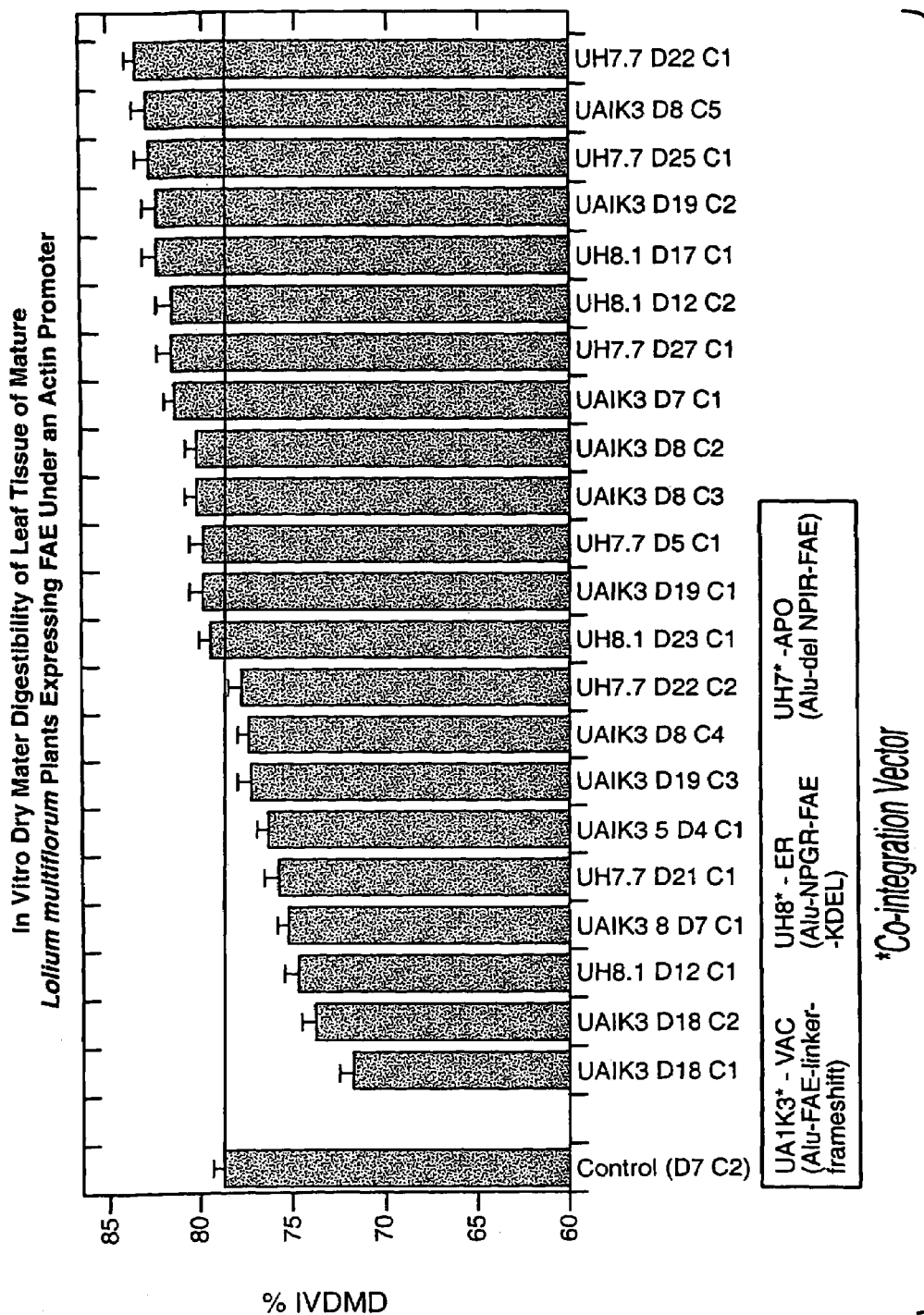
FIG._24

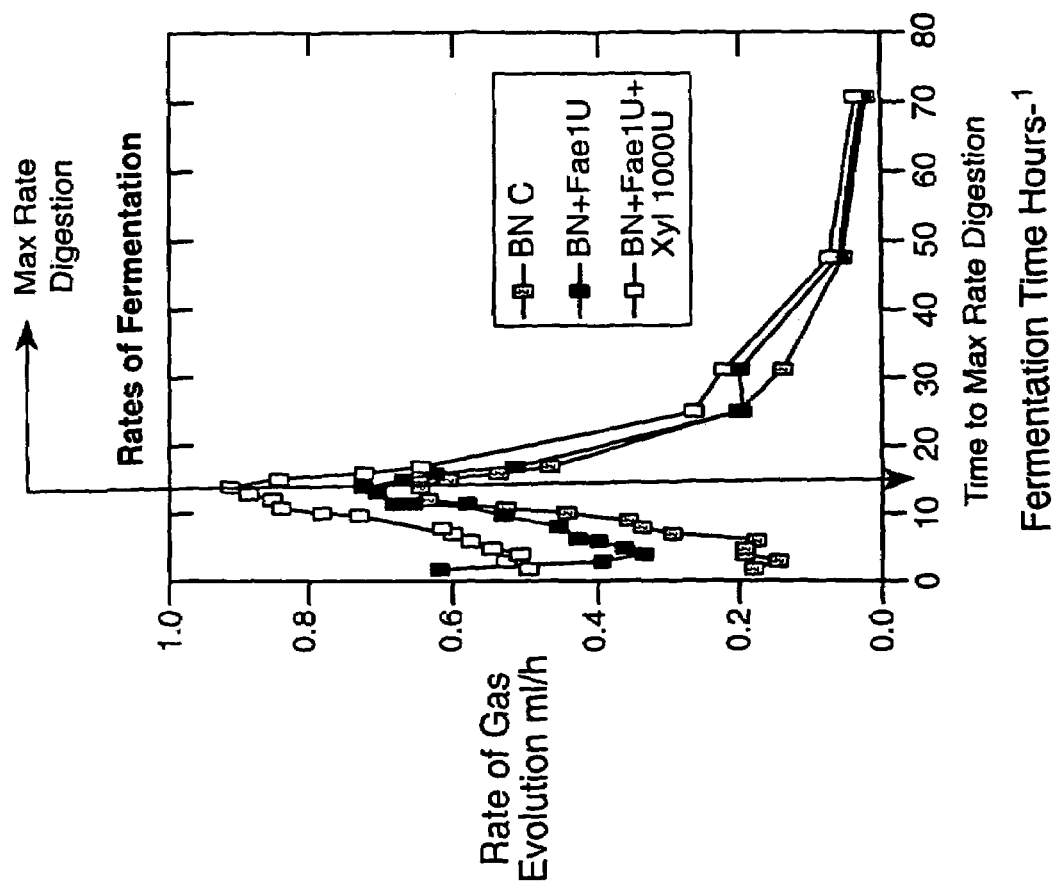
FIG._25B
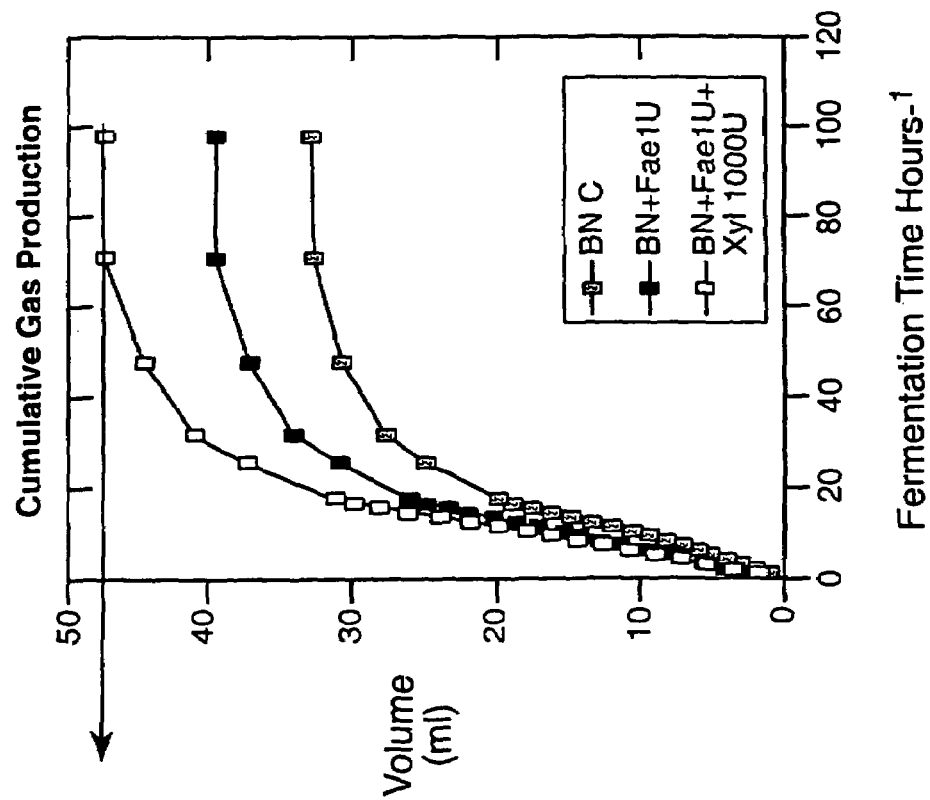
FIG._25A

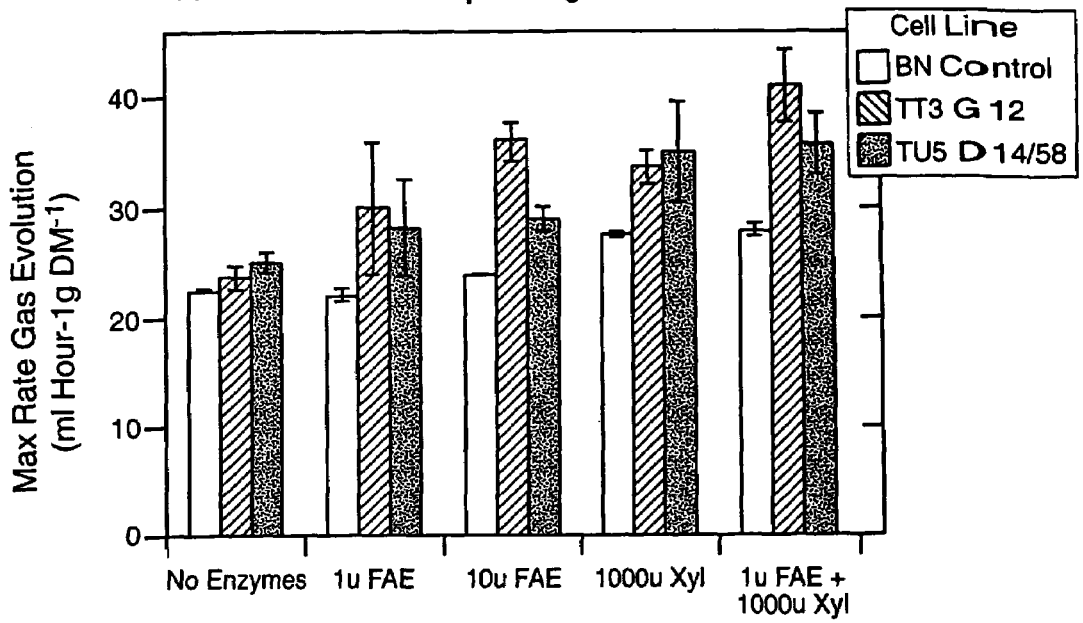
FIG._26A  Maximum Rate of Digestion
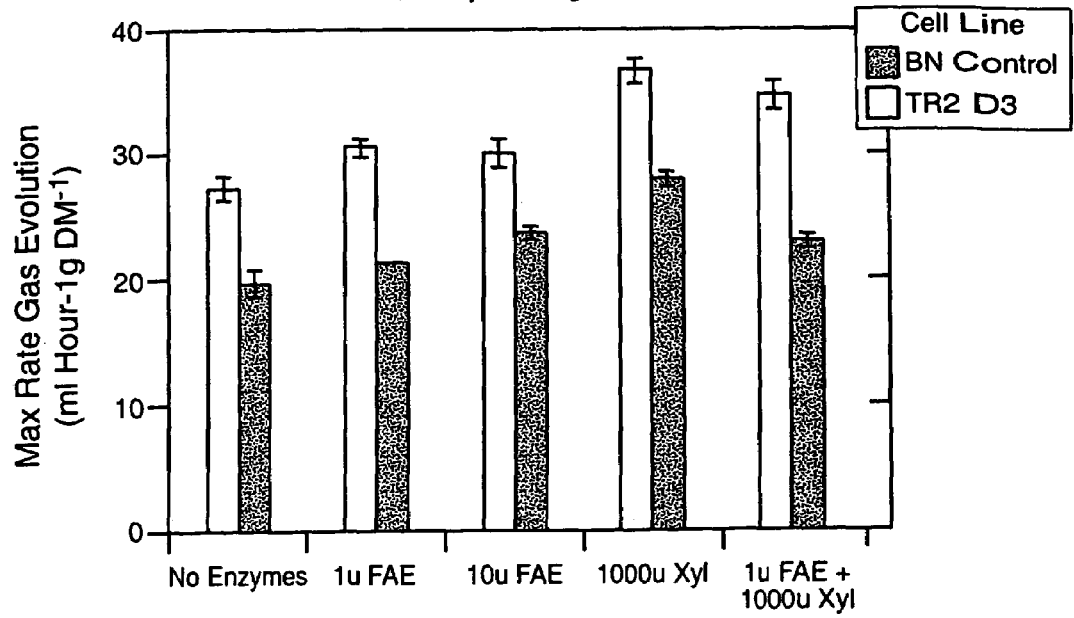
FIG._26B  Maximum Rate of Digestion

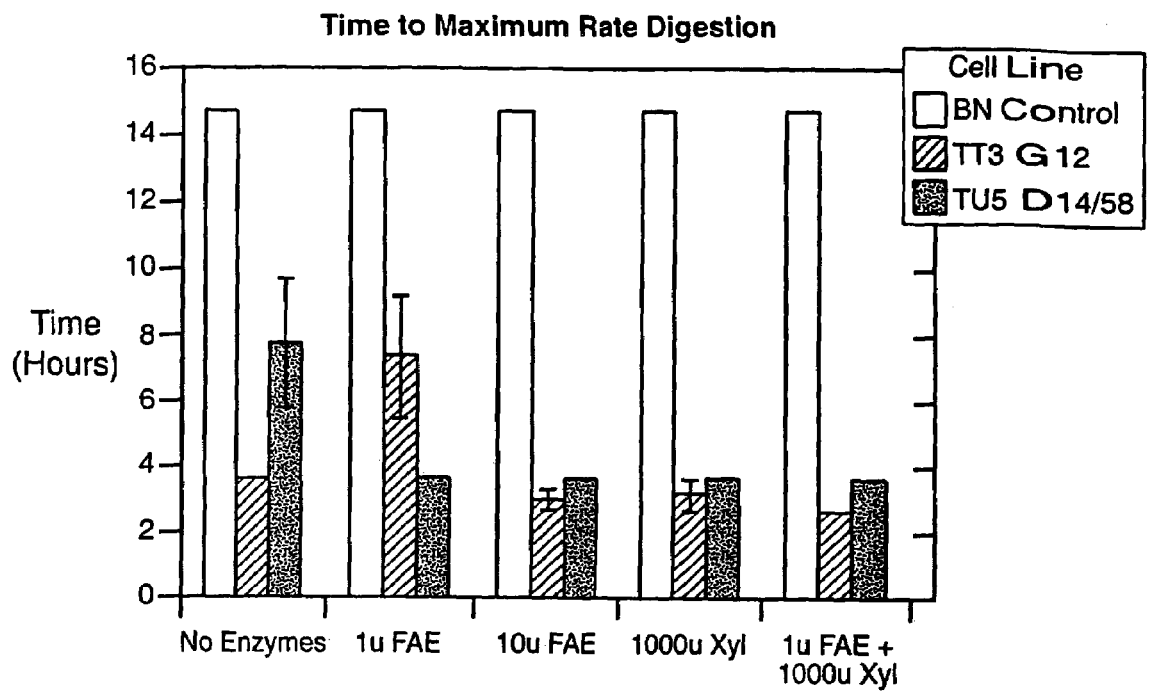
FIG._27A
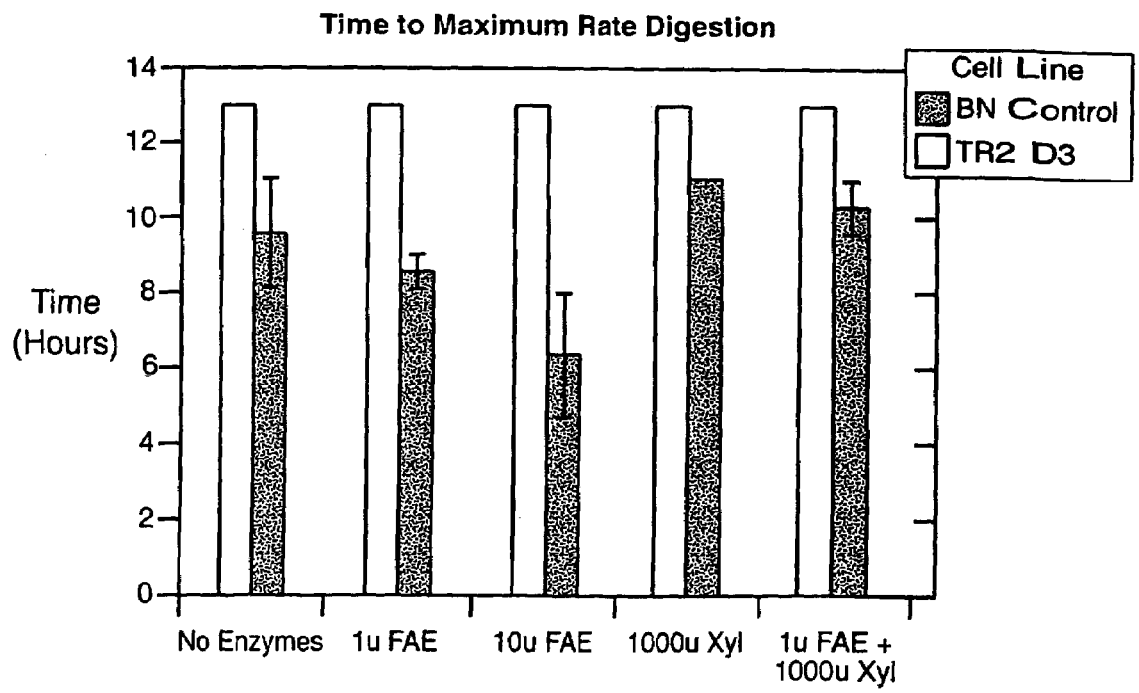
FIG._27B

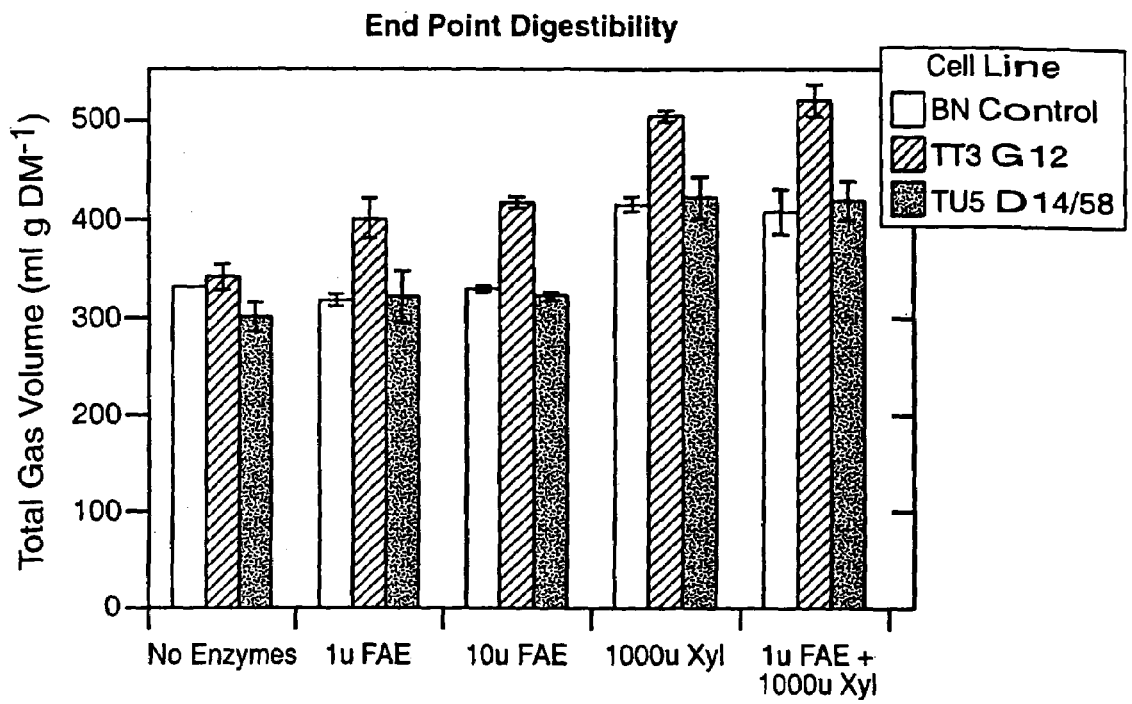
FIG._28A
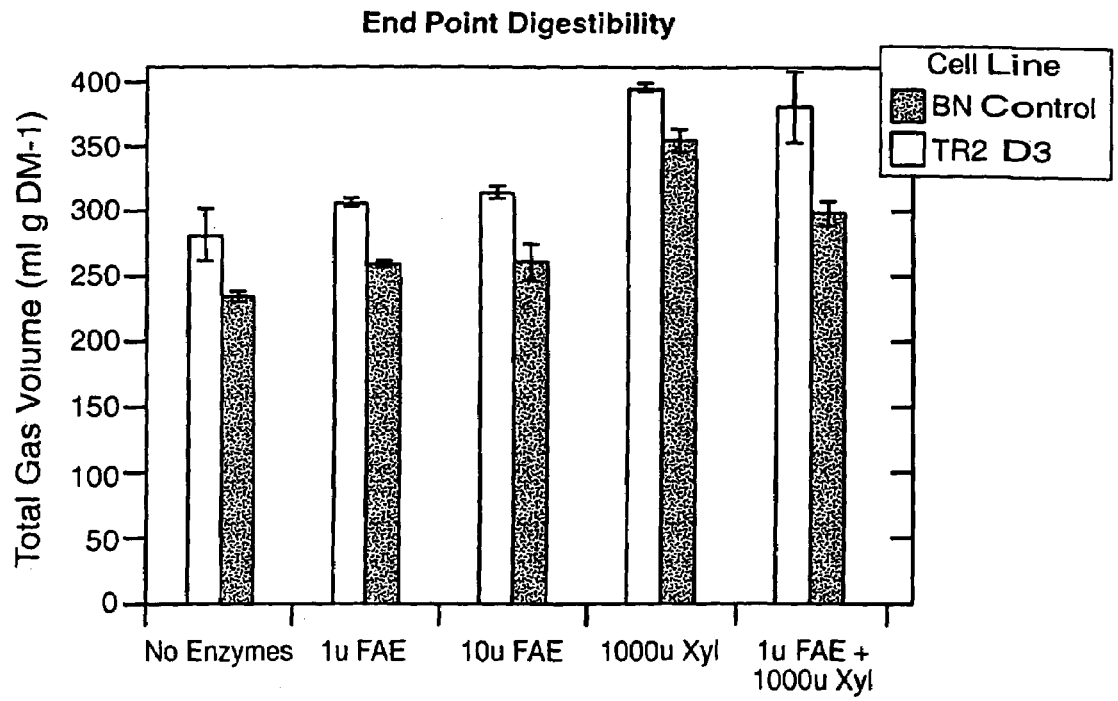
FIG._28B

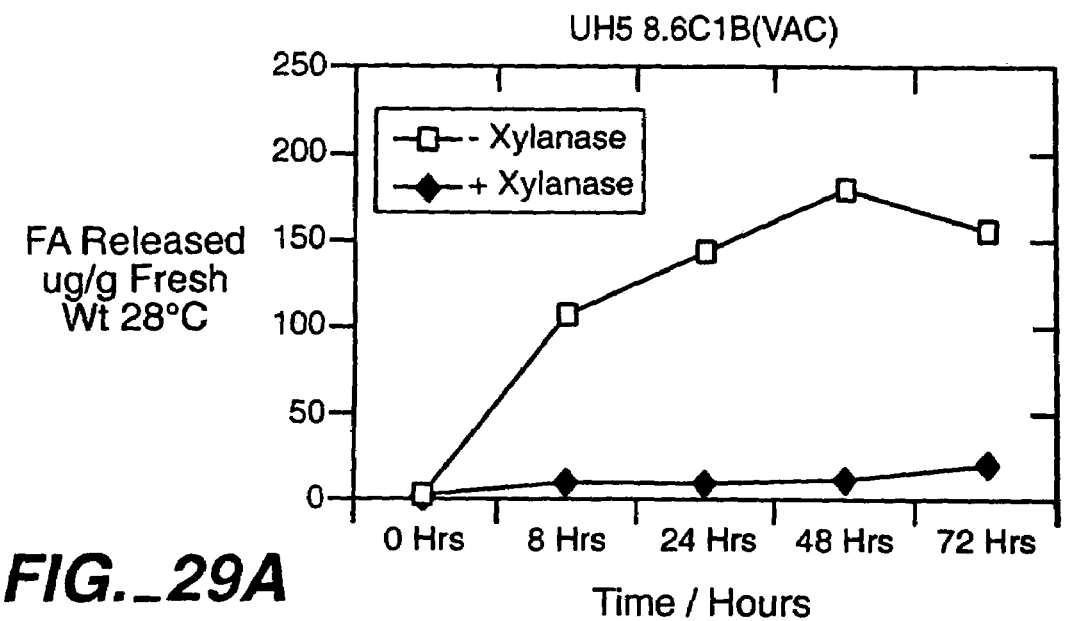
FIG._29A
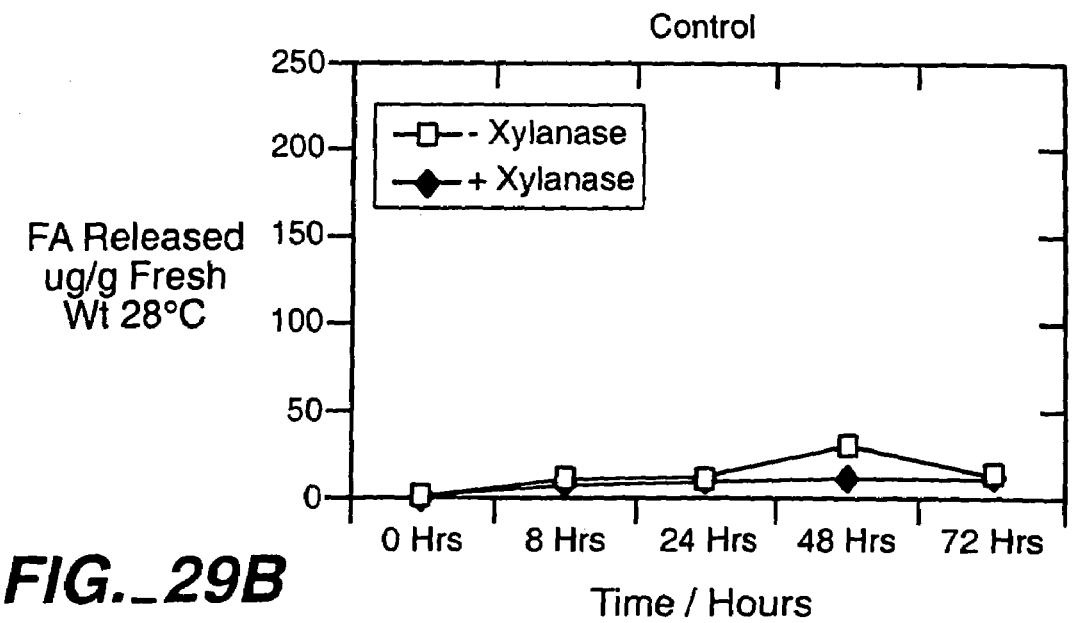
FIG._29B

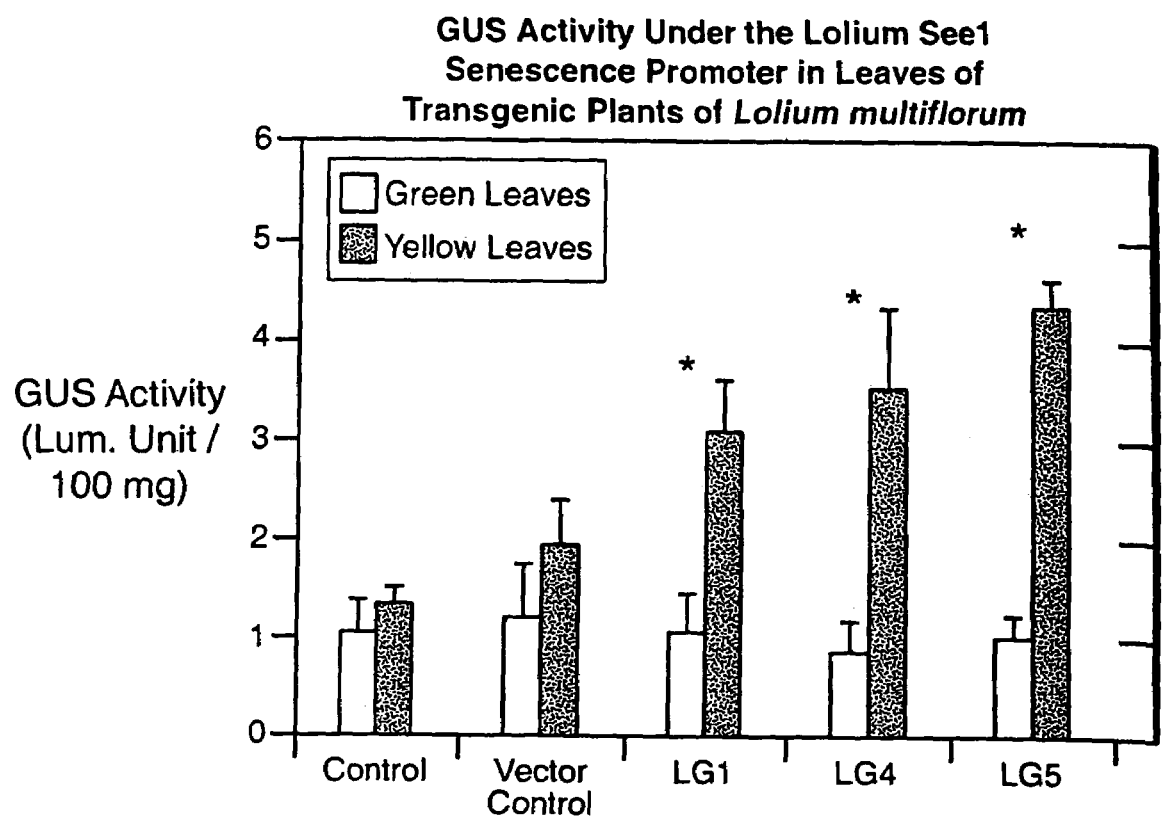
FIG._30

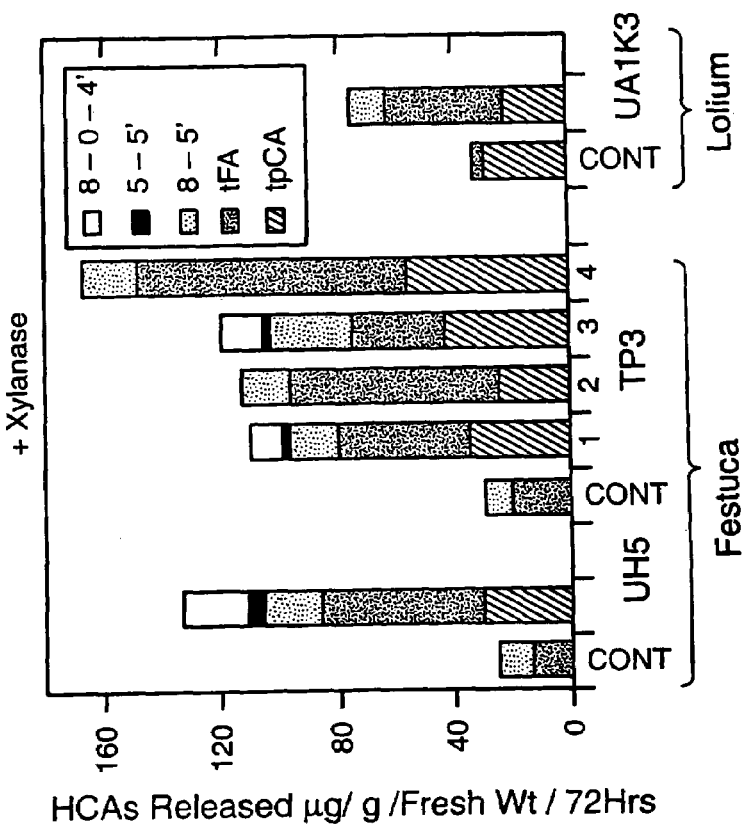
FIG._31B
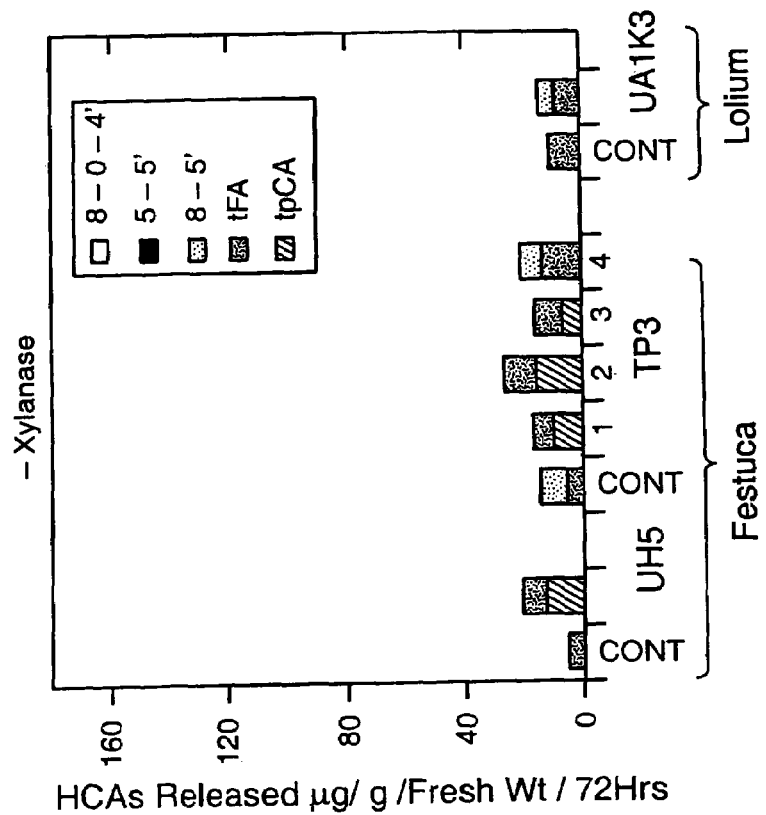
FIG._31A

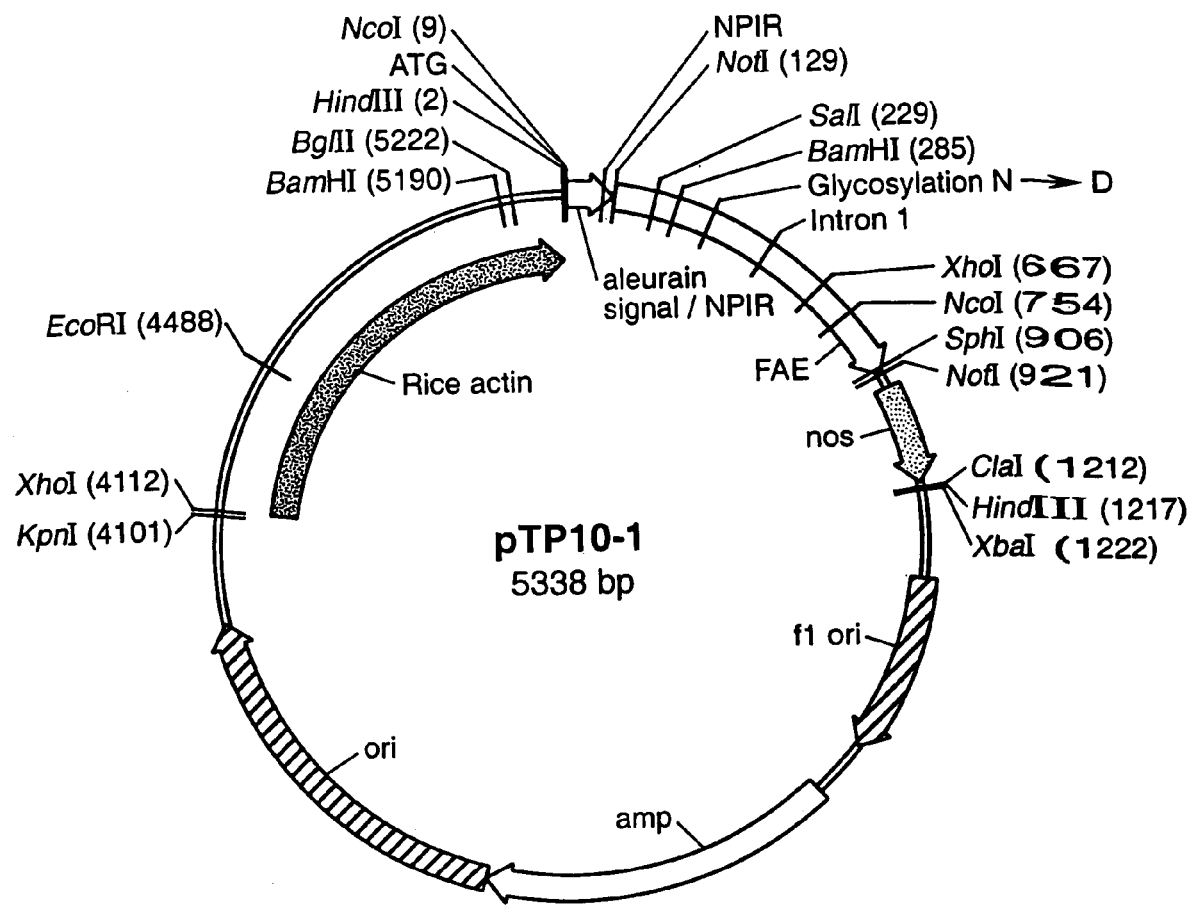
FIG._32A

```
     NcoI
     ~~~~~~
     HindIII
     ~~~~~~
                   M   A   H   A   R   V   L   L   L   A   L   A   V   L   A   T   A   A   V   A   V
  1  AAGCTTACCA TGGCCCACGC CCGCGTCCTC CTCCTGGCGC TCGCCGTGCT GGCCACGGCC GCCGTCGCCG
                                              NPIR
                                              ~~~~~~
     . A   S   S   S   S   F   A   D   S   N   P   I   R   P   V   T   D   R   A   A   A   S   T   .
                                                                                  NotI
                                                                                  ~~~~~~
 71  TCGCCTCCTC CTCCTCCTTC GCCGACTCCA ACCCGATCCG GCCCGTCACC GACCGCGCGG CCGCCTCCAC
     . Q   G   I   S   E   D   L   Y   S   R   L   V   E   M   A   T   I   S   Q   A   A   Y   A
141  GCAGGGCATC TCCGAAGACC TCTACAGCCG TTTAGTCGAA ATGGCCACTA TCTCCCAAGC TGCCTACGCC
                    SalI
                    ~~~~~~
     . D   L   C   N   I   P   S   T   I   I   K   G   E   K   I   Y   N   S   Q   T   D   I   N   G
211  GACCTGTGCA ACATTCCGTC GACTATTATC AAGGGAGAGA AAATTTACAA TTCTCAAACT GACATTAACG
        BamHI
        ~~~~~~
     . W   I   L   R   D   D   S   S   K   E   I   I   T   V   F   R   G   T   G   S   D   T   N   .
281  GATGGATCCT CCGGCGACGA CAGCAGCAAAG AAATAATCAC CGTCTTCCGT GGCACTGGTA GTGATACGAA
                                    Glycosylation
                                    ~~~~~~~~~~~~
     . L   Q   L   D   T   D   Y   T   L   T   P   F   D   T   L   P   Q   C   N   G   C   E   V
351  TCTACAACTC GATACTGACT ACACCCCTCAC GCCTTTCGAC ACCCTACCAC AATGCAACGG TTGTGAAGTA
     .     H   G   G   Y   Y   I   G   W   V   S   V   Q   D   Q   V   E   S   L   V   K   Q   Q   V   S
421  CACGGTGGAT ATTATATTGG ATGGGTCTCC GTCCAGGACC AAGTCGAGTC GCTTGTCAAA CAGCAGGTTA
     . Q   Y   P   D   Y   A   L   T   V   T   G   H   X   L   G   A   S   L   A   A   L   T   A   .
491  GCCAGTATCC GGACTACGCG CTGACCGTGA CCGGCCACKC CCTCGGCGCC TCCCTGGCGG CACTCACTGC
     . A   Q   L   S   A   T   Y   D   N   I   R   L   Y   T   F   G   E   P   R   S   G   N   Q
561  CGCCCAGCTG TCTGCGACAT ACGACAACAT CCGGCTGTAC ACCTTCGGCG AACCGCGCAG CGGCAATCAG
```

FIG._32B

```
                                                                     XhoI
         A  F  A  S     Y  M  N     D  A  F     Q  A  S  S     P  D  T     T  Q  Y     F  R  V  T
 631  GCCTTCGCGT CGTACATGAA CGATGCCTTC CAAGCCTCGA GCCCAGATAC GACGCAGTAT TTCCGGGTCA

NcoI
         .  H  A  N     D  G  I     P  N  L     P  P  V  E     Q  G  Y     A  H  G     G  V  E  Y  .
 701  CTCATGCCAA CGACGGCATC CCAAACCTGC CCCCGGTGGA GCAGGGGTAC GCCCATGGCG GTGTAGAGTA
         .  W  S  V     D  P  Y  S     A  Q  N     T  F  V     C  T  G     D  E  V  Q     C  C  E
 771  CTGGAGCGTT GATCCTTACA GCGCCCAGAA CACATTTGTC TGCACTGGGG ATGAAGTGCA GTGCTGTGAG

SphI
         A  Q  G  G     Q  G  V     N  N  A     H  T  T  Y     F  G  M     T  S  G     A  C  T  W
 841  GCCCAGGGCG GACAGGGTGT GAATAATGCG CACACGACTT ATTTGGGAT GACGAGCGGC GCATGCACCT

NotI                                 KDEL
         .  P  V  A     A  A  E     T  T  E  G  +
 911  GGCCGGTCGC GGCCGCGGAA ACCACTGAAG GATGAGCTGT AAAGAAGCAG ATCGTTCAAA CATTTGGCAA
 981  TAAAGTTTCT GCGGCTCAC TAAGATTGAA TCCTGTTGCC GGTCTTGCA CGTGACTGGG AAAACCCTGG CGTTACCCAA
1051  TTAAGCATGT AATAATTAAC ATGTAATGCA TGACGTTATT TATGAGATGG GTTTTTATGA TTAGAGTCCC ACCGATCGCC
1121  GCAATTATAC ATTTAATACG CGATAGAAAA CGAAATATAG AGGATAAATT ATCGCGCGCG

ClaI          XbaI
1191  GTGTCATCTA TGTTACTAGA TCGATAAGCT TCTAGAGCGG CCGGTGAGC TCCAATTCGC CCTATAGTGA
1261  GTCGTATTAC GCGCGCTCAC TGGCCGTCGT TTTACAACGT CGTGACTGGG AAAACCCTGG CGTTACCCAA
1331  CTTAATCGCC TTGCAGCACA TCCCCCTTTC GCCAGCTGGC GTAATAGCGA AGAGGCCCGC ACCGATCGCC
1401  CTTCCCAACA GTTGCGCAGC CTGAATGGCG AATGGGACGC GCCCTGTAGC GGCGCATTAA GCGCGGCGGG
```

FIG._32C

```
1471  TGTGGTGGTT ACGGCGCAGCG TGACCGCTAC ACTTGCCAGC GCCCTAGCGC CCGCTCCTTT CGCTTTCTTC
1541  CCTTCCTTTC TCGCCACGTT CGCCGGCTTT CGCCGGCTTT CTCTAAATCG GGGGCTCCCT TTAGGGTTCC
1611  GATTAGTGC TTTACGGCAC CTCGACCCCA TTAGGGTGAT ACGTTCACGTA GTGGGCCATC
1681  GCCCTGATAG ACGGTTTTTC GCCCTTTGAC GTTGGAGTCC AAAAACTTGA ATAGTGGACT CTTGTTCCAA
1751  ACTGGAACAA CACTCAACCC TATCTCGGTC TATTCTTTTG ACGTTCTTTA GATTTGCCG ATTTCGGCCT
1821  ATTGGTTAAA AAATGAGCTG ATTTAACAAA AATTTAACGC ATTTATAAGG AAAATATTAA CGCTTACAAT
1891  TTAGGTGGCA CTTTTCGGGG AAATGTGCGC GGAACCCCTA GAATTTTAAC TTTCTAAATA CATTCAAATA
1961  TGTATCCGCT CATGAGACAA TAACCCTGAT AAATGCTTCA AAAGGAAGA GTATGAGTAT
2031  TCAACATTTC CGTGTCGCCC TTATTCCCTT TTTTGCGGCA TTTTGCCTTC CTGTTTTTGC TCACCCAGAA
2101  ACGCTGGTGA AAGTAAAAGA TGCTGAAGAT CAGTTGGGTG CACGAGTGGG TTACATCGAA CTGGATCTCA
2171  ACAGCGGTAA GATCCTTGAG AGTTTTCGCC CCGAAGAACG TTTTCCAATG ATGAGCACTT TTAAAGTTCT
2241  GCTATGTGGC GCGGTATTAT CCCGTATTGA CGCCGGGCAA GAGCAACTCG GTCGCCGCAT ACACTATTCT
2311  CAGAATGACT TGGTTGAGTA CTCACCAGTC ACAGAAAAGC ATCTTACGGA TGGCATGACA GTAAGAGAAT
2381  TATGCAGTGC TGCCATAACC ATGAGTGATA ACACTGCGGC CAACTTACTT CTGACAACGA TCGGAGGACC
2451  GAAGGAGCTA ACCGCTTTTT TGCACAACAT GGGGGATCAT GTAAACTCGC CTTGATCGTTG GGAACCGGAG
2521  CTGAATGAAG CCATACCAAA CGACGAGCGT GACACCACGA TGCCTGTAGC AATGGCAACA ACGTTGCGCA
2591  AACTATTAAC TGGCGAACTA CTTACTCTAG CTTCCCGGCA ACAATTAATA GACTGGATGG AGGCGGATAA
2661  AGTTGCAGGA CCACTTCTGC GCTCGGCCCT TCCGGCTGGC TGGTTTATTG CTGATAAATC TGGAGCCGGT
2731  GAGCGTGGGT CTCGCGGTAT CATTGCAGCA CTGGGGCCAG ATGGTAAGCC CTCCCGTATC GTAGTTATCT
2801  ACACGACGGG GAGTCAGGCA ACTATGGATG AACGAAATAG ACAGATCGCT GAGATAGGTG CCTCACTGAT
2871  TAAGCATTGG TAACTGTCAG ACCAAGTTTA CTCATATATA CTTTAGATTG ATTAAAACT TCATTTTTAA
2941  TTTAAAAGGA TCTAGGTGAA GATCCTTTTT GATAATCTCA TGACCAAAAT CCCTTAACGT GAGTTTTCGT
3011  TCCACTGAGC GTCAGACCCC GTAGAAAAGA TCAAAGGATC TTCTTGAGAT CCTTTTTTTC TGCGCGTAAT
3081  CTGCTGCTTG CAAACAAAAA AACCACCGCT ACCAGCGGTG GTTTGTTTGC CGGATCAAGA GCTACCAACT
3151  CTTTTTCCGA AGGTAACTGG CTTCAGCAGA GCGCAGATAC CAAATACTGT CCTTCTAGTG TAGCCGTAGT
3221  TAGGCCACCA CTTCAAGAAC TCTGTAGCAC CGCCTACATA CTCGCTCTG CTAATCCTGT TACCAGTGGC
3291  TGCTGCCAGT GGCGATAAGT CGTGTCTTAC CGGGTTGGAC TCAAGACGAT AGTTACCGGA TAAGGCGCAG
3361  CGGTCGGGCT GAACGGGGGG TTCGTGCACA CAGCCCAGCT TGGAGCGAAC GACCTACACC GAACTGAGAT
3431  ACCTACAGCG TGAGCTATGA GAAAGCGCCA CGCTTCCCGA AGGGAGAAAG GCGGACAGT ATCCGGTAAG
3501  CGGCAGGGTC GGAACAGGAG AGCGCACGAG GGAGCTTCCA GGGGGAAACG CCTGGTATCT TTATAGTCCT
3571  GTCGGGTTTC GCCACCTCTG ACTTGAGCGT CGATTTTTGT GATGCTCGTC AGGGGGGCGG AGCCTATGGA
3641  AAAACGCCAG CAACGCGGCC TTTTTACGGT TCCTGGCCTT TTGCTGGCCT TTTGCTCACA TGTTCTTTCC
3711  TGCGTTATCC CCTGATTCTG TGGATAACCG TATTACCGCC TTTGAGTGAG CTGATACCGC TCGCCGCAGC
3781  CGAACGACCG AGCGCAGCGA GTCAGTGAGC GAGGAAGCGG AAGAGCGCCC AATACGCAAA CCGCCTCTCC
3851  CCGCGCGTTG GCCGATTCAT TAATGCAGCT GGCACGACAG GTTTCCCGAC TGGAAAGCGG GCAGTGAGCG
```

FIG._32D

```
3921                                          CAACGCAATT AATGTGAGTT AGCTCACTCA TTAGGCACCC CAGGCTTTAC ACTTTATGCT TCCGGCTCGT
3991  ATGTTGTGTG GAATTGTGAG CGGATAACAA TTTCACACAG GAAACAGCTA TGACCATGAT TACGCCAAGC
                                                                        XhoI
                                                                        ~~~~~~~

4061  GCGCAATTAA CCCTCACTAA AGGGAACAAA AGCTGGGTAC CGGGCCCCCC CTCGAGGTCA TTCATATGCT
4131  TGAGAAGAGA GTCGGGATAG TCCAAAATAA AACAAAGGTG AGATTACCTG GTCAAAAGTG AAAACATCAG
4201  TTAAAAGGTG GTATAAGTAA AATATCGGTA ATAAAAGGTG GCCCAAAGTG AAATTTACTC TTTTCTACTA
4271  TTATAAAAAT TGGATGTGTT TTGTCGGTAC TTTGATACGT CATTTTTGTA TGAATTGGTT TTTAAGTTTA
4341  TTCGCGATTT GGAAATGCAT ATCTGTATTT GAGTCGGTTT TTAAGTTCGT TGCTTTTTGT AATACAGAGG
4411  GATTTGTATA AGAAATATCT TTAAAAAACC CATATGCTAA TTTGACATAA TTTTTGAGAA AAATATATAT
      EcoRI
      ~~~~~

4481  TCAGGCGAAT TCCACAATGA ACAATATAAA GATTAAAATA GCTTGCCCCC GTTGCAGCGA TGGGTATTTT
4551  TTCTAGTAAA ATAAAAGATA AACTTAGACT CAAAACATTT ACAAAAAACAA CCCCTAAAGT CCTAAAGCCC
4621  AAAGTGCTAT GCACGATCCA TAGCAAGCCC AGCCCAACCC AACCCACCCC AGTGCAGCCA
4691  ACTGGCAAAT AGTCTCCACC CCCGGCACTA TCACCGTGAG TTGTCCGCAC CACCGCACGT CTCGCAGCCA
4761  AAAAAAAAAA AAGAAAGAAA AAAAAGAAAA AGAAAAACAG CAGGTGGGTC CGGGTCGTGG GGGCCGGAAA
4831  AGCGAGGAGG ATCGCGAGGC GCGACGAGGC CCGGCCCTCC CTCCGCTTCC CCACCTCCTC
4901  CACTATATAC ATACCCCCCC CTCTCCTCCC ATCCCCCCCC CCCTACCACC ACCACCACCA CCACCTCCTC
4971  CCCCCTCGCT GCCGGACGAC GAGCTCCTCC CCCCTCCCCC TCCGCCGCCG CCGGTAACCA CCCCGCCCCT
5041  CTCCTCTTTC TTTCTCCGTT TTTTTTTTCG TCTCGGTCTC GATCTTTGGC CTTGGTAGTT TGGGTGGGCG
5111  AGAGCGGCTT CGTCGCCCAG ATCGGGTGCGC GGAGGGGCG GGATCTCGCG GCTGGCGTCT CCGGGCGTGA
      BamHI                                               BglII
      ~~~~~                                              ~~~~~

5181  GTCGGCCCGG ATCCCTCGCGG GGAATGGGGC TCTCGGATGT AGATCTTCTT TCTTTCTTCT TTTTGTGGTA
5251  GAATTTGAAT CCCTCAGCAT TGTTCATCGG TAGTTTTTCT TTTCATGATT TGTGACAAAT GCAGCCCTCGT
5321  GCGGAGCTTT TTTGTAGC
```

FIG._32E

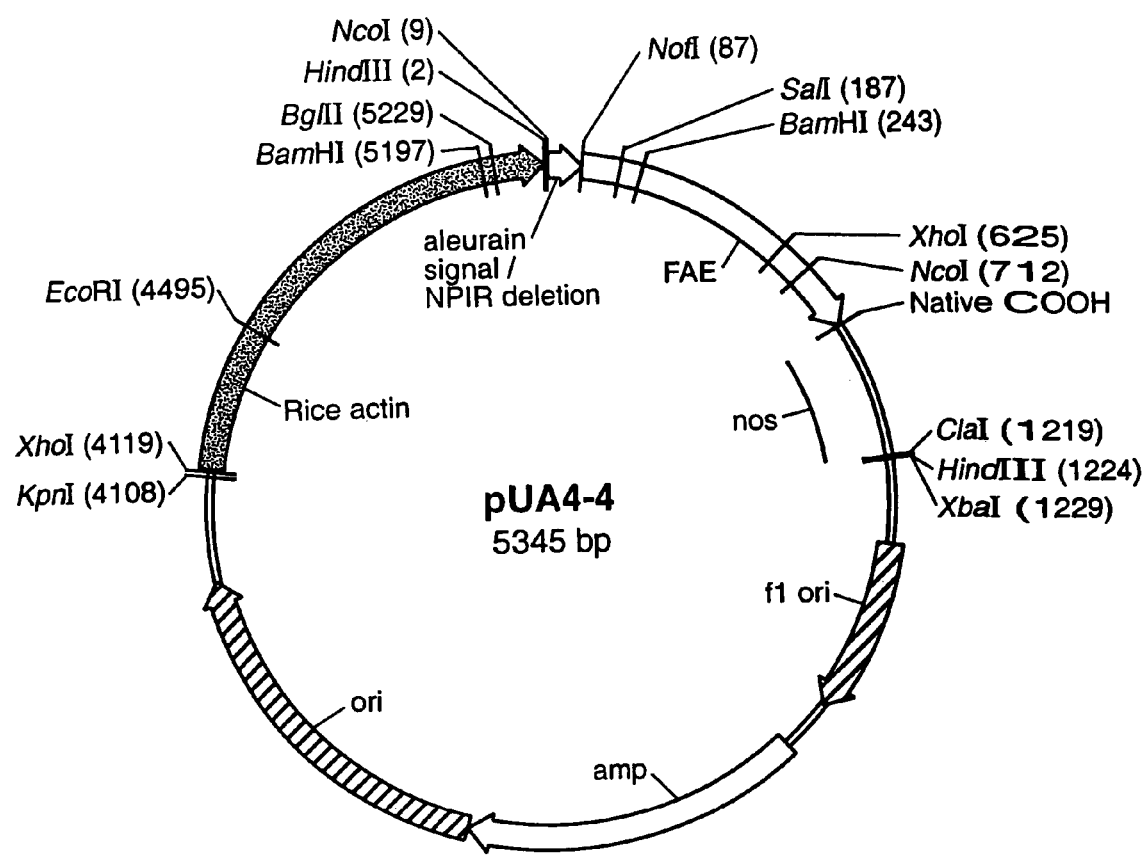
FIG._33A

```
     HindIII
     ~~~~~~~
             M   A   H   A   R   V   L   L   L   A   L   A   V   L   A   T   A   A   V   A   V
  1  AAGCTTACCA TGGCCCACGC CCGCGTCCTC CTCCTGGCGC TCGCCGTGCT GGCCACGGCC GCCGTCGCCG
                NcoI
                ~~~~
     .  A   S   S   R   A   A   A   S   T   Q   G   I   S       E   D   L   Y   S   R   L   V   E   M   .
 71  TCGCCTCCTC CCGCGCGGCC GCCTCCACGC AGGGCATCTC CGAAGACCTC TACAGCCGTT TAGTCGAAAT
                           NotI
                           ~~~~
     .  A   T   I   S   Q   A   A   Y   A   D   L   C   N       I   P   S   T   I   I   K   G   E   K
141  GGCCACTATC TCCCAAGCTG CCTACGCCGA CCTGTGCAAC ATTCCGTCGA CTATTATCAA GGGAGAGAAA
                                                              SalI
                                                              ~~~~
        I   Y   N   S   Q   T   D       I   N   G   W   I   L   R   D   D   S   S   K   E   I   I   T   V
211  ATTTACAATT CTCAAACTGA CATTAACGGA TGGATCCTCC GCGACGACAG CAGCAAAGAA ATAATCACCG
                                           BamHI
                                           ~~~~~
     .  F   R   G   T   G   S   D   T   N   L   Q   L   D   T   N   Y   T   L   T   P   F   D   T   .
281  TCTTCCGTGG CACTGGTAGT GATACGAATC TACAACTGA TACTAACTAC ACCCTCACGC CTTTCGACAC
     .  L   P   Q   C   N   G   C   E   V   H   G   G   Y   Y   I   G   W   V   S   V   Q   D   Q   .
351  CCTACCACAA TGCAACGGTT GTGAAGTACA CGGTGGATAT TATATTGGAT GGGTCTCCGT CCAGGACCAA
     .  V   E   S   L   V   K   Q       Q   V   S       Q   Y   P   D   Y   A   L   T   V   T   G   H   L   .
421  GTCGAGTCGC TTGTCAAACA GCAGGTTAGC CAGTATCCGG ACTACGCGCT GACCGTGACC GGCCACKCCC
     .  G   A   S       L   A   A   L   T   A   A   Q   L   S       A   T   Y   D   N   I   R   L   Y   T   .
491  TCGGCGCCTC CCTGGCGGCA CTCACTGCCG CCCAGCTGTC TGCGACATAC GACAACATCC GCCTGTACAC
                                                                                       XhoI
                                                                                       ~~~~
     .  F   G   E       P   R   S   G   N   Q   A       F   A   S       Y   M   N   D       A   F   Q       A   S   S
561  CTTCGGCGAA CCGGCGCAGC GCAATCAGGC CTTCGCGTCG TACATGAACG ATGCCTTCCA AGCCTCGAGC
     .  P   D   T   T   Q   Y   F   R   V   T       H   A   N   D   G   I   P       N   L   P       P   V   E       Q
631  CCAGATACGA CGCAGTATTT CCGGGTCACT CATGCCAACG ACGGCATCCC AAACCTGCCC CCGGTGGAGC
     .  G   Y   A   H   G   G   V   E   Y   W   S   V   D       P   Y   S       A   Q   N   T   F   V   C   .
```

FIG._33B

```
 701  AGGGGTACGC CCATGGCGGT GTAGAGTACT GGAGCGTTGA TCCTTACAGC GCCCAGAACA CATTTGTCTG
       .  T  G  D   E  V  Q   C  C  E  A    Q  G  G    Q  G  V  N    N  N  A  H    T  T  Y
 771  CACTGGGGAT GAAGTGCAGT GCTGTGAGGC CAGGGGCGGA CCCAGAACAA ATAATGCGCA CACGACTTAT
       F  G  M  T   S  G  A    C  T  W    *
 841  TTTGGGATGA CGAGCGGAGC CTGTACATGG TGATCAGTCA TTTCAGCCTC AGAGCGGCCG AATTCGCCCT CCAGGAAAGA
 911  TGGATGTCCT GGAGAGGGGG CCGCGTAACC ACTGAAGGAT GAGCTGTAAA ACAACGTCGT GACTGGGAAA GTTCAAACAT
 981  TTGCAATAA AGTTTCTTAA GATTGAATCC TGTTGCCGGT CTTGCGATGA AGCTGGCGTA ATAGCGAAGA GGCCCGCACC
1051  AATTACGTTA AGCATGTAAT AATTAACATG CGTTATTTAT TTATCATATA CTGTAGCGCC GCATTAAGCG
1121  GAGTCCCGCA ATTATACATT TAATACGCGA TAGAAAACAA GCAAACTAGG GATATGGGTT TTTATGATTA ATAAATTATC
                                                       HindIII
1191  GCGGCGCGGTG TCATCTATGT ATAAGCTTCT AGAGCGGCCG GTGGAGCTCC AATTCGCCCT
                          ClaI      XbaI
1261  ATAGTGAGTC GTATTACGCG CGCTCACTGG CCGTCGTTTT ACAACGTCGT GACTGGGAAA ACCCTGGCGT
1331  TACCCAACTT AATGCCCTTG CAGCACATCC CCCTTTCGCC AGCTGGCGTA ATAGCGAAGA GGCCCGCACC
1401  GATCGCCCTT CCCAACAGTT GCGCAGCCTG AATGGCGAAT GGGACGCGCC CTGTAGCGGC GCATTAAGCG
1471  CGGCGGGTGT GGTGGTTACG CGCAGCGTGA CCGCTACACT TGCCAGCGCC CTAGCGCCCG CTCCTTTCGC
1541  TTTCTTCCCT TCCTTTCTCG CCACGTTCGC CGGCTTTCCC CGTCAAGCTC TAAATCGGGG GCTCCCTTTA
1611  GGGTTCCGAT TTAGTGCTTT ACGGCACCCTC GACCCCAAAA AACTTGATTA GGGTGATGGT TCACGTAGTG
1681  GGCCATCGCC CTGATAGACG GTTTTTCGCC CTTTGACGTT GGAGTCCACG TTCTTTAATA GTGGACTCTT
1751  GTTCCAAACT GGAACAACAC TCAACCCTAT CTCGGTCTAT TCTTTTGATT TATAAGGGAT TTTGCCGATT
1821  TCGGCCTATT GGTTAAAAAA TGAGCTGATT TAACAAAAAT TTAACGCGAA TTTTAACAAA ATATTAACGC
1891  TTACAATTTA GGTGGCACTT TTCGGGGAAA TGTGCGCGGA ACCCCTATTT GTTTATTTTT CTAAATACAT
1961  TCAAATATGT ATCCGCTCAT GAGACAATAA CCCTGATAAA TGCTTCAATA ATATTGAAAA AGGAAGAGTA
2031  TGAGTATTCA ACATTTCCGT GTCGCCCTTA TTCCCTTTTT TGCGGCATTT TGCCTTCCTG TTTTTGCTCA
2101  CCCAGAAACG CTGGTGAAAG TAAAAGATGC TGAAGATCAG TTGGGTGCAC GAGTGGGTTA CATCGAACTG
2171  GATCTCAACA GCGGTAAGAT CCTTGAGAGT TTTCGCCCCG AAGAACGTTT TCCAATGATG AGCACTTTTA
2241  AAGTTCTGCT ATGTGGCGCG GTATTATCCC GTATTGACGC CGGGCAAGAG CGGCCAAGAG CAACTCGGTC GCCGCATACA
2311  CTATTCTCAG AATGACTTGG TTGAGTACTC ACCAGTCACA GAAAAGCATC TTACGGATGG CATGACAGTA
2381  AGAGAATTAT GCAGTGCTGC CATAACATG GCTTTTTGC ACAACATGGG ATGGATCATG CTTACTTCTG ACAACGATCG
2451  GAGGACCGAA GGAGCTAACC GCTTTTTTGC ACAACATGGG GATCATGTA ACTCGCCTTG ATCGTTGGGA
2521  ACCGAGCTG AATGAAGCCA TACCAAACGA CGAGCGTGAC ACCACGATGC CTGTAGCAAT GGCAACAACG
2591  TTGCGCAAAC TATTAACTGG CGAACTACTT ACTCTAGCTT CCCGGCAACA ATTAATAGAC TGGATGGAGG
2661  CGGATAAAGT TGCAGGACCA CTTCTGCGCT CGGCCCTTCC GGCTGGCTGG TTTATTGCTG ATAAATCTGG
```

FIG._33C

| | | | | | | | |
|---|---|---|---|---|---|---|---|
|2731|AGCCGGTGAG|CGTGGGTCTC|GCGTATCAT|TGCAGCACTG|GGGCCAGATG|GTAAGCCCTC|CCGTATCGTA|
|2801|GTTATCTACA|CGACGGGGAG|TCAGGCAACT|ATGGATGAAC|GAAATAGACA|GATCGCTGAG|ATAGGTGCCT|
|2871|CACTGATTAA|GCATTGGTAA|CTGTCAGACC|AAGTTTACTC|ATATATACTT|TAGATTGATT|TAAAACTTCA|
|2941|TTTTTAATTT|AAAAGGATCT|AGTGAAGAT|CCTTTTTGAT|AATCTCATGA|CCAAAATCCC|TTAACGTGAG|
|3011|TTTTCGTTCC|ACTGAGCGTC|AGACCCCGTA|GAAAAGATCA|AAGGATCTTC|TTGAGATCCT|TTTTTTCTGC|
|3081|GCGTAATCTG|CTGCTTGCAA|ACAAAAAAC|CACCGCTACC|AGCGGTGGTT|TGTTTGCCGG|ATCAAGAGCT|
|3151|ACCAACTCTT|TTTCCGAAGG|TAACTGGCTT|CAGCAGAGCG|CAGATACCAA|ATACTGTCCT|TCTAGTGTAG|
|3221|CCGTAGTTAG|GCCACCACTT|CAAGAACTCT|GTAGCACCGC|CTACATACCT|CGCTCTGCTA|ATCCTGTTAC|
|3291|CAGTGGCTGC|TGCCAGTGGC|GATAAGTCGT|GTCTTACCGG|GTTGGACTCA|AGACGATAGT|TACCGGATAA|
|3361|GGCGCAGCGG|TCGGGCTGAA|CGGGGGGTTC|GTGCACACAG|CCCAGCTTGG|AGCGAACGAC|CTACACCGAA|
|3431|CTGAGATACC|TACAGCGTGA|GCTATGAGAA|AGCGCCACGC|TTCCCGAAGG|GAGAAAGGCG|GACAGGTATC|
|3501|CGTAAGCGG|CAGGGTCGA|ACAGGAGAGC|GCACGAGGGA|GCTTCCAGGG|GGAAACGCCT|GGTATCTTTA|
|3571|TAGTCCTGTC|GGGTTTCGCC|ACCTCTGACT|TGAGCGTCGA|TTTTTGTGAT|GCTCGTCAGG|GGGGCGGAGC|
|3641|CTATGGAAAA|ACGCCAGCAA|CGCGGCCTTT|TTACGGTTCC|TGGCCTTTTG|CTGGCCTTTT|GCTCACATGT|
|3711|TCTTTCCTGC|GTTATCCCCT|GATTCTGTGG|ATAACCGTAT|TACCGCCTTT|GAGTGAGCTG|ATACCGCTCG|
|3781|CCGCAGCCGA|ACGACCGAGC|GCAGCGAGTC|AGTGAGCGAG|GAAGCGGAAG|AGCGCCCAAT|ACGCAAACCG|
|3851|CCTCTCCCCG|CGCGTTGGCC|GATTCATTAA|TGCAGCTGGC|ACGACAGGTT|TCCCGACTGG|AAAGCGGGCA|
|3921|GTGAGCGCAA|CGCAATTAAT|GTGAGTTAGC|TCACTCATTA|GGCACCCCAG|GCTTTACACT|TTATGCTTCC|
|3991|GGCTCGTATG|TTGTGTGGAA|TTGTGAGCGG|ATAACAATTT|CACACAGGAA|ACAGCTATGA|CCATGATTAC|
| | | | |EcoRI| | |KpnI|XhoI|
|4061|GCCAAGCGCG|CAATTAACCC|TCACTAAAGG|GAACAAAAGC|TGGGTACCGG|GCCCCCCCTC|GAGGTCATTC|
|4131|ATATGCTTGA|GAAGAGAGTC|GGGATAGTCC|AAAGATAAAC|AAAGGTAAGA|TTACCTGGTC|AAAAGTGAAA|
|4201|ACATCAGTTA|AAAGGTGGTA|TAAGTAAAAT|ATCGGTAATA|AAAGGTGGCC|CAACCCCAAC|TTTACTCTTT|
|4271|TCTACTATTA|TAAAAATTGA|GGATGTTTTG|TCGGTACTTT|GATACGTCAT|TTTTGTATGA|ATTGGTTTTT|
|4341|AAGTTTATTC|GCGATTTGGA|AATGCATATC|TGTATTTGAG|TCGTTTTTA|AGTTCGTTGC|TTTTGTAAAT|
|4411|ACAGAGGGAT|TTGTATAAGA|AATATCTTTA|AAAAACCCAT|ATGCTAATTT|GACATAAAT|TTGAGAAAAA|
|4481|TATATATTCA|GGCGAATTCC|ACAATGAACA|ATAATAAGAT|TAAAATAGCT|TGCCCCCGTT|GCAGCGATGG|
|4551|GTATTTTTC|TAGTAAAATA|AAAGATAAA|TTAGACTCAA|AACATTTACA|AAAACAACCC|CTAAAGTCCT|
|4621|AAAGCCCAAA|GTGCTATGCA|CGATCCATAG|CAAGCCCAGC|CCAACCCAAC|CCACCCCAGT|CCACCCCAAC|
|4691|GCAGCCAACT|GGCAAATAGT|CTCCACCCCC|GGCACTATCA|CCGTGAGTTG|TCCGCACCAC|CGCACGTCTC|
|4761|GCAGCCAAA|AAAAAAAAAG|AAGAAAAAGA|AAGAAAAAGA|AAAACAGCAG|GTGGGTCCGG|GTCGTGGGGG|
|4831|CCGGAAAAGC|GAGGAGGATC|GCGAGCAGCG|ACGAGGCCCG|ACGAGGCCCTC|CGCTTCCAAA|GAAACGCCCC|

FIG.—33D

```
4901  CCATCGCCAC TATATACATA CCCCCCCCTC TCCTCCCATC CCCCCAACCC TACCACCACC ACCACCACCA
4971  CCTCCTCCCC CCTCGCTGCC GGACGACGAG CTCCTCCCCC CTCCCCCTCC GCCGCCGCCG GTAACCACCC
5041  CGCCCCTCTC CTCTTTCTTT CTCCGTTTTT TTTTTCGTCT CGGTCTCGAT CTTTGGCCTT GGTAGTTTGG
5111  GTGGGCGAGA GCGGCTTCGT CGCCCAGATC AGGGGCGGGA TCTCGCGGCT GGCGTCTCCG
                                              BglII
                 BamHI                        ------
                 ------
5181  GGCGTGAGTC GGCCCGGATC CTCGCGGGGA ATGGGGCTCT CGGATGTAGA TCTTCTTTCT TTCTTCTTTT
5251  TGTGGTAGAA TTTGAAATCCC TCAGCATTGT TCATCGGTAG TTTTTCTTTT CATGATTTGT GACAAATGCA
5321  GCCTCGTGCG GAGCTTTTTT GTAGC
```

*FIG._33E*

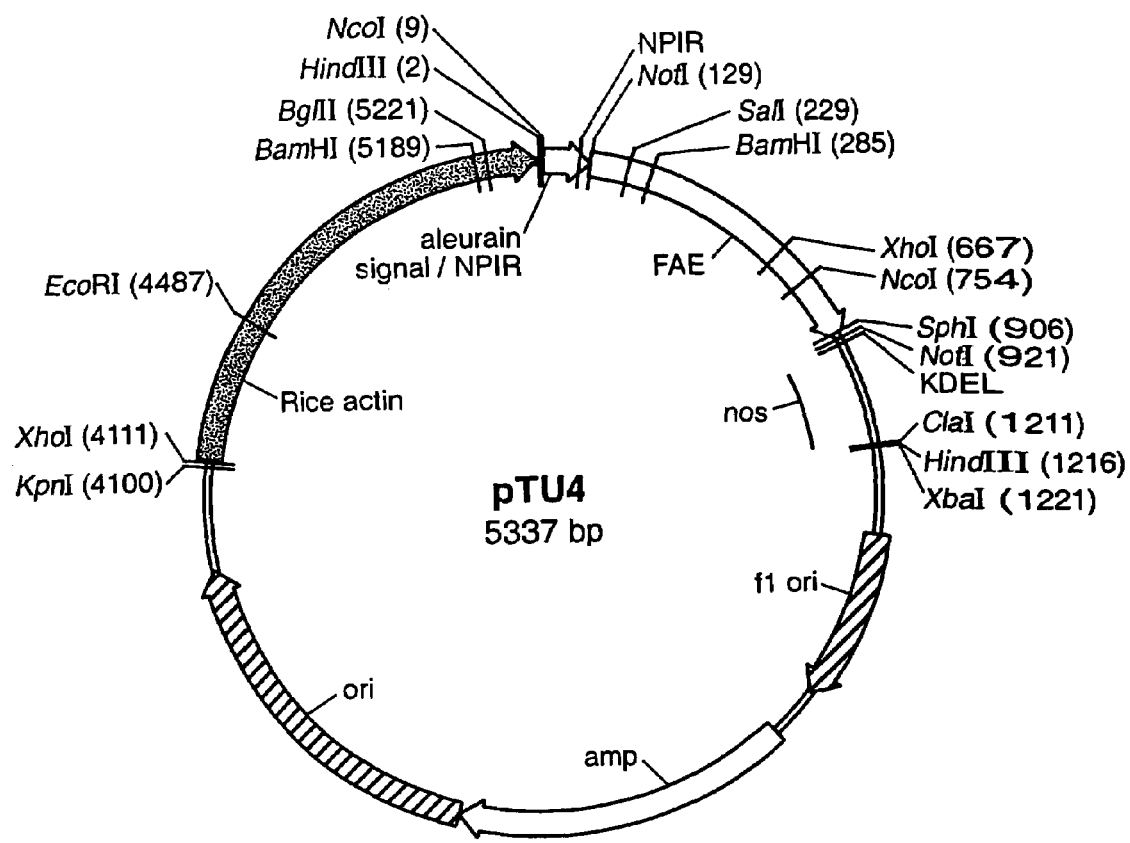
FIG._34A

```
           HindIII
           ------
                    M   A   H   A   R   V   L   L   L   A   L   A   V   L   A   T   A   A   V   A   V
    1  AAGCTTACCA TGGCCCACGC CCGCGTCCTC CTCCTGGCGC TGGCCGTGCT GGCCACGGCC GCCGTCGCCG
                                                                              NotI
                                                                              ----
        A   S   S   S   S   F   A   D   S   N   P   I   R   P   V   T   D   R   A   A   A   S   T .
   71  TCGCCTCCTC CTCCTCCTTC GCCGACTCCA ACCCGATCCG GCCCGTCACC GACCGCGCGG CCGCCTCCAC
        Q   G   I   S   E   D   L   Y   S   R   L   V   E   M   A   T   I   S   Q   A   A   Y   A
  141  GCAGGGCATC TCCGAAGACC TCTACAGCCG TTTAGTCGAA ATGGCCACTA TCTCCCAAGC TGCCTACGCC
                                     SalI
                                     ----
        D   L   C   N   I   P   S   T   I   I   K   G   E   K   I   Y   N   S   Q   T   D   I   N   G
  211  GACCTGTGCA ACATTCCGTC GACTATTATC AAGGGAGAGA AAATTTACAA TTCTCAAACT GACATTAACG
                              BamHI
                              -----
        W   I   L   R   D   D   S   S   K   E   I   I   T   V   F   R   G   T   G   S   D   T   N .
  281  GATGGATCCT CCGGCGACGA AGCAGCAAAG AAATAATCAC CGTCTTCCGT GGCACTGGTA GTGATACGAA
        L   Q   L   D   T   N   Y   T   L   T   P   F   D   A   F   L   T   P   Q   C   N   G   C   E   V
  351  TCTACAACTC GATACTAACT ACACCCTCAC GCCTTTCGAC ACCCTACCAC AATGCAACGG TTGTGAAGTA
        H   G   G   Y   Y   I   G   W   V   S   V   Q   D   Q   V   E   S   L   V   K   Q   V   S
  421  CACGGTGGAT ATTATATTGG ATGGGTCTCC GTCCAGGACC AAGTCGAGTC GCTTGTCAAA CAGCAGGTTA
        Q   Y   P   D   Y   A   L   T   V   T   G   H   X   L   G   A   S   L   A   A   L   T   A .
  491  GCCAGTATCC GGACTACGCG CTGACCGTGA CCGGCCACKC CCTCGGGGCC TCCCTGGCGG CACTCACTGC
        A   Q   L   S   A   T   Y   D   N   I   R   L   Y   T   F   G   E   P   R   S   G   N   Q .
  561  CGCCCAGCTG TCTGCCACAT ACGACAACAT CCGCCTGTAC ACCTTCGGCG AACCGCGCAG CGGCAATCAG
                                                                   XhoI
                                                                   ----
        A   F   A   S   Y   M   N   D   A   F   Q   A   S   S   P   D   T   T   Q   Y   F   R   V   T
  631  GCCTTCGCGT CGTACATGAA CGATGCCTTC CAAGCCTCGA GCCCAGATAC GACGCAGTAT TTCCGGGTCA
                                                           NcoI
                                                           ----
        . H   A   N   D   G   I   P   N   L   P   P   V   E   Q   G   Y   A   H   G   G   V   E   Y .
```

FIG._34B

```
                                                                                                                       W
       . W  S  V   D   P  Y   S   A  Q  N   T   F  V   C   T  G  D   E  V   Q   C  C  E
 701   CTCATGCCAA CGACGGCATC CCAAACCTGC CCCCGGTTGGA GCAGGGGTAC GCCCATGGCG GTGTAGAGTA
 771   CTGGAGCGTT GATCCTTACA GCGCCCAGAA CACATTTGTC TGCACTGGGG ATGAAGTGCA GTGCTGTGAG
                                                                           SphI
         A   Q   G   G   Q   G   V     N   N   A     H   T   T   Y   F   G   M     T   S   G     A   C   T   W
 841   GCCCAGGGGCG GACAGGGTGT GAATAATGCG CACACGACTT ATTTTGGGAT GACGAGCGGC GCATGCACCT
             NotI
         .   P   V   A   A   E     P   L   K   D     E   L   *
 911   GGCCGGTCGC GGCCGCGGAA CCACTGAAGG ATGAGCTGTA CTAGAGCGGC CGATAAGCTT CTATAGTGAG
 981   AAAGTTTCTT AAGATTGAAT CCTGTTGCCG GTCTTGCGAT TTACAACGTC GGCCGTCGTT GTTACCCAAC
1051   TAAGCATGTA ATAATTAACA TGTAATGCAT GACGTTATTT ATGAGATGGG CCAGCTGGCG CCGATCGCCC
1121   CAATTATACA TTTAATACGC GATAGAAAAC AAAATATAGC GCGCAAACTA GGATAAATTA TCGCGCGCGG
                            ClaI       XbaI
                            HindIII
1191   TGTCATCTAT GTTACTAGAT CGATAAGCTT CTAGAGCGGC CGGTGAGCT CCAATTCGCC CTATAGTGAG
1261   TCGTATTACG CGCGCTCACT GGCCGTCGTT TTACAACGTC GTGACTGGGA AAACCCTGGC GTTACCCAAC
1331   TTAATCGCCT TGCAGCACAT CCCCTTTCG CCAGCTGGCG TAATAGCGAA GAGGCCCGCA CCGATCGCCC
1401   TTCCCAACAG TTGCGCAGCC TGAATGGCGA ATGGGACGCG CCCTGTAGCG GCGCATTAAG CGCGGCGGGT
1471   GTGGTGGTTA CGCGCAGCGT GACCGCTACA CTTGCCAGCG CCCTAGCGCC CGCTCCTTTC GCTTTCTTCC
1541   CTTCCTTTCT CGCCACGTTC GCCGGCTTTC CCCGTCAAGC TCTAAATCGG GGGCTCCCTT TAGGGTTCCG
1611   ATTTAGTGCT TTACGGCACC TCGACCCCAA AAAACTTGAT TAGGGTGATG TGGGCCATCG
1681   CCCTGATAGA CGGTTTTTCG CCCTTTGACG TTGGAGTCCA CGTTCTTTAA CGTGACTC TTGTTCCAAA
1751   CTGGAACAAC ACTCAACCCT ATCTCGGTCT ATTCTTTTGA ATTTAACGCG TTTATAAGGG TTTCGGCCTA
1821   TTGGTTAAAA AATGAGCTGA TTTAACAAAA ATTTAACAA AAATTTAACG GCTTACAATT
1891   TAGGTGGCAC TTTTCGGGGA AATGTGCGCG GAACCCCTAT TTGTTTATTT TTCTAAATAC ATTCAAATAT
1961   GTATCCGCTC ATGAGACAAT AACCCTGATA AATGCTTCAA TAATATTGAA AAAGGAAGAG TATGAGTATT
2031   CAACATTTCC GTGTCGCCCT TATTCCCTTT TTTGCGGCAT TTTGCCTTCC TGTTTTTGCT CACCCAGAAA
2101   CGCTGGTGAA AGTAAAAGAT GCTGAAGATC AGTTGGGTGC ACGAGTGGGT TACATCGAAC TGGATCTCAA
2171   CAGCGGTAAG ATCCTTGAGA GTTTTCGCCC CGAAGAACTT TTTCCAATGA TGAGCACTTT TAAAGTTCTG
2241   CTATGTGGCG CGGTATTATC CCGTATTGAC GCCGGGCAAG AGCAACTCGG TCGCCGCATA CACTATTCTC
2311   AGAATGACTT GGTTGAGTAC TCACCAGTCA CAGAAAAGCA TCTTACGGAT GGCATGACAG TAAGAGAATT
2381   ATGCAGTGCT GCCATAACCA TGAGTGATAA CACTGCGGCC AACTTACTTC TGACAACGAT CGGAGGACCG
```

FIG._34C

| | | | | | | | |
|---|---|---|---|---|---|---|---|
| 2451 | AAGGAGCTAA | CCGCTTTTTT | GCACAACATG | GGGGATCATG | TAACTCGCCT | TGATCGTTGG | GAACCGGAGC |
| 2521 | TGAATGAAGC | CATACCAAAC | GACGAGCGTG | ACACCACGAT | GCCTGTAGCA | ATGGCAACAA | CGTTGCGCAA |
| 2591 | ACTATTAACT | GGCGAACTAC | TTACTCTAGC | TTCCCGGCAA | CAATTAATAG | ACTGGATGGA | GGCGGATAAA |
| 2661 | GTTGCAGGAC | CACTTCTGCG | CTCGGCCCTT | CCGGCTGGCT | GGTTTATTGC | TGATAAATCT | GGAGCCGGTG |
| 2731 | AGCGTGGGTC | TCGCGGTATC | ATTGCAGCAC | TGGGGCCAGA | TGGTAAGCCC | TCCCGTATCG | TAGTTATCTA |
| 2801 | CACGACGGGG | AGTCAGGCAA | CTATGGATGA | ACGAAATAGA | CAGATCGCTG | AGATAGGTGC | CTCACTGATT |
| 2871 | AAGCATTGGT | AACTGTCAGA | CCAAGTTTAC | TCATATATAC | TTTAGATTGA | TTTAAAACTT | CATTTTTAAT |
| 2941 | TTAAAAGGAT | CTAGGTGAAG | ATCCTTTTTG | ATAATCTCAT | GACCAAAATC | CCTTAACGTG | AGTTTTCGTT |
| 3011 | CCACTGAGCG | TCAGACCCCG | TAGAAAAGAT | CAAAGGATCT | TCTTGAGATC | CTTTTTTTCT | GCGCGTAATC |
| 3081 | TGCTGCTTGC | AAACAAAAAA | ACCACCGCTA | CCAGCGGTGG | TTTGTTTGCC | GGATCAAGAG | CTACCAACTC |
| 3151 | TTTTTCCGAA | GGTAACTGGC | TTCAGCAGAG | CGCAGATACC | AAATACTGTC | CTTCTAGTGT | AGCCGTAGTT |
| 3221 | AGGCCACCAC | TTCAAGAACT | CTGTAGCACC | GCCTACATAC | CTCGCTCTGC | TAATCCTGTT | ACCAGTGGCT |
| 3291 | GCTGCCAGTG | GCGATAAGTC | GTGTCTTACC | GGGTTGGACT | CAAGACGATA | GTTACCGGAT | AAGGCGCAGC |
| 3361 | GGTCGGGCTG | AACGGGGGGT | TCGTGCACAC | AGCCCAGCTT | GGAGCGAACG | ACCTACACCG | AACTGAGATA |
| 3431 | CCTACAGCGT | GAGCTATGAG | AAAGCGCCAC | GCTTCCCGAA | GGGAGAAAGG | CGGACAGGTA | TCCGGTAAGC |
| 3501 | GGCAGGGTCG | GAACAGGAGA | GCGCACGAGG | GAGCTTCCAG | GGGGAAACGC | CTGGTATCTT | TATAGTCCTG |
| 3571 | TCGGGTTTCG | CCACCTCTGA | CTTGAGCGTC | GATTTTTGTG | ATGCTCGTCA | GGGGGGCGGA | GCCTATGGAA |
| 3641 | AAACGCCAGC | AACGCGGCCT | TTTTACGGTT | CCTGGCCTTT | TGCTGGCCTT | TTGCTCACAT | GTTCTTTCCT |
| 3711 | GCGTTATCCC | CTGATTCTGT | GGATAACCGT | ATTACCGCCT | TTGAGTGAGC | TGATACCGCT | CGCCGCAGCC |
| 3781 | GAACGACCGA | GCGCAGCGAG | TCAGTGAGCG | AGGAAGCGGA | AGAGCGCCCA | ATACGCAAAC | CGCCTCTCCC |
| 3851 | CGCGCGTTGG | CCGATTCATT | AATGCAGCTG | GCACGACAGG | TTTCCCGACT | GGAAAGCGGG | CAGTGAGCGC |
| 3921 | AACGCAATTA | ATGTGAGTTA | GCTCACTCAT | TAGGCACCCC | AGGCTTTACA | CTTTATGCTT | CCGGCTCGTA |
| 3991 | TGTTGTGTGG | AATTGTGAGC | GGATAACAAT | TTCACACAGG | AAACAGCTAT | GACCATGATT | ACGCCAAGCG |

EcoRI                                                          XhoI
    ----                                                        ----

| | | | | | | | |
|---|---|---|---|---|---|---|---|
| 4061 | CGCAATTAAC | CCTCACTAAA | GGGAACAAAA | GCTGGGTACC | GGGCCCCCCC | TCGAGGTCAT | TCATATGCTT |
| 4131 | GAGAGAGAG | TCGGGATAGT | CCAAAATAAA | ACAAAGTAA | GATTACCTGG | TCAAAAGTGA | AAACATCAGT |
| 4201 | TAAAAGGTGG | TATAAGTAAA | ATATCGGTAA | TGTCGGTACT | TGATACGTC | ATTTTGTTAT | GAATTGGTTT |
| 4271 | TATAAAATT | GAGGATGTTT | TGTCGGTTT | TTGATACGTTT | AAGTTACTCT | TTCTACTAT |
| 4341 | TCGCGATTTG | GAAATGCATA | TCTGTATTTG | AGTCGGTTT | GCTTTTGTT | TTAAGTTAT |
| 4411 | ATTTGTATAA | GAAATATCTT | TAAAAACCC | ATATGCTAAT | ATATGCTAAT | TTTGACATAAT | TTTGAGAAA | ATACAGAGG |

KpnI

| | | | | | | |
|---|---|---|---|---|---|---|
| 4481 | CAGGCGAATT | CCACAATGAA | CAATAATAAG | ATTAAAAATAG | CTTGCCCCCG | TTGCAGCGAT | GGTATTTT |
| 4551 | TCTAGTAAAA | TAAAAGATAA | ACTTAGACTC | AAACATTTA | AAAACAACC | CCCTAAAGTC | CTAAAGCCCA |

FIG._34D

```
4621  AAGTGCTATG  CACGATCCAT  AGCAAGCCCA  GCCCAACCCA  ACCCAACCCA  GTGCAGCCAA
4691  CTGGCAAATA  GTCTCCACCC  CCGGCACTAT  CACCGTGAGT  TGTCCGCACC  ACCGCACGTC
4761  AAAAAAAAAA  AGAAAGAAAA  AAAAGAAAAA  GAAAAACAGC  AGGTGGGTCC  GGCCGGAAAA
4831  GCGAGGAGGA  TCGCGAGCAG  CGACGAGGCC  CGGCCTTCCC  TCCGCTTCCA  AAGAAACGCC
4901  ACTATATACA  TACCCCCCCC  TCTCCTCCCA  TCCCCCCAAC  CCTACCACCA  CCACCTCCTCC
4971  CCCCTCGCTG  CCGGACGACG  AGCTCCTCCC  CCCTCCCCCT  CCGCCGCCGC  CCCGCCCCTC
5041  TCCTCTTTCT  TTCTCCGTTT  TTTTTTTCGT  CTCGGTCTCG  ATCTTTGGCC  GGGTGGGCGA
5111  GAGCGGCTTC  GTCGCCCAGA  TCGGTGCGCG  GGAGGGGCGG  GATCTCGCGG  CTGGCGTCTC  CGGGCGTGAG
                  BamHI                                           BglII
5181  TCGGCCCCGGA  TCCTCGCGGG  GAATGGGGCT  CTCGGATGTA  GATCTTCTTT  CTTTCTTCTT  TTTGTGGTAG
5251  AATTGAAATC  CCTCAGCATT  GTTCATCGGT  AGTTTTTCTT  TTCATGATTT  GTGACAAATG  CAGCCTCGTG
5321  CGGAGCTTTT  TTGTAGC
```

FIG._34E

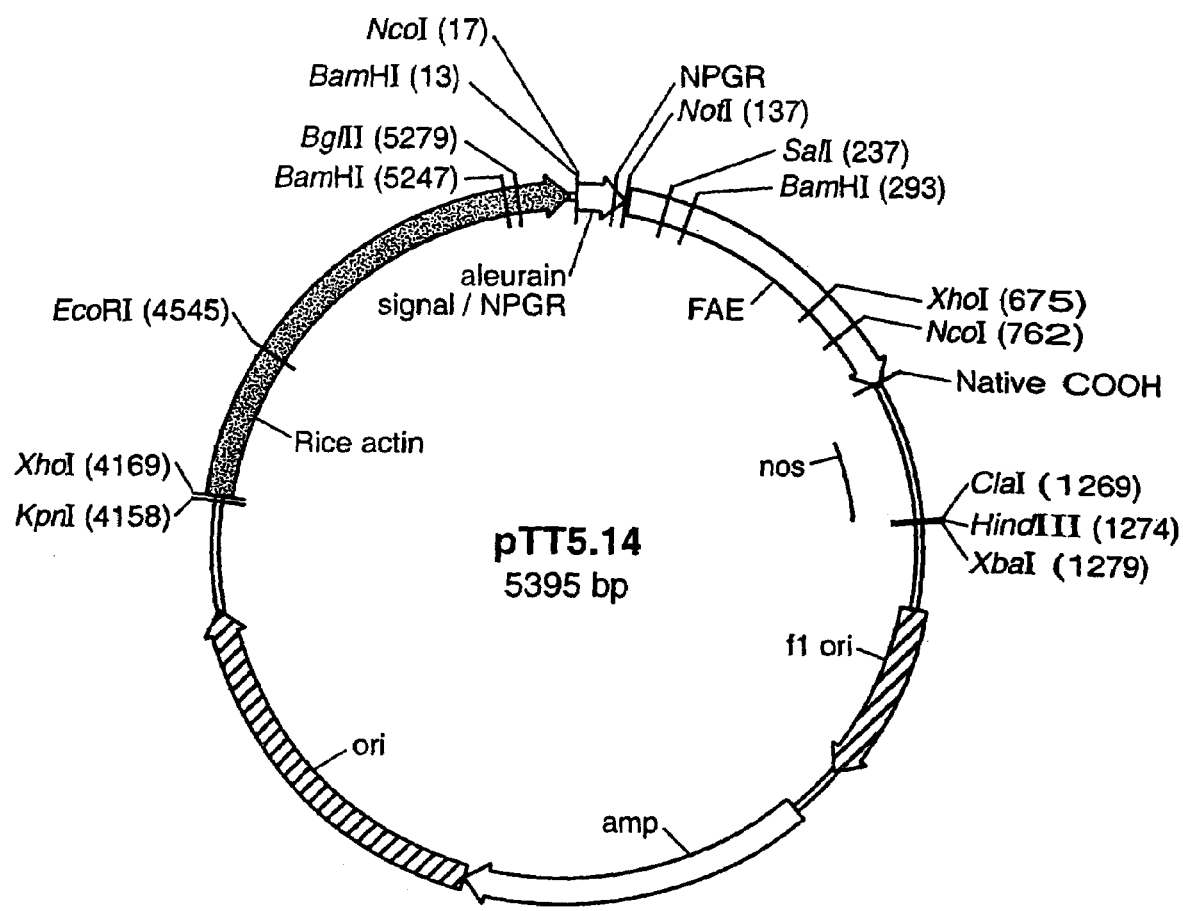
FIG._35A

```
                NcoI
              --------
              BamHI
              ------
                       M   A   H   A   R   V   L   L   L   A   L   A   V   L   A   T   A   A   .
  1    CCTGACGCCG AGGATCCATG GCCCACGCCC GGTCCTCCT CCTGGCGCTC GCCGTGCTGG CCACGGCCGC
                                                                                NotI
       . V   A   V   A   S   S   S   F   A   D   S   N   P   G   R   P   V   T   D   R   A   A
 71    CGTCGCCGTC GCCTCCTCCT CCTCCTTCGC CGACTCCAAC CCGGGCCGGC CCGTCACCGA CCGCGCGGCC
       NotI
       A   S   T   Q   G   I   S   E   D   L   Y   S   R   L   V   E   M   A   T   I   S   Q   A   A
141    GCCTCCACGC AGGGCATCTC CGAAGACCTC TACAGCCGTT TAGTCGAAAT GGCCACTATC TCCCAAGCTG
                                                    SalI
       . Y   A   D   L   C   N   I   P   S   T   I   I   K   G   E   K   I   Y   N   S   Q   T   D   .
211    CCTACGCCGA CCTGTGCAAC ATTCCGTCGA CTATTATCAA GGGAGAGAAA ATTTACAATT CTCAAACTGA
                                  BamHI
       . I   N   G   W   I   L   R   D   D   S   S   K   E   I   I   T   V   F   R   G   T   G   S
281    CATTAACGGA TGGATCCTCC GCGACGACAG CAGCAAAGAA ATAATCACCG TCTTCCGTGG CACTGGTAGT
         D   T   N   L   Q   L   D   T   N   Y   T   L   T   P   F   D   T   L   P   Q   C   N   G   C
351    GATACGAATC TACAACTCGA TACTAACTAC ACCCTCACGC CTTTCGACAC CCTACCACAA TGCAACGGTT
       . E   V   H   G   G   Y   Y   I   G   W   S   V   Q   D   Q   V   E   S   L   V   K   Q   .
421    GTGAAGTACA CGGTGGATAT TATATTGGAT GGGTCTCCGT CCAGGACCAA GTCGAGTCGC TTGTCAAACA
       . Q   V   S   Q   Y   P   D   Y   A   L   T   V   T   G   H   X   L   G   A   S   L   A   A
491    GCAGGTTAGC CAGTATCCGG ACTATGCGCT GACCGTGACC GGCCACKCCC TCGGCGCCTC CCTGGCGGCA
       L   T   A   A   Q   L   S   A   T   Y   D   N   I   R   L   Y   T   F   G   E   P   R   S   G
561    CTCACTGCCG CCCAGCTGTC TGCGACATAC GACAACATCC GCCTGTACAC CTTCGGCGAA CCGCGCAGCG
                                                                    XhoI
       . N   Q   A   F   A   S   Y   M   N   D   A   F   Q   A   S   S   P   D   T   T   Q   Y   F   .
631    GCAATCAGGC CTTCGCGTCG TACATGAACG ATGCCTTCCA AGCCTCGAGC CCAGATACGA CGCAGTATTT
                                                                                    NcoI
                                                                                    ~~~
       . R   V   T   H   A   N   D   G   I   P   N   L   P   P   V   E   Q   G   Y   A   H   G   G
```

FIG. _35B

```
701  CCGGGTCACT CATGCCAACG ACGGCATCCC AAACCTGCCC CCGGTGGAGC AGGGGTACGC CCATGGCGGT
      V  E  Y  W  S  V  D  P  Y  S  A  Q  N  T  F  V  C  T  G  D  E  V  Q  C
771  GTAGAGTACT GGAGCGTTGA TCCTTACAGC GCCCAGAACA CATTTGTCTG CACTGGGGAT GAAGTGCAGT
      .  C  E  A  Q  G  G           Q  G  V  N  A  H     T  T  Y     F  G  M  T  S  G  A
841  GCTGTGAGGC CCAGGGCGGA CAGGGTGTGA ATGCTGCGCA CACGACTTAT TTTGGGATGA CGAGCGGAGC
      .  C  T  W  *
911  CTGTACATGG TGATCAGTCA TTTCAGCCTC CCCGAGTGTA CCAGGAAAGA TGGATGTCCT GGAGAGGGGG
981  CCGCGTAACC ACTGAAGGAT GAGCTGTAAA GAAGCAGATC GTTCAAACAT TTGGCAATAA AGTTTCTTAA
1051 GATTGAATCC TGTTGCCGGT CTTGCGATGA TTATCATATA ATTTCTGTTG AATTACGTTA AGCATGTAAT
1121 AATTAACATG TAATGCATGA CGTTATTTAT GAGATGGGTT TTTATGATTA GAGTCCCGCA ATTATACATT
1191 TAATACGCGA TAGAAAACAA AATATAGCGC GCAAACTAGG ATAAATTATC GCGCGCGGTG TCATCTATGT
                           HindIII
                      ClaI    XbaI
1261 TACTAGATCG ATAAGCTTCT AGAGCGGCCG GTGGAGCTCC AATTCGCCCT ATAGTGAGTC GTATTACGCG
1331 CGCTCACTGG CCGTCGTTTT ACAACGTCGT GACTGGGAAA ACCCTGGCGT TACCCAACTT AATCGCCTTG
1401 CAGCACATCC CCCTTTCGCC AGCTGGCGTA ATAGCGAAGA GGCCCGCACC GATCGCCCTT CCCAACAGTT
1471 GCGCAGCCTG AATGGCGAAT GGGACGCGCC CTGTAGCGGC GCATTAAGCG CGGCGGGTGT GGTGGTTACG
1541 CGCAGCGTGA CCGCTACACT TGCCAGCGCC CTAGCGCCCG CTCCTTTCGC TTTCTTCCCT TCCTTTCTCG
1611 CCACGTTCGC CGGCTTTCCC CGTCAAGCTC TAAATCGGGG GCTCCCTTTA GGGTTCCGAT TTAGTGCTTT
1681 ACGGCACCTC GACCCCAAAA AACTTGATTA GGGTGATGGT TCACGTAGTG GGCCATCGCC CTGATAGACG
1751 GTTTTTCGCC CTTTGACGTT GGAGTCCACG TTCTTTAATA GTGGACTCTT GTTCCAAACT GGAACAACAC
1821 TCAACCCTAT CTCGGTCTAT TCTTTTGATT TATAAGGGAT TTTGCCGATT TCGGCCTATT GGTTAAAAAA
1891 TGAGCTGATT TAACAAAAAT TTAACGCGAA TTTTAACAAA ATATTAACGC TTACAATTTA GGTGGCACTT
1961 TTCGGGGAAA TGTGCGCGGA ACCCCTATTT GTTTATTTTT CTAAATATGT AGTATTATCA ATCCGCTCAT
2031 GAGACAATAA CCCTGATAAA TGCTTCAATA ATATTGAAAA AGGAAGAGTA CCCAGAAACG CTGGTGAAAG
2101 GTCGCCCTTA TTCCCTTTTT TGCGGCATTT TGCCTTCCTG TTTTTGCTCA CATCGAACTG GATCTCAACA GCGGTAAGAT
2171 TAAAGATGC TGAAGATCAG TTGGGTGCAC GAGTGGGTTA TCCAATGATG AGCACTTTTA AAGTTCTGCT ATGTGGCGCG
2241 CCTTGAGAGT TTTCGCCCCG AAGAACGTTT TCCAATGATG AGCACTTTTA AAGTTCTGCT ATGTGGCGCG
2311 GTATTATCCC GTATTGACGC CGGGCAAGAG CAACTCGGTC GCCGCATACA CTATTCTCAG AATGACTTGG
2381 TTGAGTACTC ACCAGTCACA GAAAAGCATC TTACGGATGG CATGACAGTA AGAGAATTAT GCAGTGCTGC
2451 CATAACCATG AGTGATAACA CTGCGGCCAA CTTACTTCTG ACAACGATCG GAGGACCGAA GGAGCTAACC
2521 GCTTTTTTGC ACAACATGGG GGATCATGTA ACTCGCCTTG ATCGTTGGGA ACCGGAGCTG AATGAAGCCA
2591 TACCAAACGA CGAGCGTGAC ACCACGATGC CTGTAGCAAT GGCAACAACG TTGCGCAAAC TATTAACTGG
2661 CGAACTACTT ACTCTAGCTT CCCGGCAACA ATTAATAGAC TGGATGGAGG CGGATAAAGT TGCAGGACCA
```

FIG._35C

| | | | | | | | |
|---|---|---|---|---|---|---|---|
| 2731 | CTTCTGCGCT | CGGCCCTTCC | GGCTGGCTGG | TTTATTGCTG | ATAAATCTGG | AGCCGGTGAG | CGTGGGTCTC |
| 2801 | GCGTATCAT | TGCAGCACTG | GGGCCAGATG | GTAAGCCCTC | CCGTATCGTA | GTTATCTACA | CGACGGGGAG |
| 2871 | TCAGCAACT | ATGCAGTGAAC | GAAATAGACA | GATCGCTGAG | ATAGGTGCCT | CACTGATTAA | GCATTGGTAA |
| 2941 | CTGTCAGACC | AAGTTTACTC | ATATATACTT | TAGATTGATT | TAAAACTTCA | TTTTTAATTT | AAAAGATCT |
| 3011 | AGGTGAAGAT | CCTTTTTTGAT | AATCTCATGA | CCAAAATCCC | TTAACGTGAG | TTTTCGTTCC | ACTGAGCGTC |
| 3081 | AGACCCCGTA | GAAAAGATCA | AAGGATCTTC | TTGAGATCCT | TTTTTTCTGC | GCGTAATCTG | CTGCTTGCAA |
| 3151 | ACAAAAAAAC | CACCGCTACC | AGCGGTGGTT | TGTTTGCCGG | ATCAAGAGCT | ACCAACTCTT | TTTCCGAAGG |
| 3221 | TAACTGGCTT | CAGCAGAGCG | CAGATACCAA | ATACTGTTCT | TCTAGTGTAG | CCGTAGTTAG | GCCACCACTT |
| 3291 | CAAGAACTCT | GTAGCACCGC | CTACATACCT | CGCTCTGCTA | ATCCTGTTAC | CAGTGGCTGC | TGCCAGTGGC |
| 3361 | GATAAGTCGT | GTCTTACCGG | GTTGGACTCA | AGACGATAGT | TACCGGATAA | AAGGCGCAGCGG | TCGGGCTGAA |
| 3431 | CGGGGGGTTC | GTGCACACAG | CCCAGCTTGG | AGCGAACGAC | CTACACCGAA | CTGAGATACC | TACAGCGTGA |
| 3501 | GCTATGAGAA | AGCGCCACGC | TTCCCGAAGG | GAGAAAGGCG | GACAGGTATC | CGGTAAGCGG | CAGGGTCGGA |
| 3571 | ACAGGAGAGC | GCACGAGGGA | GCTTCCAGGG | GGAAACGCCT | GGTATCTTTA | TAGTCCTGTC | GGGTTTCGCC |
| 3641 | ACCTCTGACT | TGAGCGTCGA | TTTTTGTGAT | GCTCGTCAGG | GGGGCGGAGC | CTATGGAAAA | ACGCCAGCAA |
| 3711 | CGCGGCCTTT | TTACGGTTCC | TGGCCTTTTG | CTGGCCTTTT | GCTCACATGT | TCTTTCCTGC | GTTATCCCCT |
| 3781 | GATTCTGTGG | ATAACCGTAT | TACCGCCTTT | GAGTGAGCTG | ATACCGCTCG | CCGCAGCCGA | ACGACCGAGC |
| 3851 | GCAGCGAGTC | AGTGAGCGAG | GAAGCGGAAG | AGCGCCCAAT | ACGCAAACCG | CCTCTCCCCG | CGCGTTGGCC |
| 3921 | GATTCATTAA | TGCAGCTGGC | ACGACAGGTT | TCCCGACTGG | AAAGCGGGCA | GTGAGCGCAA | CGCAATTAAT |
| 3991 | GTGAGTTAGC | TCACTCATTA | GGCACCCCAG | GCTTTACACT | TTATGCTTCC | GGCTCGTATG | TTGTGTGGAA |
| 4061 | TTGTGAGCGG | ATAACAATTT | CACACAGGAA | ACAGCTATGA | CCATGATTAC | GCCAAGCGCG | CAATTAACCC |
| | | | KpnI | | XhoI | | |
| 4131 | TCACTAAAGG | GAACAAAAGC | TGGGTACCGG | GCCCCCCCTC | GAGGTCATTC | GAAGAGAGTC | |
| 4201 | GGGATAGTCC | AAAATAAAAC | AAAGGTAAGA | TTACCTGGTC | AAAAGTGAAA | AAAGGTGGTA | |
| 4271 | TAAGTAAAAT | ATCGGTAATA | AAAGGTGGCC | CAAAGTCCT | TTTACTCTTT | TAAAAATTGA | |
| 4341 | GGATGTTTTG | TCGGTACTTT | GATACGTCAT | TTTTGTATGA | AGTTTATTC | GCGATTTGGA | |
| 4411 | AATGCATATC | TGTATTTGAG | TCGGTTTTTA | AGTTCGTTGC | TTTTGTAAAT | ACAGAGGGAT | TTGTATAAGA | |
| | | | | | | EcoRI | |
| 4481 | AATATCTTTA | AAAAACCCAT | ATGCTAATTT | GACATAATT | TTGAGAAAAA | TATATATTCA | GGCGAATTCC |
| 4551 | ACACTAAGAACA | ATAATAAGAT | TAAAATAGCT | TGCCCCCGTT | GCAGCGATGG | GTATTTTTC | TAGTAAAATA |
| 4621 | AAAGATAAAC | TTAGACTCAA | AACATTACA | AAACAACCC | CTAAAGTCCT | AAGCCCAAA | GTGCTATGCA |
| 4691 | CGATCCATAG | CAAGCCCAGC | CCAACCCAAC | CCACCCCAGT | CCACCCCAAC | GCAGCCAACT | GCAAAATGT |
| 4761 | CTCCACCCCC | GGCACTATCA | CCGTGAGTTG | TCCGCACCAC | CGCACGTCTC | GCAGCCAAAA | AAAAAAAAG |
| 4831 | AAAGAAAAAA | AAGAAAAAGA | AAAACAGCAG | GTGGGTCCGG | GTCGTGGGGG | CCGAAAAGC | GAGGAGGATC |

FIG._35D

```
4901  GCGAGCAGCG ACGAGGCCCG GCCCTCCCTC CGCTTCCAAA GAAACGCCCC CCATGCCCAC TATATACATA
4971  CCCCCCCTC  TCCTCCCATC CCCCAACCC  TACCACCACC ACCACCACCA CCTCCTCCCC CCTCGCTGCC
5041  GGACGACGAG CTCCTCCCCC CTCCCCCTCC GCCGCCGCCG GTAACCACCC CGCCCCTCTC CTCTTTCTTT
5111  CTCCGTTTTT TTTTTCGTCT CGGTCTCGAT CTTTGGCCCT GGTAGTTTGG GTGGGCGAGA GCGGCTTCGT
                                                                       BamHI
5181  CGCCCAGATC GGTGCGCGGG AGGGGCGGGA TCTCGCGGGCT GGCGTCTCCG GGCGTGAGTC GGCCCGGATC
                 BamHI                 BglII
5251  CTCGCGGGGA ATGGGGCTCT CGGATGTAGA TCTTCTCTTT TTCTTCTTTT TGTGGTAGAA TTTGAATCCC
5321  TCAGCATTGT TCATCGGGTAG TTTTTCTTT  CATGATTGT  GACAAATGCA GCCTCGTGCG GAGCTTTTT
5391  GTAGC
```

*FIG._35E*

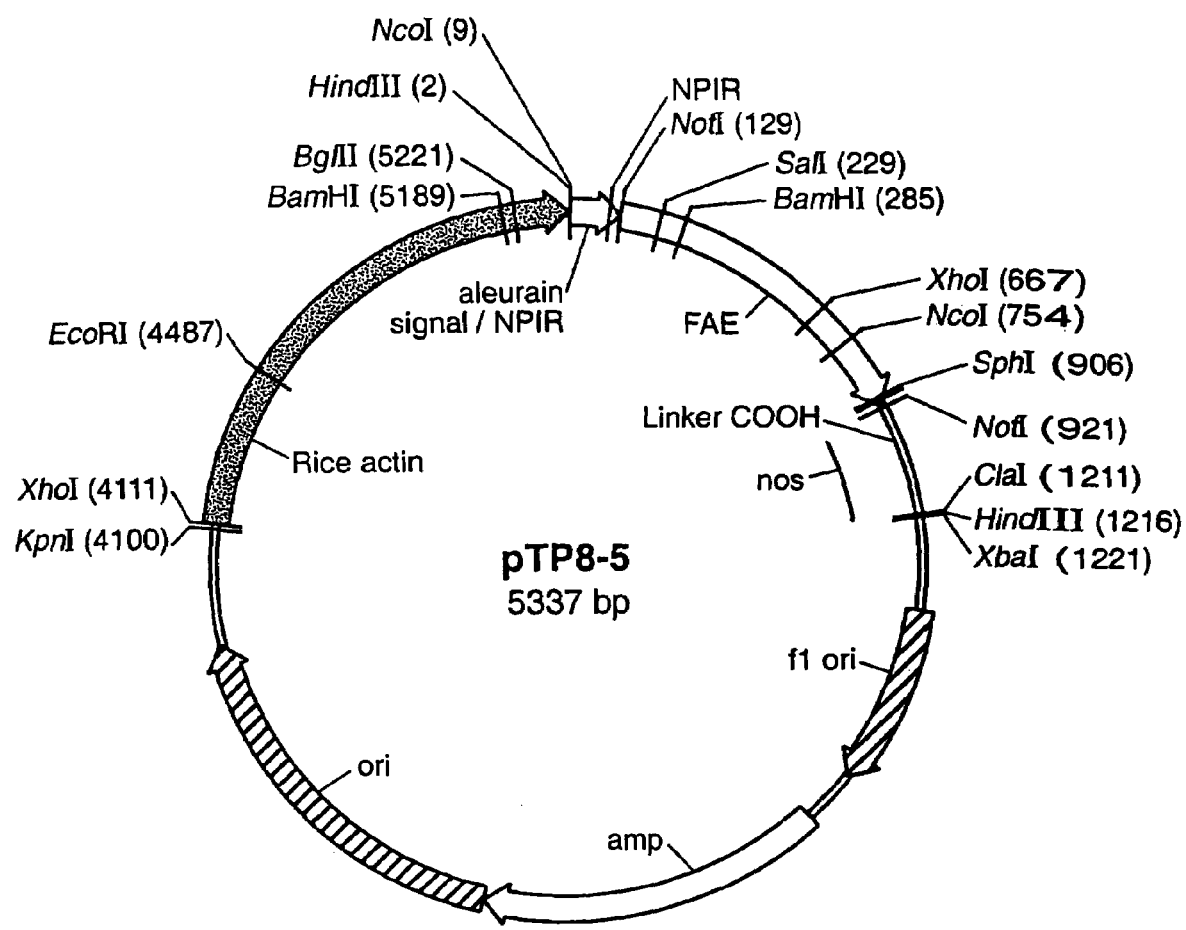
FIG._36A

```
                               HindIII
                               ~~~~~~~
                  M   A   H   A   R   V   L   L   L   A   L   A   V   L   A   T   A   A   V   A   V
  1   AAGCTTACCA TGGCCCACGC CCGCGTCCTC CTCCTGGCGC TCGCCGTGCT GGCCACGGCC GCCGTCGCCG
                                                                              NotI
                                                                              ~~~~
      .   A   S   S       S   S   F       A   D   S   N       P   I   R       P   V   T       D   R   A   A   S   T
 71   TCGGCCTCCTC CTCCTCCTTC GCCGACTCCA ACCCGATCCG GCCCGTCACC GACCGCGCGG CCGCCTCCAC
      .   Q   G   I       S   E   D   L   Y   S   R       L   V   E       M   A   T   I   S   Q   A       A   Y   A
141   GCAGGGCATC TCCGAAGACC TCTACAGCCG TTTAGTCGAA ATGGCCACTA TCTCCCAAGC TGCCTACGCC
                 SalI
                 ~~~~
      D   L   C   N       I   P   S       T   I   H       K   G   E   K   I   Y   N       S   Q   T       D   I   N   G
211   GACCTGTGCA ACATTCCGTC GACTATTATC AAGGGAGAGA AAATTTACAA TTCTCAAACT GACATTAACG
                         BamHI
                         ~~~~~
      .   W   I   L       R   D   D       S   S   K   E       I   I   T       V   F   R       G   T   G   S       D   T   N
281   GATGGATCCT CCGGCGACGAC AGCAGCAAAG AAATAATCAC CGTCTTCCGT GGCACTGGTA GTGATACGAA
      .   L   Q   L       D   T   N   Y       T   L   T       P   F   D       T   L   P   Q   C   N   G       C   E   V
351   TCTACAACTC GATACTAACT ACACCCTCAC GCCTTTCGAC ACCCTACCAC AATGCAACGG TTGTGAAGTA
      H   G   G   Y   Y   I   G       W   V   S       V   Q   D   Q   V   E   S       L   V   K       Q   Q   V   S
421   CACGGTGGAT ATTATATTGG ATGGGTCTCC GTCCAGGACC AAGTCGAGTC GCTTGTCAAA CAGCAGGTTA
      .   Q   Y   P       D   Y   A       L   T   V   T       G   H   K       L   G   A       S   L   A   A       L   T   A
491   GCCAGTATCC GGACTACGCG CTGACCGTGA CCGGCCACKC CCTCGGCGCC TCCCTGGCGG CACTCACTGC
      .   A   Q   L       S   A   T   Y       D   N   I       R   L   Y       T   F   G   E   P   R   S       G   N   Q
561   CGCCCAGCTG TCTGCGACAT ACGACAACAT CCGCCTGTAC ACCTTCGGCG AACCGCGCAG CGGCAATCAG
                                                                                                              XhoI
                                                                                                              ~~~~
      A   F   A   S       Y   M   N       D   A   F       Q   A   S       S   P   D   T       T   Q   Y       F   R   V   T
631   GCCTTCGCGT CGTACATGAA CGATGCCTTC CAAGCCTCGA GCCCAGATAC GACGCAGTAT TTCCGGGTCA
                                                                              NcoI
                                                                              ~~~~
      .   H   A   N   D   G   I       P   N   L   P   P   V   E   Q   G   Y       A   H   G   G       V   E   Y   .
```

*FIG._36B*

```
701  CTCATGCCAA CGACGGCATC CCAAACCTGC CCCCGGTGGA GCAGGGGTAC GCCCATGGCG GTGTAGAGTA
     · W  S  V   D  P  Y  S   A  Q  N    T  F  V     Q  G  Y     A  H  G      V  *  S

771  CTGGAGCCGTT GATCCTTACA GCGCCCAGAA CACATTTGTC TGCACTGGGG ATGAAGTGCA GTGCTGTGAG
       L  E  P   D  P  Y  S   A  Q  N    H  I  V    C  T  G    D  E  V  Q    C  C  E
                                                                              SphI

841  GCCCAGGGCG GACAGGGGTGT GAATAATGCG CACACGACTT ATTTTGGGAT GACGAGCGGC GCATGCACCT
      A  Q  G   G  Q  G  V   N  N  A    H  T  T  Y   F  G  M    T  S  G     A  C  T  W
                 NotI

911  GGCCGGTCGC GGCCGCGTAA CCACTGAAGG ATGAGCTGTA AAGAAGCAGA TCGTTCAAAC ATTTGGCAAT
     ·  P  V  A   A  A  *
981  AAGTTTCTT AAGATTGAAT CCTGTTGCCG GTCTTGCGAT GATTATCATA AAACCCTGGA GTTACCCAAC
1051 TAAGCATGTA ATAATTAACA TGTAATGCAT GACGTTATTT ATGAGATGGG TTTTTATGAT TAGAGTCCCG
1121 CAATTATACA TTTAATACGC GATAGAAAAC GCGCAAACTA GGATAAATTA TCGCGCGCGG
             HindIII
1191 GGCCGGTCGC GTTACTAGAT CGATAAGCTT CTAGAGCGGC CGGTGGAGCT CCAATTCGCC CTATAGTGAG
                          ClaI    XbaI
1261 TCGTATTACG CGCGCTCACT GGCCGTCGTT TTACAACGTC GTGACTGGGA AAACCCTGGC GTTACCCAAC
1331 TTAATCGCCT TGCAGCACAT CCCCCTTTCG CCAGCTGGCG TAATAGCGCG GAGGCCCGCA CCGATCGCCC
1401 TTCCCAACAG TTGCGCAGCC TGAATGGCGA ATGGGACGCG CCCTGTAGCG GCGCATTAAG CGCGGCGGGT
1471 GTGGTGGTTA CGCGCAGCGT GACCGCTACA CTTGCCAGCG CCCTAGCGCC CGCTCCTTTC GCTTTCTTCC
1541 CTTCCTTTCT CGCCACGTTC GCCGGCTTTC CCCGTCAAGC TCTAAATCGG GGGCTCCCTT TAGGGTTCCG
1611 ATTTAGTGCT TTACGGCACC TCGACCCCAA AAAACTTGAT TAGGGTGATG TGGTCACGTAG TGGGCCATCG
1681 CCCTGATAGA CGGTTTTTCG CCCTTTGACG TTGGAGTCCA CGTTCTTTAA TAGTGGACTC TTGTTCCAAA
1751 CTGGAACAAC ACTCAACCCT ATCTCGGTCT ATTCTTTTGA TTTATAAGGG ATTTTGCCGA TTTCGGCCTA
1821 TTGGTTAAAA AATGAGCTGA TTTAACAAAA ATTTAACGCG AATTTTAACA AAATATTAAC GCTTACAATT
1891 TAGGTGGCAC TTTTCGGGGA AATGTGCGCG GAACCCTATT TGTTTATTTT TCTAAATAC ATTCAAATAT
1961 GTATCCGCTC ATGAGACAAT AACCCTGATA TATTCCCTTT TTTGCCTTCC TTTGCCTTCC ACGAGTGGT ACGAGTGGT TATGAGTATT
2031 CAACATTTCC GTGTCGCCCT TATTCCCTTT TTTGCCTTTC CTTTATTTTC TGTTTTTGCT TACATCGAAC TGGATCTCAA
2101 CGGTGGTAAG ATGAAAAGAT GCTGAAGATC AGTTGGGTGC ACGAGTGGGT TACATCGAAC TGGATCTCAA
2171 CAGCGGTAAG ATCCTTGAGA GTTTTCGCCC CGAAGAACGT TTTCCAATGA TGAGCACTTT TAAAGTTCTG
2241 CTATGTGGCG CGGTATTATC CCGTATTGAC GCCGGGCAAG AGCAACTCGG TCGCCGCATA CACTATTCTC
2311 AGAATGACTT GGTTGAGTAC TCACCAGTCA CAGAAAAGCA TCTTACGGAT GGCATGACAG TAAGAGAATT
```

FIG._36C

```
2381 ATGCAGTGCT GCCATAACCA TGAGTGATAA CACTGCGGCC AACTTACTTC TGACAACGAT CGGAGGACCG
2451 AAGGAGCTAA CCGCTTTTTT GCACACATG GGGATCATG TAACTCGCCT TGATCGTTGG GAACCGGAGC
2521 TGAATGAAGC CATACCAAAC GACGAGCGTG ACACCACGAT GCCTGTAGCA ATGGCAACAA CGTTGCGCAA
2591 ACTATTAACT GGCGAACTAC TTACTCTAGC TTCCCGGCAA CAATTAATAG ACTGGATGGA GGCGGATAAA
2661 GTTGCAGGAC CACTTCTGCG CTCGGCCCTT CCGGCTGGCT GGTTTATTGC TGATAAATCT GGAGCCGGTG
2731 AGCGTGGGTC TCGCGGTATC ATTGCAGCAC TGGGGCCAGA TGGTAAGCCC TCCCGTATCG TAGTTATCTA
2801 CACGACGGGG AGTCAGGCAA CTATGGATGA ACGAAATAGA CAGATCGCTG AGATAGGTGC CTCACTGATT
2871 AAGCATTGGT AACTGTCAGA CCAAGTTTAC TCATATATAC TTTAGATTGA TTTAAAACTT CATTTTTAAT
2941 TTAAAAGGAT CTAGGTGAAG ATCCTTTTTG ATAATCTCAT GACCAAAATC CCTTAACGTG AGTTTTCGTT
3011 CCACTGAGCG TCAGACCCCG TAGAAAAGAT CAAAGGATCT TCTTGAGATC CTTTTTTTCT GCGCGTAATC
3081 TGCTGCTTGC AAACAAAAAA ACCACCGCTA CCAGCGGTGG TTTGTTTGCC GGATCAAGAG CTACCAACTC
3151 TTTTTCCGAA GGTAACTGGC TTCAGCAGAG CGCAGATACC AAATACTGTC CTTCTAGTGT AGCCGTAGTT
3221 AGGCCACCAC TTCAAGAACT CTGTAGCACC GCCTACATAC CTCGCTCTGC TAATCCTGTT ACCAGTGGCT
3291 GCTGCCAGTG GCGATAAGTC GTGTCTTACC GGGTTGGACT CAAGACGATA GTTACCGGAT AAGGCGCAGC
3361 GGTCGGGCTG AACGGGGGGT TCGTGCACAC AGCCCAGCTT GGAGCGAACG ACCTACACCG AACTGAGATA
3431 CCTACAGCGT GAGCTATGAG AAAGCGCCAC GCTTCCCGAA GGGAGAAAGG CGGACAGGTA TCCGGTAAGC
3501 GGCAGGGTCG GAACAGGAGA GCGCACGAGG GAGCTTCCAG GGGGAAACGC CTGGTATCTT TATAGTCCTG
3571 TCGGGTTTCG CCACCTCTGA CTTGAGCGTC GATTTTTGTG ATGCTCGTCA GGGGGGCGGA GCCTATGGAA
3641 AAACGCCAGC AACGCGGCCT TTTTACGGTT CCTGGCCTTT TGCTGGCCTT TTGCTCACAT GTTCTTTCCT
3711 GCGTTATCCC CTGATTCTGT GGATAACCGT ATTACCGCCT TTGAGTGAGC TGATACCGCT CGCCGCAGCC
3781 GAACGACCGA GCGCAGCGAG TCAGTGAGCG AGGAAGCGGA AGAGCGCCCA ATACGCAAAC CGCCTCTCCC
3851 CGCGCGTTGG CCGATTCATT AATGCAGCTG GCACGACAGG TTTCCCGACT GGAAAGCGGG CAGTGAGCGC
3921 AACGCAATTA ATGTGAGTTA GCTCACTCAT TAGGCACCCC AGGCTTTACA CTTTATGCTT CCGGCTCGTA
3991 TGTTGTGTGG AATTGTGAGC GGATAACAAT TTCACACAGG AAACAGCTAT GACCATGATT ACGCCAAGCG
                EcoRI                                                 XbaI
4061 CGCAATTAAC CCTCACTAAA GGGAACAAAA GCTGGGTACC GGGCCCCCCC TCGAGGTCAT TCATATGCTT
4131 GAGAAGAGAG TCGGGATAGT CCAAAATAAA ACAAAGGTAA GATTACCTGG TCAAAAGTGA AAACATCAGT
                                                 KpnI
4201 TAAAAGGTGG TATAAGTAAA ATATCGGTAA TAAAAGGTGG CCCAAAGTGA AATTACTCT TTTCTACTAT
4271 TATAAAAATT GAGGATGTTT TGTCGGTACT TTGATACGTC ATTTTTGTAT GAATTGGTTT TTAAGTTTAT
4341 TCGCGATTTG GAAATGCATA TCTGTATTTG AGTCGGTTTT TAAGTTCGTT GCTTTTGTAA ATACAGAGGG
4411 ATTTGTATAA GAAATATCTT TAAAAAACCC ATATGCTAAT TTGACATAAT TTTGAGAAAA AATATATATT

4481 CAGGCGAATT CCACAATGAA CAATAATAAG ATTAAAATAG CTTGCCCCCG TTGCAGCGAT GGGTATTTTT
```

FIG._36D

```
4551  TCTAGTAAAA TAAAAGATAA ACTTAGACTC AAAACATTTA CAAAAACAAC CCCTAAAGTC CTAAAGCCCA
4621  AAGTGCTATG CACGATCCAT AGCAAGCCCA GCCCAACCCA ACCCACCCCA GTGCAGCCAA
4691  CTGGCAAATA GTCTCCACCC CCGGCACTAT TGTCCGCACC ACCGCACGTC TCGCAGCCAA
4761  AAAAAAAAAA AGAAAGAAAA AAAAGAAAAA GAAAACAGC AGGTGGGTCC GGGTCGTGGG GGCCGGAAAA
4831  GCGAGGAGGA TCGCGAGCAG CGGCCCCTCC TCCGCTTCCA AAGAAACGCC CCCCATCGCC
4901  ACTATATACA TACCCCCCCC TCTCCTCCCA CCTACCACCA CCACCACCAC CACCTCCTCC
4971  CCCCTCGCTG CCGGACGACG AGCTCCTCCC CCCTCCCCCT CGGCCGCGC CGGTAACCAC CCCGCCCCTC
5041  TCCTCTTTCT TTCTCCGTTT TTTTTTTCGT CTCGGTCTCG ATCTTTGGCC TTGGTAGTTT GGGTGGGCGA
5111  GAGCGGCTTC GTCGCCCAGA TCGGTGCGCG GATCTCGCGG GATCTCGCGG CTGGCGTCTC CGGGCGTGAG
                BamHI                                   BglII
5181  TCGGCCCCGA TCCTCGCGGG GAATGGGGCT CTCGGATGTA GATCTTCTTT CTTTCTTCTT TTTGTGTAG
5251  AATTGAAATC CCTCAGCATT GTTCATCGGT AGTTTTTCTT TTCATGATTT GTGACAAATG CAGCCTCGTG
5321  CGGAGCTTTT TTGTAGC
```

*FIG._36E*

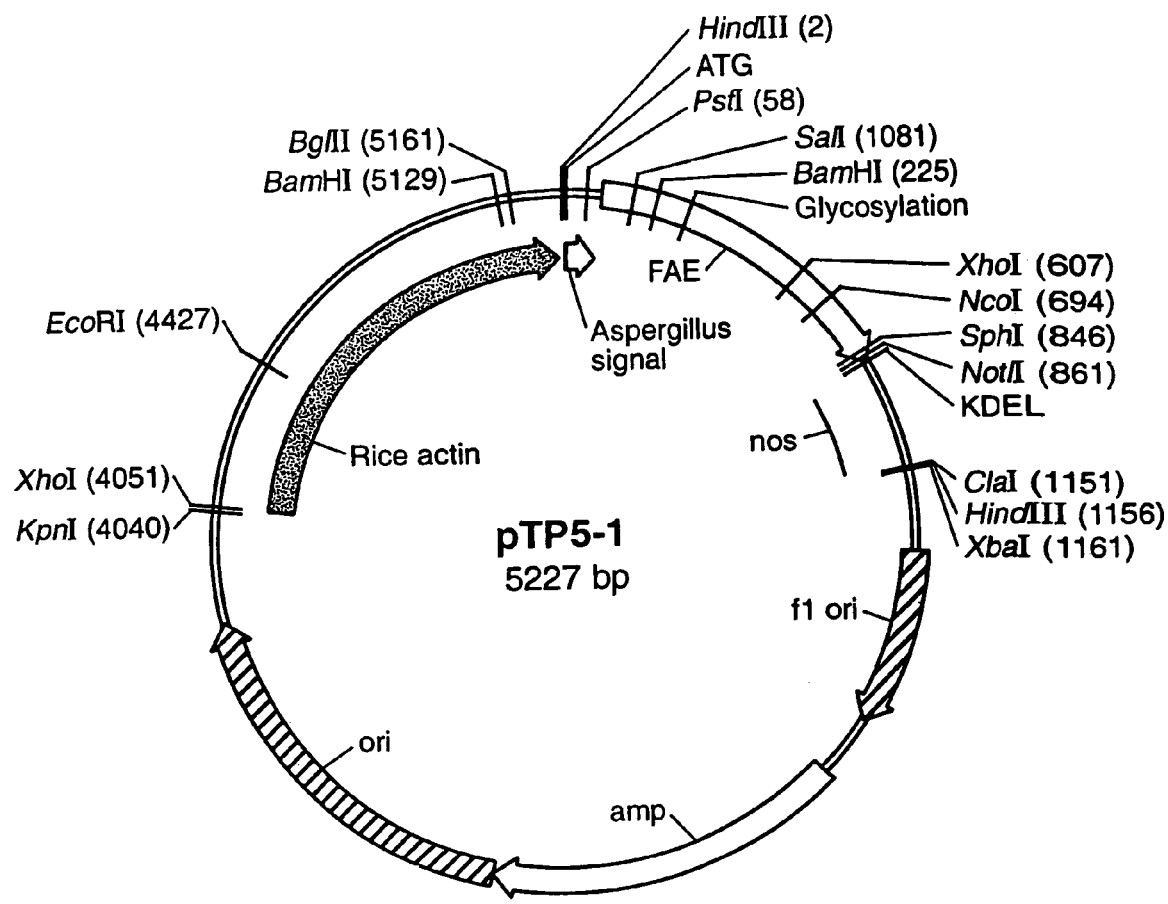
FIG._37A

```
       HindIII
       ------
                       M   K   Q   F   S   A   K   H   V   L   A   V   V   V         T   A   G   H   A   L   A
                                                                                      PstI
                                                                                      ----
  1    AAGCTTAACA TGAAGCAGTT CTCCGCCAAA CACGTCCTCG CAGTTGTGGT GACTGCAGGG CACGCCTTAG
         A   S   T   Q   G   I   S   E   D   L   Y   S   R   L   V   E   M   A   T   I   S   Q   A    .
 71    CAGCCTCTAC GCAAGGCATC TCCGAAGACC TCTACAGCCG TTTAGTCGAA ATGGCCACTA TCTCCCAAGC
                                                             SalI
                                                             ----
         A   Y   A   D   L   C   N   I   P   S   T   I   I   K   G   E   K   I   Y   N   S   Q   T
141    TGCCTACGCC GACCTGTGCA ACATTCCGTC GACTATTATC AAGGGAGAGA AAATTTACAA TTCTCAAACT
                                 BamHI
                                 -----
         D   I   N   G   W   I   L   R   D   D   S   S   K   E   I   I   T   V   F   R   G   T   G   S
211    GACATTAACG GATGGATCCT CCGCGACGAC AGCAGCAAAG AAATAATCAC CGTCTTCCGT GGCACTGGTA
         .   D   T   N   L   Q   L   D   T   N   Y   T   L   T   P   F   D   T   L   P   Q   C   N   G   .
281    GTGATACGAA TCTACAACTC GATACTAACT ACACCCTCAC GCCTTTCGAC ACCCTACCAC AATGCAACGG
         .   C   E   V   H   G   G   Y   I   G   W   V   S   V   Q   D   Q   V   E   S   L   V   K
351    TTGTGAAGTA CACGGTGGAT ATTATATTGG ATGGGTCTCC GTCCAGGACC AAGTCGAGTC GCTTGTCAAA
         Q   Q   V   S   Q   Y   P   D   Y   A   L   T   V   T   G   H   K   L   G   A   S   L   A   A
421    CAGCAGGTTA GCCAGTATCC GGACTACGCG CTGACCGTGA CCGGCCACTC CCTCGGCGCC TCCCTGGCGG
         .   L   T   A   A   Q   L   S   A   T   Y   D   N   I   R   L   Y   T   F   G   E   P   R   S   .
491    CACTCACTGC CGCCCAGCTG TCTGCGACAT ACGACAACAT CCGGCTGTAC ACCTTCGGCG AACCGCGCAG
                                                                   XhoI
                                                                   ----
         G   N   Q   A   F   A   S   Y   M   N   D   A   F   Q   A   S   S   P   D   T   T   Q   Y
561    CGGCAATCAG GCCTTCGCGT CGTACATGAA CGATGCCTTC CAAGCCTCGA GCCCAGATAC GACGCAGTAT
                                                                                     NcoI
                                                                                     ----
         F   R   V   T   H   A   N   D   G   I   P   N   L   P   P   V   E   Q   G   Y   A   H   G   G
631    TTCCGGGTCA CTCATGCCAA CGACGGCATC CCAAACCTGC CCCCGGTGGA GCAGGGGTAC GCCCATGGCG
         .   V   E   Y   W   S   V   D   P   Y   S   A   Q   N   T   F   V   C   T   G   D   E   V   Q   .
701    GTGTAGAGTA CTGGAGCGTT GATCCTTACA GCGCCCAGAA CACATTTGTC TGCACTGGGG ATGAAGTGCA
         .   C   C   E   A   Q   G   G   Q   V   N   N   A   H   T   T   Y   F   G   M   T   S   G
771    GTGCTGTGAG GCCCAGGGCG GACAGGGTGT GAATAATGCG CACACGACTT ATTTTGGGAT GACGAGCGGC
```

FIG._37B

```
       SphI              NotI
       A  C  T  W  P  V  A  A  E    P  L  K  D  E  L  *
 841  GCATGCACCT GGCCGGTCGC GGCCGCGGAA CCACTGAAGG ATGAGCTGTA AAGAAGCAGA TCGTTCAAAC
 911  ATTTGGCAAT AAAGTTTCTT AAGATTGAAT CCTGTTGCCG GTCTTGCGAT GATTATCATA TAATTTCTGT
 981  TGAATTACGT TAAGCATGTA ATAATTAACA TGTAATGCAT GACGTTATTT ATGAGATGGG TTTTTATGAT
1051  TAGAGTCCCG CAATTATACA TTTAATACGC GATAGAAAAC AAAATATAGC GCGCAAACTA GGATAAATTA
                                            HindIII
                              ClaI          XbaI
1121  TCGCGCGCGG TGTCATCTAT GTTACTAGAT CGATAAGCTT CTAGAGCGGC CGGTGGAGCT CCAATTCGCC
1191  CTATAGTGAG TCGTATTACG CGCGCTCACT GGCCGTCGTT TTACAACGTC GTGACTGGGA AAACCCTGGC
1261  GTTACCCAAC TTAATCGCCT TGCAGCACAT CCAGCTGGCG ATGGAGCGAA CCCTGTAGCG GCGCATTAAG
1331  CCGATCGCCC TTCCCAACAG TTGCGCAGCC TGAATGGCGA ATGGGACGCG CCCTAGCGCC CGCTCCTTTC
1401  CGCGGCGGGT GTGGTGGTTA CGCGCAGCGT GACCGCTACA CTTGCCAGCG CCCTAGCGCC GGGCTCCCTT
1471  GCTTTCTTCC CTTCCTTTCT CGCCACGTTC GCCGGCTTTC CCCGTCAAGC TCTAAATCGG GTTCACGTAG
1541  TAGGGTTCCG ATTTAGTGCT TTACGGCACC TCGACCCCAA AAAACTTGAT TAGGGTGATG GTTCACGTAG
1611  TGGGCCATCG CCCTGATAGA CGGTTTTTCG CCCTTTGACG TTGGAGTCCA CGTTCTTTAA TAGTGGACTC
1681  TTGTTCCAAA CTGGAACAAC ACTCAACCCT ATCTCGGTCT ATTCTTTTGA TTTATAAGGG ATTTTGCCGA
1751  TTTCGGCCTA TTGGTTAAAA AATGAGCTGA TTTAACAAAA ATTTAACGCG AATTTTAACA AAATATTAAC
1821  GCTTACAATT TAGGTGGCAC TTTTCGGGGA AATGTGCGCG GAACCCCTAT TTGTTTATTT TTCTAAATAC
1891  ATTCAAATAT GTATCCGCTC ATGAGACAAT AACCCTGATA AATGCTTCAA TAATATTGAA AAAGGAAGAG
1961  TATGAGTATT CAACATTTCC GTGTCGCCCT TATTCCCTTT TTTGCGGCAT TTTGCCTTCC TGTTTTTGCT
2031  CACCCAGAAA CGCTGGTGAA AGTAAAAGAT GCTGAAGATC AGTTGGGTGC ACGAGTGGGT TACATCGAAC
2101  TGGATCTCAA CAGCGGTAAG ATCCTTGAGA GTTTTCGCCC CGAAGAACGT TTTCCAATGA TGAGCACTTT
2171  TAAAGTTCTG CTATGTGGCG CGGTATTATC CGTATTGAC GCCGGGCAAG AGCAACTCGG TCGCCGCATA
2241  CACTATTCTC AGAATGACTT GGTTGAGTAC TCACCAGTCA CAGAAAAGCA TCTTACGGAT GGCATGACAG
2311  TAAGAGAATT ATGCAGTGCT GCCATAACCA TGAGTGATAA CACTGCGGCC AACTTACTTC TGACAACGAT
2381  CGGAGGACCG AAGGAGCTAA CCGCTTTTTT GCACAACATG GGGGATCATG TAACTCGCCT TGATCGTTGG
2451  GAACCGGAGC TGAATGAAGC CATACCAAAC GACGAGCGTG ACACCACGAT GCCTGTAGCA ATGGCAACAA
2521  CGTTGCGCAA ACTATTAACT GGCGAACTAC TTACTCTAGC TTCCCGGCAA CAATTAATAG ACTGGATGGA
2591  GGCGGATAAA GTTGCAGGAC CACTTCTGCG CTCGGCCCTT CCGGCTGGCT GGTTTATTGC TGATAAATCT
2661  GGAGCCGGTG AGCGTGGGTC TCGCGGTATC ATTGCAGCAC TGGGGCCAGA TGGTAAGCCC TCCCGTATCG
```

FIG._37C

```
2731 TAGTTATCTA CACGACGGGG AGTCAGGCAA CTATGATGA ACGAAATAGA CAGATCGCTG AGATAGGTGC
2801 CTCACTGATT AAGCATTGGT AACTGTCAGA CCAAGTTTAC TCATATATAC TTTAGATTGA TTTAAAACTT
2871 CATTTTTAAT CTAGTGAAG CTAGTGAACCCCG ATCCTTTTG ATAATCTCAT GACCAAAATC CCTTAACGTG
2941 AGTTTTCGTT CCACTGAGCG TCAGACCCCG TAGAAAAGAT CAAAGGATCT TCTTGAGATC CTTTTTTTCT
3011 GCGCGTAATC TGCTGCTTGC AAACAAAAAA ACCACCGCTA CCAGCGGTGG TTTGTTTGCC GGATCAAGAG
3081 CTACCAACTC TTTTTCCGAA GGTAACTGGC TTCAGCAGAG CGCAGATACC AAATACTGTC CTTCTAGTGT
3151 AGCCGTAGTT AGGCCACCAC TTCAAGAACT CTGTAGCACC GCCTACATAC CTCGCTCTGC TAATCCTGTT
3221 ACCAGTGGCT GCTGCCAGTG GCGATAAGTC GTGTCTTACC GGGTTGGACT CAAGACGATA GTTACCGGAT
3291 AAGGCGCAGC GGTCGGGCTG AACGGGGGT TCGTGCACAC AGCCCAGCTT GGAGCGAACG ACCTACACCG
3361 AACTGAGATA CCTACAGCGT GAGCTATGAG AAAGCGCCAC GCTTCCCGAA GGGAGAAAGG CGGACAGGTA
3431 TCCGGTAAGC GGCAGGGTCG GAACAGAGA GCGCACGAGG GAGCTTCCAG GGGAAACGC CTGGTATCTT
3501 TATAGTCCTG TCGGGTTTCG CCACCTCTGA CTTGAGCGTC GATTTTTGTG ATGCTCGTCA GGGGGGCGGA
3571 GCCTATGGAA AAACGCCAGC AACGCGGCCT TTTTACGGTT CCTGGCCTTT TGCTGGCCTT TTGCTCACAT
3641 GTTCTTTCCT GCGTTATCCC CTGATTCTGT GGATAACCGT ATTACCGCCT TTGAGTGAGC TGATACCGCT
3711 CGCCGCAGCC GAACGACCGA GCGCAGCGAG TCAGTGAGCG AGGAAGCGGA AGAGCGCCCA ATACGCAAAC
3781 CGCCTCTCCC CGCGCGTTGG CCGATTCATT AATGCAGCTG GCACGACAGG TTTCCCGACT GGAAAGCGGG
3851 CAGTGAGCGC AACGCAATTA ATGTGAGTTA GCTCACTCAT TAGGCACCCC AGGCTTTACA CTTTATGCTT
3921 CCGGCTCGTA TGTTGTGTGG AATTGTGAGC GGATAACAAT TTCACACAGG AAACAGCTAT GACCATGATT
                                     EcoRI                                    XhoI
3991 ACGCCAAGCG CGCAATTAAC CCTCACTAAA GGGAACAAAA GCTGGGTACC GGGCCCCCCC TCGAGGTCAT
4061 TCATATGCTT GAGAAGAGAG TCGGGATAGT CCAAAATAAA ACAAAGGTAA GATTACCTGG TCAAAAGTGA
                                                               KpnI
4131 AAACATCAGT TAAAAGGTGG TATAAGTAAA ATATCGGTAA TAAAAGGTGG CCCAAAGTGA AATTTACTCT
4201 TTTCTACTAT TATAAAAATT GAGGATGTTT TGTCGGTACT TTGATACGTC ATTTTTGTAT GAATTGGTTT
4271 TTAAGTTTAT TCGCGATTTG GAAATGCATA TCTGTATTTG AGTCGGTTTT TAAGTTCGTT GCTTTTGTAA
4341 ATACAGAGGG ATTTGTATAA GAAATATCTT TAAAAAACCC ATATGCTAAT TTGACATAAT TTTTGAGAAA

4411 AATATATATT CAGGCGAATT CCACAATGAA CAATAATAAG ATTAAAAATAG TTGCAGCGAT TTGCCCCCCG
4481 GGGTATTTTT TCTAGTAAAA TAAAGATAA ACTTAGACTC AAAACATTTA CAAAAACAAC CCCTAAAGTC
4551 CTAAAGCCCA AAGTGCTATG CACGATCCAT AGCAAGCCCA GCCCAACCCA ACCCACCCCA
4621 GTGCAGCCAA CTGGCAAATA GTCTCCACCC CCGGCACTAT CACCGTGAGT TGTCCGCACC ACCGCACGTC
4691 TCGCAGCCAA AAAAAAAAA AGAAAGAAAA AAAAGAAAA GAAAAACAGC AGGTGGGTCC GGGTCGTGGG
```

FIG._37D

```
4761  GGCCGGAAAA  GCGAGGAGGA  TCGCGAGCAG  CGACGAGGCC  CGGCCCTCCC  TCCGCTTCCA  AAGAAACGCC
4831  CCCCATCGCC  ACTATATACA  TACCCCCCCC  TCTCCCTCCCA  TCCCCCCAAC  CCTACCACCA  CCACCACCAC
4901  CACCTCCTCC  CCCCTCGCTG  CCGGACGACG  AGCTCCTCCC  CCCTCCCCCT  CCGCCCGCCGC  CGGTAACCAC
4971  CCCGCCCCTC  TCCTCTTTCT  TTCTCCGTTT  TTTTTTCGT  CTCGGTCTCG  ATCTTTGGCC  TTGGTAGTTT
5041  GGGTGGGCGA  GAGCGGCTTC  GTCGCCCAGA  TCGGTGCGCG  GGAGGGGCGG  GATCTCGCGG  CTGGGCGTCTC
                  BamHI                                          BglII
5111  CGGGCGTGAG  TCGGCCCGGA  TCCTCGCGGG  GAATGGGGCT  CTCGGATGTA  GATCTTCTTT  CTTTCTTCTT
5181  TTTGTGGTAG  AATTGAAATC  CCTCAGCATT  GTTCATCGGT  AGTTTTTCTT  TTCATGATTT  GTGACAAATG
5251  CAGCCTCGTG  CGGAGCTTTT  TTGTAGC

FIG._37E
```

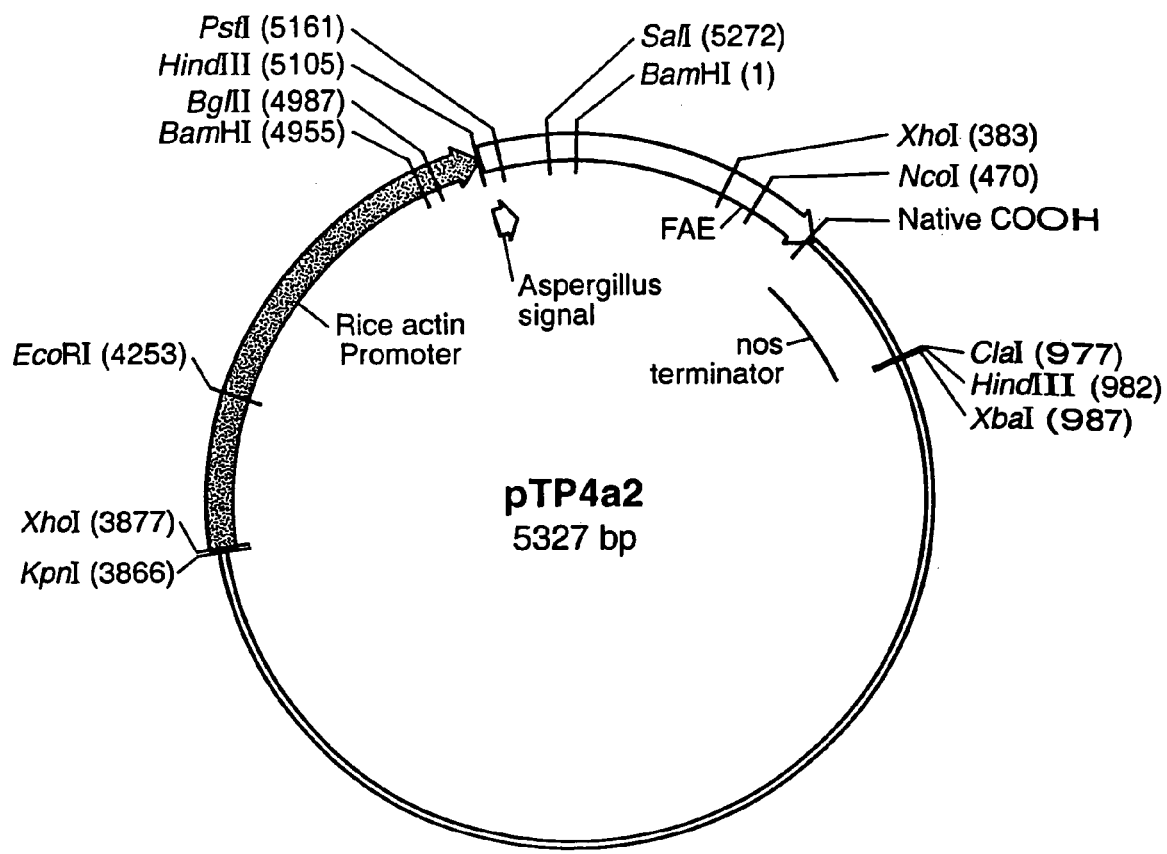
FIG._38A

```
                                                                                        .  I  L  R     D  D  D  S  S     K  E  I     I  T  V     F  R  G     T     G  S  D        T  N  L
  1 GATCCTCCGC GACGACAGCA GCAAAGAAAT AATCACCGTC TTCCGTGGCA CTGGTAGTGA TACGAATCTA
       Q L D T   N Y T       L T P     F D T L     P Q C     N G C     E V H G
 71 CAACTCGATA CTAACTACAC CCTCACGCCT TTCGACACCC TACCACAATG CAACGGTTGT GAAGTACACG
    .  G  Y  Y     I  G  W     V  S  V  Q     D  Q  V     E  S  L     V  K  Q  Q  V  S  Q  .
141 GTGGATATTA TATTGGATGG GTCTCCGTCC AGGACCAAGT CGAGTCGCTT GTCAAACAGC AGGTTAGCCA
    .  Y  P  D     Y  A  L  T     V  T  G     H  X  L     G  A  S  L     A  A  L        T  A  A
211 GTATCCGGAC TACGCGCTGA CCGTGACCGG CCACKCCCTC GGGCGCCCTC TGGCGGGCACT CACTGCCGCC
       Q L S A   T Y D       N I R     L Y T F     G E P     R S G     N Q A F
281 CAGCTGTCTG CGACATACGA CAACATCCGC CTGTACACCT TCGGCGAACC GCGCAGCGGC AATCAGGCCT
                                                                   XhoI
                                                                        .  D  T  T  Q  Y  F  R     V  T  H  .
    .  A  S  Y     M  N  D     A  F  Q  A     S  S  P
351 TCGCGTCGTA CATGAACGAT GCCTTCCAAG CCTCGAGCCC AGATACGACG CAGTATTTCC GGGTCACTCA
                                                                       NcoI
    .  A  N  D     G  I  P  N     L  P  P     V  E  Q     G  Y  A  H     G  G  V     E  Y  W
421 TGCCAACGAC GGCATCCCAA ACCTGCCCCC GGTGGAGCAG GGGTACGCCC ATGGCGGTGT AGAGTACTGG
       S V D P   Y S A       Q N T     F V C T     G D E     V Q C     C E A Q
491 AGCGTTGATC CTTACAGCGC CCAGAACACA TTTGTCTGCA CGGGGATGA AGTGCAGTGC TGTGAGGCCC
    .  G  G  Q     G  V  N     N  A  H  T     T  Y  F     G  M  T     S  G  A  C     T  W  *  .
561 AGGGCGGACA GGGTGTGAAT AATGCGCACA CGACTTATTT TGGGATGACG AGCGGAGCCT GTACATGGTG
    .  *
631 ATCAGTCATT TCAGCCTCCC CGAGTGTACC AGGAAAGATG GATGTCCTGG AGAGGGGCC GCGTAACCAC
701 TGAAGGATGA GCTGTAAAGA AGCAGATCGT TCAAACATTT GGCAATAAAG TTTCTTAAGA TTGAATCCTG
771 TTGCCGGTCT TGCGATGATT ATCATATAAT TTCTGTTGAA TTACGTTAAG CATGTAATAA TTAACATGTA
841 ATGCATGACG TTATTATGA GATGGGTTTT TATGATTAGA GTCCCGCAAT TATACATTTA ATACGCGATA
                                                                                          ClaI
911 GAAAACAAAA TATAGCGCGC AAACTAGAT AAATTATCGC GCGCGGTGTC ATCTATGTTA CTAGATCGAT
                              XbaI
                              HindIII
```

FIG._38B

```
 981 AAGCTTCTAG AGCGGCCGGT GGAGCTCCAA TTCGCCCTAT AGTGAGTCGT ATTACGCGCG CTCACTGGCC
1051 GTCGTTTTAC AACGTCGTGA CTGGGAAAAC CCTGGCGTTA CCCAACTTAA TCGCCTTGCA GCACATCCCC
1121 CTTTCGCCAG CTGGCGTAAT AGCGAAGAGG CCCGCACCGA TCGCCCTTCC CAACAGTTGC GCAGCCTGAA
1191 TGGCGAATGG GACGCGCCCT GTAGCGGCGC ATTAAGCGCG GCGGGTGTGG TGGTTACGCG CAGCGTGACC
1261 GCTACACTTG CCAGCGCCCT AGCGCCCGCT CCTTTCGCTT TCTTCCCTTC CTTTCTCGCC ACGTTCGCCG
1331 GCTTTCCCCG TCAAGCTCTA AATCGGGGGC TCCCTTTAGG GTTCCGATTT AGTGCTTTAC GGCACCTCGA
1401 CCCCAAAAAA CTTGATTAGG GTGATGGTTC ACGTAGTGGG CCATCGCCCT GATAGACGGT TTTTCGCCCT
1471 TTGACGTTGG AGTCCACGTT CTTTAATAGT GGACTCTTGT TCCAAACTGG AACAACACTC AACCCTATCT
1541 CGGTCTATTC TTTTGATTTA TAAGGGATTT TGCCGATTTC GGCCTATTGG TTAAAAAATG AGCTGATTTA
1611 ACAAAAATTT AACGCGAATT TTAACAAAAT ATTAACGCTT ACAATTTAGG TGGCACTTTT CGGGGAAATG
1681 TGCGCGGAAC CCCTATTTGT TTATTTTTCT AAATACATTC AAATATGTAT CCGCTCATGA GACAATAACC
1751 CTGATAAATG CTTCAATAAT ATTGAAAAAG GAAGAGTATG AGTATTCAAC ATTTCCGTGT CGCCCTTATT
1821 CCCTTTTTTG CGGCATTTTG CCTTCCTGTT TTTGCTCACC CAGAAACGCT GGTGAAAGTA AAAGATGCTG
1891 AAGATCAGTT GGGTGCACGA GTGGGTTACA TCGAACTGGA TCTCAACAGC GGTAAGATCC TTGAGAGTTT
1961 TCGCCCCGAA GAACGTTTTC CAATGATGAG CACTTTTAAA GTTCTGCTAT GTGGCGCGGT ATTATCCCGT
2031 ATTGACGCCG GGCAAGAGCA ACTCGGTCGC CGCATACACT ATTCTCAGAA TGACTTGGTT GAGTACTCAC
2101 CAGTCACAGA AAAGCATCTT ACGGATGGCA TGACAGTAAG AGAATTATGC AGTGCTGCCA TAACCATGAG
2171 TGATAACACT GCGGCCAACT TACTTCTGAC AACGATCGGA GGACCGAAGG AGCTAACCGC TTTTTTGCAC
2241 AACATGGGGG ATCATGTAAC TCGCCTTGAT CGTTGGGAAC CGGAGCTGAA TGAAGCCATA CCAAACGACG
2311 AGCGTGACAC CACGATGCCT GTAGCAATGG CAACAACGTT GCGCAAACTA TTAACTGGCG AACTACTTAC
2381 TCTAGCTTCC CGGCAACAAT TAATAGACTG GATGGAGGCG GATAAAGTTG CAGGACCACT TCTGCGCTCG
2451 GCCCTTCCGG CTGGCTGGTT TATTGCTGAT AAATCTGGAG CCGGTGAGCG TGGGTCTCGC GGTATCATTG
2521 CAGCACTGGG GCCAGATGGT AAGCCCTCCC GTATCGTAGT TATCTACACG ACGGGGAGTC AGGCAACTAT
2591 GGATGAACGA AATAGACAGA TCGCTGAGAT AGGTGCCTCA CTGATTAAGC ATTGGTAACT GTCAGACCAA
2661 GTTTACTCAT ATATACTTTA GATTGATTTA AAACTTCATT TTTAATTTAA AAGGATCTAG GTGAAGATCC
2731 TTTTTGATAA TCTCATGACC AAAATCCCTT AACGTGAGTT TTCGTTCCAC TGAGCGTCAG ACCCCGTAGA
2801 AAAGATCAAA GGATCTTCTT GAGATCCTTT TTTTCTGCGC GTAATCTGCT GCTTGCAAAC AAAAAAACCA
2871 CCGCTACCAG CGGTGGTTTG TTTGCCGGAT CAAGAGCTAC CAACTCTTTT TCCGAAGGTA ACTGGCTTCA
2941 GCAGAGCGCA GATACCAAAT ACTGTCCTTC TAGTGTAGCC GTAGTTAGGC CACCACTTCA AGAACTCTGT
3011 AGCACCGCCT ACATACCTCG CTCTGCTAAT CCTGTTACCA GTGGCTGCTG CCAGTGGCGA TAAGTCGTGT
3081 CTTACCGGGT TGGACTCAAG ACGATAGTTA CCGGATAAGG CGCAGCGGTC GGGCTGAACG GGGGGTTCGT
3151 GCACACAGCC CAGCTTGGAG CGAACGACCT ACACCGAACT GAGATACCTA CAGCGTGAGC TATGAGAAAG
3221 CGCCACGCTT CCCGAAGGGA GAAAGGCGGA CAGGTATCCG GTAAGCGGCA GGGTCGGAAC AGGAGAGCGC
3291 ACGAGGGAGC TTCCAGGGGG AAACGCCTGG TATCTTTATA GTCCTGTCGG GTTTCGCCAC CTCTGACTTG
3361 AGCGTCGATT TTTGTGATGC TCGTCAGGGG GGCGGAGCCT ATGGAAAAAC GCCAGCAACG CGGCCTTTTT
```

*FIG._38C*

```
3431  ACGGTTCCTG  GCCTTTTGCT  GGCCTTTTGC  TCACATGTTC  TTTCCTGCGT  TATCCCCTGA  TTCTGTGGAT
3501  AACCGTATTA  CCGCCCTTTGA  GTGAGCTGAT  ACCGCTCGCC  GCAGCCGAAC  GACCGAGCGC  AGCGAGTCAG
3571  TGAGCGAGGA  AGCGGAAGAG  CGCCCAATAC  GCAAACCGCC  TCTCCCCGCG  CGTTGGCCGA  TTCATTAATG
3641  CAGCTGGCAC  GACAGGTTTC  CCGACTGGAA  AGCGGGCAGT  GAGCGCAACG  CAATTAATGT  GAGTTAGCTC
3711  ACTCATTAGG  CACCCCAGGC  TTTACACTTT  ATGCTTCCGG  CTCGTATGTT  GTGTGGAATT  GTGAGCGGAT
3781  AACAATTTCA  CACAGAAAAC  AGCTATGACC  ATGATTACGC  CAAGCGCGCA  ATTAACCCTC  ACTAAAGGGA
                                                      KpnI                   XhoI

3851  ACAAAAGCTG  GGTACCGGGC  CCCCCCCTCGA  GGTCATTCAT  ATGCTTGAGA  AGAGAGTCGG  GATAGTCCAA
3921  AATAAAACAA  AGGTAAGATT  ACCTGGTCAA  AAGTGAAAAC  ATCAGTTAAA  AGGTGGTATA  AGTAAAATAT
3991  CGGTAATAAA  AGGTGGCCCA  CCGGGCAGT   TACTATTATA  AGCCCAAACTGG  AAAATTGAGG  ATGTTTTGTC
4061  GGTACTTTGA  TACGTCATTT  TTGTATGAAT  TGGTTTTTAA  GTTTATTCGC  GATTTGGAAA  TGCATATCTG
4131  TATTTGAGTC  GGTTTTTAAG  TTCGTTGCTT  TTGTAAATAC  AGAGGGATTT  GTATAAGAAA  TATCTTTAAA
                                                                                EcoRI

4201  AAACCCATAT  GCTAATTTGA  CATAATTTTT  GAGAAAAATA  TATATTCAGG  CGAATTCCAC  AATGAACAAT
4271  AATAAGATTA  AAATAGCTTG  CCCCCGTTGC  AGCGGATGGT  ATTTTTCTA   GTAAAATAAA  AGATAAACTT
4341  AGACTCAAAA  CATTTACAAG  AACAACCCCT  AAAGTCCTAA  AGCCCAAAGT  GCTATGCACG  ATCCATAGCA
4411  AGCCCAGCCC  AACCCAACCC  ACCCCAACCC  AGCCAGTGC   AGCCAACTGG  CAAATAGTCT  CCACCCCCGG
4481  CACTATCACC  GTGAGTTGTC  CGCACCACCG  CACGTCTCGC  AGCCAAAAAA  AAAAAAAGAA  AGAAAAAAAA
4551  GAAAAAGAAA  AACAGCAGT   GGGTCCGGGT  CGTGGGGGCC  GGAAAAGCGA  GGAGGATCGC  GAGCAGCGAC
4621  GAGGCCCGGC  CCTCCCTCCG  CTTCCAAAGA  AACGCCCCCC  ATCGCCACTA  TATACATACC  CCCCCCTCTC
4691  CTCCCATCCC  CCCAACCCTA  CCACCACCAC  AACGCCCACC  TCCTCCCCCC  TCGCTGCCGG  ACGACGAGCT
4761  CCTCCCCCCT  CCCCCTCCGC  CGCCGCCCGT  CACCACCCCG  CCCCCTCTCCT  CTTTCTTTTCT  CCGTTTTTTT
4831  TTTCGTCTCG  GTCTCGATCT  TTGGCCTTGG  TAGTTTGGGT  GGGCGAGAGC  GGCTTCGTCG  CCCAGATCGG
                                                                 BamHI

4901  TGCGCGGGAG  GGGCGGGATC  TCGCGCTGG   CGTCTCCGGG  CGTGAGTCGG  CCCGGATCCT  CGCGGGGAAT
                                                     BglII

4971  GGGGCTCTCG  GATGTAGATC  TTCTTTTCTT  CTTCTTTTTG  TGGTAGAAT   TGAATCCCTC  AGCATTGTTC
                                                                                HindIII 5041  ATCGGTAGTT  TTTCTTTTCA  TGATTTGTGA  CAAATGCAGC  CTCGTGCGGA  GCTTTTTTGT  AGCAAGCTTA
```

FIG.\_38D

```
                                                                      PstI
                                                                  ~~~~~~~~
       M   K   Q   F   S   A   K   H   V   L   A   V   V   T   A   G   H   A   L   A   A   S   .
5111 ACATGAAGCA GTTCTCCGCC AAACACGTCC TCGCAGTTGT GGTGACTGCA GGGCACGCCT TAGCAGCCTC
      .  T   Q   G   I   S   E   D   L   Y   S   R   L   V   E   M   A   T   I   S   Q   A   A   Y
5181 TACGCAAGGC ATCTCCGAAG ACCTCTACAG CCGTTTAGTC GAAATGGCCA CTATCTCCCA AGCTGCCTAC
                                                              SalI
                                                           ~~~~~~
       A   D   L   C   N   I   P   S   T   I   I   K   G   E   K   I   Y   N   S   Q   T   D   I   N
5251 GCCGACCTGT GCAACATTCC GTCGACTATT ATCAAGGGAG AGAAAATTTA CAATTCTCAA ACTGACATTA
       B
       ~
      .  G   W
5321 ACGGATG
```

FIG._38E

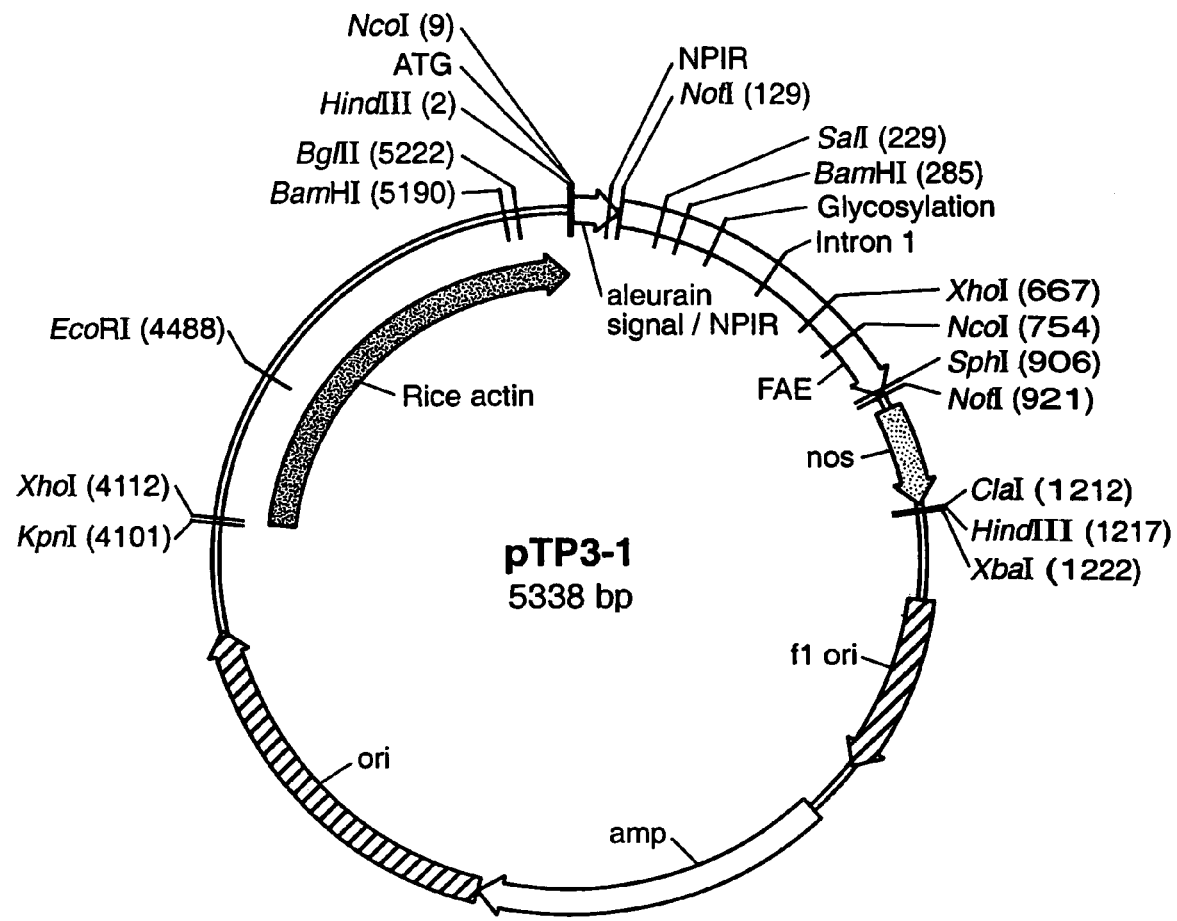
FIG._39A

```
     NcoI
     ~~~~
HindIII
~~~~~~~
                  M   A   H   A   R   V   L   L   L   A   L   A   V   L   A   T   A   A   V   A   V
  1  AAGCTTACCA TGGCCCACGC CCGGCGTCCTC CTCCTGGCGC TCGCCGTGCT GGCCACGGCC GCCGTCGCCG NotI
                                                          ~~~~
       A   S   S   S   F   A   D   S   N   P   I   R   P   V   T   D   R   A   A   A   S   T
 71  TCGCCTCCTC CTCCTCCTTC GCCGACTCCA ACCCGATCCG GCCCGTCACC GACCGGGCGG CCGCCTCCAC NPIR
                                   ~~~~
       Q   G   I   S   E   D   L   Y   S   R   L   V   E   M   A   T   I   S   Q   A   Y   A
141  GCAGGGCATC TCCGAAGACC TCTACAGCCG TTTAGTCGAA ATGGCCACTA TCTCCCAAGC TGCCTACGCC SalI
           ~~~~
       D   L   C   N   I   P   S   T   I   I   K   G   E   K   I   Y   N   S   Q   T   D   I   N   G
211  GACCTGTGCA ACATTCCGTC GACTATTATC AAGGGAGAGA AAATTTACAA TTCTCAAACT GACATTAACG BamHI
     ~~~~~
       W   I   L   R   D   D   S   S   K   E   I   I   T   V   F   R   G   T   G   S   D   T   N
281  GATGGATCCT CCGCGACGAC AGCAGCAAAG AAATAATCAC CGTCTTCCGT GGCACTGGTA GTGATACGAA Glycosylation
                 ~~~~~~~~~~~~~
       L   Q   L   D   T   N   Y   T   L   T   P   F   D   T   L   P   Q   C   N   G   C   E   V
351  TCTACAACTC GATACTAACT ACACCCTCAC GCCTTTCGAC ACCCTACCAC AATGCAAACG TTGTGAAGTA H   G   G   Y   I   G   W   V   S   V   Q   D   Q   V   E   S   L   V   K   Q   Q   V   S
421  CACGGTGGAT ATTATATTGG ATGGGTCTCC GTCCAGGACC AAGTCGAGTC GCTTGTCAAA CAGCAGGTTA Q   Y   P   D   Y   A   L   T   V   T   G   H   K   L   G   A   S   L   A   A   L   T   A
491  GCCAGTATCC GGACTACGCG CTGACCGTGA CCGGCCACKC CCTCGGCGCC TCCCTGGCGG CACTCACTGC A   Q   L   S   A   T   Y   D   N   I   R   L   Y   T   F   G   E   P   R   S   G   N   Q
561  CGCCCAGCTG TCTGCGACAT ACGACAACAT CCGCCTGTAC ACCTTCGGCG AACCGCGCAG CGGCAATCAG
```

FIG._39B

```
                    XhoI
       A  F  A  S  Y  M  N  D  A  F  Q  A  S  S  P  D  T  T  Q  Y  F  R  V  T
 631  GCCTTCGCGT CGTACATGAA CGATGCCTTC CAAGCCTCGA GCCCAGATAC GACGCAGTAT TTCCGGGTCA

NcoI
       H  A  N  D  G  I  P  N  L  P  P  V  E  Q  G  Y  A  H  G  G  V  E  Y  .
 701  CTCATGCCAA CGACGGCATC CCAAACCTGC CCCCGGTGGA GCAGGGGTAC GCCCATGGCG GTGTAGAGTA
     .  W  S  V  D  P  Y  S  A  Q  N  T  F  V  C  T  G  D  E  V  Q  C  C  E
 771  CTGGAGCGTT GATCCTTACA GCGCCCAGAA CACATTTGTC TGCACTGGGG ATGAAGTGCA GTGCTGTGAG

SphI
       A  Q  G  G  Q  G  V  N  N  A  H  T  T  Y  F  G  M  T  S  G     A  C  T  W
 841  GCCCAGGGCG GACAGGGGTGT GAATAATGCG CACACGACTT ATTTTGGGAT GACGAGCGGC GCATGCACCT

KDEL
             NotI                    T  T  E  G  *
      .  P  V  A  A  A  E
 911  GGCCGGTCGC GGCCGCGGAA ACCACTGAAG GATGAGCTGT TCTAGAGCGG AAAGAAGCAG ATCGTTCAAA CATTTGGCAA
 981  TAAAGTTTCT GCGCGCTCAC TGGCCGTCGT TGGCCTTGCC GGTCTTGCGA CGTGACTGGG AAAACCCTGG TTGAATTACG
1051  TTAAGCATGT AATAATTAAC ATGTAATGCA TGACGTTATT TATGAGATGG GTTTTTATGA TTAGAGTCCC
1121  GCAATTATAC ATTTAATACG CGATAGAAAA CGATAGCGCA CAAAATATAG CGCGCAAACT AGGATAAATT ATCGCGCGCG

HindIII
                          ClaI     XbaI
1191  GTGTCATCTA TGTTACTAGA TCGATAAGCT TCTAGAGCGG CCGGTGGAGC TCCAATTCGC CCTATAGTGA
1261  GTCGTATTAC GCGCGCTCAC TGGCCGTCGT TTACAACGT GCCAGTCGG GTGACTGGG AAAACCCTGG CGTTACCCAA
1331  CTTAATCGCC TTGCAGCACA TCCCCCTTTC GCCAGCTGGC GTAATAGCGA AGAGGCCCGC ACCGATCGCC
1401  CTTCCCAACA GTTGCGCAGC CTGAATGGCG AATGGGACGC GCCCTGTAGC GGCGCATTAA GCGCGGCGGG
```

FIG._39C

```
1471  TGTGGTGGTT  ACGGCGCAGCG  TGACCGCTAC  ACTTGCCAGC  GCCCTAGCGC  CCGCTCCTTT  CGCTTTCTTC
1541  CCTTCCTTTC  TCGCCACGTT  CGCCGGCTTT  CCCCGTCAAG  CTCTAAATCG  GGGGCTCCCT  TTAGGTTCC
1611  GATTTAGTGC  TTTACGGCAC  CTCGACCCCA  AAAAACTTGA  TTAGGTGAT   GGTTCACGTA  GTGGGCCATC
1681  GCCCTGATAG  ACGGTTTTTC  GCCCTTTGAC  GTTGGAGTCC  ACGTTCTTTA  ATAGTGGACT  CTTGTTCCAA
1751  ACTGAACAA   CACTCAACCC  TATCTCGGTC  TATTCTTTTG  ATTTATAAGG  GATTTTGCCG  ATTTCGGCCT
1821  ATTGGTTAAA  AAATGAGCTG  ATTTAACAAA  AATTAACGC   GAATTTTAAC  AAAATATTAA  CGCTTACAAT
1891  TTAGGTGGCA  CTTTTCGGGG  AAATGTGCGC  GGAACCCCTA  TTTGTTTATT  TTTCTAAATA  CATTCAAATA
1961  TGTATCCGCT  CATGAGACAA  TAACCCTGAT  AAATGCTTCA  ATAATATTGA  AAAAGGAAGA  GTATGAGTAT
2031  TCAACATTTC  CGTGTCGCCC  TTATTCCCTT  TTTTGCGGCA  TTTTGCCTTC  CTGTTTTTGC  TCACCCAGAA
2101  ACGCTGGTGA  AAGTAAAAGA  TGCTGAAGAT  CAGTTGGGTG  CACGAGTGGG  TTACATCGAA  CTGGATCTCA
2171  ACAGCGGTAA  GATCCTTGAG  AGTTTTCGCC  CCGAAGAACG  TTTTCCAATG  ATGAGCACTT  TTAAAGTTCT
2241  GCTATGTGGC  GCGGTATTAT  CCCGTATTGA  CGCCGGGCAA  GAGCAACTCG  GTCGCCGCAT  ACACTATTCT
2311  CAGAATGACT  TGGTTGAGTA  CTCACCAGTC  ACAGAAAAGC  ATCTTACGGA  TGGCATGACA  GTAAGAGAAT
2381  TATGCAGTGC  TGCCATAACC  ATGAGTGATA  ACACTGCGGC  CAACTTACTT  CTGACAACGA  TCGGAGGACC
2451  GAAGGAGCTA  ACCGCTTTTT  TGCACAACAT  GGGGGATCAT  GTAACTCGCC  TTGATCGTTG  GGAACCGGAG
2521  CTGAATGAAG  CCATACCAAA  CGACGAGCGT  GACACCACGA  TGCCTGTAGC  AATGGCAACA  ACGTTGCGCA
2591  AACTATTAAC  TGGCGAACTA  CTTACTCTAG  CTTCCCGGCA  ACAATTAATA  GACTGGATGG  AGGCGGATAA
2661  AGTTGCAGGA  CCACTTCTGC  GCTCGGCCCT  TCCGGCTGGC  TGGTTTATTG  CTGATAAATC  TGGAGCCGGT
2731  GAGCGTGGGT  CTCGCGGTAT  CATTGCAGCA  CTGGGGCCAG  ATGGTAAGCC  CTCCCGTATC  GTAGTTATCT
2801  ACACGACGGG  GAGTCAGGCA  ACTATGGATG  AACGAAATAG  ACAGATCGCT  GAGATAGTG   CCTCACTGAT
2871  TAAGCATTGG  TAACTGTCAG  ACCAAGTTTA  CTCATATATA  CTTTAGATTG  ATTTAAAACT  TCATTTTTAA
2941  TTTAAAAGGA  TCTAGGTGAA  GATCCTTTTT  GATAAATCTCA  TGACCAAAAT  CCCTTAACGT  GAGTTTTCGT
3011  TCCACTGAGC  GTCAGACCCC  GTAGAAAAGA  TCAAAGCGGT  GTTCTTGAGAT TTCTTTTTTC TGCGCGTAAT
3081  CTGCTGCTTG  CAAACAAAAA  AACCACCGCT  ACCAGCGGTG  GTTTGTTTGC  CGGATCAAGA  GCTACCAACT
3151  CTTTTTCCGA  AGGTAACTGG  CTTCAGCAGA  GCGCAGATAC  CAAATACTGT  CCTTCTAGTG  TAGCCGTAGT
3221  TAGGCCACCA  CTTCAAGAAC  TCTGTAGCAC  CGCCTACATA  GCGTCGCTCTG CTAATCCTGT  TACCAGTGGC
3291  TGCTGCCAGT  GGCGATAAGT  CGTGTCTTAC  CGGGTTGGAC  TCAAGACGAT  AGTTACCGGA  TAAGGCGCAG
3361  CGGTCGGGCT  GAACGGGGGG  TTCGTGCACA  CAGCCCAGCT  TGGAGCGAAC  GACCTACACC  GAACTGAGAT
3431  ACCTACAGCG  TGAGCTATGA  GAAAGCGCCA  CGCTTCCCGA  AGGGAGAAAG  GCGGACAGGT  ATCCGGTAAG
3501  CGGCAGGGTC  GGAACAGGAG  AGCGCACGAG  GGAGCTTCCA  GGGGGAAACG  CCTGGTATCT  TTATAGTCCT
3571  GTCGGGTTTC  GCCACCTCTG  ACTTGAGCGT  CGATTTTTGT  GATGCTCGTC  AGGGGGGCGG  AGCCTATGGA
3641  AAAACGCCAG  CAACGCGGCC  TTTTTACGGT  TCCTGGCCTT  TTGCTGGCCT  TTTGCTCACA  TGTTCTTTCC
3711  TGCGTTATCC  CCTGATTCTG  TGGATAACCG  TATTACCGCC  TTTGAGTGAG  CTGATACCGC  TCGCCGCAGC
3781  CGAACGACCG  AGCGCAGCGA  GTCAGTGAGC  GAGGAAGCGG  AAGAGCGCCC  AATACGCAAA  CCGCCTCTCC
3851  CCGCGCGTTG  GCCGATTCAT  TAATGCAGCT  GGCACGACAG  GTTTCCCGAC  TGGAAAGCGG  GCAGTGAGCG
```

*FIG._39D*

```
3921 CAACGCAATT AATGTGAGTT AGCTCACTCA TTAGGCACCC CAGGCTTTAC ACTTTATGCT TCCGGCTCGT
3991 ATGTTGTGTG GAATTGTGAG CGGATAACAA TTTCACACAG GAAACAGCTA TGACCATGAT TACGCCAAGC
                                                                    XhoI
                                                                   ~~~~~~

4061 GCGCAATTAA CCCTCACTAA AGGGAACAAA AGCTGGGTAC CGGGCCCCCC CTCGAGGTCA TTCATATGCT
4131 TGAGAAGAGA GTCGGATAG  TCCAAAATAA AACAAAGGTA AGATTACCTG GTCAAAAGTG AAAACATCAG
4201 TTAAAAGGTG GTATAAGTAA AATATCGGTA ATAAAAGGTG GCCCAAAGTG AAATTACTC  TTTTCTACTA
4271 TTATAAAAT  TGAGGATGTT TTGATACGT  TTTGATACGT CATTTTTGTA TGAATTGGTT TTTAAGTTTA
4341 TTCGCGATTT GGAAATGCAT ATCTGTATTT TAAGTCGTT  TGCTTTTGTA AATACAGAGG
4411 GATTTGTATA AGAATATCT  TTAAAAAACC CATATGCTAA TTTTGACATA TTTTTGAGAA AAATATATAT
                     EcoRI
                    ~~~~~~

4481 TCAGGCGAAT TCCACAATGA ACAATAATAA GATTAAAATA GCTTGCCCCC GTTGCAGCGA TGGGTATTTT
4551 TTCTAGTAAA ATAAAAGATA AACTTAGACT CAAAAACATT CAAAAACATT ACAAAAACAA CCCTAAAGT  CCTAAAGCCC
4621 AAAGTGCTAT GCACGATCCA TAGCAAGCCC AGCCCAACCC AACCCAACCC AGTGCAGCCA
4691 ACTGGCAAAT AGTCTCCACC CCCGGCACTA TCACCGTGAG TTGTCCGCAC CACCGCACGT CTCGCAGCCA
4761 AAAAAAAAAA AAGAAGAAAA AAAAAGAAAA AGAAAAACAG CAGGTGGGTC CGGGTCGTGG GGGCCGGAAA
4831 AGCGAGGAGG ATCGCAGCA  GCGACGAGGC CTCCGCTTCC AAAGAAACGC CCCCCATCGC
4901 CACTATATAC ATACCCCCCC CTCTCCTCCC ATCCCCCCC  ACCACCACCA CCACCTCCTC
4971 CCCCCTCGCT GCCGACGAC  GAGCTCCTCC CCGTACCACC CCGGTAACCA CCCCGCCCCT
5041 CTCTCTTTC  TTTCTCCGTT TTTTTTTCG  TCTCGGTCTC CTTGGTAGTT TGGGTGGGCG
5111 AGAGCGGCTT CGTCGCCCAG ATCGGTGCGC GGATCTCGCG GCTGGCGTCT CCGGGCGTGA
                                         BglII
                                        ~~~~~~

5181 GTCGGCCCGG ATCCTCGCGG GGAATGGGGC TCTCGGATGT AGATCTTCTT TCTTTCTTCT TTTTGTGGTA
5251 GAATTGAAT  CCCTCAGCAT TGTTCATCGG TAGTTTTTCT TTTCATGATT TGTGACAAAT GCAGCCTCGT
5321 GCGGAGCTTT TTTGTAGC
        BamHI
       ~~~~~~
```

FIG._39E

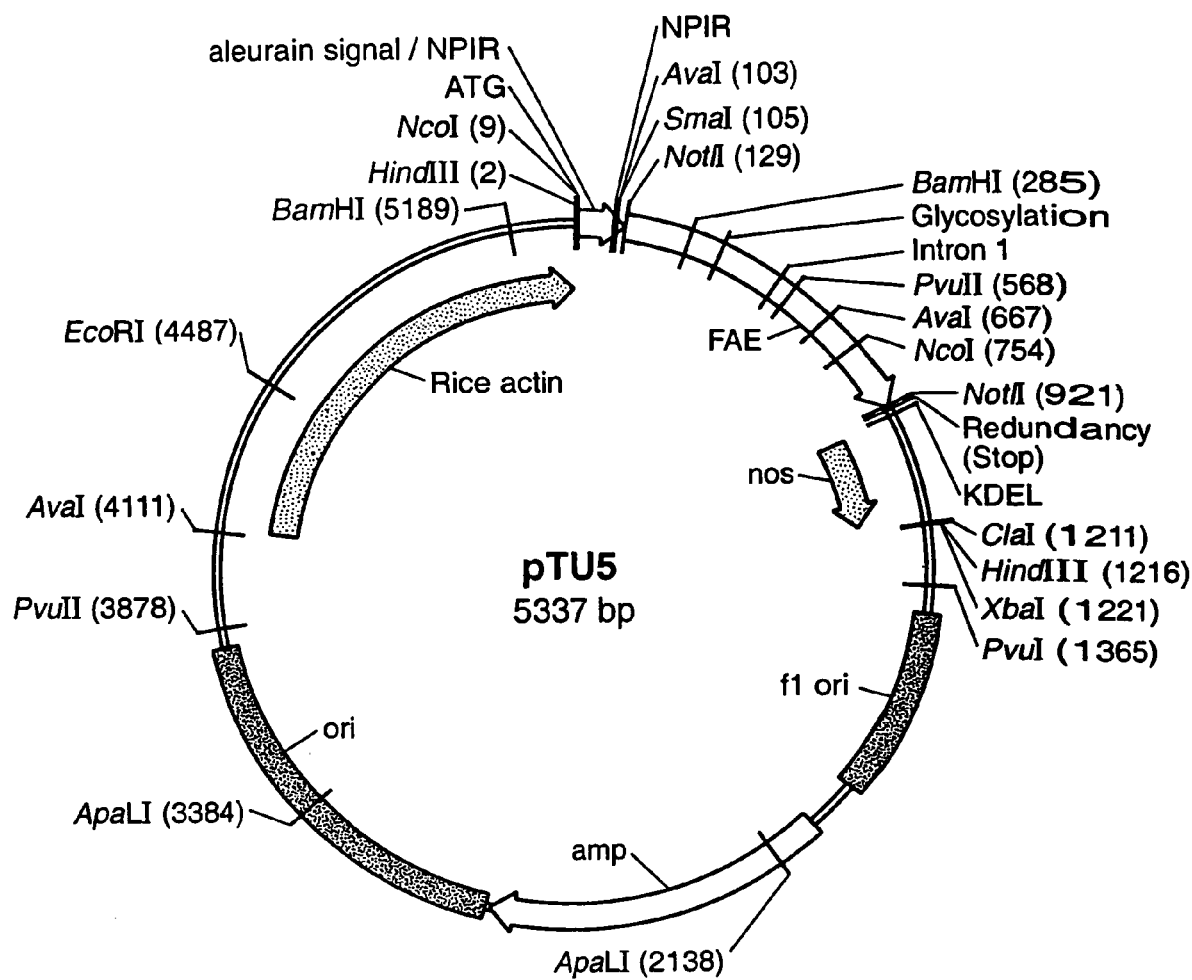
FIG._40A

```
     HindIII NcoI
     ~~~~~~ ~~~~~~~
  1  AAGCTTACCA TGGCCCACGC CCGCGTCCTC CTCCTGGCGC TCGCCGTGCT
     TTCGAATGGT ACCGGGTGCG GGCGCAGGAG GAGGACCGCG AGCGGCACGA 51  GGCCACGGCC GCCGTCGCCG TCGCCTCCTC CTCCTCCTTC GCCGACTCCA
     CCGGTGCCGG CGGCAGCGGC AGCGGAGGAG GAGGAGGAAG CGGCTGAGGT SmaI
        ~~~~~~
        AvaI                                NotI
        ~~~~~~                              ~~~~~~~~~~
101  ACCCGGGCCG GCCCGTCACC GACCGCGCGG CCGCCTCCAC GCAGGGCATC
     TGGGCCCGGC CGGGCAGTGG CTGGCGCGCC GGCGGAGGTG CGTCCCGTAG 151  TCCGAAGACC TCTACAGCCG TTTAGTCGAA ATGGCCACTA TCTCCCAAGC
     AGGCTTCTGG AGATGTCGGC AAATCAGCTT TACCGGTGAT AGAGGGTTCG 201  TGCCTACGCC GACCTGTGCA ACATTCCGTC GACTATTATC AAGGGAGAGA
     ACGGATGCGG CTGGACACGT TGTAAGGCAG CTGATAATAG TTCCCTCTCT BamHI
                                                 ~~~~~~
251  AAATTTACAA TTCTCAAACT GACATTAACG GATGGATCCT CCGCGACGAC
     TTTAAATGTT AAGAGTTTGA CTGTAATTGC CTACCTAGGA GGCGCTGCTG 301  AGCAGCAAAG AAATAATCAC CGTCTTCCGT GGCACTGGTA GTGATACGAA
     TCGTCGTTTC TTTATTAGTG GCAGAAGGCA CCGTGACCAT CACTATGCTT 351  TCTACAACTC GATACTAACT ACACCCTCAC GCCTTTCGAC ACCCTACCAC
     AGATGTTGAG CTATGATTGA TGTGGGAGTG CGGAAAGCTG TGGGATGGTG 401  AATGCAACGG TTGTGAAGTA CACGGTGGAT ATTATATTGG ATGGGTCTCC
     TTACGTTGCC AACACTTCAT GTGCCACCTA TAATATAACC TACCCAGAGG 451  GTCCAGGACC AAGTCGAGTC GCTTGTCAAA CAGCAGGTTA GCCAGTATCC
     CAGGTCCTGG TTCAGCTCAG CGAACAGTTT GTCGTCCAAT CGGTCATAGG 501  GGACTACGCG CTGACCGTGA CCGGCCACKC CCTCGGCGCC TCCCTGGCGG
     CCTGATGCGC GACTGGCACT GGCCGGTGMG GGAGCCGCGG AGGGACCGCC PvuII
             ~~~~~~
551  CACTCACTGC CGCCCAGCTG TCTGCGACAT ACGACAACAT CCGCCTGTAC
     GTGAGTGACG GCGGGTCGAC AGACGCTGTA TGCTGTTGTA GGCGGACATG 601  ACCTTCGGCG AACCGCGCAG CGGCAATCAG GCCTTCGCGT CGTACATGAA
     TGGAAGCCGC TTGGCGCGTC GCCGTTAGTC CGGAAGCGCA GCATGTACTT AvaI
             ~~~~~~
651  CGATGCCTTC CAAGCCTCGA GCCCAGATAC GACGCAGTAT TTCCGGGTCA
     GCTACGGAAG GTTCGGAGCT CGGGTCTATG CTGCGTCATA AAGGCCCAGT
```

FIG. _40B

```
701  CTCATGCCAA CGACGGCATC CCAAACCTGC CCCCGGTGGA GCAGGGGTAC
     GAGTACGGTT GCTGCCGTAG GGTTTGGACG GGGGCCACCT CGTCCCCATG

NcoI
          ~~~~~~
751  GCCCATGGCG GTGTAGAGTA CTGGAGCGTT GATCCTTACA GCGCCCAGAA
     CGGGTACCGC CACATCTCAT GACCTCGCAA CTAGGAATGT CGCGGGTCTT

801  CACATTTGTC TGCACTGGGG ATGAAGTGCA GTGCTGTGAG GCCCAGGGCG
     GTGTAAACAG ACGTGACCCC TACTTCACGT CACGACACTC CGGGTCCCGC

851  GACAGGGTGT GAATAATGCG CACGACTT ATTTTGGGAT GACGAGCGGC
     CTGTCCCACA CTTATTACGC GTGCTGAA TAAAACCCTA CTGCTCGCCG

NotI
          ~~~~~~~~~~
901  GCATGCACCT GGCCGGTCGC GGCCGCGGAA CCACTGAAGG ATGAGCTGTA
     CGTACGTGGA CCGGCCAGCG CCGGCGCCTT GGTGACTTCC TACTCGACAT

951  AAGAAGCAGA TCGTTCAAAC ATTTGGCAAT AAAGTTTCTT AAGATTGAAT
     TTCTTCGTCT AGCAAGTTTG TAAACCGTTA TTTCAAAGAA TTCTAACTTA

1001 CCTGTTGCCG GTCTTGCGAT GATTATCATA TAATTTCTGT TGAATTACGT
     GGACAACGGC CAGAACGCTA CTAATAGTAT ATTAAAGACA ACTTAATGCA

1051 TAAGCATGTA ATAATTAACA TGTAATGCAT GACGTTATTT ATGAGATGGG
     ATTCGTACAT TATTAATTGT ACATTACGTA CTGCAATAAA TACTCTACCC

1101 TTTTTATGAT TAGAGTCCCG CAATTATACA TTTAATACGC GATAGAAAAC
     AAAAATACTA ATCTCAGGGC GTTAATATGT AAATTATGCG CTATCTTTTG

1151 AAAATATAGC GCGCAAACTA GGATAAATTA TCGCGCGCGG TGTCATCTAT
     TTTTATATCG CGCGTTTGAT CCTATTTAAT AGCGCGCGCC ACAGTAGATA

XbaI
                 ~~~~~~~
          ClaI   HindIII
          ~~~~~~~~~~~~~~
1201 GTTACTAGAT CGATAAGCTT CTAGAGCGGC CGGTGGAGCT CCAATTCGCC
     CAATGATCTA GCTATTCGAA GATCTCGCCG GCCACCTCGA GGTTAAGCGG 1251 CTATAGTGAG TCGTATTACG CGCGCTCACT GGCCGTCGTT TTACAACGTC
     GATATCACTC AGCATAATGC GCGCGAGTGA CCGGCAGCAA AATGTTGCAG 1301 GTGACTGGGA AAACCCTGGC GTTACCCAAC TTAATCGCCT TGCAGCACAT
     CACTGACCCT TTTGGGACCG CAATGGGTTG AATTAGCGGA ACGTCGTGTA PvuII
                                    ~~~~~~
1351 CCCCCTTTCG CCAGCTGGCG TAATAGCGAA GAGGCCCGCA CCGATCGCCC
     GGGGGAAAGC GGTCGACCGC ATTATCGCTT CTCCGGGCGT GGCTAGCGGG 1401 TTCCCAACAG TTGCGCAGCC TGAATGGCGA ATGGGACGCG CCCTGTAGCG
     AAGGGTTGTC AACGCGTCGG ACTTACCGCT TACCCTGCGC GGGACATCGC
```

FIG._40C

```
1451  GCGCATTAAG CGCGGCGGGT GTGGTGGTTA CGCGCAGCGT GACCGCTACA
      CGCGTAATTC GCGCCGCCCA CACCACCAAT GCGCGTCGCA CTGGCGATGT

1501  CTTGCCAGCG CCCTAGCGCC CGCTCCTTTC GCTTCTTCC  CTTCCTTTCT
      GAACGGTCGC GGGATCGCGG GCGAGGAAAG CGAAAGAAGG GAAGGAAAGA

1551  CGCCACGTTC GCCGGCTTTC CCCGTCAAGC TCTAAATCGG GGGCTCCCTT
      GCGGTGCAAG CGGCCGAAAG GGGCAGTTCG AGATTTAGCC CCCGAGGGAA

1601  TAGGGTTCCG ATTTAGTGCT TTACGGCACC TCGACCCCAA AAAACTTGAT
      ATCCCAAGGC TAAATCACGA AATGCCGTGG AGCTGGGGTT TTTTGAACTA

1651  TAGGGTGATG GTTCACGTAG TGGGCCATCG CCCTGATAGA CGGTTTTTCG
      ATCCCACTAC CAAGTGCATC ACCCGGTAGC GGGACTATCT GCCAAAAAGC

1701  CCCTTTGACG TTGGAGTCCA CGTTCTTTAA TAGTGGACTC TTGTTCCAAA
      GGGAAACTGC AACCTCAGGT GCAAGAAATT ATCACCTGAG AACAAGGTTT

1751  CTGGAACAAC ACTCAACCCT ATCTCGGTCT ATTCTTTTGA TTTATAAGGG
      GACCTTGTTG TGAGTTGGGA TAGAGCCAGA TAAGAAAACT AAATATTCCC

1801  ATTTTGCCGA TTTCGGCCTA TTGGTTAAAA AATGAGCTGA TTTAACAAAA
      TAAAACGGCT AAAGCCGGAT AACCAATTTT TTACTCGACT AAATTGTTTT

1851  ATTTAACGCG AATTTTAACA AAATATTAAC GCTTACAATT TAGGTGGCAC
      TAAATTGCGC TTAAAATTGT TTTATAATTG CGAATGTTAA ATCCACCGTG

1901  TTTTCGGGGA AATGTGCGCG GAACCCCTAT TTGTTTATTT TTCTAAATAC
      AAAAGCCCCT TTACACGCGC CTTGGGGATA AACAAATAAA AAGATTTATG

1951  ATTCAAATAT GTATCCGCTC ATGAGACAAT AACCCTGATA AATGCTTCAA
      TAAGTTTATA CATAGGCGAG TACTCTGTTA TTGGGACTAT TTACGAAGTT

2001  TAATATTGAA AAAGGAAGAG TATGAGTATT CAACATTTCC GTGTCGCCCT
      ATTATAACTT TTTCCTTCTC ATACTCATAA GTTGTAAAGG CACAGCGGGA

2051  TATTCCCTTT TTTGCGGCAT TTTGCCTTCC TGTTTTTGCT CACCCAGAAA
      ATAAGGGAAA AAACGCCGTA AAACGGAAGG ACAAAAACGA GTGGGTCTTT

ApaLI
                                                    ‑‑‑‑‑‑‑‑
2101  CGCTGGTGAA AGTAAAAGAT GCTGAAGATC AGTTGGGTGC ACGAGTGGGT
      GCGACCACTT TCATTTTCTA CGACTTCTAG TCAACCCACG TGCTCACCCA

2151  TACATCGAAC TGGATCTCAA CAGCGGTAAG ATCCTTGAGA GTTTTCGCCC
      ATGTAGCTTG ACCTAGAGTT GTCGCCATTC TAGGAACTCT CAAAAGCGGG

2201  CGAAGAACGT TTTCCAATGA TGAGCACTTT TAAAGTTCTG CTATGTGGCG
      GCTTCTTGCA AAAGGTTACT ACTCGTGAAA ATTTCAAGAC GATACACCGC

2251  CGGTATTATC CCGTATTGAC GCCGGGCAAG AGCAACTCGG TCGCCGCATA
      GCCATAATAG GGCATAACTG CGGCCCGTTC TCGTTGAGCC AGCGGCGTAT

2301  CACTATTCTC AGAATGACTT GGTTGAGTAC TCACCAGTCA CAGAAAAGCA
      GTGATAAGAG TCTTACTGAA CCAACTCATG AGTGGTCAGT GTCTTTTCGT
```

FIG._40D

```
2351  TCTTACGGAT GGCATGACAG TAAGAGAATT ATGCAGTGCT GCCATAACCA
      AGAATGCCTA CCGTACTGTC ATTCTCTTAA TACGTCACGA CGGTATTGGT

2401  TGAGTGATAA CACTGCGGCC AACTTACTTC TGACAACGAT CGGAGGACCG
      ACTCACTATT GTGACGCCGG TTGAATGAAG ACTGTTGCTA GCCTCCTGGC

2451  AAGGAGCTAA CCGCTTTTTT GCACAACATG GGGGATCATG TAACTCGCCT
      TTCCTCGATT GGCGAAAAAA CGTGTTGTAC CCCCTAGTAC ATTGAGCGGA

2501  TGATCGTTGG GAACCGGAGC TGAATGAAGC CATACCAAAC GACGAGCGTG
      ACTAGCAACC CTTGGCCTCG ACTTACTTCG GTATGGTTTG CTGCTCGCAC

2551  ACACCACGAT GCCTGTAGCA ATGGCAACAA CGTTGCGCAA ACTATTAACT
      TGTGGTGCTA CGGACATCGT TACCGTTGTT GCAACGCGTT TGATAATTGA

2601  GGCGAACTAC TTACTCTAGC TTCCCGGCAA CAATTAATAG ACTGGATGGA
      CCGCTTGATG AATGAGATCG AAGGGCCGTT GTTAATTATC TGACCTACCT

2651  GGCGGATAAA GTTGCAGGAC CACTTCTGCG CTCGGCCCTT CCGGCTGGCT
      CCGCCTATTT CAACGTCCTG GTGAAGACGC GAGCCGGGAA GGCGACCGA

2701  GGTTTATTGC TGATAAATCT GGAGCCGGTG AGCGTGGGTC TCGCGGTATC
      CCAAATAACG ACTATTTAGA CCTCGGCCAC TCGCACCCAG AGCGCCATAG

2751  ATTGCAGCAC TGGGGCCAGA TGGTAAGCCC TCCCGTATCG TAGTTATCTA
      TAACGTCGTG ACCCCGGTCT ACCATTCGGG AGGGCATAGC ATCAATAGAT

2801  CACGACGGGG AGTCAGGCAA CTATGGATGA ACGAAATAGA CAGATCGCTG
      GTGCTGCCCC TCAGTCCGTT GATACCTACT TGCTTTATCT GTCTAGCGAC

2851  AGATAGGTGC CTCACTGATT AAGCATTGGT AACTGTCAGA CCAAGTTTAC
      TCTATCCACG GAGTGACTAA TTCGTAACCA TTGACAGTCT GGTTCAAATG

2901  TCATATATAC TTTAGATTGA TTTAAAACTT CATTTTTAAT TTAAAAGGAT
      AGTATATATG AAATCTAACT AAATTTTGAA GTAAAAATTA AATTTTCCTA

2951  CTAGGTGAAG ATCCTTTTTG ATAATCTCAT GACCAAAATC CCTTAACGTG
      GATCCACTTC TAGGAAAAAC TATTAGAGTA CTGGTTTTAG GGAATTGCAC

3001  AGTTTTCGTT CCACTGAGCG TCAGACCCCG TAGAAAAGAT CAAAGGATCT
      TCAAAAGCAA GGTGACTCGC AGTCTGGGGC ATCTTTTCTA GTTTCCTAGA

3051  TCTTGAGATC CTTTTTTTCT GCGCGTAATC TGCTGCTTGC AAACAAAAAA
      AGAACTCTAG GAAAAAAAGA CGCGCATTAG ACGACGAACG TTTGTTTTTT

3101  ACCACCGCTA CCAGCGGTGG TTTGTTTGCC GGATCAAGAG CTACCAACTC
      TGGTGGCGAT GGTCGCCACC AAACAAACGG CCTAGTTCTC GATGGTTGAG

3151  TTTTTCCGAA GGTAACTGGC TTCAGCAGAG CGCAGATACC AAATACTGTC
      AAAAAGGCTT CCATTGACCG AAGTCGTCTC GCGTCTATGG TTTATGACAG

3201  CTTCTAGTGT AGCCGTAGTT AGGCCACCAC TTCAAGAACT CTGTAGCACC
      GAAGATCACA TCGGCATCAA TCCGGTGGTG AAGTTCTTGA GACATCGTGG

3251  GCCTACATAC CTCGCTCTGC TAATCCTGTT ACCAGTGGCT GCTGCCAGTG
      CGGATGTATG GAGCGAGACG ATTAGGACAA TGGTCACCGA CGACGGTCAC
```

FIG._40E

```
3301  GCGATAAGTC GTGTCTTACC GGGTTGGACT CAAGACGATA GTTACCGGAT
      CGCTATTCAG CACAGAATGG CCCAACCTGA GTTCTGCTAT CAATGGCCTA

ApaLI
                                    ~~~~~~
3351  AAGGCGCAGC GGTCGGGCTG AACGGGGGGT TCGTGCACAC AGCCCAGCTT
      TTCCGCGTCG CCAGCCCGAC TTGCCCCCCA AGCACGTGTG TCGGGTCGAA

3401  GGAGCGAACG ACCTACACCG AACTGAGATA CCTACAGCGT GAGCTATGAG
      CCTCGCTTGC TGGATGTGGC TTGACTCTAT GGATGTCGCA CTCGATACTC

3451  AAAGCGCCAC GCTTCCCGAA GGGAGAAAGG CGGACAGGTA TCCGGTAAGC
      TTTCGCGGTG CGAAGGGCTT CCCTCTTTCC GCCTGTCCAT AGGCCATTCG

3501  GGCAGGGTCG GAACAGGAGA GCGCACGAGG GAGCTTCCAG GGGGAAACGC
      CCGTCCCAGC CTTGTCCTCT CGCGTGCTCC CTCGAAGGTC CCCCTTTGCG

3551  CTGGTATCTT TATAGTCCTG TCGGGTTTCG CCACCTCTGA CTTGAGCGTC
      GACCATAGAA ATATCAGGAC AGCCCAAAGC GGTGGAGACT GAACTCGCAG

3601  GATTTTTGTG ATGCTCGTCA GGGGGGCGGA GCCTATGGAA AAACGCCAGC
      CTAAAAACAC TACGAGCAGT CCCCCCGCCT CGGATACCTT TTTGCGGTCG

3651  AACGCGGCCT TTTTACGGTT CCTGGCCTTT TGCTGGCCTT TTGCTCACAT
      TTGCGCCGGA AAAATGCCAA GGACCGGAAA ACGACCGGAA AACGAGTGTA

3701  GTTCTTTCCT GCGTTATCCC CTGATTCTGT GGATAACCGT ATTACCGCCT
      CAAGAAAGGA CGCAATAGGG GACTAAGACA CCTATTGGCA TAATGGCGGA

3751  TTGAGTGAGC TGATACCGCT CGCCGCAGCC GAACGACCGA GCGCAGCGAG
      AACTCACTCG ACTATGGCGA GCGGCGTCGG CTTGCTGGCT CGCGTCGCTC

3801  TCAGTGAGCG AGGAAGCGGA AGAGCGCCCA ATACGCAAAC CGCCTCTCCC
      AGTCACTCGC TCCTTCGCCT TCTCGCGGGT TATGCGTTTG GCGGAGAGGG

PvuII
                                    ~~~~~~
3851  CGCGCGTTGG CCGATTCATT AATGCAGCTG GCACGACAGG TTTCCCGACT
      GCGCGCAACC GGCTAAGTAA TTACGTCGAC CGTGCTGTCC AAAGGGCTGA

3901  GGAAAGCGGG CAGTGAGCGC AACGCAATTA ATGTGAGTTA GCTCACTCAT
      CCTTTCGCCC GTCACTCGCG TTGCGTTAAT TACACTCAAT CGAGTGAGTA

3951  TAGGCACCCC AGGCTTTACA CTTTATGCTT CCGGCTCGTA TGTTGTGTGG
      ATCCGTGGGG TCCGAAATGT GAAATACGAA GGCCGAGCAT ACAACACACC

4001  AATTGTGAGC GGATAACAAT TTCACACAGG AAACAGCTAT GACCATGATT
      TTAACACTCG CCTATTGTTA AAGTGTGTCC TTTGTCGATA CTGGTACTAA

4051  ACGCCAAGCG CGCAATTAAC CCTCACTAAA GGGAACAAAA GCTGGGTACC
      TGCGGTTCGC GCGTTAATTG GGAGTGATTT CCCTTGTTTT CGACCCATGG

AvaI
                                    ~~~~~~~
4101  GGGCCCCCCC TCGAGGTCAT TCATATGCTT GAGAAGAGAG TCGGGATAGT
      CCCGGGGGGG AGCTCCAGTA AGTATACGAA CTCTTCTCTC AGCCCTATCA
```

FIG._40F

```
4151  CCAAAATAAA ACAAAGGTAA GATTACCTGG TCAAAAGTGA AAACATCAGT
      GGTTTTATTT TGTTTCCATT CTAATGGACC AGTTTTCACT TTTGTAGTCA

4201  TAAAAGGTGG TATAAGTAAA ATATCGGTAA TAAAAGGTGG CCCAAAGTGA
      ATTTTCCACC ATATTCATTT TATAGCCATT ATTTTCCACC GGGTTTCACT

4251  AATTTACTCT TTTCTACTAT TATAAAAATT GAGGATGTTT TGTCGGTACT
      TTAAATGAGA AAAGATGATA ATATTTTAA CTCCTACAAA ACAGCCATGA

4301  TTGATACGTC ATTTTTGTAT GAATTGGTTT TTAAGTTTAT TCGCGATTTG
      AACTATGCAG TAAAAACATA CTTAACCAAA AATTCAAATA AGCGCTAAAC

4351  GAAATGCATA TCTGTATTTG AGTCGGTTTT TAAGTTCGTT GCTTTTGTAA
      CTTTACGTAT AGACATAAAC TCAGCCAAAA ATTCAAGCAA CGAAAACATT

4401  ATACAGAGGG ATTTGTATAA GAAATATCTT TAAAAAACCC ATATGCTAAT
      TATGTCTCCC TAAACATATT CTTTATAGAA ATTTTTGGG TATACGATTA

EcoRI
                                           ‑ ‑ ‑ ‑ ‑ ‑ ‑
4451  TTGACATAAT TTTTGAGAAA AATATATATT CAGGCGAATT CCACAATGAA
      AACTGTATTA AAAACTCTTT TTATATATAA GTCCGCTTAA GGTGTTACTT

4501  CAATAATAAG ATTAAAATAG CTTGCCCCCG TTGCAGCGAT GGGTATTTTT
      GTTATTATTC TAATTTTATC GAACGGGGGC AACGTCGCTA CCCATAAAAA

4551  TCTAGTAAAA TAAAAGATAA ACTTAGACTC AAAACATTTA CAAAAACAAC
      AGATCATTTT ATTTTCTATT TGAATCTGAG TTTTGTAAAT GTTTTTGTTG

4601  CCCTAAAGTC CTAAAGCCCA AAGTGCTATG CACGATCCAT AGCAAGCCCA
      GGGATTTCAG GATTTCGGGT TTCACGATAC GTGCTAGGTA TCGTTCGGGT

4651  GCCCAACCCA ACCCAACCCA ACCCACCCCA GTGCAGCCAA CTGGCAAATA
      CGGGTTGGGT TGGGTTGGGT TGGGTGGGGT CACGTCGGTT GACCGTTTAT

4701  GTCTCCACCC CCGGCACTAT CACCGTGAGT TGTCCGCACC ACCGCACGTC
      CAGAGGTGGG GGCCGTGATA GTGGCACTCA ACAGGCGTGG TGGCGTGCAG

4751  TCGCAGCCAA AAAAAAAAAA AGAAAGAAAA AAAAGAAAAA GAAAAACAGC
      AGCGTCGGTT TTTTTTTTTT TCTTTCTTTT TTTTCTTTTT CTTTTTGTCG

4801  AGGTGGGTCC GGGTCGTGGG GGCCGGAAAA GCGAGGAGGA TCGCGAGCAG
      TCCACCCAGG CCCAGCACCC CCGGCCTTTT CGCTCCTCCT AGCGCTCGTC

4851  CGACGAGGCC CGGCCCTCCC TCCGCTTCCA AAGAAACGCC CCCCATCGCC
      GCTGCTCCGG GCCGGGAGGG AGGCGAAGGT TTCTTTGCGG GGGGTAGCGG

4901  ACTATATACA TACCCCCCCC TCTCCTCCCA TCCCCCCAAC CCTACCACCA
      TGATATATGT ATGGGGGGGG AGAGGAGGGT AGGGGGGTTG GGATGGTGGT

4951  CCACCACCAC CACCTCCTCC CCCCTCGCTG CCGGACGACG AGCTCCTCCC
      GGTGGTGGTG GTGGAGGAGG GGGGAGCGAC GGCCTGCTGC TCGAGGAGGG

5001  CCCTCCCCCT CCGCCGCCGC CGGTAACCAC CCCGCCCCTC TCCTCTTTCT
      GGGAGGGGGA GGCGGCGGCG GCCATTGGTG GGGCGGGGAG AGGAGAAAGA
```

FIG._40G

```
5051  TTCTCCGTTT TTTTTTTCGT CTCGGTCTCG ATCTTTGGCC TTGGTAGTTT
      AAGAGGCAAA AAAAAAAGCA GAGCCAGAGC TAGAAACCGG AACCATCAAA

5101  GGGTGGGCGA GAGCGGCTTC GTCGCCCAGA TCGGTGCGCG GGAGGGGCGG
      CCCACCCGCT CTCGCCGAAG CAGCGGGTCT AGCCACGCGC CCTCCCCGCC
                                                 BamHI
                                                 --------
5151  GATCTCGCGG CTGGCGTCTC CGGGCGTGAG TCGGCCCGGA TCCTCGCGGG
      CTAGAGCGCC GACCGCAGAG GCCCGCACTC AGCCGGGCCT AGGAGCGCCC

5201  GAATGGGGCT CTCGGATGTA GATCTTCTTT CTTTCTTCTT TTTGTGGTAG
      CTTACCCCGA GAGCCTACAT CTAGAAGAAA GAAAGAAGAA AAACACCATC

5251  AATTTGAATC CCTCAGCATT GTTCATCGGT AGTTTTTCTT TTCATGATTT
      TTAAACTTAG GGAGTCGTAA CAAGTAGCCA TCAAAAAGAA AAGTACTAAA

5301  GTGACAAATG CAGCCTCGTG CGGAGCTTTT TTGTAGC
      CACTGTTTAC GTCGGAGCAC GCCTCGAAAA AACATCG
```

FIG._40H

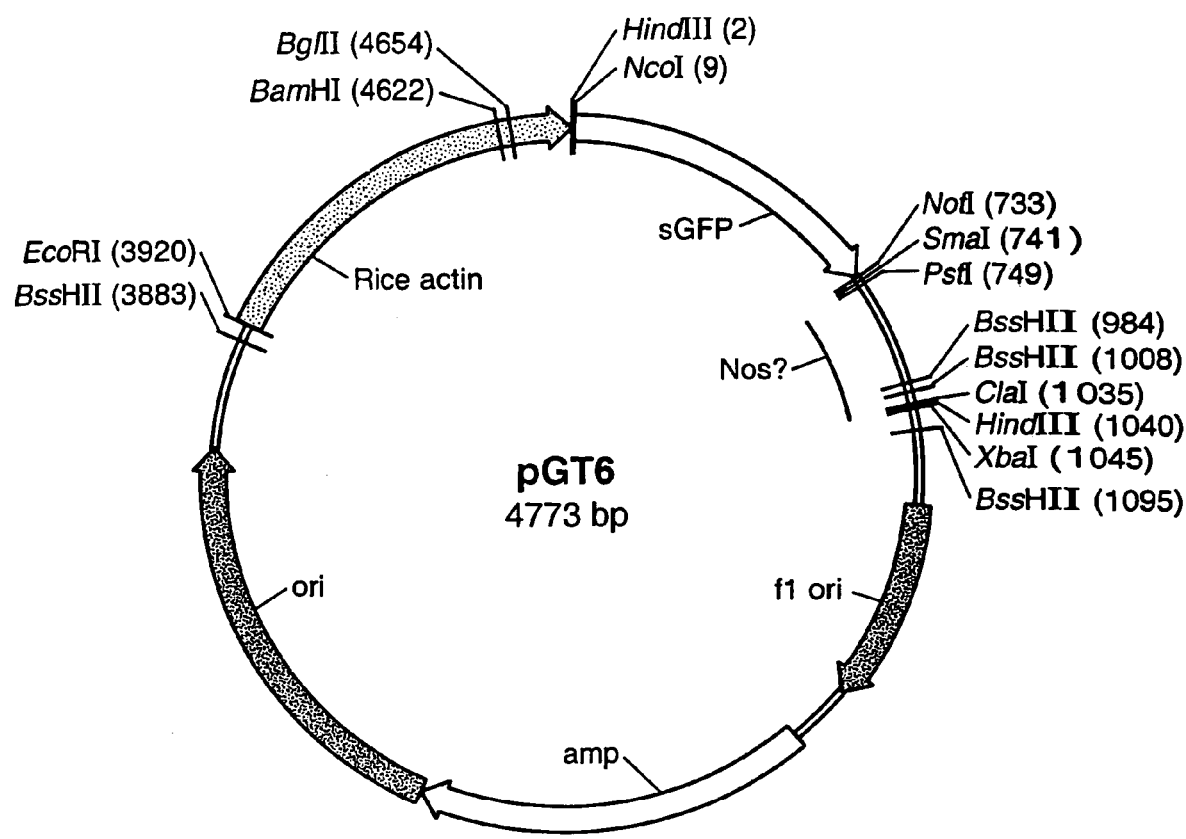
FIG._41A

```
         HindIII  NcoI
         ~~~~~~  ~~~~~
   1     AAGCTTACCA TGGTGAGCAA GGGCGAGGAG CTGTTCACCG GGTGGTGCC  CATCCTGGTC GAGCTGGACG
         TTCGAATGGT ACCACTCGTT CCCGCTCCTC GACAAGTGGC CCACCACCGG GTAGGACCAG CTCGACCTGC 71     GCGACGTGAA CGGCCACAAG TTCAGCGTGT CCGGCGAGGG CGAGGGCGAT GCCACCTACG GCAAGCTGAC
         CGCTGCACTT GCCGGTGTTC AAGTCGCACA GGCCGCTCCC GCTCCCGCTA CGGTGGATGC CGTTCGACTG 141     CCTGAAGTTC ATCTGCACCA CCGGCAAGCT GCCCGTGCCC TGGCCCACCC TCGTGACCAC CTTCACCTAC
         GGACTTCAAG TAGACGTGGT GGCCGTTCGA CGGGCACGGG ACCGGGTGGG AGCACTGGTG GAAGTGGATG 211     GGCGTGCAGT GCTTCAGCCG CTACCCCGAC AGCACGACTT CTTCAAGTCC GCCATGCCCG
         CCGCACGTCA CGAAGTCGGC GATGGGGCTG GTGTACTTCG GAAGTTCAGG CGGTACGGGC 281     AAGGCTACGT CCAGGAGCGC ACCATCTTCT TCAAGGACGA CGGCAACTAC AAGACCCGCG CCGAGGTGAA
         TTCCGATGCA GGTCCTCGCG TGGTAGAAGA AGTTCCTGCT GCCGTTGATG TTCTGGGCGC GGCTCCACTT 351     GTTCGAGGGC GACACCCTGG TGAACCGCAT CGAGCTGAAG GGCATCGACT TCAAGGAGGA CGGCAACATC
         CAAGCTCCCG CTGTGGGACC ACTTGGCGTA GCTCGACTTC CCGTAGCTGA AGTTCCTCCT GCCGTTGTAG 421     CTGGGGCACA AGCTGGAGTA CAACTACAAC AGCCACAACG TCTATATCAT GGCCGACAAG CAGAAGAACG
         GACCCCGTGT TCGACCTCAT GTTGATGTTG TCGGTGTTGC AGATATAGTA CCGGCTGTTC GTCTTCTTGC 491     GCATCAAGGT GAACTTCAAG ATCCGCCACA ACATCGAGGA CGGCAGCGTG CAGCTCGCCG ACCACTACCA
         CGTAGTTCCA CTTGAAGTTC TAGGCGGTGT TGTAGCTCCT GCCGTCGCAC GTCGAGCGGC TGGTGATGGT 561     GCAGAACACC CCCATCGGCG ACGGCCCCGT GCTGCTGCCC GACAACCACT ACCTGAGCAC CCAGTCCGCC
         CGTCTTGTGG GGGTAGCCGC TGCCGGGGCA CGACGACGGG CTGTTGGTGA TGGACTCGTG GGTCAGGCGG 631     CTGAGCAAAG ACCCCAACGA GAAGCGCGAT CACATGGTCC TGCTGGAGTT CGTGACCGCC GCCGGGATCA
         GACTCGTTTC TGGGGTTGCT CTTCGCGCTA GTGTACCAGG ACGACCTCAA GCACTGGCGG CGGCCCCTAGT
```

FIG.—41B

```
                                                  SmaI
                                      NotI        PstI
701  CTCACGGCAT GGACGAGCTG TACAAGTAAA GCGGCCGCCC GGGCTGCAGG GAAACCACTG AAGGATGAGC
     GAGTGCCGTA CCTGCTCGAC ATGTTCATTT CGCCGGCGGG CCCGACGTCC CTTTGGTGAC TTCCTACTCG

771  TGTAAAGAAG CAGATCGTTC AAACATTTGG CAATAAAGTT TCTTAAGATT GAATCCTGTT GCCGGTCTTG
     ACATTTCTTC GTCTAGCAAG TTTGTAAACC GTTATTTCAA AGAATTCTAA CTTAGGACAA CGGCCAGAAC

841  CGATGATTAT CATATAATTT CTGTTGAATT ACGTTAAGCA TGTAATAATT AACATGTAAT GCATGACGTT
     GCTACTAATA GTATATTAAA GACAACTTAA TGCAATTCGT ACATTATTAA TTGTACATTA CGTACTGCAA

911  ATTTATGAGA TGGGTTTTTA TGATTAGAGT CCCGCAATTA TACATTTAAT ACGCGATAGA AAACAAAATA
     TAAATACTCT ACCCAAAAAT ACTAATCTCA GGGCGTTAAT ATGTAAATTA TGCGCTATCT TTTGTTTTAT

XbaI
                      BssHII                                   ClaI HindIII
981  TAGCGCGCAA ACTAGGATAA ATTATCGCGC GCGGTGTCAT CTATGTTACT AGATCGATAA GCTTCTAGAG
     ATCGCGCGTT TGATCCTATT TAATAGCGCG CGCCACAGTA GATACAATGA TCTAGCTATT CGAAGATCTC 1051 CGGCCGGTGG AGCTCCAATT CGCCCTATAG TGAGTCGTAT TACGCGCGCT CACTGGCCGT CGTTTTACAA
     GCCGGCCACC TCGAGGTTAA GCGGGATATC ACTCAGCATA ATGCGCGCGA GTGACCGGCA GCAAAATGTT BssHII
1121 CGTCGTGACT GGGAAAACCC TGGCGTTACC CAACTTAATC GCCTTGCAGC ACATCCCCCT TTCGCCAGCT
     GCAGCACTGA CCCTTTTGGG ACCGCAATGG GTTGAATTAG CGGAACGTCG TGTAGGGGGA AAGCGGTCGA 1191 GGCGTAATAG CGAAGAGGCC CGCACCGATC GCCCTTCCCA ACAGTTGCGC AGCCTGAATG GCGAATGGGA
     CCGCATTATC GCTTCTCCGG GCGTGGCTAG CGGGAAGGGT TGTCAACGCG TCGGACTTAC CGCTTACCCT 1261 CGCGCCCTGT AGCGGCGCAT TAAGCGCGGC GGGTGTGGTG GTTACGCGCA GCGTGACCGC TACACTTGCC
     GCGCGGGACA TCGCCGCGTA ATTCGCGCCG CCCACACCAC CAATGCGCGT CGCACTGGCG ATGTGAACGG
```

FIG._41C

```
1331  AGCGCCCTAG CGCCCGCTCC TTTCGCTTTC TTCCCTTCCT TTCTCGCCAC GTTCGCCGGC TTTCCCCGTC
      TCGCGGGATC GCGGGCGAGG AAAGCGAAAG AAGGGAAGGA AAGAGCGGTG CAAGCGGCCG AAAGGGGCAG

1401  AAGCTCTAAA TCGGGGGCTC CCTTTAGGGT TCCGATTTAG TGCTTTACGG CACCTCGACC CCAAAAAACT
      TTCGAGATTT AGCCCCCGAG GGAAATCCCA AGGCTAAATC ACGAAATGCC GTGGAGCTGG GGTTTTTTGA

1471  TGATTAGGGT GATGGTTCAC GTAGTGGGCC ATCGCCCTGA TAGACGGTTT TTCGCCCTTT GACGTTGGAG
      ACTAATCCCA CTACCAAGTG CATCACCCGG TAGCGGGACT ATCTGCCAAA AAGCGGGAAA CTGCAACCTC

1541  TCCACGTTCT TTAATAGTGG ACTCTTGTTC CAAACTGGAA CAACACTCAA CCCTATCTCG GTCTATTCTT
      AGGTGCAAGA AATTATCACC TGAGAACAAG GTTTGACCTT GTTGTGAGTT GGGATAGAGC CAGATAAGAA

1611  TTGATTTATA AGGGATTTTG CCGATTTCGG CCTATTGGTT AAAAAATGAG CTGATTTAAC AAAAATTTAA
      AACTAAATAT TCCCTAAAAC GGCTAAAGCC GGATAACCAA TTTTTTACTC GACTAAATTG TTTTTAAATT

1681  CGCGAATTTT AACAAAATAT TAACGCTTAC AATTTAGGTG GCACTTTTCG CGCGGAACCC
      GCGCTTAAAA TTGTTTTATA ATTGCGAATG TTAAATCCAC CGTGAAAAGC GCGCCTTGGG

1751  CTATTTGTTT ATTTTTCTAA ATACATTCAA ATATGTATCC GCTCATGAGA CAATAACCCT GATAAATGCT
      GATAAACAAA TAAAAAGATT TATGTAAGTT TATACATAGG CGAGTACTCT GTTATTGGGA CTATTTACGA

1821  TCAATAATAT TGAAAAAGAA AGAGTATGAG TATTCAACAT TTCCGTGTCG TAAGATCCTT GCCCCGAAGA
      AGTTATTATA ACTTTTTCCT TCTCATACTC ATAAGTTGTA AGGCACAGC ATTCTAGGAA CGGGGCTTCT

1891  GCATTTTGCC TTCCTGTTTT TGCTCACCCA GAAACGCTGG TGAAAGTAAA AGATGCTGAA GATCAGTTGG
      CGTAAAACGG AAGGACAAAA ACGAGTGGGT CTTTGCGACC ACTTTCATTT TCTACGACTT CTAGTCAACC

1961  GTGCACGAGT GGGTTACATC GAACTGGATC TCAACAGCGG TAAGATCCTT GAGAGTTTTC GCCCCGAAGA
      CACGTGCTCA CCCAATGTAG CTTGACCTAG AGTTGTCGCC ATTCTAGGAA CTCTCAAAAG CGGGGCTTCT

2031  ACGTTTTCCA ATGATGAGCA CTTTTAAAGT TCTGCTATGT GGCGCGGTAT TATCCCGTAT TGACGCCGGG
      TGCAAAAGGT TACTACTCGT GAAAATTTCA AGACGATACA CCGCGCCATA ATAGGGCATA ACTGCGGCCC

2101  CAAGAGCAAC TCGGTCGCCG CATACACTAT TCTCAGAATG ACTTGGTTGA GTACTCACCA GTCACAGAAA
      GTTCTCGTTG AGCCAGCGGC GTATGTGATA AGAGTCTTAC TGAACCAACT CATGAGTGGT CAGTGTCTTT
```

FIG.–41D

```
2171  AGCATCTTAC GGATGGCATG ACAGTAAGAG AATTATGCAG TGCTGCCATA ACCATGAGTG ATAACACTGC
      TCGTAGAATG CCTACCGTAC TGTCATTCTC TTAATACGTC ACGACGGTAT TGGTACTCAC TATTGTGACG

2241  GGCCAACTTA CTTCTGACAA CGATCGGAGG ACCGAAGGAG CTAACCGCTT TTTTGCACAA CATGGGGAT
      CCGGTTGAAT GAAGACTGTT GCTAGCCTCC TGGCTTCCTC GATTGGCGAA AAAACGTGTT GTACCCCTA

2311  CATGTAACTC GCCTTGATCG TTGGGAACCG GAGCTGAATG AAGCCATACC AAACGACGAG CGTGACACCA
      GTACATTGAG CGGAACTAGC AACCCTTGGC CTCGACTTAC TTCGGTATGG TTTGCTGCTC GCACTGTGGT

2381  CGATGCCTGT AGCAATGGCA ACAACGTTGC GCAAACTATT AACTGGCGAA CTACTTACTC TAGCTTCCCG
      GCTACGGACA TCGTTACCGT TGTTGCAACG CGTTTGATAA TTGACCGCTT GATGAATGAG ATCGAAGGGC

2451  GCAACAATTA ATAGACTGGA TGGAGGCGGA TAAAGTTGCA GGACCACTTC CCTTCCGGCT
      CGTTGTTAAT TATCTGACCT ACCTCCGCCT ATTTCAACGT CCTGGTGAAG ACGCAGCCG GGAAGGCCGA

2521  GGCTGGTTTA ATCTGGAGCC GGTGAGCGTG GGTCTCGCGG TATCATTGCA GCACTGGGGC
      CCGACCAAAT AACGACTATT TAGACCTCGG CCACTCGCAC CCAGAGCGCC ATAGTAACGT CGTGACCCCG

2591  CAGATGGTAA GCCCTCCCGT ATCGTAGTTA TCTACACGAC GGGGAGTCAG GCAACTATGG ATGAACGAAA
      GTCTACCATT CGGGAGGCCA TAGCATCAAT AGATGTGCTG CCCCTCAGTC CGTTGATACC TACTTGCTTT

2661  TAGACAGATC GCTGAGATAG GTGCCTCACT GATTAAGCAT TGGTAACTGT CAGACCAAGT TTACTCATAT
      ATCTGTCTAG CGACTCTATC CACGGAGTGA CTAATTCGTA ACCATTGACA GTCTGGTTCA AATGAGTATA

2731  ATACTTTAGA TTGATTTAAA ACTTCATTTT TAATTTAAAA ATTAAATTTT GGATCTAGT GAAGATCCTT TTTGATAATC
      TATGAAATCT AACTAAATCT TGAAGTAAAA ATTAAATTTT CCTAGATCCA CTTCTAGGAA AAACTATTAG

2801  TCATGACCAA AATCCCTTAA CGTGAGTTTT CGTTCCACTG AGCGTCAGAC CCCGTAGAAA AGATCAAAGG
      AGTACTGGTT TTAGGGAATT GCACTCAAAA GCAAGGTGAC TCGCAGTCTG GGGCATCTTT TCTAGTTTCC

2871  ATCTTCTTGA GATCCTTTTT TTCTGCGCGT AATCTGCTGC TTGCAAACAA AAAAACCACC GCTACCAGCG
      TAGAAGAACT CTAGGAAAAA AAGACGCGCA TTAGACGACG AACGTTTGTT TTTTTGGTGG CGATGGTCGC

2941  GTGGTTTGTT TGCCGGATCA AGAGCTACCA ACTCTTTTTC CGAAGGTAAC TGGCTTCAGC AGAGCGCAGA
      CACCAAACAA ACGGCCCTAGT TCTCGATGGT TGAGAAAAG GCTTCCATTG ACCGAAGTCG TCTCGCGTCT
```

FIG.—41E

```
3011  TACCAAATAC TGTCCTTCTA GTGTAGCCGT AGTTAGGCCA CCACTTCAAG AACTCTGTAG CACCGCCTAC
      ATGGTTTATG ACAGGAAGAT CACATCGGCA TCAATCCGGT GGTGAAGTTC TTGAGACATC GTGGCGGATG

3081  ATACCTCGCT CTGCTAATCC TGTTACCAGT GGCTGCTGCC CCGACGACGG AGTCGTGTCT TACCGGGTTG
      TATGGAGCGA GACGATTAGG ACAATGGTCA CCGACGACGG GGCTGCTGCC CCGACGACGG TCAGCACAGA ATGGCCCAAC

3151  GACTCAAGAC GATAGTTACC GGATAAGGCG CAGCGGGTCGG GCTGAACGGG GGGTTCGTGC ACACAGCCCA
      CTGAGTTCTG CTATCAATGG CCTATTCCGC GTCGCCAGCC CGACTTGCCC CCCAAGCACG TGTGTCGGGT

3221  GCTTGGAGCG AACGACCTAC ACCGAACTGA GATACCTACA GCGTGAGCTA TGAGAAAGCG CCACGCTTCC
      CGAACCTCGC TTGCTGGATG TGGCTTGACT CTATGGATGT CGCACTCGAT ACTCTTTCGC GGTGCGAAGG

3291  CGAAGGGAGA AAGGCGGACA GGTATCCGGT AAGCGGCAGG GTCGGAACAG GAGAGCGCAC GAGGGAGCTT
      GCTTCCCTCT TTCCGCCTGT CCATAGGCCA TTCGCCGTCC CAGCCTTGTC CTCTCGCGTG CTCCCTCGAA

3361  CCAGGGGAAA ACGCCTGGTA TCTTTATAGT CCTGTCGGGT TTCGCCACCT CTGACTTGAG CGTCGATTTT
      GGTCCCCTTT TGCGGACCAT AGAAATATCA GGACAGCCCA AAGCGGTGGA GACTGAACTC GCAGCTAAAA

3431  TGTGATGCTC GTCAGGGGGG CGGAGCCTAT CAGCAACGCG CAGCAACGCG GGCTTTTTAC GGTTCCTGGC
      ACACTACGAG CAGTCCCCCC GCCTCGGATA GTCGTTGCGC GTCGTTGCGC CCGAAAAATG CCAAGGACCG

3501  CTTTGCTGG CCTTTGCTC ACATGTTCTT TCCCCTGTTA TCCCCCTGATT CTGTGGATAA CCGTATTACC
      GAAAACGACC GGAAAACGAG TGTACAAGAA AGGGACTAA AGGGGACTAA GACACCTATT GGCATAATGG

3571  GCCTTTGAGT GAGCTGATAC CGCTCGCCGC AGCCGAACGA CCGAGCGCAG CGAGTCAGTG AGCGAGGAAG
      CGGAAACTCA CTCGACTATG GCGAGCGGCG TCGGCTTGCT GGCTCGCGTC GCTCAGTCAC TCGCTCCTTC

3641  CGGAAGAGCG CCCAATACGC AAACCGCCTC TCCCCGCGCG TTGGCCGATT CATTAATGCA GCTGGCACGA
      GCCTTCTCGC GGGTTATGCG TTTGGCGGAG AGGGGCGCGC AACCGGCTAA GTAATTACGT CGACCGTGCT

3711  CAGGTTTCCC GACTGGAAAG CGGGCAGTGA GCGCAACGCA ATTAATGTGA GTTAGCTCAC TCATTAGGCA
      GTCCAAAGGG CTGACCTTTC GCCCGTCACT CGCGTTGCGT TAATTACACT CAATCGAGTG AGTAATCCGT

3781  CCCCAGGCTT TACACTTTAT GCTTCCGGCT CGTATGTTGT GTGGAATTGT GAGCGGATAA CAATTTCACA
      GGGGTCCGAA ATGTGAAATA CGAAGGCCGA GCATACAACA CACCTTAACA CTCGCCTATT GTTAAAGTGT
```

FIG._41F

```
                                                   BssHII                                            EcoRI
                                                   ------                                            -----
3851  CAGGAAACAG CTATGACCAT GATTACGCCA AGCGCGCAAT TAACCCTCAC TAAAGGGAAC AAAAGCTGGA
      GTCCTTTGTC GATACTGGTA CTAATGCGGT TCGCGCGTTA ATTGGGAGTG ATTTCCCTTG TTTTCGACCT
      EcoRI
      -----
3921  ATTCCACAAT GAACAATAAT AAGATTAAAA AGCGCGCAAT TAGCTTGCCC CGTTGCAGC GATGGGTATT TTTTCTAGTA
      TAAGGTGTTA CTTGTTATTA TTCTAATTTT ATCGAACGTCG GGCAACGTCG CTACCCATAA AAAAGATCAT
3991  AAATAAAGA TAAACTTAGA CTCAAAAACAT TTACAAAAAC AACCCCTAAA GTCCTAAAGC CCAAAGTGCT CAACTGGCAA
      TTTATTTCT ATTTGAATCT GAGTTTTGTA AATGTTTTTG TTGGGGATTT CAGGATTTCG GGTTTCACGA GTTGACCGTT
4061  ATGCACGATC CATAGCAAGC CCAGCCAAG CCAACCCAAC CCAACCCACC CCAGTGCAGC GTCTCGCAGC CAAAAAAAAA
      TACGTGCTAG GTATCGTTCG GGTCGGGTTCG GGTTGGGTTG GGTTGGGTGG GGTCACGTCG CAGAGCGTCG GTTTTTTTTT
4131  ATAGTCTCCA CCCCCGGCAC TATCACCGTG AGTTGTCCGC ACCACCGCAC TGGTGGCGTG CAGAGCGTCG GTTTTTTTTT
      TATCAGAGGT GGGGGCCGTG ATAGTGGCAC TCAACAGGCG ACCACCGCAC TGGTGGCGTG CAGAGCGTCG
4201  AAAAGAAAGA AAAGAAAAGAA AAAGAAAAAAC AGCAGGTGGG TCCGGGTCGT GGGGGCCGGA AAAGCGAGGA
      TTTTCTTTCT TTTCTTTTCTT TTTCTTTTTG TCGTCCACCC AGGCCCAGCA CCCCCGGCCT TTTCGCTCCT
4271  GGATCGCGAG CAGCGACGAG GCCCGGCCCT CCCTCCGCTT CCAAAGAAAC GCCACTATAT GCCACTATAT
      CCTAGCGCTC GTCGCTGCTC CGGGCCGGGA GGGAGGCGAA GGTTTCTTTG CGGTGATATA CGGTGATATA
4341  ACATACCCCC CCCTCCTCTC CCATCCCCCC AACCCTACCA CCACCACTCC TCCCCCCTCG
      TGTATGGGGG GGGAGGAGAG GGTAGGGGGG TTGGGATGGT GTGGTGGTGAGG AGGGGGAGC
4411  CTGCCGGACC ACGAGCTCCT CCCTCCGCCGC CCCTCCGCCC CACCCCGCCC CTCTCCTCTT
      GACGGCCTGC TGCTCGAGGA GGAGGCGGCG GGAGGCGGG GTGGGGCGGG GAGAGGAGAA
4481  TCTTTCTCCG TTTTTTTTT CGTCTCGGTC TCGATCTTTG GCCTTGGTAG TTTGGGTGGG CGAGAGCGGC
      AGAAAGAGGC AAAAAAAAA GCAGAGCCAG AGCTAGAAAC CGGAACCATC AAACCCACCC GCTCTCGCCG
4551  TTCGTCGCCC AGATCGGTGC GCGGGAGGGG CGGGATCTCG CGGCTGGCGT CTCCGGGCGT GAGTCGGCCC
      AAGCAGCGGG TCTAGCCACG CGCCCTCCCC GCCCTAGAGC GCCGACCGCA GAGGCCCGCA CTCAGCCGGG
```

FIG._41G

```
             BamHI                                Bg1II
             ~~~~~~                               ~~~~~~
4621  GGATCCTCGC GGGGAATTGGG GCTCTCGGAT GTAGATCTTC TTTCTTTCTT CTTTTTGTGG TAGAATTTGA
      CCTAGGAGCG CCCCTTACCC CGAGAGCCTA CATCTAGAAG AAAGAAAGAA GAAAAACACC ATCTTAAACT

4691  ATCCCTCAGC ATTGTTCATC GGTAGTTTTT CTTTTCATGA TTTGTGACAA ATGCAGCCTC GTGCGGAGCT
      TAGGGAGTCG TAACAAGTAG CCATCAAAAA GAAAAGTACT AAACACTGTT TACGTCGGAG CACGCCTCGA

4761  TTTTTGTAGG TAG
      AAAAACATCC ATC
```

FIG._41H

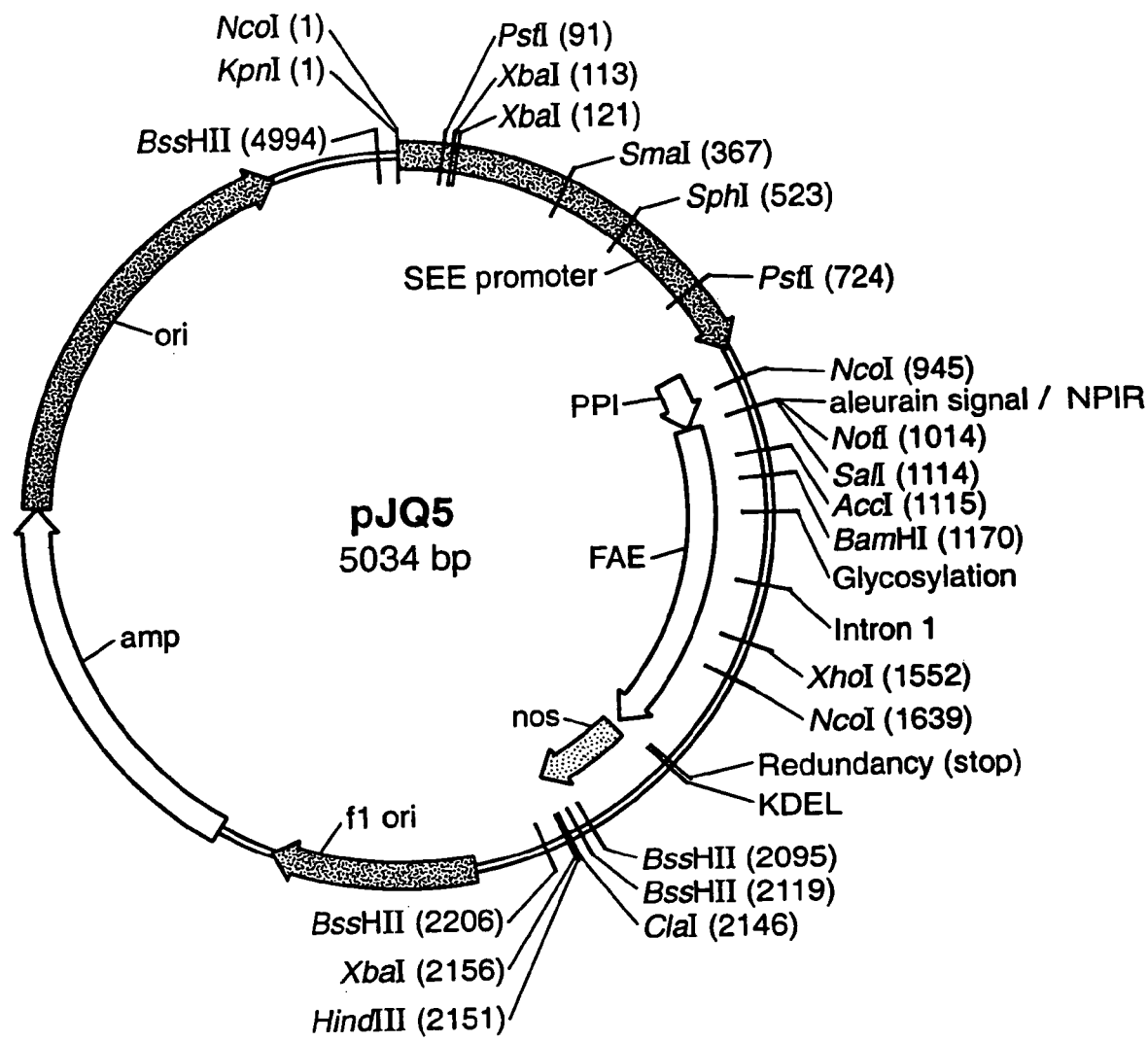
FIG._42A

```
     NcoI
     -----
     KpnI
     ~
  1  CATGGGCCAG GTATAATTAT GGGATATCTC AAGCAAATAA TCGAAATATC ACCATTGGCT ACAATATCTG
     GTACCCGGTC CATATTAATA CCCTATAGAG TTCGTTTATT AGCTTTATAG TGGTAACCGA TGTTATAGAC

PstI                                            XbaI       XbaI
               ----                                            ----       ----
 71  AGCTCCGAGT TCTGACTGCA GTCTGGATGA CGCGTGTTGT TCAAGATCCC ATCTAGAACT CTAGATAGCA CAGCCACAGC
     TCGAGGCTCA AGACTGACGT CAGACCTACT GCGCACAACA AGTTCTAGGG TAGATCTTGA GATCTATCGT GTCGGTGTCG

141  ACCTACAGGA GTGCGACACT TGTGGACTGT AGTAGTGTTG GAGACGGAGC TCTTTCCTAC CTCCTGACGT
     TGGATGTCCT CACGCTGTGA ACACCTGACA TCATCACAAC CTCTGCCTCG AGAAAGGATG GAGGACTGCA

211  TGCCGCCGTT GTCCATTCCA ACGGCATCAC TCTCAACCAA TCACGCGCTC CCAACAAAAT ATCGTCCCCC
     ACGGCGGCAA CAGGTAAGGT TGCCGTAGTG AGAGTTGGTT AGTGCGCGAG GGTTGTTTTA TAGCAGGGGG

SmaI
           ----
281  ATGTCTTGGC GGAGAGAGAG TACATACATG CTGTCGCGCC GTTTTTGTCT GAATCTCGCT TCCACTGCC
     TACAGAACCG CCTCTCTCTC ATGTATGTAC GACAGCGCGG CAAAAACAGA CTTAGAGCGA AGGTGACCGG

351  AATCAGCTCA GCTCCCGGGA GCTCACTCAT TCAAGATCCC ATCGTCGTCG TCACCCCTGG CGTCATGGGA
     TTAGTCGAGT CGAGGGCCCT CGAGTGAGTA AGTTCTAGGG TAGCAGCAGC AGTGGGGACC GCAGTACCCT

421  TGGAAAAGAA CCTCCGTTGC TCGGATGAGT CAGCCATATC CCCGAACAGA GTACTGCAAG ATAACCCAAT
     ACCTTTTCTT GGAGGCAACG AGCCTACTCA GTCGGTATAG GGGCTTGTCT CATGACGTTC TATTGGGTTA

SphI
                                                         ----
491  TCAGATTCCC CCAATAGAGA AAGTATAGCA TGCTTTCGGG TTTTGTTTGG CTTAATTGAC TTTATTTTTG
     AGTCTAAGGG GGTTATCTCT TTCATATCGT ACGAAAGCCC AAAACAAACC GAATTAACTG AAATAAAAAC

561  TTGGAGTTGA ATGCTGATTT GTTGTGTAAA ATGCCCAACC ATCTGAATAT CGAGACGGAT AATAGGCTGG
     AACCTCAACT TACGACTAAA CAACACATTT TACGGGTTGG TAGACTTATA GCTCTGCCTA TTATCCGACC
```

FIG. 42B

```
631  CTAATTAATT TATAGCAAGA TTCTGTAGTG CACATCGCAA ATATCTTTCT GGGCATTACA GCTGGAGGCT
     GATTAATTAA ATATCGTTCT AAGACATCAC GTGTAGCGTT TATAGAAAGA CCCGTAATGT CGACCTCCGA
                                PstI
                                -------

701  TCATCAGCCT GAAACACTCT GCAGAGCCTG AAGCAAGTGG TGAAGCGTGG CGATGAGATG GGTATAAAAC
     AGTAGTCGGA CTTTGTGAGA CGTCTCGGAC TTCGTTCACC ACTTCGCACC GCTACTCTAC CCATATTTTG

771  CCCCGGCACC GGGACGCGAG CTCCCCGCCTA CCAGTACCAT CTCGCCTCGC TCCCCCTGCC GGACGACCCA
     GGGGCCGTGG CCCTGCGCTC GAGGGCGGAT GGTCATGGTA GAGCGGAGCG AGGGGGACGG CCTGCTGGGT

841  GTAAAATACT GTTGCCCACT CGCCGGCGAG ATGGMCGTGC ACAAGGAGGT SAACTTCGTS GCCTACCTCC
     CATTTTATGA CAACGGGTGA GCGGCCGCTC TACCKGCACG TGTTCCTCCA STTGAAGCAS CGGATGGAGG
                                       NcoI
                                       -------

911  TGATCGTSCT CGGCCCTCTC TTGCTCGTST CCGCCATGGA GCACGTGGAC GCCAAGGCCT GCACCCKCGA
     ACTAGCASGA GCCGGGAGAG AACGAGCASA GGCGGTACCT CGTGCACCTG CGGTTCCGGA CGTGGGMGCT
                                                NotI
                                                -------

981  GTGCGGCAAC CTCGGCTTCG GCATCTGCCC GGCGGCCGCC TCCACGCAGG GCATCTCCGA AGACCTCTAC
     CACGCCGTTG GAGCCGAAGC CGTAGACGGG CCGCCGGCGG AGGTGCGTCC CGTAGAGGCT TCTGGAGATG
                                                                          SalI
                                                                          -------
                                                                          AccI
                                                                          -------

1051 AGCCGTTTAG TCGAAATGGC CACTATCTCC CAAGCTGCCT ACGCCGACCT GTGCAACATT CCGTCGACTA
     TCGGCAAATC AGCTTTACCG GTGATAGAGG GTTCGACGGA TGCGGCTGGA CACGTTGTAA GGCAGCTGAT
                                                                  BamHI
                                                                  -------

1121 TTATCAAGGG AGAGAAAATT TACAATTCTC AAACTGACAT TAACGGATGG ATCCTCCGCG ACGACAGCAG
     AATAGTTCCC TCTCTTTTAA ATGTTAAGAG TTTGACTGTA ATTGCCTACC TAGGAGGCGC TGCTGTCGTC
```

FIG._42C

```
1191  CAAAGAAATA ATCACCGTCT TCCGTGGCAC TGGTAGTGAT ACGAATCTAC AACTCGATAC TAACTACACC
      GTTTCTTTAT TAGTGGCAGA AGGCACCGTG ACCATCACTA TGCTTAGATG TTGAGCTATG ATTGATGTGG

1261  CTCACGCCTT TCGACACCCT ACCACAATGC AACGGTTGTG AAGTACACGG TGGATATTAT ATTGGATGGG
      GAGTGCGGAA AGCTGTGGGA TGGTGTTACG TTGCCAACAC TTCATGTGCC ACCTATAATA TAACCTACCC

1331  TCTCCGTCCA GGACCAAGTC GAGTCGCTTG TCAAACAGCA GGTTAGCCAG TATCCGGACT ACGCGCTGAC
      AGAGGCAGGT CCTGGTTCAG CTCAGCGAAC AGTTTGTCGT CCAATCGGTC ATAGGCCTGA TGCGCGACTG

1401  CGTGACCGGC CACKCCCTCG GCGCCTCCCT GGCGGCACTC ACTGCCGCCC AGCTGTCTGC GACATACGAC
      GCACTGGCCG GTGMGGGAGC CGCGGAGGGA CCGCCGTGAG TGACGGCGGG TCGACAGACG CTGTATGCTG

1471  AACATCCGCC TGTACACCTT CGGCGAACCG CGCAGCGGCA ATCAGGCCTT CGCGTCGTAC ATGAACGATG
      TTGTAGGCGG ACATGTGGAA GCCGCTTGGC GCGTCGCCGT TAGTCCGGAA GCGCAGCATG TACTTGCTAC

XhoI
                                              ------
1541  CCTTCCAAGC CTCGAGCCCA GATACGACGC AGTATTTCCG GGTCACTCAT GCCAACGACG GCATCCCAAA
      GGAAGGTTCG GAGCTCGGGT CTATGCTGCG TCATAAAGGC CCAGTGAGTA CGGTTGCTGC CGTAGGGTTT

NcoI
                                                 -------
1611  CCTGCCCCCG GTGGAGCAGG GGTACGCCCA TGGCGGTGTA GAGTACTGGA GCGTTGATCC TTACAGCGCC
      GGACGGGGGC CACCTCGTCC CCATGCGGGT ACCGCCACAT CTCATGACCT CGCAACTAGG AATGTCGCGG

1681  CAGAACACAT TTGTCTGCAC TGGGATGAA GTGCAGTGCT CACGTCACGA GGGCGGACAG GGTGTGAATA
      GTCTTGTGTA AACAGACGTG ACCCCTACTT CACGTCACGA CCCGCCTGTC CCACACTTAT

1751  ATGCGCACAC GACTTATTTT GGGATGACGA GCGGAGCCTG TACATGGTGA TCAGTCATTT CAGCCCTCCCC
      TACGCGTGTG CTGAATAAAA CCCTACTGCT CGCCTCGGAC ATGTACCACT AGTCAGTAAA GTCGGAGGGG

1821  GAGTGTACCA GGAAAGATGG ATGTCCTGGA GAGGGGGCCG CGTAACCACT GAAGGATGAG CTGTAAAGAA
      CTCACATGGT CCTTTCTACC TACAGGACCT CTCCCCCGGC GCATTGGTGA CTTCCTACTC GACATTTCTT
```

FIG.–42D

```
1891  GCAGATCGTT CAAACATTTG GCAATAAAGT TTCTTAAGAT TGAATCCTGT TGCCGGTCTT GCGATGATTA
      CGTCTAGCAA GTTTGTAAAC CGTTATTTCA AGAATTCTA ACTTAGGACA ACGGCCAGAA CGCTACTAAT

1961  TCATATAATT TCTGTTGAAT TACGTTAAGC ATGTAATAAT TAACATGTAA TGCATGACGT TATTTATGAG
      AGTATATTAA AGACAACTTA ATGCAATTCG TACATTATTA ATTGTACATT ACGTACTGCA ATAAATACTC
                                                                      BssHII
                                                                      -----

2031  ATGGGTTTTT ATGATTAGAG TCCCGCAATT ATACATTTAA TACGCGATAG AAAACAAAAT ATAGCGCGCA
      TACCCAAAAA TACTAATCTC AGGGCGTTAA TATGTAAATT ATGCGCTATC TTTTGTTTTA TATCGCGCGT
                          BssHII                             XbaI
                          ------                             ----
                                                 ClaI HindIII
                                                 ----------

2101  AACTAGGATA AATTATCGCG CGCGGTGTCA TCTATGTTAC TAGATCGATA AGCTTCTAGA GCGGCCGGTG
      TTGATCCTAT TTAATAGCGC GCGCCACAGT AGATACAATG ATCTAGCTAT TCGAAGATCT CGCCGGCCAC
                             BssHII
                             ------

2171  GAGCTCCAAT TCGCCCTATA GTGAGTCGTA TTACGCGCGC TCACTGGCCG TCGTTTTACA ACGTCGTGAC
      CTCGAGGTTA AGCGGGATAT CACTCAGCAT AATGCGCGCG AGTGACCGGC AGCAAAATGT TGCAGCACTG

2241  TGGGAAAACC CTGGCGTTAC CCAACTTAAT CGCCCTTGCAG AACAGTTGCG CAGCCTGAAT GGCGAATGGG
      ACCCTTTTGG GACCGCAATG GGTTGAATTA GCGGGAACGTC TTGTCAACGC GTCGGACTTA CCGCTTACCC

2311  GCGAAGAGGC CCGCACCGAT CGCCCTTCCC AACAGTTGCG CAGCCTGAAT GGCGAATGGG ACGCGCCCTG
      CGCTTCTCCG GGCGTGGCTA GCGGGAAGGG TTGTCAACGC GTCGGACTTA CCGCTTACCC TGCGCGGGAC

2381  TAGCGGCGCA TTAAGCGCGG CGGGTGTGGT GGTTACGCGC AGCGTGACCG CTACACTTGC CAGCGCCCTA
      ATCGCCGCGT AATTCGCGCC GCCCACACCA CCAATGCGCG TCGCACTGGC GATGTGAACG GTCGCGGGAT

2451  GCGCCCGCTC CTTTCGCTTT CTTCCCTTCC TTTCTCGCCA CGTTCGCCGG CTTTCCCCGT CAAGCTCTAA
      CGCGGGCGAG GAAAGCGAAA GAAGGGAAGG AAAGAGCGGT GCAAGCGGCC GAAAGGGGCA GTTCGAGATT
```

FIG.-42E

```
2521  ATCGGGGGCT CCCTTTAGGG TTCCGATTTA GTGCTTTACG GCACCTCGAC CCCAAAAAAC TTGATTAGGG
      TAGCCCCCGA GGGAAATCCC AAGCTAAAT  CACGAAATGC CGTGGAGCTG GGGTTTTTTG AACTAATCCC

2591  TGATGGTTCA CGTAGTGGGC CATCGCCCTG ATAGACGGTT TTTCGCCCTT TGACGTTGGA GTCCACGTTC
      ACTACCAAGT GCATCACCCG GTAGCGGGAC TATCTGCCAA AAAGCGGGAA ACTGCAACCT CAGGTGCAAG

2661  TTTAATAGTG GACTCTTGTT CCAAACTGGA ACAACACTCA ACCCTATCTC GGTCTATTCT TTTGATTTAT
      AAATTATCAC CTGAGAACAA GGTTTGACCT TGTTGTGAGT TGGGATAGAG CCAGATAAGA AAACTAAATA

2731  AAGGGATTTT GCCTATTCG GCCTATTGGT TAAAAAATGA GCTGATTTAA CAAAAATTTA ACGCGAATTT
      TTCCCTAAAA CGGCTAAAGC CGGATAACCA ATTTTTTACT CGACTAAATT GTTTTAAAT  TGCGCTTAAA

2801  TAACAAAATA TTAACGCTTA CAATTAGGT  GGCACTTTTC GGGGAAATGT GCGCGGAACC CCTATTGTT
      ATTGTTTTAT AATTGCGAAT GTTAAATCCA CCGTGAAAAG CGCGCCTTGG GGATAAACAA

2871  TATTTTTCTA AATACATTCA AATATGTATC GTATTCAACA CGCTCATGAG ACAATAACCC TTCAATAATA
      ATAAAAAGAT TTATGTAAGT TTATACATAG CATAAGTTGT GCGAGTACTC TGTTATTGGG AAGTTATTAT

2941  TTGAAAAAGG AAGAGTATGA GTATTCAACA TTTCCGTGTC GCCCTTATTC CCTTTTTGC  GGCATTTTGC
      AACTTTTCC  TTCTCATACT CATAAGTGT  AAAGGCACAG CGGGAATAAG GGAAAAAACG CCGTAAAACG

3011  CTTCCTGTTT TTGCTCACCC AGAAACGCTG GTGAAAGTAA AAGATGCTGA AGATCAGTTG GGTGCACGAG
      GAAGGACAAA AACGAGTGGG TCTTTGCGAC CACTTTCATT TTCTACGACT TCTAGTCAAC CCACGTGCTC

3081  TGGGTTACAT CGAACTGGAT CTCAACAGCG GTAAGATCCT TGAGAGTTTT CGCCCCGAAG AACGTTTTCC
      ACCCAATGTA GCTTGACCTA GAGTTGTCGC CATTCTAGGA ACTCTCAAAA GCGGGGCTTC TTGCAAAAGG

3151  AATGATGAGC ACTTTTAAAG TTCTGCTATG TGGCGCGGTA TTATCCCGTA TTGACGCCGG GCAAGAGCAA
      TTACTACTCG TGAAAATTTC AAGACGATAC ACCGCGCCAT AATAGGGCAT AACTGCGGCC CGTTCTCGTT

3221  CTCGGTCGCC GCATACACTA TTCTCAGAAT GACTTGGTTG AGTACTCACC AGTCACAGAA AAGCATCTTA
      GAGCCAGCGG CGTATGTGAT AAGAGTCTTA CTGAACGAAC TCATGAGTGG TCAGTGTCTT TTCGTAGAAT

3291  CGGATGGCAT GACAGTAAGA GAATTATGCA GTGCTGCCAT AACCATGAGT GATAACACTG CGGCCAACTT
      GCCTACCGTA CTGTCATTCT CTTAATACGT CACGACGGTA TTGGTACTCA CTATTGTGAC GCCGGTTGAA
```

*FIG._42F*

```
3361  ACTTCTGACA ACGATCGGAG GACCGAAGGA GCTAACCGCT TTTTTGCACA ACATGGGGGA TCATGTAACT
      TGAAGACTGT TGCTAGCCTC CTGGCTTCCT CGATTGGCGA AAAAACGTGT TGTACCCCCT AGTACATTGA

3431  CGCCTTGATC GTTGGGAACC GGAGCTGAAT GAAGCCATAC CAAACGACGA GCGTGACACC ACGATGCCTG
      GCGGAACTAG CAACCCTTGG CCTCGACTTA CTTCGGTATG GTTTGCTGCT CGCACTGTGG TGCTACGGAC

3501  TAGCAATGGC AACAACGTTG CGCAAACTAT TAACTGGCGA ACTACTTACT CTAGCTTCCC GGCAACAATT
      ATCGTTACCG TTGTTGCAAC GCGTTTGATA ATTGACCGCT TGATGAATGA GATCGAAGGG CCGTTGTTAA

3571  AATAGACTGG ATGGAGGCGG ATAAAGTTGC AGGACCACTT CTGCGCTCGG CCCTTCCGGC TGGCTGGTTT
      TTATCTGACC TACCTCCGCC TATTTCAACG TCCTGGTGAA GACGCGAGCC GGGAAGGCCG ACCGACCAAA

3641  ATTGCTGATA AATCTGGAGC CGGTGAGCGT GGGTCTCGCG AGCACTGGC GTATCATTGC CCAGATGGTA
      TAACGACTAT TTAGACCTCG GCCACTCGCA CCCAGAGCGC TCGTGACCCG CATAGTAACG GGTCTACCAT

3711  AGCCCTCCCG TATCGTAGTT ATCTACACGA CGGGAGTCA GGCAACTATG GATGAACGAA ATAGACAGAT
      TCGGGAGGGC ATAGCATCAA TAGATGTGCT GCCCCTCAGT CCGTTGATAC CTACTTGCTT TATCTGTCTA

3781  CGCTGAGATA GGTGCCTCAC TGGTAAGCA TTGGTAACTG TCAGACCAAG TTTACTCATA TATACTTTAG
      GCGACTCTAT CCACGGAGTG ACTAATTCGT AACCATTGAC AGTCTGGTTC AAATGAGTAT ATATGAAATC

3851  ATTGATTTAA AACTTCATT TTAATTTAAA AGGATCTAGG TGAAGATCCT TTTTGATAAT CTCATGACCA
      TAACTAAATT TTGAAGTAAA AATTAAATT TCCTAGATCC ACTTCTAGGA AAAACTATTA GAGTACTGGT

3921  AAATCCCTTA ACGTGAGTTT TCGTTCCACT GAGCGTCAGA CCCCGTAGAA AAGATCAAAG GATCTTCTTG
      TTTAGGGAAT TGCACTCAAA AGCAAGGTGA CTCGCAGTCT GGGGCATCTT TTCTAGTTTC CTAGAAGAAC

3991  AGATCCTTTT TTTCTGCGCG TAATCTGCTG CTTGCAAACA AAAAAACCAC CGCTACCAGC GGTGGTTTGT
      TCTAGGAAAA AAAGACGCGC ATTAGACGAC GAACGTTTGT TTTTTTGGTG GCGATGGTCG CCACCAAACA

4061  TTGCCGGATC AAGAGCTACC AACTCTTTTT CCGAAGGTAA CTGGCTTCAG CAGAGCGCAG ATACCAAATA
      AACGGCCTAG TTCTCGATGG TTGAGAAAAA GGCTTCCATT GACCGAAGTC GTCTCGCGTC TATGGTTTAT

4131  CTGTCCTTCT AGTGTAGCCG TAGTTAGGCC ACCACTTCAA GAACTCTGTA GCACCGCCTA CATACCTCGC
      GACAGGAAGA TCACATCGGC ATCAATCCGG TGGTGAAGTT CTTGAGACAT CGTGGCGGAT GTATGGAGCG
```

FIG. 42G

```
4201  TCTGCTAATC CTGTTACCAG TGGCTGCTGC CAGTGGCGAT AAGTCGTGTC TTACCGGGTT GGACTCAAGA
      AGACGATTAG GACAATGGTC ACCGACGACG GTCACCGCTA TTCAGCACAG AATGGCCCAA CCTGAGTTCT

4271  CGATAGTTAC CGGATAAGGC GCAGCGGTCG GGCTGAACGG GGGGTTCGTG CACACAGCCC AGCTTGGAGC
      GCTATCAATG GCCTATTCCG CGTCGCCAGC CCGACTTGCC CCCCAAGCAC GTGTGTCGGG TCGAACCTCG

4341  GAACGACCTA CACCGAACTG AGATACCTAC AGCGTGAGCT ATGAGAAAGC GCCACGCTTC CCGAAGGGAG
      CTTGCTGGAT GTGGCTTGAC TCTATGGATG TCGCACTCGA TACTCTTTCG CGGTGCGAAG GGCTTCCCTC

4411  AAAGGCGGAC AGGTATCCGG TAAGCGGCAG GGTCGGAACA GGAGAGCGCA CGAGGGAGCT TCCAGGGGGA
      TTTCCGCCTG TCCATAGGCC ATTCGCCGTC CCAGCCTTGT CCTCTCGCGT GCTCCCTCGA AGGTCCCCCT

4481  AACGCCTGGT ATCTTTATAG TCCTGTCGGG TTTCGCCACC TCTGACTTGA GCGTCGATTT TTGTGATGCT
      TTGCGGACCA TAGAAATATC AGGACAGCCC AAAGCGGTGG AGACTGAACT CGCAGCTAAA AACACTACGA

4551  CGTCAGGGGG GCGGAGCCTA TGGAAAAACG CCAGCAACGC GGTTCCTG CCTTTTGCTG
      GCAGTCCCCC CGCCTCGGAT ACCTTTTGCG GGTCGTTGCG CCGGAAGACC GGAAAACGAC

4621  GCCTTTTGCT CACATGTTCT TTCCTGCGTT ATCCCCTGAT TCTGTGGATA CGCCTTTGAG
      CGGAAAACGA GTGTACAAGA AAGGACGCAA TAGGGGACTA AGACACCTAT GCGGAAACTC

4691  TGAGCTGATA CCGCTCGCCG CAGCCGAACG ACCGAGCGCA GCGAGTCAGT GCGGAAGAGC
      ACTCGACTAT GGCGAGCGGC GTCGGCTTGC TGGCTCGCGT CGCTCAGTCA CTCGCTTCTCG

4761  GCCCAATACG CAAAACCGCCT CTCCCCGCGC GTTGGCCGAT TCATTAATGC ACAGGTTTCC
      CGGGTTATGC GTTTGGCGGA GAGGGGCGCG CAACCGGCTA AGTAATTACG TGTCCAAAGG

4831  CGACTGGAAA GCGGGCAGTG AGCGCAACGC AATTAATGTG AGTTAGCTCA CTCATTAGGC ACCCCAGGCT
      GCTGACCTTT CGCCCGTCAC TCGCGTTGCG TTAATTACAC TCAATCGAGT GAGTAATCCG TGGGGTCCGA

4901  TTACACTTTA TGCTTCCGGC TCGTATGTTG TGTGGAATTG TGAGCGGATA ACAATTTCAC ACAGGAAACA
      AATGTGAAAT ACGAAGGCCG AGCATACAAC ACACCTTAAC ACTCGCCTAT TGTTAAAGTG TGTCCTTTGT
```

FIG._42H

```
                          BssHII                              NcoI            KpnI
4971  GCTATGACCA TGATTACGCC AAGCGCGCAA TTAACCCTCA CTAAAGGGAA CAAAAGCTGG GTAC
      CGATACTGGT ACTAATGCGG TTCGCGCGTT AATTGGGAGT GATTTCCCTT GTTTTCGACC CATG
```

FIG. _42I

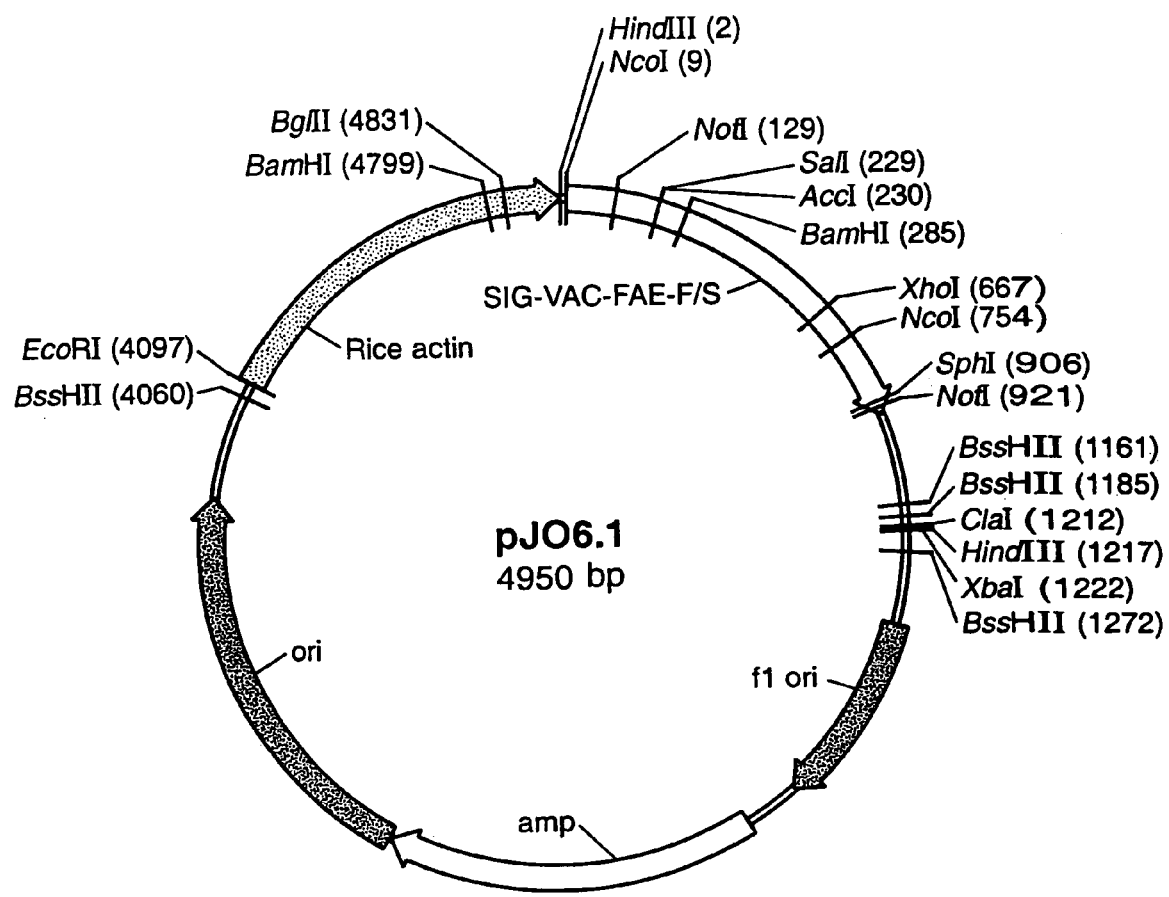
FIG._43A

```
    HindIII NcoI
    -------  ----
  1 AAGCTTACCA TGGCCCACGC CCGCGTCCTC CTCCTGGGCG CTCGCCGTGCT GGCCACGGCC GCCGTCGCCG
    TTCGAATGGT ACCGGGTGCG GGCGCAGGAG GAGGACCGCG AGCGGCACGA CCGGTGCCGG CGGCAGCGGC
                                                                 NotI
                                                                 ------
 71 TCGCCCTCCTC CTCCTCCTTC GCCGACTCCA ACCCGATCCG GCCCGTCACC GACCGCGCGG CCGCCTCCAC
    AGCGGGAGGAG GAGGAGGAAG CGGCTGAGGT TGGGCTAGGC CGGGCAGTGG CTGGCGCGCC GGCGGAGGTG 141 GCAGGGCATC TCCGAAGACC TCTACAGCCG TTTAGTCGAA ATGGCCACTA TCTCCCAAGC TGCCTACGCC
    CGTCCCGTAG AGGCTTCTGG AGATGTCGGC AAATCAGCTT TACCGGTGAT AGAGGGTTCG ACGGATGCGG
                              SalI
                              ------
                              AccI
                              ------
211 GACCTGTGCA ACATTCCGTC GACTATTATC AAGGGAGAGA AAATTTACAA TTCTCAAACT GACATTAACG
    CTGGACACGT TGTAAGGCAG CTGATAATAG TTCCCTCTCT TTTAAATGTT AAGAGTTTGA CTGTAATTGC
          BamHI
          ------
281 GATGGATCCT CCGCGACGAC AGCAGCAAAG AAATAATCAC CGTCTTCCGT GGCACTGGTA GTGATACGAA
    CTACCTAGGA GGCGCTGCTG TCGTCGTTTC TTTATTAGTG GCAGAAGGCA CCGTGACCAT CACTATGCTT 351 TCTACAACTC GATACTAACT ACACCCTCAC GCCTTTCGAC ACCCTACCAC AATGCAACGG TTGTGAAGTA
    AGATGTTGAG CTATGATTGA TGTGGGAGTG CGGAAAGCTG TGGGATGGTG TTACGTTGCC AACACTTCAT 421 CACGGTGGAT ATTATATTGG TAATATAACC ATGGGTCTCC GTCCAGGACC AAGTCGAGTC GCTTGTCAAA CAGCAGGTTA
    GTGCCACCTA TAATATAACC ATTAC-- CAGGGTCTGG TTCAGCTCAG CGAACAGTTT GTCGTCCAAT 491 GCCAGTATCC GGACTACGCG CTGACCGTGA CCGGCCACKC CCTCGGCGCC TCCCTGGCGG CACTCACTGC
    CGGTCATAGG CCTGATGCGC GACTGGCACT GGCCGGTGMG GGAGCCGCGG AGGGACCGCC GTGAGTGACG 561 CGCCCAGCTG TCTGCGACAT ACGACAAACAT CCGCCTGTAC ACCTTCGGCG AACCGCGCAG CGGCAATCAG
    GCGGGTCGAC AGACGCTGTA TGCTGTTGTA GGCGGACATG TGGAAGCCGC TTGGCGCGTC GCCGTTAGTC
```

FIG._43B

```
                                  XhoI
                                  ------
 631  GCCTTCGCGT CGTACAATGAA CGATGCCTTC CAAGCCTCGA GCCCAGATAC GACGCAGTAT TTCCGGGTCA
      CGGAAGCGCA GCATGTACTT GCTACGGAAG GTTCGGAGCT CGGGTCTATG CTGCGTCATA AAGGCCCAGT

NcoI
                                                              ------
 701  CTCATGCCAA CGACGGCATC CCAAACCTGC CCCCGGTGGA GCAGGGGTAC GCCCATGGCG GTGTAGAGTA
      GAGTACGGTT GCTGCCGTAG GGTTTGGACG GGGGCCACCT CGTCCCCATG CGGGTACCGC CACATCTCAT

771  CTGGGAGCGT GATCCTTACA GCGCCCAGAA CACATTTGTC TGCACTGGGG ATGAAGTGCA GTGCTGTGAG
      GACCCTCGCA CTAGGAATGT CGCGGGTCTT GTGTAAACAG ACGTGACCCC TACTTCACGT CACGACACTC

SphI
                                                                         ------
 841  GCCCAGGGCG GACAGGGTGT GAATAATGCG CACACGACTT ATTTTGGGAT GACGAGCCGC GCATGCACCT
      CGGGTCCCGC CTGTCCCACA CTTATTACGC GTGTGCTGAA TAAAACCCTA CTGCTCGGCG CGTACGTGGA

NotI
              ----------
 911  GGCCGGTCGC GGCCGCGGAA ACCACTGAAG GATGAGCTGT AAAGAAGCAG ATCGTTCAAA CATTTGGCAA
      CCGGCCAGCG CCGGCGCCTT TGGTGACTTC CTACTCGACA TTTCTTCGTC TAGCAAGTTT GTAAACCGTT

981  TAAAGTTTCT TAAGATTGAA TCCTGTTGCC GGTCTTGCGA TGATTATCAT ATAATTTCTG TTGAATTACG
      ATTTCAAAGA ATTCTAACTT AGGACAACGG CCAGAACGCT ACTAATAGTA TATTAAAGAC AACTTAATGC

1051  TTAAGCATGT AATAATTAAC ATGTAATGCA TATGAGATGG TGACGTTATT TATGAGATGG GTTTTTATGA TTAGAGTCCC
      AATTCGTACA TTATTAATTG TACATTACGT ACTGCAATAA ATACTCTACC CAAAAATACT AATCTCAGGG

BssHII                                                     BssHII
              ------                                                     ------
1121  GCAATTATAC ATTTAATACG CGATAGAAAA CAAAATATAG CCGCGCAAACT AGGATAAATT ATCGCGCGCG
      CGTTAATATG TAAATTATGC GCTATCTTTT GTTTTATATC GGCGCGTTTGA TCCTATTTAA TAGCGCGCGC
```

FIG._43C

```
                                                                    XbaI
                                                       ClaI  HindIII
                                                     ~~~~~~~~~~~~~
1191  GTGTCATCTA TGTTACTAGA TCGATAAGCT TCTAGAGCGG CCGGTGGAGC TCCAATTCGC CCTATAGTGA
      CACAGTAGAT ACAATGATCT AGCTATTCGA AGATCTCGCC GGCCACCTCG AGGTTAAGCG GGATATCACT
               BssHII
               ~~~~~~
1261  GTCGTATTAC GCGCGCTCAC TGGCCGTCGT TTTACAACGT CGTGACTGGG AAAACCCTGG CGTTACCCAA
      CAGCATAATG CGCGCGAGTG ACCGGCAGCA AAATGTTGCA GCACTGACCC TTTTGGGACC GCAATGGGTT 1331  CTTAATCGCC TTGCAGCACA TCCCCCTTTC GCCAGCTGGC GTAATAGCGA AGAGGCCCGC ACCGATCGCC
      GAATTAGCGG AACGTCGTGT AGGGGGAAAG CGGTCGACCG CATTATCGCT TCTCCGGGCG TGGCTAGCGG 1401  CTTCCCAACA GTTGCGCAGC CTGAATGGCG AATGGGACGC GCCCTGTAGC GGCGCATTAA GCGCGGCGGG
      GAAGGGTTGT CAACGCGTCG GACTTACCGC TTACCCTGCG CGGGACATCG CCGCGTAATT CGCGCCGCCC 1471  TGTGGTGGTT ACGCGCAGCG TGACCGCTAC ACTTGCCAGC GCCCTAGCGC CCGCTCCTTT CGCTTTCTTC
      ACACCACCAA TGCGCGTCGC ACTGGCGATG TGAACGGTCG CGGGATCGCG GGCGAGGAAA GCGAAAGAAG 1541  CCTTCCTTTC TCGCCACGTT CGCCGGCTTT CCCCGTCAAG CTCTAAATCG GGGGCTCCCT TTAGGGTTCC
      GGAAGGAAAG AGCGGTGCAA GCGGCCGAAA GGGGCAGTTC GAGATTTAGC CCCCGAGGGA AATCCCAAGG 1611  GATTTAGTGC TTTACGGCAC CTCGACCCCA AAAAACTTGA TTAGGGTGAT GGTTCACGTA GTGGGCCATC
      CTAAATCACG AAATGCCGTG GAGCTGGGGT TTTTTGAACT AATCCCACTA CCAAGTGCAT CACCCGGTAG 1681  GCCCTGATAG ACGGTTTTTC GCCCTTTGAC GTTGGAGTCC ACGTTCTTTA ATAGTGGACT CTTGTTCCAA
      CGGGACTATC TGCCAAAAAG CGGGAAACTG CAACCTCAGG TGCAAGAAAT TATCACCTGA GAACAAGGTT 1751  ACTGAACAA CACTCAACCC TATCTCGGTC TATTCTTTTG ATAGTGGTTC AATTATAAGG GATTTGCCGC ATTTCGCCT
      TGACTTGTT GTGAGTTGGG ATAGAGCCAG ATAAGAAAAC TAAATGCG    CTAAAACGGC TAAAGCCGGA 1821  ATTGGTTAAA AAATGAGCTG ATTTAACAAA AATTTAACGC GAATTTTAAC AAAATATTAA CGCTTACAAT
      TAACCAATTT TTTACTCGAC TAAATTGTTT TTAAATTGCG CTTAAAATTG TTTTATAATT GCGAATGTTA

FIG._43D
```

```
1891  TTAGTTGGCA CTTTTCGGGG AAATGTGCGC GGAACCCCTA TTTGTTTATT TTTCTAAATA CATTCAAATA
      AATCCACCGT GAAAAGCCCC TTTACACGCG CCTTGGGGAT AAACAAATAA AAAGATTTAT GTAAGTTTAT

1961  TGTATCCGCT CATGAGACAA TAACCCTGAT AAATGCTTCA ATAATATTGA AAAAGGAAGA GTATGAGTAT
      ACATAGGCGA GTACTCTGTT ATTGGGACTA TTTACGAAGT TATTATAACT TTTTCCTTCT CATACTCATA

2031  TCAACATTTC CGTGTCGCCC TTATTCCCTT TTTTGCGGCA TTTTGCCTTC CTGTTTTTGC TCACCCAGAA
      AGTTGTAAAG GCACAGCGGG AATAAGGGAA AAAACGCCGT AAAACGGAAG GACAAAAACG AGTGGGTCTT

2101  ACGCTGGTGA AAGTAAAAGA TGCTGAAGAT CAGTTGGGTG CACGAGTGGT TTACATCGAA CTGGATCTCA
      TGCGACCACT TTCATTTTCT ACGACTTCTA GTCAACCCAC GTGCTCACCC AATGTAGCTT GACCTAGAGT

2171  ACAGCGGTAA GATCCTTGAG AGTTTCGCCC CCGAAGAACG TTTTCCAATG ATGAGCACTT TTAAAGTTCT
      TGTCGCCATT CTAGGAACTC TCAAAGCGGG GGCTTCTTGC AAAAGGTTAC TACTCGTGAA AATTTCAAGA

2241  GCTATGTGGC GCGGTATTAT CCCGTATTGA CGCCGGGCAA GAGCAACTCG GTCGCCGCAT ACACTATTCT
      CGATACACCG CGCCATAATA GGGCATAACT GCGGCCCGTT CTCGTTGAGC CAGCGGCGTA TGTGATAAGA

2311  CAGAATGACT TGGTTGAGTA CTCACCAGTC ACAGAAAAGC ATCTTACGGA TGGCATGACA GTAAGAGAAT
      GTCTTACTGA ACCAACTCAT GAGTGGTCAG TGTCTTTTCG TAGAATGCCT ACCGTACTGT CATTCTCTTA

2381  TATGCAGTGC TGCCATAACC ATGAGTGATA ACACTGCGGC CAACTTACTT CTGACAACGA TCGGAGGACC
      ATACGTCACG ACGGTATTGG TACTCACTAT TGTGACGCCG GTTGAATGAA GACTGTTGCT AGCCTCCTGG

2451  GAAGGAGCTA ACCGCTTTTT TGCACAACAT GGGGGATCAT GTAACTCGCC TTGATCGTTG GGAACCGGAG
      CTTCCTCGAT TGGCGAAAAA ACGTGTTGTA CCCCCTAGTA CATTGAGCGG AACTAGCAAC CCTTGGCCTC

2521  CTGAATGAAG CCATACCAAA CGACGAGCGT GACACCACGA TGCCTGTAGC AATGGCAACA ACGTTGCGCA
      GACTTACTTC GGTATGGTTT GCTGCTCGCA CTGTGGTGCT ACGGACATCG TTACCGTTGT TGCAACGCGT

2591  AACTATTAAC TGGCGAACTA CTTACTCTAG CTTCCCGGCA ACAATTAATA GACTGGATGG AGGCGGATAA
      TTGATAATTG ACCGCTTGAT GAATGAGATC GAAGGGCCGT TGTTAATTAT CTGACCTACC TCCGCCTATT

2661  AGTTGCAGGA CCACTTCTGC GCTCGGCCCT TCCGGCTGGC TGGTTTATTG CTGATAAATC TGGAGCCGGT
      TCAACGTCCT GGTGAAGACG CGAGCCGGGA AGGCCGACCG ACCAAATAAC GACTATTTAG ACCTCGGCCA
```

FIG._43E

```
2731  GAGCGTGGGT CTCGCGTAT CATTGCAGCA CTGGGGCCAG ATGGTAAGCC CTCCCGTATC GTAGTTATCT
      CTCGCACCCA GAGCGCCATA GTAACGTCGT GACCCCGGTC TACCATTCGG GAGGGCATAG CATCAATAGA

2801  ACACGACGGG GAGTCAGGCA ACTATGGATG AACGAAATAG ACAGATCGCT GAGATAGGTG CCTCACTGAT
      TGTGCTGCCC CTCAGTCCGT TGATACCTAC TTGCTTTATC TGTCTAGCGA CTCTATCCAC GGAGTGACTA

2871  TAAGCATTGG TAACTGTCAG ACCAAGTTTA CTCATATATA CTTTAGATTG ATTTAAAACT TCATTTTAA
      ATTCGTAACC ATTGACAGTC TGGTTCAAAT GAGTATATAT GAAATCTAAC TAAATTTGA AGTAAAAATT

2941  TTTAAAAGGA TCTAGGTGAA GATCCTTTTT GATAATCTCA TGACCAAAAT CCCTTAACGT GAGTTTTCGT
      AAATTTTCCT AGATCCACTT CTAGGAAAAA CTATTAGAGT ACTGGTTTTA GGGAATTGCA CTCAAAAGCA

3011  TCCACTGAGC GTCAGACCCC GTAGAAAAGA TCAAAGGATC TTCTTGAGAT CCTTTTTTTC TGCGCGTAAT
      AGGTGACTCG CAGTCTGGGG CATCTTTTCT AGTTTCCTAG AAGAACTCTA GGAAAAAAAG ACGCGCATTA

3081  CTGCTGCTTG CAAACAAAAA AACCACCGCT ACCAGCGGTG GTTTGTTTGC CGGATCAAGA GCTACCAACT
      GACGACGAAC GTTTGTTTTT TTGGTGGCGA TGGTCGCCAC CAAACAAACG GCCTAGTTCT CGATGGTTGA

3151  CTTTTTCCGA AGGTAACTGG CTTCAGCAGA GCGCAGATAC CAAATACTGT TCTTCTAGTG TAGCCGTAGT
      GAAAAAGGCT TCCATTGACC GAAGTCGTCT CGCGTCTATG GTTTATGACA AGAAGATCAC ATCGGCATCA

3221  TAGGCCACCA CTTCAAGAAC TCTGTAGCAC CGCCTACATA CCCTCGCTCT CTAATCCTGT TACCAGTGGC
      ATCCGGTGGT GAAGTTCTTG AGACATCGTG GCGGATGTAT GGGAGCGAGA GATTAGGACA ATGGTCACCG

3291  TGCTGCCAGT GGCGATAAGT CGTGTCTTAC CGGGTTGGAC TCAAGACGAT AGTTACCGGA TAAGGCGCAG
      ACGACGGTCA CCGCTATTCA GCACAGAATG GCCCAACCTG AGTTCTGCTA TCAATGGCCT ATTCCGCGTC

3361  CGGTCGGGCT GAACGGGGGG TTCGTGCACA CAGCCCAGCT TGGAGCGAAC GACCTACACC GAACTGAGAT
      GCCAGCCCGA CTTGCCCCCC AAGCACGTGT GTCGGGTCGA ACCTCGCTTG CTGGATGTGG CTTGACTCTA

3431  ACCTACAGCG TGAGCTATGA GAAAGCGCCA CGCTTCCCGA AGGGAGAAAG GCGGACAGGT ATCCGGTAAG
      TGGATGTCGC ACTCGATACT CTTTCGCGGT GCGAAGGGCT TCCCTCTTTC CGCCTGTCCA TAGGCCATTC

3501  CGGCAGGGTC GGAACAGGAG AGCGCACGAG GGAGCTTCCA GGGGGAAACG CCTGGTATCT TTATAGTCCT
      GCCGTCCCAG CCTTGTCCTC TCGCGTGCTC CCTCGAAGGT CCCCCTTTGC GGACCATAGA AATATCAGGA
```

FIG._43F

```
3571  GTCGGGTTTC GCCACCTCTG ACTTGAGCGT CGATTTTTGT GATGCTCGTC AGGGGGGCGG AGCCTATGGA
      CAGCCCAAAG CGGTGGAGAC TGAACTCGCA GCTAAAAACA CTACGAGCAG TCCCCCCGCC TCGGATACCT

3641  AAAACGCCAG CAACGCGGCC TCCTGGCCTT TTGCTGGCCT TATTACCGCC TTTGCTCACA TGTTCTTTCC
      TTTTGCGGTC GTTGCGCCGG AGGACCGGAA AACGACCGGA ATAATGGCGG AAACGAGTGT ACAAGAAAGG

3711  TGCGTTATCC CCTGATTCTG TGGATAACCG TATTACCGCC TTTGAGTGAG CTGATACCGC TCGCCGCAGC
      ACGCAATAGG GGACTAAGAC ACCTATTGGC ATAATGGCGG AAACTCACTC GACTATGGCG AGCGGCGTCG

3781  CGAACGACCG AGCGCAGCGA GTCAGTGAGC GAGGAAGCGG AAGAGCGCCC AATACGCAAA CCGCCTCTCC
      GCTTGCTGGC TCGCGTCGCT CAGTCACTCG CTCCTTCGCC TTCTCGCGGG TTATGCGTTT GGCGGAGAGG

3851  CCGCGCGTTG GCCGATTCAT TAATGCAGCT GGCACGACAG GTTTCCCGAC TGGAAAGCGG GCAGTGAGCG
      GGCGCGCAAC CGGCTAAGTA ATTACGTCGA CCGTGCTGTC CAAAGGGCTG ACCTTTCGCC CGTCACTCGC

3921  CAACGCAATT AATGTGAGTT AGCTCACTCA TTAGGCACCC CAGGCTTTAC ACTTTATGCT TCCGGCTCGT
      GTTGCGTTAA TTACACTCAA TCGAGTGAGT AATCCGTGGG GTCCGAAATG TGAAATACGA AGGCCGAGCA
                                                                            BssHII

3991  ATGTTGTGTG GAATTGTGAG CGGATAACAA TTTCACACAG GAAACAGCTA TGACCATGAT TACGCCAAGC
      TACAACACAC CTTAACACTC GCCTATTGTT AAAGTGTGTC CTTTGTCGAT ACTGGTACTA ATGCGGTTCG
      BssHII                         EcoRI

4061  GCGCAATTAA CCCTCACTAA AGGGAACAAA AGCTGGAATT CCACAATGAA CAATAATAAG ATTAAAATAG
      CGCGTTAATT GGGAGTGATT TCCCTTGTTT TCGACCTTAA GGTGTTACTT GTTATTATTC TAATTTTATC

4131  CTTGCCCCCG TTGCAGCGAT GGGTATTTTT TCTAGTAAAA TAAAAGATAA ACTTAGACTC AAAACATTTA
      GAACGGGGGC AACGTCGCTA CCCATAAAAA AGATCATTTT ATTTTCTATT TGAATCTGAG TTTTGTAAAT

4201  CAAAAACAAC CCCTAAAGTC CTAAAGCCCA AAGTGCTATG CACGATCCAT AGCAAGCCCA GCCCAACCCA
      GTTTTTGTTG GGGATTTCAG GATTTCGGGT GTTCACGATAC GTGCTAGGTA TCGTTCGGGT CGGGTTGGGT
```

FIG._43G

```
4271  ACCCAACCCA  ACCCACCCCA  GTGCAGCCAA  CTGGCAAATA  GTCTCCACCC  CCGGCACTAT  CACCGTGAGT
      TGGGTTGGGT  TGGGTGGGGT  CACGTCGGTT  GACCGTTTAT  CAGAGGTGGG  GGCCGTGATA  GTGGCACTCA

4341  TGTCCGCACC  ACCGCACGTC  TCGCAGCCAA  AAAAAAAAAA  AGAAAGAAAA  AAAAGAAAAA  GAAAAACAGC
      ACAGGCGTGG  TGGCGTGCAG  AGCGTCGGTT  TTTTTTTTTT  TCTTTCTTTT  TTTTCTTTTT  CTTTTTGTCG

4411  AGGTGGGTCC  GGGTCGTGGG  GGCCGGAAAA  GCGAGGAGGA  TCGCGAGCAG  CGACGAGGCC  CGGCCCTCCC
      TCCACCCAGG  CCCAGCACCC  CCGGCCTTTT  CGCTCCTCCT  AGCGCTCGTG  GCTGCTCCGG  GCCGGGAGGG

4481  TCCGCTTCCA  AAGAAACGCC  CCCCATCGCC  ACTATATACA  TACCCCCCCC  TCTCCTCCCA  TCCCCCCAAC
      AGGCGAAGGT  TTCTTTGCGG  GGGGTAGCGG  TGATATATGT  ATGGGGGGGG  AGAGGAGGGT  AGGGGGGTTG

4551  CCTACCACCA  CCACCACCAC  CCCCTCCTCC  CCCCTCGCTG  CCGGACGACG  AGCTCCTCCC  CCCTCCCCCT
      GGATGGTGGT  GGTGGTGGTG  GGGGAGGAGG  GGGGAGCGAC  GGCCTGCTGC  TCGAGGAGGG  GGGAGGGGGA

4621  CCGCCGCCGC  CGGTAACCAC  CCCGCCCCTC  TCCTCTTTCT  TTCTCCGTTT  TTTTTTTCGT  CTCGGTCTCG
      GGCGGCGGCG  GCCATTGGTG  GGGCGGGGAG  AGGAGAAAGA  AAGAGGCAAA  AAAAAAAGCA  GAGCCAGAGC

4691  ATCTTTGGCC  TTGGTAGTTT  GGGTGGGCGA  GAGCGGCTTC  GTCGCCCAGA  TCGGTGCGCG  GGAGGGGCGG
      TAGAAACCGG  AACCATCAAA  CCCACCCGCT  CTCGCCGAAG  CAGCGGGTCT  AGCCACGCGC  CCTCCCCGCC

BamHI                    BglII

4761  GATCTCGCGG  CTGGCGTCTC  CGGGGCGTGA  TCGGGCCCGA  TCCTCGCGGG  GAATGGGGCT  CTCGGATGTA
      CTAGAGCGCC  GACCGCAGAG  GCCCCGCACT  AGCCCGGGCT  AGGAGCGCCC  CTTACCCCGA  GAGCCTACAT
      BglII

4831  GATCTTCTTT  CTTTCTTTCTT  TTTGTGGTAG  AATTTGAAATC  CCTCAGCATT  GTTCATCGGT  AGTTTTCTT
      CTAGAAGAAA  GAAAGAAAGAA  AAACACCATC  TTAAACTTAG  GGAGTCGTAA  CAAGTAGCCA  TCAAAAAGAA

4901  TTCATGATTT  GTGACAAATG  CAGCCCTCGTG  CGGAGCTTTT  TTGTAGGTAG
      AAGTACTAAA  CACTGTTTAC  GTCGGAGCAC  GCCTGAAAA  AACATCCATC
```

FIG._43H

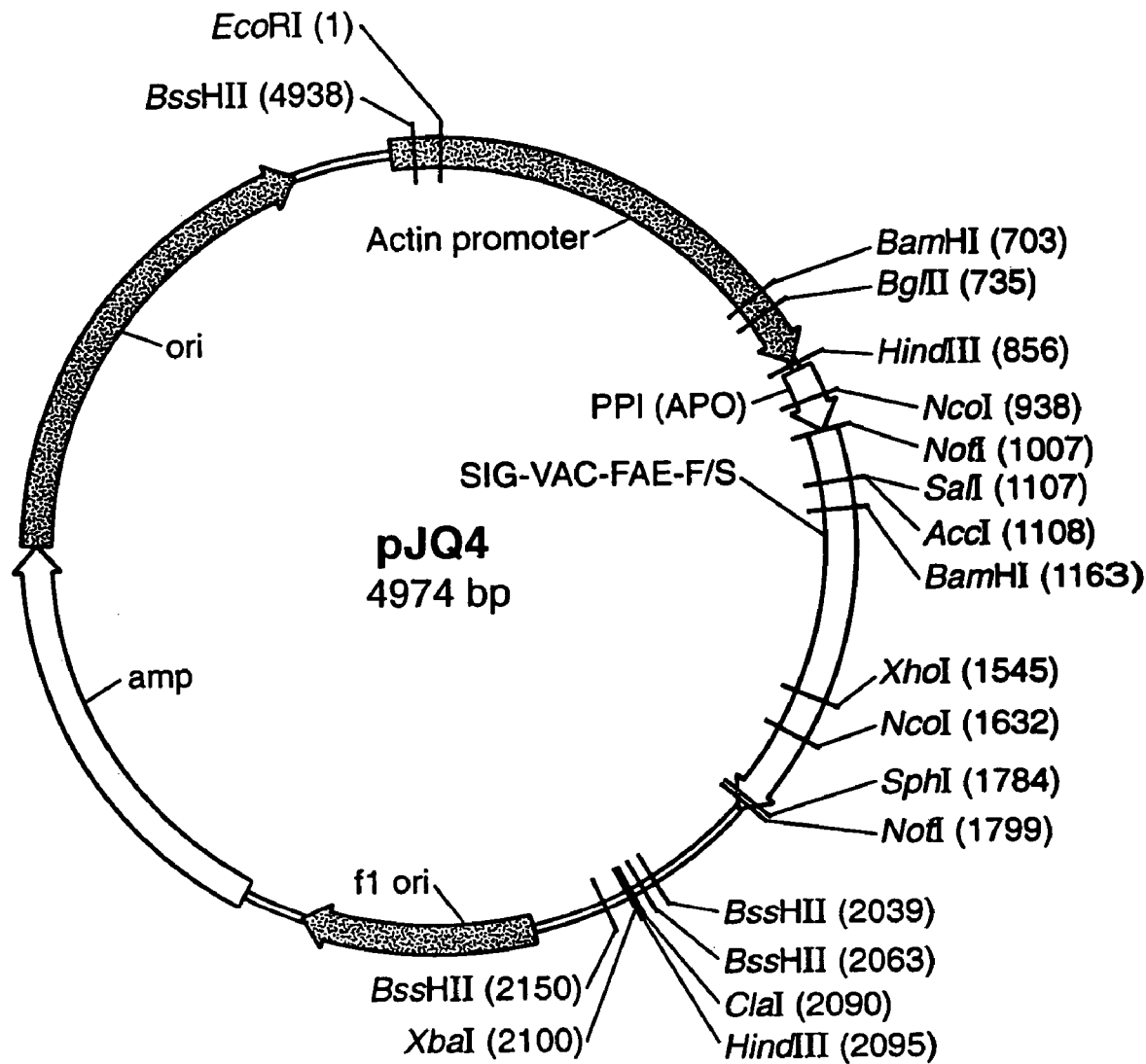
FIG._44A

```
      EcoRI
      -----
  1   AATTCCACAA TGAACAATAA TAAGATTAAA ATAGCTTGCC CCCGTTGCAG CGATGGGTAT TTTTTCTAGT
      TTAAGGTGTT ACTTGTTATT ATTCTAATTT TATCGAACGG GGGCAACGTC GCTACCCATA AAAAAGATCA

71   AAAATAAAAG ATAAACTTAG ACTCAAAACA TTTACAAAAA CCCAACCCTAA AGTCCTAAAG CCCAAAGTGC
      TTTTATTTTC TATTTGAATC TGAGTTTTGT AAATGTTTTT GTTGGGGATT TCAGGATTTC GGGTTTCACG

141   TATGCACGAT CCATAGCAAG CCCAGCCCAA CCCAACCCAC CCCAGTGCAG CCAACTGGCA
      ATACGTGCTA GGTATCGTTC GGGTCGGGTT GGGTTGGGTG GGGTCACGTC GGTTGACCGT

211   AATAGTCTCC ACCCCCGGCA CTATCACCGT GAGTTGTCCG CACCACCGCA CGTCTCCGCAG CCAAAAAAAA
      TTATCAGAGG TGGGGGCCGT GATAGTGGCA CTCAACAGGC GTGGTGGCGT GCAGAGCGTC GGTTTTTTTT

281   AAAAGAAAG AAAAGAAAAA TTTTCTTTT CAGCAGGTGG GTCCGGGTCG TGGGGCCGG AAAAGCGAGG
      TTTTCTTTC TTTTCTTTTT GTCGTCCACC CAGGCCCAGC ACCCCGGCC TTTTCGCTCC

351   AGGATCGCGA GCAGCGACGA GGCCCGGCCC TCCAAAGAAA CGCCCCCAT CGCCACTATA
      TCCTAGCGCT CGTCGCTGCT CCGGGCCGGG AGGTTTCTTT GCGGGGGGTA GCGGTGATAT

421   TACATACCCC CCCCTCTCCT CCCATCCCCC CAACCCTACC ACCACCACCA CTCCCCCCTC
      ATGTATGGGG GGGGAGAGGA GGGTAGGGGG GTTGGGATGG TGGTGGTGGT GAGGGGGAG

491   GCTGCCGGAC GACGAGCTCC TCCCCCCTCC CCGCCCGGTAA CCGCCGGTAA CCTCTCCTCT
      CGACGGCCTG CTGCTCGAGG AGGGGGAGG GGGAGGGGG GGCGGCCATT GGTGGGGCGG GGAGAGGAGA

561   TTCTTTCTCC GTTTTTTTTT TCGTCTCGGT CTCGATCTTT GGCCTTGGTA GTTTGGGTGG GCGAGAGCGG
      AAGAAAGAGG CAAAAAAAAA AGCAGAGCCA GAGCTAGAAA CCGGAACCAT CAAACCCACC CGCTCTCGCC

631   CTTCGTCGCC CAGATCGGTG CGCGGGAGGG GCGGGATCTC GCGGCTGGCG TCTCCGGGCG TGAGTCGGCC
      GAAGCAGCGG GTCTAGCCAC GCGCCCTCCC CGCCCTAGAG CGCCGACCGC AGAGGCCCGC ACTCAGCCGG

BamHI                                   BglII
      -----                                   -----
701   CGGATCCTCG CGGGGAATGG GGCTCTCGGA TGTAGATCTT CTTTCTTTCT TCTTTTTGTG GTAGAATTTG
      GCCTAGGAGC GCCCCTTACC CCGAGAGCCT ACATCTAGAA GAAAGAAAGA AGAAAAACAC CATCTTAAAC
```

FIG._44B

```
 771  AATCCCTCAG CATTGTTCAT CGGTAGTTTT TCTTTTCATG AATGCAGCCT CGTGCGGAGC
      TTAGGGAGTC GTAACAAGTA GCCATCAAAA AGAAAAGTAC ATTTGTGACA TTACGTCCGA GCACGCCTCG
                                                  TAAACACTGT

HindIII
                            --------

841  TTTTTTGTAG GTAGAAGCTT ACMATGGMCG TGCACAAGGA GGTSAACTTC TCCTGATCGT
      AAAAAACATC CATCTTCGAA TGKTACCCKGC ACGTGTTCCT CCASTTGAAG CASCGGATGG AGGACTAGCA
                                                                GTSGCCTACC

NcoI
                                        --------

911  SCTCGGCCTC CTCTTGCTCG TSTCCGCCAT GGAGCACGTG GACGCCAAGG CCTGCACCCK CGAGTGCGGC
      SGAGCCGGAG GAGAACGAGC ASAGGCGGTA CCTCGTGCAC CTGCGGGTTCC GGACGTGGGM GCTCACGCCG

NotI
                                                              --------

981  AACCTCGGCT TCGGCATCTG CCCGGCGCGCC GCCTCCACGC AGGGCATCTC CGAAGACCTC TACAGCCGTT
      TTGGAGCCGA AGCCGTAGAC GGGCCGCCGG CGGAGGTGCG TCCCGTAGAG GCTTCTGGAG ATGTCGGCAA

SalI
                                                                        --------
                                                                        AccI
                                                                        --------

1051  TAGTCGAAAT GGCCACTATC TCCCAAGCTG CCTGTGCAAC ATTCCGTCGA CTATTATCAA
      ATCAGCTTTA CCGGTGATAG AGGGTTCGAC GGACACGTTG TAAGGCAGCT GATAATAGTT

BamHI
                                                  --------

1121  GGGAGAGAAA ATTTACAATT CTCAAACTGA TGGATCCTCC GCGACGACAG CAGCAAAGAA
      CCCTCTCTTT TAAATGTTAA GAGTTTGACT ACCTAGGAGG CGCTGCTGTC GTCGTTTCTT

1191  ATAAATCACCG TCTTCCGTGG CACTGGTAGT GATACGAAATC TACTAACTGA ACCCTCACGC
      TATTAGTGGC AGAAGGCACC GTGACCATCA CTATGCTTAG ATGTTGAGCT TGGGAGTGCG

1261  CTTCGACACA CCTACCACAA TGCAACGGTT GTGAAGTACA CGGTGGATAT TATATTGGAT GGGTCTCCGT
      GAAAGCTGTG GGATGGTGTT ACGTTGCCAA CACTTCATGT GCCACCTATA ATATAACCTA CCCAGAGGCA
```

*FIG. 44C*

```
1331  CCAGGACCAA GTCGAGTCGC TTGTCAAACA GCAGGTTAGC CAGTATCCGG ACTACGCGCT GACCGTGACC
      GGTCCTGGTT CAGCTCAGCG AACAGTTTGT CGTCCAATCG GTCATAGGCC TGATGCGCGA CTGGCACTGG

1401  GGCCACKCCC TCGGCGCCTC CCTGGCGGCA CTCACTGCCG CCCAGCTGTC TGCGACATAC GACAACATCC
      CCGGTGMGGG AGCCGCGGAG GGACCGCCGT GAGTGACGGC GGGTCGACAG ACGCTGTATG CTGTTGTAGG

1471  GCCTGTACAC CTTCGGCGAA CCGCGCAGCG GCAATCAGGC CTTCGCGTCG TACATGAACG ATGCCTTCCA
      CGGACATGTG GAAGCCGCTT GGCGCGTCGC CGTTAGTCCG GAAGCGCAGC ATGTACTTGC TACGGAAGGT

1541  AGCCTCGAGC CCAGATACGA CGCAGTATTT CCGGGTCACT CATGCCAACG ACGGCATCCC AAACCTGCCC
      TCGGAGCTCG GGTCTATGCT GCGTCATAAA GGCCCAGTGA GTACGGTTGC TGCCGTAGGG TTTGGACGGG
            XhoI                                    NcoI

1611  CCGGTGGAGC AGGGGTACGC CCATGGCGGT GTAGAGTACT GGAGCGTTGA TCCTTACAGC GCCCAGAACA
      GGCCACCTCG TCCCCATGCG GGTACCGCCA CATCTCATGA CCTCGCAACT AGGAATGTCG CGGGTCTTGT

1681  CATTTGTCTG CACTGGGGAT GAAGTGCAGT GCTGTGAGGC CCAGGGCGGA CAGGGTGTGA ATAATGCGCA
      GTAAACAGAC GTGACCCCTA CTTCACGTCA CGACACTCCG GGTCCCGCCT GTCCCACACT TATTACGCGT
                                          SphI

1751  CACGACTTAT TTTGGGATGA CGAGCGGCGC ATGCACCTGG AAGTTCTTTA AGATTGAATC CTGTTGCCGG
      GTGCTGAATA AAACCCTACT GCTCGCCGCG TACGTGGACC TTCAAAGAAT TCTAACTTAG GACAACGGCC
                                                                    NotI

1821  TGAGCTGTAA AGAAGCAGAT CGTTCAAACA TTTGGCAATA AAGCATGTAA TAATTAACAT GTAATGCATG
      ACTCGACATT TCTTCGTCTA GCAAGTTTGT AAACCGTTAT TTCGTACATT ATTAATTGTA CATTACGTAC

1891  TCTTGCGATG ATTATCATAT AATTTCTGTT GAATTACGTT AAGCATGTAA TAATTAACAT TTAATACGCG
      AGAACGCTAC TAATAGTATA TTAAAGACAA CTTAATGCAA TTCGTACATT ATTAATTGTA AATTATGCGC

1961  ACGTTATTTA TGAGATGGGT TTTTATGATT AGAGTCCCGC AATTATACAT TTAATACGCG ATAGAAAACA
      TGCAATAAAT ACTCTACCCA AAAATACTAA TCTCAGGGCG TTAATATGTA AATTATGCGC TATCTTTTGT
```

FIG._44D

```
                     BssHII                                                                    XbaI
                   ~~~~~~~~                                                                    ~~~~
                                                                                ClaI   HindIII
                                                      BssHII                    ~~~~   ~~~~~~~
                                                    ~~~~~~~~
2031  AAATATAGCG CGCAAACTAG GATAAATTAT CGCGCGCGGT GTCATCTATG TTACTAGATC GATAAGCTTC
      TTTATATCGC GCGTTTGATC CTATTTAATA GCGCGCGCCA CAGTAGATAC AATGATCTAG CTATTCGAAG XbaI                                                   BssHII
      ~~~~                                                  ~~~~~~~~
2101  TAGAGCGGCC GGTGGAGCTC CAATTCGCCC TATAGTGAGT CGTATTACGC GCGCTCACTG GCCGTCGTTT
      ATCTCGCCGG CCACCTCGAG GTTAAGCGGG ATATCACTCA GCATAATGCG CGCGAGTGAC CGGCAGCAAA 2171  TACAACGTCG TGACTGGGAA AACCCTGGCG TTACCCAACT TAATCGCCTT GCAGCACATC CCCCTTTCGC
      ATGTTGCAGC ACTGACCCTT TTGGGACCGC AATGGGTTGA ATTAGCGGAA CGTCGTGTAG GGGGAAAGCG 2241  CAGCTGGCGT AATAGCGAAG AGCCCGCAC  CGATCGCCCT TCCCAACAGT TGCGCAGCCT GAATGGCGAA
      GTCGACCGCA TTATCGCTTC TCCGGGCGTG GCTAGCGGGA AGGGTTGTCA ACGCGTCGGA CTTACCGCTT 2311  TGGGACGCGC CCTGTAGCGG CGCATTAAGC GCGGCGGGTG TGGTGGTTAC GCGCAGCGTG ACCGCTACAC
      ACCCTGCGCG GGACATCGCC GCGTAATTCG CGCCGCCCAC ACCACCAATG CGCGTCGCAC TGGCGATGTG 2381  TTGCCAGCGC CCTAGCGCCC GCTCCTTTCG CTTTCTTCCC TTCCTTTCTC GCCACGTTCG CCGGCTTTCC
      AACGGTCGCG GGATCGCGGG CGAGGAAAGC GAAAGAAGGG AAGGAAAGAG CGGTGCAAGC GGCCGAAAGG 2451  CCGTCAAGCT CTAAATCGGG GGCTCCCTTT AGGGTTCCGA TTTAGTGCTT TACGGCACCT CGACCCCAAA
      GGCAGTTCGA GATTTAGCCC CCGAGGGAAA TCCCAAGGCT AAATCACGAA ATGCCGGTGGA GCTGGGGTTT 2521  AAACTTGATT AGGGTGATGG TTCACGTAGT GGGCCATCGC CCTGATAGAC GGTTTTTCGC CCTTTGACGT
      TTTGAACTAA TCCCACTACC AAGTGCATCA CCCGGTAGCG GGACTATCTG CCAAAAAGCG GGAAACTGCA 2591  TGGAGTCCAC GTTCTTTAAT AGTGGACTCT TGTTCCAAAC TGGAACAACA CTCAACCCTA TCTCGGTCTA
      ACCTCAGGTG CAAGAAATTA TCACCTGAGA ACAAGGTTTG ACCTTGTTGT GAGTTGGGAT AGAGCCAGAT 2661  TTCTTTTGAT TTATAAGGGA TTTTGCCGAT TTCGGCCTAT TGGTTAAAAA ATGAGCTGAT TTAACAAAAA
      AAGAAAACTA AATATTCCCT AAAACGGCTA AAGCCGGATA ACCAATTTTT TACTCGACTA AATTGTTTT
```

FIG._44E

```
2731  TTTAACGCGA ATTTTAACAA AATATTAACG CTTACAATTT AGGTGCACT TTTCGGGGAA ATGTGCGCGG
      AAATTGCGCT TAAAATTGTT TTATAATTGC GAATGTTAAA TCCACCGTGA AAAGCCCCTT TACACGCGCC

2801  AACCCCTATT TGTTTATTTT TCTAAATACA TTCAAATATG TATCCGCTCA TGAGACAATA ACCCTGATAA
      TTGGGGATAA ACAAATAAAA AGATTTATGT AAGTTTATAC ATAGGCGAGT ACTCTGTTAT TGGGACTATT

2871  ATGCTTCAAT AATATTGAAA AAGGAAGAGT ATGAGTATTC AACATTTCCG TGTCGCCCTT ATTCCCTTTT
      TACGAAGTTA TTATAACTTT TTCCTTCTCA TACTCATAAG TTGTAAAGGC ACAGCGGGAA TAAGGGAAAA

2941  TTGCGGCATT TTGCCTTCCT GTTTTTGCTC ACCCAGAAAC GCTGGTGAAA GTAAAAGATG CTGAAGATCA
      AACGCCGTAA AACGGAAGGA CAAAAACGAG TGGGTCTTTG CGACCACTTT CATTTTCTAC GACTTCTAGT

3011  GTTGGGTGCA CGAGTGGGTT ACATCGAACT GGATCTCAAC AGCGGTAAGA TCCTTGAGAG TTTTCGCCCC
      CAACCCACGT GCTCACCCAA TGTAGCTTGA CCTAGAGTTG TCGCCATTCT AGGAACTCTC AAAAGCGGGG

3081  GAAGAACGTT TTCCAATGAT GAGCACTTTT AAAGTTCTGC TATGTGGCGC GGTATTATCC CGTATTGACG
      CTTCTTGCAA AAGGTTACTA CTCGTGAAAA TTTCAAGACG ATACACCGCG CCATAATAGG GCATAACTGC

3151  CCGGGCAAGA GCAACTCGGT CGCCGCATAC ACTATTCTCA GAATGACTTG GTTGAGTACT CACCAGTCAC
      GGCCCGTTCT CGTTGAGCCA GCGGCGTATG TGATAAGAGT CTTACTGAAC CAACTCATGA GTGGTCAGTG

3221  AGAAAAGCAT CTTACGGATG GCATGACAGT AAGAGAATTA TGCAGTGCTG CCATAACCAT GAGTGATAAC
      TCTTTTCGTA GAATGCCTAC CGTACTGTCA TTCTCTTAAT ACGTCACGAC GGTATTGGTA CTCACTATTG

3291  ACTGCGGCCA ACTTACTTCT GACAACGATC GGAGGACCGA AGGAGCTAAC CGCTTTTTTG CACACAATGG
      TGACGCCGGT TGAATGAAGA CTGTTGCTAG CCTCCTGGCT TCCTCGATTG GCGAAAAAAC GTGTTGTACC

3361  GGGATCATGT AACTCGCCTT GATCGTTGGG AACCGGAGCT GAATGAAGCC ATACCAAACG ACGAGCGTGA
      CCCTAGTACA TTGAGCGGAA CTAGCAACCC TTGGCCTCGA CTTACTTCGG TATGGTTTGC TGCTCGCACT

3431  CACCACGATG CCTGTAGCAA TGGCAACAAC GTTGCGCAAA CTATTAACTG GCGAACTACT TACTCTAGCT
      GTGGTGCTAC GGACATCGTT ACCGTTGTTG CAACGCGTTT GATAATTGAC CGCTTGATGA ATGAGATCGA

3501  TCCCGGCAAC AATTAATAGA CTGGATGGAG GCGGATAAAG TTGCAGGACC ACTTCTGCGC TCGGCCCTTC
      AGGGCCGTTG TTAATTATCT GACCTACCTC CGCCTATTTC AACGTCCTGG TGAAGACGCG AGCCGGGAAG
```

FIG._44F

```
3571  CGGCTGGCTG GTTTATTGCT GATAAATCTG GAGCCGGTGA GCGTGGGTCT CGCGGTATCA TTGCAGCACT
      GCCGACCGAC CAAATAACGA CTATTTAGAC CTCGGCCACT CGCACCCAGA GCGCCATAGT AACGTCGTGA

3641  GGGGCCAGAT GGTAAGCCCT CCCGTATCGT AGTTATCTAC ACGACGGGGA GTCAGGCAAC TATGGATGAA
      CCCCGGTCTA CCATTCGGGA GGGCATAGCA TCAATAGATG TGCTGCCCCT CAGTCCGTTG ATACCTACTT

3711  CGAAATAGAC AGATCGCTGA GATAGGTGCC TCACTGATTA AGCATTGGTA ACTGTCAGAC CAAGTTTACT
      GCTTTATCTG TCTAGCGACT CTATCCACGG AGTGACTAAT TCGTAACCAT TGACAGTCTG GTTCAAATGA

3781  CATATATACT TTAGATTGAT TTAAAACTTC ATTTTTAATT TAAAAGGATC TAGGTGAAGA TCCTTTTTGA
      GTATATATGA AATCTAACTA AATTTTGAAG TAAAAATTAA ATTTTCCTAG ATCCACTTCT AGGAAAAACT

3851  TAATCTCATG ACCAAAATCC CTTAACGTGA GTTTTCGTTC CACTGAGCGT CAGACCCCGT AGAAAAGATC
      ATTAGAGTAC TGGTTTTAGG GAATTGCACT CAAAAGCAAG GTGACTCGCA GTCTGGGGCA TCTTTTCTAG

3921  AAAGGATCTT CTTGAGATCC TTTTTTTCTG CGCGTAATCT GCTGCTTGCA AACAAAAAAA CCACCGCTAC
      TTTCCTAGAA GAACTCTAGG AAAAAAAGAC GCGCATTAGA CGACGAACGT TTGTTTTTTT GGTGGCGATG

3991  CAGCGGTGGT TTGTTTGCCG GATCAAGAGC TACCAACTCT TTTTCCGAAG GTAACTGGCT TCAGCAGAGC
      GTCGCCACCA AACAAACGGC CTAGTTCTCG ATGGTTGAGA AAAAGGCTTC CATTGACCGA AGTCGTCTCG

4061  GCAGATACCA AATATACTGTCC TTCTAGTGTA GCCGTAGTTA GGCCACCACT TCAAGAACTC TGTAGCACCG
      CGTCTATGGT TTATGACAGG AAGATCACAT CGGCATCAAT CCGGTGGTGA AGTTCTTGAG ACATCGTGGC

4131  CCTACATACC TCGCTCTGCT AATCCTGTTA CCAGTGGCTG CTGCCAGTGG CGATAAGTCG TGTCTTACCG
      GGATGTATGG AGCGAGACGA TTAGGACAAT GGTCACCGAC GACGGTCACC GCTATTCAGC ACAGAATGGC

4201  GGTTGGACTC AAGACGATAG TTACCGGATA AGGCGCAGCG GTCGGGCTGA ACGGGGGGTT CGTGCACACA
      CCAACCTGAG TTCTGCTATC AATGGCCTAT TCCGCGTCGC CAGCCCGACT TGCCCCCCAA GCACGTGTGT

4271  GCCCAGCTTG GAGCGAACGA CCTACACCGA ACTGAGATAC CTACAGCGTG AGCTATGAGA AAGCGCCACG
      CGGGTCGAAC CTCGCTTGCT GGATGTGGCT TGACTCTATG GATGTCGCAC TCGATACTCT TTCGCGGTGC

4341  CTTCCCGAAG GGAGAAAGGC GGACAGGTAT CCGGTAAGCG GCAGGGTCGG AACAGGAGAG CGCACGAGGG
      GAAGGGCTTC CCTCTTTCCG CCTGTCCATA GGCCATTCGC CGTCCCAGCC TTGTCCTCTC GCGTGCTCCC
```

FIG._44G

```
4411  AGCTTCCAGG GGGAAACGCC TGGTATCTTT ATAGTCCTGT CGGGTTTCGC CACCTCTGAC TTGAGCGTCG
      TCGAAGGTCC CCCTTTGCGG ACCATAGAAA TATCAGGACA GCCCAAAGCG GTGGAGACTG AACTCGCAGC

4481  ATTTTTGTGA TGCTCGTCAG GGGGGCGGAG CCTATGGAAA AACGCCAGCA ACGCGGCCTT TTTACGGTTC
      TAAAAACACT ACGAGCAGTC CCCCCGCCTC GGATACCTTT TTGCGGTCGT TGCGCCGGAA AAATGCCAAG

4551  CTGGCCTTTT GCTGGCCTTT TGCTCACATG TTCTTTCCTG CGTTATCCCC TGATTCTGTG GATAACCGTA
      GACCGGAAAA CGACCGGAAA ACGAGTGTAC AAGAAAGGAC GCAATAGGGG ACTAAGACAC CTATTGGCAT

4621  TTACCGCCTT TGAGTGAGCT GATACCGCTC GCCGCAGCCG AACGACCGAG CGCAGCGAGT CAGTGAGCGA
      AATGGCGGAA ACTCACTCGA CTATGGCGAG CGGCGTCGGC TTGCTGGCTC GCGTCGCTCA GTCACTCGCT

4691  GGAAGCGGAA GAGCGCCCAA TACGCAAACC GCCTCTCCCC GCGCGTTGGC CGATTCATTA ATGCAGCTGG
      CCTTCGCCTT CTCGCGGGTT ATGCGTTTGG CGGAGAGGGG CGCGCAACCG GCTAAGTAAT TACGTCGACC

4761  CACGACAGGT TTCCCGACTG GAAAGCGGGC AGTGAGCGCA ACGCAATTAA TGTGAGTTAG CTCACTCATT
      GTGCTGTCCA AAGGGCTGAC CTTTCGCCCG TCACTCGCGT TGCGTTAATT ACACTCAATC GAGTGAGTAA

4831  AGGCACCCCA GGCTTTACAC TTTATGCTTC CGGCTCGTAT GTTGTGTGGA ATTGTGAGCG GATAACAATT
      TCCGTGGGGT CCGAAATGTG AAATACGAAG GCCGAGCATA CAACACACCT TAACACTCGC CTATTGTTAA
                                                                   BssHII
                                                                   ~~~~~~
4901  TCACACAGGA AACAGCTATG ACCATGATTA CGCCAAGCGC GCAATTAACC CTCACTAAAG GGAACAAAAG
      AGTGTGTCCT TTGTCGATAC TGGTACTAAT GCGGTTCGCG CGTTAATTGG GAGTGATTTC CCTTGTTTTC
      EcoR

4971  CTGG
      GACC
```

FIG. 44H

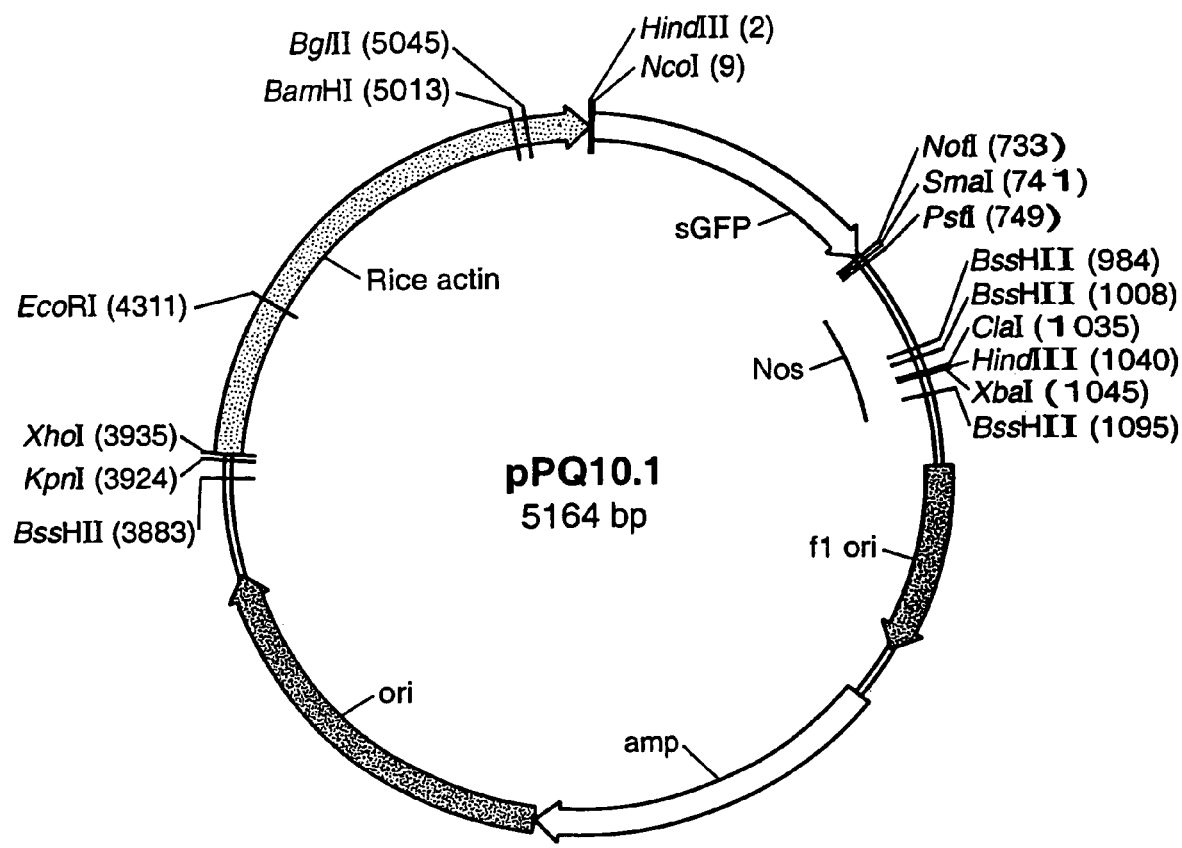
FIG._45A

```
     HindIII  NcoI
     ~~~~~~~  ~~~~~~~
  1  AAGCTTACCA TGGTGAGCAA GGGCGAGGAG CTGTTCACCG GGGTGGTGCC CATCCTGGTC GAGCTGGACG
     TTCGAATGGT ACCACTCGTT CCCGCTCCTC GACAAGTGGC CCCACCACGG GTAGGACCAG CTCGACCTGC 71  GCGACGTGAA CGGCCACAAG TTCAGCGTGT CCGGCGAGGG CGAGGGCGAT GCCACCTACG GCAAGCTGAC
     CGCTGCACTT GCCGGTGTTC AAGTCGCACA GGCCGCTCCC GCTCCCGCTA CGGTGGATGC CGTTCGACTG 141  CCTGAAGTTC ATCTGCACCA CCGGCAAGCT GCCCGTGCCC TGGCCCACCC TCGTGACCAC CTTCACCTAC
     GGACTTCAAG TAGACGTGGT GGCCGTTCGA CGGGCACGGG ACCGGGTGGG AGCACTGGTG GAAGTGGATG 211  GGCGTGCAGT GCTTCAGCCG CTACCCCGAC CACATGAAGC AGCACGACTT CTTCAAGTCC GCCATGCCCG
     CCGCACGTCA CGAAGTCGGC GATGGGGCTG GTGTACTTCG TCGTGCTGAA GAAGTTCAGG CGGTACGGGC 281  AAGGCTACGT CCAGGAGCGC ACCATCTTCT TCAAGGACGA CGGCAACTAC AAGACCCGCG CCGAGGTGAA
     TTCCGATGCA GGTCCTCGCG TGGTAGAAGA AGTTCCTGCT GCCGTTGATG TTCTGGGCGC GGCTCCACTT 351  GTTCGAGGGC GACACCCTGG TGAACCGCAT CGAGCTGAAG GGCATCGACT TCAAGGAGGA CGGCAACATC
     CAAGCTCCCG CTGTGGGACC ACTTGGCGTA GCTCGACTTC CCGTAGCTGA AGTTCCTCCT GCCGTTGTAG 421  CTGGGGCACA AGCTGGAGTA CAACTACAAC AGCCACAACG TCTATATCAT GGCCGACAAG CAGAAGAACG
     GACCCCGTGT TCGACCTCAT GTTGATGTTG TCGGTGTTGC AGATATAGTA CCGGCTGTTC GTCTTCTTGC 491  GCATCAAGGT GAACTTCAAG ATCCGCCACA ACATCGAGGA CGGCAGCGTG CAGCTCGCCG ACCACTACCA
     CGTAGTTCCA CTTGAAGTTC TAGGCGGTGT TGTAGCTCCT GCCGTCGCAC GTCGAGCGGC TGGTGATGGT 561  GCAGAACACC CCCATCGGCG ACGGCCCCGT GCTGCTGCCC GACAACCACT ACCTGAGCAC CCAGTCCGCC
     CGTCTTGTGG GGGTAGCCGC TGCCGGGGCA CGACGACGGG CTGTTGGTGA TGGACTCGTG GGTCAGGCGG 631  CTGAGCAAAG ACCCCAACGA GAAGCGCGAT CACATGGTCC TGCTGGAGTT CGTGACCGCC GCCGGGATCA
     GACTCGTTTC TGGGGTTGCT CTTCGCGCTA GTGTACCAGG ACGACCTCAA GCACTGGCGG CGGCCCTAGT
```

FIG._45B

```
                         SmaI
                        -------
                  NotI            PstI
                 -------         -------
 701 CTCACGGCAT GGACGAGCTG TACAAGTAAA GCGGCCGCCC GGGCTGCAGG GAAACCACTG AAGGATGAGC
     GAGTGCCGTA CCTGCTCGAC ATGTTCATTT CGCCGGCGGG CCCGACGTCC CTTTGGTGAC TTCCTACTCG

771 TGTAAAGAAG CAGATCGTTC AAACATTTGG TCTTAAGATT TCTTAAGATT GAATCCTGTT GCCGGTCTTG
     ACATTTCTTC GTCTAGCAAG TTTGTAAACC AGAATTCTAA AGAATTCTAA CTTAGGACAA CGGCCAGAAC

841 CGATGATTAT CATATAATTT CTGTTGAATT ACGTTAAGCA TGTAATAATT AACATGTAAT GCATGACGTT
     GCTACTAATA GTATATTAAA GACAACTTAA TGCAATTCGT ACATTATTAA TTGTACATTA CGTACTGCAA

911 ATTTATGAGA TGGGTTTTTA TGATTAGAGT CCCGCAATTA TACATTTAAT ACGCGATAGA AAACAAAATA
     TAAATACTCT ACCCAAAAAT ACTAATCTCA GGGCGTTAAT ATGTAAATTA TGCGCTATCT TTTGTTTTAT

XbaI
                                                               -------
                                    BssHII
                                   -------
 981 TAGCGCGCAA ACTAGGATAA ATTATCGCGC GCGGTGTCAT CTATGTTACT AGATCGATAA GCTTCTAGAG
     ATCGCGCGTT TGATCCTATT TAATAGCGCG CGCCACAGTA GATACAATGA TCTAGCTATT CGAAGATCTC

ClaI HindIII
                                                              ----- -------
1051 CGGCCCGGTGG AGCTCCAATT CGCCCTATAG TGAGTCGTAT TACGCGCGCT CACTGGCCGT CGTTTTACAA
     GCCGGGCCACC TCGAGGTTAA GCGGGATATC ACTCAGCATA ATGCGCGCGA GTGACCGGCA GCAAAATGTT BssHII
                                                    -------
1121 CGTCGTGACT GGGAAAACCC TGGCGTTACC CAACTTAATC GCCTTGCAGC ACATCCCCCT TTCGCCAGCT
     GCAGCACTGA CCCTTTTGGG ACCGCAATGG GTTGAATTAG CGGAACGTCG TGTAGGGGGA AAGCGGTCGA 1191 GGCGTAATAG CGAAGAGGCC CGCACCGATC GCCCTTCCCA ACAGTTGCGC AGCCTGAATG GCGAATGGGA
     CCGCATTATC GCTTCTCCGG GCGTGGCTAG CGGGAAGGGT TGTCAACGCG TCGGACTTAC CGCTTACCCT
```

FIG._45C

```
1261  CGCGCCCTGT AGCGGCGCAT TAAGCGCGGC GGGTGTGGTG GTTACGCGCA GCGTGACCGC TACACTTGCC
      GCGCGGGACA TCGCCGCGTA ATTCGCGCCG CCCACACCAC CAATGCGCGT CGCACTGGCG ATGTGAACGG

1331  AGCGCCCTAG CGCCCGCTCC TTTCGCTTTC TTCCCTTCCT TTCTCGCCAC GTTCGCCGGC TTTCCCCGTC
      TCGCGGGATC GCGGGCGAGG AAAGCGAAAG AAGGGAAGGA AAGAGCGGTG CAAGCGGCCG AAAGGGGCAG

1401  AAGCTCTAAA TCGGGGGCTC CCTTTAGGGT TCCGATTTAG TGCTTTACGG CACCTCGACC CCAAAAAACT
      TTCGAGATTT AGCCCCCGAG GGAAATCCCA AGGCTAAATC ACGAAATGCC GTGGAGCTGG GGTTTTTTGA

1471  TGATTAGGGT GATGGTTCAC GTAGTGGGCC ATCGCCCTGA TAGACGGTTT TTCGCCCTTT GACGTTGGAG
      ACTAATCCCA CTACCAAGTG CATCACCCGG TAGCGGGACT ATCTGCCAAA AAGCGGGAAA CTGCAACCTC

1541  TCCACGTTCT TTAATAGTGG ACTCTTGTTC CAAACTGAA CAACACTCAA CCCTATCTCG GTCTATTCTT
      AGGTGCAAGA AATTATCACC TGAGAACAAG GTTTGACCTT GTTGTGAGTT GGGATAGAGC CAGATAAGAA

1611  TTGATTTATA AGGGATTTTG CCGATTTCGG CCTATTGGTT AAAAAATGAG CTGATTTAAC AAAAATTTAA
      AACTAAATAT TCCCTAAAAC GGCTAAAGCC GGATAACCAA TTTTTTACTC GACTAAATTG TTTTTAAATT

1681  CGCGAATTTT AACAAAATAT TAAGCTTAC AATTAGTG ATATGTATCC GCACTTTCG CGGGAACCC
      GCGCTTAAAA TTGTTTTATA ATTCGCGAATG TTAAATCCAC TATACATAGG CGTGAAAAGC CCCTTTGGG

1751  CTATTTGTTT ATTTTTCTAA AATACATTCAA ATATGTATCC GCTCATGAGA TTCCGTGTCG GATAAATGCT
      GATAAACAAA TAAAAGATT TATGTAAGTT TATACATAGG CGAGTACTCT AAGGCACAGC CTATTACGA

1821  TCAATAATAT TGAAAAAGGA AGAGTATGAG TATTCAACAT TTCCGTGTCG CCCTTATTCC CTTTTTGCG
      AGTTATTATA ACTTTTTCCT TCTCATACTC ATAAGTTGTA AGGCACAGC GGGAATAAGG GAAAAAACGC

1891  GCATTTTGCC TTCCTGTTTT TGCTCACCCA GAAACGCTGG TGAAAGTAAA AGATGCTGAA GATCAGTTGG
      CGTAAAACGG AAGGACAAAA ACGAGTGGGT CTTTGCGACC ACTTTCATTT TCTACGACTT CTAGTCAACC

1961  GTGCACGAGT GGGTTACATC GAACTGGATC TCAACAGCGG TAAGATCCTT GAGAGTTTTC GCCCCGAAGA
      CACGTGCTCA CCCAATGTAG CTTGACCTAG AGTTGTCGCC ATTCTAGGAA CTCTCAAAAG CGGGGCTTCT

2031  ACGTTTTCCA ATGATGAGCA CTTTTAAAGT TCTGCTATGT GGGCGCGGTAT TATCCCGTAT TGACGCCGGG
      TGCAAAAGGT TACTACTCGT GAAAATTTCA AGACGATACA CCCGCGCCATA ATAGGGCATA ACTGCGGCCC
```

FIG._45D

```
2101  CAAGAGCAAC TCGGTCGCCG CATACACTAT TCTCAGAATG ACTTGGTTGA GTACTCACCA GTCACAGAAA
      GTTCTCGTTG AGCCAGCGGC GTATGTGATA AGAGTCTTAC TGAACCAACT CATGAGTGGT CAGTGTCTTT

2171  AGCATCTTAC GGATGGCATG ACAGTAAGAG AATTATGCAG TGCTGCCATA ACCATGAGTG ATAACACTGC
      TCGTAGAATG CCTACCGTAC TGTCATTCTC TTAATACGTC ACGACGGTAT TGGTACTCAC TATTGTGACG

2241  GGCCAACTTA CTTCTGACAA CGATCGGAGG ACCGAAGGAG CTAACCGCTT TTTTGCACAA CATGGGGGAT
      CCGGTTGAAT GAAGACTGTT GCTAGCCTCC TGGCTTCCTC GATTGGCGAA AAAACGTGTT GTACCCCTA

2311  CATGTAACTC GCCTTGATCG TTGGGAACCG GAGCTGAATG CTCGACTTAC AAGCCATACC CGTGACACCA
      GTACATTGAG CGGAACTAGC AACCCTTGGC CTCGACTTAC GAGCTGAATG TTCGGTATGG GCACTGTGGT

2381  CGATGCCTGT AGCAATGGCA ACAACGTTGC GCAAACTATT AACTGGCGAA CTACTTACTC TAGCTTCCCG
      GCTACGGACA TCGTTACCGT TGTTGCAACG CGTTTGATAA TTGACCGCTT GATGAATGAG ATCGAAGGGC

2451  GCAACAATTA ATAGACTGGA TGGAGGCGGA TAAAGTTGCA GGACCACTTC TGCGCTCGGC CCTTCCGGCT
      CGTTGTTAAT TATCTGACCT ACCTCCGCCT ATTTCAACGT CCTGGTGAAG ACGCGAGCCG GGAAGGCCGA

2521  GGCTGGTTTA TTGCTGATAA ATCTGGAGCC GGTGAGCGTG GGTCTCGCGG TATCATTGCA GCACTGGGGC
      CCGACCAAAT AACGACTATT TAGACCTCGG CCACTCGCAC CCAGAGCGCC ATAGTAACGT CGTGACCCCG

2591  CAGATGGTAA GCCCTCCCGT ATCGTAGTTA TCTACACGAC GGGGAGTCAG GCAACTATGG ATGAACGAAA
      GTCTACCATT CGGGAGGGCA TAGCATCAAT AGATGTGCTG CCCCTCAGTC CGTTGATACC TACTTGCTTT

2661  TAGACAGATC GCTGAGATAG GTGCCTCACT GATTAAGCAT TGGTAACTGT CAGACCAAGT TTACTCATAT
      ATCTGTCTAG CGACTCTATC CACGGAGTGA CTAATTCGTA ACCATTGACA GTCTGGTTCA AATGAGTATA

2731  ATACTTTAGA TTGATTTAAA ACTTCATTTT TAATTAAAA GGATCTAGGT GAAGATCCTT TTTGATAATC
      TATGAAATCT AACTAAATT TGAAGTAAAA ATTAAAATTT CCTAGATCCA CTTCTAGGAA AAACTATTAG

2801  TCATGACCAA AATCCCTTAA CGTGAGTTTT CGTTCCACTG AGCGTCAGAC CCCGTAGAAA AGATCAAAGG
      AGTACTGGTT TTAGGGAATT GCACTCAAAA GCAAGGTGAC TCGCAGTCTG GGGCATCTTT TCTAGTTTCC

2871  ATCTTCTTGA GATCCTTTTT TTCTGCGCGT AATCTGCTGC TTGCAAACAA AAAAACCACC GCTACCAGCG
      TAGAAGAACT CTAGGAAAAA AAGACGCGCA TTAGACGACG AACGTTTGTT TTTTTGGTGG CGATGGTCGC
```

FIG._45E

```
2941  GTGGTTTGTT  TGCCGGATCA  AGAGCTACCA  ACTCTTTTTC  CGAAGGTAAC  TGGCTTCAGC  AGAGCGCAGA
      CACCAAACAA  ACGGCCTAGT  TCTCGATGGT  TGAGAAAAAG  GCTTCCATTG  ACCGAAGTCG  TCTCGCGTCT

3011  TACCAAATAC  TGTCCTTCTA  GTGTAGCCGT  AGTTAGGCCA  CCACTTCAAG  AACTCTGTAG  CACCGCCTAC
      ATGGTTTATG  ACAGGAAGAT  CACATCGGCA  TCAATCCGGT  GGTGAAGTTC  TTGAGACATC  GTGGCGGATG

3081  ATACCTCGCT  CTGCTAATCC  TGTTACCAGT  GGCTGCTGCC  AGTGGCGATA  AGTCGTGTCT  TACCGGGTTG
      TATGGAGCGA  GACGATTAGG  ACAATGGTCA  CCGACGACGG  TCACCGCTAT  TCAGCACAGA  ATGGCCCAAC

3151  GACTCAAGAC  GATAGTTACC  GGATAAGGCG  CAGCGGTCGG  GCTGAACGGG  GGGTTCGTGC  ACACAGCCCA
      CTGAGTTCTG  CTATCAATGG  CCTATTCCGC  GTCGCCAGCC  CGACTTGCCC  CCCAAGCACG  TGTGTCGGGT

3221  GCTTGGAGCG  AACGACCTAC  ACCGAACTGA  GATACCTACA  GCGTGAGCTA  TGAGAAAGCG  CCACGCTTCC
      CGAACCTCGC  TTGCTGGATG  TGGCTTGACT  CTATGGATGT  CGCACTCGAT  ACTCTTTCGC  GGTGCGAAGG

3291  CGAAGGGAGA  AAGGCGGACA  GGTATCCGGT  AAGCGGCAGG  GTCGGAACAG  GAGAGCGCAC  GAGGGAGCTT
      GCTTCCCTCT  TTCCGCCTGT  CCATAGGCCA  TTCGCCGTCC  CAGCCTTGTC  CTCTCGCGTG  CTCCCTCGAA

3361  CCAGGGGAA   ACGCCTGGTA  TCTTTATAGT  CCTGTCGGGT  TTCGCCACCT  CTGACTTGAG  CGTCGATTTT
      GGTCCCCCTT  TGCGGACCAT  AGAAATATCA  GGACAGCCCA  AAGCGGTGGA  GACTGAACTC  GCAGCTAAAA

3431  TGTGATGCTC  GTCAGGGGGG  CGGAGCCTAT  GGAAAAACGC  CAGCAACGCG  GCCTTTTTAC  GGTTCCTGGC
      ACACTACGAG  CAGTCCCCCC  GCCTCGGATA  CCTTTTTGCG  GTCGTTGCGC  CGGAAAAATG  CCAAGGACCG

3501  CTTTTGCTGG  CCTTTTGCTC  ACATGTTCTT  TCCTGCGTTA  TCCCCCTGATT  CTGTGGATAA  CCGTATTACC
      GAAAACGACC  GGAAAACGAG  TGTACAAGAA  AGGACGCAAT  AGGGGACTAA  GACACCTATT  GGCATAATGG

3571  GCCTTTGAGT  GAGCTGATAC  CGCTCGCCGC  AGCCGAACGA  CCGAGCGCAG  CGAGTCAGTG  AGCGAGGAAG
      CGGAAACTCA  CTCGACTATG  GCGAGCGGCG  TCGGCTTGCT  GGCTCGCGTC  GCTCAGTCAC  TCGCTCCTTC

3641  CGGAAGAGCG  CCCAATACGC  AAACCGCCTC  TCCCCGCGCG  TTGGCCGATT  CATTAATGCA  GCTGGCACGA
      GCCTTCTCGC  GGGTTATGCG  TTTGGCGGAG  AGGGGCGCGC  AACCGGCTAA  GTAATTACGT  CGACCGTGCT

3711  CAGGTTTCCC  GACTGGAAAG  CGGGCAGTGA  GCGCAACGCA  ATTAATGTGA  GTTAGCTCAC  TCATTAGGCA
      GTCCAAAGGG  CTGACCTTTC  GCCCGTCACT  CGCGTTGCGT  TAATTACACT  CAATCGAGTG  AGTAATCCGT
```

*FIG._45F*

```
3781  CCCCAGGCTT  TACACTTTAT  GCTTCCGGCT  CGTATGTTGT  GAGCGGATAA  CAATTTCACA
      GGGGTCCGAA  ATGTGAAATA  CGAAGGCCGA  GCATACAACA  CTCGCCTATT  GTTAAAGTGT
                                              BssHII                     KpnI
                                              ------                     ----
3851  CAGGAAACAG  CTATGACCAT  GATTACGCCA  AGCGCGCAAT  TAACCCTCAC  TAAAGGGAAC  AAAAGCTGGG
      GTCCTTTGTC  GATACTGGTA  CTAATGCGGT  TCGCGCGTTA  ATTGGGAGTG  ATTTCCCTTG  TTTTCGACCC
      KpnI        XhoI
      ----        ----
3921  TACCGGGCCC  CCCCTCGAGG  TCATTCATAT  GCTTGAGAAG  AGAGTCGGGA  TAGTCCAAAA  TAAAACAAAG
      ATGGCCCGGG  GGGGAGCTCC  AGTAAGTATA  CGAACTCTTC  TCTCAGCCCT  ATCAGTTTTT  ATTTTGTTTC
3991  GTAAGATTAC  CTGGTCAAAA  GTGAAAACAT  CAGTTAAAAG  GTGGTATAAG  TAAAATATCG  GTAATAAAAG
      CATTCTAATG  GACCAGTTTT  CACTTTTGTA  GTCAATTTTC  CACCATATTC  ATTTTATAGC  CATTATTTTC
4061  GTGGCCCAAA  GTGAAATTTA  CTCTTTTCTA  CTATTATAAA  AATTGAGGAT  GTTTTGTCGG  TACTTTGATA
      CACCGGGTTT  CACTTTAAAT  GAGAAAAGAT  GATAATATTT  TTAACTCCTA  CAAAACAGCC  ATGAAACTAT
4131  CGTCATTTTT  GTATGAATTG  GTTTTAAGT  CATATCTGTA  TTTGAGTCGG
      GCAGTAAAAA  CATATCTTAAC  CAAAAATTCA  AATAAGCGCT  GTATAGACAT  AAACTCAGCC
4201  TTTTAAGTT  CGTTGCTTTT  GTAAATACAG  AGGGATTTGT  ATAAGAAATA  TCTTTAAAAA  ACCCATATGC
      AAAAATTCAA  GCAACGAAAA  CATTTATGTC  TCCCTAAACA  TATTCTTTAT  AGAAATTTTT  TGGGTATACG
                                                              EcoRI
                                                              -----
4271  TAATTTGACA  TAATTTTTGA  GAAAAATATA  TATTCAGGCG  AATTCCACAA  TGAACAATAA  TAAGATTAAA
      ATTAAACTGT  ATTAAAAACT  CTTTTTATAT  ATAAGTCCGC  TTAAGGTGTT  ACTTGTTATT  ATTCTAATTT
4341  ATAGCTTGCC  CCCGTTGCAG  CGATGGGTAT  TTTTTCTAGT  AAAATAAAAG  ATAAACTTAG  ACTCAAAACA
      TATCGAACGG  GGGCAACGTC  GCTACCCATA  AAAAAGATCA  TTTTATTTTC  TATTTGAATC  TGAGTTTTGT
4411  TTTACAAAAA  CAACCCCTAA  AGTCCTAAAG  CCCAAAGTGC  TATGCACGAT  CCATAGCCAAG  CCCAGCCCAA
      AAATGTTTTT  GTTGGGGATT  TCAGGATTTC  GGGTTTCACG  ATACGTGCTA  GGTATCGTTC   GGGTCGGGTT
```

FIG._45G

```
4481  CCCAACCCAA  CCCAACCCAC  CCCAGTGCAG  CCAACTGGCA  AATAGTCTCC  ACCCCCGGCA  CTATCACCGT
      GGGTTGGGTT  GGGTTGGGTG  GGGTCACGTC  GGTTGACCGT  TTATCAGAGG  TGGGGGCCGT  GATAGTGGCA

4551  GAGTTGTCCG  CACCACCGCA  CGTCTCGCAG  CCAAAAAAAG  AAAAAAAAGA  AAAAGAAAAA
      CTCAACAGGC  GTGGTGGCGT  GCAGAGCGTC  GGTTTTTTTC  TTTTTTTTCT  TTTTCTTTTT

4621  CAGCAGGTGG  GTCCGGGTCG  TGGGGGCCGG  AAAAGCGAGG  AGGATCGCGA  GCAGCGACGA  GGCCCGGCCC
      GTCGTCCACC  CAGGCCCAGC  ACCCCCGGCC  TTTTCGCTCC  TCCTAGCGCT  CGTCGCTGCT  CCGGGCCGGG

4691  TCCCTCCGCT  TCCAAAGAAA  CGCCCCCCAT  TACATACCCC  CCCCTCTCCT  CCCATCCCCC
      AGGGAGGCGA  AGGTTTCTTT  GCGGGGGGTA  ATGTATGGGG  GGGGAGAGGA  GGGTAGGGGG

4761  CAACCCTACC  ACCACCACCA  CCACCACCTC  CTCCCCCCTC  GCTGCCGGAC  GACGAGCTCC  TCCCCCCTCC
      GTTGGGATGG  TGGTGGTGGT  GGTGGTGGAG  GAGGGGGGAG  CGACGGCCTG  CTGCTCGAGG  AGGGGGGAGG

4831  CCCTCCGCCC  CCGGCCGGTAA  CCACCCCCGCC  CCTCTCCTCT  TTCTTTCTCC  GTTTTTTTTT  TCGTCTCGT
      GGGAGGCGGG  GGCGGCCATT  GGTGGGGCGG  GGAGAGGAGA  AAGAAAGAGG  CAAAAAAAAA  AGCAGAGCCA

4901  CTCGATCTTT  GGCCTTGGTA  GTTTGGGTGG  GCGAGAGCGG  CTTCGTCGCC  CAGATCGGTG  CGCGGGAGGG
      GAGCTAGAAA  CCGGAACCAT  CAAACCCACC  CGCTCTCGCC  GAAGCAGCGG  GTCTAGCCAC  GCGCCCTCCC
                                                                  BamHI
                                                                  ------

4971  GCGGGATCTC  GCGGCTGGGCG  TCTCCGGGCG  TGAGTCGGCC  CGGATCCTCG  CGGGGAATGG  GGCTCTCGGA
      CGCCCTAGAG  CGCCGACCGC  AGAGGCCCGC  ACTCAGCCGG  GCCTAGGAGC  GCCCCTTACC  CCGAGAGCCT
      BglII
      ------

5041  TGTAGATCTT  CTTTCTTTCT  CTTTTTTGTG  GTAGAATTTG  AATCCCTCAG  CATTGTTCAT  CGGTAGTTTT
      ACATCTAGAA  GAAAGAAAGA  GAAAAAACAC  CATCTTAAAC  TTAGGGAGTC  GTAACAAGTA  GCCATCAAAA

5111  TCTTTTCATG  ATTTGTGACA  AATGCAGCCT  CGTGCGGAGC  TTTTTGTAG   GTAG
      AGAAAAGTAC  TAAACACTGT  TTACGTCGGA  GCACGCCTCG  AAAAAACATC  CATC
```

FIG._45H

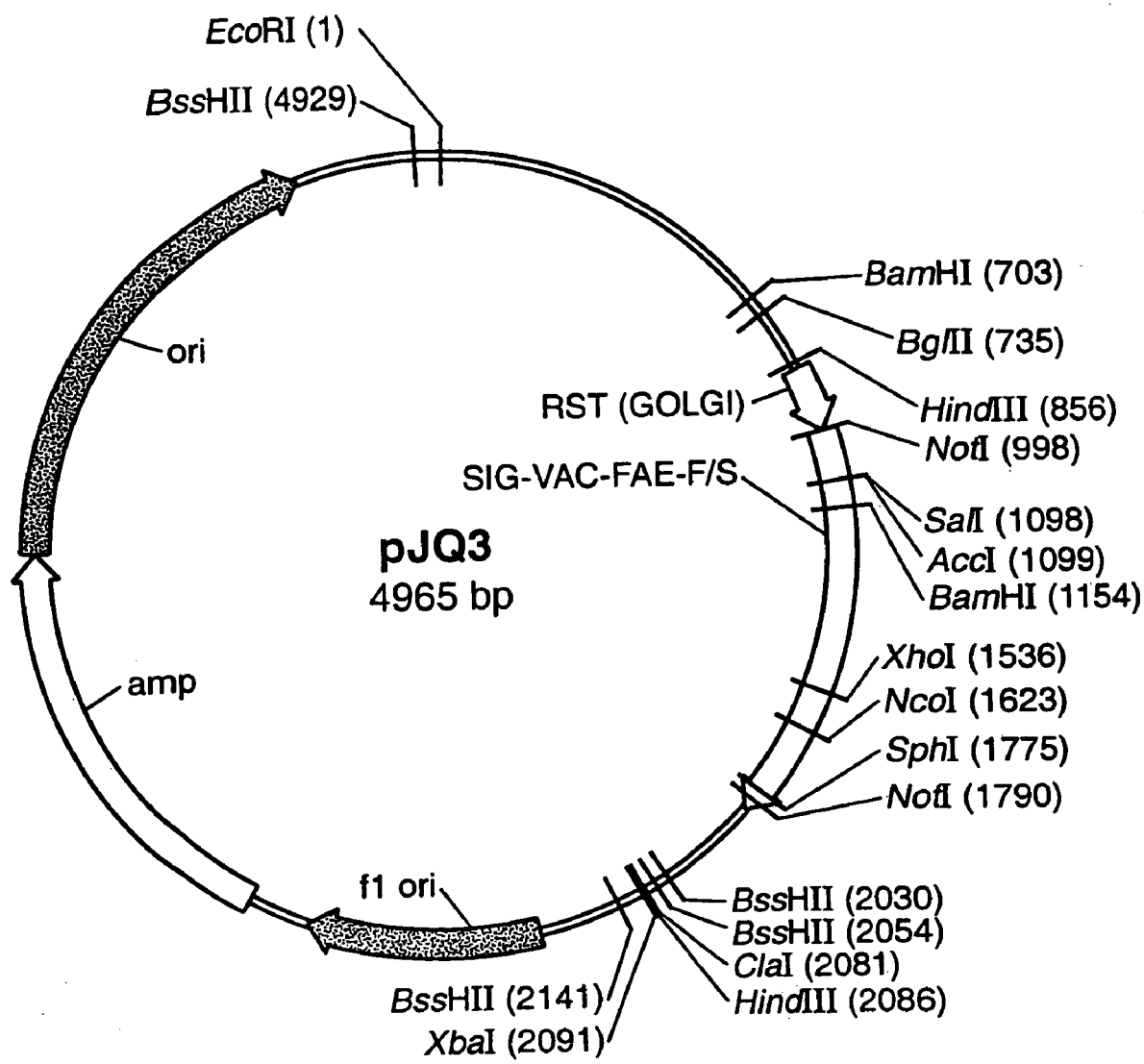
FIG._46A

```
     EcoRI
     ~~~~~
   1 AATTCCACAA TGAACAATAA TAAGATTAAA ATAGCTTGCC CCCGTTGCAG CGATGGGTAT TTTTTCTAGT
     TTAAGGTGTT ACTTGTTATT ATTCTAATTT TATCGAACGG GGGCAACGTC GCTACCCATA AAAAAGATCA

71 AAAATAAAAG ATAAACTTAG ACTCAAAACA TTTACAAAAA CAACCCCTAA AGTCCTAAAG CCCAAAGTGC
     TTTTATTTTC TATTTGAATC TGAGTTTTGT AAATGTTTTT GTTGGGGATT TCAGGATTTC GGGTTTCACG

141 TATGCACGAT CCATAGCAAG CTATCACCGT CCCAGCCCAA CCCAACCCAC CCCAGTGCAG CCAACTGGCA
     ATACGTGCTA GGTATCGTTC GATAGTGGCA GGGTCGGGTT GGGTTGGGTG GGGTCACGTC GGTTGACCGT

211 AATAGTCTCC ACCCCCGGCA CTATCACCGT GAGTGTCCG CACCACCGCA CGTCTCGCAG CCAAAAAAAA
     TTATCAGAGG TGGGGGCCGT GATAGTGGCA CTCAACAGGC GTGGTGGCGT GCAGAGCGTC GGTTTTTTTT

281 AAAAGAAAAG AAAAAAAAGA AAAAGAAAAA CAGCAGGTGG GTCCGGGGTCG TGGGGGCCGG AAAAGCGAGG
     TTTTCTTTTC TTTTTTTTCT TTTTCTTTTT GTCGTCCACC CAGGCCCAGC ACCCCGGCC TTTTCGCTCC

351 AGGATCGCGA GCAGCGACGA GGCCCGGCCC TCCCCTCCGCT TCCAAAGAAA CGCCCACTATA
     TCCTAGCGCT CGTCGCTGCT CCGGGCCCGGG AGGGAGGCGA AGGTTTCTTT GCGGGTGATAT

421 TACATACCCC CCCCTCTCCT CCCATCCCCC CAACCCTACC ACCACCACCA CCACCACCTC CTCCCCCCTC
     ATGTATGGGG GGGGAGAGGA GGGTAGGGGG GTTGGGATGG TGGTGGTGGT GGTGGTGGAG GAGGGGGGAG

491 GCTGCCGGAC GACGAGCTCC TCCCCCCTCC CCTCCGCCG CCGCCGGTAA CCACCCCGCC CCTCTCCTCT
     CGACGGCCTG CTGCTCGAGG AGGGGGGAGG GGAGGCGGC GGCGGCCATT GGTGGGGCGG GGAGAGGAGA

561 TTCTTTCTCC GTTTTTTTT TCGTCTCGGT AGCAGAGCCA CTCGATCTTT GGCCTTGGTA GCGAGAGCGG
     AAGAAAGAGG CAAAAAAAA AGCAGAGCCA TCGTCTCGGT GAGCTAGAAA CCGGAACCAT CGCTCTCGCC

631 CTTCGTCGCC CAGATCGGTG CGCGGAGGG GCGGGATCTC GCGGGATCTC GCGGCTGGCG TGAGTCGGCC
     GAAGCAGCGG GTCTAGCCAC GCGCCCTCCC CGCCCTAGAG CGCCGACCGC AGAGCCCGC ACTCAGCCGG

BglII
                                        ~~~~~
 701 CGGGGATCCCTCG CGGGGAATGG GGCTCTCGGA TGTAGATCTT CTTTTCTTCT TCTTTTTTGTG GTAGAATTTG
     GCCCCTAGGG GCCCCTTACC CCGAGAGCCT ACATCTAGAA GAAAGAAAGA AGAAAAACAC CATCTTAAAC
```

FIG._46B

```
771   AATCCCTCAG CATTGTTCAT CGGTAGTTTT TCTTTTCATG ATTTGTGACA AATGCAGCCT CGTGCGGAGC
      TTAGGGAGTC GTAACAAGTA GCCATCAAAA AGAAAAGTAC TAAACACTGT TTACGTCGGA GCACGCCTCG
                 HindIII
                 ------

841   TTTTTGTAG GTAGAAGCTT ACCATGATCC ACACCAACCT CAAAAAGAAG TTCTCCCTCT TCATCCTCGT
      AAAAAACATC CATCTTCGAA TGGTACTAGG TGTGGTTGGA GTTTTTCTTC AAGAGGGAGA AGTAGGAGCA

911   CTTCCCTCTC TTCGCCGTGA TCTGCGTGTG GAAGAAGGGC TCCGACTACG AGGCCCTCAC CCTCCAAGCC
      GAAGGGAGAG AAGCGGCACT AGACGCACAC CTTCTTCCCG AGGCTGATGC TCCGGGAGTG GGAGGTTCGG
                                                   NotI
                                                   ------

981   AAGGAGTTCC AAATGGCGGC CGCCTCCACG CAGGGCATCT CCGAAGACCT CTACAGCCGT TTAGTCGAAA
      TTCCTCAAGG TTTACCGCCG GCGGAGGTGC GTCCCGTAGA GGCTTCTGGA GATGTCGGCA AATCAGCTTT
                                                                SalI
                                                                ------
                                                                 AccI
                                                                 ------

1051  TGGCCACTAT CTCCCAAGCT GCCTACGCCG ACCTGTGCAA CATTCCGTCG ACTATTATCA AGGGAGAGAA
      ACCGGTGATA GAGGGTTCGA CGGATGCGGC TGGACACGTT GTAAGGCAGC TGATAATAGT TCCCTCTCTT
                                  BamHI
                                  ------

1121  AATTTACAAT TCTCAAACTG ACATTAACGG ATGGATCCTC CGCGACGACA GCAGCAAAGA AATAATCACC
      TTAAATGTTA AGAGTTTGAC TGTAATTGCC TACCTAGGAG GCGCTGCTGT CGTCGTTTCT TTATTAGTGG

1191  GTCTTCCGTG GCACTGGTAG TGATACGAAT CTACAACTCG ATACTAACTA CACCCCTCACG CCTTTCGACA
      CAGAAGGCAC CGTGACCATC ACTATGCTTA GATGTTGAGC TATGATTGAT GTGGGAGTGC GGAAAGCTGT

1261  CCCTACCACA ATGCAACGGT TGTGAAGTAC ACGGTGGATA TTATATTGGA TGGGTCTCCG TCCAGGACCA
      GGGATGGTGT TACGTTGCCA ACACTTCATG ACACTTCCA AATATAACCT ACCCAGAGGC AGGTCCTGGT
```

FIG._46C

```
1331  AGTCGAGTCG  CTTGTCAAAC  AGCAGGTTAG  CCAGTATCCG  GACTACGCGC  TGACCGTGAC  CGGCCACKCC
      TCAGCTCAGC  GAACAGTTTG  TCGTCCAATC  GGTCATAGGC  CTGATGCGCG  ACTGGCACTG  GCCGGTGMGG

1401  CTCGGCGCCT  CCCTGGCGGC  ACTCACTGCC  GCCCAGTCGT  CTGCGACATA  CGACAACATC  CGCCTGTACA
      GAGCCGCGGA  GGGACCGCCG  TGAGTGACGG  CGGGTCAGCA  GACGCTGTAT  GCTGTTGTAG  GCGGACATGT
                                                                              XhoI
                                                                              -------
1471  CCTTCGGCGA  ACCGCGCAGC  GGCAATCAGG  CCTTCGCGTC  GTACATGAAC  GATGCCTTCC  AAGCCTCGAG
      GGAAGCCGCT  TGGCGCGTCG  CCGTTAGTCC  GGAAGCGCAG  CATGTACTTG  CTACGGAAGG  TTCGGAGCTC

1541  CCCAGATACG  ACGCAGTATT  TCCGGGTCAC  CCTGTGCAAC  TCATGCCAAC  GACGGCATCC  CAAACCTGCC
      GGGTCTATGC  TGCGTCATAA  AGGCCCAGTG  GGACACGTTG  AGTACGGTTG  CTGCCGTAGG  GTTTGGACGG
                  NcoI
                  ------
1611  CAGGGGTACG  CCCATGGCGG  TGTAGAGTAC  TGGAGCGTTG  ATCCTTACAG  CGCCCAGAAC  ACATTTGTCT
      GTCCCCATGC  GGGTACCGCC  ACATCTCATG  ACCTCGCAAC  TAGGAATGTC  GCGGGTCTTG  TGTAAACAGA

1681  GCACTGGGGA  TGCTGTGAGG  TGCTGTGCAG  CCCAGGGCGG  ACAGGGTGTG  AATAATGCGC  ACACGACTTA
      CGTGACCCCT  ACGACACTCC  ACGACACGTC  GGGTCCCGCC  TGTCCCACAC  TTATTACGCG  TGTGCTGAAT

1751  TTTTGGGATG  ACGAGCGGGC  CATGCACCTG  GCCGGTCGCG  GCCGGCGCCG  CCACTGAAGG  ATGAGCTGTA
      AAAACCCTAC  TGCTCGCCCG  GTACGTGGAC  CGGCCAGCGC  CGGCCGCGGC  GGTGACTTCC  TACTCGACAT
                              SphI                                NotI
                              -------                             ------
1821  AAGAAGCAGA  TCGTTCAAAC  ATTTGGCAAT  AAAGTTTCTT  AAGATTGAAT  CCTGTTGCCG  GTCTTGCGAT
      TTCTTCGTCT  AGCAAGTTTG  TAAACCGTTA  TTTCAAAGAA  TTCTAACTTA  GGACAACGGC  CAGAACGCTA

1891  GATTATCATA  TAATTTCTGT  TGAATTACGT  TAAGCATGTA  ATAATTAACA  TGTAATGCAT  GACGTTATTT
      CTAATAGTAT  ATTAAAGACA  ACTTAATGCA  ATTCGTACAT  TATTAATTGT  ACATTACGTA  CTGCAATAAA
```

FIG.\_46D

```
                                                                              BssHII
                                                                              ----
1961  ATGAGATGGG TTTTTATGAT TAGAGTCCCG CAATTATACA TTTAATACGC GATAGAAAAC AAAATATAGC
      TACTCTACCC AAAAATACTA ATCTCAGGGC GTTAATATGT AAATTATGCG CTATCTTTTG TTTTATATCG

BssHII                    BssHII                         XbaI
        ------                    ------                         ----
2031  GCGCAAACTA GGATAAATTA TCGCGCGCGG TGTCATCTAT GTTACTAGAT CGATAAGCTT CTAGAGCGGC
      CGCGTTTGAT CCTATTTAAT AGCGCGCGCC ACAGTAGATA CAATGATCTA GCTATTCGAA GATCTCGCCG

ClaI  HindIII
                                                ----  -------
2101  CGGTGGGAGCT CCAATTCGCC CTATAGTGAG TCGTATTACG CGGCGCTCACT GGCCGTCGTT TTACAACGTC
      GCCACCCTCGA GGTTAAGCGG GATATCACTC AGCATAATGC GCCGCGAGTGA CCGGCAGCAA AATGTTGCAG BssHII
                                       ------
2171  GTGACTGGGA AAACCCTGGC GTTACCCAAC TTAATCGCCT TGCAGCACAT ACGTCGTGTA CCAGCTGGCG
      CACTGACCCT TTTGGGACCG CAATGGGTTG AATTAGCGGA ACGTCGTGTA TGCAGCACAT GGTCGACCGC 2241  TAATAGCGAA GAGGCCCGCA CCGATCGCCC TTCCCAACAG TTGCGCAGCC TGAATGGCGA ATGGGACGCG
      ATTATCGCTT CTCCGGGCGT GGCTAGCGGG AAGGGTTGTC AACGCGTCGG ACTTACCGCT TACCCTGCGC 2311  CCCTGTAGCG GCGCATTAAG CGCGGCGGGT GTGGTGGTTA CGCGCAGCGT GACCGCTACA CTTGCCAGCG
      GGGATCGCGC CGCGTAATTC GCGCCGCCCA CACCACCAAT GCGCGTCGCA CTGGCGATGT GAACGGTCGC 2381  CCCTAGCGCC CGCTCCTTTC GCTTTCTTCC CTTCCTTTCT GCCGGCTTTC CCCGTCAAGC
      GGGATCGCGG GCGAGGAAAG CGAAAGAAGG GAAGGAAAGA CGGCCGAAAG GGGCAGTTCG 2451  TCTAAATCGG GGGCTCCCTT TAGGGTTCCG ATTTAGTGCT TTACGGCACC TCGACCCCAA AAAACTTGAT
      AGATTTAGCC CCCGAGGGAA ATCCCAAGGC TAAATCACGA AATGCCGTGG AGCTGGGGTT TTTTGAACTA 2521  TAGGGTGATG GTTCACGTAG TGGGCCATCG ACCCGGTAGC CGGTTTTTCG CCCTTTGACG TTGGAGTCCA
      ATCCCACTAC CAAGTGCATC ACCCGGTAGC TGGGCCATCG GCCAAAAAGC GGGAAACTGC AACCTCAGGT
```

*FIG._46E*

```
2591  CGTTCTTTAA TAGTGGACTC TTGTTCCAAA CTGGAACAAC ACTCAACCCT ATCTCGGTCT ATTCTTTTGA
      GCAAGAAATT ATCACCTGAG AACAAGGTTT GACCTTGTTG TGAGTTGGGA TAGAGCCAGA TAAGAAAACT

2661  TTTATAAGGG ATTTTGCCGA TTTCGGCCTA AATGAGCTGA TTTAACAAAA ATTTAACGCG
      AAATATTCCC TAAAACGGCT AAAGCCCGAT AACCAATTTT TTACTCGACT AAATTGTTTT TAAATTGCGC

2731  AATTTTAACA AAATATTAAC GCTTACAAAT TAGGTGGCAC TTTTCGGGGA AATGTGCGCG GAACCCCTAT
      TTAAAATTGT TTTATAATTG CGAATGTTAA ATCCACCGTG AAAAGCCCCT TTACACGCGC CTTGGGGATA

2801  TTGTTTATTT TTCTAAATAT ATTCAAATAT GTATCCGCTC ATGAGACAAT AACCCTGATA AATGCTTCAA
      AACAAATAAA AAGATTTATA TAAGTTTATA CATAGGCGAG TACTCTGTTA TTGGGACTAT TTACGAAGTT

2871  TAATATTGAA AAAGGAAGAG TATGAGTATT CAACATTTCC GTGTCGCCCT TATTCCCTTT TTTGCGGCAT
      ATTATAACTT TTTCCTTCTC ATACTCATAA GTTGTAAAGG CACAGCGGGA ATAAGGGAAA AAACGCCGTA

2941  TTTGCCTTCC TGTTTTTGCT CACCCAGAAA CGCTGGTGAA AGTAAAAGAT GCTGAAGATC AGTTGGGTGC
      AAACGGAAGG ACAAAAACGA GTGGGTCTTT GCGACCACTT TCATTTTCTA CGACTTCTAG TCAACCCACG

3011  ACGAGTGGGT TACATCGAAC TGGATCTCAA CAGCGGTAAG ATCCTTGAGA GTTTTCGCCC CGAAGAACGT
      TGCTCACCCA ATGTAGCTTG ACCTAGAGTT GTCGCCATTC TAGGAACTCT CAAAAGCGGG GCTTCTTGCA

3081  TTTCCAATGA TGAGCACTTT TAAAGTTCTG CTATGTGGCG CGGTATTATC CCGTATTGAC GCCGGGCAAG
      AAAGGTTACT ACTCGTGAAA ATTTCAAGAC GATACACCGC GGCATAATAG GGCATAACTG CGGCCCGTTC

3151  AGCAACTCGG TCGCCGCATA CACTATTCTC AGAATGACTT GGTTGAGTAC TCACCAGTCA CAGAAAAGCA
      TCGTTGAGCC AGCGGCGTAT GTGATAAGAG TCTTACTGAA CCAACTCATG AGTGGTCAGT GTCTTTTCGT

3221  TCTTACGGAT GGCATGACAG TAAGAGAATT ATGCAGTGCT GCCATAACCA CCGCTTTTTT CACTGCGGCC
      AGAATGCCTA CCGTACTGTC ATTCTCTTAA TACGTCACGA CGGTATTGGT GGCGAAAAAA GTGACGCCGG

3291  AACTTACTTC TGACAACGAT CGGAGGACCG AAGGAGCTAA CCGCTTTTTT GCACAACATG GGGGATCATG
      TTGAATGAAG ACTGTTGCTA GCCTCCTGGC TTCCTCGATT GGCGAAAAAA CGTGTTGTAC CCCCTAGTAC

3361  TAACTCGCCT TGATCGTTGG GAACCGGGAG TGAATGAAGC CATACCAAAC GACGAGCGTG ACACCACGAT
      ATTGAGCGGA ACTAGCAACC CTTGGCCCTC ACTTACTTCG GTATGGTTTG CTGCTCGCAC TGTGGTGCTA
```

FIG._46F

```
3431  GCCTGTAGCA ATGGCAACAA CGTTGCGCAA ACTATTAACT GGCGAACTAC TTACTCTAGC TTCCCGGCAA
      CGGACATCGT TACCGTTGTT GCAACGCGTT TGATAATTGA CCGCTTGATG AATGAGATCG AAGGGCCGTT

3501  CAATTAATAG ACTGGATGGA GTTGCAGGAC CCGCCTATTT CAACGTCCTG GTGAAGACGC GAGCCGGGAA GGCCGACCGA
      GTTAATTATC TGACCTACCT CCGCCTATTT CAACGTCCTG GTGAAGACGC GAGCCGGGAA GGCCGACCGA

3571  GGTTATTGC TGATAAATCT GGAGCCGGTG AGCGTGGGTC TCGCGGTATC ATTGCAGCAC TGGGGCCAGA
      CCAATAAACG ACTATTAGA CCTCGGCCAC TCGCACCCAG AGCGCCATAG TAACGTCGTG ACCCCGGTCT

3641  TGGTAAGCCC TCCCGTATCG TAGTTATCTA CACGACGGGG AGTCAGGCAA CTATGGATGA ACGAAATAGA
      ACCATTCGGG AGGGCATAGC ATCAATAGAT GTGCTGCCCC TCAGTCCGTT GATACCTACT TGCTTTATCT

3711  CAGATCGCTG AGATAGGTGC AAGCATTGGT AACTGTCAGA CCAAGTTTAC TCATATATAC
      GTCTAGCGAC TCTATCCACG TTCGTAACCA TTGACAGTCT GGTTCAAATG AGTATATATG

3781  TTTAGATTGA TTTAAAACTT CATTTTTAAT TTAAAAGAT CTAGGTGAAG ATCCTTTTG ATAATCTCAT
      AAATCTAACT AAATTTTGAA GTAAAAATTA AATTTTCCTA GATCCACTTC TAGGAAAAAC TATTAGAGTA

3851  GACCAAAATC CCTTAACGTG AGTTTTCGTT CCACTGAGCG TCAGAGCCCG TAGAAAAGAT CAAAGGATCT
      CTGGTTTTAG GGAATTGCAC TCAAAGCAA GGTGACTCGC AGTCTCGGGC ATCTTTTCTA GTTTCCTAGA

3921  TCTTGAGATC CTTTTTTTCT GCGCGTAATC TGCTGCTTGC AAACAAAAAA ACCACCGCTA CCAGCGGTGG
      AGAACTCTAG GAAAAAAAGA CGCGCATTAG ACGACGAACG TTTGTTTTTT TGGTGGCGAT GGTCGCCACC

3991  TTTGTTTGCC GGATCAAGAG CTACCAACTC TTTTTCCGAA GGTAACTGGC TTCAGCAGAG CGCAGATACC
      AAACAAACGG CCTAGTTCTC GATGGTTGAG AAAAAGGCTT CCATTGACCG AAGTCGTCTC GCGTCTATGG

4061  AAATACTGTC CTTCTAGTGT AGCCGTAGTT AGGCCACCAC TTCAAGAACT CTGTAGCACC GCCTACATAC
      TTTATGACAG GAAGATCACA TCGGCATCAA TCCGGTGGTG AAGTTCTTGA GACATCGTGG CGGATGTATG

4131  CTCGCTCTGC TAATCCTGTT ACCAGTGGCT GCTGCCAGTG GCGATAAGTC CGCTATTCAG GTGTCTTACC GGGTTGGACT
      GAGCGAGACG ATTAGGACAA TGGTCACCGA CGACGGTCAC CGCTATTCAG GTGTCTTACC CCCAACCTGA

4201  CAAGACGATA GTTACCGGAT AAGGCGCAGC GGTCGGGCTG AACGGGGGGT TCGTGCACAC AGCCCAGCTT
      GTTCTGCTAT CAATGGCCTA TTCCGCGTCG CCAGCCCGAC TTGCCCCCCA AGCACGTGTG TCGGGTCGAA
```

FIG._46G

```
4271  GGAGCGAACG ACCTACACCG AACTGAGATA CCTACAGCGT GAGCTATGAG AAAGCGCCAC GCTTCCCGAA
      CCTCGCTTGC TGGATGTGGC TTGACTCTAT GGATGTCGCA CTCGATACTC TTTCGCGGTG CGAAGGGCTT

4341  GGGAGAAAGG CGGACAGGTA TCCGGTAAGC GGCAGGGTCG GAACAGGAGA GCGCACGAGG GAGCTTCCAG
      CCCTCTTTCC GCCTGTCCAT AGGCCATTCG CCGTCCCAGC CTTGTCCTCT CGCGTGCTCC CTCGAAGGTC

4411  GGGGAAACGC CTGGTATCTT TATAGTCCTG TCGGGTTTCG CCACCTCTGA CTTGAGCGTC GATTTTGTG
      CCCCTTTGCG GACCATAGAA ATATCAGGAC AGCCCAAAGC GGTGGAGACT GAACTCGCAG CTAAAAACAC

4481  ATGCTCGTCA GGGGGGCGGA GCCTATGGAA AAACGCCAGC AACGCGGCCT TTTTACGGTT CCTGGCCTTT
      TACGAGCAGT CCCCCCGCCT CGGATACCTT TTTGCGGTCG TTGCGCCGGA AAAATGCCAA GGACCGGAAA

4551  TGCTGGCCTT TTGCTCACAT GTTCTTTCCT GCGTTATCCC CTGATTCTGT GGATAACCGT ATTACCGCCT
      ACGACCGGAA AACGAGTGTA CAAGAAAGGA CGCAATAGGG GACTAAGACA CCTATTGGCA TAATGGCGGA

4621  TTGAGTGAGC TGATACCGCT CGCCGCAGCC GAACGACCGA GCGCAGCGAG TCAGTGAGCG AGGAAGCGGA
      AACTCACTCG ACTATGGCGA GCGGCGTCGG CTTGCTGGCT CGCGTCGCTC AGTCACTCGC TCCTTCGCCT

4691  AGAGCGCCCA ATACGCAAAC CGCCTCTCCC CGCGCGTTGG CCGATTCATT AATGCAGCTG GCACGACAGG
      TCTCGCGGGT TATGCGTTTG GCGGAGAGGG GCGCGCAACC GGCTAAGTAA TTACGTCGAC CGTGCTGTCC

4761  TTTCCCGACT GGAAAGCGGG CAGTGAGCGC AACGCAATTA ATGTGAGTTA GCTCACTCAT TAGGCACCCC
      AAAGGGCTGA CCTTTCGCCC GTCACTCGCG TTGCGTTAAT TACACTCAAT CGAGTGAGTA ATCCGTGGGG

4831  AGGCTTTACA CTTTATGCTT CCGGCTCGTA TGTTGTGTGG AATTGTGAGC GGATAACAAT TTCACACAGG
      TCCGAAATGT GAAATACGAA GGCCGAGCAT ACAACACACC TTAACACTCG CCTATTGTTA AAGTGTGTCC

BssHII                                        EcoRI
                         ~~~~~~                                        ~~~~~
4901  AAACAGCTAT GACCATGATT ACGCCAAGCG CGCAATTAAC CCTCACTAAA GGGAACAAAA GCTGG
      TTTGTCGATA CTGGTACTAA TGCGGTTCGC GCGTTAATTG GGAGTGATTT CCCTTGTTTT CGACC
```

FIG._46H

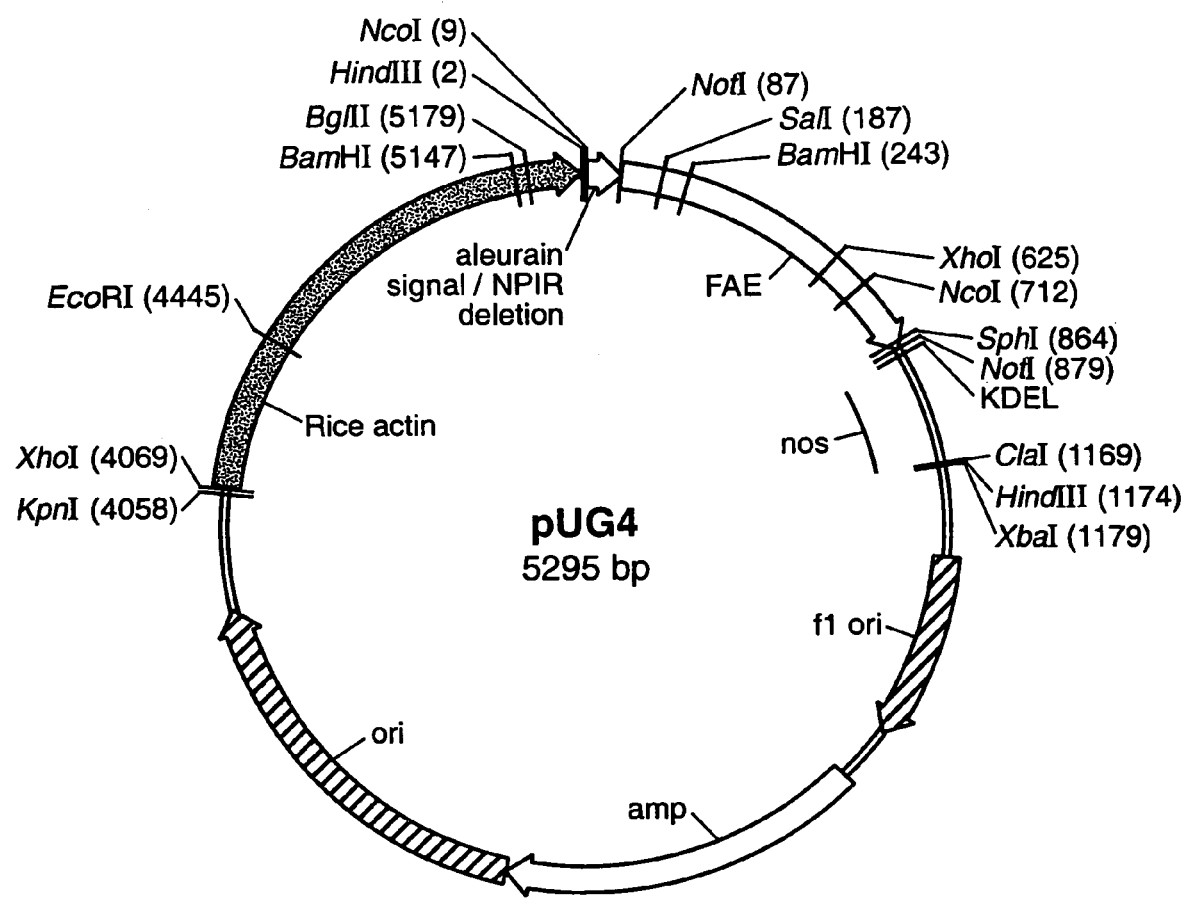
FIG._47A

```
     NcoI
     ~~~~~~
     HindIII
     ~~~~~~           M   A   H   A   R   V   L   L   L   A   L   A   V   L   A   T   A   A   V   A   V
  1  AAGCTTACCA TGGCCCACGC CCGCGTCCTC CTCCTGGCGC TCGGCCGTGCT GGCCACGGCC GCCGTCGCCG
     .  A   S   S   R   A   A   A   S   T   Q   G   I   S   E   D   L   Y   S   R   L   V   E   M   .
 71  TCGGCCTCCTC CCGCGCGGCC GCCTCCACGC AGGGCATCTC CGAAGACCTC TACAGCCGTT TAGTCGAAAT
                 NotI                                                  SalI
     .  A   T   I   S   Q   A   A   Y   A   D   L   C   N   I   P   S   T   I   I   K   G   E   K
141  GGCCACTATC TCCCAAGCTG CCTACGCCGA CCTGTGCAAC ATTCCGTCGA CTATTATCAA GGGAGAGAAA
                                                           BamHI
        I   Y   N   S   Q   T   D   I   N   G   W   I   L   R   D   D   S   K   E   I   I   T   V
211  ATTTACAATT CTCAAACTGA CATTAACGGA TGGATCCTCC GCGACGACAG CAGCAAAGAA ATAATCACCG
     .  F   R   G   T   G   S   D   T   N   L   Q   L   D   T   N   Y   T   L   T   P   F   D   T   .
281  TCTTCCGTGG CACTGGTAGT GATACGAATC TACAAACTCGA TACTAACTAC ACCCTCACGC CTTTCGACAC
     .  L   P   Q   C   N   G   C   E   V   H   G   G   Y   I   G   W   S   V   Q   D   Q
351  CCTACCACAA TGCAACGGTT GTGAAGTACA CGGTGGATAT TATATTGGAT GGGTCTCCGT CCAGGACCAA
        V   E   S   L   V   K   Q   Q   V   S   Q   Y   P   D   Y   A   L   T   V   T   G   H   X   L   .
421  GTCGAGTCGC TTGTCAAACA GCAGGTTAGC CAGTATCCGG ACTACGCGCT GACCGTGACC GGCCACKCCC
     .  G   A   S   L   A   A   L   T   A   A   Q   L   S   A   T   Y   D   N   I   R   L   Y   T   .
491  TCGGCGCCTC CCTGGCGGCA CTCACTGCCG CCCAGCTGTC TGCGACATAC GACAACATCC GCCTGTACAC
                                                                                  XhoI
                                                                                  ~
     .  F   G   E   P   R   S   G   N   Q   A   F   A   S   Y   M   N   D   A   F   Q   A   S   S
561  CTTCGGGCGAA CCGGCGCAGCG GCAATCAGGC CTTCGCGTCG TACATGAACG ATGCCTTCCA AGCCTCGAGC
     .  P   D   T   Q   Y   F   R   V   T   H   A   N   D   G   I   P   N   L   P   P   V   E   Q
631  CCAGATACGA CGCAGTATTT CCGGGTCACT CATGCCAACG ACGGCATCCC AAACCTGCCC CCGGTGGAGC
     NcoI
     ~~~~~~
```

FIG._47B

```
              .  G  Y  A   H  G  G   V  E  Y  W   S  V  D   P  Y  S   A  Q  N  T   F  V  C
 701 AGGGGTACGC CCATGGCGGT GTAGAGTACT GGAGCGTTGA TCCTTACAGC GCCCAGAACA CATTTGTCTG
      . T  G  D   E  V  Q   C  C  E  A   Q  G  G   Q  G  V  N   A  H   T  T  Y
 771 CACTGGGGAT GAAGTGCAGT GCTGTGAGGC CCAGGGCGGA CAGGGTGTGA ATAATGCGCA CACGACTTAT
                                         NotI
       F  G  M  T   S  G  A   C  T  W   P  V  A  A   A  E  P   L  K  D   E  L  *
 841 TTTGGGATGA CGAGCGGCGC ATGCACCTGG CCGGTCGCGG CCGGAAACC ACTGAAGGAT GAGCTGTAAA
 911 GAAGCAGATC GTTCAAACAT TGGCAATAA AGTTTCTTAA GATTGAATCC TGTTGCCGGT CTTGCGATGA
 981 TTATCATATA ATTTCTGTTG AATTACGTTA AGCATGTAAT AATTAACATG TAATGCATGA CGTTATTTAT
1051 GAGATGGGTT TTTATGATTA GAGTCCCGCA ATTATATACATT TAATACGCGA TAGAAAACAA AATATAGCGC
                                                              HindIII
                                                    ClaI       XbaI
1121 GCAAACTAGG ATAAATTATC GCGCGCGGTG TCATCTATGT TACTAGATCG ATAAGCTTCT AGAGCGGCCG
1191 GTGGAGCTCC AATTCGCCCT ATAGTGAGTC CGCTCACTGG CGGTCGTTTT ACAACGTCGT
1261 GACTGGGAAA ACCCTGGCGT TACCCAACTT AATCGCCTTG CAGCACATCC CCCTTTCGCC AGCTGGCGTA
1331 ATAGCGAAGA GGCCCGCACC GATCGCCCTT CCCAACAGTT GCGCAGCCTG AATGGCGAAT GGGACGCGCC
1401 CTGTAGCGGC GCATTAAGCG CGGCGGGTGT GGTGGTTACG CGCAGCGTGA CCGCTACACT TGCCAGCGCC
1471 CTAGCGCCCG CTCCTTTCGC TTTCTTCCCT TCCTTTCTCG CCACGTTCGC CGGCTTTCCC CGTCAAGCTC
1541 TAAATCGGGG GCTCCCTTTA GGGTTCCGAT TTAGTGCTTT ACGGCACCTC GACCCCAAAA AACTTGATTA
1611 GGGTGATGGT TCACGTAGTG GGCCATCGCC CTGATAGACG GTTTTTCGCC CTTTGACGTT GGAGTCCACG
1681 TTCTTTAATA GTGGACTCTT GTTCCAAACT GGAACAACAC TCAACCCTAT CTCGGTCTAT TCTTTTGATT
1751 TATAAGGGAT TTGCCCGATT TCGGCCTATT GGTTAAAAAA TGAGCTGATT TAACAAAAAT TTAACGCGAA
1821 TTTTAACAAA ATATTAACGC TTACAATTTA GGTGGCACTT TTCGGGGAAA TGTGCGCGGA ACCCCTATTT
1891 GTTTATTTTT CTAAATACAT TCAAATATGT ATCCGCTCAT GAGACAATAA CCCTGATAAA TGCTTCAATA
1961 ATATTGAAAA AGGAAGAGTA TGAGTATTCA ACATTTCCGT GTCGCCCTTA TTCCCTTTTT TGCGGCATTT
2031 TGCCTTCCTG TTTTTGCTCA CCCAGAAACG CTGGTGAAAG TAAAAGATGC TGAAGATCAG TTGGGTGCAC
2101 GAGTGGGTTA CATCGAACTG GATCTCAACA GCGGTAAGAT CCTTGAGAGT TTTCGCCCCG AAGAACGTTT
2171 TCCAATGATG AGCACTTTTA AAGTTCTGCT ATGTGGCGCG GTATTATCCC GTATTGACGC CGGGCAAGAG
2241 CAACTCGGTC GCCGCATACA CTATTCTCAG AATGACTTGG TTGAGTACTC ACCAGTCACA GAAAAGCATC
2311 TTACGGATGG CATGACAGTA AGAGAATTAT GCAGTGCTGC CATAACCATG AGTGATAACA CTGCGGCCAA
2381 CTTACTTCTG ACAACGATCG GAGGACCGAA GGAGCTAACC GCTTTTTTGC ACAACATGGG GGATCATGTA
2451 ACTCGCCTTG ATCGTTGGGA ACCGGAGCTG ATGAAGCCA TACCAAACGA CGAGCGTGAC ACCACGATGC
2521 CTGTAGCAAT GGCAACAACG TTGCGCAAAC TATTAACTGG CGAACTACTT ACTCTAGCTT CCCGGCAACA
```

*FIG. 47C*

```
2591  ATTAATAGAC TGGATGGAGG CGGATAAAGT TGCAGGACCA CTTCTGCGCT CGGCCCTTCC GGCTGGCTGG
2661  TTTATTGCTG ATAAATCTGG AGCCGGTGAG CGTGGGTCTC GCGGTATCAT TGCAGCACTG GGGCCAGATG
2731  GTAAGCCCTC CCGTATCGTA GTTATCTACA CACGGGGAG TCAGGCAACT ATGGATGAAC GAAATAGACA
2801  GATCGCTGAG ATAGGTGCCT CACTGATTAA GCATTGGTAA CTGTCAGACC AAGTTTACTC ATATATACTT
2871  TAGATTGATT TAAAACTTCA TTTTTAATTT AAAAGGATCT AGGTGAAGAT CCTTTTTGAT AATCTCATGA
2941  CCAAAATCCC TTAACGTGAG TTTTCGTTCC ACTGAGCGTC AGACCCCGTA GAAAAGATCA AAGGATCTTC
3011  TTGAGATCCT TTTTTTCTGC GCGTAATCTG CTGCTTGCAA ACAAAAAAAC CACCGCTACC AGCGGTGGTT
3081  TGTTTGCCGG ATCAAGAGCT ACCAACTCTT TTTCCGAAGG TAACTGGCTT CAGCAGAGCG CAGATACCAA
3151  ATACTGTCCT TCTAGTGTAG CCGTAGTTAG GCCACCACTT CAAGAACTCT GTAGCACCGC CTACATACCT
3221  CGCTCTGCTA ATCCTGTTAC CAGTGGCTGC TGCCAGTGGC GATAAGTCGT GTCTTACCGG GTTGGACTCA
3291  AGACGATAGT TACCGGATAA GGCGCAGCGG TCGGGCTGAA CGGGGGGTTC GTGCACACAG CCCAGCTTGG
3361  AGCGAACGAC CTACACCGAA CTGAGATACC TACAGCGTGA GCTATGAGAA AGCGCCACGC TTCCCGAAGG
3431  GAGAAAGGCG GACAGGTATC CGGTAAGCGG CAGGGTCGGA ACAGGAGAGC GCACGAGGGA GCTTCCAGGG
3501  GGAAACGCCT GTATCTTTA TAGTCCTGTC GGGTTTCGCC ACCTCTGACT TGAGCGTCGA TTTTTGTGAT
3571  GCTCGTCAGG GGGGCGGAGC CTATGGAAAA ACGCCAGCAA CGCGGCCTTT TTACGGTTCC TGGCCTTTTG
3641  CTGGCCTTTT GCTCACATGT TCTTTCCTGC GTTATCCCCT GATTCTGTGG ATAACCGTAT TACCGCCTTT
3711  GAGTGAGCTG ATACCGCTCG CCGCAGCCGA ACGACCGAGC GCAGCGAGTC AGTGAGCGAG GAAGCGGAAG
3781  AGCGCCCAAT ACGCAAACCG CCTCTCCCCG CGCGTTGGCC GATTCATTAA TGCAGCTGGC ACGACAGGTT
3851  TCCCGACTGG AAAGCGGGCA GTGAGCGCAA CGCAATTAAT GTGAGTTAGC TCACTCATTA GGCACCCCAG
3921  GCTTTACACT TTATGCTTCC GGCTCGTATG TTGTGTGGAA TTGTGAGCGG ATAACAATTT CACACAGGAA
                   XhoI                                                  KpnI
                  --------                                                  --
3991  ACAGCTATGA CCATGATTAC GCCAAGCGCG CAATTAACCC TCACTAAAGG GAACAAAAGC TGGGTACCGG
4061  GCCCCCCCTC GAGGTCATTC ATATGCTTGA GAAGAGAGTC GGGATAGTCC AAAATAAAAC AAAGGTAAGA
4131  TTACCTGGTC AAAAGTGAAA TTTACTCTTT ACATCAGTTA AAAGGTGGTA TAAGTAAAAT ATCGGTAATA AAAGGTGGCC
4201  CAAAGTGAAA TTTGTGCCTT CTAACTATTA TCTACTATTA GGATGTTTTG TCGGTACTTT GATACGTCAT
4271  TTTTGTATGA ATTGGTTTTT AAGTTTATTC TAAAAATTGA GCGATTTGGA TGTATTGAG TCGGTTTTA
4341  AGTTCGTTGC TTTTGTAAAT ACAGAGGGAT TTGTATAAGA AATATCTTTA AAAACCCAT ATGCTAATTT
                                                        EcoRI
                                                        -----
4411  GACATAATTT TTGAGAAAAA TATATATTCA GGCGAATTCC ACAATGAACA ATAATAAGAT TAAAATAGCT
4481  TGCCCCCCGTT GCAGCGATGG GTATTTTTTC TAGTAAAATA AAAGATAAAC TTAGACTCAA AACATTACA
4551  AAAACAACCC CTAAAGTCCT AAAGCCCAAA GTGCTATGCA CGATCCATAG CAAGCCCAGC CCAACCCAAC
4621  CCAACCCAAC CCACCCCAGT GCAGCCAACT GGCAAATAGT CTCCACCCCC CTCCACTATCA GGCACTATCA CCGTGAGTTG
```

FIG.\_47D

```
4691  TCCGCACCAC CGCACGTCTC GCAGCCAAAA AAAAAAAAG AAAGAAAAAA AAGAAAAAGA AAAACAGCAG
4761  GTGGGTCCGG GTCGTGGGGG CCGGAAAAGC GAGGAGGATC GCGAGCAGCG ACGAGGCCCG GCCCTCCCTC
4831  CGCTTCCAAA GAAACGCCCC CCATCGCCAC TATATACATA CCCCCCCCTC TCCTCCCATC CCCCAACCC
4901  TACCACCACC ACCACCACCA CCTCCTCCCC CCTCGCTGCC GGACGACGAG CTCCCTCCCC CTCCCCTCC
4971  GCCGCCGCCG GTAACCACCC CGCCCCCTC CTCTTTCTTT CTCCGTTTTT TTTTTCGTCT CGGTCTCGAT
5041  CTTTGGCCTT GGTAGTTTGG GTGGGCGAGA GCGGCTTCGT CGCCCAGATC CGCCCAGATC GGTGCGCGGG AGGGGCGGGA
                                                   BamHI                              BglII
5111  TCTCGCGGCT GGCGTCTCCG GGCGTGAGTC GGCCCCGGATC CTCGCGGGGA ATGGGGCTCT CGGATGTAGA
      BglII
5181  TCTTCTTTCT TTCTTTCTTT TGTGGTAGAA TTTGAATCCC TCAGCATTGT TCATCGGTAG TTTTTCTTTT
5251  CATGATTTGT GACAAATGCA GCCTCGTGCG GAGCTTTTTT GTAGC
```

FIG. 47E

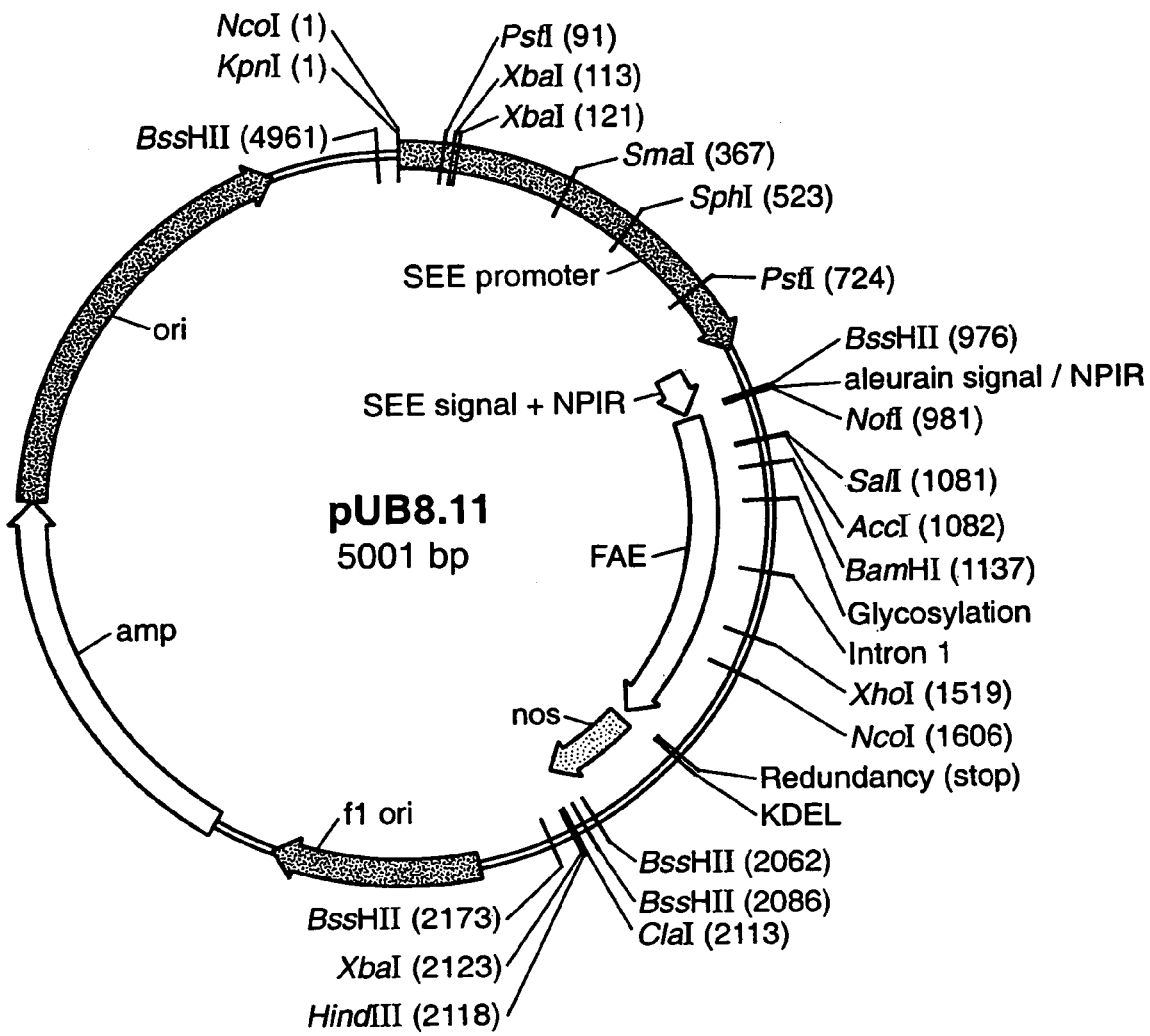
FIG._48A

```
      NcoI
      ~~~~~
      KpnI
      ~
  1   CATGGGCCAG GTATAATTAT GGGATATCTC AAGCAAATAA TCGAAATATC ACCATTGGCT ACAATATCTG
      GTACCCGGTC CATATTAATA CCCTATAGAG TTCGTTTATT AGCTTTATAG TGGTAACCGA TGTTATAGAC

PstI                                    XbaI
                          ~~~~~                                   ~~~~~
 71   AGCTCCGAGT TCTGACTGCA GTCTGGATGA CGCGTGTTGT ATCTAGAACT CTAGATAGCA CAGCCACAGC
      TCGAGGCTCA AGACTGACGT CAGACTACT GCGCACAACA TAGATCTTGA GATCTATCGT GTCGGTGTCG

141   ACCTACAGGA GTGCGACACT TGTGGACTGT AGTAGTGTTG GAGACGGAGC TCTTCCTAC CTCCTGACGT
      TGGATGTCCT CACGCTGTGA ACACCTGACA TCATCACAAC CTCTGCCTCG AGAAAGGATG GAGGACTGCA

211   TGCCGCCGTT GTCCATTCCA ACGGCATCAC TCTCAACCAA TCACGCGCTC CCAACAAAAT ATCGTCCCCC
      ACGGCGGCAA CAGGTAAGGT TGCCGTAGTG AGAGTTGGTT AGTGCGCGAG GGTTGTTTTA TAGCAGGGGG

SmaI
                          ~~~~~
281   ATGTCTTGGC GGAGAGAGAG TACATACATG CTGTCGCGCC GTTTTGTCT GAATCTCGCT TCCACTGGCC
      TACAGAACCG CCTCTCTCTC ATGTATGTAC GACAGCGCGG CAAAAACAGA CTTAGAGCGA AGGTGACCGG

351   AATCAGCTCA GCTCCCGGGA GCTCACTCAT TCAAGATCCC ATCGTCGTCG TCACCCCTGG CGTCATGGGA
      TTAGTCGAGT CGAGGGCCCT CGAGTGAGTA AGTTCTAGGG TAGCAGCAGC AGTGGGGACC GCAGTACCCT

421   TGGAAAAGAA CCTCCGTTGC TCGGATGAGT CAGCCATATC CCCGAACAGA GTACTGCAAG ATAACCCAAT
      ACCTTTTCTT GGAGGCAACG AGCCTACTCA GTCGGTATAG GGGCTTGTCT CATGACGTTC TATTGGGTTA

SphI
                                                 ~~~~~
491   TCAGATTCCC CCAATAGAGA AAGTATAGCA TGCTTTCGGG TTTTGTTTGG TTTATTTTTG CTTAATTGAC
      AGTCTAAGGG GGTTATCTCT TTCATATCGT ACGAAAGCCC AAAACAAACC AAATAAAAAC GAATTAACTG

561   TTGGAGTTGA ATGCTGATTT GTTGTGTAAA ATGCCCAACC ATCTGAATAT CGAGACGGAT AATAGGCTGG
      AACCTCAACT TACGACTAAA CAACACATTT TACGGGTTGG TAGACTTATA GCTCTGCCTA TTATCCGACC
```

*FIG._48B*

```
631   CTAATTAATT TATAGCAAGA TTCTGTAGTG CACATCGCAA ATATCTTTCT GGGCATTACA GCTGGAGGCT
      GATTAATTAA ATATCGTTCT AAGACATCAC GTGTAGCGTT TATAGAAAGA CCCGTAATGT CGACCTCCGA
                            PstI
                            -----

701   TCATCAGCCT GAAACACTCT GCAGAGCCTG AAGCAAGTGG TGAAGCGTGG CGATGAGATG GGTATAAAAC
      AGTAGTCGGA CTTTGTGAGA CGTCTCGGAC TTCGTTCACC ACTTCGCACC GCTACTCTAC CCATATTTTG

771   CCCCGGCACC GGGACGCGAG CTCCCGCCTA CCAGTACCAT CTCGCCTCGC TCCCCCTGCC GGACGACCCA
      GGGGCCGTGG CCCTGCGCTC GAGGGCGGAT GGTCATGGTA GAGCGGAGCG AGGGGGACGG CCTGCTGGGT

841   GTAAAATACT GTTGCCCACT CGCCGGCGAG ATGGCCCACG GCCGCATCCT CTTCTTGGCG CTCGCCGTCT
      CATTTTATGA CAACGGGTGA GCGGCCGCTC TACCGGGTGC CGGCGTAGGA GAAGAACCGC GAGCGGCAGA
                                                                     BssHII
                                                                     ------
                                                                        NotI
                                                                        ----

911   TGGCCACCGC CGCGGGTGGCC GCCGCATCNT TGGCGGACTC CAACCCGATC CGGCCCCGTCA CCGAGCGCGC
      ACCGGTGGCG GCGCCCACCGG CGGCGTAGNA ACCGCCTGAG GTTGGGCTAG GCCGGGGCAGT GGCTCGCGCG
      NotI
      ----

981   GGCCGCCCTCC ACGCAGGGCA TCTCCGAAGA CCTCTACAGC CGTTTAGTCG AAATGGCCAC TATCTCCCAA
      CCGGCGGGAGG TGCGTCCCGT AGAGGCTTCT GGAGATGTCG GCAAATCAGC TTTACCGGTG ATAGAGGGTT
                                                 SalI
                                                 ------
                                                 AccI
                                                 ------

1051  GCTGCCTACG CCGACCTGTG CAACATTCCG TCGACTATTA TCAAGGGAGA GAAAATTTAC AATTCTCAAA
      CGACGGATGC GGCTGGACAC GTTGTAAGGC AGCTGATAAT AGTTCCCTCT CTTTTAAATG TTAAGAGTTT
```

FIG._48C

```
               BamHI
               ------
1121  CTGACATTAA CGGATGGATC CTCCGCGACG ACAGCAGCAA AGAAATAATC ACCGTCTTCC GTGGCACTGG
      GACTGTAATT GCCTACCTAG GAGGCGCTGC TGTCGTCGTT TCTTTATTAG TGGCAGAAGG CACCGTGACC

1191  TAGTGATACG AATCTACAAC TCGATACTAA CTACACCCTC ACGCCTTTCG ACACCCTACC ACAATGCAAC
      ATCACTATGC TTAGATGTTG AGCTATGATT GATGTGGGAG TGCGGAAAGC TGTGGGATGG TGTTACGTTG

1261  GGTTGTGAAG TACACGGTGG ATATTATATT GGATGGGTCT CCGTCCAGGA CCAAGTCGAG TCGCTTGTCA
      CCAACACTTC ATGTGCCACC TATAATATAA CCTACCCAGA GGCAGGTCCT GGTTCAGCTC AGCGAACAGT

1331  AACAGCAGGT TAGCCAGTAT CCGGACTACG CGCTGACCGT GACCGGCCAC KCCCTCGGCG CCTCCCTGGC
      TTGTCGTCCA ATCGGTCATA GGCCTGATGC GCGACTGGCA CTGGCCGGTG MGGGAGCCGC GGAGGGACCG

1401  GGCACTCACT GCCGCCCAGC TGTCTGCGAC ATACGACAAC ATCCGCCTGT ACACCTTCGG CGAACCGCGC
      CCGTGAGTGA CGGCGGGTCG ACAGACGCTG TATGCTGTTG TAGGCGGACA TGTGGAAGCC GCTTGGCGCG

XhoI
                                                              ------
1471  AGCGGCAATC AGGCCTTCGC GTCGTACATG AACGATGCCT TCCAAGCCTC GAGCCCAGAT ACGACGCAGT
      TCGCCGTTAG TCCGGAAGCG CAGCATGTAC TTGCTACGGA AGGTTCGGAG CTCGGGTCTA TGCTGCGTCA

NcoI
                                                                          ------
1541  ATTTCCGGGT CACTCATGCC AACGACGGCA TCCCAAACCT GCCCCCGGTG GAGCAGGGGT ACGCCCATGG
      TAAAGGCCCA GTGAGTACGG TTGCTGCCGT AGGGTTTGGA CGGGGGCCAC CTCGTCCCCA TGCGGGTACC

1611  CGGTGTAGAG TACTGGAGCG TTGATCCTTA CAGCGCCCAG AACACATTTG TCTGCACTGG GGATGAAGTG
      GCCACATCTC ATGACCTCGC AACTAGGAAT GTCGCGGGTC TTGTGTAAAC AGACGTGACC CCTACTTCAC

1681  CAGTGCTGTG AGGCCCAGGG CGGACAGGGT GTGAATAATG CGCACACGAC TTATTTTGGG ATGACGAGCG
      GTCACGACAC TCCGGGTCCC GCCTGTCCCA CACTTATTAC GCGTGTGCTG AATAAAACCC TACTGCTCGC

1751  GAGCCTGTAC ATGGTGATCA GTCATTTCAG CCTCCCCGAG TGTACCAGGA AAGATGGATG TCCTGGAGAG
      CTCGGACATG TACCACTAGT CAGTAAAGTC GGAGGGGCTC ACATGGTCCT TTCTACCTAC AGGACCTCTC

FIG._48D
```

```
1821  GGGGCCGCGT AACCACTGAA GGATGAGCTG TAAAGAAGCA GATCGTTCAA ACATTGGCCA ATAAAGTTTC
      CCCCGGCGCA TTGGTGACTT CCTACTCGAC ATTTCTTCGT CTAGCAAGTT TGTAAACCGT TATTTCAAAG

1891  TTAAGATTGA ATCCTGTTGC CGGTCTTGCG ATGATTATCA TATAATTTCT GTTGAATTAC GTTAAGCATG
      AATTCTAACT TAGGACAACG GCCAGAACGC TACTAATAGT ATATTAAAGA CAACTTAATG CAATTCGTAC

1961  TAATAATTAA CATGTAATGC ATGACGTTAT TTATGAGATG GGTTTTTATG ATTAGAGTCC CGCAATTATA
      ATTATTAATT GTACATTACG TACTGCAATA AATACTCTAC CCAAAAATAC TAATCTCAGG GCGTTAATAT
                                                  BssHII              BssHII
                                                  ~~~~~~              ~~~~~~

2031  CATTAATAC GCGATAGAAA ACAAAAATATA GCGCGCAAAC TAGGATAAAT TATCGCGCGC GGTGTCATCT
      GTAATTATG CGCTATCTTT TGTTTTATAT CGCGCGTTTG ATCCTATTTA ATAGCGCGCG CCACAGTAGA
                          XbaI
                          ~~~~
                          ClaI HindIII
                          ~~~~~~~~~~~~

2101  ATGTTACTAG ATCGATAAGC TTCTAGAGCG GCCGGTGACG CTCCAATTCG CCCTATAGTG AGTCGTATTA
      TACAATGATC TAGCTATTCG AAGATCTCGC CGGCCACTGC GAGGTTAAGC GGGATATCAC TCAGCATAAT
      BssHII
      ~~~~~~

2171  CGGCGCGCTCA CTGGCCGTCG TTTTACAACG TCGTGACTGG GAAAACCCTG GCGTTACCCA ACTTAATCGC
      GCCGCGCGAGT GACCGGCAGC AAAATGTTGC AGCACTGACC CTTTTGGGAC CGCAATGGGT TGAATTAGCG

2241  CTTGCAGCAC ATCCCCCTTT CGCCAGCTGG CGTAATAGCG AAGAGGCCCG CACCGATCGC CCTTCCCAAC
      GAACGTCGTG TAGGGGGAAA GCGGTCGACC GCATTATCGC TTCTCCGGGC GTGGCTAGCG GGAAGGGTTG

2311  AGTTGCGCAG CCTGAATGGC GAATGGGACG CTTACCTGC CGCCCTGTAG CGGCGCATTA AGCGCGGCGG GTGTGGTGGT
      TCAACGCGTC GGACTTACCG CTTACCCTGC GCGGGACATC GCCGCGTAAT TCGCGCCGCC CACACCACCA

2381  TACGCGCAGC GTGACCGCTA CACTTGCCAG CGCCCTAGCG CCCGCTCCTT TCGCTTTCTT CCCTTCCTTT
      ATGCGCGTCG CACTGGCGAT GTGAACGGTC GCGGGATCGC GGGCGAGGAA AGCGAAAGAA GGGAAGGAAA
```

FIG._48E

```
2451  CTCGCCACGT TCGCCCGGCTT TCCCCGTCAA GCTCTAAATC GGGGGCTCCC TTTAGGGTTC CGATTTAGTG
      GAGCGGTGCA AGCGGGCCGAA AGGGGCAGTT CGAGATTTAG CCCCCGAGGG AAATCCCAAG GCTAAATCAC

2521  CTTTACGGCA CCTCGACCCC AAAAAACTTG ATTAGGGTGA TGGTTCACGT AGTGGGCCAT CGCCCTGATA
      GAAATGCCGT GGAGCTGGGG TTTTTTGAAC TAATCCCACT ACCAAGTGCA TCACCCGGTA GCGGGACTAT

2591  GACGGTTTTT CGCCCTTTGA CGTTGGAGTC CACGTTCTTT AATAGTGGAC TCTTGTTCCA AACTGGAACA
      CTGCCAAAAA GCGGGAAACT GCAACCTCAG GTGCAAGAAA TTATCACCTG AGAACAAGGT TTGACCTTGT

2661  ACACTCAACC CTATCTCGT CTATTCTTTT GATTATAAG GGATTTTGCC GATTTCGGCC TATTGGTTAA
      TGTGAGTTGG GATAGAGCCA CTAAGAGAAA CCTAAAACGG CTAAAGCCGG ATAACCAATT

2731  AAAATGAGCT GATTAAACAA AAATTAACG CGAATTTTAA CAAAATATTA ACGCTTACAA TTTAGGTGGC
      TTTTACTCGA CTAAATTGTT TTTAAATTGC GCTTAAAATT GTTTATAAAT TGCGAATGTT AAATCCACCG

2801  ACTTTTCGGG GAAATGTGCG CGGAACCCCT ATTTGTTTAT TTTTCTAAAT ACATTCAAAT ATGTATCCGC
      TGAAAAGCCC CTTTACACGC GCCTTGGGGA TAAACAAATA AAAAGATTTA TGTAAGTTTA TACATAGGCG

2871  TCATGAGACA ATAACCCTGA TAAATGCTTC AATAATATTG AAAAAGGAAG AGTATGAGTA TTCAACATTT
      AGTACTCTGT TATTGGGACT ATTTACGAAG TTATTATAAC TTTTCCTTC TCATACTCAT AAGTTGTAAA

2941  CCGTGTCGCC CTTATTCCCT TTTTTGCGGC ATTTTGCCTT TAAAACGCCG CCTGTTTTTG CTCACCCAGA AACGCTGGTG
      GGCACAGCGG GAATAAGGGA AAAAACGCCG TAAAACGCCG GGACAAAAAC GAGTGGGTCT TTGCGACCAC

3011  AAAGTAAAAG ATGCTGAAGA TCAGTTGGGT GCACGAGTGG GTTACATCGA ACTGGATCTC AACAGCGGTA
      TTTCATTTTC TACGACTTCT AGTCAACCCA CGTGCTCACC CAATGTAGCT TGACCTAGAG TTGTCGCCAT

3081  AGATCCTTGA GAGTTTTCGC CCCGAAGAAC GTTTTCCAAT GATGAGCACT TTTAAAGTTC TGCTATGTGG
      TCTAGGAACT CTCAAAAGCG GGGCTTCTTG CAAAAGGTTA CTACTCGTGA AAATTTCAAG ACGATACACC

3151  CGCGGTATTA TCCCGTATTG ACGCCGGGCA AGAGCAACTC GGTCGCCGCA TACACTATTC TCAGAATGAC
      GCGCCATAAT AGGGCATAAC TGCGGCCCGT TCTCGTTGAG CCAGCGGCGT ATGTGATAAG AGTCTTACTG

3221  TTGGTTGAGT ACTCACCAGT CACAGAAAAG CATCTTACGG ATGGCATGAC AGTAAGAGAA TTATGCAGTG
      AACCAACTCA TGAGTGGTCA GTGTCTTTTC GTAGAATGCC TACCGTACTG TCATTCTCTT AATACGTCAC
```

*FIG._48F*

```
3291  CTGCCATAAC CATGAGTGAT AACACTGCGG CCAACTTACT TCTGACAACG ATCGGAGGAC CGAAGGAGCT
      GACGGTATTG GTACTCACTA TTGTGACGCC GGTTGAATGA AGACTGTTGC TAGCCTCCTG GCTTCCTCGA

3361  AACCGCTTTT TTGCACAACA TGGGGGATCA CGCTCGGCCC TTCCGGCTGG CTTGATCGTT GGGAACCGGA GCTGAATGAA
      TTGGCGAAAA AACGTGTTGT ACCCCCTAGT GCGAGCCGGG AAGGCCGACC GAACTAGCAA CCCTTGGCCT CGACTTACTT

3431  GCCATACCAA ACGACGAGCG TGACACCACG ATGCCTGTAG CAATGGCAAC AACGTTGCGC AAACTATTAA
      CGGTATGGTT TGCTGCTCGC ACTGTGGTGC TACGGACATC GTTACCGTTG TTGCAACGCG TTTGATAATT

3501  CTGGCGAACT ACTTACTCTA GCTTCCCGGC AACAATTAAT AGACTGGATG GAGGCGGATA AAGTTGCAGG
      GACCGCTTGA TGAATGAGAT CGAAGGGCCG TTGTTAATTA TCTGACCTAC CTCCGCCTAT TTCAACGTCC

3571  ACCACTTCTG CGCTCGGCCC TTCCGGCTGG CTGGTTTATT GCTGATAAAT CTGGAGCCGG TGAGCGTGGG
      TGGTGAAGAC GCGAGCCGGG AAGGCCGACC GACCAAATAA CGACTATTTA GACCTCGGCC ACTCGCACCC

3641  TCTCGCGGTA TCATTGCAGC ACTGGGGGCCA GATGGTAAGC CCTCCCCGTAT CGTAGTTATC TACACGACGG
      AGAGCGCCAT AGTAACGTCG TGACCCCGGT CTACCATTCG GGAGGGCATA GCATCAATAG ATGTGCTGCC

3711  GGAGTCAGGC AACTATGGAT GAACGAAATA CTTGCTTTAT AGACAGATCGC TGAGATAGGT GCCTCACTGA TTAAGCATTG
      CCTCAGTCCG TTGATACCTA CTTGCTTTAT CTGTCTAGCG ACTCTATCCA CGGAGTGACT AATTCGTAAC

3781  GTAACTGTCA GACCAAGTTT ACTCATATAT ACTTTAGATT GATTAAAAC TTCATTTTTA ATTAAAAGG
      CATTGACAGT CTGGTTCAAA TGAGTATATA TGAAATCTAA CTAAATTTTG AAGTAAAAT TAAATTTTCC

3851  ATCTAGGTGA AGATCCTTTT TGATAATCTC ATGACCAAAA TCCCTTAACG TGAGTTTTCG TTCCACTGAG
      TAGATCCACT TCTAGGAAAA ACTATTAGAG TACTGGTTTA AGGGAATTGC ACTCAAAAGC AAGGTGACTC

3921  CGTCAGACCC CGTAGAAAAG ATCAAAGGAT CTTCTTGAGA TCCTTTTTTT CTGCGCGTAA TCTGCTGCTT
      GCAGTCTGGG GCATCTTTTC TAGTTTCCTA GAAGAACTCT AGGAAAAAAA GACGCGCATT AGACGACGAA

3991  GCAAACAAAA AAACCACCGC TACCAGCGGT GGTTTGTTTG CCGGATCAAG AGCTACCAAC TCTTTTTCCG
      CGTTTGTTTT TTTGGTGGCG ATGGTCGCCA CCAAACAAAC GGCCTAGTTC TCGATGGTTG AGAAAAAGGC

4061  AAGGTAACTG GCTTCAGCAG AGCGCAGATA CCAAATACTG TCCTTCTAGT GTAGCCGTAG TTAGGCCACC
      TTCCATTGAC CGAAGTCGTC TCGCGTCTAT GGTTTATGAC AGGAAGATCA CATCGGCATC AATCCGGTGG
```

FIG._48G

```
4131  ACTTCAAGAA CTCTGTAGCA CCGGCCTACAT ACCTCGCTCT GCTAATCCTG TTACCAGTGG CTGCTGCCAG
      TGAAGTTCTT GAGACATCGT GGCGGATGTA TGGAGCGAGA CGATTAGGAC AATGGTCACC GACGACGGTC

4201  TGGCGATAAG TCGTGTCTTA CCGGGTTGGA CTCAAGACGA TAGTTACCGG ATAAGGCGCA GCGGTCGGGC
      ACCGCTATTC AGCACAGAAT GGCCCAACCT GAGTTCTGCT ATCAATGGCC TATTCCGCGT CGCCAGCCCG

4271  TGAACGGGGG GTTCGTGCAC ACAGCCCAGC TTGGAGCGAA CGACCTACAC CGAACTGAGA TACCTACAGC
      ACTTGCCCCC CAAGCACGTG TGTCGGGTCG AACCTCGCTT GCTGGATGTG GCTTGACTCT ATGGATGTCG

4341  GTGAGCTATG AGAAAGCGCC ACGCTTCCCG AAGGAGAAA TATCCGGTAA GCGGCAGGGT
      CACTCGATAC TCTTTCGCGG TGCGAAGGGC TTCCCTCTTT CCGGCGACAGG ATAGGCCATT CGCCGTCCCA

4411  CGGAACAGGA GAGCGCACGA GGGAGCTTCC GCCTGGTATC CAGGGGGGCG GAGCCTATGG AAAAACGCCA
      GCCTTGTCCT CTCGCGTGCT CCCTCGAAGG CGGACCATAG GTCCCCCCGC CTCGGATACC TTTTTGCGGT

4481  CGCCACCTCT GACTTGAGCG TCGATTTTTG TGATGCTCGT CAGGGGAAAC GCCTGGTATC TGTCGGGTTT
      GCGGTGGAGA CTGAACTCGC AGCTAAAAAC ACTACGAGCA GTCCCCTTTG CGGACCATAG ACAGCCCAAA

4551  GCAACGCGGC CTTTTTACGG TTCCCTGGCCT TTTGCTCAC ATGTTCTTTC CTGCGTTATC
      CGTTGCGCCG GAAAAATGCC AAGGACCGGA AAACGACCGG TACAAGAAAG GACGCAATAG

4621  CCCTGATTCT GTGGATAACC GTATTACCGC CTTTGAGTGA GCTGATACCG CCGAACGACC
      GGGACTAAGA CACCTATTGG CATAATGGCG GAAACTCACT CGACTATGGC GGCTTGCTGG

4691  GAGCGCAGCG AGTCAGTGAG CGAGGAAGCG GAAGAGCGCC CAATACGCAA ACCGCCTCTC CCCGCGCGTT
      CTCGCGTCGC TCAGTCACTC GCTCCTTCGC CTTCTCGCGG GTTATGCGTT TGGCGGAGAG GGGCGCGCAA

4761  GGCCGATTCA TTAATGCAGC TGGCACGACA GGTTTCCCGA CTGGAAAGCG GGCAGTGAGC GCAACGCAAT
      CCGGCTAAGT AATTACGTCG ACCGTGCTGT CCAAAGGGCT GACCTTTCGC CCGTCACTCG CGTTGCGTTA

4831  TAATGTGAGT TAGCTCACTC ATTAGGCACC CCAGGCTTTA CACTTTATGC TTCCGGCTCG TATGTTGTGT
      ATTACACTCA ATCGAGTGAG TAATCCGTGG GGTCCGAAAT GTGAAATACG AAGGCCGAGC ATACAACACA
```

```
                                                                    BssHII
                                                                    ~~~~~~
4901  GGAATTGTGA GCGGATAACA ATTTCACACA GGAAACAGCT ATGACCATGA TTACGCCAAG CGCGCAATTA
      CCTTAACACT CGCCTATTGT TAAAGTGTGT CCTTTGTCGA TACTGGTACT AATGCGGTTC GCGCGTTAAT
                                           NcoI
                                           KpnI
                                           ~~~~
4971  ACCCTCACTA AAGGGAACAA AAGCTGGGTA C
      TGGGAGTGAT TTCCCTTGTT TTCGACCCAT G
```

FIG._48I

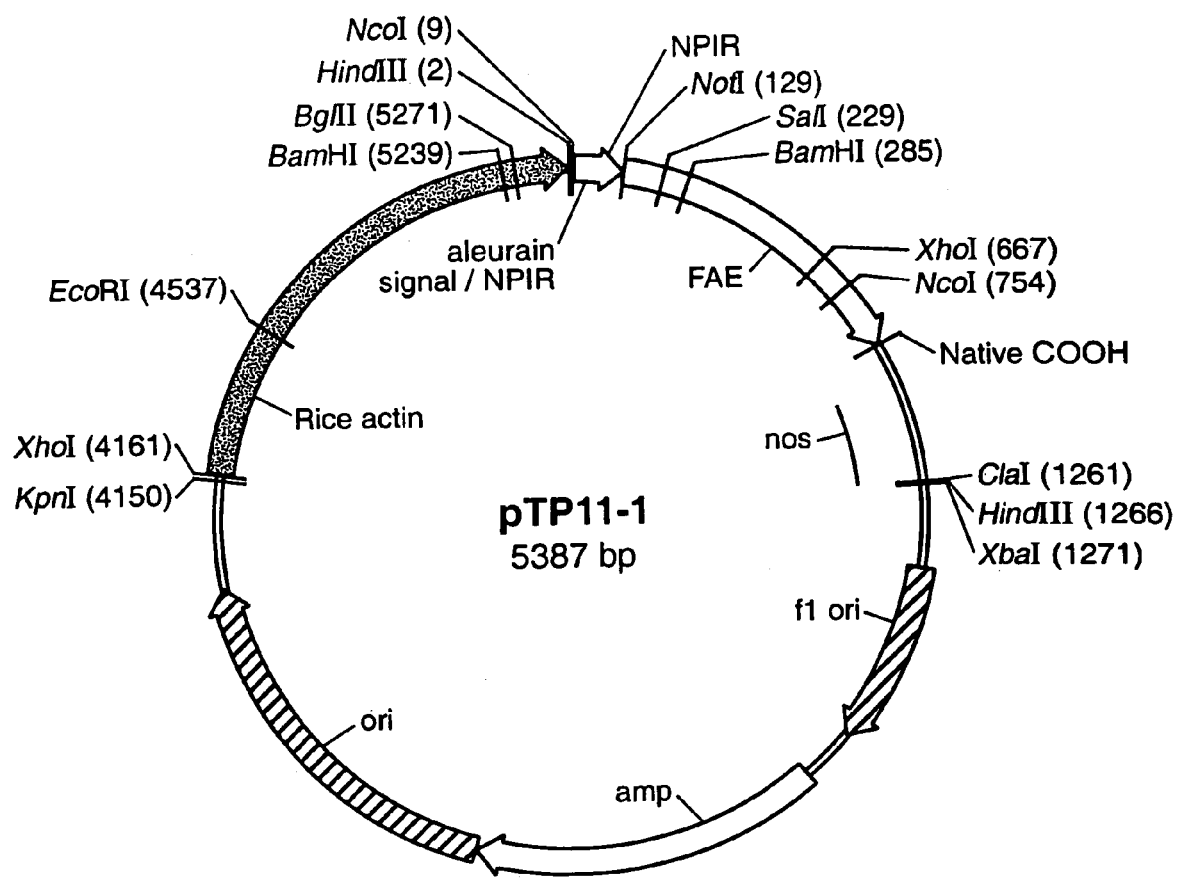
FIG._49A

```
                                    HindIII
                                    ~~~~~~~
                       M   A   H   A   R   V   L   L   L   A   L   A   V   L   A   T   A   A   V   A   V
  1  AAGCTTACCA TGGCCCACGC CCGCGTCCTC CTCCTGGCGC TCGCCGTGCT GGCCACGGCC GCCGTCGCCG
                NcoI                                                   NotI
                ~~~~~~~                                                ~~~~
       .  A   S   S   S   F   A   D   S   N   P   I   R   P   V   T   D   R   A   A   A   S   T
 71  TCGCCTCCTC CTCCTCCTTC GCCGACTCCA ACCCGATCCG GCCCGTCACC GACCGGGCGG CCGCCTCCAC
       .  Q   G   I   S   E   D   L   Y   S   R   L   V   E   M   A   T   I   S   Q   A   A   Y   A
141  GCAGGGCATC TCCGAAGACC TCTACAGCCG TTTAGTCGAA ATGGCCACTA TCTCCCAAGC TGCCTACGCC
                           SalI
                           ~~~~
                                         AccI
                                         ~~~~
       D   L   C   N   I   P   S   T   I   H   K   G   E   K   I   Y   N   S   Q   T   D   I   N   G
211  GACCTGTGCA ACATTCCGTC GACTATTATC AAGGGAGAGA AAATTTACAA TTCTCAAACT GACATTAACG
     BamHI
     ~~~~~
       .  W   I   L   R   D   D   S   S   K   E   I   I   T   V   F   R   G   T   G   S   D   T   N
281  GATGGATCCT CCGCGACGAC AGCAGCAAAG AAATAATCAC CGTCTTCCGT GGCACTGGTA GTGATACGAA
       .  L   Q   L   D   T   N   Y   T   L   T   P   F   D   T   L   P   Q   C   N   G   C   E   V
351  TCTACAACTC GATACTAACT ACACCCTCAC GCCTTTCGAC ACCCTACCAC AATGCAACGG TTGTGAAGTA
       H   G   G   Y   Y   I   G   W   V   S   V   Q   D   Q   V   E   S   L   V   K   Q   Q   V   S
421  CACGGTGGAT ATTATATTGG ATGGGTCTCC GTCCAGGACC AAGTCGAGTC GCTTGTCAAA CAGCAGGTTA
       .  Q   Y   P   D   Y   A   L   T   V   T   G   H   K   L   G   A   S   L   A   A   L   T   A
491  GCCAGTATCC GGACTACGCG CTGACCGTGA CCGGCCACKC CCTCGGGGCC TCCCTGGCGG CACTCACTGC
       .  A   Q   L   S   A   T   Y   D   N   I   R   L   Y   T   F   G   E   P   R   S   G   N   Q
561  CGCCCAGCTG TCTGCGACAT ACGACAACAT CCGCCTGTAC ACCTTCGGCG AACCGCGCAG CGGCAATCAG
                                                 XhoI
                                                 ~~~~
       A   F   A   S   Y   M   N   D   A   F   Q   A   S   P   D   T   Q   Y   F   R   V   T
631  GCCTTCGCGT CGTACATGAA CGATGCCTTC CAAGCCTCGA GCCCAGATAC GACGCAGTAT TTCCGGGTCA
```

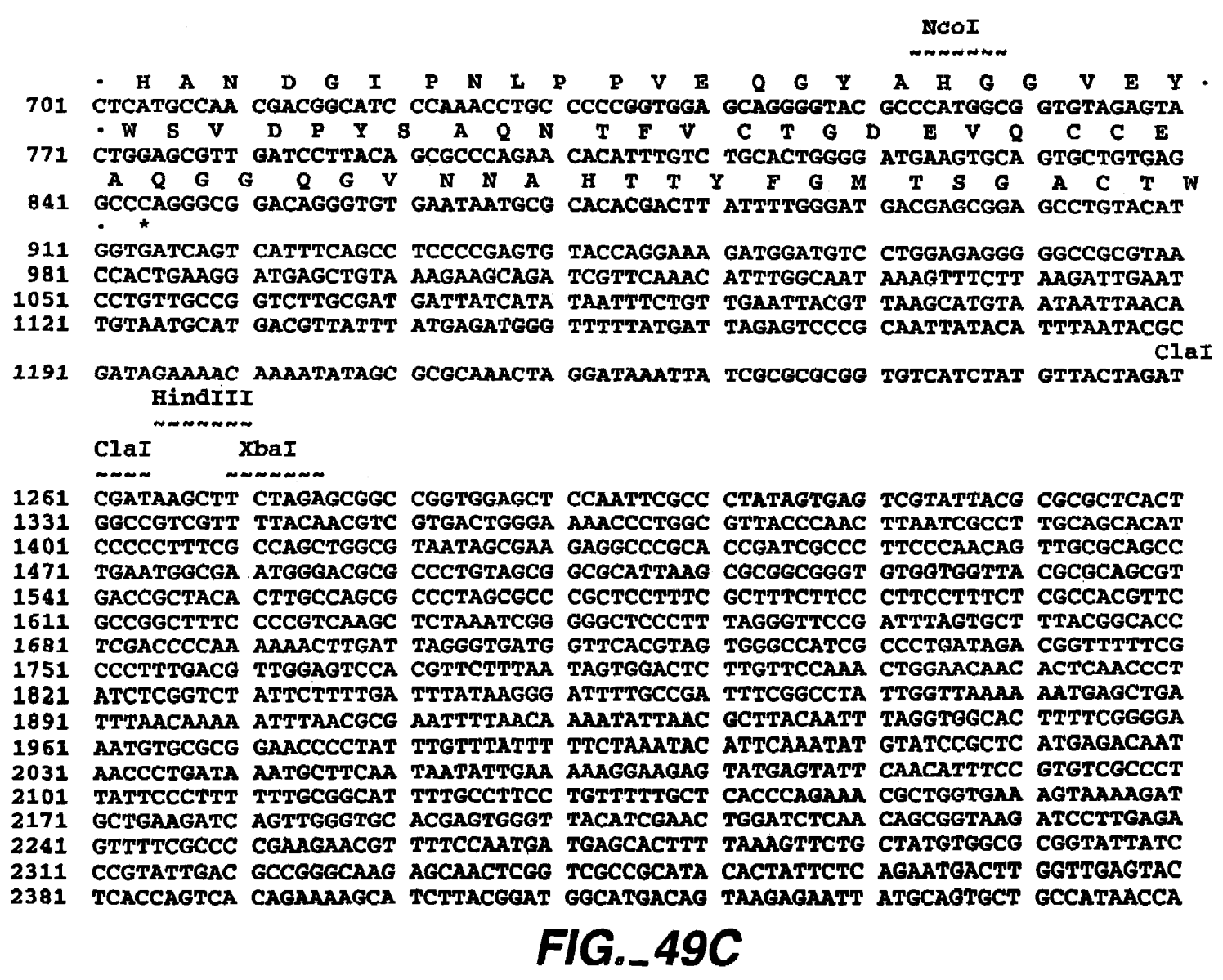

```
2451  TGAGTGATAA  CACTGCGCGCC  AACTTACTTC  TGACAACGAT  CGGAGGACCG  AAGGAGCTAA  CCGCTTTTTT
2521  GCACAACATG  GGGGATCATG  TAACTCGCCT  TGATCGTTGG  GAACCGGAGC  TGAATGAAGC  CATACCAAAC
2591  GACGAGCGTG  ACACCACGTG  GCCTGTAGCA  ATGGCAACAA  CGTTGCGCAA  ACTATTAACT  GGCGAACTAC
2661  TTACTCTAGC  TTCCCGGCTG  CAATTAATAG  ACTGGATGGA  GGCGGATAAA  GTTGCAGGAC  CACTTCTGCG
2731  CTCGGCCCTT  CCGGCTGGCT  GGTTTATTGC  TGATAAATCT  GGAGCCGGTG  AGCGTGGGTC  TCGCGGTATC
2801  ATTGCAGCAC  TGGGGCCAGA  TGGTAAGCCC  TCCCGTATCG  TAGTTATCTA  CACGACGGGG  AGTCAGGCAA
2871  CTATGGATGA  ACGAAATAGA  CAGATCGCTG  AGATAGGTGC  CTCACTGATT  AAGCATTGGT  AACTGTCAGA
2941  CCAAGTTTAC  TCATATATAC  TTTAGATTGA  TTTAAAACTT  CATTTTTAAT  TTAAAAGGAT  CTAGGTGAAG
3011  ATCCTTTTTG  ATAATCTCAT  GACCAAAATC  CCTTAACGTG  AGTTTTCGTT  CCACTGAGCG  TCAGACCCCG
3081  TAGAAAAGAT  CAAAGGATCT  TCTTGAGATC  CTTTTTTTCT  GCGCGTAATC  TGCTGCTTGC  AAACAAAAAA
3151  ACCACCGCTA  CCAGCGGTGG  TTTGTTTGCC  GGATCAAGAG  CTACCAACTC  TTTTTCCGAA  GGTAACTGGC
3221  TTCAGCAGAG  CGCAGATACC  AAATACTGTC  CTTCTAGTGT  AGCCGTAGTT  AGGCCACCAC  TTCAAGAACT
3291  CTGTAGCACC  GCCTACATAC  CTCGCTCTGC  TAATCCTGTT  ACCAGTGGCT  GCTGCCAGTG  GCGATAAGTC
3361  GTGTCTTACC  GGGTTGGACT  CAAGACGATA  GTTACCGGAT  AAGGCGCAGC  GGTCGGGCTG  AACGGGGGGT
3431  TCGTGCACAC  AGCCCAGCTT  GGAGCGAACG  ACCTACACCG  AACTGAGATA  CCTACAGCGT  GAGCTATGAG
3501  AAAGCGCCAC  GCTTCCCGAA  GGGAGAAAGG  CGGACAGGTA  TCCGGTAAGC  GGCAGGGTCG  GAACAGGAGA
3571  GCGCACGAGG  GAGCTTCCAG  GGGGAAACGC  CTGGTATCTT  TATAGTCCTG  TCGGGTTTCG  CCACCTCTGA
3641  CTTGAGCGTC  GATTTTTGTG  ATGCTCGTCA  GGGGGGCGGA  GCCTATGGAA  AAACGCCAGC  AACGCGGCCT
3711  TTTTACGGTT  CCTGGCCTTT  TGCTGGCCTT  TTGCTCACAT  GTTCTTTCCT  GCGTTATCCC  CTGATTCTGT
3781  GGATAACCGT  ATTACCGCCT  TTGAGTGAGC  TGATACCGCT  CGCCGCAGCC  GAACGACCGA  GCGCAGCGAG
3851  TCAGTGAGCG  AGGAAGCGGA  AGAGCGCCCA  ATACGCAAAC  CGCCTCTCCC  CGCGCGTTGG  CCGATTCATT
3921  AATGCAGCTG  GCACGACAGG  TTTCCCGACT  GGAAAGCGGG  CAGTGAGCGC  AACGCAATTA  ATGTGAGTTA
3991  GCTCACTCAT  TAGGCACCCC  AGGCTTTACA  CTTTATGCTT  CCGGCTCGTA  TGTTGTGTGG  AATTGTGAGC
4061  GGATAACAAT  TTCACACAGG  AAACAGCTAT  GACCATGATT  ACGCCAAGCG  CGCAATTAAC  CCTCACTAAA
                                                                  EcoRI
4131  GGGAACAAAA  GCTGGGTACC  GGGCCCCCCC  TCGAGGTCAT  TCATATGCTT  GAGAAGAGAG  TCGGGATAGT
      KpnI                               XhoI
4201  CCAAAATAAA  ACAAGGTAA   GATTACCTGG  TCAAAAGTGA  AAACATCAGT  TAAAAGGTGG  TATAAGTAAA
4271  ATATCGGTAA  TAAAAGGTGG  CCCAAAGTGA  AATTTACTCT  TTTCTACTAT  TATAAAAATT  GAGGATGTTT
4341  TGTCGGTACT  TTGATACGTC  ATTTTTGTAT  GAATTGGTTT  TTAAGTTTAT  TCGCGATTTG  GAAATGCATA
4411  TCTGTATTTG  AGTCGGTTTT  TAAGTTCGTT  GCTTTGTAA   ATACAGAGGG  ATTTGTATAA  GAAATATCTT

4481  TAAAAACCC   ATATGCTAAT  TTTGACATAA  TTTTGAGAAA  AATATATATT  CAGGCGAATT  CCACAATGAA
4551  CAATAATAAG  ATTAAAATAG  CTTGCCCCCG  TTGCAGCGAT  GGGTATTTTT  TCTAGTAAAA  TAAAAGATAA
4621  ACTTAGACTC  AAAACATTTA  CAAAACAAC   CCCTAAAGTC  CTAAAGCCCA  AAGTGCTATG  CACGATCCAT
```

*FIG._49D*

```
4691  AGCAAGCCCA  GCCCAACCCA  ACCCACCCCA  GTGCAGCCAA  CTGGCAAATA  GTCTCCACCC
4761  CCGGCACTAT  CACCGTGAGT  TGTCCGCACC  ACCGCACGTC  AAAAAAAAA   AGAAAGAAAA
4831  AAAGAAAAAA  GAAAAACAGC  AGGTGGTCC   GGGTCGTGGG  GCGAGGAGGA  TCGCGAGCAG
4901  CGACGAGGCC  CGGCCCTCCC  TCCGCTTCCA  CCCCATCGCC  ACTATATACA  TACCCCCCCC
4971  TCTCCTCCCA  TCCCCCCAAC  CCTACCACCA  CACCTCCTCC  CCCCTCGCTG  CCGGACGACG
5041  AGCTCCTCCC  CCCTCCCCCT  CCGCCGCCGC  CCCGCCCCTC  TCCTCTTTCT  TTCTCCGTTT
5111  TTTTTTTCGT  CTCGGTCTCG  ATCTTTGGCC  TTGGTAGTTT  GGGTGGGCGA  GAGCGGCTTC  GTCGCCCAGA
                                                                BamHI
5181  TCGGTGCGCG  GGAGGGGCGG  GATCTCGCGG  CTGGCGTCTC  CGGGCGTGAG  TCCTCGCGGG
                              BglII
5251  GAATGGGGCT  CTCGGATGTA  GATCTTCTT   CTTTCTTCTT  TTTGTGGTAG  AATTTGAATC  CCTCAGCATT
5321  GTTCATCGGT  AGTTTTTCTT  TTCATGATTT  GTGACAAATG  CAGCCTCGTG  CGGAGCTTTT  TTGTAGC
```

*FIG._49E*

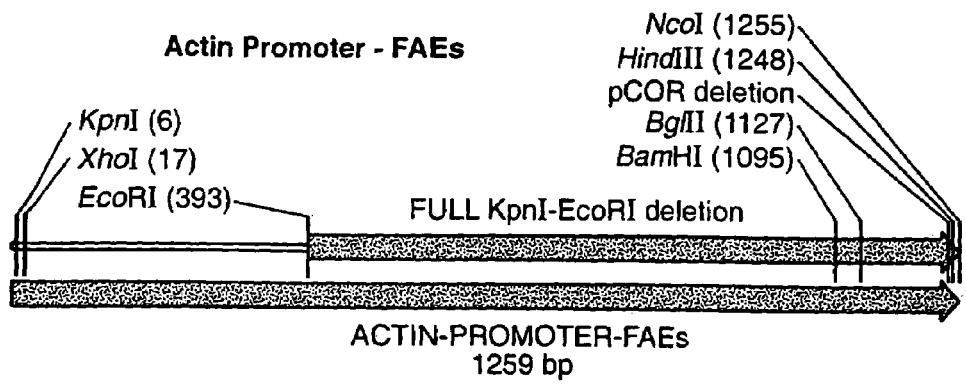

```
                             NcoI (1255)
       Actin Promoter - FAEs  HindIII (1248)
                              pCOR deletion
      KpnI (6)                BglII (1127)
      XhoI (17)               BamHI (1095)
      EcoRI (393)
                       FULL KpnI-EcoRI deletion ACTIN-PROMOTER-FAEs
                          1259 bp
```

```
     KpnI            XhoI
     ----            ------

1  GGTACCGGGC CCCCCCTCGA GGTCATTCAT ATGCTTGAGA AGAGAGTCGG GATAGTCCAA AATAAAACAA
     CCATGGCCCG GGGGGGAGCT CCAGTAAGTA TACGAACTCT TCTCTCAGCC CTATCAGGTT TTATTTTGTT

71  AGGTAAGATT ACCTGGTCAA AAGTGAAAAC ATCAGTTAAA AGGTGGTATA AGTAAAATAT CGGTAATAAA
     TCCATTCTAA TGGACCAGTT TTCACTTTTG TAGTCAATTT TCCACCATAT TCATTTTATA GCCATTATTT

141  AGGTGGCCCA AAGTGAAATT TACTCTTTTC TACTATTATA AAAATTGAGG ATGTTTTGTC GGTACTTTGA
     TCCACCGGGT TTCACTTTAA ATGAGAAAAG ATGATAATAT TTTTAACTCC TACAAAACAG CCATGAAACT

211  TACGTCATTT TTGTATGAAT TGGTTTTTAA GTTATTCGC GATTTGGAAA TGCATATCTG TATTTGAGTC
     ATGCAGTAAA AACATACTTA ACCAAAAATT CAATAAGCG CTAAACCTTT ACGTATAGAC ATAAACTCAG

281  GGTTTTTAAG TTCGTTGCTT TTGTAAATAC AGAGGGATTT GTATAAGAAA TATCTTTAAA AAACCCATAT
     CCAAAAATTC AAGCAACGAA AACATTTATG TCTCCCTAAA CATATTCTTT ATAGAAATTT TTTGGGTATA

EcoRI
                                           -----

351  GCTAATTTGA CATAATTTTT GAGAAAAATA TATATTCAGG CGAATTCCAC AATGAACAAT AATAAGATTA
     CGATTAAACT GTATTAAAAA CTCTTTTTAT ATATAAGTCC GCTTAAGGTG TTACTTGTTA TTATTCTAAT

421  AAATAGCTTG CCCCCGTTGC AGCGATGGGT ATTTTTTCTA GTAAATAAA AGATAAACTT AGACTCAAAA
     TTTATCGAAC GGGGGCAACG TCGCTACCCA TAAAAAAGAT CATTTTATTT TCTATTTGAA TCTGAGTTTT

491  CATTTACAAA AACAACCCCT AAAGTCCTAA AGCCCAAAGT GCTATGCACG ATCCATAGCA AGCCCAGCCC
     GTAAATGTTT TTGTTGGGGA TTTCAGGATT TCGGGTTTCA CGATACGTGC TAGGTATCGT TCGGGTCGGG

561  AACCCAACCC AACCCAACCC ACCCCAGTGC AGCCAACTGG CAAATAGTCT CCACCCCCGG CACTATCACC
     TTGGGTTGGG TTGGGTTGGG TGGGGTCACG TCGGTTGACC GTTTATCAGA GGTGGGGGCC GTGATAGTGG

631  GTGAGTTGTC CGCACCACCG CACGTCTCGC AGCCAAAAAA AAAAAAAGAA AGAAAAAAAA GAAAAAGAAA
     CACTCAACAG GCGTGGTGGC GTGCAGAGCG TCGGTTTTTT TTTTTTTCTT TCTTTTTTTT CTTTTTCTTT

701  AACAGCAGGT GGGTCCGGGT CGTGGGGGCC GGAAAAGCGA GGAGGATCGC GAGCAGCGAC GAGGCCCGGC
     TTGTCGTCCA CCCAGGCCCA GCACCCCCGG CCTTTTCGCT CCTCCTAGCG CTCGTCGCTG CTCCGGGCCG
```

FIG._50A

```
771   CCTCCCTCCG CTTCCAAAGA AACGCCCCCC ATCGCCACTA TATACATACC CCCCCCTCTC CTCCCATCCC
      GGAGGGAGGC GAAGGTTTCT TTGCGGGGGG TAGCGGTGAT ATATGTATGG GGGGGAGAG GAGGGTAGGG

841   CCCAACCCTA CCACCACCAC CACCACCACC TCCTCCCCCC TCGCTGCCGG ACGACGAGCT CCTCCCCCCT
      GGGTTGGGAT GGTGGTGGTG GTGGTGGTGG AGGAGGGGGG AGCGACGGCC TGCTGCTCGA GGAGGGGGA

911   CCCCCTCCGC CGCCGCCGGT AACCACCCCG CCCCTCTCCT CTTTCTTTCT CCGTTTTTTT TTTCGTCTCG
      GGGGGAGGCG GCGGCGGCCA TTGGTGGGGC GGGGAGAGGA GAAAGAAAGA GGCAAAAAAA AAAGCAGAGC

981   GTCTCGATCT TTGGCCTTGG TAGTTTGGGT GGGCGAGAGC GGCTTCGTCG CCCAGATCGG TGCGCGGGAG
      CAGAGCTAGA AACCGGAACC ATCAAACCCA CCCGCTCTCG CCGAAGCAGC GGGTCTAGCC ACGCGCCCTC

BamHI
                                                                ------
1051  GGGCGGGATC TCGCGGCTGG CGTCTCCGGG CGTGAGTCGG CCCGGATCCT CGCGGGGAAT GGGGCTCTCG
      CCCGCCCTAG AGCGCCGACC GCAGAGGCCC GCACTCAGCC GGGCCTAGGA GCGCCCCTTA CCCCGAGAGC

BglII
              ------
1121  GATGTAGATC TTCTTTCTTT CTTCTTTTTG TGGTAGAATT TGAATCCCTC AGCATTGTTC ATCGGTAGTT
      CTACATCTAG AAGAAAGAAA GAAGAAAAAC ACCATCTTAA ACTTAGGGAG TCGTAACAAG TAGCCATCAA

HindIII  NcoI
                                                            -------  ----
1191  TTTCTTTTCA TGATTTGTGA CAAATGCAGC CTCGTGCGGA GCTTTTTTGT AGGTAGAAGC TTACCATGG
      AAAGAAAAGT ACTAAACACT GTTTACGTCG GAGCACGCCT CGAAAAAACA TCCATCTTCG AATGGTACC
```

KpnI-EcoRI - deletion underlined and restored NCO site in bold in vectors pJQ4.9, pJQ3.2 and pJO6.3.

FIG._50B

ALEURAIN_deleted NPIR (Apoplast) Structure and Sequence

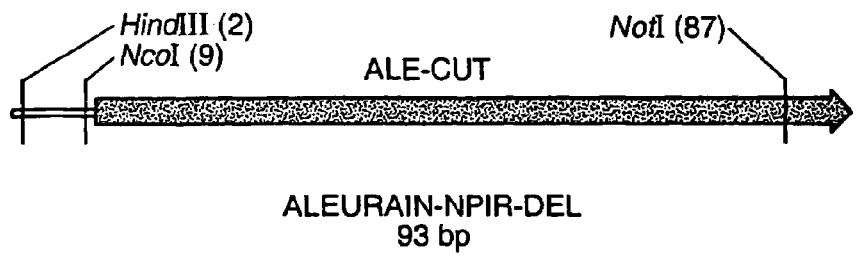

ALEURAIN-NPIR-DEL
93 bp

```
+1         M   A   H   A   R   V   L   L   L   A   L   A   V   L   A   T   A   A   V   A
    HindIII NcoI
    ------  --------
1   AAGCTTACCA TGGCCCACGC CCGCGTCCTC CTCCTGGCGC TCGCCGTGCT GGCCACGGCC GCCGTCGCCG
    TTCGAATGGT ACCGGGTGCG GGCGCAGGAG GAGGACCGCG AGCGGCACGA CCGGTGCCGG CGGCAGCGGC +1  V   A   S   S   R   A   A
                        NotI
                        ----------
71  TCGCCTCCTC CCGCGCGGCC GCC
    AGCGGAGGAG GGCGCGCCGG CGG
```

FIG._51

SEE1 ( Senescence enhanced ) PROMOTER sequence

```
  1  CATGGGCCAG GTATAATTAT GGGATATCTC AAGCAAATAA TCGAAATATC ACCATTGGCT ACAATATCTG
                          PstI                             XbaI       XbaI
                          --------                         --------   ------
 71  AGCTCCGAGT TCTGACTGCA GTCTGGATGA CGCGTGTTGT ATCTAGAACT CTAGATAGCA CAGCCACAGC
141  ACCTACAGGA GTGCGACACT TGTGGACTGT AGTAGTGTTG GAGACGGAGC TCTTTCCTAC CTCCTGACGT
211  TGCCGCCGTT GTCCATTCCA ACGGCATCAC TCTCAACCAA TCACGCGCTC CCAACAAAAT ATCGTCCCCC
281  ATGTCTTGGC GGAGAGAGAG TACATACATG CTGTCGCGCC GTTTTTGTCT GAATCTCGCT TCCACTGGCC
                SmaI
                --------
351  AATCAGCTCA GCTCCCGGGA GCTCACTCAT TCAAGATCCC ATCGTCGTCG TCACCCCTGG CGTCATGGGA
421  TGGAAAAGAA CCTCCGTTGC TCGGATGAGT CAGCCATATC CCCGAACAGA GTACTGCAAG ATAACCCAAT
                                                SphI
                                                --------
491  TCAGATTCCC CCAATAGAGA AAGTATAGCA TGCTTTCGGG TTTTGTTTGG CTTAATTGAC TTTATTTTTG
561  TTGGAGTTGA ATGCTGATTT GTTGTGTAAA ATGCCCAACC ATCTGAATAT CGAGACGGAT AATAGGCTGG
631  CTAATTAATT TATAGCAAGA TTCTGTAGTG CACATCGCAA ATATCTTTCT GGGCATTACA GCTGGAGGCT
                          PstI
                          --------
701  TCATCAGCCT GAAACACTCT GCAGAGCCTG AAGCAAGTGG TGAAGCGTGG CGATGAGATG GGTATAAAAC
771  CCCCGGCACC GGGACGCGAG CTCCCGCCTA CCAGTACCAT CTCGCCTCGC TCCCCCTGCC GGACGACCCA
841  GTAAAATACT GTTGCCCACT CGCCGGCGAG ATG
```

FIG._52

SEE1 ( Senescence enhanced ) PROMOTER plus vacuolar aleurain SIGNAL/NPIR sequence

```
  1  CATGGGCCAG GTATAATTAT GGGATATCTC AAGCAAATAA TCGAAATATC ACCATTGGCT ACAATATCTG
                          PstI                             XbaI       XbaI
                          --------                         --------   ------
 71  AGCTCCGAGT TCTGACTGCA GTCTGGATGA CGCGTGTTGT ATCTAGAACT CTAGATAGCA CAGCCACAGC
141  ACCTACAGGA GTGCGACACT TGTGGACTGT AGTAGTGTTG GAGACGGAGC TCTTTCCTAC CTCCTGACGT
211  TGCCGCCGTT GTCCATTCCA ACGGCATCAC TCTCAACCAA TCACGCGCTC CCAACAAAAT ATCGTCCCCC
281  ATGTCTTGGC GGAGAGAGAG TACATACATG CTGTCGCGCC GTTTTTGTCT GAATCTCGCT TCCACTGGCC
                SmaI
                --------
351  AATCAGCTCA GCTCCCGGGA GCTCACTCAT TCAAGATCCC ATCGTCGTCG TCACCCCTGG CGTCATGGGA
421  TGGAAAAGAA CCTCCGTTGC TCGGATGAGT CAGCCATATC CCCGAACAGA GTACTGCAAG ATAACCCAAT
                                                SphI
                                                --------
491  TCAGATTCCC CCAATAGAGA AAGTATAGCA TGCTTTCGGG TTTTGTTTGG CTTAATTGAC TTTATTTTTG
561  TTGGAGTTGA ATGCTGATTT GTTGTGTAAA ATGCCCAACC ATCTGAATAT CGAGACGGAT AATAGGCTGG
631  CTAATTAATT TATAGCAAGA TTCTGTAGTG CACATCGCAA ATATCTTTCT GGGCATTACA GCTGGAGGCT
                          PstI
                          --------
701  TCATCAGCCT GAAACACTCT GCAGAGCCTG AAGCAAGTGG TGAAGCGTGG CGATGAGATG GGTATAAAAC
771  CCCCGGCACC GGGACGCGAG CTCCCGCCTA CCAGTACCAT CTCGCCTCGC TCCCCCTGCC GGACGACCCA
                                                       M  A H G  R I L  F L A  L A V  L
841  GTAAAATACT GTTGCCCACT CGCCGGCGAG ATGGCCCACG GCCGCATCCT CTTCTTGGCG CTCGCCGTCT
                                                                                BssHII
                                                                                NotI
      · A T A    A V A    A A S L    A D S    N P I    R P V    T    E R A
911  TGGCCACCGC CGCGGTGGCC GCCGCATCNT TGGCGGACTC CAACCCGATC CGGCCCGTCA CCGAGCGCGC
        NotI
        ------
      · A A
981  GGCCGCC
```

FIG._53

SEQUENCE LISTING

```
<160> NUMBER OF SEQ ID NOS: 97

<210> SEQ ID NO 1
<211> LENGTH: 2436
<212> TYPE: DNA
<213> ORGANISM: Aspergillus niger

<400> SEQUENCE: 1
ccatggtggt gtcgatatcg gcagtagtct ttgccgaaac gttgagggtt acagtgatct      60
gcgtcggaca tacttcgggg aatctacggc ggaatatcaa agtcttcgga atatccatat     120
tgggaaagga cagaagctcc ggggtagttt gatagatgag ctccggtgta ttaaatcggg     180
agctgacagg agtgagcgtc atgtagacca tctagtaatg tcagtcgcgc gcaatttcgc     240
acatgaaaca agttgatttc gggaccccat tgttacatct ctcggctaca gctcgagatg     300
tgcctgccga gtatacttag aagccatgcc agcgtgttgt tatacgacca aaagtcaggg     360
aatatgaaac gatcgtcgga tatttcttgt ttttatccta aattagtctt ccagtggttt     420
atttaagaga tagatccctt cacaaacact catccaacgg acttctcata ccactcattg     480
acataatttc aaacagctcc aggcgcattt agttcaacat gaagcaattc tccgccaaac     540
acgtcctcgc agttgtggtg actgcagggc acgccttagc agcctctacg caaggcatct     600
ccgaagacct ctacagccgt ttagtcgaaa tggccactat ctcccaagct gcctacgccg     660
acctgtgcaa cattccgtcg actattatca agggagagaa aatttacaat tctcaaactg     720
acattaacgg atggatcctc cgcgacgaca gcagcaaaga aataatcacc gtcttccgtg     780
gcactggtag tgatacgaat ctacaactcg atactaacta caccctcacg cctttcgaca     840
ccctaccaca atgcaacggt tgtgaagtac acggtggata ttatattgga tgggtctccg     900
tccaggacca agtcgagtcg cttgtcaaac agcaggttag ccagtatccg gactatgcgc     960
tgactgtgac gggccacagg tatgccctcg tgatttcttt caattaagtg tataatactc    1020
```

-continued

```
actaactcta cgatagtctc ggagcgtccc tggcagcact cactgccgcc cagctgtctg   1080
cgacatacga caacatccgc ctgtacacct tcggcgaacc gcgcagcggc aatcaggcct   1140
tcgcgtcgta catgaacgat gccttccaag cctcgagccc agatacgacg cagtatttcc   1200
gggtcactca tgccaacgac ggcatcccaa acctgccccc ggtggagcag gggtacgccc   1260
atggcggtgt agagtactgg agcgttgatc cttacagcgc ccagaacaca tttgtctgca   1320
ctggggatga agtgcagtgc tgtgaggccc agggcggaca gggtgtgaat aatgcgcaca   1380
cgacttattt tgggatgacg agcggagcct gtacatggtg atcagtcatt tcagcctccc   1440
cgagtgtacc aggaaagatg gatgtcctgg agagggcatg catgtacgta tacccgaagc   1500
acacttttc ggtaaatcag gacatgtaat aagttccttc catgaataga tatggttacc    1560
ctcaccataa gccttgaggt tgcctttctc ttttgattgt gaatatatat ttaaagtaga   1620
tgacagatat ctctaaacac cttatccgct taaacccatc atagattgtg tcacgtgata   1680
gaccccttga atgatgagcg aaatgtatca gtcccgttta aatcaaaccc tttcagccta   1740
gcacagtcag aatacaccaa ccccattcta aggtagtact aaatatgaat acagcctaaa   1800
tgcatcgcta tatgatccca taaagaagca acaaccttc agatctcgtt ttgcgctgcg    1860
aagagctagc tctaccatgg tctcaattat gagtggagcg tttagtctcg tttaagccta   1920
gctatcttat aaggacaaca catgtacatg gcttacttg tagagaggta ggatcccggg    1980
cttcttcaca tctcgaggag ttgtctacac gtcgcgtcca tgtcataagc cggtactcga   2040
cgttgtcgtg accgtgaccc agaccctgt tgatagcgtt gagaaggccc tatatttgaa    2100
tttccaatct cagctttacg aagatatgcc catggtggag ggttagtaaa ccgatgatga   2160
tcgtgtgcag catgagatga gaccgtggcc aatcctgttc aaatgccaag acccgcctcc   2220
taccacatgt aaggcatccg tcggccgcac gttgaattgt gcaaatgccg agatcataaa   2280
agcggccaca cttccacgtc ggtactggat ggggttgcgcg tggccatact gtgttttcca   2340
ttgcgtgggt cgttcgtgtt actgcgacgc agattctgta ggcaaggcgc agggctctct   2400
tctgaggtag aaaacacccc atattaatct gaattc                             2436
```

<210> SEQ ID NO 2
<211> LENGTH: 281
<212> TYPE: PRT
<213> ORGANISM: Aspergillus niger

<400> SEQUENCE: 2

```
Met Lys Gln Phe Ser Ala Lys His Val Leu Ala Val Val Thr Ala
  1               5                  10                  15

Gly His Ala Leu Ala Ala Ser Thr Gln Gly Ile Ser Glu Asp Leu Tyr
             20                  25                  30

Ser Arg Leu Val Glu Met Ala Thr Ile Ser Gln Ala Ala Tyr Ala Asp
         35                  40                  45

Leu Cys Asn Ile Pro Ser Thr Ile Ile Lys Gly Glu Lys Ile Tyr Asn
     50                  55                  60

Ser Gln Thr Asp Ile Asn Gly Trp Ile Leu Arg Asp Asp Ser Lys
 65                  70                  75                  80

Glu Ile Ile Thr Val Phe Arg Gly Thr Gly Ser Asp Thr Asn Leu Gln
                 85                  90                  95

Leu Asp Thr Asn Tyr Thr Leu Thr Pro Phe Asp Thr Leu Pro Gln Cys
            100                 105                 110

Asn Gly Cys Glu Val His Gly Gly Tyr Tyr Ile Gly Trp Val Ser Val
```

-continued

```
                115                 120                 125
Gln Asp Gln Val Glu Ser Leu Val Lys Gln Gln Val Ser Gln Tyr Pro
    130                 135                 140

Asp Tyr Ala Leu Thr Val Thr Gly His Ser Leu Gly Ala Ser Leu Ala
145                 150                 155                 160

Ala Leu Thr Ala Ala Gln Leu Ser Ala Thr Tyr Asp Asn Ile Arg Leu
                165                 170                 175

Tyr Thr Phe Gly Glu Pro Arg Ser Gly Asn Gln Ala Phe Ala Ser Tyr
                180                 185                 190

Met Asn Asp Ala Phe Gln Ala Ser Ser Pro Asp Thr Thr Gln Tyr Phe
                195                 200                 205

Arg Val Thr His Ala Asn Asp Gly Ile Pro Asn Leu Pro Pro Val Glu
                210                 215                 220

Gln Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asn Ala His Thr Thr Tyr Phe
                260                 265                 270

Gly Met Thr Ser Gly Ala Cys Thr Trp
                275                 280

<210> SEQ ID NO 3
<211> LENGTH: 40
<212> TYPE: DNA
<213> ORGANISM: Artificial Sequence
<220> FEATURE:
<223> OTHER INFORMATION: funcional PCR product reading frame

<400> SEQUENCE: 3
ggactacgcg ctgaccgtga ccggccactc cctcggcgcc                          40

<210> SEQ ID NO 4
<211> LENGTH: 35
<212> TYPE: DNA
<213> ORGANISM: Artificial Sequence
<220> FEATURE:
<223> OTHER INFORMATION: inactivated PCR product reading frame

<400> SEQUENCE: 4
ccggccacgc cctcggcgcc tccctggcgg cactc                               35

<210> SEQ ID NO 5
<211> LENGTH: 10
<212> TYPE: PRT
<213> ORGANISM: Artificial Sequence
<220> FEATURE:
<223> OTHER INFORMATION: retention sequence

<400> SEQUENCE: 5

Ala Ala Ala Glu Pro Leu Lys Asp Glu Leu
1               5                  10

<210> SEQ ID NO 6
<211> LENGTH: 33
<212> TYPE: DNA
<213> ORGANISM: Artificial Sequence
<220> FEATURE:
<223> OTHER INFORMATION: retention sequence encoding sequence

<400> SEQUENCE: 6
```
gcggccgcgg aaccactgaa ggatgagctg taa                                    33

<210> SEQ ID NO 7
<211> LENGTH: 15
<212> TYPE: PRT
<213> ORGANISM: Artificial Sequence
<220> FEATURE:
<223> OTHER INFORMATION: FAE-linker-frameshift sequence

<400> SEQUENCE: 7

Gly Ala Cys Thr Trp Pro Val Ala Ala Ala Glu Thr Thr Glu Gly
 1               5                  10                  15

<210> SEQ ID NO 8
<211> LENGTH: 48
<212> TYPE: DNA
<213> ORGANISM: Artificial Sequence
<220> FEATURE:
<223> OTHER INFORMATION: FAE-linker-frameshift sequence

<400> SEQUENCE: 8
ggcgcatgca cctggccggt cgcggccgcg gaaaccactg aaggatga                    48

<210> SEQ ID NO 9
<211> LENGTH: 41
<212> TYPE: PRT
<213> ORGANISM: Hordeum sp.

<400> SEQUENCE: 9

Met Ala His Ala Arg Val Leu Leu Ala Leu Ala Val Leu Ala Thr
 1               5                  10                  15

Ala Ala Val Ala Val Ala Ser Ser Ser Phe Ala Asp Ser Asn Pro
                20                  25                  30

Ile Arg Pro Val Thr Asp Arg Ala Ala
                35                  40

<210> SEQ ID NO 10
<211> LENGTH: 134
<212> TYPE: DNA
<213> ORGANISM: Hordeum sp.

<400> SEQUENCE: 10
aagcttacca tgcccacgc ccgcgtcctc ctcctggcgc tcgccgtgct ggccacggcc       60
gccgtcgccg tcgcctcctc ctcctccttc gccgactcca acccgatccg gcccgtcacc     120
gaccgcgcgg ccgc                                                       134

<210> SEQ ID NO 11
<211> LENGTH: 46
<212> TYPE: PRT
<213> ORGANISM: Rattus sp.

<400> SEQUENCE: 11

Met Ile His Thr Asn Leu Lys Lys Phe Ser Leu Phe Ile Leu Val
 1               5                  10                  15

Phe Leu Leu Phe Ala Val Ile Cys Val Trp Lys Lys Gly Ser Asp Tyr
                20                  25                  30

Glu Ala Leu Thr Leu Gln Ala Lys Glu Phe Gln Met Ala Ala
                35                  40                  45

<210> SEQ ID NO 12
<211> LENGTH: 149
<212> TYPE: DNA

```
<213> ORGANISM: Rattus sp.

<400> SEQUENCE: 12
aagcttacca tgatccacac caacctcaaa aagaagttct ccctcttcat cctcgtcttc    60
ctcctcttcg ccgtgatctg cgtgtggaag aagggctccg actacgaggc cctcaccctc   120
caagccaagg agttccaaat ggcggccgc                                     149

<210> SEQ ID NO 13
<211> LENGTH: 50
<212> TYPE: PRT
<213> ORGANISM: Solanum sp.
<220> FEATURE:
<221> NAME/KEY: VARIANT
<222> LOCATION: (1)...(50)
<223> OTHER INFORMATION: Xaa = Any Amino Acid

<400> SEQUENCE: 13

Met Xaa Val His Lys Glu Val Asn Phe Val Ala Tyr Leu Leu Ile Val
  1               5                  10                  15

Leu Gly Leu Leu Leu Leu Val Ser Ala Met Glu His Val Asp Ala Lys
             20                  25                  30

Ala Cys Thr Xaa Glu Cys Gly Asn Leu Gly Phe Gly Ile Cys Pro Ala
         35                  40                  45

Ala Ala
     50

<210> SEQ ID NO 14
<211> LENGTH: 159
<212> TYPE: DNA
<213> ORGANISM: Solanum sp.

<400> SEQUENCE: 14
aagcttacma tggmcgtgca caaggaggts aacttcgtsg cctacctcct gatcgtsctc    60
ggcctcctct tgctcgtstc cgccatggag cacgtggacg ccaaggcctg caccckcgag   120
tgcggcaacc tcggcttcgg catctgcccg gcggccgcc                          159

<210> SEQ ID NO 15
<211> LENGTH: 5338
<212> TYPE: DNA
<213> ORGANISM: Artificial Sequence
<220> FEATURE:
<223> OTHER INFORMATION: pTP10-1 vector

<400> SEQUENCE: 15
aagcttacca tggcccacgc ccgcgtcctc ctcctggcgc tcgccgtgct ggccacggcc    60
gccgtcgccg tcgcctcctc ctcctccttc gccgactcca cccgatccg gcccgtcacc   120 gaccgcgcgg ccgcctccac gcagggcatc tccgaagacc tctacagccg tttagtcgaa   180
atggccacta tctcccaagc tgcctacgcc gacctgtgca acattccgtc gactattatc   240
aagggagaga aaatttacaa ttctcaaact gacattaacg gatggatcct ccgcgacgac   300
agcagcaaag aaataatcac cgtcttccgt ggcactggta gtgatacgaa tctacaactc   360
gatactgact acaccctcac gcctttcgac accctaccac aatgcaacgg ttgtgaagta   420
cacggtggat attatattgg atgggtctcc gtccaggacc aagtcgagtc gcttgtcaaa   480
cagcaggtta gccagtatcc ggactacgcg ctgaccgtga ccggccackc cctcggcgcc   540
tccctggcgg cactcactgc cgcccagctg tctgcgacat cgacaacat ccgcctgtac   600 accttcggcg aaccgcgcag cggcaatcag gccttcgcgt cgtacatgaa cgatgccttc   660
```

```
caagcctcga gcccagatac gacgcagtat ttccgggtca ctcatgccaa cgacggcatc     720
ccaaacctgc ccccggtgga gcaggggtac gcccatggcg gtgtagagta ctggagcgtt     780
gatccttaca gcgcccagaa cacatttgtc tgcactgggg atgaagtgca gtgctgtgag     840
gcccagggcg gacagggtgt gaataatgcg cacacgactt attttgggat gacgagcggc     900
gcatgcacct ggccggtcgc ggccgcggaa accactgaag gatgagctgt aaagaagcag     960
atcgttcaaa catttggcaa taaagtttct taagattgaa tcctgttgcc ggtcttgcga    1020
tgattatcat ataatttctg ttgaattacg ttaagcatgt aataattaac atgtaatgca    1080
tgacgttatt tatgagatgg gttttatga ttagagtccc gcaattatac atttaatacg    1140
cgatagaaaa caaatatag cgcgcaaact aggataaatt atcgcgcgcg gtgtcatcta    1200
tgttactaga tcgataagct tctagagcgg ccggtggagc tccaattcgc cctatagtga    1260
gtcgtattac gcgcgctcac tggccgtcgt tttacaacgt cgtgactggg aaaaccctgg    1320
cgttacccaa cttaatcgcc ttgcagcaca tcccccttc gccagctggc gtaatagcga    1380
agaggcccgc accgatcgcc cttcccaaca gttgcgcagc ctgaatggcg aatgggacgc    1440
gccctgtagc ggcgcattaa gcgcggcggg tgtggtggtt acgcgcagcg tgaccgctac    1500
acttgccagc gccctagcgc ccgctccttt cgctttcttc ccttcctttc tcgccacgtt    1560
cgccggcttt ccccgtcaag ctctaaatcg ggggctccct ttagggttcc gatttagtgc    1620
tttacggcac ctcgacccca aaaaacttga ttagggtgat ggttcacgta gtgggccatc    1680
gccctgatag acgttttttc gccctttgac gttggagtcc acgttcttta atagtggact    1740
cttgttccaa actggaacaa cactcaaccc tatctcggtc tattcttttg atttataagg    1800
gattttgccg atttcggcct attggttaaa aaatgagctg atttaacaaa aatttaacgc    1860
gaattttaac aaaatattaa cgcttacaat ttaggtggca cttttcgggg aaatgtgcgc    1920 ggaacccta tttgtttatt tttctaaata cattcaaata tgtatccgct catgagacaa    1980
taaccctgat aaatgcttca ataatattga aaaggaaga gtatgagtat tcaacatttc    2040
cgtgtcgccc ttattccctt ttttgcggca ttttgccttc ctgttttgc tcacccagaa    2100 acgctggtga agtaaaaga tgctgaagat cagttgggtg cacgagtggg ttacatcgaa    2160
ctggatctca acagcggtaa gatccttgag agttttcgcc ccgaagaacg ttttccaatg    2220
atgagcactt ttaaagttct gctatgtggc gcggtattat cccgtattga cgccgggcaa    2280
gagcaactcg gtcgccgcat acactattct cagaatgact tggttgagta ctcaccagtc    2340
acagaaaagc atcttacgga tggcatgaca gtaagagaat tatgcagtgc tgccataacc    2400
atgagtgata acactgcggc caacttactt ctgacaacga tcggaggacc gaaggagcta    2460
accgcttttt tgcacaacat gggggatcat gtaactcgcc ttgatcgttg gaaccggag    2520 ctgaatgaag ccataccaaa cgacgagcgt gacaccacga tgcctgtagc aatggcaaca    2580
acgttgcgca aactattaac tggcgaacta cttactctag cttcccggca acaattaata    2640
gactggatgg aggcggataa agttgcagga ccacttctgc gctcggccct tccggctggc    2700
tggtttattg ctgataaatc tggagccggt gagcgtgggt ctcgcggtat cattgcagca    2760
ctggggccag atggtaagcc ctcccgtatc gtagttatct acacgacggg gagtcaggca    2820
actatggatg aacgaaatag acagatcgct gagataggtg cctcactgat taagcattgg    2880
taactgtcag accaagttta ctcatatata ctttagattg atttaaaact tcatttttaa    2940
tttaaaagga tctaggtgaa gatcctttt gataatctca tgaccaaaat cccttaacgt    3000
```

-continued

```
gagttttcgt tccactgagc gtcagacccc gtagaaaaga tcaaaggatc ttcttgagat    3060
cctttttttc tgcgcgtaat ctgctgcttg caaacaaaaa aaccaccgct accagcggtg    3120
gtttgtttgc cggatcaaga gctaccaact cttttttccga aggtaactgg cttcagcaga    3180
gcgcagatac caaatactgt ccttctagtg tagccgtagt taggccacca cttcaagaac    3240
tctgtagcac cgcctacata cctcgctctg ctaatcctgt taccagtggc tgctgccagt    3300
ggcgataagt cgtgtcttac cgggttggac tcaagacgat agttaccgga taaggcgcag    3360
cggtcgggct gaacggggggg ttcgtgcaca cagcccagct tggagcgaac gacctacacc    3420
gaactgagat acctacagcg tgagctatga aaagcgccca cgcttcccga agggagaaag    3480
gcggacaggt atccggtaag cggcagggtc ggaacaggag agcgcacgag ggagcttcca    3540
gggggaaacg cctggtatct ttatagtcct gtcgggtttc gccacctctg acttgagcgt    3600 cgattttgt gatgctcgtc agggggggcgg agcctatgga aaaacgccag caacgcggcc    3660
ttttacggtt tcctgccctt tgctggcct tttgctcaca tgttctttcc tgcgttatcc    3720
cctgattctg tggataaccg tattaccgcc tttgagtgag ctgataccgc tcgccgcagc    3780
cgaacgaccg agcgcagcga gtcagtgagc gaggaagcgg aagagcgccc aatacgcaaa    3840
ccgcctctcc ccgcgcgttg gccgattcat taatgcagct ggcacgacag gtttcccgac    3900
tggaaagcgg gcagtgagcg caacgcaatt aatgtgagtt agctcactca ttaggcaccc    3960
caggctttac actttatgct tccggctcgt atgttgtgtg gaattgtgag cggataacaa    4020
tttcacacag gaaacagcta tgaccatgat tacgccaagc gcgcaattaa ccctcactaa    4080
agggaacaaa agctgggtac cgggccccccc ctcgaggtca ttcatatgct tgagaagaga    4140
gtcgggatag tccaaaataa aacaaaggta agattacctg gtcaaaagtg aaaacatcag    4200
ttaaaaggtg gtataagtaa aatatcggta ataaaaggtg gcccaaagtg aaatttactc    4260
ttttctacta ttataaaaat tgaggatgtt ttgtcggtac tttgatacgt cattttgta    4320 tgaattggtt tttaagttta tcgcgatttt ggaaatgcat atctgtattt gagtcggttt    4380
ttaagttcgt tgcttttgta aatacagagg gatttgtata agaaatatct ttaaaaaacc    4440
catatgctaa tttgacataa ttttttgagaa aaatatatat tcaggcgaat tccacaatga    4500
acaataataa gattaaaata gcttgccccc gttgcagcga tgggtatttt ttctagtaaa    4560
ataaaagata aacttagact caaaacattt acaaaaacaa cccctaaagt cctaaagccc    4620
aaagtgctat gcacgatcca tagcaagccc agcccaaccc aacccaaccc aacccacccc    4680
agtgcagcca actggcaaat agtctccacc cccggcacta tcaccgtgag ttgtccgcac    4740
caccgcacgt ctcgcagcca aaaaaaaaaa aagaaagaaa aaaagaaaa agaaaaacag    4800 caggtgggtc cgggtcgtgg gggccggaaa agcgaggagg atcgcgagca gcgacgaggc    4860
ccggccctcc ctccgcttcc aaagaaacgc ccccatcgc cactatatac ataccccccc    4920
ctctcctccc atccccccaa ccctaccacc accaccacca ccacctcctc cccccctcgct    4980 gccggacgac gagctcctcc cccctccccc tccgccgccg ccggtaacca ccccgcccct    5040
ctcctctttc tttctccgtt tttttttcg tctcggtctc gatctttggc cttggtagtt    5100
tgggtgggcg agagcggctt cgtcgcccag atcggtgcgc gggaggggcg ggatctcgcg    5160
gctggcgtct ccgggcgtga gtcggcccgg atcctcgcgg ggaatggggc tctcggatgt    5220
agatcttctt tctttcttct ttttgtggta gaatttgaat ccctcagcat tgttcatcgg    5280
tagttttcct tttcatgatt tgtgacaaat gcagcctcgt gcggagcttt tttgtagc     5338
```

-continued

```
<210> SEQ ID NO 16
<211> LENGTH: 311
<212> TYPE: PRT
<213> ORGANISM: Artificial Sequence
<220> FEATURE:
<223> OTHER INFORMATION: pTP10-1 vector
<220> FEATURE:
<221> NAME/KEY: VARIANT
<222> LOCATION: (1)...(311)
<223> OTHER INFORMATION: Xaa = Any Amino Acid

<400> SEQUENCE: 16

Met Ala His Ala Arg Val Leu Leu Ala Leu Ala Val Leu Ala Thr
 1               5                  10                  15

Ala Ala Val Ala Val Ala Ser Ser Ser Phe Ala Asp Ser Asn Pro
                20                  25                  30

Ile Arg Pro Val Thr Asp Arg Ala Ala Ser Thr Gln Gly Ile Ser
                35                  40                  45

Glu Asp Leu Tyr Ser Arg Leu Val Glu Met Ala Thr Ile Ser Gln Ala
 50                  55                  60

Ala Tyr Ala Asp Leu Cys Asn Ile Pro Ser Thr Ile Ile Lys Gly Glu
 65                  70                  75                  80

Lys Ile Tyr Asn Ser Gln Thr Asp Ile Asn Gly Trp Ile Leu Arg Asp
                 85                  90                  95

Asp Ser Ser Lys Glu Ile Ile Thr Val Phe Arg Gly Thr Gly Ser Asp
                100                 105                 110

Thr Asn Leu Gln Leu Asp Thr Asp Tyr Thr Leu Thr Pro Phe Asp Thr
                115                 120                 125

Leu Pro Gln Cys Asn Gly Cys Glu Val His Gly Gly Tyr Tyr Ile Gly
130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
                180                 185                 190

Asn Ile Arg Leu Tyr Thr Phe Gly Glu Pro Arg Ser Gly Asn Gln Ala
                195                 200                 205

Phe Ala Ser Tyr Met Asn Asp Ala Phe Gln Ala Ser Ser Pro Asp Thr
210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
                260                 265                 270

Val Gln Cys Cys Glu Ala Gln Gly Gly Gln Gly Val Asn Asn Ala His
                275                 280                 285

Thr Thr Tyr Phe Gly Met Thr Ser Gly Ala Cys Thr Trp Pro Val Ala
                290                 295                 300

Ala Ala Glu Thr Thr Glu Gly
305                 310

<210> SEQ ID NO 17
<211> LENGTH: 5345
<212> TYPE: DNA
<213> ORGANISM: Artificial Sequence
<220> FEATURE:
```

<223> OTHER INFORMATION: pUA4-4 vector

<400> SEQUENCE: 17

```
aagcttacca tggcccacgc ccgcgtcctc ctcctggcgc tcgccgtgct ggccacggcc      60
gccgtcgccg tcgcctcctc ccgcgcggcc gcctccacgc agggcatctc cgaagacctc     120
tacagccgtt tagtcgaaat ggccactatc tcccaagctg cctacgccga cctgtgcaac     180
attccgtcga ctattatcaa gggagagaaa atttacaatt ctcaaactga cattaacgga     240
tggatcctcc gcgacgacag cagcaaagaa ataatcaccg tcttccgtgg cactggtagt     300
gatacgaatc tacaactcga tactaactac accctcacgc ctttcgacac cctaccacaa     360
tgcaacggtt gtgaagtaca cggtggatat tatattggat gggtctccgt ccaggaccaa     420
gtcgagtcgc ttgtcaaaca gcaggttagc cagtatccgg actacgcgct gaccgtgacc     480
ggccackccc tcggcgcctc cctggcggca ctcactgccg cccagctgtc tgcgacatac     540
gacaacatcc gcctgtacac cttcggcgaa ccgcgcagcg gcaatcaggc cttcgcgtcg     600
tacatgaacg atgccttcca agcctcgagc ccagatacga cgcagtattt ccgggtcact     660
catgccaacg acggcatccc aaacctgccc ccggtggagc aggggtacgc ccatggcggt     720
gtagagtact ggagcgttga tccttacagc gcccagaaca catttgtctg cactggggat     780
gaagtgcagt gctgtgaggc ccagggcgga cagggtgtga ataatgcgca cacgacttat     840
tttgggatga cgagcggagc ctgtacatgg tgatcagtca tttcagcctc cccgagtgta     900
ccaggaaaga tggatgtcct ggagaggggg ccgcgtaacc actgaaggat gagctgtaaa     960
gaagcagatc gttcaaacat ttggcaataa agtttcttaa gattgaatcc tgttgccggt    1020
cttgcgatga ttatcatata atttctgttg aattacgtta agcatgtaat aattaacatg    1080
taatgcatga cgttatttat gagatgggtt tttatgatta gagtcccgca attatacatt    1140
taatacgcga tagaaaacaa atatagcgc gcaaactagg ataaattatc gcgcgcggtg    1200
tcatctatgt tactagatcg ataagcttct agagcggccg gtggagctcc aattcgccct    1260
atagtgagtc gtattacgcg cgctcactgg ccgtcgtttt acaacgtcgt gactgggaaa    1320
accctggcgt tacccaactt aatcgccttg cagcacatcc ccctttcgcc agctggcgta    1380
atagcgaaga ggcccgcacc gatcgccctt cccaacagtt gcgcagcctg aatggcgaat    1440
gggacgcgcc ctgtagcggc gcattaagcg cggcgggtgt ggtggttacg cgcagcgtga    1500
ccgctacact tgccagcgcc ctagcgcccg ctcctttcgc tttcttccct cctttctcg    1560
ccacgttcgc cggctttccc cgtcaagctc taaatcgggg gctcccttta gggttccgat    1620
ttagtgcttt acggcacctc gaccccaaaa aacttgatta gggtgatggt tcacgtagtg    1680
ggccatcgcc ctgatagacg ttttttcgcc ctttgacgtt ggagtccacg ttctttaata    1740
gtggactctt gttccaaact ggaacaacac tcaaccctat ctcggtctat tcttttgatt    1800
tataagggat tttgccgatt tcggcctatt ggttaaaaaa tgagctgatt taacaaaaat    1860
ttaacgcgaa ttttaacaaa atattaacgc ttacaattta ggtggcactt tcggggaaa    1920
tgtgcgcgga accctatttt gtttattttt ctaaatacat tcaaatatgt atccgctcat    1980
gagacaataa ccctgataaa tgcttcaata atattgaaaa aggaagagta tgagtattca    2040
acatttccgt gtcgccctta ttccctttt tgcggcattt tgccttcctg ttttgtgctca    2100
cccagaaacg ctggtgaaag taaaagatgc tgaagatcag ttgggtgcac gagtgggtta    2160
catcgaactg gatctcaaca gcggtaagat ccttgagagt tttcgccccg aagaacgttt    2220
tccaatgatg agcacttttta aagttctgct atgtggcgcg gtattatccc gtattgacgc    2280
```

```
cgggcaagag caactcggtc gccgcataca ctattctcag aatgacttgg ttgagtactc    2340
accagtcaca gaaaagcatc ttacggatgg catgacagta agagaattat gcagtgctgc    2400
cataaccatg agtgataaca ctgccggcaa cttacttctg acaacgatcg gaggaccgaa    2460
ggagctaacc gcttttttgc acaacatggg ggatcatgta actcgccttg atcgttggga    2520
accggagctg aatgaagcca taccaaacga cgagcgtgac accacgatgc ctgtagcaat    2580
ggcaacaacg ttgcgcaaac tattaactgg cgaactactt actctagctt cccggcaaca    2640
attaatagac tggatggagg cggataaagt tgcaggacca cttctgcgct cggcccttcc    2700
ggctggctgg tttattgctg ataaatctgg agccggtgag cgtgggtctc gcggtatcat    2760
tgcagcactg gggccagatg gtaagccctc ccgtatcgta gttatctaca cgacggggag    2820
tcaggcaact atggatgaac gaaatagaca gatcgctgag ataggtgcct cactgattaa    2880
gcattggtaa ctgtcagacc aagtttactc atatatactt tagattgatt taaaacttca    2940
tttttaattt aaaaggatct aggtgaagat cctttttgat aatctcatga ccaaaatccc    3000
ttaacgtgag ttttcgttcc actgagcgtc agaccccgta gaaaagatca aaggatcttc    3060
ttgagatcct ttttttctgc gcgtaatctg ctgcttgcaa acaaaaaaac caccgctacc    3120
agcggtggtt tgtttgccgg atcaagagct accaactctt tttccgaagg taactggctt    3180
cagcagagcg cagataccaa atactgtcct tctagtgtag ccgtagttag gccaccactt    3240
caagaactct gtagcaccgc ctacatacct cgctctgcta atcctgttac cagtggctgc    3300
tgccagtggc gataagtcgt gtcttaccgg gttggactca agacgatagt taccggataa    3360
ggcgcagcgg tcgggctgaa cggggggttc gtgcacacag cccagcttgg agcgaacgac    3420
ctacaccgaa ctgagatacc tacagcgtga gctatgagaa agcgccacgc ttcccgaagg    3480
gagaaaggcg gacaggtatc cggtaagcgg cagggtcgga acaggagagc gcacgaggga    3540
gcttccaggg ggaaacgcct ggtatcttta tagtcctgtc gggtttcgcc acctctgact    3600
tgagcgtcga tttttgtgat gctcgtcagg ggggcggagc ctatggaaaa acgccagcaa    3660
cgcggccttt ttacggttcc tggccttttg ctggccttt gctcacatgt tctttcctgc    3720
gttatcccct gattctgtgg ataaccgtat taccgccttt gagtgagctg ataccgctcg    3780
ccgcagccga acgaccgagc gcagcgagtc agtgagcgag gaagcggaag agcgcccaat    3840
acgcaaaccg cctctccccg cgcgttggcc gattcattaa tgcagctggc acgacaggtt    3900
tcccgactgg aaagcgggca gtgagcgcaa cgcaattaat gtgagttagc tcactcatta    3960 ggcacccccag gctttacact ttatgcttcc ggctcgtatg ttgtgtggaa ttgtgagcgg    4020
ataacaattt cacacaggaa acagctatga ccatgattac gccaagcgcg caattaaccc    4080
tcactaaagg gaacaaaagc tgggtaccgg gccccccctc gaggtcattc atatgcttga    4140
gaagagagtc gggatagtcc aaaataaaac aaaggtaaga ttacctggtc aaaagtgaaa    4200
acatcagtta aaaggtggta agtaaaat atcggtaata aaaggtggcc caaagtgaaa    4260
tttactcttt tctactatta taaaaattga ggatgttttg tcggtacttt gatacgtcat    4320
ttttgtatga attggttttt aagtttattc gcgatttgga aatgcatatc tgtatttgag    4380
tcggttttta agttcgttgc ttttgtaaat acagagggat ttgtataaga aatatcttta    4440 aaaacccat atgctaattt gacataattt ttgagaaaaa tatatattca ggcgaattcc    4500
acaatgaaca ataataagat taaaatagct tgccccgtt gcagcgatgg gtattttttc    4560
tagtaaaata aagataaac ttagactcaa acatttaca aaaacaaccc ctaaagtcct    4620
```

```
aaagcccaaa gtgctatgca cgatccatag caagcccagc ccaacccaac ccaacccaac    4680
ccaccccagt gcagccaact ggcaaatagt ctccaccccc ggcactatca ccgtgagttg    4740
tccgcaccac cgcacgtctc gcagccaaaa aaaaaaaaag aaagaaaaaa aagaaaaaga    4800
aaaacagcag gtgggtccgg gtcgtggggg ccggaaaagc gaggaggatc gcgagcagcg    4860
acgaggcccg gccctccctc cgcttccaaa gaaacgcccc ccatcgccac tatatacata    4920
cccccccctc tcctcccatc cccccaaccc taccaccacc accaccacca cctcctcccc    4980
cctcgctgcc ggacgacgag ctcctccccc ctcccctcc gccgccgccg gtaaccaccc     5040
cgcccctctc ctctttcttt ctccgttttt ttttcgtct cggtctcgat ctttggcctt     5100
ggtagtttgg gtgggcgaga gcggcttcgt cgcccagatc ggtgcgcggg aggggcggga    5160
tctcgcggct ggcgtctccg ggcgtgagtc ggcccggatc ctcgcgggga atggggctct    5220
cggatgtaga tcttctttct ttcttctttt tgtggtagaa tttgaatccc tcagcattgt    5280
tcatcggtag ttttcttt catgatttgt gacaaatgca gcctcgtgcg gagcttttt      5340 gtagc                                                                5345
```

<210> SEQ ID NO 18
<211> LENGTH: 287
<212> TYPE: PRT
<213> ORGANISM: Artificial Sequence
<220> FEATURE:
<223> OTHER INFORMATION: pUA4-4 vector
<220> FEATURE:
<221> NAME/KEY: VARIANT
<222> LOCATION: (1)...(287)
<223> OTHER INFORMATION: Xaa = Any Amino Acid

<400> SEQUENCE: 18

```
Met Ala His Ala Arg Val Leu Leu Ala Leu Ala Val Leu Ala Thr
 1               5                  10                  15

Ala Ala Val Ala Val Ala Ser Ser Arg Ala Ala Ala Ser Thr Gln Gly
                20                  25                  30

Ile Ser Glu Asp Leu Tyr Ser Arg Leu Val Glu Met Ala Thr Ile Ser
            35                  40                  45

Gln Ala Ala Tyr Ala Asp Leu Cys Asn Ile Pro Ser Thr Ile Ile Lys
        50                  55                  60

Gly Glu Lys Ile Tyr Asn Ser Gln Thr Asp Ile Asn Gly Trp Ile Leu
65                  70                  75                  80

Arg Asp Asp Ser Ser Lys Glu Ile Ile Thr Val Phe Arg Gly Thr Gly
                85                  90                  95

Ser Asp Thr Asn Leu Gln Leu Asp Thr Asn Tyr Thr Leu Thr Pro Phe
            100                 105                 110

Asp Thr Leu Pro Gln Cys Asn Gly Cys Glu Val His Gly Gly Tyr Tyr
        115                 120                 125

Ile Gly Trp Val Ser Val Gln Asp Gln Val Glu Ser Leu Val Lys Gln
    130                 135                 140

Gln Val Ser Gln Tyr Pro Asp Tyr Ala Leu Thr Val Thr Gly His Xaa
145                 150                 155                 160

Leu Gly Ala Ser Leu Ala Ala Leu Thr Ala Ala Gln Leu Ser Ala Thr
                165                 170                 175

Tyr Asp Asn Ile Arg Leu Tyr Thr Phe Gly Glu Pro Arg Ser Gly Asn
            180                 185                 190

Gln Ala Phe Ala Ser Tyr Met Asn Asp Ala Phe Gln Ala Ser Ser Pro
        195                 200                 205
```

-continued

```
Asp Thr Thr Gln Tyr Phe Arg Val Thr His Ala Asn Asp Gly Ile Pro
    210                 215                 220

Asn Leu Pro Pro Val Glu Gln Gly Tyr Ala His Gly Gly Val Glu Tyr
225                 230                 235                 240

Trp Ser Val Asp Pro Tyr Ser Ala Gln Asn Thr Phe Val Cys Thr Gly
                245                 250                 255

Asp Glu Val Gln Cys Cys Glu Ala Gln Gly Gly Gln Gly Val Asn Asn
                260                 265                 270

Ala His Thr Thr Tyr Phe Gly Met Thr Ser Gly Ala Cys Thr Trp
            275                 280                 285

<210> SEQ ID NO 19
<211> LENGTH: 5337
<212> TYPE: DNA
<213> ORGANISM: Artificial Sequence
<220> FEATURE:
<223> OTHER INFORMATION: pTU4 vector

<400> SEQUENCE: 19
aagcttacca tggcccacgc ccgcgtcctc ctcctggcgc tcgccgtgct ggccacggcc     60
gccgtcgccg tcgcctcctc ctcctccttc gccgactcca acccgatccg gcccgtcacc    120
gaccgcgcgg ccgcctccac gcagggcatc tccgaagacc tctacagccg tttagtcgaa    180
atggccacta tctcccaagc tgcctacgcc gacctgtgca acattccgtc gactattatc    240
aagggagaga aaatttacaa ttctcaaact gacattaacg gatggatcct ccgcgacgac    300
agcagcaaag aaataatcac cgtcttccgt ggcactggta gtgatacgaa tctacaactc    360
gatactaact acaccctcac gcctttcgac accctaccac aatgcaacgg ttgtgaagta    420
cacggtggat attatattgg atgggtctcc gtccaggacc aagtcgagtc gcttgtcaaa    480
cagcaggtta gccagtatcc ggactacgcg ctgaccgtga ccggccackc cctcggcgcc    540
tccctggcgg cactcactgc cgcccagctg tctgcgacat acgacaacat ccgcctgtac    600
accttcggcg aaccgcgcag cggcaatcag gccttcgcgt cgtacatgaa cgatgccttc    660
caagcctcga gccagatac gacgcagtat tccgggtca ctcatgccaa cgacggcatc    720
ccaaacctgc ccccggtgga gcaggggtac gcccatggcg gtgtagagta ctggagcgtt    780
gatccttaca cgcgcccagaa cacatttgtc tgcactgggg atgaagtgca gtgctgtgag    840
gcccagggcg gacagggtgt gaataatgcg cacacgactt attttgggat gacgagcggc    900
gcatgcacct ggccggtcgc ggccgcggaa ccactgaagg atgagctgta agaagcaga    960 tcgttcaaac atttggcaat aaagtttctt aagattgaat cctgttgccg gtcttgcgat   1020
gattatcata taatttctgt tgaattacgt taagcatgta ataattaaca tgtaatgcat   1080
gacgttattt atgagatggg tttttatgat tagagtcccg caattataca tttaatacgc   1140
gatagaaaac aaaatatagc gcgcaaacta ggataaatta tcgcgcgcgg tgtcatctat   1200
gttactagat cgataagctt ctagagcggc cggtggagct ccaattcgcc ctatagtgag   1260
tcgtattacg cgcgctcact ggccgtcgtt ttacaacgtc gtgactggga aaaccctggc   1320
gttacccaac ttaatcgcct tgcagcacat cccccttttcg ccagctggcg taatagcgaa   1380
gaggcccgca ccgatcgccc ttcccaacag ttgcgcagcc tgaatggcga atgggacgcg   1440
ccctgtagcg gcgcattaag cgcggcgggt gtggtggtta cgcgcagcgt gaccgctaca   1500
cttgccagcg ccctagcgcc cgctcctttc gctttcttcc cttcctttct cgccacgttc   1560
gccggctttc cccgtcaagc tctaaatcgg gggctccctt tagggttccg atttagtgct   1620
```

```
ttacggcacc tcgaccccaa aaaacttgat tagggtgatg gttcacgtag tgggccatcg    1680
ccctgataga cggttttttcg cccctttgacg ttggagtcca cgttcttttaa tagtggactc   1740 ttgttccaaa ctggaacaac actcaaccct atctcggtct attcttttga tttataaggg    1800
attttgccga tttcggccta ttggttaaaa aatgagctga tttaacaaaa atttaacgcg    1860
aattttaaca aaatattaac gcttacaatt taggtggcac ttttcgggga aatgtgcgcg    1920 gaaccccctat ttgtttattt ttctaaatac attcaaatat gtatccgctc atgagacaat    1980
aaccctgata aatgcttcaa taatattgaa aaaggaagag tatgagtatt caacatttcc    2040
gtgtcgccct tattccctttt tttgcggcat tttgccttcc tgttttttgct cacccagaaa    2100 cgctggtgaa agtaaaagat gctgaagatc agttgggtgc acgagtgggt tacatcgaac    2160
tggatctcaa cagcggtaag atccttgaga gttttcgccc cgaagaacgt tttccaatga    2220
tgagcacttt taaagttctg ctatgtggcg cggtattatc ccgtattgac gccgggcaag    2280
agcaactcgg tcgccgcata cactattctc agaatgactt ggttgagtac tcaccagtca    2340
cagaaaagca tcttacggat ggcatgacag taagagaatt atgcagtgct gccataacca    2400
tgagtgataa cactgcggcc aacttacttc tgacaacgat cggaggaccg aaggagctaa    2460 ccgcttttttt gcacaacatg ggggatcatg taactcgcct tgatcgttgg aaccggagc    2520 tgaatgaagc cataccaaac gacgagcgtg acaccacgat gcctgtagca atggcaacaa    2580
cgttgcgcaa actattaact ggcgaactac ttactctagc ttcccggcaa caattaatag    2640
actggatgga ggcggataaa gttgcaggac cacttctgcg ctcggccctt ccggctggct    2700
ggtttattgc tgataaatct ggagccggtg agcgtgggtc tcgcggtatc attgcagcac    2760
tggggccaga tggtaagccc tcccgtatcg tagttatcta cacgacgggg agtcaggcaa    2820
ctatggatga acgaaataga cagatcgctg agataggtgc ctcactgatt aagcattggt    2880
aactgtcaga ccaagtttac tcatatatac tttagattga tttaaaactt cattttttaat    2940 ttaaaaggat ctaggtgaag atcctttttg ataatctcat gaccaaaatc ccttaacgtg    3000
agttttcgtt ccactgagcg tcagacccccg tagaaaagat caaaggatct tcttgagatc    3060 cttttttttct gcgcgtaatc tgctgcttgc aaacaaaaaa accaccgcta ccagcggtgg    3120
tttgtttgcc ggatcaagag ctaccaactc tttttccgaa ggtaactggc ttcagcagag    3180
cgcagatacc aaatactgtc cttctagtgt agccgtagtt aggccaccac ttcaagaact    3240
ctgtagcacc gcctacatac ctcgctctgc taatcctgtt accagtggct gctgccagtg    3300
gcgataagtc gtgtcttacc gggttggact caagacgata gttaccggat aaggcgcagc    3360
ggtcgggctg aacggggggt tcgtgcacac agcccagctt ggagcgaacg acctacaccg    3420
aactgagata cctacagcgt gagctatgag aaagcgccac gcttcccgaa gggagaaagg    3480
cggacaggta tccggtaagc ggcagggtcg gaacaggaga gcgcacgagg gagcttccag    3540
ggggaaacgc ctggtatctt tatagtcctg tcgggtttcg ccacctctga cttgagcgtc    3600
gatttttgtg atgctcgtca gggggggcgga gcctatggaa aaacgccagc aacgcggcct    3660
ttttacggtt cctggccttt tgctggcctt ttgctcacat gttctttcct gcgttatccc    3720
ctgattctgt ggataaccgt attaccgcct ttgagtgagc tgataccgct cgccgcagcc    3780
gaacgaccga gcgcagcgag tcagtgagcg aggaagcgga agagcgccca atacgcaaac    3840
cgcctctccc cgcgcgttgg ccgattcatt aatgcagctg gcacgacagg tttcccgact    3900
ggaaagcggg cagtgagcgc aacgcaatta atgtgagtta gctcactcat taggcacccc    3960
aggctttaca ctttatgctt ccggctcgta tgttgtgtgg aattgtgagc ggataacaat    4020
```

```
ttcacacagg aaacagctat gaccatgatt acgccaagcg cgcaattaac cctcactaaa    4080
gggaacaaaa gctgggtacc gggccccccc tcgaggtcat tcatatgctt gagaagagag    4140
tcgggatagt ccaaaataaa acaaggtaa gattacctgg tcaaaagtga aaacatcagt     4200 taaaggtgg tataagtaaa atatcggtaa taaaaggtgg cccaaagtga aatttactct     4260
tttctactat tataaaaatt gaggatgttt tgtcggtact ttgatacgtc attttttgtat   4320 gaattggttt ttaagtttat tcgcgatttg gaaatgcata tctgtatttg agtcggtttt    4380
taagttcgtt gcttttgtaa atacagaggg atttgtataa gaaatatctt taaaaaaccc    4440
atatgctaat ttgacataat ttttgagaaa aatatatatt caggcgaatt ccacaatgaa    4500
caataataag attaaaatag cttgcccccg ttgcagcgat gggtattttt tctagtaaaa    4560
taaaagataa acttagactc aaaacattta caaaaacaac ccctaaagtc ctaaagccca    4620
aagtgctatg cacgatccat agcaagccca gcccaaccca acccaaccca acccacccca    4680
gtgcagccaa ctggcaaata gtctccaccc ccggcactat caccgtgagt tgtccgcacc    4740
accgcacgtc tcgcagccaa aaaaaaaaaa agaaagaaaa aaaagaaaaa gaaaacagc     4800 aggtgggtcc gggtcgtggg ggccggaaaa gcgaggagga tcgcgagcag cgacgaggcc    4860
cggccctccc tccgcttcca agaaacgccc cccatcgcc actatataca taccccccccc   4920 tctcctccca tcccccaac cctaccacca ccaccaccac cacctcctcc ccctcgctg     4980 ccggacgacg agctcctccc ccctccccct ccgccgccgc cggtaaccac cccgcccctc    5040
tcctctttct ttctccgttt ttttttcgt ctcggtctcg atctttggcc ttggtagttt     5100
gggtgggcga gagcggcttc gtcgcccaga tcggtgcgcg ggaggggcgg gatctcgcgg    5160
ctggcgtctc cgggcgtgag tcggcccgga tcctcgcggg gaatgggggct ctcggatgta   5220 gatcttcttt cttcttctt tttgtggtag aatttgaatc cctcagcatt gttcatcggt     5280 agttttctt ttcatgattt gtgacaaatg cagcctcgtg cggagctttt ttgtagc        5337
```

<210> SEQ ID NO 20
<211> LENGTH: 313
<212> TYPE: PRT
<213> ORGANISM: Artificial Sequence
<220> FEATURE:
<223> OTHER INFORMATION: pTU4 vector
<220> FEATURE:
<221> NAME/KEY: VARIANT
<222> LOCATION: (1)...(313)
<223> OTHER INFORMATION: Xaa = Any Amino Acid

<400> SEQUENCE: 20

```
Met Ala His Ala Arg Val Leu Leu Ala Leu Ala Val Leu Ala Thr
 1               5                  10                  15

Ala Ala Val Ala Val Ala Ser Ser Ser Phe Ala Asp Ser Asn Pro
                20                  25                  30

Ile Arg Pro Val Thr Asp Arg Ala Ala Ala Ser Thr Gln Gly Ile Ser
            35                  40                  45

Glu Asp Leu Tyr Ser Arg Leu Val Glu Met Ala Thr Ile Ser Gln Ala
 50                  55                  60

Ala Tyr Ala Asp Leu Cys Asn Ile Pro Ser Thr Ile Lys Gly Glu
 65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110
```

Thr Asn Leu Gln Leu Asp Thr Asn Tyr Thr Leu Thr Pro Phe Asp Thr
    115                 120                 125

Leu Pro Gln Cys Asn Gly Cys Glu Val His Gly Gly Tyr Tyr Ile Gly
130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp Pro Val Ala
    290                 295                 300

Ala Ala Glu Pro Leu Lys Asp Glu Leu
305                 310

<210> SEQ ID NO 21
<211> LENGTH: 5395
<212> TYPE: DNA
<213> ORGANISM: Artificial Sequence
<220> FEATURE:
<223> OTHER INFORMATION: pTT5.14 vector

<400> SEQUENCE: 21
cctgacgccg aggatccatg gcccacgccc gcgtcctcct cctggcgctc gccgtgctgg     60
ccacggccgc cgtcgccgtc gcctcctcct cctccttcgc cgactccaac ccgggccggc    120
ccgtcaccga ccgcgcggcc gcctccacgc agggcatctc cgaagacctc tacagccgtt    180
tagtcgaaat ggccactatc tcccaagctg cctacgccga cctgtgcaac attccgtcga    240
ctattatcaa gggagagaaa atttacaatt ctcaaactga cattaacgga tggatcctcc    300
gcgacgacag cagcaaagaa ataatcaccg tcttccgtgg cactggtagt gatacgaatc    360
tacaactcga tactaactac acccctcacg cttttcgaca cctaccacaa tgcaacggtt    420
gtgaagtaca cggtggatat tatattggat gggtctccgt ccaggaccaa gtcgagtcgc    480
ttgtcaaaca gcaggttagc cagtatccgg actacgcgct gaccgtgacc ggccackccc    540
tcggcgcctc cctggcggca ctcactgccg cccagctgtc tgcgacatac gacaacatcc    600
gcctgtacac cttcggcgaa ccgcgcagcg gcaatcaggc cttcgcgtcg tacatgaacg    660
atgccttcca agcctcgagc ccagatacga cgcagtattt ccgggtcact catgccaacg    720
acggcatccc aaacctgccc ccggtggagc agggggtacgc ccatggcggt gtagagtact    780
ggagcgttga tccttacagc gcccagaaca catttgtctg cactggggat gaagtgcagt    840
gctgtgaggc ccagggcgga cagggtgtga ataatgcgca cacgacttat tttgggatga    900

```
cgagcggagc ctgtacatgg tgatcagtca tttcagcctc cccgagtgta ccaggaaaga    960
tggatgtcct ggagagggggg ccgcgtaacc actgaaggat gagctgtaaa gaagcagatc   1020
gttcaaacat ttggcaataa agtttcttaa gattgaatcc tgttgccggt cttgcgatga   1080
ttatcatata atttctgttg aattacgtta agcatgtaat aattaacatg taatgcatga   1140
cgttatttat gagatgggtt tttatgatta gagtcccgca attatacatt taatacgcga   1200
tagaaaacaa aatatagcgc gcaaactagg ataaattatc gcgcgcggtg tcatctatgt   1260
tactagatcg ataagcttct agagcggccg gtggagctcc aattcgccct atagtgagtc   1320
gtattacgcg cgctcactgg ccgtcgtttt acaacgtcgt gactgggaaa accctggcgt   1380
tacccaactt aatcgccttg cagcacatcc ccctttcgcc agctggcgta atagcgaaga   1440
ggcccgcacc gatcgccctt cccaacagtt gcgcagcctg aatggcgaat gggacgcgcc   1500
ctgtagcggc gcattaagcg cggcgggtgt ggtggttacg cgcagcgtga ccgctacact   1560
tgccagcgcc ctagcgcccg ctcctttcgc tttcttccct cctttctcg ccacgttcgc    1620
cggctttccc cgtcaagctc taaatcgggg gctcccttta gggttccgat ttagtgcttt   1680
acggcacctc gaccccaaaa aacttgatta gggtgatggt tcacgtagtg ggccatcgcc   1740
ctgatagacg gttttttcgcc ctttgacgtt ggagtccacg ttctttaata gtggactctt   1800
gttccaaact ggaacaacac tcaaccctat ctcggtctat tcttttgatt tataagggat   1860
tttgccgatt tcggcctatt ggttaaaaaa tgagctgatt taacaaaaat ttaacgcgaa   1920
ttttaacaaa atattaacgc ttacaattta ggtggcactt ttcggggaaa tgtgcgcgga   1980
accctatttt gtttattttt ctaaatacat tcaaatatgt atccgctcat gagacaataa   2040
ccctgataaa tgcttcaata atattgaaaa aggaagagta tgagtattca acatttccgt   2100
gtcgccctta ttccctttttt tgcggcattt tgccttcctg ttttttgctca cccagaaacg   2160
ctggtgaaag taaagatgc tgaagatcag ttgggtgcac gagtgggtta catcgaactg   2220
gatctcaaca gcggtaagat ccttgagagt tttcgccccg aagaacgttt tccaatgatg   2280
agcactttta aagttctgct atgtggcgcg gtattatccc gtattgacgc cgggcaagag   2340
caactcggtc gccgcataca ctattctcag aatgacttgg ttgagtactc accagtcaca   2400
gaaaagcatc ttacgatgg catgacagta agagaattat gcagtgctgc cataaccatg   2460
agtgataaca ctgcggccaa cttacttctg acaacgatcg gaggaccgaa ggagctaacc   2520
gctttttttgc acaacatggg ggatcatgta actcgccttg atcgttggga accggagctg   2580
aatgaagcca taccaaacga cgagcgtgac accacgatgc ctgtagcaat ggcaacaacg   2640
ttgcgcaaac tattaactgg cgaactactt actctagctt cccggcaaca attaatagac   2700
tggatggagg cggataaagt tgcaggacca cttctgcgct cggcccttcc ggctggctgg   2760
tttattgctg ataaatctgg agccggtgag cgtgggtctc gcggtatcat tgcagcactg   2820
gggccagatg gtaagccctc ccgtatcgta gttatctaca cgacggggag tcaggcaact   2880
atggatgaac gaaatagaca gatcgctgag ataggtgcct cactgattaa gcattggtaa   2940
ctgtcagacc aagtttactc atatatactt tagattgatt taaaacttca ttttaatttt   3000
aaaaggatct aggtgaagat cctttttgat aatctcatga ccaaaatccc ttaacgtgag   3060
ttttcgttcc actgagcgtc agaccccgta gaaaagatca aaggatcttc ttgagatcct   3120
ttttttctgc gcgtaatctg ctgcttgcaa acaaaaaaac caccgctacc agcggtggtt   3180
tgtttgccgg atcaagagct accaactctt tttccgaagg taactggctt cagcagagcg   3240
```

-continued

```
cagataccaa atactgtcct tctagtgtag ccgtagttag gccaccactt caagaactct    3300
gtagcaccgc ctacatacct cgctctgcta atcctgttac cagtggctgc tgccagtggc    3360
gataagtcgt gtcttaccgg gttggactca agacgatagt taccggataa ggcgcagcgg    3420
tcgggctgaa cggggggttc gtgcacacag cccagcttgg agcgaacgac ctacaccgaa    3480
ctgagatacc tacagcgtga gctatgagaa agcgccacgc ttcccgaagg gagaaaggcg    3540
gacaggtatc cggtaagcgg cagggtcgga acaggagagc gcacgaggga gcttccaggg    3600
ggaaacgcct ggtatcttta tagtcctgtc gggtttcgcc acctctgact tgagcgtcga    3660
tttttgtgat gctcgtcagg ggggcggagc ctatggaaaa acgccagcaa cgcggccttt    3720
ttacggttcc tggccttttg ctggccttt  gctcacatgt tctttcctgc gttatcccct    3780
gattctgtgg ataaccgtat taccgccttt gagtgagctg ataccgctcg ccgcagccga    3840
acgaccgagc gcagcgagtc agtgagcgag gaagcggaag agcgcccaat acgcaaaccg    3900
cctctccccg cgcgttggcc gattcattaa tgcagctggc acgacaggtt cccgactgg     3960 aaagcgggca gtgagcgcaa cgcaattaat gtgagttagc tcactcatta ggcacccag     4020 gctttacact ttatgcttcc ggctcgtatg ttgtgtggaa ttgtgagcgg ataacaattt    4080
cacacaggaa acagctatga ccatgattac gccaagcgcg caattaaccc tcactaaagg    4140
gaacaaaagc tgggtaccgg gccccccctc gaggtcattc atatgcttga agagagtc     4200 gggatagtcc aaaataaaac aaaggtaaga ttacctggtc aaaagtgaaa acatcagtta    4260
aaaggtggta taagtaaaat atcggtaata aaaggtggcc caaagtgaaa tttactcttt    4320
tctactatta taaaaattga ggatgtttg tcggtacttt gatacgtcat ttttgtatga     4380
attggttttt aagtttattc gcgatttgga aatgcatatc tgtatttgag tcggttttta    4440
agttcgttgc ttttgtaaat acagagggat ttgtataaga aatatcttta aaaaacccat    4500
atgctaattt gacataattt ttgagaaaaa tatatattca ggcgaattcc acaatgaaca    4560
ataataagat taaatagct tgcccccgtt gcagcgatgg gtattttttc tagtaaaata     4620
aaagataaac ttagactcaa acatttaca aaaacaaccc ctaaagtcct aaagcccaaa     4680
gtgctatgca cgatccatag caagcccagc ccaacccaac ccaacccaac ccaccccagt    4740
gcagccaact ggcaaatagt ctccacccc  ggcactatca ccgtgagttg tccgcaccac    4800
cgcacgtctc gcagccaaaa aaaaaaaag aaagaaaaa aagaaaaaga aaacagcag     4860 gtgggtccgg gtcgtggggg ccggaaaagc gaggaggatc gcgagcagcg acgaggcccg    4920
gccctccctc cgcttccaaa gaaacgcccc ccatcgccac tatatacata cccccccctc    4980
tcctcccatc cccccaaccc taccaccacc accaccacca cctcctcccc cctcgctgcc    5040
ggacgacgag ctcctccccc ctccccctcc gccgccgccg gtaaccaccc cgcccctctc    5100
ctctttcttt ctccgttttt tttttcgtct cggtctcgat ctttggcctt ggtagtttgg    5160
gtgggcgaga gcggcttcgt cgcccagatc ggtgcgcggg aggggcggga tctcgcggct    5220
ggcgtctccg ggcgtgagtc ggcccggatc ctcgcgggga atgggctct  cggatgtaga   5280 tcttctttct ttcttctttt tgtggtagaa tttgaatccc tcagcattgt tcatcggtag    5340 ttttctttt  catgatttgt gacaaatgca gcctcgtgcg gagctttttt gtagc         5395
```

<210> SEQ ID NO 22
<211> LENGTH: 301
<212> TYPE: PRT
<213> ORGANISM: Artificial Sequence
<220> FEATURE:
<223> OTHER INFORMATION: pTT5.14 vector

```
<220> FEATURE:
<221> NAME/KEY: VARIANT
<222> LOCATION: (1)...(301)
<223> OTHER INFORMATION: Xaa = Any Amino Acid

<400> SEQUENCE: 22

Met Ala His Ala Arg Val Leu Leu Leu Ala Leu Ala Val Leu Ala Thr
 1               5                  10                  15
Ala Ala Val Ala Val Ala Ser Ser Ser Phe Ala Asp Ser Asn Pro
            20                  25                  30
Gly Arg Pro Val Thr Asp Arg Ala Ala Ser Thr Gln Gly Ile Ser
        35                  40                  45
Glu Asp Leu Tyr Ser Arg Leu Val Glu Met Ala Thr Ile Ser Gln Ala
 50                  55                  60
Ala Tyr Ala Asp Leu Cys Asn Ile Pro Ser Thr Ile Ile Lys Gly Glu
 65                  70                  75                  80
Lys Ile Tyr Asn Ser Gln Thr Asp Ile Asn Gly Trp Ile Leu Arg Asp
                85                  90                  95
Asp Ser Ser Lys Glu Ile Ile Thr Val Phe Arg Gly Thr Gly Ser Asp
            100                 105                 110
Thr Asn Leu Gln Leu Asp Thr Asn Tyr Thr Leu Thr Pro Phe Asp Thr
        115                 120                 125
Leu Pro Gln Cys Asn Gly Cys Glu Val His Gly Tyr Tyr Ile Gly
    130                 135                 140
Trp Val Ser Val Gln Asp Gln Val Glu Ser Leu Val Lys Gln Val
145                 150                 155                 160
Ser Gln Tyr Pro Asp Tyr Ala Leu Thr Val Thr Gly His Xaa Leu Gly
                165                 170                 175
Ala Ser Leu Ala Ala Leu Thr Ala Ala Gln Leu Ser Ala Thr Tyr Asp
            180                 185                 190
Asn Ile Arg Leu Tyr Thr Phe Gly Glu Pro Arg Ser Gly Asn Gln Ala
        195                 200                 205
Phe Ala Ser Tyr Met Asn Asp Ala Phe Gln Ala Ser Ser Pro Asp Thr
 210                 215                 220
Thr Gln Tyr Phe Arg Val Thr His Ala Asn Asp Gly Ile Pro Asn Leu
225                 230                 235                 240
Pro Pro Val Glu Gln Gly Tyr Ala His Gly Gly Val Glu Tyr Trp Ser
                245                 250                 255
Val Asp Pro Tyr Ser Ala Gln Asn Thr Phe Val Cys Thr Gly Asp Glu
            260                 265                 270
Val Gln Cys Cys Glu Ala Gln Gly Gly Gln Gly Val Asn Asn Ala His
        275                 280                 285
Thr Thr Tyr Phe Gly Met Thr Ser Gly Ala Cys Thr Trp
 290                 295                 300

<210> SEQ ID NO 23
<211> LENGTH: 5337
<212> TYPE: DNA
<213> ORGANISM: Artificial Sequence
<220> FEATURE:
<223> OTHER INFORMATION: pTP8-5 vector

<400> SEQUENCE: 23
aagcttacca tggcccacgc ccgcgtcctc ctcctggcgc tcgccgtgct ggccacggcc    60
gccgtcgccg tcgcctcctc ctcctccttc gccgactcca acccgatccg gcccgtcacc   120
gaccgcgcgg ccgcctccac gcagggcatc tccgaagacc tctacagccg tttagtcgaa   180
```

-continued

```
atggccacta tctcccaagc tgcctacgcc gacctgtgca acattccgtc gactattatc      240
aagggagaga aaatttacaa ttctcaaact gacattaacg gatggatcct ccgcgacgac      300
agcagcaaag aaataatcac cgtcttccgt ggcactggta gtgatacgaa tctacaactc      360
gatactaact acaccctcac gcctttcgac accctaccac aatgcaacgg ttgtgaagta      420
cacggtggat attatattgg atgggtctcc gtccaggacc aagtcgagtc gcttgtcaaa      480
cagcaggtta gccagtatcc ggactacgcg ctgaccgtga ccggccackc cctcggcgcc      540
tccctggcgg cactcactgc cgcccagctg tctgcgacat acgacaacat ccgcctgtac      600
accttcggcg aaccgcgcag cggcaatcag gccttcgcgt cgtacatgaa cgatgccttc      660
caagcctcga gccagatac gacgcagtat ttccgggtca ctcatgccaa cgacggcatc       720
ccaaacctgc ccccggtgga gcaggggtac gcccatggcg gtgtagagta ctggagcgtt      780
gatccttaca cgcgcccagaa cacatttgtc tgcactgggg atgaagtgca gtgctgtgag      840
gcccagggcg gacagggtgt gaataatgcg cacacgactt attttgggat gacgagcggc      900
gcatgcacct ggccggtcgc ggccgcgtaa ccactgaagg atgagctgta aagaagcaga      960
tcgttcaaac atttggcaat aaagtttctt aagattgaat cctgttgccg gtcttgcgat     1020
gattatcata taatttctgt tgaattacgt taagcatgta ataattaaca tgtaatgcat     1080
gacgttattt atgagatggg tttttatgat tagagtcccg caattataca tttaatacgc     1140
gatagaaaac aaaatatagc gcgcaaacta ggataaatta tcgcgcgcgg tgtcatctat     1200
gttactagat cgataagctt ctagagcggc cggtggagct ccaattcgcc ctatagtgag     1260
tcgtattacg cgcgctcact ggccgtcgtt ttacaacgtc gtgactggga aaaccctggc     1320
gttacccaac ttaatcgcct tgcagcacat ccccctttcg ccagctggcg taatagcgaa     1380
gaggcccgca ccgatcgccc ttcccaacag ttgcgcagcc tgaatggcga atgggacgcg     1440
ccctgtagcg cgcattaag cgcggcgggt gtggtggtta cgcgcagcgt gaccgctaca     1500
cttgccagcg ccctagcgcc cgctcctttc gctttcttcc cttcctttct cgccacgttc     1560
gccggctttc cccgtcaagc tctaaatcgg ggctcccctt tagggttccg atttagtgct     1620
ttacggcacc tcgaccccaa aaaacttgat tagggtgatg gttcacgtag tgggccatcg     1680
ccctgataga cggtttttcg ccctttgacg ttggagtcca cgttctttaa tagtggactc     1740
ttgttccaaa ctggaacaac actcaaccct atctcggtct attcttttga tttataaggg     1800
attttgccga tttcggccta ttggttaaaa aatgagctga tttaacaaaa atttaacgcg     1860
aattttaaca aaatattaac gcttacaatt taggtggcac ttttcgggga aatgtgcgcg     1920 gaaccc ctat ttgtttattt ttctaaatac attcaaatat gtatccgctc atgagacaat     1980
aaccctgata aatgcttcaa taatattgaa aaaggaagag tatgagtatt caacatttcc     2040
gtgtcgccct tattcccttt tttgcggcat tttgccttcc tgtttttgct cacccagaaa     2100
cgctggtgaa agtaaaagat gctgaagatc agttgggtgc acgagtgggt tacatcgaac     2160
tggatctcaa cagcggtaag atccttgaga gttttcgccc cgaagaacgt tttccaatga     2220
tgagcacttt taaagttctg ctatgtggcg cggtattatc ccgtattgac gccgggcaag     2280
agcaactcgg tcgccgcata cactattctc agaatgactt ggttgagtac tcaccagtca     2340
cagaaaagca tcttacggat ggcatgacag taagagaatt atgcagtgct gccataacca     2400
tgagtgataa cactgcggcc aacttacttc tgacaacgat cggaggaccg aaggagctaa     2460 ccgcttttttt gcacaacatg ggggatcatg taactcgcct tgatcgttgg gaaccggagc     2520
```

```
tgaatgaagc cataccaaac gacgagcgtg acaccacgat gcctgtagca atggcaacaa    2580
cgttgcgcaa actattaact ggcgaactac ttactctagc ttcccggcaa caattaatag    2640
actggatgga ggcggataaa gttgcaggac cacttctgcg ctcggccctt ccggctggct    2700
ggtttattgc tgataaatct ggagccgtg agcgtgggtc tcgcggtatc attgcagcac     2760
tggggccaga tggtaagccc tcccgtatcg tagttatcta cacgacgggg agtcaggcaa    2820
ctatggatga acgaaataga cagatcgctg agataggtgc ctcactgatt aagcattggt    2880
aactgtcaga ccaagtttac tcatatatac tttagattga tttaaaactt catttttaat    2940
ttaaaaggat ctaggtgaag atccttttg ataatctcat gaccaaaatc ccttaacgtg     3000
agttttcgtt ccactgagcg tcagaccccg tagaaaagat caaaggatct tcttgagatc    3060
ctttttttct gcgcgtaatc tgctgcttgc aaacaaaaaa accaccgcta ccagcggtgg    3120
tttgtttgcc ggatcaagag ctaccaactc tttttccgaa ggtaactggc ttcagcagag    3180
cgcagatacc aaatactgtc cttctagtgt agccgtagtt aggccaccac ttcaagaact    3240
ctgtagcacc gcctacatac ctcgctctgc taatcctgtt accagtggct gctgccagtg    3300
gcgataagtc gtgtcttacc gggttggact caagacgata gttaccggat aaggcgcagc    3360
ggtcgggctg aacggggggt tcgtgcacac agcccagctt ggagcgaacg acctacaccg    3420
aactgagata cctacagcgt gagctatgag aaagcgccac gcttcccgaa gggagaaagg    3480
cggacaggta tccggtaagc ggcagggtcg gaacaggaga gcgcacgagg gagcttccag    3540
ggggaaacgc ctggtatctt tatagtcctg tcgggtttcg ccacctctga cttgagcgtc    3600
gatttttgtg atgctcgtca gggggcgga gcctatggaa aaacgccagc aacgcggcct    3660
ttttacggtt cctggccttt tgctggcctt ttgctcacat gttctttcct gcgttatccc    3720
ctgattctgt ggataaccgt attaccgcct ttgagtgagc tgataccgct cgccgcagcc    3780
gaacgaccga gcgcagcgag tcagtgagcg aggaagcgga agagcgccca atacgcaaac    3840
cgcctctccc cgcgcgttgg ccgattcatt aatgcagctg gcacgacagg tttcccgact    3900
ggaaagcggg cagtgagcgc aacgcaatta atgtgagtta gctcactcat taggcacccc    3960
aggctttaca ctttatgctt ccggctcgta tgttgtgtgg aattgtgagc ggataacaat    4020
ttcacacagg aaacagctat gaccatgatt acgccaagcg cgcaattaac cctcactaaa    4080
gggaacaaaa gctgggtacc gggccccccc tcgaggtcat tcatatgctt gagaagagag    4140
tcgggatagt ccaaaataaa acaaaggtaa gattacctgg tcaaaagtga aaacatcagt    4200
taaaaggtgg tataagtaaa atatcggtaa taaaaggtgg cccaaagtga aatttactct    4260
tttctactat tataaaaatt gaggatgttt tgtcggtact ttgatacgtc atttttgtat    4320
gaattggttt ttaagtttat tcgcgatttg gaaatgcata tctgtatttg agtcggtttt    4380
taagttcgtt gcttttgtaa atacagaggg atttgtataa gaaatatctt taaaaacccc    4440
atatgctaat ttgacataat ttttgagaaa atatatatt caggcgaatt ccacaatgaa     4500
caataataag attaaaatag cttgcccccg ttgcagcgat gggtattttt tctagtaaaa    4560
taaaagataa acttagactc aaaacatttta caaaacaac ccctaaagtc ctaaagccca    4620
aagtgctatg cacgatccat agcaagccca gcccaaccca acccaaccca acccaccccca    4680 gtgcagccaa ctggcaaata gtctccaccc ccggcactat caccgtgagt tgtccgcacc    4740
accgcacgtc tcgcagccaa aaaaaaaaaa agaaagaaaa aaaagaaaaa gaaaaacagc    4800
aggtgggtcc gggtcgtggg ggccggaaaa gcgaggagga tcgcgagcag cgacgaggcc    4860
cggccctccc tccgcttcca aagaaacgcc ccccatcgcc actatataca tacccccccc    4920
```

```
tctcctccca tcccccaac cctaccacca ccaccaccac cacctcctcc cccctcgctg    4980
ccggacgacg agctcctccc ccctcccct cgccgccgc cggtaaccac cccgcccctc    5040
tcctctttct ttctccgttt ttttttcgt ctcggtctcg atctttggcc ttggtagttt    5100
gggtgggcga gagcggcttc gtcgcccaga tcggtgcgcg ggaggggcgg gatctcgcgg    5160
ctggcgtctc cgggcgtgag tcggcccgga tcctcgcggg gaatgggct ctcggatgta    5220 gatcttcttt ctttcttctt tttgtggtag aatttgaatc cctcagcatt gttcatcggt    5280 agttttctt ttcatgattt gtgacaaatg cagcctcgtg cggagctttt ttgtagc      5337
```

<210> SEQ ID NO 24
<211> LENGTH: 306
<212> TYPE: PRT
<213> ORGANISM: Artificial Sequence
<220> FEATURE:
<223> OTHER INFORMATION: pTP8-5 vector
<220> FEATURE:
<221> NAME/KEY: VARIANT
<222> LOCATION: (1)...(306)
<223> OTHER INFORMATION: Xaa = Any Amino Acid

<400> SEQUENCE: 24

```
Met Ala His Ala Arg Val Leu Leu Ala Leu Ala Val Leu Ala Thr
 1               5                  10                  15

Ala Ala Val Ala Val Ala Ser Ser Ser Phe Ala Asp Ser Asn Pro
                20                  25                  30

Ile Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270
```

Val Gln Cys Cys Glu Ala Gln Gly Gly Gln Gly Val Asn Asn Ala His
    275                 280                 285

Thr Thr Tyr Phe Gly Met Thr Ser Gly Ala Cys Thr Trp Pro Val Ala
    290                 295                 300

Ala Ala
305

<210> SEQ ID NO 25
<211> LENGTH: 5277
<212> TYPE: DNA
<213> ORGANISM: Artificial Sequence
<220> FEATURE:
<223> OTHER INFORMATION: pTP5-1 vector

<400> SEQUENCE: 25

| | |
|---|---:|
| aagcttaaca tgaagcagtt ctccgccaaa cacgtcctcg cagttgtggt gactgcaggg | 60 |
| cacgccttag cagcctctac gcaaggcatc tccgaagacc tctacagccg tttagtcgaa | 120 |
| atggccacta tctcccaagc tgcctacgcc gacctgtgca acattccgtc gactattatc | 180 |
| aagggagaga aaatttacaa ttctcaaact gacattaacg gatggatcct ccgcgacgac | 240 |
| agcagcaaag aaataatcac cgtcttccgt ggcactggta gtgatacgaa tctacaactc | 300 |
| gatactaact acaccctcac gccttttcgac accctaccac aatgcaacgg ttgtgaagta | 360 |
| cacggtggat attatattgg atgggtctcc gtccaggacc aagtcgagtc gcttgtcaaa | 420 |
| cagcaggtta gccagtatcc ggactacgcg ctgaccgtga ccggccackc cctcggcgcc | 480 |
| tccctggcgg cactcactgc cgcccagctg tctgcgacat acgacaacat ccgcctgtac | 540 |
| accttcggcg aaccgcgcag cggcaatcag gccttcgcgt cgtacatgaa cgatgccttc | 600 |
| caagcctcga gcccagatac gacgcagtat ttccgggtca ctcatgccaa cgacggcatc | 660 |
| ccaaacctgc ccccggtgga gcaggggtac gcccatggcg tgtagagta ctggagcgtt | 720 |
| gatccttaca gcgcccagaa cacatttgtc tgcactgggg atgaagtgca gtgctgtgag | 780 |
| gcccagggcg gacagggtgt gaataatgcg cacacgactt attttgggat gacgagcggc | 840 |
| gcatgcacct ggccggtcgc ggccgcggaa ccactgaagg atgagctgta agaagcaga | 900 |
| tcgttcaaac attggcaat aaagtttctt aagattgaat cctgttgccg gtcttgcgat | 960 |
| gattatcata taatttctgt tgaattacgt taagcatgta ataattaaca tgtaatgcat | 1020 |
| gacgttattt atgagatggg tttttatgat tagagtcccg caattataca tttaatacgc | 1080 |
| gatagaaaac aaaatatagc gcgcaaacta ggataaatta tcgcgcgcgg tgtcatctat | 1140 |
| gttactagat cgataagctt ctagagcggc cggtggagct ccaattcgcc ctatagtgag | 1200 |
| tcgtattacg cgcgctcact ggccgtcgtt ttacaacgtc gtgactggga aaaccctggc | 1260 |
| gttacccaac ttaatcgcct tgcagcacat ccccctttcg ccagctggcg taatagcgaa | 1320 |
| gaggcccgca ccgatcgccc ttcccaacag ttgcgcagcc tgaatggcga atgggacgcg | 1380 |
| ccctgtagcg gcgcattaag cgcggcgggt gtggtggtta cgcgcagcgt gaccgctaca | 1440 |
| cttgccagcg ccctagcgcc cgctcctttc gctttcttcc cttcctttct cgccacgttc | 1500 |
| gccggctttc cccgtcaagc tctaaatcgg gggctccctt agggttccg atttagtgct | 1560 |
| ttacggcacc tcgaccccaa aaaacttgat tagggtgatg gttcacgtag tgggccatcg | 1620 |
| ccctgataga cggtttttcg ccctttgacg ttggagtcca cgttctttaa tagtggactc | 1680 |
| ttgttccaaa ctggaacaac actcaaccct atctcggtct attcttttga tttataaggg | 1740 |
| attttgccga tttcggccta ttggttaaaa aatgagctga tttaacaaaa atttaacgcg | 1800 |

-continued

```
aattttaaca aaatattaac gcttacaatt taggtggcac ttttcgggga aatgtgcgcg    1860
gaacccctat tgtttattt ttctaaatac attcaaatat gtatccgctc atgagacaat    1920
aaccctgata aatgcttcaa taatattgaa aaggaagag tatgagtatt caacatttcc    1980
gtgtcgccct tattccctt tttgcggcat tttgccttcc tgtttttgct cacccagaaa    2040
cgctggtgaa agtaaaagat gctgaagatc agttgggtgc acgagtgggt tacatcgaac    2100
tggatctcaa cagcggtaag atccttgaga gttttcgccc cgaagaacgt tttccaatga    2160
tgagcacttt taaagttctg ctatgtggcg cggtattatc ccgtattgac gccgggcaag    2220
agcaactcgg tcgccgcata cactattctc agaatgactt ggttgagtac tcaccagtca    2280
cagaaaagca tcttacggat ggcatgacag taagagaatt atgcagtgct gccataacca    2340
tgagtgataa cactgcggcc aacttacttc tgacaacgat cggaggaccg aaggagctaa    2400
ccgcttttt gcacaacatg ggggatcatg taactcgcct tgatcgttgg aaccggagc    2460
tgaatgaagc cataccaaac gacgagcgtg acaccacgat gcctgtagca atggcaacaa    2520
cgttgcgcaa actattaact ggcgaactac ttactctagc ttcccggcaa caattaatag    2580
actggatgga ggcggataaa gttgcaggac cacttctgcg ctcggccctt ccggctggct    2640
ggtttattgc tgataaatct ggagccggtg agcgtgggtc tcgcggtatc attgcagcac    2700
tggggccaga tggtaagccc tcccgtatcg tagttatcta cacgacgggg agtcaggcaa    2760
ctatggatga acgaaataga cagatcgctg agataggtgc ctcactgatt aagcattggt    2820
aactgtcaga ccaagtttac tcatatatac tttagattga tttaaaactt catttttaat    2880
ttaaaaggat ctaggtgaag atcctttttg ataatctcat gaccaaaatc ccttaacgtg    2940
agttttcgtt ccactgagcg tcagaccccg tagaaaagat caaaggatct tcttgagatc    3000
ctttttttct gcgcgtaatc tgctgcttgc aaacaaaaaa accaccgcta ccagcggtgg    3060
tttgtttgcc ggatcaagag ctaccaactc tttttccgaa ggtaactggc ttcagcagag    3120
cgcagatacc aaatactgtc cttctagtgt agccgtagtt aggccaccac ttcaagaact    3180
ctgtagcacc gcctacatac ctcgctctgc taatcctgtt accagtggct gctgccagtg    3240
gcgataagtc gtgtcttacc gggttggact caagacgata gttaccggat aaggcgcagc    3300
ggtcgggctg aacggggggt tcgtgcacac agcccagctt ggagcgaacg acctacaccg    3360
aactgagata cctacagcgt gagctatgag aaagcgccac gcttcccgaa gggagaaagg    3420
cggacaggta tccggtaagc ggcagggtcg gaacaggaga gcgcacgagg gagcttccag    3480
ggggaaacgc ctggtatctt tatagtcctg tcgggtttcg ccacctctga cttgagcgtc    3540
gatttttgtg atgctcgtca ggggggcgga gcctatggaa aaacgccagc aacgcggcct    3600
ttttacggtt cctggccttt tgctggcctt ttgctcacat gttctttcct gcgttatccc    3660
ctgattctgt ggataaccgt attaccgcct ttgagtgagc tgataccgct cgccgcagcc    3720
gaacgaccga gcgcagcgag tcagtgagcg aggaagcgga agagcgccca atacgcaaac    3780
cgcctctccc cgcgcgttgg ccgattcatt aatgcagctg gcacgacagg tttcccgact    3840
ggaaagcggg cagtgagcgc aacgcaatta atgtgagtta gctcactcat taggcacccc    3900
aggctttaca ctttatgctt ccggctcgta tgttgtgtgg aattgtgagc ggataacaat    3960
ttcacacagg aaacagctat gaccatgatt acgccaagcg cgcaattaac cctcactaaa    4020
gggaacaaaa gctgggtacc gggccccccc tcgaggtcat tcatatgctt gagaagagag    4080
tcgggatagt ccaaaataaa acaaaggtaa gattacctgg tcaaaagtga aaacatcagt    4140
```

-continued

```
taaaaggtgg tataagtaaa atatcggtaa taaaaggtgg cccaaagtga aatttactct    4200
tttctactat tataaaaatt gaggatgttt tgtcggtact tgatacgtc attttttgtat    4260
gaattggttt ttaagtttat tcgcgatttg gaaatgcata tctgtatttg agtcggtttt    4320
taagttcgtt gcttttgtaa atacagaggg atttgtataa gaaatatctt taaaaaaccc    4380
atatgctaat ttgacataat ttttgagaaa aatatatatt caggcgaatt ccacaatgaa    4440
caataataag attaaaatag cttgcccccg ttgcagcgat gggtattttt tctagtaaaa    4500
taaaagataa acttagactc aaaacattta caaaaacaac ccctaaagtc ctaaagccca    4560
aagtgctatg cacgatccat agcaagccca gcccaaccca acccaaccca acccaccca    4620
gtgcagccaa ctggcaaata gtctccaccc ccggcactat caccgtgagt tgtccgcacc    4680
accgcacgtc tcgcagccaa aaaaaaaaaa agaaagaaaa aaaagaaaaa gaaaacagc    4740
aggtgggtcc gggtcgtggg ggccggaaaa gcgaggagga tcgcgagcag cgacgaggcc    4800
cggccctccc tccgcttcca agaaacgcc cccatcgcc actatataca taccccccc    4860
tctcctccca tcccccaac cctaccacca ccaccaccac cacctcctcc ccctcgctg    4920
ccggacgacg agtcctccc ccctccccct cgccgccgc cggtaaccac cccgcccctc    4980
tcctctttct ttctccgttt ttttttttcgt ctcggtctcg atctttggcc ttggtagttt    5040
gggtgggcga gagcggcttc gtcgcccaga tcggtgcgcg ggaggggcgg gatctcgcgg    5100
ctggcgtctc cgggcgtgag tcggcccgga tcctcgcggg gaatgggggct ctcggatgta    5160
gatcttcttt ctttcttctt tttgtggtag aatttgaatc cctcagcatt gttcatcggt    5220
agttttctt ttcatgattt gtgacaaatg cagcctcgtg cggagctttt ttgtagc       5277
```

<210> SEQ ID NO 26
<211> LENGTH: 293
<212> TYPE: PRT
<213> ORGANISM: Artificial Sequence
<220> FEATURE:
<223> OTHER INFORMATION: pTP5-1 vector
<220> FEATURE:
<221> NAME/KEY: VARIANT
<222> LOCATION: (1)...(293)
<223> OTHER INFORMATION: Xaa = Any Amino Acid

<400> SEQUENCE: 26

```
Met Lys Gln Phe Ser Ala Lys His Val Leu Ala Val Val Thr Ala
 1               5                  10                  15

Gly His Ala Leu Ala Ala Ser Thr Gln Gly Ile Ser Glu Asp Leu Tyr
            20                  25                  30

Ser Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ser Gln Thr Asp Ile Asn Gly Trp Ile Leu Arg Asp Asp Ser Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Gly Cys Glu Val His Gly Gly Tyr Tyr Ile Gly Trp Val Ser Val
        115                 120                 125

Gln Asp Gln Val Glu Ser Leu Val Lys Gln Gln Val Ser Gln Tyr Pro
    130                 135                 140
```

```
Asp Tyr Ala Leu Thr Val Thr Gly His Xaa Leu Gly Ala Ser Leu Ala
145                 150                 155                 160

Ala Leu Thr Ala Ala Gln Leu Ser Ala Thr Tyr Asp Asn Ile Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Ala Ser Ser Pro Asp Thr Thr Gln Tyr Phe
        195                 200                 205

Arg Val Thr His Ala Asn Asp Gly Ile Pro Asn Leu Pro Pro Val Glu
    210                 215                 220

Gln Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asn Ala His Thr Thr Tyr Phe
                260                 265                 270

Gly Met Thr Ser Gly Ala Cys Thr Trp Pro Val Ala Ala Ala Glu Pro
            275                 280                 285

Leu Lys Asp Glu Leu
    290
```

```
<210> SEQ ID NO 27
<211> LENGTH: 5327
<212> TYPE: DNA
<213> ORGANISM: Artificial Sequence
<220> FEATURE:
<223> OTHER INFORMATION: pTP4a2 vector

<400> SEQUENCE: 27
gatcctccgc gacgacagca gcaaagaaat aatcaccgtc ttccgtggca ctggtagtga      60
tacgaatcta caactcgata ctaactacac cctcacgcct ttcgacccc taccacaatg     120 caacggttgt gaagtacacg gtggatatta tattggatgg gtctccgtcc aggaccaagt    180
cgagtcgctt gtcaaacagc aggttagcca gtatccggac tacgcgctga ccgtgaccgg    240
ccackccctc ggcgcctccc tggcggcact cactgccgcc cagctgtctg cgacatacga    300
caacatccgc ctgtacacct tcggcgaacc gcgcagcggc aatcaggcct tcgcgtcgta    360
catgaacgat gccttccaag cctcgagccc agatacgacg cagtatttcc gggtcactca    420
tgccaacgac ggcatcccaa acctgccccc ggtggagcag gggtacgccc atggcggtgt    480
agagtactgg agcgttgatc cttacagcgc ccagaacaca tttgtctgca ctggggatga    540
agtgcagtgc tgtgaggccc agggcggaca gggtgtgaat aatgcgcaca cgacttattt    600
tgggatgacg agcggagcct gtacatggtg atcagtcatt tcagcctccc cgagtgtacc    660
aggaaagatg gatgtcctgg agaggggcc gcgtaaccac tgaaggatga gctgtaaaga    720
agcagatcgt tcaaacattt ggcaataaag tttcttaaga ttgaatcctg ttgccggtct    780
tgcgatgatt atcatataat ttctgttgaa ttacgttaag catgtaataa ttaacatgta    840
atgcatgacg ttatttatga gatgggtttt tatgattaga gtcccgcaat tatacattta    900
atacgcgata gaaaacaaaa tatagcgcgc aaactaggat aaattatcgc gcgcggtgtc    960
atctatgtta ctagatcgat aagcttctag agcggccggt ggagtccaa ttcgccctat   1020 agtgagtcgt attacgcgcg ctcactggcc gtcgttttac aacgtcgtga ctgggaaaac   1080
cctggcgtta cccaacttaa tcgccttgca gcacatcccc ctttcgccag ctggcgtaat   1140
agcgaagagg cccgcaccga tcgcccttcc caacagttgc gcagcctgaa tggcgaatgg   1200
```

-continued

```
gacgcgccct gtagcggcgc attaagcgcg gcgggtgtgg tggttacgcg cagcgtgacc    1260
gctacacttg ccagcgccct agcgcccgct cctttcgctt tcttcccttc ctttctcgcc    1320
acgttcgccg gctttccccg tcaagctcta atcggggc tcccttta gttccgattt        1380 agtgctttac ggcacctcga ccccaaaaaa cttgattagg gtgatggttc acgtagtggg    1440
ccatcgccct gatagacggt ttttcgccct tgacgttgg agtccacgtt ctttaatagt     1500
ggactcttgt tccaaactgg aacaacactc aaccctatct cggtctattc ttttgattta    1560
taagggattt tgccgatttc ggcctattgg ttaaaaatg agctgattta acaaaaattt     1620
aacgcgaatt ttaacaaaat attaacgctt acaatttagg tggcacttt cggggaaatg     1680 tgcgcggaac ccctatttgt ttatttttct aaatacattc aaatatgtat ccgctcatga    1740
gacaataacc ctgataaatg cttcaataat attgaaaaag gaagagtatg agtattcaac    1800
atttccgtgt cgcccttatt cccttttttg cggcattttg ccttcctgtt tttgctcacc    1860
cagaaacgct ggtgaaagta aaagatgctg aagatcagtt gggtgcacga gtgggttaca    1920
tcgaactgga tctcaacagc ggtaagatcc ttgagagttt tcgccccgaa gaacgttttc    1980
caatgatgag cacttttaaa gttctgctat gtggcgcggt attatcccgt attgacgccg    2040
ggcaagagca actcggtcgc cgcatacact attctcagaa tgacttggtt gagtactcac    2100
cagtcacaga aaagcatctt acggatggca tgacagtaag agaattatgc agtgctgcca    2160
taaccatgag tgataacact gcggccaact tacttctgac aacgatcgga ggaccgaagg    2220
agctaaccgc ttttttgcac aacatggggg atcatgtaac tcgccttgat cgttgggaac    2280
cggagctgaa tgaagccata ccaaacgacg agcgtgacac cacgatgcct gtagcaatgg    2340
caacaacgtt gcgcaaacta ttaactggcg aactacttac tctagcttcc cggcaacaat    2400
taatagactg gatggaggcg gataaagttg caggaccact tctgcgctcg gcccttccgg    2460
ctggctggtt tattgctgat aaatctggag ccggtgagcg tgggtctcgc ggtatcattg    2520
cagcactggg gccagatggt aagccctccc gtatcgtagt tatctacacg acggggagtc    2580
aggcaactat ggatgaacga atagacaga tcgctgagat aggtgcctca ctgattaagc      2640
attggtaact gtcagaccaa gtttactcat atatacttta gattgattta aaacttcatt    2700
tttaatttaa aaggatctag gtgaagatcc tttttgataa tctcatgacc aaaatccctt    2760
aacgtgagtt ttcgttccac tgagcgtcag accccgtaga aaagatcaaa ggatcttctt    2820
gagatccttt ttttctgcgc gtaatctgct gcttgcaaac aaaaaaacca ccgctaccag    2880
cggtggtttg tttgccggat caagagctac caactctttt tccgaaggta actggcttca    2940
gcagagcgca gataccaaat actgtccttc tagtgtagcc gtagttaggc caccacttca    3000
agaactctgt agcaccgcct acatacctcg ctctgctaat cctgttacca gtggctgctg    3060
ccagtggcga taagtcgtgt cttaccgggt tggactcaag acgatagtta ccggataagg    3120
cgcagcggtc gggctgaacg gggggttcgt gcacacagcc cagcttggag cgaacgacct    3180
acaccgaact gagatacta cagcgtgagc tatgagaaag cgccacgctt cccgaaggga    3240
gaaaggcgga caggtatccg gtaagcggca gggtcggaac aggagagcgc acgagggagc    3300
ttccaggggg aaacgcctgg tatctttata gtcctgtcgg gtttcgccac ctctgacttg    3360
agcgtcgatt tttgtgatgc tcgtcagggg ggcggagcct atggaaaaac gccagcaacg    3420
cggccttttt acggttcctg gccttttgct ggccttttgc tcacatgttc tttcctgcgt    3480
tatcccctga ttctgtggat aaccgtatta ccgcctttga gtgagctgat accgctcgcc    3540
```

-continued

```
gcagccgaac gaccgagcgc agcgagtcag tgagcgagga agcggaagag cgcccaatac    3600
gcaaaccgcc tctccccgcg cgttggccga ttcattaatg cagctggcac gacaggtttc    3660
ccgactggaa agcgggcagt gagcgcaacg caattaatgt gagttagctc actcattagg    3720
caccccaggc tttacacttt atgcttccgg ctcgtatgtt gtgtggaatt gtgagcggat    3780
aacaatttca cacaggaaac agctatgacc atgattacgc caagcgcgca attaaccctc    3840
actaaaggga acaaaagctg gtaccgggcc cccccctcga ggtcattcat atgcttgaga    3900
agagagtcgg gatagtccaa aataaaacaa aggtaagatt acctggtcaa aagtgaaaac    3960
atcagttaaa aggtggtata agtaaaatat cggtaataaa aggtggccca aagtgaaatt    4020
tactcttttc tactattata aaaattgagg atgttttgtc ggtactttga tacgtcattt    4080
ttgtatgaat tggtttttaa gtttattcgc gatttggaaa tgcatatctg tatttgagtc    4140 ggttttaag ttcgttgctt ttgtaaatac agagggattt gtataagaaa tatctttaaa     4200
aaacccatat gctaatttga cataattttt gagaaaaata tatattcagg cgaattccac    4260
aatgaacaat aataagatta aaatagcttg ccccccgttgc agcgatgggt attttttcta    4320
gtaaaataaa agataaaactt agactcaaaa catttacaaa acaacccct aaagtcctaa     4380 agcccaaagt gctatgcacg atccatagca agcccagccc aacccaaccc aacccaaccc    4440
accccagtgc agccaactgg caaatagtct ccaccccccgg cactatcacc gtgagttgtc   4500
cgcaccaccg cacgtctcgc agccaaaaaa aaaaaagaa agaaaaaaa gaaaagaaa      4560 aacagcaggt gggtccgggt cgtggggggcc ggaaaagcga ggaggatcgc gagcagcgac   4620
gaggcccggc cctccctccg cttccaaaga aacgcccccc atcgccacta tatacatacc    4680
cccccctctc ctcccatccc cccaacccta ccaccaccac caccaccacc tcctccccc     4740 tcgctgccgg acgacgagct cctcccccct cccctccgc cgccgccggt aaccaccccg     4800 ccctctcct ctttctttct ccgttttttt tttcgtctcg gtctcgatct ttggccttgg     4860
tagtttgggt gggcgagagc ggcttcgtcg cccagatcgg tgcgcgggag gggcgggatc    4920
tcgcggctgg cgtctccggg cgtgagtcgg cccggatcct cgcggggaat ggggctctcg    4980
gatgtagatc ttctttctt cttctttttg tggtagaatt tgaatccctc agcattgttc     5040
atcggtagtt tttctttca tgatttgtga caaatgcagc ctcgtgcgga gcttttttgt     5100
agcaagctta acatgaagca gttctccgcc aaacacgtcc tcgcagttgt ggtgactgca    5160
gggcacgcct tagcagcctc tacgcaaggc atctccgaag acctctacag ccgtttagtc    5220
gaaatggcca ctatctccca agctgcctac gccgacctgt gcaacattcc gtcgactatt    5280
atcaagggag agaaaattta caattctcaa actgacatta acggatg                 5327
```

<210> SEQ ID NO 28
<211> LENGTH: 209
<212> TYPE: PRT
<213> ORGANISM: Artificial Sequence
<220> FEATURE:
<223> OTHER INFORMATION: pTP4a2 vector
<220> FEATURE:
<221> NAME/KEY: VARIANT
<222> LOCATION: (1)...(209)
<223> OTHER INFORMATION: Xaa = Any Amino Acid

<400> SEQUENCE: 28

```
Ile Leu Arg Asp Asp Ser Ser Lys Glu Ile Ile Thr Val Phe Arg Gly
1               5                   10                  15

Thr Gly Ser Asp Thr Asn Leu Gln Leu Asp Thr Asn Tyr Thr Leu Thr
            20                  25                  30
```

```
Pro Phe Asp Thr Leu Pro Gln Cys Asn Gly Cys Glu Val His Gly Gly
         35                  40                  45
Tyr Tyr Ile Gly Trp Val Ser Val Gln Asp Gln Val Glu Ser Leu Val
 50                  55                  60
Lys Gln Gln Val Ser Gln Tyr Pro Asp Tyr Ala Leu Thr Val Thr Gly
 65                  70                  75                  80
His Xaa Leu Gly Ala Ser Leu Ala Ala Leu Thr Ala Ala Gln Leu Ser
                 85                  90                  95
Ala Thr Tyr Asp Asn Ile Arg Leu Tyr Thr Phe Gly Glu Pro Arg Ser
                100                 105                 110
Gly Asn Gln Ala Phe Ala Ser Tyr Met Asn Asp Ala Phe Gln Ala Ser
                115                 120                 125
Ser Pro Asp Thr Thr Gln Tyr Phe Arg Val Thr His Ala Asn Asp Gly
        130                 135                 140
Ile Pro Asn Leu Pro Pro Val Glu Gln Gly Tyr Ala His Gly Gly Val
145                 150                 155                 160
Glu Tyr Trp Ser Val Asp Pro Tyr Ser Ala Gln Asn Thr Phe Val Cys
                165                 170                 175
Thr Gly Asp Glu Val Gln Cys Cys Glu Ala Gln Gly Gly Gln Gly Val
                180                 185                 190
Asn Asn Ala His Thr Thr Tyr Phe Gly Met Thr Ser Gly Ala Cys Thr
            195                 200                 205
Trp

<210> SEQ ID NO 29
<211> LENGTH: 5338
<212> TYPE: DNA
<213> ORGANISM: Artificial Sequence
<220> FEATURE:
<223> OTHER INFORMATION: pTP3-1 vector

<400> SEQUENCE: 29
aagcttacca tggcccacgc ccgcgtcctc ctcctggcgc tcgccgtgct ggccacggcc      60
gccgtcgccg tcgcctcctc ctcctccttc gccgactcca acccgatccg gcccgtcacc     120
gaccgcgcgg ccgcctccac gcagggcatc tccgaagacc tctacagccg tttagtcgaa     180
atggccacta tctcccaagc tgcctacgcc gacctgtgca cattccgtc gactattatc      240 aagggagaga aaatttacaa ttctcaaact gacattaacg gatggatcct ccgcgacgac     300
agcagcaaag aaataatcac cgtcttccgt ggcactggta gtgatacgaa tctacaactc     360
gatactaact acaccctcac gcctttcgac accctaccac aatgcaacgg ttgtgaagta     420
cacggtggat attatattgg atgggtctcc gtccaggacc aagtcgagtc gcttgtcaaa     480
cagcaggtta gccagtatcc ggactacgcg ctgaccgtga ccggccackc cctcggcgcc     540
tccctggcgg cactcactgc cgcccagctg tctgcgacat acgacaacat ccgcctgtac     600
accttcggcg aaccgcgcag cggcaatcag gccttcgcgt cgtacatgaa cgatgccttc     660
caagcctcga gccagatac gacgcagtat ttccgggtca ctcatgccaa cgacggcatc      720
ccaaacctgc ccccggtgga gcagggctac gcccatggcg gtgtagagta ctggagcgtt     780
gatccttaca gcgcccagaa cacatttgtc tgcactgggg atgaagtgca gtgctgtgag     840
gcccagggcg gacagggtgt gaataatgcg cacacgactt attttgggat gacgagcggc     900
gcatgcacct ggccggtcgc ggccgcggaa accactgaag gatgagctgt aaagaagcag     960
atcgttcaaa catttggcaa taaagttcct taagattgaa tcctgttgcc ggtcttgcga    1020
```

-continued

```
tgattatcat ataatttctg ttgaattacg ttaagcatgt aataattaac atgtaatgca    1080
tgacgttatt tatgagatgg gttttttatga ttagagtccc gcaattatac atttaatacg   1140
cgatagaaaa caaatatag cgcgcaaact aggataaatt atcgcgcgcg gtgtcatcta     1200
tgttactaga tcgataagct tctagagcgg ccggtggagc tccaattcgc cctatagtga    1260
gtcgtattac gcgcgctcac tggccgtcgt tttacaacgt cgtgactggg aaaaccctgg    1320
cgttacccaa cttaatcgcc ttgcagcaca tccccctttc gccagctggc gtaatagcga    1380
agaggcccgc accgatcgcc cttcccaaca gttgcgcagc ctgaatggcg aatgggacgc    1440
gccctgtagc ggcgcattaa gcgcggcggg tgtggtggtt acgcgcagcg tgaccgctac    1500
acttgccagc gccctagcgc ccgctccttt cgctttcttc ccttcctttc tcgccacgtt    1560
cgccggcttt ccccgtcaag ctctaaatcg ggggctccct ttagggttcc gatttagtgc    1620
tttacggcac ctcgacccca aaaaacttga ttagggtgat ggttcacgta gtgggccatc    1680
gccctgatag acggtttttc gccctttgac gttggagtcc acgttcttta atagtggact    1740
cttgttccaa actggaacaa cactcaaccc tatctcggtc tattcttttg atttataagg    1800
gattttgccg atttcggcct attggttaaa aaatgagctg atttaacaaa aatttaacgc    1860
gaattttaac aaaatattaa cgcttacaat ttaggtggca cttttcgggg aaatgtgcgc    1920 ggaacccta tttgtttatt tttctaaata cattcaaata tgtatccgct catgagacaa    1980
taaccctgat aaatgcttca ataatattga aaaggaaga gtatgagtat tcaacatttc    2040
cgtgtcgccc ttattccctt ttttgcggca ttttgccttc ctgttttgc tcacccagaa    2100 acgctggtga agtaaaaga tgctgaagat cagttgggtg cacgagtggg ttacatcgaa    2160
ctggatctca acagcggtaa gatccttgag agttttcgcc ccgaagaacg ttttccaatg    2220
atgagcactt ttaaagttct gctatgtggc gcggtattat cccgtattga cgccgggcaa    2280
gagcaactcg gtcgccgcat acactattct cagaatgact tggttgagta ctcaccagtc    2340
acagaaaagc atcttacgga tggcatgaca gtaagagaat tatgcagtgc tgccataacc    2400
atgagtgata acactgcggc caacttactt ctgacaacga tcggaggacc gaaggagcta    2460
accgcttttt tgcacaacat gggggatcat gtaactcgcc ttgatcgttg ggaaccggag    2520
ctgaatgaag ccataccaaa cgacgagcgt gacaccacga tgcctgtagc aatggcaaca    2580
acgttgcgca aactattaac tggcgaacta cttactctag cttcccggca acaattaata    2640
gactggatga aggcggataa agttgcagga ccacttctgc gctcggccct tccggctggc    2700
tggtttattg ctgataaatc tggagccggt gagcgtgggt ctcgcggtat cattgcagca    2760
ctggggccag atggtaagcc ctcccgtatc gtagttatct acacgacggg gagtcaggca    2820
actatggatg aacgaaatag acagatcgct gagataggtg cctcactgat taagcattgg    2880
taactgtcag accaagttta ctcatatata ctttagattg atttaaaact tcattttaa    2940 tttaaaagga tctaggtgaa gatccttttt gataatctca tgaccaaaat cccttaacgt    3000
gagttttcgt tccactgagc gtcagacccc gtagaaaaga tcaaaggatc ttcttgagat    3060
cctttttttc tgcgcgtaat ctgctgcttg caaacaaaaa aaccaccgct accagcggtg    3120
gtttgtttgc cggatcaaga gctaccaact cttttccga aggtaactgg cttcagcaga    3180
gcgcagatac caaatactgt ccttctagtg tagccgtagt taggccacca cttcaagaac    3240
tctgtagcac cgcctacata cctcgctctg ctaatcctgt taccagtggc tgctgccagt    3300
ggcgataagt cgtgtcttac cgggttggac tcaagacgat agttaccgga taaggcgcag    3360
```

```
cggtcgggct gaacgggggg ttcgtgcaca cagcccagct tggagcgaac gacctacacc   3420
gaactgagat acctacagcg tgagctatga gaaagcgcca cgcttcccga agggagaaag   3480
gcggacaggt atccggtaag cggcagggtc ggaacaggag agcgcacgag ggagcttcca   3540
gggggaaacg cctggtatct ttatagtcct gtcgggtttc gccacctctg acttgagcgt   3600
cgattttttgt gatgctcgtc agggggggcgg agcctatgga aaaacgccag caacgcggcc   3660
ttttttacggt tcctggcctt tgctggcct tttgctcaca tgttctttcc tgcgttatcc   3720
cctgattctg tggataaccg tattaccgcc tttgagtgag ctgataccgc tcgccgcagc   3780
cgaacgaccg agcgcagcga gtcagtgagc gaggaagcgg aagagcgccc aatacgcaaa   3840
ccgcctctcc ccgcgcgttg gccgattcat taatgcagct ggcacgacag gtttcccgac   3900
tggaaagcgg gcagtgagcg caacgcaatt aatgtgagtt agctcactca ttaggcaccc   3960
caggctttac actttatgct tccggctcgt atgttgtgtg gaattgtgag cggataacaa   4020
tttcacacag gaaacagcta tgaccatgat tacgccaagc gcgcaattaa ccctcactaa   4080
agggaacaaa agctgggtac cgggcccccc ctcgaggtca ttcatatgct tgagaagaga   4140
gtcgggatag tccaaaataa aacaaaggta agattacctg gtcaaaagtg aaaacatcag   4200
ttaaaaggtg gtataagtaa aatatcggta ataaaggtg gcccaaagtg aaatttactc   4260
ttttctacta ttataaaaat tgaggatgtt ttgtcggtac tttgatacgt cattttttgta   4320
tgaattggtt tttaagttta ttcgcgattt ggaaatgcat atctgtattt gagtcggttt   4380
ttaagttcgt tgcttttgta aatacagagg gatttgtata agaaatatct ttaaaaaacc   4440
catatgctaa tttgacataa tttttgagaa aaatatatat tcaggcgaat ccacaatga    4500
acaataataa gattaaaata gcttgccccc gttgcagcga tgggtatttt ttctagtaaa   4560
ataaaagata aacttagact caaaacattt acaaaaacaa cccctaaagt cctaaagccc   4620
aaagtgctat gcacgatcca tagcaagccc agcccaaccc aacccaaccc aacccacccc   4680
agtgcagcca actggcaaat agtctccacc cccggcacta tcaccgtgag ttgtccgcac   4740
caccgcacgt ctcgcagcca aaaaaaaaaa aagaaagaaa aaaagaaaa agaaaaacag    4800
caggtgggtc cgggtcgtgg gggccggaaa agcgaggagg atcgcgagca gcgacgaggc   4860
ccggccctcc ctccgcttcc aaagaaacgc ccccatcgc cactatatac ataccccccc    4920
ctctcctccc atccccccaa ccctaccacc accaccacca ccacctcctc cccctcgct    4980
gccggacgac gagctcctcc cccctcccc tccgccgccg ccgtaaccaa ccccgccccct   5040
ctcctctttc tttctccgtt ttttttttcg tctcggtctc gatctttggc cttggtagtt   5100
tgggtgggcg agagcggctt cgtcgcccag atcggtgcgc gggagggggcg ggatctcgcg   5160
gctggcgtct ccgggcgtga gtcggcccgg atcctcgcgg ggaatgggc tctcggatgt    5220
agatcttctt tctttcttct ttttgtggta gaatttgaat ccctcagcat tgttcatcgg   5280
tagttttttct tttcatgatt tgtgacaaat gcagcctcgt gcggagcttt tttgtagc    5338
```

<210> SEQ ID NO 30
<211> LENGTH: 311
<212> TYPE: PRT
<213> ORGANISM: Artificial Sequence
<220> FEATURE:
<223> OTHER INFORMATION: pTP3-1 vector
<220> FEATURE:
<221> NAME/KEY: VARIANT
<222> LOCATION: (1)...(311)
<223> OTHER INFORMATION: Xaa = Any Amino Acid

<400> SEQUENCE: 30

```
Met Ala His Ala Arg Val Leu Leu Ala Leu Ala Val Leu Ala Thr
1               5                   10                  15

Ala Ala Val Ala Val Ala Ser Ser Ser Phe Ala Asp Ser Asn Pro
            20                  25                  30

Ile Arg Pro Val Thr Asp Arg Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Lys Gly Glu
65              70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
            115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
                195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
    275                 280                 285

Thr Thr Tyr Phe Gly Met Thr Ser Gly Ala Cys Thr Trp Pro Val Ala
290                 295                 300

Ala Ala Glu Thr Thr Glu Gly
305                 310

<210> SEQ ID NO 31
<211> LENGTH: 5337
<212> TYPE: DNA
<213> ORGANISM: Artificial Sequence
<220> FEATURE:
<223> OTHER INFORMATION: pTU5 vector

<400> SEQUENCE: 31
aagcttacca tggcccacgc ccgcgtcctc ctcctggcgc tcgccgtgct ggccacggcc      60
gccgtcgccg tcgcctcctc ctcctccttc gccgactcca acccgggccg gcccgtcacc     120
gaccgcgcgg ccgcctccac gcagggcatc tccgaagacc tctacagccg tttagtcgaa     180
atggccacta tctcccaagc tgcctacgcc gacctgtgca acattccgtc gactattatc     240
```

```
aagggagaga aaatttacaa ttctcaaact gacattaacg gatggatcct ccgcgacgac      300
agcagcaaag aaataatcac cgtcttccgt ggcactggta gtgatacgaa tctacaactc      360
gatactaact acaccctcac gcctttcgac accctaccac aatgcaacgg ttgtgaagta      420
cacggtggat attatattgg atgggtctcc gtccaggacc aagtcgagtc gcttgtcaaa      480
cagcaggtta gccagtatcc ggactacgcg ctgaccgtga ccggccactc cctcggcgcc      540
tccctggcgg cactcactgc cgcccagctg tctgcgacat acgacaacat ccgcctgtac      600
accttcggcg aaccgcgcag cggcaatcag gccttcgcgt cgtacatgaa cgatgccttc      660
caagcctcga gcccagatac gacgcagtat ttccgggtca ctcatgccaa cgacggcatc      720
ccaaacctgc cccgggtgga gcaggggtac gcccatggcg gtgtagagta ctggagcgtt      780
gatccttaca gcgcccagaa cacatttgtc tgcactgggg atgaagtgca gtgctgtgag      840
gcccagggcg gacagggtgt gaataatgcg cacacgactt attttgggat gacgagcggc      900
gcatgcacct ggccggtcgc ggccgcggaa ccactgaagg atgagctgta aagaagcaga      960
tcgttcaaac atttggcaat aaagtttctt aagattgaat cctgttgccg gtcttgcgat     1020
gattatcata taatttctgt tgaattacgt taagcatgta ataattaaca tgtaatgcat     1080
gacgttattt atgagatggg ttttatgat tagagtcccg caattataca tttaatacgc     1140
gatagaaaac aaaatatagc gcgcaaacta ggataaatta tcgcgcgcgg tgtcatctat     1200
gttactagat cgataagctt ctagagcggc cggtggagct ccaattcgcc ctatagtgag     1260
tcgtattacg cgcgctcact ggccgtcgtt ttacaacgtc gtgactggga aaaccctggc     1320
gttacccaac ttaatcgcct tgcagcacat ccccctttcg ccagctggcg taatagcgaa     1380
gaggcccgca ccgatcgccc ttcccaacag ttgcgcagcc tgaatggcga atgggacgcg     1440
ccctgtagcg gcgcattaag cgcggcgggt gtggtggtta cgcgcagcgt gaccgctaca     1500
cttgccagcg ccctagcgcc cgctcctttc gctttcttcc cttcctttct cgccacgttc     1560
gccggctttc cccgtcaagc tctaaatcgg gggctccctt tagggttccg atttagtgct     1620
ttacggcacc tcgaccccaa aaaacttgat tagggtgatg gttcacgtag tgggccatcg     1680
ccctgataga cggtttttcg ccctttgacg ttggagtcca cgttctttaa tagtggactc     1740
ttgttccaaa ctggaacaac actcaaccct atctcggtct attcttttga tttataaggg     1800
attttgccga tttcggccta ttggttaaaa aatgagctga tttaacaaaa atttaacgcg     1860
aattttaaca aaatattaac gcttacaatt taggtggcac ttttcgggga atgtgcgcg     1920 gaaccccctat ttgtttattt ttctaaatac attcaaatat gtatccgctc atgagacaat     1980
aaccctgata aatgcttcaa taatattgaa aaaggaagag tatgagtatt caacatttcc     2040
gtgtcgccct tattccctt tttgcggcat tttgccttcc tgttttgct cacccagaaa     2100 cgctggtgaa agtaaaagat gctgaagatc agttgggtgc acgagtgggt tacatcgaac     2160
tggatctcaa cagcggtaag atccttgaga gttttcgccc cgaagaacgt tttccaatga     2220
tgagcacttt taaagttctg ctatgtggcg cggtattatc ccgtattgac gccgggcaag     2280
agcaactcgg tcgccgcata cactattctc agaatgactt ggttgagtac tcaccagtca     2340
cagaaaagca tcttacggat ggcatgacag taagagaatt atgcagtgct gccataacca     2400
tgagtgataa cactgcggcc aacttacttc tgacaacgat cggaggaccg aaggagctaa     2460 ccgcttttt gcacaacatg gggatcatg taactcgcct tgatcgttgg gaaccggagc     2520
tgaatgaagc cataccaaac gacgagcgtg acaccacgat gcctgtagca atggcaacaa     2580
cgttgcgcaa actattaact ggcgaactac ttactctagc ttcccggcaa caattaatag     2640
```

-continued

```
actggatgga ggcggataaa gttgcaggac cacttctgcg ctcggccctt ccggctggct   2700
ggtttattgc tgataaatct ggagccggtg agcgtgggtc tcgcggtatc attgcagcac   2760
tggggccaga tggtaagccc tcccgtatcg tagttatcta cacgacgggg agtcaggcaa   2820
ctatggatga acgaaataga cagatcgctg agataggtgc ctcactgatt aagcattggt   2880
aactgtcaga ccaagtttac tcatatatac tttagattga tttaaaactt catttttaat   2940
ttaaaaggat ctaggtgaag atcctttttg ataatctcat gaccaaaatc ccttaacgtg   3000
agttttcgtt ccactgagcg tcagaccccg tagaaaagat caaggatctc ttgagatc    3060 cttttttct gcgcgtaatc tgctgcttgc aaacaaaaaa accaccgcta ccagcggtgg    3120
tttgtttgcc ggatcaagag ctaccaactc tttttccgaa ggtaactggc ttcagcagag   3180
cgcagatacc aaatactgtc cttctagtgt agccgtagtt aggccaccac ttcaagaact   3240
ctgtagcacc gcctacatac ctcgctctgc taatcctgtt accagtggct gctgccagtg   3300
gcgataagtc gtgtcttacc gggttggact caagacgata gttaccggat aaggcgcagc   3360
ggtcgggctg aacggggggt tcgtgcacac agcccagctt ggagcgaacg acctacaccg   3420
aactgagata cctacagcgt gagctatgag aaagcgccac gcttcccgaa gggagaaagg   3480
cggacaggta tccggtaagc ggcagggtcg gaacaggaga gcgcacgagg gagcttccag   3540
ggggaaacgc ctggtatctt tatagtcctg tcgggtttcg ccacctctga cttgagcgtc   3600 gattttgtg atgctcgtca gggggcgga gcctatggaa aaacgccagc aacgcggcct    3660
ttttacggtt cctggccttt tgctggcctt ttgctcacat gttctttcct gcgttatccc   3720
ctgattctgt ggataaccgt attaccgcct ttgagtgagc tgataccgct cgccgcagcc   3780
gaacgaccga gcgcagcgag tcagtgagcg aggaagcgga gagcgccca atacgcaaac    3840 cgcctctccc cgcgcgttgg ccgattcatt aatgcagctg gcacgacagg tttcccgact   3900
ggaaagcggg cagtgagcgc aacgcaatta atgtgagtta gctcactcat taggcacccc   3960
aggctttaca ctttatgctt ccggctcgta tgttgtgtgg aattgtgagc ggataacaat   4020
ttcacacagg aaacagctat gaccatgatt acgccaagcg cgcaattaac cctcactaaa   4080
gggaacaaaa gctgggtacc gggccccccc tcgaggtcat tcatatgctt gagaagagag   4140
tcgggatagt ccaaaataaa acaaaggtaa gattacctgg tcaaaagtga aaacatcagt   4200
taaaaggtgg tataagtaaa atatcggtaa taaaaggtgg cccaaagtga aatttactct   4260
tttctactat tataaaaatt gaggatgttt tgtcggtact ttgatacgtc atttttgtat   4320
gaattggttt ttaagtttat tcgcgatttg gaaatgcata tctgtatttg agtcggtttt   4380
taagttcgtt gcttttgtaa atacagaggg atttgtataa gaaatatctt taaaaaccc    4440 atatgctaat ttgacataat ttttgagaaa aatatatatt caggcgaatt ccacaatgaa   4500
caataataag attaaaatag cttgcccccg ttgcagcgat gggtattttt tctagtaaaa   4560 taaagataa acttagactc aaaacattta caaaacaac ccctaaagtc ctaaagccca     4620
aagtgctatg cacgatccat agcaagccca gcccaaccca acccaaccca acccacccca   4680
gtgcagccaa ctggcaaata gtctccaccc ccggcactat caccgtgagt tgtccgcacc   4740
accgcacgtc tcgcagccaa aaaaaaaaaa agaaagaaaa aaaagaaaaa gaaaacagc    4800 aggtgggtcc gggtcgtggg ggccggaaaa gcgaggagga tcgcgagcag cgacgaggcc   4860
cggccctccc tccgcttcca agaaacgcc cccatcgcc actatataca tacccccccc     4920
tctcctccca tcccccaac cctaccacca ccaccaccac cacctcctcc ccctcgctg     4980
```

```
ccggacgacg agctcctccc ccctccccct ccgccgccgc cggtaaccac cccgcccctc    5040
tcctctttct ttctccgttt ttttttttcgt ctcggtctcg atctttggcc ttggtagttt    5100
gggtgggcga gagcggcttc gtcgcccaga tcggtgcgcg ggaggggcgg gatctcgcgg    5160
ctggcgtctc cgggcgtgag tcggcccgga tcctcgcggg gaatgggget ctcggatgta    5220 gatcttcttt ctttcttctt tttgtggtag aatttgaatc cctcagcatt gttcatcggt    5280
agtttttctt ttcatgattt gtgacaaatg cagcctcgtg cggagctttt ttgtagc      5337
```

<210> SEQ ID NO 32
<211> LENGTH: 4773
<212> TYPE: DNA
<213> ORGANISM: Artificial Sequence
<220> FEATURE:
<223> OTHER INFORMATION: pGT6 vector
<400> SEQUENCE: 32

```
aagcttacca tggtgagcaa gggcgaggag ctgttcaccg gggtggtgcc catcctggtc     60
gagctggacg gcgacgtgaa cggccacaag ttcagcgtgt ccggcgaggg cgagggcgat   120
gccacctacg gcaagctgac cctgaagttc atctgcacca ccggcaagct gcccgtgccc   180
tggcccaccc tcgtgaccac cttcacctac ggcgtgcagt gcttcagccg ctaccccgac   240
cacatgaagc agcacgactt cttcaagtcc gccatgcccg aaggctacgt ccaggagcgc   300
accatcttct tcaaggacga cggcaactac aagacccgcg ccgaggtgaa gttcgagggc   360
gacaccctgg tgaaccgcat cgagctgaag ggcatcgact tcaaggagga cggcaacatc   420
ctggggcaca agctggagta caactacaac agccacaacg tctatatcat ggccgacaag   480
cagaagaacg gcatcaaggt gaacttcaag atccgccaca acatcgagga cggcagcgtg   540
cagctcgccg accactacca gcagaacacc cccatcggcg acggccccgt gctgctgccc   600
gacaaccact acctgagcac ccagtccgcc ctgagcaaag accccaacga gaagcgcgat   660
cacatggtcc tgctggagtt cgtgaccgcc gccgggatca ctcacggcat ggacgagctg   720
tacaagtaaa gcggccgccc gggctgcagg gaaaccactg aaggatgagc tgtaaagaag   780
cagatcgttc aaacatttgg caataaagtt tcttaagatt gaatcctgtt gccggtcttg   840
cgatgattat catataattt ctgttgaatt acgttaagca tgtaataatt aacatgtaat   900
gcatgacgtt atttatgaga tgggttttta tgattagagt cccgcaatta tacatttaat   960
acgcgataga aaacaaaata tagcgcgcaa actaggataa attatcgcgc gcggtgtcat  1020
ctatgttact agatcgataa gcttctagag cggccggtgg agctccaatt cgccctatag  1080
tgagtcgtat tacgcgcgct cactggccgt cgttttacaa cgtcgtgact gggaaaaccc  1140
tggcgttacc caacttaatc gccttgcagc acatccccct ttcgccagct ggcgtaatag  1200
cgaagaggcc cgcaccgatc gcccttccca acagttgcgc agcctgaatg gcgaatggga  1260
cgcgccctgt agcggcgcat taagcgcggc gggtgtggtg gttacgcgca gcgtgaccgc  1320
tacacttgcc agcgccctag cgcccgctcc tttcgctttc ttcccttcct ttctcgccac  1380
gttcgccggc tttccccgtc aagctctaaa tcggggctc cctttagggt tccgatttag  1440
tgctttacgg cacctcgacc ccaaaaaact tgattagggt gatggttcac gtagtgggcc  1500
atcgccctga tagacggttt ttcgcccttt gacgttggag tccacgttct ttaatagtgg  1560
actcttgttc caaactggaa caacactcaa ccctatctcg gtctattctt tgatttata  1620 agggattttg ccgatttcgg cctattggtt aaaaaatgag ctgatttaac aaaaatttaa  1680
cgcgaatttt aacaaaatat taacgcttac aatttaggtg cacttttcg gggaaatgtg  1740
```

```
cgcggaaccc ctatttgttt attttttctaa atacattcaa atatgtatcc gctcatgaga   1800 caataacccct gataaatgct tcaataatat tgaaaaagga agagtatgag tattcaacat   1860
ttccgtgtcg cccttattcc cttttttgcg gcattttgcc ttcctgtttt tgctcaccca   1920
gaaacgctgg tgaaagtaaa agatgctgaa gatcagttgg gtgcacgagt gggttacatc   1980
gaactggatc tcaacagcgg taagatcctt gagagttttc gccccgaaga acgttttcca   2040
atgatgagca cttttaaagt tctgctatgt ggcgcggtat tatcccgtat tgacgccggg   2100
caagagcaac tcggtcgccg catacactat tctcagaatg acttggttga gtactcacca   2160
gtcacagaaa agcatcttac ggatggcatg acagtaagag aattatgcag tgctgccata   2220
accatgagtg ataacactgc ggccaactta cttctgacaa cgatcggagg accgaaggag   2280
ctaaccgctt ttttgcacaa catgggggat catgtaactc gccttgatcg ttgggaaccg   2340
gagctgaatg aagccatacc aaacgacgag cgtgacacca cgatgcctgt agcaatggca   2400
acaacgttgc gcaaactatt aactggcgaa ctacttactc tagcttcccg gcaacaatta   2460
atagactgga tggaggcgga taaagttgca ggaccacttc tgcgctcggc ccttccggct   2520
ggctggttta ttgctgataa atctggagcc ggtgagcgtg ggtctcgcgg tatcattgca   2580
gcactggggc cagatggtaa gccctcccgt atcgtagtta tctacacgac ggggagtcag   2640
gcaactatgg atgaacgaaa tagacagatc gctgagatag gtgcctcact gattaagcat   2700
tggtaactgt cagaccaagt ttactcatat atactttaga ttgatttaaa acttcatttt   2760
taatttaaaa ggatctaggt gaagatcctt tttgataatc tcatgaccaa aatcccttaa   2820
cgtgagtttt cgttccactg agcgtcagac cccgtagaaa agatcaaagg atcttcttga   2880 gatcctttttt ttctgcgcgt aatctgctgc ttgcaaacaa aaaaaccacc gctaccagcg   2940
gtggtttgtt tgccggatca agagctacca actctttttc cgaaggtaac tggcttcagc   3000
agagcgcaga taccaaatac tgtccttcta gtgtagccgt agttaggcca ccacttcaag   3060
aactctgtag caccgcctac atacctcgct ctgctaatcc tgttaccagt ggctgctgcc   3120
agtggcgata agtcgtgtct taccgggttg gactcaagac gatagttacc ggataaggcg   3180
cagcggtcgg gctgaacggg gggttcgtgc acacagccca gcttggagcg aacgacctac   3240
accgaactga gatacctaca gcgtgagcta tgagaaagcg ccacgcttcc cgaagggaga   3300
aaggcggaca ggtatccggt aagcggcagg gtcggaacag gagagcgcac gagggagctt   3360
ccagggggaa acgcctggta tctttatagt cctgtcgggt ttcgccacct ctgacttgag   3420
cgtcgatttt tgtgatgctc gtcaggggggg cggagcctat ggaaaaacgc cagcaacgcg   3480
gcctttttac ggttcctggc cttttgctgg ccttttgctc acatgttctt tcctgcgtta   3540
tcccctgatt ctgtggataa ccgtattacc gcctttgagt gagctgatac cgctcgccgc   3600
agccgaacga ccgagcgcag cgagtcagtg agcgaggaag cggaagagcg cccaatacgc   3660
aaaccgcctc tccccgcgcg ttggccgatt cattaatgca gctggcacga caggtttccc   3720
gactggaaag cgggcagtga gcgcaacgca attaatgtga gttagctcac tcattaggca   3780
ccccaggctt tacactttat gcttccggct cgtatgttgt gtggaattgt gagcggataa   3840
caatttcaca caggaaacag ctatgaccat gattacgcca agcgcgcaat taaccctcac   3900
taaagggaac aaaagctgga attccacaat gaacaataat aagattaaaa tagcttgccc   3960
ccgttgcagc gatgggtatt ttttctagta aaataaaaga taaacttaga ctcaaaacat   4020
ttacaaaaac aaccccctaaa gtcctaaagc ccaaagtgct atgcacgatc catagcaagc   4080
```

-continued

```
ccagcccaac ccaacccaac ccaacccacc ccagtgcagc caactggcaa atagtctcca    4140 ccccggcac tatcaccgtg agttgtccgc accaccgcac gtctcgcagc caaaaaaaaa    4200
aaaagaaaga aaaaaagaa aaagaaaaac agcaggtggg tccgggtcgt ggggccgga     4260 aaagcgagga ggatcgcgag cagcgacgag gcccggccct ccctccgctt ccaaagaaac   4320 gcccccatc gccactatat acataccccc ccctctcctc ccatccccc aaccctacca    4380 ccaccaccac caccacctcc tcccccctcg ctgccggacg acgagctcct cccccctccc   4440
cctccgccgc cgccggtaac caccccgccc ctctcctctt tctttctccg tttttttttt   4500
cgtctcggtc tcgatctttg gccttggtag tttgggtggg cgagagcggc ttcgtcgccc   4560
agatcggtgc gcgggagggg cgggatctcg cggctggcgt ctccgggcgt gagtcggccc   4620
ggatcctcgc ggggaatggg gctctcggat gtagatcttc tttctttctt cttttgtgg    4680 tagaatttga atccctcagc attgttcatc ggtagttttt cttttcatga tttgtgacaa   4740
atgcagcctc gtgcggagct tttttgtagg tag                                4773

<210> SEQ ID NO 33
<211> LENGTH: 5034
<212> TYPE: DNA
<213> ORGANISM: Artificial Sequence
<220> FEATURE:
<223> OTHER INFORMATION: pJQ5 vector

<400> SEQUENCE: 33
catgggccag gtataattat gggatatctc aagcaaataa tcgaaatatc accattggct     60
acaatatctg agctccgagt tctgactgca gtctggatga cgcgtgttgt atctagaact    120
ctagatagca cagccacagc acctacagga gtgcgacact tgtggactgt agtagtgttg    180
gagacggagc tctttcctac ctcctgacgt tgccgccgtt gtccattcca acggcatcac    240
tctcaaccaa tcacgcgctc ccaacaaaat atcgtccccc atgtcttggc ggagagagag    300
tacatacatg ctgtcgcgcc gttttgtct gaatctcgct tccactggcc aatcagctca     360
gctcccggga gctcactcat tcaagatccc atcgtcgtcg tcaccctgg cgtcatggga    420 tggaaaagaa cctccgttgc tcggatgagt cagccatatc cccgaacaga gtactgcaag    480
ataacccaat tcagattccc ccaatagaga aagtatagca tgctttcggg ttttgtttgg    540
cttaattgac tttatttttg ttggagttga atgctgattt gttgtgtaaa atgcccaacc    600
atctgaatat cgagacggat aataggctgg ctaattaatt tatagcaaga ttctgtagtg    660
cacatcgcaa atatctttct gggcattaca gctggaggct tcatcagcct gaaacactct    720
gcagagcctg aagcaagtgg tgaagcgtgg cgatgagatg ggtataaaac ccccggcacc    780
gggacgcgag ctcccgccta ccagtaccat ctcgcctcgc tccccctgcc ggacgaccca    840
gtaaaatact gttgcccact cgccggcgag atggmcgtgc acaaggaggt saacttcgts   900
gcctacctcc tgatcgtsct cggcctcctc ttgctcgtst ccgccatgga gcacgtggac    960
gccaaggcct gcaccckcga gtgcggcaac ctcggcttcg gcatctgccc ggcggccgcc   1020
tccacgcagg gcatctccga agacctctac agccgtttag tcgaaatggc cactatctcc   1080
caagctgcct acgccgacct gtgcaacatt ccgtcgacta ttatcaaggg agagaaaatt   1140
tacaattctc aaactgacat taacggatgg atcctccgcg acgacagcag caaagaaata   1200
atcaccgtct tccgtggcac tggtagtgat acgaatctac aactcgatac taactacacc   1260
ctcacgcctt tcgacaccct accacaatgc aacggttgtg aagtacacgg tggatattat   1320
attggatggg tctccgtcca ggaccaagtc gagtcgcttg tcaaacagca ggttagccag   1380
```

```
tatccggact acgcgctgac cgtgaccggc cackccctcg gcgcctccct ggcggcactc    1440
actgccgccc agctgtctgc gacatacgac aacatccgcc tgtacacctt cggcgaaccg    1500
cgcagcggca atcaggcctt cgcgtcgtac atgaacgatg ccttccaagc ctcgagccca    1560
gatacgacgc agtatttccg ggtcactcat gccaacgacg gcatcccaaa cctgccccg     1620 gtggagcagg gtacgccca tggcggtgta gagtactgga gcgttgatcc ttacagcgcc    1680
cagaacacat ttgtctgcac tggggatgaa gtgcagtgct gtgaggccca gggcggacag    1740
ggtgtgaata tgcgcacac gacttatttt gggatgacga gcggagcctg tacatggtga    1800
tcagtcattt cagcctcccc gagtgtacca ggaaagatgg atgtcctgga gagggggccg    1860
cgtaaccact gaaggatgag ctgtaaagaa gcagatcgtt caaacatttg caataaagt     1920 ttcttaagat tgaatcctgt tgccggtctt gcgatgatta tcatataatt tctgttgaat    1980
tacgttaagc atgtaataat taacatgtaa tgcatgacgt tatttatgag atgggttttt    2040
atgattagag tcccgcaatt atacatttaa tacgcgatag aaaacaaaat atagcgcgca    2100
aactaggata aattatcgcg cgcggtgtca tctatgttac tagatcgata agcttctaga    2160
gcggccggtg gagctccaat tcgccctata gtgagtcgta ttacgcgcgc tcactggccg    2220
tcgttttaca acgtcgtgac tgggaaaacc ctggcgttac ccaacttaat cgccttgcag    2280
cacatccccc tttcgccagc tggcgtaata gcgaagaggc ccgcaccgat cgcccttccc    2340
aacagttgcg cagcctgaat ggcgaatggg acgcgccctg tagcggcgca ttaagcgcgg    2400
cgggtgtggt ggttacgcgc agcgtgaccg ctacacttgc cagcgcccta gcgcccgctc    2460
ctttcgcttt cttcccttcc tttctcgcca cgttcgccgg ctttccccgt caagctctaa    2520
atcgggggct ccctttaggg ttccgattta gtgctttacg gcacctcgac cccaaaaaac    2580
ttgattaggg tgatggttca cgtagtgggc catcgccctg atagacggtt tttcgccctt    2640
tgacgttgga gtccacgttc tttaatagtg gactcttgtt ccaaactgga acaacactca    2700
accctatctc ggtctattct tttgatttat aagggatttt gccgatttcg gcctattggt    2760
taaaaaatga gctgatttaa caaaaattta acgcgaattt taacaaaata ttaacgctta    2820
caatttaggt ggcacttttc ggggaaatgt gcgcggaacc cctatttgtt tatttttcta    2880
aatacattca aatatgtatc cgctcatgag acaataaccc tgataaatgc ttcaataata    2940
ttgaaaaagg aagagtatga gtattcaaca tttccgtgtc gcccttattc cctttttgc     3000 ggcattttgc cttcctgttt ttgctcaccc agaaacgctg gtgaaagtaa aagatgctga    3060
agatcagttg ggtgcacgag tgggttacat cgaactggat ctcaacagcg gtaagatcct    3120
tgagagtttt cgccccgaag aacgttttcc aatgatgagc acttttaaag ttctgctatg    3180
tggcgcggta ttatcccgta ttgacgccgg gcaagagcaa ctcggtcgcc gcatacacta    3240
ttctcagaat gacttggttg agtactcacc agtcacagaa aagcatctta cggatggcat    3300
gacagtaaga gaattatgca gtgctgccat aaccatgagt gataacactg cggccaactt    3360
acttctgaca acgatcggag gaccgaagga gctaaccgct tttttgcaca acatggggga    3420
tcatgtaact cgccttgatc gttgggaacc ggagctgaat gaagccatac caaacgacga    3480
gcgtgacacc acgatgcctg tagcaatggc aacaacgttg cgcaaactat taactggcga    3540
actacttact ctagcttccc ggcaacaatt aatagactgg atggaggcgg ataaagttgc    3600
aggaccactt ctgcgctcgg cccttccggc tggctggttt attgctgata aatctggagc    3660
cggtgagcgt gggtctcgcg gtatcattgc agcactgggg ccagatggta agccctcccg    3720
```

-continued

```
tatcgtagtt atctacacga cggggagtca ggcaactatg gatgaacgaa atagacagat    3780
cgctgagata ggtgcctcac tgattaagca ttggtaactg tcagaccaag tttactcata    3840
tatactttag attgatttaa aacttcattt ttaatttaaa aggatctagg tgaagatcct    3900
ttttgataat ctcatgacca aaatccctta acgtgagttt cgttccact gagcgtcaga    3960
ccccgtagaa aagatcaaag gatcttcttg agatcctttt tttctgcgcg taatctgctg    4020
cttgcaaaca aaaaaaccac cgctaccagc ggtggtttgt ttgccggatc aagagctacc    4080
aactcttttt ccgaaggtaa ctggcttcag cagagcgcag ataccaaata ctgtccttct    4140
agtgtagccg tagttaggcc accacttcaa gaactctgta gcaccgccta catacctcgc    4200
tctgctaatc ctgttaccag tggctgctgc cagtggcgat aagtcgtgtc ttaccgggtt    4260
ggactcaaga cgatagttac cggataaggc gcagcggtcg ggctgaacgg ggggttcgtg    4320
cacacagccc agcttggagc gaacgaccta caccgaactg agatacctac agcgtgagct    4380
atgagaaagc gccacgcttc ccgaagggag aaaggcggac aggtatccgg taagcggcag    4440
ggtcggaaca ggagagcgca cgagggagct tccaggggga aacgcctggt atctttatag    4500
tcctgtcggg tttcgccacc tctgacttga gcgtcgattt ttgtgatgct cgtcaggggg    4560
gcggagccta tggaaaaacg ccagcaacgc ggccttttta cggttcctgg ccttttgctg    4620
gccttttgct cacatgttct ttcctgcgtt atccccctgat tctgtggata accgtattac    4680
cgcctttgag tgagctgata ccgctcgccg cagccgaacg accgagcgca gcgagtcagt    4740
gagcgaggaa gcggaagagc gcccaatacg caaaccgcct ctccccgcgc gttggccgat    4800
tcattaatgc agctggcacg acaggtttcc cgactggaaa gcgggcagtg agcgcaacgc    4860
aattaatgtg agttagctca ctcattaggc accccaggct ttacacttta tgcttccggc    4920
tcgtatgttg tgtggaattg tgagcggata acaatttcac acaggaaaca gctatgacca    4980
tgattacgcc aagcgcgcaa ttaaccctca ctaaagggaa caaaagctgg gtac           5034
```

<210> SEQ ID NO 34
<211> LENGTH: 4950
<212> TYPE: DNA
<213> ORGANISM: Artificial Sequence
<220> FEATURE:
<223> OTHER INFORMATION: pJO6.1 vector

<400> SEQUENCE: 34

```
aagcttacca tggcccacgc ccgcgtcctc ctcctggcgc tcgccgtgct ggccacggcc      60
gccgtcgccg tcgcctcctc ctcctccttc gccgactcca acccgatccg gcccgtcacc     120
gaccgcgcgg ccgcctccac gcagggcatc tccgaagacc tctacagccg tttagtcgaa     180
atggccacta tctcccaagc tgcctacgcc gacctgtgca acattccgtc gactattatc     240
aagggagaga aaatttacaa ttctcaaact gacattaacg gatggatcct ccgcgacgac     300
agcagcaaag aaataatcac cgtcttccgt ggcactggta gtgatacgaa tctacaactc     360
gatactaact acaccctcac gcctttcgac accctaccac aatgcaacgg ttgtgaagta     420
cacggtggat attatattgg atgggtctcc gtccaggacc aagtcgagtc gcttgtcaaa     480
cagcaggtta gccagtatcc ggactacgcg ctgaccgtga ccggccackc cctcggcgcc     540
tccctggcgg cactcactgc cgcccagctg tctgcgacat acgacaacat ccgcctgtac     600
accttcggcg aaccgcgcag cggcaatcag gccttcgcgt cgtacatgaa cgatgccttc     660
caagcctcga gccagatac gacgcagtat ttccgggtca ctcatgccaa cgacggcatc     720
ccaaacctgc ccccggtgga gcaggggtac gcccatggcg gtgtagagta ctggagcgtt     780
```

-continued

```
gatccttaca gcgcccagaa cacatttgtc tgcactgggg atgaagtgca gtgctgtgag    840
gcccagggcg gacagggtgt gaataatgcg cacacgactt attttgggat gacgagcggc    900
gcatgcacct ggccggtcgc ggccgcggaa accactgaag gatgagctgt aaagaagcag    960
atcgttcaaa catttggcaa taaagtttct taagattgaa tcctgttgcc ggtcttgcga   1020
tgattatcat ataatttctg ttgaattacg ttaagcatgt aataattaac atgtaatgca   1080
tgacgttatt tatgagatgg ttttttatga ttagagtccc gcaattatac atttaatacg   1140
cgatagaaaa caaatatag cgcgcaaact aggataaatt atcgcgcgcg tgtcatcta    1200
tgttactaga tcgataagct tctagagcgg ccggtggagc tccaattcgc cctatagtga   1260
gtcgtattac gcgcgctcac tggccgtcgt tttacaacgt cgtgactggg aaaaccctgg   1320
cgttacccaa cttaatcgcc ttgcagcaca tccccctttc gccagctggc gtaatagcga   1380
agaggcccgc accgatcgcc cttcccaaca gttgcgcagc ctgaatggcg aatgggacgc   1440
gccctgtagc ggcgcattaa gcgcggcggg tgtggtggtt acgcgcagcg tgaccgctac   1500
acttgccagc gccctagcgc ccgctccttt cgctttcttc ccttcctttc tcgccacgtt   1560
cgccggcttt ccccgtcaag ctctaaatcg ggggctccct ttagggttcc gatttagtgc   1620
tttacggcac ctcgacccca aaaaacttga ttagggtgat ggttcacgta gtgggccatc   1680
gccctgatag acggtttttc gccctttgac gttggagtcc acgttcttta atagtggact   1740
cttgttccaa actggaacaa cactcaaccc tatctcggtc tattcttttg atttataagg   1800
gattttgccg atttcggcct attggttaaa aatgagctg atttaacaaa aatttaacgc    1860
gaattttaac aaaatattaa cgcttacaat ttaggtggca cttttcgggg aaatgtgcgc   1920
ggaacccta tttgtttatt tttctaaata cattcaaata tgtatccgct catgagacaa    1980
taaccctgat aaatgcttca ataatattga aaaggaaga gtatgagtat tcaacatttc    2040
cgtgtcgccc ttattcccct tttttgcggca ttttgccttc ctgtttttgc tcacccagaa   2100
acgctggtga agtaaaaga tgctgaagat cagttgggtg cacgagtggg ttacatcgaa    2160
ctggatctca acagcggtaa gatccttgag agttttcgcc ccgaagaacg ttttccaatg   2220
atgagcactt ttaaagttct gctatgtggc gcggtattat cccgtattga cgccgggcaa   2280
gagcaactcg gtcgccgcat acactattct cagaatgact tggttgagta ctcaccagtc   2340
acagaaaagc atcttacgga tggcatgaca gtaagagaat tatgcagtgc tgccataacc   2400
atgagtgata acactgcggc caacttactt ctgacaacga tcggaggacc gaaggagcta   2460
accgcttttt tgcacaacat gggggatcat gtaactcgcc ttgatcgttg ggaaccggag   2520
ctgaatgaag ccataccaaa cgacgagcgt gacaccacga tgcctgtagc aatggcaaca   2580
acgttgcgca aactattaac tggcgaacta cttactctag cttcccggca acaattaata   2640
gactggatgg aggcggataa agttgcagga ccacttctgc gctcggccct tccggctggc   2700
tggtttattg ctgataaatc tggagccggt gagcgtgggt ctcgcggtat cattgcagca   2760
ctggggccag atggtaagcc ctcccgtatc gtagttatct acacgacggg gagtcaggca   2820
actatggatg aacgaaatag acagatcgct gagataggtg cctcactgat taagcattgg   2880
taactgtcag accaagttta ctcatatata ctttagattg atttaaaact tcatttttaa   2940
tttaaaagga tctaggtgaa gatcctttt gataatctca tgaccaaaat cccttaacgt    3000
gagttttcgt tccactgagc gtcagacccc gtagaaaaga tcaaaggatc ttcttgagat   3060
cctttttttc tgcgcgtaat ctgctgcttg caaacaaaaa aaccaccgct accagcggtg   3120
```

```
gtttgtttgc cggatcaaga gctaccaact cttttttccga aggtaactgg cttcagcaga    3180
gcgcagatac caaatactgt ccttctagtg tagccgtagt taggccacca cttcaagaac    3240
tctgtagcac cgcctacata cctcgctctg ctaatcctgt taccagtggc tgctgccagt    3300
ggcgataagt cgtgtcttac cgggttggac tcaagacgat agttaccgga taaggcgcag    3360
cggtcgggct gaacggggg ttcgtgcaca cagcccagct tggagcgaac gacctacacc    3420
gaactgagat acctacagcg tgagctatga gaaagcgcca cgcttcccga agggagaaag    3480
gcggacaggt atccggtaag cggcagggtc ggaacaggag agcgcacgag ggagcttcca    3540
gggggaaacg cctggtatct ttatagtcct gtcgggtttc gccacctctg acttgagcgt    3600
cgattttgt gatgctcgtc agggggcgg agcctatgga aaaacgccag caacgcggcc    3660
ttttttacggt tcctggcctt tgctggcct tttgctcaca tgttctttcc tgcgttatcc    3720
cctgattctg tggataaccg tattaccgcc tttgagtgag ctgataccgc tcgccgcagc    3780
cgaacgaccg agcgcagcga gtcagtgagc gaggaagcgg aagagcgccc aatacgcaaa    3840
ccgcctctcc ccgcgcgttg gccgattcat taatgcagct ggcacgacag gtttcccgac    3900
tggaaagcgg gcagtgagcg caacgcaatt aatgtgagtt agctcactca ttaggcaccc    3960
caggctttac actttatgct tccggctcgt atgttgtgtg gaattgtgag cggataacaa    4020
tttcacacag gaaacagcta tgaccatgat tacgccaagc gcgcaattaa ccctcactaa    4080
agggaacaaa agctggaatt ccacaatgaa caataataag attaaaatag cttgcccccg    4140
ttgcagcgat gggtattttt tctagtaaaa taaaagataa acttagactc aaaacattta    4200
caaaaacaac ccctaaagtc ctaaagccca agtgctatg cacgatccat agcaagccca    4260
gcccaaccca acccaaccca acccacccca gtgcagccaa ctggcaaata gtctccaccc    4320
ccggcactat caccgtgagt tgtccgcacc accgcacgtc tcgcagccaa aaaaaaaaaa    4380
agaaagaaaa aaaagaaaaa gaaaacagc aggtgggtcc gggtcgtggg ggccggaaaa    4440
gcgaggagga tcgcgagcag cgacgaggcc cggccctccc tccgcttcca aagaaacgcc    4500
ccccatcgcc actatataca taccccccc tctcctccca tcccccaac cctaccacca    4560
ccaccaccac cacctcctcc ccctcgctg ccggacgacg agtcctccc ccctcccct    4620
ccgccgccgc cggtaaccac cccgcccctc tcctctttct ttctccgttt tttttttcgt    4680
ctcggtctcg atctttggcc ttggtagttt gggtgggcga gagcggcttc gtcgcccaga    4740
tcggtgcgcg ggaggggcgg gatctcgcgg ctggcgtctc cgggcgtgag tcggcccgga    4800
tcctcgcggg gaatggggct ctcggatgta gatcttcttt cttctttctt tttgtggtag    4860
aatttgaatc cctcagcatt gttcatcggt agttttctt ttcatgattt gtgacaaatg    4920
cagcctcgtg cggagctttt ttgtaggtag                                     4950
```

<210> SEQ ID NO 35
<211> LENGTH: 4974
<212> TYPE: DNA
<213> ORGANISM: Artificial Sequence
<220> FEATURE:
<223> OTHER INFORMATION: pJQ4 vector

<400> SEQUENCE: 35

```
aattccacaa tgaacaataa taagattaaa atagcttgcc cccgttgcag cgatgggtat       60
ttttctagt aaaataaaag ataaacttag actcaaaaca tttacaaaaa caaccctaa      120
agtcctaaag cccaaagtgc tatgcacgat ccatagcaag cccagcccaa cccaacccaa     180
cccaacccac cccagtgcag ccaactggca aatagtctcc accccggca ctatcaccgt      240
```

```
gagttgtccg caccaccgca cgtctcgcag ccaaaaaaaa aaaagaaag aaaaaaaga      300
aaagaaaaa  cagcaggtgg gtccgggtcg tgggggccgg aaaagcgagg aggatcgcga    360
gcagcgacga ggcccggccc tccctccgct tccaaagaaa cgcccccat cgccactata    420
tacataccc  cccctctcct cccatccccc caaccctacc accaccacca ccaccacctc    480
ctccccctc  gctgccggac gacgagctcc tcccccctcc cctccgccg ccgccggtaa    540
ccacccgcc  cctctcctct ttctttctcc gttttttttt tcgtctcggt ctcgatcttt    600
ggccttggta gtttgggtgg gcgagagcgg cttcgtcgcc cagatcggtg cgcgggaggg    660
gcgggatctc gcggctggcg tctccgggcg tgagtcggcc cggatcctcg cggggaatgg    720
ggctctcgga tgtagatctt ctttctttct tcttttgtg gtagaatttg aatccctcag    780
cattgttcat cggtagtttt tcttttcatg atttgtgaca aatgcagcct cgtgcggagc    840
tttttttgtag gtagaagctt acmatggmcg tgcacaagga ggtsaacttc gtsgcctacc    900
tcctgatcgt sctcggcctc ctcttgctcg tstccgccat ggagcacgtg gacgccaagg    960
cctgcacck cgagtgcggc aacctcggct tcggcatctg cccggcggcc gcctccacgc   1020
agggcatctc cgaagacctc tacagccgtt tagtcgaaat ggccactatc tcccaagctg   1080
cctacgccga cctgtgcaac attccgtcga ctattatcaa gggagagaaa atttacaatt   1140
ctcaaactga cattaacgga tggatcctcc gcgacgacag cagcaaagaa ataatcaccg   1200
tcttccgtgg cactggtagt gatacgaatc tacaactcga tactaactac acctcacgc    1260
ctttcgacac cctaccacaa tgcaacggtt gtgaagtaca cggtggatat tatattggat   1320
gggtctccgt ccaggaccaa gtcgagtcgc ttgtcaaaca gcaggttagc cagtatccgg   1380
actacgcgct gaccgtgacc ggccackccc tcggcgcctc cctggcggca ctcactgccg   1440
cccagctgtc tgcgacatac gacaacatcc ggctgtacac cttcggcgaa ccgcgcagcg   1500
gcaatcaggc cttcgcgtcg tacatgaacg atgccttcca agcctcgagc ccagatacga   1560
cgcagtattt ccgggtcact catgccaacg acggcatccc aaacctgccc ccggtggagc   1620
agggtacgc  ccatggcggt gtagagtact ggagcgttga tccttacagc gcccagaaca   1680
catttgtctg cactggggat gaagtgcagt gctgtgaggc ccagggcgga cagggtgtga   1740
ataatgcgca cacgacttat tttgggatga cgagcggcgc atgcacctgg ccggtcgcgg   1800
ccgcggaaac cactgaagga tgagctgtaa agaagcagat cgttcaaaca tttggcaata   1860
aagtttctta agattgaatc ctgttgccgg tcttgcgatg attatcatat aatttctgtt   1920
gaattacgtt aagcatgtaa taattaacat gtaatgcatg acgttattta tgagatgggt   1980
ttttatgatt agagtcccgc aattatacat ttaatacgcg atagaaaaca aaatatagcg   2040
cgcaaactag gataaattat cgcgcgcggt gtcatctatg ttactagatc gataagcttc   2100
tagagcggcc ggtggagctc caattcgccc tatagtgagt cgtattacgc gcgctcactg   2160
gccgtcgttt tacaacgtcg tgactgggaa accctggcg ttacccaact taatcgcctt    2220
gcagcacatc cccctttcgc cagctggcgt aatagcgaag aggcccgcac cgatcgccct   2280
tcccaacagt tgcgcagcct gaatggcgaa tgggacgcgc cctgtagcgg cgcattaagc   2340
gcggcgggtg tggtggttac gcgcagcgtg accgctacac ttgccagcgc cctagcgccc   2400
gctcctttcg ctttcttccc ttcctttctc gccacgttcg ccggctttcc ccgtcaagct   2460
ctaaatcggg ggctcccttt agggttccga tttagtgctt tacggcacct cgaccccaaa   2520
aaacttgatt agggtgatgg ttcacgtagt gggccatcgc cctgatagac ggttttcgc    2580
```

```
cctttgacgt tggagtccac gttctttaat agtggactct tgttccaaac tggaacaaca    2640
ctcaaccct a tctcggtcta ttcttttgat ttataaggga ttttgccgat ttcggcctat   2700
tggttaaaaa atgagctgat ttaacaaaaa tttaacgcga attttaacaa aatattaacg    2760
cttacaattt aggtggcact tttcggggaa atgtgcgcgg aaccccctatt tgtttatttt   2820
tctaaataca ttcaaatatg tatccgctca tgagacaata accctgataa atgcttcaat   2880
aatattgaaa aaggaagagt atgagtattc aacatttccg tgtcgccctt attcccttt t  2940
ttgcggcatt ttgccttcct gttttt gctc acccagaaac gctggtgaaa gtaaaagatg   3000
ctgaagatca gttgggtgca cgagtgggtt acatcgaact ggatctcaac agcggtaaga   3060
tccttgagag ttttcgcccc gaagaacgtt ttccaatgat gagcactttt aaagttctgc    3120
tatgtggcgc ggtattatcc cgtattgacg ccgggcaaga gcaactcggt cgccgcatac    3180
actattctca gaatgacttg gttgagtact caccagtcac agaaaagcat cttacggatg    3240
gcatgacagt aagagaatta tgcagtgctg ccataaccat gagtgataac actgcggcca   3300
acttacttct gacaacgatc ggaggaccga aggagctaac cgcttttttg cacaacatgg    3360
gggatcatgt aactcgcctt gatcgttggg aaccggagct gaatgaagcc ataccaaacg    3420
acgagcgtga caccacgatg cctgtagcaa tggcaacaac gttgcgcaaa ctattaactg    3480
gcgaactact tactctagct tcccggcaac aattaataga ctggatggag gcggataaag    3540
ttgcaggacc acttctgcgc tcggcccttc cggctggctg gtttattgct gataaatctg    3600
gagccggtga gcgtgggtct cgcggtatca ttgcagcact ggggccagat ggtaagccct    3660
cccgtatcgt agttatctac acgacgggga gtcaggcaac tatggatgaa cgaaatagac    3720
agatcgctga gataggtgcc tcactgatta agcattggta actgtcagac caagtttact    3780
catatatact ttagattgat ttaaaacttc atttttaatt taaaaggatc taggtgaaga    3840
tcctttttga taatctcatg accaaaatcc cttaacgtga gttttcgttc cactgagcgt    3900
cagaccccgt agaaaagatc aaaggatctt cttgagatcc ttttttttctg cgcgtaatct   3960
gctgcttgca acaaaaaaa ccaccgctac cagcggtggt ttgtttgccg gatcaagagc     4020
taccaactct ttttccgaag gtaactggct tcagcagagc gcagatacca aatactgtcc    4080
ttctagtgta gccgtagtta ggccaccact tcaagaactc tgtagcaccg cctacatacc    4140
tcgctctgct aatcctgtta ccagtggctg ctgccagtgg cgataagtcg tgtcttaccg    4200
ggttggactc aagacgatag ttaccggata aggcgcagcg gtcgggctga acggggggtt    4260
cgtgcacaca gcccagcttg gagcgaacga cctacaccga actgagatac ctacagcgtg    4320
agctatgaga aagcgccacg cttcccgaag gagaaaggc ggacaggtat ccggtaagcg     4380
gcagggtcgg aacaggagag cgcacgaggg agcttccagg gggaaacgcc tggtatcttt    4440
atagtcctgt cgggtttcgc cacctctgac ttgagcgtcg attttt gtga tgctcgtcag   4500
gggggcggag cctatggaaa aacgccagca acgcggcctt tttacggttc ctggcctttt    4560
gctggccttt tgctcacatg ttctttcctg cgttatcccc tgattctgtg ataaccgta    4620
ttaccgcctt tgagtgagct gataccgctc gccgcagccg aacgaccgag cgcagcgagt    4680
cagtgagcga ggaagcggaa gagcgcccaa tacgcaaacc gcctctcccc gcgcgttggc    4740
cgattcatta atgcagctgg cacgacaggt ttcccgactg gaaagcgggc agtgagcgca    4800
acgcaattaa tgtgagttag ctcactcatt aggcacccca ggctttacac tttatgcttc    4860
cggctcgtat gttgtgtgga attgtgagcg ataacaatt tcacacagga aacagctatg    4920
accatgatta cgccaagcgc gcaattaacc ctcactaaag ggaacaaaag ctgg           4974
```

<210> SEQ ID NO 36
<211> LENGTH: 5164
<212> TYPE: DNA
<213> ORGANISM: Artificial Sequence
<220> FEATURE:
<223> OTHER INFORMATION: pPQ10.1 vector

<400> SEQUENCE: 36

```
aagcttacca tggtgagcaa gggcgaggag ctgttcaccg ggtggtgcc catcctggtc      60
gagctggacg gcgacgtgaa cggccacaag ttcagcgtgt ccggcgaggg cgagggcgat    120
gccacctacg gcaagctgac cctgaagttc atctgcacca ccggcaagct gcccgtgccc    180
tggcccaccc tcgtgaccac cttcacctac ggcgtgcagt gcttcagccg ctaccccgac    240
cacatgaagc agcacgactt cttcaagtcc gccatgcccg aaggctacgt ccaggagcgc    300
accatcttct tcaaggacga cggcaactac aagacccgcg ccgaggtgaa gttcgagggc    360
gacaccctgg tgaaccgcat cgagctgaag ggcatcgact tcaaggagga cggcaacatc    420
ctggggcaca gctggagta caactacaac agccacaacg tctatatcat ggccgacaag    480
cagaagaacg gcatcaaggt gaacttcaag atccgccaca acatcgagga cggcagcgtg    540
cagctcgccg accactacca gcagaacacc cccatcggcg acggccccgt gctgctgccc    600
gacaaccact acctgagcac ccagtccgcc ctgagcaaag accccaacga gaagcgcgat    660
cacatggtcc tgctggagtt cgtgaccgcc gccgggatca ctcacggcat ggacgagctg    720
tacaagtaaa gcggccgccc gggctgcagg gaaaccactg aaggatgagc tgtaaagaag    780
cagatcgttc aaacatttgg caataaagtt tcttaagatt gaatcctgtt gccggtcttg    840
cgatgattat catataattt ctgttgaatt acgttaagca tgtaataatt aacatgtaat    900
gcatgacgtt atttatgaga tgggttttta tgattagagt cccgcaatta tacatttaat    960
acgcgataga aaacaaaata tagcgcgcaa actaggataa attatcgcgc gcggtgtcat   1020
ctatgttact agatcgataa gcttctagag cggccggtgg agctccaatt cgccctatag   1080
tgagtcgtat tacgcgcgct cactggccgt cgttttacaa cgtcgtgact gggaaaaccc   1140
tggcgttacc caacttaatc gccttgcagc acatccccct ttcgccagct ggcgtaatag   1200
cgaagaggcc cgcaccgatc gcccttccca acagttgcgc agcctgaatg gcgaatggga   1260
cgcgccctgt agcggcgcat taagcgcggc gggtgtggtg gttacgcgca gcgtgaccgc   1320
tacacttgcc agcgccctag cgcccgctcc tttcgctttc ttcccttcct ttctcgccac   1380
gttcgccggc tttccccgtc aagctctaaa tcggggctc cctttagggt tccgatttag   1440
tgctttacgg cacctcgacc ccaaaaaact tgattaggt gatggttcac gtagtgggcc   1500
atcgccctga tagacggttt ttcgcccttt gacgttggag tccacgttct ttaatagtgg   1560
actcttgttc caaactggaa caacactcaa ccctatctcg gtctattctt ttgatttata   1620
agggattttg ccgatttcgg cctattggtt aaaaaatgag ctgatttaac aaaaatttaa   1680
cgcgaatttt aacaaaatat taacgcttac aatttaggtg cacttttcg gggaaatgtg   1740
cgcggaaccc ctatttgttt attttttctaa atacattcaa atatgtatcc gctcatgaga   1800
caataaccct gataaatgct tcaataatat tgaaaaagga agagtatgag tattcaacat   1860
ttccgtgtcg cccttattcc cttttttgcg cattttgcc ttcctgtttt tgctcaccca   1920
gaaacgctgg tgaaagtaaa agatgctgaa gatcagttgg gtgcacgagt gggttacatc   1980
gaactggatc tcaacagcgg taagatcctt gagagttttc gccccgaaga acgttttcca   2040
```

```
atgatgagca cttttaaagt tctgctatgt ggcgcggtat tatcccgtat tgacgccggg    2100
caagagcaac tcggtcgccg catacactat tctcagaatg acttggttga gtactcacca    2160
gtcacagaaa agcatcttac ggatggcatg acagtaagag aattatgcag tgctgccata    2220
accatgagtg ataacactgc ggccaactta cttctgacaa cgatcggagg accgaaggag    2280
ctaaccgctt ttttgcacaa catgggggat catgtaactc gccttgatcg ttgggaaccg    2340
gagctgaatg aagccatacc aaacgacgag cgtgacacca cgatgcctgt agcaatggca    2400
acaacgttgc gcaaactatt aactggcgaa ctacttactc tagcttcccg gcaacaatta    2460
atagactgga tggaggcgga taaagttgca ggaccacttc tgcgctcggc ccttccggct    2520
ggctggttta ttgctgataa atctggagcc ggtgagcgtg ggtctcgcgg tatcattgca    2580
gcactggggc cagatggtaa gccctcccgt atcgtagtta tctacacgac ggggagtcag    2640
gcaactatgg atgaacgaaa tagacagatc gctgagatag gtgcctcact gattaagcat    2700
tggtaactgt cagaccaagt ttactcatat atactttaga ttgatttaaa acttcatttt    2760
taatttaaaa ggatctaggt gaagatcctt tttgataatc tcatgaccaa aatcccttaa    2820
cgtgagtttt cgttccactg agcgtcagac cccgtagaaa agatcaaagg atcttcttga    2880
gatccttttt ttctgcgcgt aatctgctgc ttgcaaacaa aaaaaccacc gctaccagcg    2940
gtggtttgtt tgccggatca agagctacca actcttttcc gaaggtaac tggcttcagc    3000 agagcgcaga taccaaatac tgtccttcta gtgtagccgt agttaggcca ccacttcaag    3060
aactctgtag caccgcctac atacctcgct ctgctaatcc tgttaccagt ggctgctgcc    3120
agtggcgata agtcgtgtct taccgggttg gactcaagac gatagttacc ggataaggcg    3180
cagcggtcgg gctgaacggg gggttcgtgc acacagccca gcttggagcg aacgacctac    3240
accgaactga gatacctaca gcgtgagcta tgagaaagcg ccacgcttcc cgaagggaga    3300
aaggcggaca ggtatccggt aagcggcagg gtcggaacag gagagcgcac gagggagctt    3360
ccagggggaa acgcctggta tctttatagt cctgtcgggt ttcgccacct ctgacttgag    3420
cgtcgatttt tgtgatgctc gtcagggggg cggagcctat ggaaaaacgc cagcaacgcg    3480
gcctttttac ggttcctggc cttttgctgg ccttttgctc acatgttctt tcctgcgtta    3540
tcccctgatt ctgtggataa ccgtattacc gcctttgagt gagctgatac cgctcgccgc    3600
agccgaacga ccgagcgcag cgagtcagtg agcgaggaag cggaagagcg cccaatacgc    3660
aaaccgcctc tccccgcgcg ttggccgatt cattaatgca gctggcacga caggtttccc    3720
gactggaaag cgggcagtga gcgcaacgca attaatgtga gttagctcac tcattaggca    3780
ccccaggctt tacactttat gcttccggct cgtatgttgt gtggaattgt gagcggataa    3840
caatttcaca caggaaacag ctatgaccat gattacgcca agcgcgcaat taaccctcac    3900
taaagggaac aaaagctggg taccgggccc cccctcgagg tcattcatat gcttgagaag    3960
agagtcggga tagtccaaaa taaaacaaag gtaagattac tggtcaaaa gtgaaaacat    4020 cagttaaaag gtggtataag taaaatatcg gtaataaaag gtgcccaaa gtgaaattta    4080 ctcttttcta ctattataaa aattgaggat gttttgtcgg tactttgata cgtcattttt    4140
gtatgaattg gttttaagt ttattcgcga tttggaaatg catatctgta tttgagtcgg    4200
tttttaagtt cgttgctttt gtaaatacag agggatttgt ataagaaata tctttaaaaa    4260
acccatatgc taatttgaca taattttttga gaaaaatata tattcaggcg aattccacaa    4320
tgaacaataa taagattaaa atagcttgcc cccgttgcag cgatgggtat ttttttctagt    4380 aaaataaaag ataaacttag actcaaaaca tttacaaaaa caaccccctaa agtcctaaag    4440
```

-continued

| | |
|---|---|
| cccaaagtgc tatgcacgat ccatagcaag cccagcccaa cccaacccaa cccaacccac | 4500 |
| cccagtgcag ccaactggca aatagtctcc accccggca ctatcaccgt gagttgtccg | 4560 |
| caccaccgca cgtctcgcag ccaaaaaaaa aaaagaaaag aaaaaaaaga aaaagaaaaa | 4620 |
| cagcaggtgg gtccgggtcg tgggggccgg aaaagcgagg aggatcgcga gcagcgacga | 4680 |
| ggcccggccc tccctccgct tccaaagaaa cgccccccat cgccactata tacataccccc | 4740 |
| ccctctcct cccatccccc caaccctacc accaccacca ccaccacctc ctcccccctc | 4800 |
| gctgccggac gacgagctcc tccccctcc cctccgccg ccgccggtaa ccaccccgcc | 4860 |
| cctctcctct ttctttctcc gtttttttt tcgtctcggt ctcgatcttt ggccttggta | 4920 |
| gtttgggtgg gcgagagcgg cttcgtcgcc cagatcggtg cgcgggaggg gcgggatctc | 4980 |
| gcggctggcg tctccgggcg tgagtcggcc cggatcctcg cggggaatgg ggctctcgga | 5040 |
| tgtagatctt ctttctttct tcttttttgtg gtagaatttg aatccctcag cattgttcat | 5100 |
| cggtagtttt tcttttcatg atttgtgaca aatgcagcct cgtgcggagc ttttttgtag | 5160 |
| gtag | 5164 |

<210> SEQ ID NO 37
<211> LENGTH: 4965
<212> TYPE: DNA
<213> ORGANISM: Artificial Sequence
<220> FEATURE:
<223> OTHER INFORMATION: pJQ3 vector

<400> SEQUENCE: 37

| | |
|---|---|
| aattccacaa tgaacaataa taagattaaa atagcttgcc cccgttgcag cgatgggtat | 60 |
| tttttctagt aaaataaaag ataaacttag actcaaaaca tttacaaaaa caaccccctaa | 120 |
| agtcctaaag cccaaagtgc tatgcacgat ccatagcaag cccagcccaa cccaacccaa | 180 |
| cccaacccac cccagtgcag ccaactggca aatagtctcc accccggca ctatcaccgt | 240 |
| gagttgtccg caccaccgca cgtctcgcag ccaaaaaaaa aaaagaaaag aaaaaaaaga | 300 |
| aaaagaaaaa cagcaggtgg gtccgggtcg tgggggccgg aaaagcgagg aggatcgcga | 360 |
| gcagcgacga ggcccggccc tccctccgct tccaaagaaa cgccccccat cgccactata | 420 |
| tacataccccc ccctctcct cccatccccc caaccctacc accaccacca ccaccacctc | 480 |
| ctcccccctc gctgccggac gacgagctcc tccccctcc cctccgccg ccgccggtaa | 540 |
| ccaccccgcc cctctcctct ttctttctcc gtttttttt tcgtctcggt ctcgatcttt | 600 |
| ggccttggta gtttgggtgg gcgagagcgg cttcgtcgcc cagatcggtg cgcgggaggg | 660 |
| gcgggatctc gcggctggcg tctccgggcg tgagtcggcc cggatcctcg cggggaatgg | 720 |
| ggctctcgga tgtagatctt ctttctttct tcttttttgtg gtagaatttg aatccctcag | 780 |
| cattgttcat cggtagtttt tcttttcatg atttgtgaca aatgcagcct cgtgcggagc | 840 |
| ttttttgtag gtagaagctt accatgatcc acaccaacct caaaagaag ttctccctct | 900 |
| tcatcctcgt cttcctcctc ttcgccgtga tctgcgtgtg gaagaagggc tccgactacg | 960 |
| aggccctcac cctccaagcc aaggagttcc aaatggcggc cgcctccacg cagggcatct | 1020 |
| ccgaagacct ctacagccgt ttagtcgaaa tggccactat ctcccaagct gcctacgccg | 1080 |
| acctgtgcaa cattccgtcg actattatca agggagagaa aatttacaat tctcaaactg | 1140 |
| acattaacgg atggatcctc cgcgacgaca gcagcaaaga aataatcacc gtcttccgtg | 1200 |
| gcactggtag tgatacgaat ctacaactcg atactaacta caccctcacg cctttcgaca | 1260 |

```
ccctaccaca atgcaacggt tgtgaagtac acggtggata ttatattgga tgggtctccg   1320
tccaggacca agtcgagtcg cttgtcaaac agcaggttag ccagtatccg gactacgcgc   1380
tgaccgtgac cggccackcc ctcggcgcct ccctggcggc actcactgcc gcccagctgt   1440
ctgcgacata cgacaacatc cgcctgtaca ccttcggcga accgcgcagc ggcaatcagg   1500
ccttcgcgtc gtacatgaac gatgccttcc aagcctcgag cccagatacg acgcagtatt   1560
tccgggtcac tcatgccaac gacggcatcc caaacctgcc cccggtggag caggggtacg   1620
cccatggcgg tgtagagtac tggagcgttg atccttacag cgcccagaac acatttgtct   1680
gcactgggga tgaagtgcag tgctgtgagg cccagggcgg acagggtgtg aataatgcgc   1740
acacgactta ttttgggatg acgagcggcg catgcacctg gccggtcgcg gccgcggaaa   1800
ccactgaagg atgagctgta aagaagcaga tcgttcaaac atttggcaat aaagtttctt   1860
aagattgaat cctgttgccg gtcttgcgat gattatcata taatttctgt tgaattacgt   1920
taagcatgta ataattaaca tgtaatgcat gacgttattt atgagatggg tttttatgat   1980
tagagtcccg caattataca tttaatacgc gatagaaaac aaaatatagc gcgcaaacta   2040
ggataaatta tcgcgcgcgg tgtcatctat gttactagat cgataagctt ctagagcggc   2100
cggtggagct ccaattcgcc ctatagtgag tcgtattacg cgcgctcact ggccgtcgtt   2160
ttacaacgtc gtgactggga aaaccctggc gttacccaac ttaatcgcct tgcagcacat   2220
cccccttttcg ccagctggcg taatagcgaa gaggcccgca ccgatcgccc ttcccaacag   2280
ttgcgcagcc tgaatggcga atgggacgcg ccctgtagcg cgcattaag cgcggcgggt   2340
gtggtggtta cgcgcagcgt gaccgctaca cttgccagcg ccctagcgcc cgctcctttc   2400
gctttcttcc cttcctttct cgccacgttc gccggctttc cccgtcaagc tctaaatcgg   2460
gggctcccctt tagggttccg atttagtgct ttacggcacc tcgaccccaa aaaacttgat   2520
tagggtgatg gttcacgtag tgggccatcg ccctgataga cggtttttcg ccctttgacg   2580
ttggagtcca cgttctttaa tagtggactc ttgttccaaa ctggaacaac actcaaccct   2640
atctcggtct attcttttga tttataaggg attttgccga tttcggccta ttggttaaaa   2700
aatgagctga tttaacaaaa atttaacgcg aattttaaca aaatattaac gcttacaatt   2760
taggtggcac ttttcgggga aatgtgcgcg gaacccctat ttgtttattt ttctaaatac   2820
attcaaatat gtatccgctc atgagacaat aaccctgata aatgcttcaa taatattgaa   2880
aaaggaagag tatgagtatt caacatttcc gtgtcgccct tattcccttt tttgcggcat   2940
tttgccttcc tgtttttgct cacccagaaa cgctggtgaa agtaaaagat gctgaagatc   3000
agttgggtgc acgagtgggt tacatcgaac tggatctcaa cagcggtaag atccttgaga   3060
gttttcgccc cgaagaacgt tttccaatga tgagcacttt taaagttctg ctatgtggcg   3120
cggtattatc ccgtattgac gccgggcaag agcaactcgg tcgccgcata cactattctc   3180
agaatgactt ggttgagtac tcaccagtca cagaaaagca tcttacggat ggcatgacag   3240
taagagaatt atgcagtgct gccataacca tgagtgataa cactgcggcc aacttacttc   3300
tgacaacgat cggaggaccg aaggagctaa ccgcttttt gcacaacatg ggggatcatg   3360
taactcgcct tgatcgttgg aaccggagc tgaatgaagc cataccaaac gacgagcgtg   3420
acaccacgat gcctgtagca atggcaacaa cgttgcgcaa actattaact ggcgaactac   3480
ttactctagc ttcccggcaa caattaatag actggatgga ggcggataaa gttgcaggac   3540
cacttctgcg ctcggccctt ccggctggct ggtttattgc tgataaatct ggagccggtg   3600
agcgtgggtc tcgcggtatc attgcagcac tggggccaga tggtaagccc tcccgtatcg   3660
```

```
tagttatcta cacgacgggg agtcaggcaa ctatggatga acgaaataga cagatcgctg    3720
agataggtgc ctcactgatt aagcattggt aactgtcaga ccaagtttac tcatatatac    3780
tttagattga tttaaaactt cattttaat ttaaaaggat ctaggtgaag atccttttg    3840 ataatctcat gaccaaaatc ccttaacgtg agttttcgtt ccactgagcg tcagaccccg    3900
tagaaaagat caaaggatct tcttgagatc cttttttct gcgcgtaatc tgctgcttgc    3960
aaacaaaaaa accaccgcta ccagcggtgg tttgtttgcc ggatcaagag ctaccaactc    4020
tttttccgaa ggtaactggc ttcagcagag cgcagatacc aaatactgtc cttctagtgt    4080
agccgtagtt aggccaccac ttcaagaact ctgtagcacc gcctacatac ctcgctctgc    4140
taatcctgtt accagtggct gctgccagtg gcgataagtc gtgtcttacc gggttggact    4200
caagacgata gttaccggat aaggcgcagc ggtcgggctg aacggggggt tcgtgcacac    4260
agcccagctt ggagcgaacg acctacaccg aactgagata cctacagcgt gagctatgag    4320
aaagcgccac gcttcccgaa gggagaaagg cggacaggta tccggtaagc ggcagggtcg    4380
gaacaggaga gcgcacgagg gagcttccag ggggaaacgc ctggtatctt tatagtcctg    4440
tcgggtttcg ccacctctga cttgagcgtc gatttttgtg atgctcgtca gggggcgga    4500 gcctatggaa aaacgccagc aacgcggcct ttttacggtt cctggccttt tgctggcctt    4560
ttgctcacat gttctttcct gcgttatccc ctgattctgt ggataaccgt attaccgcct    4620
ttgagtgagc tgataccgct cgccgcagcc gaacgaccga gcgcagcgag tcagtgagcg    4680
aggaagcgga agagcgccca atacgcaaac cgcctctccc cgcgcgttgg ccgattcatt    4740
aatgcagctg gcacgacagg tttcccgact ggaaagcggg cagtgagcgc aacgcaatta    4800
atgtgagtta gctcactcat taggcacccc aggctttaca ctttatgctt ccggctcgta    4860
tgttgtgtgg aattgtgagc ggataacaat ttcacacagg aaacagctat gaccatgatt    4920
acgccaagcg cgcaattaac cctcactaaa gggaacaaaa gctgg                     4965
```

<210> SEQ ID NO 38
<211> LENGTH: 5295
<212> TYPE: DNA
<213> ORGANISM: Artificial Sequence
<220> FEATURE:
<223> OTHER INFORMATION: pUG4 vector

<400> SEQUENCE: 38

```
aagcttacca tggcccacgc ccgcgtcctc ctcctggcgc tcgccgtgct ggccacggcc      60
gccgtcgccg tcgcctcctc ccgcgcggcc gcctccacgc agggcatctc cgaagacctc     120
tacagccgtt tagtcgaaat ggccactatc tcccaagctg cctacgccga cctgtgcaac     180
attccgtcga ctattatcaa gggagagaaa atttacaatt ctcaaactga cattaacgga     240
tggatcctcc gcgacgacag cagcaaagaa ataatcaccg tcttccgtgg cactggtagt     300
gatacgaatc tacaactcga tactaactac accctcacgc ctttcgacac cctaccacaa     360
tgcaacggtt gtgaagtaca cggtggatat tatattggat gggtctccgt ccaggaccaa     420
gtcgagtcgc ttgtcaaaca gcaggttagc cagtatccgg actacgcgct gaccgtgacc     480
ggccackccc tcggcgcctc cctggcggca ctcactgccg cccagctgtc tgcgacatac     540
gacaacatcc gcctgtacac cttcggcgaa ccgcgcagcg gcaatcaggc cttcgcgtcg     600
tacatgaacg atgccttcca agcctcgagc ccagatacga cgcagtattt ccgggtcact     660
catgccaacg acggcatccc aaacctgccc ccggtggagc aggggtacgc ccatggcggt     720
```

```
gtagagtact ggagcgttga tccttacagc gcccagaaca catttgtctg cactggggat    780
gaagtgcagt gctgtgaggc ccagggcgga cagggtgtga ataatgcgca cacgacttat    840
tttgggatga cgagcggcgc atgcacctgg ccggtcgcgg ccgcggaacc actgaaggat    900
gagctgtaaa gaagcagatc gttcaaacat ttggcaataa agtttcttaa gattgaatcc    960
tgttgccggt cttgcgatga ttatcatata atttctgttg aattacgtta agcatgtaat   1020
aattaacatg taatgcatga cgttatttat gagatgggtt tttatgatta gagtcccgca   1080
attatacatt taatacgcga tagaaaacaa aatatagcgc gcaaactagg ataaattatc   1140
gcgcgcggtg tcatctatgt tactagatcg ataagcttct agagcggccg gtggagctcc   1200
aattcgccct atagtgagtc gtattacgcg cgctcactgg ccgtcgtttt acaacgtcgt   1260
gactgggaaa accctggcgt tacccaactt aatcgccttg cagcacatcc cccttccgcc   1320
agctggcgta atagcgaaga ggcccgcacc gatcgccctt cccaacagtt gcgcagcctg   1380
aatggcgaat gggacgcgcc ctgtagcggc gcattaagcg cggcgggtgt ggtggttacg   1440
cgcagcgtga ccgctacact tgccagcgcc ctagcgcccg ctcctttcgc tttcttccct   1500
tcctttctcg ccacgttcgc cggctttccc cgtcaagctc taaatcgggg gctccctta   1560
gggttccgat ttagtgcttt acggcacctc gaccccaaaa aacttgatta gggtgatggt   1620
tcacgtagtg ggccatcgcc ctgatagacg gttttcgcc ctttgacgtt ggagtccacg   1680
ttctttaata gtggactctt gttccaaact ggaacaacac tcaaccctat ctcggtctat   1740
tcttttgatt tataagggat tttgccgatt tcggcctatt ggttaaaaaa tgagctgatt   1800
taacaaaaat ttaacgcgaa ttttaacaaa atattaacgc ttacaattta ggtggcactt   1860
ttcggggaaa tgtgcgcgga acccctattt gtttattttt ctaaatacat tcaaatatgt   1920
atccgctcat gagacaataa ccctgataaa tgcttcaata atattgaaaa aggaagagta   1980
tgagtattca acatttccgt gtcgccctta ttccctttttt tgcggcattt tgccttcctg   2040
ttttgctca cccagaaacg ctggtgaaag taaaagatgc tgaagatcag ttgggtgcac   2100
gagtgggtta catcgaactg gatctcaaca gcggtaagat ccttgagagt tttcgccccg   2160
aagaacgttt tccaatgatg agcactttta agttctgct atgtggcgcg gtattatccc   2220
gtattgacgc cgggcaagag caactcggtc gccgcataca ctattctcag aatgacttgg   2280
ttgagtactc accagtcaca gaaaagcatc ttacggatgg catgacagta agagaattat   2340
gcagtgctgc cataaccatg agtgataaca ctgcggccaa cttacttctg acaacgatcg   2400
gaggaccgaa ggagctaacc gcttttttgc acaacatggg ggatcatgta actcgccttg   2460
atcgttggga accggagctg aatgaagcca taccaaacga cgagcgtgac accacgatgc   2520
ctgtagcaat ggcaacaacg ttgcgcaaac tattaactgg cgaactactt actctagctt   2580
cccggcaaca attaatagac tggatggagg cggataaagt tgcaggacca cttctgcgct   2640
cggcccttcc ggctggctgg tttattgctg ataaatctgg agccggtgag cgtgggtctc   2700
gcggtatcat tgcagcactg gggccagatg gtaagccctc ccgtatcgta gttatctaca   2760
cgacggggag tcaggcaact atggatgaac gaaatagaca gatcgctgag ataggtgcct   2820
cactgattaa gcattggtaa ctgtcagacc aagtttactc atatatactt tagattgatt   2880
taaaacttca ttttttaattt aaaaggatct aggtgaagat ccttttttgat aatctcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
```

-continued

```
taactggctt cagcagagcg cagataccaa atactgtcct tctagtgtag ccgtagttag      3180
gccaccactt caagaactct gtagcaccgc ctacatacct cgctctgcta atcctgttac      3240
cagtggctgc tgccagtggc gataagtcgt gtcttaccgg gttggactca agacgatagt      3300
taccggataa ggcgcagcgg tcgggctgaa cgggggggttc gtgcacacag cccagcttgg     3360
agcgaacgac ctacaccgaa ctgagatacc tacagcgtga gctatgagaa agcgccacgc      3420
ttcccgaagg gagaaaggcg gacaggtatc cggtaagcgg cagggtcgga acaggagagc      3480
gcacgaggga gcttccaggg ggaaacgcct ggtatcttta tagtcctgtc gggtttcgcc      3540
acctctgact tgagcgtcga ttttgtgat gctcgtcagg ggggcggagc ctatggaaaa       3600
acgccagcaa cgcggccttt ttacggttcc tggccttttg ctggcctttt gctcacatgt      3660
tctttcctgc gttatcccct gattctgtgg ataaccgtat taccgccttt gagtgagctg     3720
ataccgctcg ccgcagccga acgaccgagc gcagcgagtc agtgagcgag gaagcggaag      3780
agcgcccaat acgcaaaccg cctctccccg cgcgttggcc gattcattaa tgcagctggc     3840
acgacaggtt tcccgactgg aaagcgggca gtgagcgcaa cgcaattaat gtgagttagc      3900
tcactcatta ggcaccccag gctttacact ttatgcttcc ggctcgtatg ttgtgtggaa      3960
ttgtgagcgg ataacaattt cacacaggaa acagctatga ccatgattac gccaagcgcg      4020
caattaaccc tcactaaagg gaacaaaagc tgggtaccgg gccccccctc gaggtcattc      4080
atatgcttga agagagagtc gggatagtcc aaaataaaac aaaggtaaga ttacctggtc      4140
aaaagtgaaa acatcagtta aaaggtggta taagtaaaat atcggtaata aaaggtggcc     4200
caaagtgaaa tttactcttt tctactatta taaaaattga ggatgttttg tcggtacttt      4260
gatacgtcat ttttgtatga attggttttt aagtttattc gcgatttgga aatgcatatc      4320
tgtatttgag tcggttttta agttcgttgc ttttgtaaat acagagggat ttgtataaga     4380
aatatcttta aaaacccat atgctaattt gacataattt ttgagaaaaa tatatattca      4440
ggcgaattcc acaatgaaca ataataagat taaatagct tgcccccgtt gcagcgatgg      4500
gtattttttc tagtaaaata aaagataaac ttagactcaa acatttaca aaacaaccc       4560 ctaaagtcct aaagcccaaa gtgctatgca cgatccatag caagcccagc ccaacccaac     4620
ccaacccaac ccaccccagt gcagccaact ggcaaatagt ctccaccccc ggcactatca     4680
ccgtgagttg tccgcaccac cgcacgtctc gcagccaaaa aaaaaaaag aaagaaaaaa      4740 aagaaaaaga aaaacagcag gtgggtccgg gtcgtggggg ccggaaaagc gaggaggatc     4800
gcgagcagcg acgaggcccg gccctccctc cgcttccaaa gaaacgcccc ccatcgccac     4860
tatatacata cccccccctc tcctcccatc ccccaacc taccaccacc accaccacca       4920
cctcctcccc cctcgctgcc ggacgacgag ctcctccccc ctcccctcc gccgccgccg      4980 gtaaccaccc cgccctctc ctctttctttt ctccgtttt ttttcgtct cggtctcgat       5040 ctttggcctt ggtagtttgg gtgggcgaga gcggcttcgt cgcccagatc ggtgcgcggg     5100
aggggcggga tctcgcggct ggcgtctccg ggcgtgagtc ggcccggatc ctcgcgggga     5160
atggggctct cggatgtaga tcttctttct ttcttctttt tgtggtagaa tttgaatccc     5220
tcagcattgt tcatcggtag ttttttcttt catgatttgt gacaaatgca gcctcgtgcg     5280 gagcttttttt gtagc                                                    5295
```

<210> SEQ ID NO 39
<211> LENGTH: 299
<212> TYPE: PRT

```
<213> ORGANISM: Artificial Sequence
<220> FEATURE:
<223> OTHER INFORMATION: pUG4 vector
<220> FEATURE:
<221> NAME/KEY: VARIANT
<222> LOCATION: (1)...(299)
<223> OTHER INFORMATION: Xaa = Any Amino Acid

<400> SEQUENCE: 39
```

Met Ala His Ala Arg Val Leu Leu Ala Leu Ala Val Leu Ala Thr
1               5                   10                  15

Ala Ala Val Ala Val Ala Ser Ser Arg Ala Ala Ser Thr Gln Gly
            20                  25                  30

Ile Ser Glu Asp Leu Tyr Ser Arg Leu Val Glu Met Ala Thr Ile Ser
        35                  40                  45

Gln Ala Ala Tyr Ala Asp Leu Cys Asn Ile Pro Ser Thr Ile Ile Lys
    50                  55                  60

Gly Glu Lys Ile Tyr Asn Ser Gln Thr Asp Ile Asn Gly Trp Ile Leu
65              70                  75                  80

Arg Asp Asp Ser Ser Lys Glu Ile Ile Thr Val Phe Arg Gly Thr Gly
                85                  90                  95

Ser Asp Thr Asn Leu Gln Leu Asp Thr Asn Tyr Thr Leu Thr Pro Phe
            100                 105                 110

Asp Thr Leu Pro Gln Cys Asn Gly Cys Glu Val His Gly Gly Tyr Tyr
        115                 120                 125

Ile Gly Trp Val Ser Val Gln Asp Gln Val Glu Ser Leu Val Lys Gln
    130                 135                 140

Gln Val Ser Gln Tyr Pro Asp Tyr Ala Leu Thr Val Thr Gly His Xaa
145             150                 155                 160

Leu Gly Ala Ser Leu Ala Ala Leu Thr Ala Ala Gln Leu Ser Ala Thr
                165                 170                 175

Tyr Asp Asn Ile Arg Leu Tyr Thr Phe Gly Glu Pro Arg Ser Gly Asn
            180                 185                 190

Gln Ala Phe Ala Ser Tyr Met Asn Asp Ala Phe Gln Ala Ser Ser Pro
        195                 200                 205

Asp Thr Thr Gln Tyr Phe Arg Val Thr His Ala Asn Asp Gly Ile Pro
    210                 215                 220

Asn Leu Pro Pro Val Glu Gln Gly Tyr Ala His Gly Gly Val Glu Tyr
225             230                 235                 240

Trp Ser Val Asp Pro Tyr Ser Ala Gln Asn Thr Phe Val Cys Thr Gly
                245                 250                 255

Asp Glu Val Gln Cys Cys Glu Ala Gln Gly Gly Gln Gly Val Asn Asn
            260                 265                 270

Ala His Thr Thr Tyr Phe Gly Met Thr Ser Gly Ala Cys Thr Trp Pro
        275                 280                 285

Val Ala Ala Glu Pro Leu Lys Asp Glu Leu
    290                 295

```
<210> SEQ ID NO 40
<211> LENGTH: 5001
<212> TYPE: DNA
<213> ORGANISM: Artificial Sequence
<220> FEATURE:
<223> OTHER INFORMATION: pUB8.11 vector
<220> FEATURE:
<221> NAME/KEY: misc_feature
<222> LOCATION: (1)...(5001)
<223> OTHER INFORMATION: n = A,T,C or G
```

<400> SEQUENCE: 40

```
catgggccag gtataattat gggatatctc aagcaaataa tcgaaatatc accattggct        60
acaatatctg agctccgagt tctgactgca gtctggatga cgcgtgttgt atctagaact       120
ctagatagca cagccacagc acctacagga gtgcgacact tgtggactgt agtagtgttg       180
gagacggagc tctttcctac ctcctgacgt tgccgccgtt gtccattcca acggcatcac       240
tctcaaccaa tcacgcgctc ccaacaaaat atcgtccccc atgtcttggc ggagagagag       300
tacatacatg ctgtcgcgcc gttttttgtct gaatctcgct tccactggcc aatcagctca       360
gctcccggga gctcactcat tcaagatccc atcgtcgtcg tcaccctgg cgtcatggga       420
tggaaaagaa cctccgttgc tcggatgagt cagccatatc cccgaacaga gtactgcaag       480
ataacccaat tcagattccc ccaatagaga agtatagca tgctttcggg ttttgtttgg       540
cttaattgac tttattttg ttggagttga atgctgattt gttgtgtaaa atgcccaacc       600
atctgaatat cgagacggat aataggctgg ctaattaatt tatagcaaga ttctgtagtg       660
cacatcgcaa atatctttct gggcattaca gctggaggct tcatcagcct gaaacactct       720
gcagagcctg aagcaagtgg tgaagcgtgg cgatgagatg ggtataaaac ccccggcacc       780
gggacgcgag ctcccgccta ccagtaccat ctcgcctcgc tcccctgcc ggacgaccca       840
gtaaaatact gttgcccact cgccggcgag atgcccacg gccgcatcct cttcttggcg       900
ctcgccgtct tggccaccgc cgcggtggcc gccgcatcnt tggcggactc caacccgatc       960
cggcccgtca ccgagcgcgc ggccgcctcc acgcagggca tctccgaaga cctctacagc      1020
cgtttagtcg aaatggccac tatctcccaa gctgcctacg ccgacctgtg caacattccg      1080
tcgactatta tcaagggaga gaaaatttac aattctcaaa ctgacattaa cggatggatc      1140
ctccgcgacg acagcagcaa agaaataatc accgtcttcc gtggcactgg tagtgatacg      1200
aatctacaac tcgatactaa ctacaccctc acgcctttcg acaccctacc acaatgcaac      1260
ggttgtgaag tacacggtgg atattatatt ggatgggtct ccgtccagga ccaagtcgag      1320
tcgcttgtca acagcaggt tagccagtat ccggactacg cgctgaccgt gaccggccac      1380
kccctcggcg cctccctggc ggcactcact gccgcccagc tgtctgcgac atacgacaac      1440
atccgcctgt acaccttcgg cgaaccgcgc agcggcaatc aggccttcgc gtcgtacatg      1500
aacgatgcct tccaagcctc gagccagat acgacgcagt atttccgggt cactcatgcc      1560
aacgacggca tcccaaacct gccccggtg gagcaggggt acgcccatgg cggtgtagag      1620
tactggagcg ttgatcctta cagcgcccag aacacatttg tctgcactgg ggatgaagtg      1680
cagtgctgtg aggcccaggg cggacagggt gtgaataatg cgcacacgac ttattttggg      1740
atgacgagcg gagcctgtac atggtgatca gtcatttcag cctccccgag tgtaccagga      1800
aagatggatg tcctggagag ggggccgcgt aaccactgaa ggatgagctg taaagaagca      1860
gatcgttcaa acatttggca ataaagtttc ttaagattga atcctgttgc cggtcttgcg      1920
atgattatca tataatttct gttgaattac gttaagcatg taataattaa catgtaatgc      1980
atgacgttat ttatgagatg ggtttttatg attagagtcc cgcaattata catttaatac      2040
gcgatagaaa acaaaatata gcgcgcaaac taggataaat tatcgcgcgc ggtgtcatct      2100
atgttactag atcgataagc ttctagacgc gccggtggag ctccaattcg ccctatagtg      2160
agtcgtatta cgcgcgctca ctggccgtcg ttttacaacg tcgtgactgg gaaaaccctg      2220
gcgttaccca acttaatcgc cttgcagcac atccccctt cgccagctgg cgtaatagcg      2280
aagaggcccg caccgatcgc ccttcccaac agttgcgcag cctgaatggc gaatgggacg      2340
```

```
cgccctgtag cggcgcatta agcgcggcgg gtgtggtggt tacgcgcagc gtgaccgcta   2400
cacttgccag cgccctagcg cccgctcctt tcgctttctt cccttccttt ctcgccacgt   2460
tcgccggctt tccccgtcaa gctctaaatc ggggctccc tttagggttc cgatttagtg    2520
ctttacggca cctcgacccc aaaaaacttg attagggtga tggttcacgt agtgggccat   2580
cgccctgata gacggttttt cgcccttga cgttggagtc cacgttcttt aatagtggac    2640
tcttgttcca aactggaaca acactcaacc ctatctcggt ctattctttt gatttataag   2700
ggattttgcc gatttcggcc tattggttaa aaaatgagct gatttaacaa aaatttaacg   2760
cgaattttaa caaaatatta acgcttacaa tttaggtggc acttttcggg gaaatgtgcg   2820
cggaacccct atttgtttat ttttctaaat acattcaaat atgtatccgc tcatgagaca   2880
ataaccctga taaatgcttc aataatattg aaaaggaag agtatgagta ttcaacattt    2940
ccgtgtcgcc cttattccct tttttgcggc attttgcctt cctgtttttg ctcacccaga   3000
aacgctggtg aaagtaaaag atgctgaaga tcagttgggt gcacgagtgg gttacatcga   3060
actggatctc aacagcggta agatccttga gagttttcgc cccgaagaac gttttccaat   3120
gatgagcact tttaaagttc tgctatgtgg cgcggtatta tcccgtattg acgccgggca   3180
agagcaactc ggtcgccgca tacactattc tcagaatgac ttggttgagt actcaccagt   3240
cacagaaaag catcttacgg atggcatgac agtaagagaa ttatgcagtg ctgccataac   3300
catgagtgat aacactgcgg ccaacttact tctgacaacg atcggaggac cgaaggagct   3360
aaccgctttt ttgcacaaca tggggggatca tgtaactcgc cttgatcgtt gggaaccgga   3420
gctgaatgaa gccataccaa acgacgagcg tgacaccacg atgcctgtag caatggcaac   3480
aacgttgcgc aaactattaa ctggcgaact acttactcta gcttcccggc aacaattaat   3540
agactggatg gaggcggata aagttgcagg accacttctg cgctcggccc ttccggctgg   3600
ctggtttatt gctgataaat ctggagccgg tgagcgtggg tctcgcggta tcattgcagc   3660
actggggcca gatggtaagc cctcccgtat cgtagttatc tacacgacgg ggagtcaggc   3720
aactatggat gaacgaaata gacagatcgc tgagataggt gcctcactga ttaagcattg   3780
gtaactgtca gaccaagttt actcatatat actttagatt gatttaaaac ttcatttta   3840 atttaaaagg atctaggtga agatccttt tgataatctc atgaccaaaa tcccttaacg   3900
tgagttttcg ttccactgag cgtcagaccc cgtagaaaag atcaaaggat cttcttgaga   3960 tcctttttt ctgcgcgtaa tctgctgctt gcaaacaaaa aaaccaccgc taccagcggt    4020
ggtttgtttg ccggatcaag agctaccaac tctttttccg aaggtaactg gcttcagcag   4080
agcgcagata ccaaatactg tccttctagt gtagccgtag ttaggccacc acttcaagaa   4140
ctctgtagca ccgcctacat acctcgctct gctaatcctg ttaccagtgg ctgctgccag   4200
tggcgataag tcgtgtctta ccgggttgga ctcaagacga tagttaccgg ataaggcgca   4260
gcggtcgggc tgaacggggg gttcgtgcac acagcccagc ttggagcgaa cgacctacac   4320
cgaactgaga tacctacagc gtgagctatg agaaagcgcc acgcttcccg aagggagaaa   4380
ggcggacagg tatccggtaa gcggcagggt cggaacagga gagcgcacga gggagcttcc   4440
agggggaaac gcctggtatc tttatagtcc tgtcgggttt cgccacctct gacttgagcg   4500
tcgatttttg tgatgctcgt caggggggcg gagcctatgg aaaaacgcca gcaacgcggc   4560
ctttttacgg ttcctggcct tttgctggcc ttttgctcac atgttctttc ctgcgttatc   4620
ccctgattct gtggataacc gtattaccgc ctttgagtga gctgataccg ctcgccgcag   4680
```

```
ccgaacgacc gagcgcagcg agtcagtgag cgaggaagcg gaagagcgcc caatacgcaa    4740
accgcctctc cccgcgcgtt ggccgattca ttaatgcagc tggcacgaca ggtttcccga    4800
ctggaaagcg ggcagtgagc gcaacgcaat taatgtgagt tagctcactc attaggcacc    4860
ccaggcttta cactttatgc ttccggctcg tatgttgtgt ggaattgtga gcggataaca    4920
atttcacaca ggaaacagct atgaccatga ttacgccaag cgcgcaatta accctcacta    4980
aagggaacaa aagctgggta c                                              5001

<210> SEQ ID NO 41
<211> LENGTH: 5387
<212> TYPE: DNA
<213> ORGANISM: Artificial Sequence
<220> FEATURE:
<223> OTHER INFORMATION: pTP11-1 vector

<400> SEQUENCE: 41
aagcttacca tggcccacgc ccgcgtcctc ctcctggcgc tcgccgtgct ggccacggcc      60
gccgtcgccg tcgcctcctc ctcctccttc gccgactcca acccgatccg gcccgtcacc     120
gaccgcgcgg ccgcctccac gcagggcatc tccgaagacc tctacagccg tttagtcgaa     180
atggccacta tctcccaagc tgcctacgcc gacctgtgca acattccgtc gactattatc     240
aagggagaga aaatttacaa ttctcaaact gacattaacg gatggatcct ccgcgacgac     300
agcagcaaag aaataatcac cgtcttccgt ggcactggta gtgatacgaa tctacaactc     360
gatactaact acaccctcac gcctttcgac accctaccac aatgcaacgg ttgtgaagta     420
cacggtggat attatattgg atgggtctcc gtccaggacc aagtcgagtc gcttgtcaaa     480
cagcaggtta gccagtatcc ggactacgcg ctgaccgtga ccggccackc cctcggcgcc     540
tccctggcgg cactcactgc cgcccagctg tctgcgacat acgacaacat ccgcctgtac     600
accttcggcg aaccgcgcag cggcaatcag gccttcgcgt cgtacatgaa cgatgccttc     660
caagcctcga gcccagatac gacgcagtat ttccgggtca ctcatgccaa cgacggcatc     720
ccaaacctgc cccggtgga gcaggggtac gcccatggcg gtgtagagta ctggagcgtt     780
gatccttaca gcgcccagaa cacatttgtc tgcactgggg atgaagtgca gtgctgtgag     840
gcccagggcg acagggtgt gaataatgcg cacacgactt attttgggat gacgagcgga     900
gcctgtacat ggtgatcagt catttcagcc tccccgagtg taccaggaaa gatggatgtc     960
ctggagaggg ggccgcgtaa ccactgaagg atgagctgta aagaagcaga tcgttcaaac    1020
atttggcaat aaagtttctt aagattgaat cctgttgccg gtcttgcgat gattatcata    1080
taatttctgt tgaattacgt taagcatgta ataattaaca tgtaatgcat gacgttattt    1140
atgagatggg ttttttatgat tagagtcccg caattataca tttaatacgc gatagaaaac    1200
aaaatatagc gcgcaaacta ggataaatta tcgcgcgcgg tgtcatctat gttactagat    1260
cgataagctt ctagagcggc cggtggagct ccaattcgcc ctatagtgag tcgtattacg    1320
cgcgctcact ggccgtcgtt ttacaacgtc gtgactggga aaaccctggc gttacccaac    1380
ttaatcgcct tgcagcacat ccccctttcg ccagctggcg taatagcgaa gaggcccgca    1440
ccgatcgccc ttcccaacag ttgcgcagcc tgaatggcga atgggacgcg ccctgtagcg    1500
gcgcattaag cgcggcgggt gtggtggtta cgcgcagcgt gaccgctaca cttgccagcg    1560
ccctagcgcc cgctcctttc gctttcttcc cttcctttct cgccacgttc gccggctttc    1620
cccgtcaagc tctaaatcgg gggctccctt tagggttccg atttagtgct ttacggcacc    1680
tcgaccccaa aaaacttgat tagggtgatg gttcactag tgggccatcg ccctgataga    1740
```

```
cggttttcg ccctttgacg ttggagtcca cgttctttaa tagtggactc ttgttccaaa   1800
ctggaacaac actcaaccct atctcggtct attcttttga tttataaggg attttgccga   1860
tttcggccta ttggttaaaa aatgagctga tttaacaaaa atttaacgcg aattttaaca   1920
aaatattaac gcttacaatt taggtggcac ttttcgggga aatgtgcgcg gaacccctat   1980
ttgtttattt ttctaaatac attcaaatat gtatccgctc atgagacaat aaccctgata   2040
aatgcttcaa taatattgaa aaaggaagag tatgagtatt caacatttcc gtgtcgccct   2100
tattcccttt tttgcggcat tttgccttcc tgtttttgct cacccagaaa cgctggtgaa   2160
agtaaaagat gctgaagatc agttgggtgc acgagtgggt tacatcgaac tggatctcaa   2220
cagcggtaag atccttgaga gttttcgccc cgaagaacgt tttccaatga tgagcacttt   2280
taaagttctg ctatgtggcg cggtattatc ccgtattgac gccgggcaag agcaactcgg   2340
tcgccgcata cactattctc agaatgactt ggttgagtac tcaccagtca cagaaaagca   2400
tcttacggat ggcatgacag taagagaatt atgcagtgct gccataacca tgagtgataa   2460
cactgcggcc aacttacttc tgacaacgat cggaggaccg aaggagctaa ccgcttttt   2520 gcacaacatg ggggatcatg taactcgcct tgatcgttgg gaaccggagc tgaatgaagc   2580
cataccaaac gacgagcgtg acaccacgat gcctgtagca atggcaacaa cgttgcgcaa   2640
actattaact ggcgaactac ttactctagc ttcccggcaa caattaatag actggatgga   2700
ggcggataaa gttgcaggac cacttctgcg ctcggccctt ccggctggct ggtttattgc   2760
tgataaatct ggagccggtg agcgtgggtc tcgcggtatc attgcagcac tggggccaga   2820
tggtaagccc tcccgtatcg tagttatcta cacgacgggg agtcaggcaa ctatggatga   2880
acgaaataga cagatcgctg agataggtgc ctcactgatt aagcattggt aactgtcaga   2940
ccaagtttac tcatatatac tttagattga tttaaaactt catttttaat ttaaaaggat   3000
ctaggtgaag atccttttg ataatctcat gaccaaaatc ccttaacgtg agttttcgtt   3060
ccactgagcg tcagaccccg tagaaaagat caaaggatct tcttgagatc cttttttct   3120 gcgcgtaatc tgctgcttgc aaacaaaaaa accaccgcta ccagcggtgg tttgtttgcc   3180
ggatcaagag ctaccaactc tttttccgaa ggtaactggc ttcagcagag cgcagatacc   3240
aaatactgtc cttctagtgt agccgtagtt aggccaccac ttcaagaact ctgtagcacc   3300
gcctacatac ctcgctctgc taatcctgtt accagtggct gctgccagtg gcgataagtc   3360
gtgtcttacc gggttggact caagacgata gttaccggat aaggcgcagc ggtcgggctg   3420
aacggggggt tcgtgcacac agcccagctt ggagcgaacg acctacaccg aactgagata   3480
cctacagcgt gagctatgag aaagcgccac gcttcccgaa gggagaaagg cggacaggta   3540
tccggtaagc ggcagggtcg gaacaggaga gcgcacgagg gagcttccag ggggaaacgc   3600
ctggtatctt tatagtcctg tcgggtttcg ccacctctga cttgagcgtc gatttttgtg   3660
atgctcgtca ggggggcgga gcctatggaa aaacgccagc aacgcggcct ttttacggtt   3720
cctggccttt tgctggcctt ttgctcacat gttctttcct gcgttatccc ctgattctgt   3780
ggataaccgt attaccgcct ttgagtgagc tgataccgct cgccgcagcc gaacgaccga   3840
gcgcagcgag tcagtgagcg aggaagcgga agagcgccca atacgcaaac cgcctctccc   3900
cgcgcgttgg ccgattcatt aatgcagctg gcacgacagg tttcccgact ggaaagcggg   3960
cagtgagcgc aacgcaatta atgtgagtta gctcactcat taggcacccc aggctttaca   4020
ctttatgctt ccggctcgta tgttgtgtgg aattgtgagc ggataacaat ttcacacagg   4080
```

```
aaacagctat gaccatgatt acgccaagcg cgcaattaac cctcactaaa gggaacaaaa    4140
gctgggtacc gggccccccc tcgaggtcat tcatatgctt gagaagagag tcgggatagt    4200
ccaaaataaa acaaaggtaa gattacctgg tcaaaagtga aaacatcagt taaaaggtgg    4260
tataagtaaa atatcggtaa taaaaggtgg cccaaagtga aatttactct tttctactat    4320
tataaaaatt gaggatgttt tgtcggtact ttgatacgtc atttttgtat gaattggttt    4380
ttaagtttat tcgcgatttg gaaatgcata tctgtatttg agtcggtttt taagttcgtt    4440
gcttttgtaa atacagaggg atttgtataa gaaatatctt taaaaaaccc atatgctaat    4500
ttgacataat ttttgagaaa aatatatatt caggcgaatt ccacaatgaa caataataag    4560
attaaaatag cttgcccccg ttgcagcgat gggtattttt tctagtaaaa taaaagataa    4620
acttagactc aaaacattta caaaaacaac ccctaaagtc ctaaagccca aagtgctatg    4680
cacgatccat agcaagccca gcccaaccca acccaaccca acccaccca gtgcagccaa    4740 ctggcaaata gtctccaccc ccggcactat caccgtgagt gtccgcacc accgcacgtc    4800 tcgcagccaa aaaaaaaaaa agaaagaaaa aaaagaaaaa gaaaacagc aggtgggtcc    4860 gggtcgtggg ggccggaaaa gcgaggagga tcgcgagcag cgacgaggcc cggccctccc    4920
tccgcttcca agaaacgcc cccatcgcc actatataca tacccccccc tctcctccca    4980 tcccccaac cctaccacca ccaccaccac cactcctcc ccctcgctg ccggacgacg    5040 agctcctccc ccctccccct ccgccgccgc cggtaaccac cccgcccctc tcctctttct    5100
ttctccgttt ttttttcgt ctcggtctcg atctttggcc ttggtagttt gggtgggcga    5160
gagcggcttc gtcgcccaga tcggtgcgcg ggaggggcgg gatctcgcgg ctggcgtctc    5220
cgggcgtgag tcggcccgga tcctcgcggg gaatgggggct ctcggatgta gatcttcttt    5280
ctttcttctt tttgtggtag aatttgaatc cctcagcatt gttcatcggt agtttttctt    5340
ttcatgattt gtgacaaatg cagcctcgtg cggagctttt ttgtagc                  5387
```

<210> SEQ ID NO 42
<211> LENGTH: 301
<212> TYPE: PRT
<213> ORGANISM: Artificial Sequence
<220> FEATURE:
<223> OTHER INFORMATION: pTP11-1 vector
<220> FEATURE:
<221> NAME/KEY: VARIANT
<222> LOCATION: (1)...(301)
<223> OTHER INFORMATION: Xaa = Any Amino Acid

<400> SEQUENCE: 42

```
Met Ala His Ala Arg Val Leu Leu Ala Leu Ala Val Leu Ala Thr
  1               5                  10                  15

Ala Ala Val Ala Val Ala Ser Ser Ser Ser Phe Ala Asp Ser Asn Pro
                 20                  25                  30

Ile Arg Pro Val Thr Asp Arg Ala Ala Ala Ser Thr Gln Gly Ile Ser
             35                  40                  45

Glu Asp Leu Tyr Ser Arg Leu Val Glu Met Ala Thr Ile Ser Gln Ala
         50                  55                  60

Ala Tyr Ala Asp Leu Cys Asn Ile Pro Ser Thr Ile Ile Lys Gly Glu
     65                  70                  75                  80

Lys Ile Tyr Asn Ser Gln Thr Asp Ile Asn Gly Trp Ile Leu Arg Asp
                 85                  90                  95

Asp Ser Ser Lys Glu Ile Ile Thr Val Phe Arg Gly Thr Gly Ser Asp
            100                 105                 110
```

```
Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Tyr Tyr Ile Gly
    130                 135                 140

Trp Val Ser Val Gln Asp Gln Val Glu Ser Leu Val Lys Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp
    290                 295                 300

<210> SEQ ID NO 43
<211> LENGTH: 1259
<212> TYPE: DNA
<213> ORGANISM: Artificial Sequence
<220> FEATURE:
<223> OTHER INFORMATION: actin promoter

<400> SEQUENCE: 43
ggtaccgggc cccccctcga ggtcattcat atgcttgaga agagagtcgg gatagtccaa      60
aataaaacaa aggtaagatt acctggtcaa aagtgaaaac atcagttaaa aggtggtata     120
agtaaaatat cggtaataaa aggtggccca aagtgaaatt tactcttttc tactattata     180
aaaattgagg atgttttgtc ggtactttga tacgtcattt ttgtatgaat tggttttaa      240 gtttattcgc gatttggaaa tgcatatctg tatttgagtc ggttttttaag ttcgttgctt    300 ttgtaaatac agagggattt gtataagaaa tatctttaaa aaacccatat gctaatttga     360
cataattttt gagaaaaata tatattcagg cgaattccac aatgaacaat aataagatta     420
aaatagcttg cccccgttgc agcgatgggt attttttcta gtaaaataaa agataaactt     480
agactcaaaa catttacaaa aacaacccct aaagtcctaa agcccaaagt gctatgcacg     540
atccatagca agcccagccc aacccaaccc aacccaaccc accccagtgc agccaactgg     600
caaatagtct ccaccccgg cactatcacc gtgagttgtc cgcaccaccg cacgtctcgc      660
agccaaaaaa aaaaaagaa agaaaaaaaa gaaaagaaa aacagcaggt gggtccgggt       720
cgtgggggcc ggaaaagcga ggaggatcgc gagcagcgac gaggcccggc cctccctccg     780
cttccaaaga aacgcccccc atcgccacta tatacatacc cccccctctc ctcccatccc     840
cccaacccta ccaccaccac caccaccacc tcctcccccc tcgctgccgg acgacgagct     900
cctccccctc cccctccgc cgccgccggt aaccaccccg cccctctcct ctttctttct     960
ccgttttttt tttcgtctcg gtctcgatct ttggccttgg tagtttgggt gggcgagagc    1020
```

```
ggcttcgtcg cccagatcgg tgcgcgggag gggcgggatc tcgcggctgg cgtctccggg    1080
cgtgagtcgg cccggatcct cgcggggaat ggggctctcg gatgtagatc ttctttcttt    1140 cttcttttg tggtagaatt tgaatccctc agcattgttc atcggtagtt tttcttttca     1200
tgatttgtga caaatgcagc ctcgtgcgga gcttttttgt aggtagaagc ttaccatgg     1259

<210> SEQ ID NO 44
<211> LENGTH: 27
<212> TYPE: PRT
<213> ORGANISM: Artificial Sequence
<220> FEATURE:
<223> OTHER INFORMATION: aleurain-NPIR delete structure

<400> SEQUENCE: 44

Met Ala His Ala Arg Val Leu Leu Leu Ala Leu Ala Val Leu Ala Thr
 1               5                  10                  15

Ala Ala Val Ala Val Ala Ser Ser Arg Ala Ala
            20                  25

<210> SEQ ID NO 45
<211> LENGTH: 93
<212> TYPE: DNA
<213> ORGANISM: Artificial Sequence
<220> FEATURE:
<223> OTHER INFORMATION: aleurain-NPIR delete structure encoding
      sequence

<400> SEQUENCE: 45
aagcttacca tggcccacgc ccgcgtcctc ctcctggcgc tcgccgtgct ggccacggcc     60
gccgtcgccg tcgcctcctc ccgcgcggcc gcc                                 93

<210> SEQ ID NO 46
<211> LENGTH: 873
<212> TYPE: DNA
<213> ORGANISM: Artificial Sequence
<220> FEATURE:
<223> OTHER INFORMATION: SEE1 (senescence enhanced) promoter

<400> SEQUENCE: 46
catgggccag gtataattat gggatatctc aagcaaataa tcgaaatatc accattggct     60
acaatatctg agctccgagt tctgactgca gtctggatga cgcgtgttgt atctagaact    120
ctagatagca cagccacagc acctacagga gtgcgacact tgtggactgt agtagtgttg    180
gagacggagc tctttcctac ctcctgacgt tgccgccgtt gtccattcca acggcatcac    240
tctcaaccaa tcacgcgctc ccaacaaaat atcgtccccc atgtcttggc ggagagagag    300
tacatacatg ctgtcgcgcc gttttgtct gaatctcgct tccactggcc aatcagctca     360
gctcccggga gctcactcat tcaagatccc atcgtcgtcg tcaccctgg cgtcatggga     420 tggaaaagaa cctccgttgc tcggatgagt cagccatatc cccgaacaga gtactgcaag    480
ataacccaat tcagattccc ccaatagaga agtatagca tgctttcggg ttttgtttgg     540
cttaattgac tttatttttg ttggagttga atgctgattt gttgtgtaaa atgcccaacc    600
atctgaatat cgagacggat aataggctgg ctaattaatt tatagcaaga ttctgtagtg    660
cacatcgcaa atatctttct gggcattaca gctggaggct tcatcagcct gaaacactct    720
gcagagcctg aagcaagtgg tgaagcgtgg cgatgagatg ggtataaaac ccccggcacc    780
gggacgcgag ctcccgccta ccagtaccat ctcgcctcgc tccccctgcc ggacgaccca    840
gtaaaatact gttgcccact cgccggcgag atg                                 873
```

<210> SEQ ID NO 47
<211> LENGTH: 39
<212> TYPE: PRT
<213> ORGANISM: Artificial Sequence
<220> FEATURE:
<223> OTHER INFORMATION: SEE1 promoter plus vacuolar aleurain signal/
     NPIR sequence

<400> SEQUENCE: 47

Met Ala His Gly Arg Ile Leu Phe Leu Ala Leu Ala Val Leu Ala Thr
1               5                   10                  15

Ala Ala Val Ala Ala Ser Leu Ala Asp Ser Asn Pro Ile Arg Pro
            20                  25                  30

Val Thr Glu Arg Ala Ala Ala
        35

<210> SEQ ID NO 48
<211> LENGTH: 987
<212> TYPE: DNA
<213> ORGANISM: Artificial Sequence
<220> FEATURE:
<223> OTHER INFORMATION: SEE1 promoter plus vacuolar aleurain signal/
     NPIR encoding sequence
<220> FEATURE:
<221> NAME/KEY: misc_feature
<222> LOCATION: (1)...(987)
<223> OTHER INFORMATION: n = A,T,C or G

<400> SEQUENCE: 48
catgggccag gtataattat gggatatctc aagcaaataa tcgaaatatc accattggct      60
acaatatctg agctccgagt tctgactgca gtctggatga cgcgtgttgt atctagaact     120
ctagatagca cagccacagc acctacagga gtgcgacact tgtggactgt agtagtgttg     180
gagacggagc tctttcctac ctcctgacgt tgccgccgtt gtccattcca acggcatcac     240
tctcaaccaa tcacgcgctc ccaacaaaat atcgtccccc atgtcttggc ggagagagag     300
tacatacatg ctgtcgcgcc gttttgtct gaatctcgct tccactggcc aatcagctca      360
gctcccggga gctcactcat tcaagatccc atcgtcgtcg tcaccctgg cgtcatggga      420 tggaaaagaa cctccgttgc tcggatgagt cagccatatc cccgaacaga gtactgcaag     480
ataacccaat tcagattccc ccaatagaga aagtatagca tgctttcggg ttttgtttgg     540
cttaattgac tttatttttg ttggagttga atgctgattt gttgtgtaaa atgcccaacc     600
atctgaatat cgagacggat aataggctgg ctaattaatt tatagcaaga ttctgtagtg     660
cacatcgcaa atatctttct gggcattaca gctggaggct tcatcagcct gaaacactct     720
gcagagcctg aagcaagtgg tgaagcgtgg cgatgagatg gtataaaac ccccggcacc      780 gggacgcgag ctcccgccta ccagtaccat ctcgcctcgc tcccctgcc ggacgaccca      840 gtaaatact gttgcccact cgccggcgag atggcccacg gccgcatcct cttcttggcg      900
ctcgccgtct tggccaccgc cgcggtggcc gccgcatcnt tggcggactc caacccgatc     960
cggcccgtca ccgagcgcgc ggccgcc                                         987

<210> SEQ ID NO 49
<211> LENGTH: 40
<212> TYPE: DNA
<213> ORGANISM: Artificial Sequence
<220> FEATURE:
<223> OTHER INFORMATION: primer

<400> SEQUENCE: 49

-continued

```
ggcgccgagg gagtggccgg tcacggtcag cgcgtagtcc                            40

<210> SEQ ID NO 50
<211> LENGTH: 35
<212> TYPE: DNA
<213> ORGANISM: Artificial Sequence
<220> FEATURE:
<223> OTHER INFORMATION: primer

<400> SEQUENCE: 50
ccggccacgc cctcggcgcc tccctggcgg cactc                                 35

<210> SEQ ID NO 51
<211> LENGTH: 44
<212> TYPE: DNA
<213> ORGANISM: Artificial Sequence
<220> FEATURE:
<223> OTHER INFORMATION: primer

<400> SEQUENCE: 51
ctaaagctta ccatggcggc cgcctccacg cagggcatct ccga                       44

<210> SEQ ID NO 52
<211> LENGTH: 50
<212> TYPE: DNA
<213> ORGANISM: Artificial Sequence
<220> FEATURE:
<223> OTHER INFORMATION: primer

<400> SEQUENCE: 52
tctaagcttg cggccgcgac cggccaggtg catgcgccgc tcgtcatccc                 50

<210> SEQ ID NO 53
<211> LENGTH: 325
<212> TYPE: DNA
<213> ORGANISM: Artificial Sequence
<220> FEATURE:
<223> OTHER INFORMATION: amplified nos terminator sequence from pMA406
      vector

<400> SEQUENCE: 53
agactgcaga ccatggcggc cgcgkaacca ctgaaggatg agctgtaaag aagcagatcg      60
ttcaaacatt tggcaataaa gtttcttaag attgaatcct gttgccggtc ttgcgatgat    120
tatcatataa tttctgttga attacgttaa gcatgtaata attaacatgt aatgcatgac    180
gttatttatg agatgggttt ttatgattag agtcccgcaa ttatacattt aatacgcgat    240
agaaaacaaa atatagcgcg caaactagga taaattatcg cgcgcggtgt catctatgtt    300
actagatcga taagcttcta gatct                                          325

<210> SEQ ID NO 54
<211> LENGTH: 72
<212> TYPE: DNA
<213> ORGANISM: Artificial Sequence
<220> FEATURE:
<223> OTHER INFORMATION: primer

<400> SEQUENCE: 54
agactgcaga ccatggcggc cgcgkaacca ctgaaggatg agctgtaaag aagcagatcg      60
ttcaaacatt tg                                                          72

<210> SEQ ID NO 55
<211> LENGTH: 20
```

```
<212> TYPE: DNA
<213> ORGANISM: Artificial Sequence
<220> FEATURE:
<223> OTHER INFORMATION: primer

<400> SEQUENCE: 55
aagactgcag accatggcgg                                              20

<210> SEQ ID NO 56
<211> LENGTH: 40
<212> TYPE: DNA
<213> ORGANISM: Artificial Sequence
<220> FEATURE:
<223> OTHER INFORMATION: primer

<400> SEQUENCE: 56
agatctagaa gcttatcgat ctagtaacat agatgacacc                        40

<210> SEQ ID NO 57
<211> LENGTH: 33
<212> TYPE: DNA
<213> ORGANISM: Artificial Sequence
<220> FEATURE:
<223> OTHER INFORMATION: primer

<400> SEQUENCE: 57
ctaggcggcc gcgcgggagg aggcgacggc gac                               33

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
gagggtgtat tcggtatcga gttgcaggtt cgtatc                            36

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
ctcgataccc attacaccct cacgcctttc ga                                32

<210> SEQ ID NO 60
<211> LENGTH: 10
<212> TYPE: DNA
<213> ORGANISM: Artificial Sequence
<220> FEATURE:
<223> OTHER INFORMATION: Acc1 site

<400> SEQUENCE: 60
gtaggtagac                                                         10

<210> SEQ ID NO 61
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 61
```
ctcaccatgg taagcttcta cctacaaaaa agctccgca    39

<210> SEQ ID NO 62
<211> LENGTH: 36
<212> TYPE: DNA
<213> ORGANISM: Artificial Sequence
<220> FEATURE:
<223> OTHER INFORMATION: primer

<400> SEQUENCE: 62
aaccatggcg gccgcgcgct cggtgacggg ccggat    36

<210> SEQ ID NO 63
<211> LENGTH: 29
<212> TYPE: DNA
<213> ORGANISM: Artificial Sequence
<220> FEATURE:
<223> OTHER INFORMATION: primer

<400> SEQUENCE: 63
ttcggtacca tggccaggta taattatgg    29

<210> SEQ ID NO 64
<211> LENGTH: 31
<212> TYPE: DNA
<213> ORGANISM: Artificial Sequence
<220> FEATURE:
<223> OTHER INFORMATION: primer

<400> SEQUENCE: 64
ctgcgccggc gagatggmcg tgcacaagga g    31

<210> SEQ ID NO 65
<211> LENGTH: 42
<212> TYPE: DNA
<213> ORGANISM: Artificial Sequence
<220> FEATURE:
<223> OTHER INFORMATION: primer

<400> SEQUENCE: 65
ggaattcgta gacaagctta cmatggccca cgcccgcgtc ct    42

<210> SEQ ID NO 66
<211> LENGTH: 55
<212> TYPE: DNA
<213> ORGANISM: Artificial Sequence
<220> FEATURE:
<223> OTHER INFORMATION: primer

<400> SEQUENCE: 66
tatccatggc ggccgcgcgg tcggtgacgg gccggmycgg gttggagtcg gcgaa    55

<210> SEQ ID NO 67
<211> LENGTH: 33
<212> TYPE: DNA
<213> ORGANISM: Artificial Sequence
<220> FEATURE:
<223> OTHER INFORMATION: primer

<400> SEQUENCE: 67
ctaggcggcc gcgcgggagg aggcgacggc gac    33

<210> SEQ ID NO 68
<211> LENGTH: 54
<212> TYPE: DNA
<213> ORGANISM: Artificial Sequence

```
<220> FEATURE:
<223> OTHER INFORMATION: primer

<400> SEQUENCE: 68
gcgacggcga cggcggccgt ggccagcacg gcgagcgcca ggaggaggac gcgg        54

<210> SEQ ID NO 69
<211> LENGTH: 33
<212> TYPE: DNA
<213> ORGANISM: Artificial Sequence
<220> FEATURE:
<223> OTHER INFORMATION: primer

<400> SEQUENCE: 69
tcgccgtcgc ctcctcctcc tccttcgccg act                              33

<210> SEQ ID NO 70
<211> LENGTH: 43
<212> TYPE: DNA
<213> ORGANISM: Artificial Sequence
<220> FEATURE:
<223> OTHER INFORMATION: primer

<400> SEQUENCE: 70
actaagctta aggagatata acaatgatcc acaccaacct caa                   43

<210> SEQ ID NO 71
<211> LENGTH: 45
<212> TYPE: DNA
<213> ORGANISM: Artificial Sequence
<220> FEATURE:
<223> OTHER INFORMATION: primer

<400> SEQUENCE: 71
ttccatgatc cacaccaacc tcaaaaagaa gttctccctc ttcat                 45

<210> SEQ ID NO 72
<211> LENGTH: 55
<212> TYPE: DNA
<213> ORGANISM: Artificial Sequence
<220> FEATURE:
<223> OTHER INFORMATION: primer

<400> SEQUENCE: 72
agagtgatca cggcgaagag gaggaagacg aggatgaaga gggagaactt ctttt      55

<210> SEQ ID NO 73
<211> LENGTH: 61
<212> TYPE: DNA
<213> ORGANISM: Artificial Sequence
<220> FEATURE:
<223> OTHER INFORMATION: primer

<400> SEQUENCE: 73
tatagatctg cgtgtggaag aagggctccg actacgaggc cctcaccctc caagccaagg 60
a                                                                 61

<210> SEQ ID NO 74
<211> LENGTH: 28
<212> TYPE: DNA
<213> ORGANISM: Artificial Sequence
<220> FEATURE:
<223> OTHER INFORMATION: primer

<400> SEQUENCE: 74
```
catttggaac tccttggctt ggagggtg   28

<210> SEQ ID NO 75
<211> LENGTH: 34
<212> TYPE: DNA
<213> ORGANISM: Artificial Sequence
<220> FEATURE:
<223> OTHER INFORMATION: primer

<400> SEQUENCE: 75
aaccatggcg gccgccattt ggaactcctt ggct   34

<210> SEQ ID NO 76
<211> LENGTH: 61
<212> TYPE: DNA
<213> ORGANISM: Artificial Sequence
<220> FEATURE:
<223> OTHER INFORMATION: primer

<400> SEQUENCE: 76
tatagatctg cgtgtggaag aagggctccg actacgaggc cctcaccctc caagccaagg   60
a   61

<210> SEQ ID NO 77
<211> LENGTH: 42
<212> TYPE: DNA
<213> ORGANISM: Artificial Sequence
<220> FEATURE:
<223> OTHER INFORMATION: primer

<400> SEQUENCE: 77
ggaattcgta gacaagctta cmatggmcgt gcacaaggag gt   42

<210> SEQ ID NO 78
<211> LENGTH: 37
<212> TYPE: DNA
<213> ORGANISM: Artificial Sequence
<220> FEATURE:
<223> OTHER INFORMATION: primer

<400> SEQUENCE: 78
gatcaggagg taggcwacga agttwacctc cttgtgc   37

<210> SEQ ID NO 79
<211> LENGTH: 37
<212> TYPE: DNA
<213> ORGANISM: Artificial Sequence
<220> FEATURE:
<223> OTHER INFORMATION: primer

<400> SEQUENCE: 79
cctacctcct gatcgtsctc ggcctcctct tgctcgt   37

<210> SEQ ID NO 80
<211> LENGTH: 43
<212> TYPE: DNA
<213> ORGANISM: Artificial Sequence
<220> FEATURE:
<223> OTHER INFORMATION: primer

<400> SEQUENCE: 80
ccttggcgtc cacgtgctcc atggcggawa cgagcaagag gag   43

<210> SEQ ID NO 81
<211> LENGTH: 39

```
<212> TYPE: DNA
<213> ORGANISM: Artificial Sequence
<220> FEATURE:
<223> OTHER INFORMATION: primer

<400> SEQUENCE: 81
gtggacgcca aggcctgcac cckcgagtgc ggcaacctc                              39

<210> SEQ ID NO 82
<211> LENGTH: 47
<212> TYPE: DNA
<213> ORGANISM: Artificial Sequence
<220> FEATURE:
<223> OTHER INFORMATION: primer

<400> SEQUENCE: 82
ggaattcgcg gccgccgggc agatgccgaa gccgaggttg ccgcact                    47

<210> SEQ ID NO 83
<211> LENGTH: 32
<212> TYPE: DNA
<213> ORGANISM: Artificial Sequence
<220> FEATURE:
<223> OTHER INFORMATION: primer

<400> SEQUENCE: 83
ctaaagctta acatgaagca gttctccgcc aa                                    32

<210> SEQ ID NO 84
<211> LENGTH: 8
<212> TYPE: DNA
<213> ORGANISM: Oryza sp.

<400> SEQUENCE: 84 gtaggtag                                                                8

<210> SEQ ID NO 85
<211> LENGTH: 7
<212> TYPE: PRT
<213> ORGANISM: Artificial Sequence
<220> FEATURE:
<223> OTHER INFORMATION: KDEL fusion peptide

<400> SEQUENCE: 85

Lys Pro Leu Lys Asp Glu Leu
 1               5

<210> SEQ ID NO 86
<211> LENGTH: 7
<212> TYPE: PRT
<213> ORGANISM: Artificial Sequence
<220> FEATURE:
<223> OTHER INFORMATION: designated KDEL fusion peptide

<400> SEQUENCE: 86

Glu Pro Leu Lys Asp Glu Leu
 1               5

<210> SEQ ID NO 87
<211> LENGTH: 5
<212> TYPE: PRT
<213> ORGANISM: Artificial Sequence
<220> FEATURE:
<223> OTHER INFORMATION: frameshifted terminal peptide

<400> SEQUENCE: 87
```

```
Glu Thr Thr Glu Gly
 1               5
```

<210> SEQ ID NO 88
<211> LENGTH: 27
<212> TYPE: PRT
<213> ORGANISM: Aspergillus niger

<400> SEQUENCE: 88

```
Met Lys Gln Phe Ser Ala Lys His Val Leu Ala Val Val Val Thr Ala
 1               5                  10                  15

Gly His Ala Leu Ala Ala Ser Thr Gln Gly Ile
            20                  25
```

<210> SEQ ID NO 89
<211> LENGTH: 9
<212> TYPE: PRT
<213> ORGANISM: Aspergillus niger

<400> SEQUENCE: 89

```
Met Ala Ala Ala Ser Thr Gln Gly Ile
 1               5
```

<210> SEQ ID NO 90
<211> LENGTH: 7
<212> TYPE: PRT
<213> ORGANISM: Artificial Sequence
<220> FEATURE:
<223> OTHER INFORMATION: ER retention vector

<400> SEQUENCE: 90

```
Lys Pro Leu Lys Asp Glu Leu
 1               5
```

<210> SEQ ID NO 91
<211> LENGTH: 5
<212> TYPE: PRT
<213> ORGANISM: Artificial Sequence
<220> FEATURE:
<223> OTHER INFORMATION: c-terminal targeting sequence

<400> SEQUENCE: 91

```
Pro Val Ala Ala Ala
 1               5
```

<210> SEQ ID NO 92
<211> LENGTH: 55
<212> TYPE: DNA
<213> ORGANISM: Artificial Sequence
<220> FEATURE:
<223> OTHER INFORMATION: primer

<400> SEQUENCE: 92
tatccatggc ggccgcgcgg tcggtgacgg gccggcccgg gttggagtcg gcgaa        55

<210> SEQ ID NO 93
<211> LENGTH: 8
<212> TYPE: PRT
<213> ORGANISM: Artificial Sequence
<220> FEATURE:
<223> OTHER INFORMATION: ferulic esterase end

<400> SEQUENCE: 93

```
Cys Thr Trp Pro Val Ala Ala Ala
 1               5
```

```
<210> SEQ ID NO 94
<211> LENGTH: 72
<212> TYPE: PRT
<213> ORGANISM: Artificial Sequence
<220> FEATURE:
<223> OTHER INFORMATION: pTP4a2 vector

<400> SEQUENCE: 94

Met Lys Gln Phe Ser Ala Lys His Val Leu Ala Val Val Thr Ala
1               5                   10                  15

Gly His Ala Leu Ala Ala Ser Thr Gln Gly Ile Ser Glu Asp Leu Tyr
            20                  25                  30

Ser Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ser Gln Thr Asp Ile Asn Gly Trp
65                  70

<210> SEQ ID NO 95
<211> LENGTH: 17
<212> TYPE: PRT
<213> ORGANISM: Artificial Sequence
<220> FEATURE:
<223> OTHER INFORMATION: protein encoded by functional reading frame

<400> SEQUENCE: 95

Tyr Ala Leu Thr Val Thr Gly His Ser Leu Gly Ala Ser Leu Ala Ala
1               5                   10                  15

Leu

<210> SEQ ID NO 96
<211> LENGTH: 17
<212> TYPE: PRT
<213> ORGANISM: Artificial Sequence
<220> FEATURE:
<223> OTHER INFORMATION: protein encoded by inactivated reading frame

<400> SEQUENCE: 96

Tyr Ala Leu Thr Val Thr Gly His Ala Leu Gly Ala Ser Leu Ala Ala
1               5                   10                  15

Leu

<210> SEQ ID NO 97
<211> LENGTH: 4
<212> TYPE: PRT
<213> ORGANISM: Artificial Sequence
<220> FEATURE:
<223> OTHER INFORMATION: retention sequence

<400> SEQUENCE: 97

Lys Asp Glu Leu
1
```

MANIPULATION OF THE PHENOLIC ACID CONTENT AND DIGESTIBILITY OF PLANT CELL WALLS BY TARGETED EXPRESSION OF GENES ENCODING CELL WALL DEGRADING ENZYMES

CROSS-REFERENCE TO RELATED APPLICATIONS

This application is a continuation of U.S. Ser. No. 09/991,209, filed Nov. 16, 2001, now U.S. Pat. No. 7,132,589, which claims benefit of and priority to U.S. Ser. No. 60/249,608 pursuant to 35 U.S.C. § 119(e), entitled "MANIPULATION OF THE PHENOLIC ACID CONTENT AND DIGESTIBILITY OF FORAGE GRASS CELL WALLS BY TARGETED EXPRESSION OF A FERULIC ACID ESTERASE GENE", filed Nov. 17, 2000 by Morris et al.

FIELD OF THE INVENTION

This invention relates to methods to enhance to availability of fermentable carbohydrates.

BACKGROUND OF THE INVENTION

The present crisis in livestock agriculture has prompted a resurgence of interest in grass-fed animals. However, while a high-forage diet may be desirable, it does not currently satisfy the demands of modern animal production. For the animal to make efficient use of the forage it consumes, the energy demands of the micro-organisms in the rumen must be met and synchronized with the availability of plant proteins. Otherwise this lack of synchrony will lead to (a) proteins and other nutrients being poorly utilized in the rumen, (b) loss of nitrogen, in urine and feces and therefore, the environment and (c) the need to feed excessive amounts of protein concentrates as supplements to the ruminant diet.

Cellulose and hemicellulose in grass and maize tissues could meet the energy requirements of the ruminant or provide new feed-stocks for industrial fermentation to ethanol. This potential is not currently realized because the cell walls are lignified and the cell wall polysaccharides highly cross-linked with phenolic residues and lignin, resulting in low rates of plant cell wall digestion in comparison to rates of protein breakdown in ruminants. This is a particular problem for the most important forages in Europe, the ryegrasses *Lolium perenne* and *L. mutiflorum* as well as one of the major impediments to the wider use of better adapted species, such as *Festuca arundinacea*, as a forage crop. Increasing the digestibility index of grasses has therefore been a major breeding objective for several decades but progress has been slow due to difficulties in fixing natural variation in the synthetic varieties derived from these outbreeding species (Hayward, et al., *TAG* 70:48 (1985)).

Removing labile phenolics by chemical treatment with alkali is known to increase the biodegradability and nutritional value of low-quality feed such as cereal straw, and is employed commercially for feed upgrading. Reducing phenolic cross-linking of cell wall carbohydrates is therefore a predictable way of improving the rate of digestion and digestibility of ryegrass. However chemical modification may have other disadvantages. Therefore, genetic modification would be a preferable method of changing the cell wall chemistry of highly digestible varieties. Many in the field are pursuing this approach. An alternative, however, is to use genetic modification to reduce the levels of phenolic acids in the cell walls available for crosslinking either by directly disrupting ester bonds linking phenolics and lignins to cell wall polysaccharides or by preventing excessive ferulation of cell wall carbohydrates prior to their incorporation into the cell wall.

This invention meets this and other needs by using targeted or inducible expression of cell wall degrading enzymes in plants.

SUMMARY OF THE INVENTION

Provided herein are methods for enhancing the availability of fermentable carbohydrates. In one aspect, there is provided an expression cassette comprising a DNA sequence encoding at least one cell wall degrading enzyme. The DNA sequence encoding at least one cell wall degrading enzyme may be operatively linked to a promoter sequence. The promoter may be constitutive or inducible. The expression cassette may further comprise a targeting sequence.

In one embodiment, the cell wall degrading enzyme is selected from the group consisting of ferulic acid esterase, xylanase, xylosidase, cellulase, endoglucanase, and cellbiohydrolase. In a preferred embodiment cell wall degrading enzyme is derived from a fungal source. In a more preferred embodiment, the fungal ferulic acid esterase is an *Aspergillus* ferulic acid esterase, preferably *A. niger*. In another embodiment the xylanase is derived from *Trichoderma*, preferably *T. reesei*.

In another aspect of the invention, there is provided a plant transformed with the expression cassette comprising a DNA sequence encoding at least one cell degrading enzyme. The plant may be selected from the group consisting of *Festuca, Lolium, Avena* and *Zea*. In a preferred embodiment the plant is a forage grass. In another embodiment, the plant is maize.

Further provided herein is a method of controlling the level of phenolic acids in plant cell walls of a transgenic plant. The method, in one embodiment, comprises introducing to a plant cell an expression cassette comprising a DNA sequence encoding at least one cell wall degrading enzyme, preferably a ferulic acid esterase.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE FIGURES

FIG. 1 illustrates a restriction map of a DNA fragment containing the gene encoding the 38 kd ferulic acid esterase.

FIGS. 2 A-E illustrate the complete DNA (SEQ. ID NO:1), with highlighting to point out the signal sequence, intron and various restriction endonuclease sites, and amino acid sequence (SEQ. ID. NO:2) corresponding to the gene encoding the 38 kD ferulic acid esterase isolated from *Aspergillus niger*.

FIG. 3 illustrates the DNA sequence of the gene encoding the 38 kD esterase (SEQ. ID. NO:1).

FIG. 4 illustrates the construction of the intronless ferulic acid esterase isolated from *Aspergillus niger*.

FIG. 5 illustrates that the overlapping of PCR products made with primers FAE-I5 (SEQ ID NO:49) and FAE-I3 (SEQ ID NO:50) creates two possible uninterrupted reading frames—the top in the figure below is functional (SEQ ID NO:3) (highlighted serine is at active site), the bottom is inactivated (SEQ ID NO:4).

FIG. 6 illustrates the possible vector constructions useful in the present invention. Various combinations are possible. Although and FAE gene is depicted another cell wall degrading enzyme may be used alone (i.e., instead of) or in conjunction with the FAE gene. Amp=ampicillin resistance gene.

FIG. 7 illustrates pCOR105.

FIG. 8 illustrates a generic ALE-TER vector.

FIG. 9 illustrates the KDEL-COOH ER retention sequences (SEQ ID NO:6).

FIG. 10 illustrates the FAE-LINKER-FRAMESHIFT structure and sequence (SEQ ID NO:7 and 8).

FIG. 11 illustrates plant transformation cassettes.

FIG. 12 is a table of the vectors used herein.

FIG. 14 illustrates the rat sialyl transferase structure and sequence (SEQ ID NO:11 and 12).

FIG. 15 illustrates the potato protease inhibitor II (PPI) motif structure and sequence (SEQ ID NO:13 and 14).

FIG. 16 illustrates the targeted expression of gfp to different cell compartments. Also shown are schematics of the vectors used.

FIG. 17 illustrates the FAE activity in transgenic *Festuca arundinacea* leaves of different ages under ER and APO targeting sequences.

FIG. 18 illustrates the FAE activity in transgenic *Festuca arundinacea* leaves of different ages under Vac targeting sequence.

FIG. 19 illustrates the FAE activity in transgenic *Lolium mutflorum* leaves of different ages.

FIG. 20 illustrates the FAE activity in transgenic *Lolium mutflorum* leaves under Vac, ER and APO targeting sequences.

FIG. 21 illustrates the levels of esterified monomeric and dimeric hydroxycinnamic acids in *Festuca arundinacea* plants expressing FAE under Vac targeting sequence.

FIG. 22 illustrates the levels of esterified monomeric and dimeric hydroxycinnamic acids in *Festuca arundinacea* plants expressing FAE under APO and ER targeting sequence.

FIG. 24 illustrates the in vitro dry matter digestibility of leaf tissue of mature *Lolium mutflorum* plants expressing FAE under an actin promoter.

FIG. 25 illustrates the rate of fermentation and cumulative gas production in *Festuca arundinacea* cells.

FIG. 26 illustrates the in vitro fermentation of *Festuca arundinacea* cell walls from cell cultures expressing recombinant FAE1.

FIG. 27 illustrates the Time to maximum rate digestion for *Festuca arundinacea* cells.

FIG. 28 illustrates the total gas production in *Festuca arundinacea* cells.

FIG. 29 illustrates the kinetics of FAE activity by ferulic acid release from cell wall under self digestion in *Festuca arundinacea* and stimulation by xylanase.

FIG. 30 illustrates the beta-glucoronidase activity under the *Lolium* See1 senescence promoter in leaves of transgenic plants of *Lolium mutflorum*.

FIG. 31 illustrates the release of monomeric and dimeric HCAs on self digestion of leaves of vacuolar targeted FAE expressing plants.

FIG. 32A is a schematic of the pTP10-1 vector. Also shown in FIGS. 32B-32E is the 5338 bp nucleotide sequence of the vector (SEQ ID NO:15).

FIG. 33A is a schematic of the pUA4-4 vector. Also shown in FIGS. 33B-33E is the 5345 bp nucleotide sequence of the vector (SEQ ID NO:17).

FIG. 34A is a schematic of the pTU4 vector. Also shown in FIGS. 34B-34E is the 5337 bp nucleotide sequence of the vector (SEQ ID NO:19).

FIG. 35A is a schematic of the pTT5.14 vector. Also shown in FIGS. 35B-35E is the 5395 bp nucleotide sequence of the vector (SEQ ID NO:21).

FIG. 36A is a schematic of the pTP8-5 vector. Also shown in FIGS. 36B-36E is the 5337 bp nucleotide sequence of the vector (SEQ ID NO:23).

FIG. 37A is a schematic of the pTP5-1 vector. Also shown in FIGS. 37B-37E is the 5277 bp nucleotide sequence of the vector (SEQ ID NO:25).

FIG. 38A is a schematic of the pTP4a2 vector. Also shown in FIGS. 38B-38E is the 5327 bp nucleotide sequence of the vector (SEQ ID NO:27).

FIG. 39A is a schematic of the pTP3-1 vector. Also shown in FIGS. 39B-39E is the 5338 bp nucleotide sequence of the vector (SEQ ID NO:29).

FIG. 40A is a schematic of the pTU5 vector. Also shown in FIGS. 40B-40H is the 5337 bp nucleotide sequence of the vector (SEQ ID NO:31).

FIG. 41A is a schematic of the pGT6 vector. Also shown in FIGS. 41B-41H is the 4773 bp nucleotide sequence of the vector (SEQ ID NO:32).

FIG. 42A is a schematic of the pJQ5 vector. Also shown in FIGS. 42B-42I is the 5034 bp nucleotide sequence of the vector (SEQ ID NO:33).

FIG. 43A is a schematic of the pJO6.1 vector. Also shown in FIGS. 43B-43H is the 4950 bp nucleotide sequence of the vector (SEQ ID NO:34).

FIG. 44A is a schematic of the pJQ4 vector. Also shown in FIGS. 44B-44H is the 4974 bp nucleotide sequence of the vector (SEQ ID NO:35).

FIG. 45A is a schematic of the pPQ10.1 vector. Also shown in FIGS. 45B-45H is the 5164 bp nucleotide sequence of the vector (SEQ ID NO:36).

FIG. 46A is a schematic of the pJQ3 vector. Also shown in FIGS. 46B-46H is the 4965 bp nucleotide sequence of the vector (SEQ ID NO:37).

FIG. 47A is a schematic of the pUG4 vector. Also shown in FIGS. 47B-47E is the 5295 bp nucleotide sequence of the vector (SEQ ID NO:38).

FIG. 48A is a schematic of the pUB8.11 vector. Also shown in FIGS. 48B-48I is the 5001 bp nucleotide sequence of the vector (SEQ ID NO:40).

FIG. 49A is a schematic of the pTP11-1 vector. Also shown in FIGS. 49B-49E is the 5387 bp nucleotide sequence of the vector (SEQ ID NO:41).

FIGS. 50A-B illustrate the actin promoter and its corresponding nucleotide sequence (SEQ ID NO:43).

FIG. 51 illustrates the Aleurain-NPIR delete structure. The corresponding nucleotide sequences are also shown (SEQ ID NO:45).

FIG. 52 illustrates the SEE1 (senescence enhanced) promoter sequence (SEQ ID NO:46).

FIG. 53 illustrates the SEE1 (senescence enhanced) promoter sequence plus the vacuolar aleurain signal/NPIR sequence (SEQ ID NO:47 and 48).

DETAILED DESCRIPTION OF THE INVENTION

Figure 13:
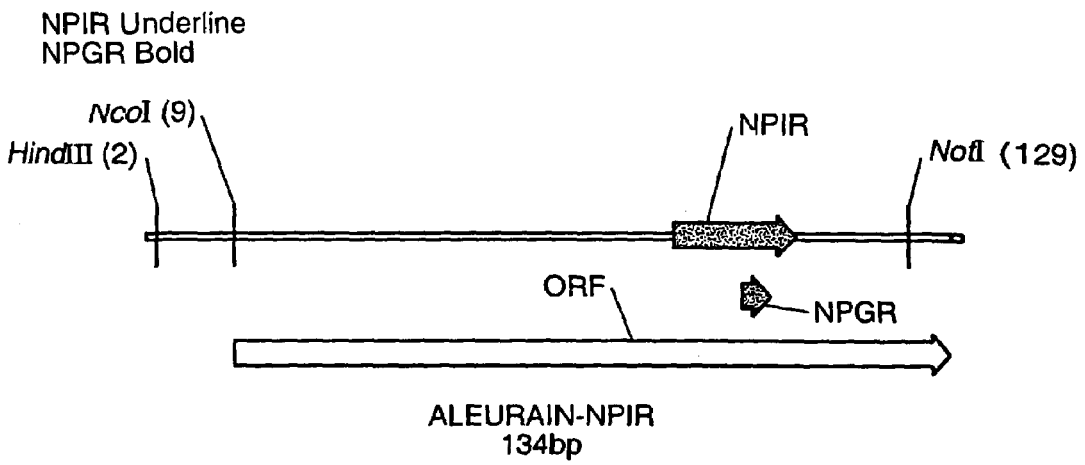
FIG. 13 depicts the barley aleurain vacuolar and apoplast signal sequence (SEQ ID NO:9 and 10).

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

DEFINITIONS

It should be noted that, as used in this specification and the appended claims, the singular forms "a," "an," "and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

"Conservatively modified variants" applies to both amino acid sequences and polynucleotides. With respect to particular polynucleotides, conservatively modified variants refers to those polynucleotides that encode identical or essentially identical amino acid sequences, or where the polynucleotide does not encode an amino acid sequence, to essentially identical sequences. Because of the degeneracy of the genetic code, a large number of functionally identical polynucleotides encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every polynucleotide herein which encodes a polypeptide also describes every possible silent variation of the nucleic acid. One of skill will recognize that each codon in a polynucleotide (except AUG, which is ordinarily the only codon for methionine) can be modified to yield a functionally identical molecule. Accordingly, each silent variation of a polynucleotide which encodes a polypeptide is implicit in each described sequence. For purposes of protein expression, there are "sub-optimal codons." These are codons that are not preferred by a particular genus or species. Altering these "sub-optimal codons" to "preferred codons" is a silent mutation in that the amino acid encoded by the codons is the same but one codon is preferentially expressed by the particular genus, e.g., *Triticum* spp.

As to amino acid sequences, one of skill will recognize that individual substitutions, deletions or additions to a polynucleotide, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

"Pyroglutamic acid" is the cyclized internal amide of L-glutamic acid

The phrase "controlling the level of phenolic acids" refers to the manipulation of phenolic acid expression in plants, particularly plant cell walls. The manipulation can be either positive; e.g., increasing the levels of phenolic acids; negative, e.g., decreasing the level of phenolic acids; or neutral, e.g., changing the relative amounts of specific phenolic acids in the cell walls but keeping the total amount relatively the same. The timing of manipulation can be during plant growth or after plant growth, e.g., after a plant has been cut or pulled from the ground or ingested. "Plant cell walls" refers to the cell walls of any cell of the plant.

The term "derived" means that a polynucleotide or protein is related to another polynucleotide or protein. The relations can be one of homology, e.g., nucleotides and proteins from certain species are homologous to similar polynucleotides and proteins of other species; analogy, e.g., proteins perform the same function and therefore are related to each other regardless of organism of origin. The relationship can be a man-made one, e.g., a protein (and a polynucleotide) can be derived from another protein by mutation; or chemical manipulation (peptidomimetics). Furthermore, a protein or a polynucleotide can be derived from an organism if, in the natural state, the protein or polynucleotide is found in one organism but recombinantly produced in another.

The term "exogenous polynucleotide" refers to a polynucleotide which is introduced into the plant by any means other than a sexual cross or sexual reproduction. Examples of means by which this can be accomplished are described below, and include *Agrobacterium*-mediated transformation, biolistic methods, electroporation, in planta techniques, and the like. Such a plant containing the exogenous polynucleotide is referred to here as an $R_1$ generation transgenic plant. Transgenic plants which arise from sexual cross or by selfing are progeny of such a plant.

The term "isolated polynucleotide molecule" or "isolated protein" refers to a polynucleotide or protein which is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated FAE1 gene is separated from open reading frames which flank the gene and encode a protein other than FAE1.

A "FAE1 encoding polynucleotide" is a nucleic acid sequence comprising (or consisting of) a coding region of an FAE 1 gene or which encodes a FAE1 polypeptide. FAE1 polynucleotides can also be identified by their ability to hybridize under low stringency conditions (see below) to nucleic acid probes having a sequence of 8 to 300 bases, preferably a sequence of 80 to 100 bases in the sequence disclosed in WO 98/14594.

The term "nucleic acid encoding," "nucleic acid sequence encoding" or "polynucleotide encoding" refers to a polynucleotide which directs the expression of a specific protein or peptide. The polynucleotides include both the DNA strand sequence that is transcribed into RNA and the RNA sequence that is translated into protein. The polynucleotides include both full length polynucleotides as well as shorter sequences derived from the full length sequences. It is understood that a particular polynucleotide includes the degenerate codons of the native sequence or sequences which may be introduced to provide codon preference in a specific host cell. The polynucleotide includes both the sense and antisense strands as either individual single strands or in the duplex form.

The term "operably linked" refers to functional linkage between a promoter and a second sequence, wherein the promoter sequence initiates transcription of RNA corresponding to the second sequence.

The term "plasmid" refers to a circular double stranded DNA molecule which comprises the coding sequence of interest, regulatory elements, a selection marker and optionally an amplification marker. A plasmid can transform prokaryotic cells or transfect eukaryotic cells. An "expression cassette" means a portion of a plasmid (or the entire plasmid) containing the regulatory elements desired for transcription, translation and/or expression and the coding region of a polynucleotide. A plasmid may contain one or more expression cassettes. If multiple expression cassettes are introduced into a plant, they can be introduced simultaneously or at different times. If simultaneous introduction is desired, the expression cassettes can be on one plasmid or more. Typically, an expression cassette comprises a promoter, poly A+ tail, and signal sequences that target the expressed polypeptide to a specific region of a cell or to be secreted, if desired. Examples of signal sequences that "target expression" of ferulic acid esterase include sequences located upstream of the FAE coding sequence. The polynucleotide that encodes the signal sequence is found preferably within the 100 nucleotides "upstream" (in the 5' direction) from the initiation codon (AUG). More preferably, the polynucleotide that encodes the signal sequence is found within the 50 nucleotides upstream from the initiation codon. Many different cellular organelles are targeted by the signal sequences used in this invention. The organelles include, but are not limited to, vacuoles, Golgi apparati, endoplasmic reticula, and apoplasts. In addition to upstream signal sequences, the expression cassette of this invention may include a polynucleotide that encodes a signal sequence at the 3' end. These signal sequences include, but are not limited to stop codons and the KDEL sequence. In addition to KDEL, other similar sequences are contemplated by this invention, including but not limited to RDEL. In addition to a KDEL sequence, a signal sequence can include a linker to a KDEL sequence. A linker is an extension of the reading frame of the encoding polynucleotide to the signal sequence. Preferably, the polynucleotide encoding the signal sequence is directly downstream from the coding sequence, more preferably less than 100 base pairs from the stop codon, more preferably less than 20 base pairs from the stop codon.

The term "polynucleotide," "polynucleotide" or "nucleic acid sequence" refers to deoxyribonucleotides or ribonucleotides and polymers thereof in either single- or double-stranded form. Unless specifically limited, the term encompasses polynucleotides containing known analogues of natural nucleotides which have similar binding properties as the reference polynucleotide and are metabolized in a manner similar to naturally occurring nucleotides. Unless otherwise indicated, a particular FAE1 polynucleotide of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al., 1992; Rossolini et al., *Mol. Cell. Probes* 8:91-98 (1994)). The term polynucleotide is used interchangeably with gene, cDNA, and mRNA encoded by a gene.

The term "polypeptide," "peptide," and "protein" are used interchangeably and refer to amino acids connected by peptide bonds. Polypeptides can be entire proteins or portions thereof. For Example. a FAE1 polypeptide may refer to the entire FAE1 protein or fragments of the FAE1 protein. A "ferulic acid esterase with an altered glycosylation site" refers to a FAE protein wherein a mutation has changed the glycosylation pattern of the protein. Mutations that effect such changes are well known in the art and include, but are not limited to, amino acid substitutions, and mutations in the proteins of the Golgi apparatus and endoplasmic reticulum that effect glycosylation of proteins.

The term "promoter" refers to a polynucleotide that directs expression of a coding sequence. A promoter can be constitutive, i.e., relatively independent of the stage of differentiation of the cell in which it is contained or it can be inducible, i.e., induced be specific environmental factors, such as the length of the day, the temperature, etc. or a promoter can be tissue-specific, i.e., directing the expression of the coding sequence in cells of a certain tissue type. A "senescence" promoter is an inducible promoter that causes transcription to be initiated upon a certain event relating to age of the organism. A "heat shock promoter" is an inducible promoter that causes transcription to be initiated upon a change in temperature. An example of a heat shock protein promoter is the Soybean Gmhsp promoter. In addition to these inducible promoters, one of skill will realize that other inducible promoters can be used. For example, a wound induced promoter, like LAP. See, U.S. Pat. No. 5,962,670.

The term "purified" denotes that a polynucleotide or protein gives rise to essentially one band in an electrophoretic gel. Particularly, it means that the polynucleotide or protein is at least 85% pure, more preferably at least 95% pure, and most preferably at least 99% pure.

The term "specifically hybridizes" refers to a nucleic acid probe that hybridizes, duplexes or binds to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., MOLECULAR CLONING: A LABORATORY MANUAL (2ND ED.), Vols. 1-3, Cold Spring Harbor Laboratory, (1989) ("Sambrook") or CURRENT PROTOCOLS IN MOLECULAR BIOLOGY, F. Ausubel et al., ed. Greene Publishing and Wiley-Interscience, New York (1987) ("Ausubel").

The term "stringent conditions" in the context of polynucleotide hybridization experiments such as Southern and northern hybridizations refers to sequence dependent, binding and washing environments. An extensive guide to the hybridization of polynucleotides is found in Tijssen (1993) LABORATORY TECHNIQUES IN BIOCHEMISTRY AND MOLECULAR BIOLOGY—HYBRIDIZATION WITH NUCLEIC ACID PROBES part I chapter 2 "overview of principles of hybridization and the strategy of nucleic acid probe assays", Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary polynucleotides which have more than 100 complementary residues on a filter in a Southern or northern blot is 50% formalin with 1 mg of heparin at between 40 and 50° C., preferably 42° C., with the hybridization being carried out overnight. An example of highly stringent wash conditions is 0.15M NaCl at from 70 to 80° C. with 72° C. being preferable for about 15 minutes. An example of stringent wash conditions is a 0.2×SSC wash at about 60 to 70° C., preferably 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 40 to 50° C., preferably 45° C. for 15 minutes. An example low stringency wash for a duplex of, e.g., more than 100 nucleotides, is 4-6×SSC at 35 to 45° C., with 40° C. being preferable, for 15 minutes. In general, a signal to noise ratio of 2× (or higher) than that observed for an unrelated probe in the particular hybridization assay indicates detection of a specific hybridization. Polynucleotides which do not hybridize to each other under stringent conditions are still substantially identical if the polypeptides which they encode are substantially identical. This occurs, e.g., when a copy of a polynucleotide is created using the maximum codon degeneracy permitted by the genetic code.

The term "transgenic plant" refers to a plant into which exogenous polynucleotides have been introduced and their progeny. Typically, cells of a plant are transformed with the exogenous polynucleotide and a transgenic plant is regenerated from the transformed cells. The regenerated plant is then bred to produce a strain of transgenic plants.

"Xylanase" (EC 3.2.1.8) refers to a well described class of gylcosyl hydrolases that hydrolize xylan. Commercial applications of xylanase include the degradation and bleaching of wood pulp for paper making. Xylanase can also be added to animal feed to improve the digestibility of plant matter. Typically, commercial xylanase is derived from fungi. A preferred xylanase is derived from *Trichoderma*.

PREFERRED EMBODIMENTS

Plant cell walls contain a range of alkali-labile ester-linked phenolic acids. In particular, grass cell walls are characterized by the presence of large amounts of esterified ferulic and p-coumaric acids (mainly in their E configurations), linked to arabinoxylans at the C5 of arabinose. These are released as ferulated oligosaccharides (FAX and PAX) by cellulase treatment but in vivo provide a substrate for peroxidase-catalyzed cross-linking of cell wall polysaccharides and lignin. The high levels of these phenolic acids and their dimers have a dramatic influence on the mechanical properties, digestibility and rates of digestion of grasses by ruminants.

Previous work has shown that ferulic acid is the predominant p-hydroxycinnamic acid esterified to grass polysaccharide but until recently the only ferulic acid dehydrodimer to have been isolated was 5,5'-diferulic acid. Recently new dehydrodiferulate dimers and cyclobutane-type dimer mixtures have been isolated from plant cell walls (Waldron, et al., *Phytochemical Analysis* 7:305 (1996)). As can be seen in FIG. 1, these mixtures are present in large amounts in grass cells. Ether linked ferulic acid-coniferyl alcohol dimers, have also been isolated from cell walls (Jacquet, et al., *Polyphenol Comm. Bordeaux* pp 451 (1996)) establishing for the first time that ferulate esters are oxidatively co-polymerized with lignin precursors which may anchor lignins to cell wall polysaccharides. The yield of these dimers in grass cells indicates that phenolic dehydrodimer cross-linking of cell wall polysaccharides is much more extensive than was previously thought.

An enzyme system has been reported from parsley endomembranes that catalyses the ferulation of endogenous polysaccharide acceptors from feruloyl CoA, pointing to the ER/golgi as the site of polysaccharide esterification and the CoA ester as the physiological co-substrate (Meyer, et al., *FEBS Lett.* 290:209 (1991)). Further evidence for this has been found in water-soluble extracellular polysaccharides excreted in large amounts into the medium by grass cell cultures. This material is highly esterified with ferulic and p-coumaric acid at levels similar to the cell walls of the cultured cells.

Feruloyl esterase activity has been detected in several fungal species including, anaerobic gut fungi, yeasts, actinomycetes, and a few fiber-degrading ruminal bacteria, which enables them to de-esterify arabinoxylans and pectins.

Two ferulic acid esterases (FAE), distinguished on the basis of molecular weight and substrate specificity, have been isolated from *Aspergillus niger* and have been shown to quantitatively hydrolyze ferulic acid and release dehydrodiferulate dimers from plant cell walls. Furthermore, FAE has been observed to act synergistically with xylanase to release ferulic acid from plant cell walls at a higher rate. Recently, a ferulic acid esterase (FAE) gene has been cloned from *Aspergillus niger* (Michelson, et al. European Patent Application No. 9510370.1). The inventors have found the recombinant enzyme releases ferulic acid and diferulate dimers from grass cell walls in a concentration dependent manner and that this enzyme is stable at 30° C. pH 5.0 in the presence of substrate and has a half life of 61 h at 30° C. in the presence of vacuolar extracts (pH 4.6) of grass cells. This gene was, therefore, a candidate for targeted and inducible expression of FAE in grasses (e.g., *Lolium multiflorum*).

The present invention provides for methods of changing the cell wall structure of transgenic plants and therefore, making them more digestible. The method comprises introducing a ferulic acid esterase coding sequence into the cells of a plant. Operably linked to the coding sequence is a promoter that can be either constitutive or inducible and signal sequences that serve to target expression of the coding sequence in the desired organelle in the desired cell of the plant. The signal sequences can be either or both N terminal or C terminal sequences.

Optionally, a second and/or third coding sequence is introduced into the plant. It is preferred that a fungal xylanase coding sequence be coexpressed with the FAE coding sequence.

This invention also provides for transgenic plants which contain FAE1 coding sequences, leading to more digestible grasses.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook, et al., MOLECULAR CLONING, A LABORATORY MANUAL, 2ND ED. (1989); Kriegler, GENE TRANSFER AND EXPRESSION: A LABORATORY MANUAL (1990); and Ausubel et al., (eds.), CURRENT PROTOCOLS IN MOLECULAR BIOLOGY (1994)).

A. Isolation of Polynucleotides

The isolation of the polynucleotides, e.g., FAE1 and xylanase of the invention may be accomplished by a number of techniques. See, for example, U.S. Pat. No. 6,368,833 which describes the isolation of a FAE from *Aspergillus niger*, and U.S. Pat. No. 6,555,335 which describes the isolation of a xylanase from *T. reesei*.

For instance, oligonucleotide probes based on the sequences cited here can be used to identify the desired gene in a cDNA or genomic DNA library from a desired species. To construct genomic libraries, large segments of genomic DNA are generated by random fragmentation, e.g., using restriction endonucleases, and are ligated with vector DNA to form concatemers that can be packaged into the appropriate vector. To prepare a library of cDNA from a specific cell culture, e.g., *Aspergillus niger*, mRNA is isolated from the culture and a cDNA library containing the gene transcripts is prepared from the mRNA.

The cDNA or genomic library can then be screened using a probe based upon the sequence of a known polynucleotide such as the polynucleotides cited here. Probes may be used to hybridize with genomic DNA or cDNA sequences to isolate homologous genes in the same or different plant species. In addition to probes derived from known polynucleotides, degenerate probes may be used. Techniques for making and using degenerate probes are well known in the art and can be found in Sambrook and Ausubel.

Alternatively, the polynucleotides of interest can be amplified from polynucleotide samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone polynucleotides that code for proteins to be expressed, to make polynucleotides to use as probes for detecting the presence of the desired mRNA in samples, for polynucleotide sequencing, or for other purposes.

Appropriate primers and probes for identifying ferulic acid esterase-specific genes, as well as xylanase sequences, from fungi and plant tissues are generated from comparisons of the sequences provided herein. For a general overview of PCR see PCR PROTOCOLS: A GUIDE TO METHODS AND APPLICATIONS, (Innis, M, Gelfand, D., Sninsky, J. and White, T., eds.), Academic Press, San Diego (1990). Reaction components are typically: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per mL Taq polymerase. Program: 96° C. for 3 min., 30 cycles of 96° C. for 45 sec., 50° C. for 60 sec., 72° C. for 60 sec, followed by 72° C. for 5 min.

Polynucleotides may also be synthesized by well-known techniques as described in the technical literature. See, e.g., Carruthers, et al., *Cold Spring Harbor Symp. Quant Biol.* 47:411-418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Suitable sources for the ferulic acid esterase used in this invention include but are not limited to, *Neurospora crassa*, *Aspergillus* spp. and specifically, *Aspergillus niger*. The xylanase used in this invention can be derived from any suitable source including, but not limited to, *Trichoderma reesei* and *Aspergillus* spp.

B. Preparation of Recombinant Vectors

To use isolated sequences in the above techniques, recombinant DNA vectors suitable for transformation of plant cells are prepared. Techniques for transforming a wide variety of plant species are well known and described in the technical and scientific literature. See, for example, Weising, et al., *Ann. Rev. Genet.* 22:421-477 (1988). A DNA sequence coding for the desired polypeptide, for example a cDNA sequence encoding the full length FAE1 protein, will preferably be combined with transcriptional and translational initiation and targeting regulatory sequences which will direct the transcription of the sequence from the gene in the intended tissues of the transformed plant under the desired conditions.

Promoters can be identified by analyzing the 5' sequences of a desired gene. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. Messing, et al., in GENETIC ENGINEERING IN PLANTS, pp. 221-227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855-866 (1989); Bustos, et al., *Plant Cell* 1:839-854 (1989); Green, et al., *EMBO J.* 7:4035-4044 (1988); Meier, et al., *Plant Cell* 3:309-316 (1991); and Zhang, et al., *Plant Physiology* 110: 1069-1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, the actin and ubiquitin promoters and other transcription initiation regions from various plant genes known to those of skill. A particularly preferred constitutive promoter is the rice actin promoter (see, McElroy, *Plant Cell*, 2:163 (1990)).

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as leaves, roots or seeds.

In one aspect of the instant invention, expression of FAE occurs after the plant has been cut, removed from the ground or ingested. Thus an appropriate promoter would be a senescence promoter. For example, BFN1 has recently been shown to be a nuclease expressed in senescing leaves, Perez-Amador, et al., *Plant Physiol.* 122:169 (2000). Similarly, SAG12, a cysteine protease is also found in senescing leaves (Noh & Amasino, *Plant Mol. Biol.* 41:181 (1999). In a preferred embodiment, the promoter from the gem gene of *Festuca pratensis* is used to direct expression of FAE in senescing leaves.

In another aspect, the FAE would be expressed upon ingestion by a foraging animal. Exemplary promoters for this aspect would include Soybean Gmhsp 17.5 promoter and the leucine aminopeptidase (LAP) promoter. The GMhsp promoter is from a heat shock protein gene and initiates expression if the temperature of the environment is increased. In the laboratory, an increase of 15° C. for 2 hours is the preferred heat shock. However, in non-laboratory conditions suitable increases in temperature will occur in silos and in the rumen of animals that have ingested the plants of this invention. The LAP promoter initiates the expression of the FAE gene upon wounding of the plant. Such wounding would occur after cutting the plant or after mastication by a foraging animal. Tissue specific promoters that could be used in this invention include promoters of genes that are differentially expressed in the leaves of grasses. An example of a leaf specific promoter is the rbcS promoter of tomato (*Proc. Nat'l Acad. Sci. USA* 84:7104 (1987)). This promoter normally regulates a gene determined to be important in photosynthesis.

For proper polypeptide expression, a polyadenylation region at the 3'-end of the coding region should be included. The polyadenylation region can be derived from the natural fungal gene, from a variety of other fungal or plant genes, or from T-DNA. These sequences are well known and readily available to those of skill in the art.

In addition to a promoter and poly A+ sequences, the preferred expression vectors of this invention also will contain signal sequences. These are polynucleotides found at the 5' and/or 3' ends of the coding region and serve to target expression of the gene to specific cellular organelles. These signal sequences can be both upstream or downstream of the coding region. Some preferred examples of upstream signal sequences include the barley aleurain sequence (Rogers, *Proc. Nat'l Acad. Sci. USA* 82:6512 (1985) which targets vacuoles and the *Aspergillus* apoplast signal. This signal sequence targets expression to the apoplast.

In addition to targeting expression to specific organelles, it may be desirable to retain the expressed FAE in the Golgi or endoplasmic reticulum. The well known ER retention signal, KDEL (SEQ ID NO:97), can be added to the 3' end of the coding polynucleotide.

The vector comprising the expression cassettes (e.g., promoters and/or coding regions) of the invention will typically comprise a marker gene which confers a selectable phenotype on plant cells. For example, the marker may encode biocide resistance, particularly antibiotic resistance, such as resistance to hygromycin, kanamycin, G418, bleomycin, or herbicide resistance, such as resistance to chlorosluforon or Basta.

C. Production of Transgenic Plants

DNA constructs of the invention may be introduced into the genome of the desired plant host by a variety of conventional techniques. For example, the DNA construct can be introduced directly to plant tissue using ballistic methods, such as DNA particle bombardment or the constructs may be introduced directly into the genomic DNA of the plant cell using techniques such as electroporation and microinjection of plant cell protoplasts. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

See Dalton et al. (Co-transformed, diploid *Lolium perenne* (Perennial Ryegrass), *Lolium multiflorum* (Italian Ryegrass) and *Lolium temulentum* (Darnel) plants produced by microprojectile bombardment. Plant Cell Reports (1999) 18(9), 721-726) for exemplary methods for culturing and transformation of grasses.

Microinjection techniques are known in the art and well described in the scientific and patent literature. The introduction of DNA constructs using polyethylene glycol precipitation is described in Paszkowski, et al., *Embo J.* 3:2717-2722 (1984). Electroporation techniques are described in Fromm, et al., *Proc. Natl. Acad. Sci. USA* 82:5824 (1985).

*Agrobacterium tumefaciens*-mediated transformation techniques, including disarming and use of binary vectors, are well described in the scientific literature. See, for example Horsch, et al., *Science* 233:496-498 (1984), and Fraley, et al., *Proc. Nat'l. Acad. Sci. USA* 80:4803 (1983). U.S. Pat. No. 5,591,616 discloses *Agrobacterium* mediated transformation techniques in monocotyledons.

Ballistic transformation techniques are described in Klein, et al., *Nature* 327:70-73 (1987). In a preferred embodiment, a particle in-flow gun (PIG) is used to transform the plant cells of this invention.

Transformed plant cells which are derived by any of the above transformation techniques can be cultured to regenerate a whole plant that possesses the transformed genotype and thus the desired phenotype such as improved digestibility. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124-176, Macmillian Publishing Company, New York, 1983; and Binding, REGENERATION OF PLANTS, PLANT PROTOPLASTS, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987).

To determine the presence of or increase of FAE1 activity, an enzymatic assay can be used or an assay to measure increases and decreases in rates of fermentation. These assays are readily available in the literature and those of skill in the art can readily find them.

One of skill will recognize that other assays can be used to detect the presence or absence of FAE1. These assays include but are not limited to; immunoassays and electrophoretic detection assays (either with staining or western blotting).

The polynucleotides of the invention can be used to confer desired traits on essentially any plant. However, the main utility of this invention is in the improved digestibility of forage plants. Thus, it is envisioned the transgenic plants of this invention will include but not be limited to the following genera *Lolium, Festuca, Triticum, Avena,* and *Medicago*. The FAE1 genes of the invention are particularly useful in the production of transgenic plants in the genus *Lolium*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

As mentioned above, the transgenic plants of this invention can be used as a foraging crop for animals, such as cattle, sheep, goats and horses. In addition, the methods of this invention can be used to transform any plant into which FAE expression is desired. For example, it is advantageous to break down cell walls during biomass conversion or during processing of plants for foodstuffs. This invention would help to achieve this goal more effectively and inexpensively.

The inventive methods herein may also be used to provide additional enzymes to enhance the availability of fermentable sugars in plants. Plant carbohydrates may be subject to further modification, either exogenously or endogenously, by the action of other enzymes. Such enzymes include, but are not limited to, endoglucanases, xylosidases and/or cellbiohydrolases. These enzymes may be provided either in an expression cassette provided for herein (i.e., endogenous) or applied to the plant cell walls (i.e., exogenous) to enhance the availability of mono- and/or di-saccharides.

Plants other than grasses may find a use in the present invention. For example, corn (or maize) is specifically contemplated to be useful. The grass *Festuca* is similar to maize in cell wall structure and therefore provides a good model of the ability to enhance fermentable carbohydrates in corn. Other useful plants contemplated for use in the present invention are *Festuca, Lolium, Zea, Avena, Sorghum, Millet* (tropical cereals), *Miscanthus* (a grass with potential for use as a biomass energy crop), *Cenchrus, Dichanthium, Brachiaria* and *Paspalum* (apomictic tropical range grasses) and *Poa* (Kentucky bluegrass).

Cell walls of forage grasses makes up 30-80% of forage dray matter representing a major source of energy for ruminants, but less than 50% of this fraction is digested by the animal. Conversion of low-value biomass to sugars and ethanol is also less than optimal due to the carbohydrate unavailability of the feedstocks, including but not limited to bagasse, race straw, corn stover and corn fiber.

Ferulic and other hydroxycinnamic acids are ester linked to arabinosyl residues in arabinoxylans, and play a key role in crosslinking xylans to liginin, resulting in less degradable cell walls. Ferulic acid esterase (FAE) can release both monomeric and dimeric ferulic acid (FA) from arabinoxylans making the cell wall more susceptible to further enzymatic attack. Transgenic plants have been produced expressing an FAE gene following microprojectile bombardment of cell cultures. Measurements of the level of FAE activity from different vectors targeting FAE to the vacuole, ER and apoplast under constitutive or inducible (heat shock) promoters shows that at least for constitutive expression of vacuolar targeted FAE, the activity was highest in young leaves and increased along the leaf lamina. We also show that FAE expression results in release of monomeric and dimeric FA from cell walls on cell death and this was enhanced several fold by the addition of xylanase. An effect of FAE expression on the monomeric and dimeric cell wall ester linked ferulate content in comparison to control (non-transformed) plants is seen. Generally, the lower the levels of monomers and, in particular, dimers of hydroxycinnamic acids in leaves, the higher the digestibility and/or availability of complex carbohydrates for conversion.

Senescence is the terminal phase in leaf development and occurs without grouth or morphogenesis. Therefore the metabolism/physiology of this stage of the leaf's lifespan can be targeted directly for alteration with minimal detrimental impact on early development. Senescence follows leaf maturity and is associated with the expression of specific genes. These genes and their controlling elements can be exploited to manipulate development, adaptation, productivity and quality traits in crop plants. There seems to be good conservation of senescence physiology across the range of higher plant species and thus these promoters are useful in the present invention.

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); Et (ethyl), Me (methyl).

EXAMPLE 1

Preparation of Enzyme Encoding DNA Sequences

A genomic clone for FAE1 (see FIGS. 1-3, SEQ ID NO:1 and 2) was used as the starting point for the preparation of an intronless FAE1 encoding DNA sequence. The sequence for the genomic clone is given in FIGS. 2 and 3 (SEQ ID NO:1 and 2). Separate fragments for both FAE exons were recovered by PCR from a 5.5 kb EcoRI fragment of the genomic clone in pLITMUS28, and 'cDNA' created by overlapping PCR. See FIG. 4.

Two 5' primers were used. FAE-S5 which amplifies the entire reading frame (including the *Aspergillus* signal), and FAE-N5 which amplifies only the mature protein (i.e. has no signal). A number of codons are optimized (underlined in primer sequences below). The overlap product may be derived from either FAE-I5 (wild type, SEQ ID NO:49) or FAE-I3 (conserved Ser changed to Ala, SEQ ID NO:50) primers, allowing production of enzymatically inactive protein to check toxicity. As shown in FIG. 5, overlapping of PCR products made with FAE-I5 and FAE-I3 creates two possible uninterrupted reading frames (SEQ ID NO:3 and 4). If the complement to FAE-I5 serves as the template when recombined then the encoded protein retains the serine moiety and the esterase is functional (highlighted serine is at active site, SEQ ID NO:95). If the FAE-I3 primer serves as the template the serine is replaced with an alanine and the esterase is inactivated (highlighted alanine in bottom amino acid sequence given in FIG. 5, SEQ ID NO:96).

Where possible, codon usage has been optimized optimized in constructed reading frames (codon choice based on published barley preferences).

```
FAE-I5
                                                (SEQ ID NO: 49)
GGCGCCGAGGGAGTGGCCGGTCACGGTCAGCGCGTAGTCC  40-mer FAE-I3
                                                (SEQ ID NO: 50)
CCGGCCACGCCCTCGGCGCCTCCCTGGCGGCACTC  35-mer FAE-N5
                                                (SEQ ID NO: 51)
CTAAAGCTTACCATGGCGGCCGCCTCCACGCAGGGCATCTCCGA
44-mer FAE-S5
                                                (SEQ ID NO: 83)
CTAAAGCTTAACATGAAGCAGTTCTCCGCCAA  32-mer FAE-3
                                                (SEQ ID NO: 52)
TCTAAGCTTGCGGCCGCGACCGGCCAGGTGCATGCGCCGCTCGTCATCCC
50-MER
```

EXAMPLE 2

Preparation of Vectors

Vectors had the general structure shown in FIG. 6.

A. Plant Transformation Vector Series

Initial expression vectors were based on pCOR105 [rice actin promoter—McElroy et al. MGG 231:150-160 (1991)] (FIG. 7). pCOR105 Not and SstII sites were first destroyed [cut with NotI and SstI, followed by heat inactivation and T4 DNA polymerase treatment in the presence of dNTPs] using standard methods as described in Maniatis et al. or following the manufacturer's instructions for enzymes to simplify subsequent Not cassette manipulation and allow use of unique Sst site (see below).

The nos terminator from pMA406 (Ainley & Key (1990) PMB 14:949-60) was amplified by PCR using primers TER5 and TER3 to generate a fragment with the following sequence (SEQ ID NO:53):

```
  (PstI)     (Not 1)
(AGACTGCAGACCATGGCGGCCGCGKAACCACTGAAGGATGAGCTGTAAAG

AAGCAGATCGTTCAAACATTTGGCAATAAAGTTTCTTAAGATTGAATCCT

GTTGCCGGTCTTGCGATGATTATCATATAATTTCTGTTGAATTACGTTAA

GCATGTAATAATTAACATGTAATGCATGACGTTATTTATGAGATGGGTTT

TTATGATTAGAGTCCCGCAATTATACATTTAATACGCGATAGAAAACAAA

ATATAGCGCGCAAACTAGGATAAATTATCGCGCGCGGTGTCATCTATGTT

ACTAGATCGATAAGCTT CTA GATCT (HindIII)  (XbaI)
(where K = G or T)
```

A redundancy in the TER5 primer (GCGKAA) creates fragments having either a stop codon (TAA) or glutamate codon (GAA) in one reading frame. The glutamate codon is in frame with a downstream KDEL motif.

The fragment and modified pCOR105 vector were cut with PstI and XbaI, according to manufacturers instructions, relevant fragments gel-purified, ligated with T4 DNA ligase and transformed into E. coli. Resulting clones were then sequenced to establish which TER5 alternatives were present.

Initial FAE expression vectors were then constructed from these vectors by inserting FAE-S5/FAE-3 PCR products (T4 DNA polymerase 'polished' in the presence of dNTPs, purified and digested with NotI, cloned into EcoRV and NotI digested vector) or FAE-N5/FAE-3 PCR products (purified and NotI digested, cloned into NotI digested and calf intestinal alkaline phosphatase treated vector).

The initial pCOR105-nos terminator clones were also modified by the addition of ALE-5/ALE-3 PCR products (encoding wild-type and modified barley aleurain signal peptides, see below for details). The products were 'polished' with T4 DNA polymerase in the presence of dNTPs, purified and cut with NotI, then cloned into EcoRV and NotI digested vectors. Addition of the ALE sequences creates a series of vectors which can express a reading frame inserted at the NotI or NcoI sites as a fusion to the barley aleurain signal, with or without vacuolar targeting motif, and with or without an ER retention motif. HindIII sites flanking the translation initiation codon and transcriptional terminator allow easy movement of transcription units between expression vectors providing different promoter sequences. (See FIG. 8 depicting the generic ALE-TER vector.)

Vector sequences were confirmed by sequencing. Two artifacts were found. Firstly, the redundant codon in TER5 was found to be AAA in one clone, which was subsequently used as the source of all KDEL fusions (ie peptide sequence is KPLKDEL (SEQ ID NO:85), rather than EPLKDEL (SEQ ID NO:86) as designed). See FIG. 9. Secondly, an additional base is found at the site of the redundant codon in one clone, creating a frameshifted terminal peptide (ETTEG, FIG. 10 (SEQ ID NO:87) which was used as a control in some constructs.

Exploitation of the modular arrangement of signal peptides in the above vector series allowed various combinations of FAE and targeting motifs to be created using standard molecular biology procedures (i.e., restriction digest, purification of relevant fragments and ligation as appropriate). For example, the NotI fragment containing the FAE reading frame was inserted into the NotI site of the frameshifted clone described above to create vector pTP3.1. The native *Aspergillus* COOH-terminus was inserted into a FAE-S5/FAE-3 clone as a SphI (T4 DNA polymerase polished)—NcoI fragment from the FAE genomic clone (replacing the NotI (T4 DNA polymerase polished)—NcoI fragment), creating vector pTP4a2, which then encodes the entire, unmodified, *Aspergillus* FAE. Replacement of the SalI/XbaI fragment of pTP3.1 with that of pTP4a2 then created pTP11.1, which encodes FAE with a native *Aspergillus* COOH-terminus but a barley aleurain N-terminal signal.

Briefly, other vectors made in this series were; pTP8.5, the FAE NotI fragment inserted into the NotI site of an ALE-frameshifted COOH-terminus construct, aleurain N-terminus; pTP5.1, replacement of the native *Aspergillus* COOH terminus with a KDEL peptide (NotI/XbaI fragment exchange), *Aspergillus* N-terminal signal retained; pTU4.4, BamHI fragment of pTP11.1 replaces BamHI fragment of pTP5.1, creates FAE reading frame fused to heterologous N- and C-termini (aleurain signal and KDEL).

Vectors in which the aleurain vacuolar targeting motif NPIR was replaced by NPGR (found to be inactive in some plant assays) were created by replacing an EcoRV/NotI fragment with ALE PCR product which had been cut with AccI (T4 DNA polymerase polished) and NotI (vectors pTT5.5 and pTT5.14, *Aspergillus* COOH-terminus). The BamHI fragment of pTT5.5 was used to replace that of pTP5.1 to produce pTU5, creating an FAE reading frame fused to heterologous N- and C-termini (NPGR modification of aleurain signal and KDEL). The aleurain signal was also modified by PCR mutagenesis to remove the vacuolar targeting NPIR motif in its entirety (directed by primer ALECUT, which contains a NotI site to allow exchange of BglII/NotI fragments). NPIR deletion was created in this way in pTP11.1 (creating pUA4.4), and in pTP5.1 by exchange of BamHI fragments with pUA4.4 (creating pUG4).

Finally, PCR mutagenesis, using overlap of fragments generated by primers GLY3 and GLYB, was also used to alter a potential glycosylation site (asparagine codon changed to aspartate, as carried out for example in Chen, H. M., C. Ford & P. J. Reilly (1994) Biochem J 301 275-281 Substitution of asparagine residues in *Aspergillus awamori* glucoamylase by site-directed mutagenesis to eliminate N-glycosylation and inactivation by deamidation; see sequence data for exact change, vector pTP10.1).

```
PCR primers
TER-5
AGACTGCAGACCATGGCGGCCGCGKAACCACTGAAG   (SEQ ID NO:54)
GATGAGCTGTAAAGAAGCAGATCGTTCAAACATTTG
72-MER (The KDEL stop codon is
underlined.)

TER-NOT
AAGACTGCAGACCATGGCGG 20-MER            (SEQ ID NO:55)

TER-3
AGATCTAGAAGCTTATCGATCTAGTAACATAGA      (SEQ ID NO:56)
TGACACC

ALECUT
CTAGGCGGCCGCGCGGGAGGAGGCGACGGCGAC      (SEQ ID NO:57)

GLYB
GAGGGTGTATTCGGTATCGAGTTGCAGGTTCGTATC   (SEQ ID NO:58)

GLY3
CTCGATACCCATTACACCCTCACGCCTTTCGA       (SEQ ID NO:59)
```

B. Construction of Different Promoter Vectors

Various promoters were used to optimize expression and to establish constitutive, heat-shock inducibility and senescence enhancement.

i. Rice Actin Promoter and 1$^{st}$ Intron

Initial vectors (FIGS. 11 and 12) were constructed from pCOR105 which was subsequently found to contain a 5 bp deletion relative to the published sequence which destroys the AccI site (GTAGGTAGAC, SEQ ID NO:60 deleted bases underlined) and may affect splicing at the adjacent 3' site. The original rice actin sequence in this region (GTAGGTAG, SEQ ID NO:84) was therefore restored using oligonucleotide NCO-ACT (CTCACCATGGTAAGCTTCTACC TACAAAAAAGCTCCGCA, SEQ ID NO:61) by replacing the BglII/HindIII fragment with a PCR product, to produce vector pPQ10.1.

A rice repetitive element is present in the upstream region of the actin promoter used in pCOR105; as this may have unpredictable effects on vector expression it was removed from pPQ10.1 by deletion of the KpnI/EcoRI fragment (end-filled with T4 polymerase and ligated following digest, restoring EcoRI but not KpnI, to produce vector pGT6. The HindIII fragment containing the FAE reading frame and nos terminator of pTP3.1 (see Example 2A) was then inserted into pGT6 to produce construct pJO6.3.

ii. Soybean Heat-Shock Promoter

A soybean heat shock promoter from a 23 kD HSP was obtained from pMA406 (Ainley & Key (1990) PMB 14:949-60). This promoter when fused to β-glucuronidase (Jefferson et al 1987 EMBO J. 6:3901-3907) had previously been shown to be inducible by a 10° C. heat-shock and show stable expression for 24-48 hours (data not shown). β-glucuronidase fusions are a sensitive and versatile fusion marker in higher plants. The construction of the co-integration HS vectors is given below.

iii. Senescence Enhanced Expression (See 1) Promoter from *Lolium multiflorum*

The promoter and signal sequence (including NPIR motif) of the LSee1 gene was amplified from *Lolium multiflorum* cv Tribune with oligonucleotides SEE-NCO and SEE-VAC, and cloned as an Asp718/NotI replacement of the promoter region of vector pTP11.1. Following sequencing to screen for PCR artifacts, one of three identical clones was chosen (pUB8.11).

The See1 promoter from maize has been cloned previously and has EMBL accession number is AX050343. See WO0070061.

The *Lolium* version of See1 was also cloned previously (Qiang Li (2000) Studies on leaf senescence and its genetic manipulation in *Lolium mutiflorum* PhD Thesis University of Wales, Aberystwyth) and has been shown to be senescence inducible when used to drive both β-glucuronidase and the *Agrobacterium* ipt gene.

An apoplast-targeted derivative was constructed by amplifying the Potato Protease Inhibitor (PPI) motif with primers PPI-AP6 and SEE-ATG, and cloning the product as an NgoMIV/NotI fragment into pUB8.11 (NgoMIV partial digest), to produce vector pJQ5.2. This vector has both the senescence induced promoter and the apoplast target sequence with the gene to be expressed inserted downstream of the apoplast sequence.

```
PCR Primers
SEE-VAC
AACCATGGCGGCCGCGCGCTCGGTGACGGGCCGGAT   (SEQ ID NO: 62)

SEE-NCO
TTCGGTACCATGGCCAGGTATAATTATGG          (SEQ ID NO: 63)

SEE-ATG
CTGCGCCGGCGAGATGGMCGTGCACAAGGAG        (SEQ ID NO: 64)
```

C. Construction of Targeting Sequences

In order to examine whether or not the localization of the enzyme would have an effect on the phenolic acid content of the cell wall various signal sequences were utilized. The targeting sequences were added either to the N-terminus or to the C-terminus of the gene of interest.

i. N-Terminal Signal Sequences

Six N-terminal signal sequences were utilized:

(a) The native *Aspergillus* end of FAE, plus excretion signal [apoplast localisation]

This is from the original clone and has the peptide sequence: MKQFSAKHVLAVVVTAGHALAASTQGI (SEQ ID NO:88).

(b) The mature *Aspergillus* end, with no excretion signal [cytoplasmic localisation]

Peptide sequence is MAAASTQGI (SEQ ID NO:89) (underlined motif is common to all constructs). Truncation of the signal sequence in (a) above was carried out by PCR with mutagenic primer FAE-N5.

(c) The barley aleurain signal, including intact NPIR motif [vacuole localisation]

The barley aleurain vacuolar signal sequence (See FIG. 13; Swissprot database accession number P05167, SEQ ID NO:10) was derived entirely from overlapping primers (ALE-5, ALE-3, ALE-CUT ALE-CAP-5 and ALE CAP-3). Following primer annealing at 37° C. and extension with T4 DNA polymerase in the presence of dNTPs according to manufacturers instructions, PCR with flanking primers ALE-5 and ALE-3 was carried out. The product was 'polished' with T4 DNA polymerase, purified, digested with NotI and cloned into EcoRV/NotI digested pCOR105-nos terminator vector (see above). ALE-3 contains redundancies so that clones encoding NPIR or NPGR motifs may be recovered. Two versions of the signal, with and without the vacuole targeting motif, were produced, to give putative vacuolar NPIR and apoplast (NPGR) signal sequences.

```
PCR Primers
ALE-5
GGAATTCGTAGACAAGCTTACMATGGCCCACGCCCG    (SEQ ID NO: 65)
CGTCCT 41-MER ALE-3
TATCCATGGCGGCCGCGCGGTCGGTGACGGGCCGGM    (SEQ ID NO: 66)
YCGGGTTGGAGTCGGCGAA 55-MER ALE-CUT
CTAGGCGGCCGCGCGGGAGGAGGCGACGGCGAC       (SEQ ID NO: 67)
33-mer ALECAP-5
GCGACGGCGACGGCGGCCGTGGCCAGCACGGCGAGC    (SEQ ID NO: 68)
GCCAGGAGGAGGACGCGG 54-MER

ALECAP-3
TCGCCGTCGCCTCCTCCTCCTCCTTCGCCGACT       (SEQ ID NO: 69)
33-MER
```

(d) The barley aleurain signal, mutated to a NPGR motif [cytoplasmic localisation]
(e) The rat sialyl transferase golgi targeting motif [golgi localisation]

A Golgi targeting vector, pJQ3.2, was made by inserting a reading frame encoding the relevant rat sialyl transferase (RST) motif (See FIG. 14, SEQ ID NO:11 and 12. RST motif shown to function in plants by Boevink P, Oparka K, Cruz S S, Martin B, Betteridge A, Hawes C, (1998) PLANT JOURNAL 15 441-447 Stacks on tracks: the plant Golgi apparatus traffics on an actin/ER network) into vector pPQ10.1, and replacing the EcoRI/NotI promoter/signal fragment of pJO6.3 with the fragment from this vector. Briefly, the RST motif was constructed by annealing oligonucleotides RST-F1A, RST-F1B, RST-F2A and RST-F2B, and amplifying the product with RST-5AD and RST-3A. This product was cloned and sequenced. Clones were found to have a deletion which was corrected by PCR with RST-RPT, followed by overlap-PCR and cloning of products.

```
PCR primers
RST-5AD
ACTAAGCTTAAGGAGATATAACAATGATCCACACCA    (SEQ ID NO: 70)
ACCTCAA

RST-F1A
TTCCATGATCCACACCAACCTCAAAAAGAAGTTCTC    (SEQ ID NO: 71)
CCTCTTCAT

RST-F1B
AGAGTGATCACGGCGAAGAGGAGGAAGACGAGGATG    (SEQ ID NO: 72)
AAGAGGGAGAACTTCTTTT

RST-F2A
TATAGATCTGCGTGTGGAAGAAGGGCTCCGACTACG    (SEQ ID NO: 73)
AGGCCCTCACCCTCCAAGCCAAGGA

RST-F2B
CATTTGGAACTCCTTGGCTTGGAGGGTG            (SEQ ID NO: 74)

RST-3A
AACCATGGCGGCCGCCATTTGGAACTCCTTGGCT      (SEQ ID NO: 75)

RST-RPT
TATAGATCTGCGTGTGGAAGAAGGGCTCCGACTACG    (SEQ ID NO: 76)
AGGCCCTCACCCTCCAAGCCAAGGA
```

(f) otif [cytoplasmic localisation]
(g) The potato protease inhibitor II (PPI) apoplast motif [apoplast localisation]

An apoplast targeting reading frame was designed to encode the relevant potato protease inhibitor II (PPI) motif (See FIG. 15) and cloned into pJO6.3, to produce vector pJQ4.9. Briefly, the PPI motif was constructed by annealing oligonucleotides PPI-AP1, PPI-AP2, PPI-AP3, PPI-AP4, PPI-AP5 and PPI-AP6, and cloning this product as a HindIII/NotI fragment into vector pPQ10.1; the EcoRI/NotI promoter/signal fragment of pJO6.3 was then replaced with the equivalent fragment from the modified pPQ10.1 vector.

```
PCR primers
PPI-AP1
GGAATTCGTAGACAAGCTTACMATGGMCGTGCACAA    (SEQ ID NO: 77)
GGAGGT

PPI-AP2
GATCAGGAGGTAGGCWACGAAGTTWACCTC          (SEQ ID NO: 78)
CTTGTGC

PPI-AP3
CCTACCTCCTGATCGTSCTCGGCCTCCTC           (SEQ ID NO: 79)
TTGCTCGT

PPI-AP4
CCTTGGCGTCCACGTGCTCCATGGCGGAWACGAGCA    (SEQ ID NO: 80)
AGAGGAG

PPI-AP5
GTGGACGCCAAGGCCTGCACCCKCGAGTGC          (SEQ ID NO: 81)
GGCAACCTC

PPI-AP6
GGAATTCGCGGCCGCCGGGCAGATGCCGAAGCCGAG    (SEQ ID NO: 82)
GTTGCCGCACT
``` ii. C-Terminal End Signal Sequences

Four C-terminal signal sequences were utilized:

(a) Native *Aspergillus* end, [CTW] (vacuole and apoplast vectors)

This was derived directly from the genomic clone (see Example 1) as a Nco1-Sph1 fragment (Sph end filled with T4 polymerase) which replaces the Nco1-Not1 region of a standard actin -FAE vector (Not1 end filled with T4 DNA polymerase).

(b) Expression vector linker alone [CTW-PVAAA, SEQ ID NO:93](plant optimised C-terminus for vacuole, golgi and apoplast vectors)

CTW is the peptide sequence of the *Aspergillus* FAE COOH end and is here provided by oligo FAE3. In this primer the reading frame is extended to provide the additional amino acids PVAAA (SEQ ID NO:91) which are partially encoded by the Not1 site used for cloning downstream signals see c) and d) below. Some COOH amino acids/motifs may affect compartment targeting, the PVAAA sequences (SEQ ID NO:91) are expected to be neutral in this respect while the native *Aspergillus* end may not be.

(c) Linker plus KPLKDEL (SEQ ID NO:90) [first K is primer artifact, intended to be E] {ER retention vectors)

These sequences are provided by primer TER5 introduced during PCR to generate the nos terminator fragment, and identified by sequencing within a specific clone. KDEL targeting has been demonstrated in plants by Denecke et al.

((1992) EMBO J. 11: 2345-2355 Plant and mammalian sorting signals for protein retention in the endoplasmic reticulum contain a conserved epitope).

(d) Linker plus ETTEG [frameshift of (c)] (loss of ER retention–vacuole vectors)

These sequences are provided by primer TER5 introduced during PCR to generate the nos terminator fragment, and identified by sequencing within a specific clone (see Example 2A).

The KDEL signal is for ER retention, while others provide controls. A frameshift in the TER5 region [additional A] was used in subsequent constructs to destroy the ER KDEL retention signal.

The linker used in the above C-terminal targeting sequences was PVAAA (SEQ ID NO:91).

D. Co-Integration and Co-Transformation Vectors.

Co-Transformation Vectors

A Hygromycin resistance gene driven by a CaMV345S promoter (pRob5) (35S-HYG-CMV in pUC18 (modified HYG, derived from pGL2) Bilang et al (1991) Gene 100:247-50) was used for co-transformation experiments with pTT3 and pTP3.1, pJQ4.9, pJQ3.2, pJO6.3, pJQ5.2, pUB8.11 vectors.

Co-Integration Vectors

1. Actin Promoter Constructs—pTR2.22, pTR6.1, pTR8.1, pTR9.4, pTR7.1, pTT5.5 and 5.1.

The CAMV35S-hyg region from pAJEB64TCA [a plant expression vector constructed by Andy Bettany at IGER containing CaMV-HYG from pTRA151 (Zheng et al 1991 Plant Physiol 97:832-835) (CaMV35S-HYG-tml terminator as clonable cassette in pUC4) cloned into KpnI site of pCOR105] was added as a HindIII fragment at the KpnI site (T4 polymerase blunt) of pTP4a2, in divergent orientation to FAE to create pTR2.22. The FAE/Nos HindIII fragment of this vector was replaced as follows in co-expression vectors. From pTP5.1 for pTR6.1, from pTP10.1 to pTR8.1, from pTP11.1 to pTR9.4. Signal sequences of FAE in pTR2.22 were replaced as HindIII/BglII fragments in pTR7.1 (fragment from pT09.1). PCR products (ALE5/ALE-G) was digested with Acc1 and T4 polymerase, polished, followed by NotI digest and cloning into EcoRV/NotI digested pTR2.22 to give clones pTT5.5 and 5.1.

```
PCR primer
ALE-G(SEQ ID NO :92)
TATCCATGGCGGCCGCGCGGTCGGTGACGGGCCGGCCCGGGTTGGAGTCG

GCGAA
```

2. Actin Promoter Constructs -pUF1, pUA1K$_3$, pUH4, pUH5, pUH6, pUH7, pUH8, pUH9.

The HygR gene from pAJEB64TCA, driven by the CaMV promoter, was first cloned as an end-filled HindIII fragment at the end-filled XbaI site of pTP3.1, to give pHOX3. For ease of cloning the downstream HindIII site was destroyed to create pUA1K3 and replacement of the FAE/Nos terminator HindIII fragment in this vector was carried out as follows. From pTP5.1 for pUF1, from pTP11.1 for pUH4, from pTP8.5 for UH5, from pTT5 for pUH6, from pUA4.4 for pUH7, from pTU5 for pUH8 and from pUG4 for pUH9.

3. Heat-Shock Promoter Constructs—pUH10, pUH12, pUC5.11.

A co-transformation vector in which FAE is expressed from the soybean heat shock promoter was made by first modifying pMA406 to remove the nos terminator (BglII linearised and gel purified, KpnI digested, T4 DNA polymerase polished in the presence of dNTPs and recircularised), and then inserting the FAE HindIII fragment from pTP11.1, creating pTT3.1, which encodes the full aleurain signal and the native *Aspergillus* COOH-terminus.

Following assays of various constructs, co-integration vectors were constructed with FAE and HygR genes arranged in tandem.

The HygR gene from pAJEB-64-TCA, driven by the CaMV promoter, was first cloned as an end-filled HindIII fragment at the end-filled XbaI site of pTP3.1, to give pHOX3 and subsequently excised as a HindIII/SacI fragment (partial SacI digest, relevant sites found in flanking pTP3.1 sequences) which was cloned into the HindIII/SacI sites of pMA406, in tandem orientation (vector pUH1a20). FAE sequences were then cloned into the HindIII site of pUH1a20 downstream of the heat-shock promoter (HindIII fragment from pTU5 for pUH10, HindIII fragment from pTT5 for pUH12). A pTP3.1 derivative was made by cloning the CaMV/HygR HindIII cassette from pAJEB-64-TCA in tandem orientation downstream of the FAE gene in pTP3.1, inactivating the middle HindIII site by partial digestion and end-filling, and excising the combined FAE/HygR cassette as a single HindIII fragment, which was inserted at the HindIII site in pMA406 to produce pUC5.11.

EXAMPLE 3

Transformation of Plant Cells

Eight to ten weeks old embryogenic *F. arundinacea* and *L. multiflorum* suspension cultures were bombarded either with a single co-integration plasmid DNA vector containing FAE and hyg resistance genes, or with a co-transformation vector containing FAE and with plasmid pROB5 conferring hygromycin resistance (CAMV35S-hpt-nos) using a Particle Inflow Gun (PIG) (Finer et al. (1992) Development of the particle inflow gun for DNA delivery to plant cells Plant Cell Reports 11:323-328) and 1.5-3.0 μm gold particles as in Dalton et al (Dalton et al. (1999) Co-transformed diploid *Lolium perenne* (Perennial ryegrass), *Lolium multiflorum* (Italian ryegrass) and *Lolium temulentum* (Darnel) plants produced by microprojectile bombardment. Plant Cell Reports. 18: 721-726) and Kuai et al (Regeneration of fertile transgenic tall fescue (*Festuca arundinacea*) plants with a stable highly expressed foreign gene. Plant Cell Tissue and Organ Culture (1999) 58:149-154). Transformants were selected with hygromycin (25 to 50 mg/l) over a 10-12 week selection period at 25° C. under continuous white fluorescent light (60 μm$^2$ s$^{-1}$) and plants regenerated via somatic embryogenesis as in Dalton et al 1999, supra. Regenerated plants were screened for FAE activity on transfer to soil and expressing plants grown to maturity in a containment growth room at 18° C. under 16 h fluorescent lights (350 μE m$^2$ s$^{-1}$). Mature plants (6-8 weeks old) were re-assayed for FAE activity and fresh tissue harvested for Southern, Northern and Western analysis, and for self digestion analysis. The remaining tissue was freeze dried and powdered for cell wall structure analysis, in vitro-dry matter digestibility (IVDMD) determinations and for in-vitro gas production determinations of rates of tissue digestion.

EXAMPLE 4

Targeting of Expression Product

To verify that the targeting sequences are effective in delivering the gene the targeting sequences were operably linked to a green fluorescent protein GFP. The vector constructs are shown in FIG. 16. Cells were transformed by particle bombardment as in Example 3. Localization of the GFP could be visualized under a microscope 1 day after bombardment (i.e., shooting). See FIG. 16.

EXAMPLE 5

FAE1 Activity

Plants regenerated from transformed cells showed FAE activity in all plant tissues tested. Cells were transformed as above under the direction of the ER and APO targeting sequences. FAE activity in transformed *Festuca arundinacea* leaves of different ages was elevated compared to control (untransformed) plants. See FIGS. 17 and 18.

Similar results were seen with *Lolium mutiflorum* leaves at different ages transformed as above under the direction of vacuolar, ER and APO targeting sequence. See FIGS. 19 and 20.

FAE expression under a heat shock promoter can also be induced. (Data not shown.)

Thus, we have demonstrated FAE expression in *Festuca* and *Lolium* leaves under constitutive and HS promoters with effective FAE targeting to the vac, ER and apo.

FAE Assay

FAE activity was determined in soluble extracts of fresh (or frozen at—70° C.) leaves or cell cultures (0.5 g) with 0.1 M NaAc, pH 5.0 extraction buffer. Extracts were incubated with 24 mM EF (ethyl 4-hydroxy-3-methoxycinnamate) or 1% FAXX as substrate, at 28° C. for 24 hrs and FAE activity calculated as the amount of ferulic acid released. FAE activity was also determined by measuring the release of monomeric and dimeric ferulic acid from self-digested leaf or cell culture samples. Fresh, or frozen, leaves or cell cultures (0.5 g) were ground in 0.1 M NaAc, pH5.0 extraction buffer in the presence and absence of xylanase (1000U GC140/sample) without added substrate and incubated at 28° C. for 72 hrs. Following incubation, and centrifugation, soluble extracts were loaded onto an activated reverse phase C18 μNova sep-pak column (Waters), eluted with 100% MeOH and the MeOH sample analysed by HPLC.

EXAMPLE 6

Chemical Analysis of Cell Wall Extracts

Ester bound compounds were extracted from freeze dried powdered leaves or cell cultures (50-100 mg) with NaOH (5 ml of 1 M) followed by incubation at 25° C. for 23 hrs under N2. After centrifugation and acidification of the soluble extract with concentrated HCl, the extracted phenolics were loaded onto an activated reverse phase C18 μNova sep-pak column (Waters) and eluted with 100% MeOH. and the MeOH sample analysed by HPLC.

HPLC was carried out with methanol: 5% acetic acid either with a 35-65% MeOH gradient in 15 min (FAE assay) or with a 30-70% MeOH gradient in 25 min (monomer and dimer cell wall components) at 2 ml/min on a μNova Pak C18 8×10 RCM (Waters). Extracts were detected and quantified with a diode array detector (240-400 nm Waters 996PDA) monitored at 280 nm for aldehydes and 340 nm for hydroxycinnamic acids.

Levels of esterified monomeric and dimeric hydroxycinnamic acids in *Festuca arundinacea* plants expressing FAE under VAC, and ER and APO targeting sequences are reduced compared to control (untransformed) plants. The results can be seen in FIGS. 21 and 22, respectively. Thus, we show where this does not result in reduced cell wall phenolics in growing plants with vac targeting but does result in lower phenolics with ER and apo targeting. In addition, Levels of esterified monomeric and dimeric hydroxycinnamic acids in Festuca arundinacea plants expressing FAE are not significantly reduced when FAE is VAC, targeting (FIG. 21) which is as predicted for correct vacuolar targeting, but are significantly reduced, as predicted, in some plants when FAE was ER and APO targeted, compared to control (untransformed) plants. The results can be seen in FIG. 22.

EXAMPLE 7

In Vitro Dry Matter Digestibility. (IVDMD)

The in vitro dry matter digestibility (IVDMD) was estimated on 1.0 g dry weight of leaf or cell culture tissue using the pepsin/cellulase method of Jones and Hayward (The effect of pepsin treatment of herbage on the prediction of dry matter digestibility from solubility in fungal cellulase solutions. Journal of the Science of Food and Agriculture (1975) 26:711-718).

We show that the presence of FAE in the plants results in higher digestibility of the leaves. This may be due to internal FAE activity acting on normal cell walls with vacuole located FAE and to both FAE activity and the lower cell wall crosslinking with ER and apo targeted FAE (as also found with cell cultures).

End point digestibility as determined by IVDMD were higher in leaf tissue of some transformed plants of *Festuca* expressing FAE, compared to control (untransformed) plants. Examples are shown where vacuolar, ER or apoplast targeted FAE under a constitutive actin promoter have been effective at increasing IVDMD. Similar results were obtained with in leaves of *Lolium*, but were less pronounced.

Figure 23:
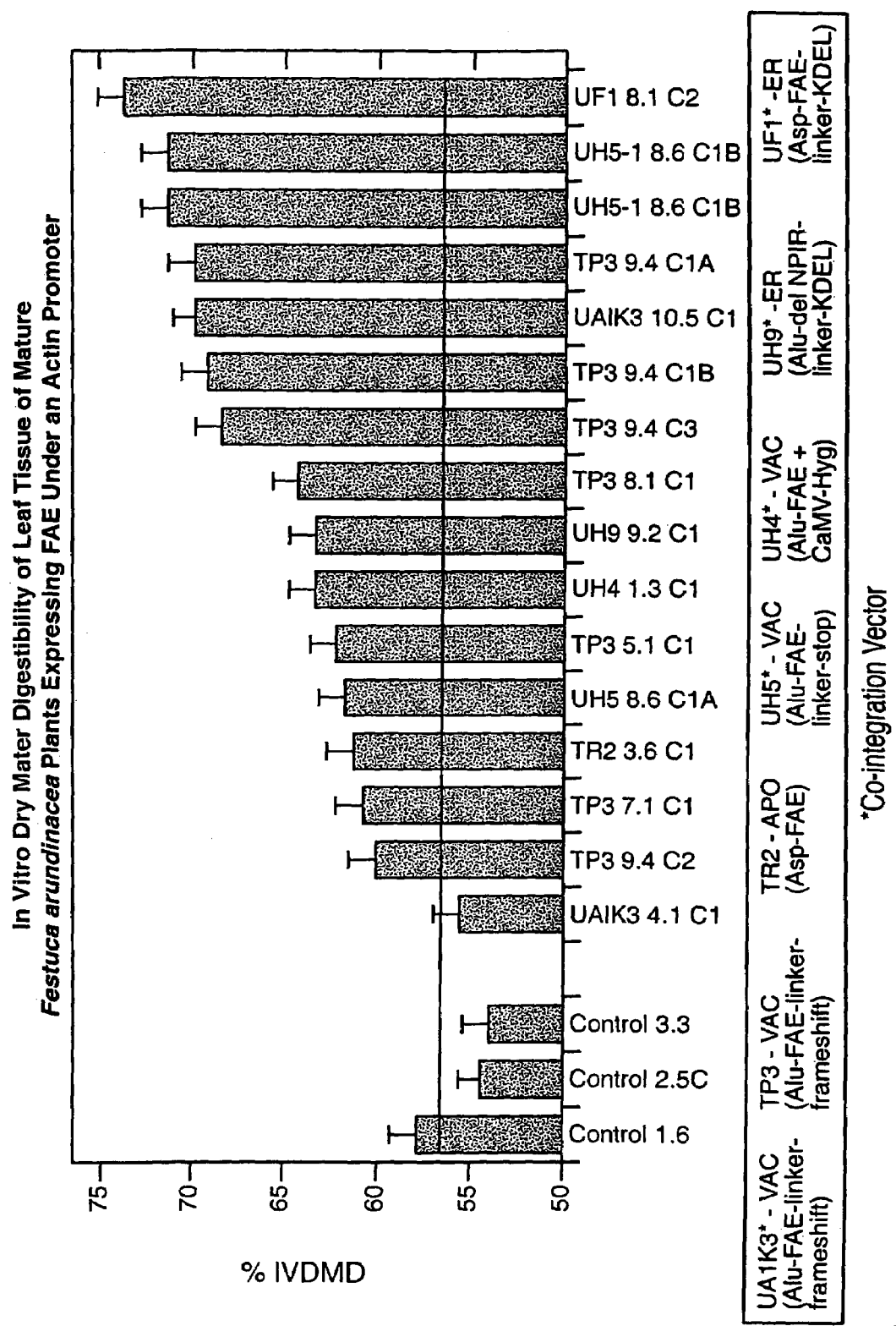
FIG. 23 illustrates the in vitro dry matter digestibility of leaf tissue of mature *Festuca arundinacea* plants expressing FAE under an actin promoter.

The results can be seen in FIGS. 23 and 24.

EXAMPLE 8

In Vitro Gas Production Measurements

In each experiment, 1.0-g samples of freeze dried powdered leaf tissue or cell culture were fermented in three 165-ml capacity serum bottles according to the pressure transducer technique of Theodorou et al. (Theodorou et al. (1994) A new gas production method using a pressure transducer to determine the fermentation kinetics of ruminant feeds. Animal Feed Science and Technology 48: 185-197). Grab samples of rumen-digesta were taken at 8.00 h before the morning feeding from fistulated wethers fed grass hay, and transported to the laboratory in a pre-warmed (39° C.) vacuum flask. The microbial inoculum and culture media were prepared as described by Theodorou et al. (1994). Each serum bottle received 10 ml of microbial inoculum, 85 ml of buffer and 4 ml of reducing agent.

At the end of the incubation period, (144 h) the contents of each serum bottle were filtered through pre-weighed sintered glass funnels and freeze dried to constant weight. Dry matter loss was calculated as the difference between the dry weight of the sample pre- and post-incubation. Additionally, the concentration of volatile fatty acids (VFA) in the liquid fraction of the culture media at the end of the 144-h incubation period was determined by gas chromatography. A Chrompack CP 9000 chromatograph fitted with an automatic sampler (Chrompack 911) and a flame-ionisation detector, linked to a Dell PC with A1-450 integration software, was used for VFA quantification.

Gas production data were fitted to the model of France et al. (France, J., Dhanoa, M. S., Theodorou, M. K, Lister, S. J., Davies. D. R. and Isac, D. 1993. A model to interpret gas accumulation profiles associated with in vitro degradation of ruminant feeds. *Journal of Theoretical Biology*. 163: 99-111.) using the MLP (Ross, G. J. S. 1987. *MLP, Maximum Likelihood Program Version* 3.08. Oxford Numerical Algorithms Group) package. The equation is in the form, $Y=A\{1-e^{[-b(t-T)-c(\sqrt{t}-\sqrt{T})]}\}$ where Y is the cumulative gas production (ml), A is the asymptote (i.e. gas pool), T is lag time, and b ($h^{-1}$) and c ($h^{-0.5}$) are decay rate constants. A combined fractional rate ($h^{-1}$) of gas production ($\mu$) was calculated as, $\mu=b+c/2\sqrt{t}$, where t is the incubation time (h).

It can be seen for *Festuca arundiancea* (denoted as BN in FIG. 25) that cell cultures have a higher rate of digestion and cumulative gas production in the presence of FAE and that the addition of an exogenous xylanase further enhance the availability of fermentable carbohydrates. Similar results are found in FAE expressing cultures without added FAE. Fermentation rates are further increased compared with controls by the addition of exogenous FAE or xylanaase as these cultures expressing FAE have a reduced cell wall phenolic composition to controls FIGS. 26-28.

EXAMPLE 9

FAE & Xylanase Transformed Plants

Addition of exogenous xylanase (GC140) greatly increased FAE mediated release of phenolics from *Festuca* and *Lolium* leaves expressing *A. niger* FAE. See FIGS. 29-31 which show that phenolic release from leaf cell walls is increased in all FAE expressing plants on cell death and this is stimulated by xylanase irrespective of the targeting. Therefore expression of a fungal xylanase in plant cells is tested.

The FAE expression cassette is modified to comprise a fungal xylanase gene (either *T. reesei* or *A. niger*) to yield a FAE-xylanase expression cassette. The FAE-xylanase expression cassette is used to transform plant cells in a manner similar to those described in Example 3. The transformed cells are allowed to grow and are selected on an appropriate medium. The enzymes so expressed increase the availability of fermentable carbohydrates to a greater extent than the FAE expression cassette.

Although the foregoing invention has been described in some detail by way of illustration and example for purposes of clarity and understanding, it will be obvious that certain changes and modifications may be practiced within the scope of the appended claims.

---

What is claimed is:

1. A method of controlling the level of phenolic acids in plant cell walls of a transgenic plant, the method comprising:
introducing into the plant an expression cassette comprising a promoter operably linked to a polynucleotide encoding a ferulic acid esterase having the sequence of SEQ ID NO:2 and a signal sequence that targets expression of the ferulic acid esterase to the endoplasmic reticulum, vacuole, apoplast, or golgi apparatus, wherein the plant is selected from *Festuca, Lolium, Sorghum, Zea, Triticum, Avena,* and *Poa*; and
producing a transgenic plant that expresses the ferulic acid esterase, wherein said ferulic acid esterase increases digestibility of the plant.

2. A method for increasing digestibility of a plant for a grass-fed animal, the method comprising introducing into a plant an expression cassette comprising a promoter operably linked to a polynucleotide encoding a ferulic acid esterase having the sequence of SEQ ID NO:2 and a signal sequence that targets expression of the ferulic acid esterase to the endoplasmic reticulum, vacuole, apoplast, or golgi apparatus, wherein the plant is selected from *Festuca, Lolium, Sorghum, Zea, Triticum, Avena*, and *Poa*, wherein the ferulic acid esterase is expressed in said plant, and wherein said ferulic acid esterase increases digestibility of the plant.

3. The method of claim 2, wherein the polynucleotide further comprises a polynucleotide that encodes CTW-PVAAA (SEQ ID NO:93) at the 3' end.

4. The method of claim 2, wherein sub-optimal codons are modified to *Triticum* spp. preferred codons.

5. The method of claim 2, wherein the introduction of the ferulic acid esterase polynucleotide into the plant is by sexual reproduction.

6. The method of claim 2, wherein the introduction of the ferulic acid esterase polynucleotide into the plant is by transformation of cell cultures.

7. The method of claim 6, wherein the cell cultures are regenerated to plants.

8. The method of claim 2, wherein the promoter is an inducible promoter, senescence promoter, a heat shock promoter, or a constitutive promoter.

9. The method of claim 2, wherein the signal sequence is upstream of the 5' end of the polynucleotide encoding ferulic acid esterase.

10. The method of claim 2, wherein the signal sequence is obtained from the signal sequence of a vacuolar targeted gene.

11. The method of claim 10, wherein the vacuolar targeted gene is a barley aleurain gene.

12. The method of claim 2, wherein the signal sequence is obtained from a vacuolar targeted senescence gene.

13. The method of claim 12, wherein the signal sequence is a *Lolium* See1 signal sequence.

14. The method of claim 2, wherein the signal sequence is derived obtained from the signal sequence of a golgi targeted gene.

15. The method of claim 14, wherein the signal sequence is a rat sialyl transferase signal sequence.

16. The method of claim 2, wherein the signal sequence is obtained from the signal sequence of an apoplast signal sequence.

17. The method of claim 2, wherein the signal sequence is obtained from the signal sequence of an *Aspergillus niger* ferulic acid esterase.

18. The method of claim 2, wherein the signal sequence is downstream of the 3' end of the ferulic acid esterase encoding polynucleotide.

19. The method of claim 2, wherein the signal sequence is a KDEL sequence.

20. The method of claim 2, wherein the second signal sequence is a stop codon.

21. The method of claim 2, wherein the signal sequence is an extension of the ferulic acid esterase reading frame to provide a linker to KDEL.

22. The method of claim 2, further comprising simultaneous introduction into the plant of a second expression cassette comprising a promoter operably linked to a polynucleotide encoding a xylanase.

23. The method of claim 22, wherein the xylanase is a fungal xylanase.

24. The method of claim 23, wherein the polynucleotide encoding a xylanase is from *Trichoderma reesei*.

25. The method of claim 22, wherein the first and second expression cassettes are present on separate plasmids.

* * * * *